US011999694B2

(12) United States Patent
Hooker et al.

(10) Patent No.: US 11,999,694 B2
(45) Date of Patent: Jun. 4, 2024

(54) DELIVERY OF THERAPEUTIC ALKALOID COMPOUNDS

(71) Applicant: Sensorium Therapeutics, Inc., Boston, MA (US)

(72) Inventors: Jacob M. Hooker, Winchester, MA (US); Michael S. Placzek, Waltham, MA (US)

(73) Assignee: Sensorium Therapeutics, Inc., Boston, MA (US)

( * ) Notice: Subject to any disclaimer, the term of this patent is extended or adjusted under 35 U.S.C. 154(b) by 0 days.

(21) Appl. No.: 17/976,150

(22) Filed: Oct. 28, 2022

(65) Prior Publication Data

US 2023/0159455 A1   May 25, 2023

Related U.S. Application Data

(60) Provisional application No. 63/352,810, filed on Jun. 16, 2022, provisional application No. 63/273,688, filed on Oct. 29, 2021.

(51) Int. Cl.

| *C07D 209/12* | (2006.01) |
| *C07D 401/12* | (2006.01) |
| *C07D 405/12* | (2006.01) |
| *C07D 409/12* | (2006.01) |
| *C07D 475/04* | (2006.01) |
| *C07D 491/113* | (2006.01) |
| *C07D 491/20* | (2006.01) |
| *C07D 495/04* | (2006.01) |
| *C07D 495/10* | (2006.01) |
| *C07D 497/10* | (2006.01) |
| *C07D 498/10* | (2006.01) |
| *C07D 519/00* | (2006.01) |
| *C07F 7/18* | (2006.01) |

(52) U.S. Cl.
CPC ......... *C07D 209/12* (2013.01); *C07D 401/12* (2013.01); *C07D 405/12* (2013.01); *C07D 409/12* (2013.01); *C07D 475/04* (2013.01); *C07D 491/113* (2013.01); *C07D 491/20* (2013.01); *C07D 495/04* (2013.01); *C07D 495/10* (2013.01); *C07D 497/10* (2013.01); *C07D 498/10* (2013.01); *C07D 519/00* (2013.01); *C07F 7/1804* (2013.01)

(58) Field of Classification Search
None
See application file for complete search history.

(56) References Cited

U.S. PATENT DOCUMENTS

| 6,288,104 | B1 | 9/2001 | Gericke et al. |
| 8,344,001 | B2 | 1/2013 | Hohlweg et al. |
| 8,552,051 | B2 | 10/2013 | Harvey et al. |
| 8,865,723 | B2 | 10/2014 | Gurney et al. |
| 8,980,338 | B2 | 3/2015 | Gericke et al. |
| 9,220,708 | B2 | 12/2015 | Ruecroft et al. |
| 9,381,220 | B2 | 7/2016 | Gericke et al. |
| 10,758,544 | B2 | 9/2020 | Wang et al. |
| 10,864,239 | B1 | 12/2020 | Bytton |
| 11,173,142 | B2 | 11/2021 | Davies |
| 11,266,651 | B2 | 3/2022 | Wang et al. |
| 11,491,159 | B2 | 11/2022 | Wang et al. |
| 2004/0044029 | A1 | 3/2004 | Dart et al. |
| 2005/0239841 | A1 | 10/2005 | Browning et al. |
| 2018/0064685 | A1 | 3/2018 | Davies |
| 2019/0070184 | A1 | 3/2019 | Wang et al. |
| 2019/0231786 | A1 | 8/2019 | Wang et al. |

FOREIGN PATENT DOCUMENTS

| CN | 102000069 A | 4/2011 |
| CN | 102153501 A | 8/2011 |
| CN | 113072576 A | 7/2021 |
| EP | 1671651 A1 | 6/2006 |
| WO | WO-1997/046234 A1 | 12/1997 |
| WO | WO-00/00184 A2 | 1/2000 |
| WO | WO-2005/051381 A1 | 6/2005 |
| WO | WO-2006/050057 A2 | 5/2006 |
| WO | WO-2008/019106 A1 | 2/2008 |
| WO | WO-2010/106494 A1 | 9/2010 |
| WO | WO-2010/106495 A1 | 9/2010 |
| WO | WO-2012/101058 A1 | 8/2012 |
| WO | WO-2014/155351 A1 | 10/2014 |
| WO | WO-2015/048590 A1 | 4/2015 |
| WO | WO-2016/049595 A1 | 3/2016 |
| WO | WO-2016/157045 A1 | 10/2016 |
| WO | WO-2016/203347 A1 | 12/2016 |
| WO | WO-2019/021196 A1 | 1/2019 |
| WO | WO-2019/021196 A9 | 5/2019 |
| WO | WO-2021/086345 A1 | 5/2021 |
| WO | WO-2022/140417 A1 | 6/2022 |

(Continued)

OTHER PUBLICATIONS

Database Registry Chemical Abstracts Service, Columbus, Ohio, Accession No. RN 41855-11-2, Entered STN: Nov. 16, 1984.*
Database Registry Chemical Abstracts Service, Columbus, Ohio, Accession No. RN 41759-66-4, Entered STN: Nov. 16, 1984.*
Database Registry Chemical Abstracts Service, Columbus, Ohio, Accession No. RN 109645-39-8, Entered STN: Aug. 8, 1987.*
International Search Report and Written Opinion for International Application No. PCT/US22/48152 dated Mar. 1, 2023.
Pubchem CID 499683 (2005).
Gericke, "Kabbo's! Kwai?: the past, present and possible future of kanna", The ethnopharmacological search for psychoactive drugs: 122-150 (2018).
International Search Report and Written Opinion for International Application No. PCT/US22/48206 dated Mar. 29, 2023.

(Continued)

*Primary Examiner* — Samantha L Shterengarts
(74) *Attorney, Agent, or Firm* — Foley Hoag LLP; Dana M. Gordon

(57) ABSTRACT

Disclosed are prodrug compounds that can be converted to mesembrine under biologically relevant conditions, such as hydrolysis in vivo; and related methods of preparing and using these compounds. Stable preparations of isolated mesembrine stereoisomers are also provided.

21 Claims, 13 Drawing Sheets

(56) References Cited

FOREIGN PATENT DOCUMENTS

| | | |
|---|---|---|
| WO | WO-2023/004428 A1 | 1/2023 |
| WO | WO-2023/069455 A1 | 4/2023 |
| WO | WO-2023/076534 A1 | 5/2023 |
| WO | WO-2023/076547 A1 | 5/2023 |
| WO | WO-2023/076586 A1 | 5/2023 |

OTHER PUBLICATIONS

Olatunji et al., "Sceletium tortuosum: A review on its phytochemistry, pharmacokinetics, biological, pre-clinical and clinical activities," Journal of Ethnopharmacology, 287 (2022) Article 114711, pp. 1-16.

Parrott et al., "Incorporation and controlled release of silyl ether prodrugs from PRINT nanoparticles", Journal of the American Chemical Society 134(18): 7978-7982 (2012).

Baillie et al., "Therapeutic targeting of 3′,5′-cyclic nucleotide phosphodiesterases: inhibition and beyond," Nature Reviews Drug Discovery, 18: 770-796 (2019).

Berkov et al., "GC-MS analysis of Amaryllidaceae and Sceletium-type alkaloids in bioactive fractions from Narcissus cv. Hawera" Rapid Commun Mass Spectrom, 35:e9116 (2021).

Chiu et al., "Proof-of-Concept Randomized Controlled Study of Cognition Effects of the Proprietary Extract Sceletium tortuosum (Zembrin) Targeting Phosphodiesterase-4 in Cognitively Healthy Subjects: Implications for Alzheimer's Dementia," Evidence-Based Complementary and Alternative Medicine, vol. 2014: Article ID 682014 pp. 1-9 (2014).

Dimpfel et al., "Effect of Zembrin and four of its alkaloid constituents on electric excitability of the rat hippocampus," Journal of Ethnopharmacology, 223: pp. 135-141 (2018).

Dimpfel et al., "Electropharmacogram of Sceletium tortuosum extract based on spectral local field power in conscious freely moving rats," Journal of Ethnopharmacology, 177: 140-147 (2016).

Dimpfel et al., "Psychophysiological Effects of Zembrin® Using Quantitative EEG Source Density in Combination with Eye-Tracking in 60 Healthy Subjects. A Double-Blind, Randomized, Placebo-Controlled, 3-Armed Study with Parallel Design," Neuroscience and Medicine, 7: 114-132 (2016).

Fountain., "The Effects of Sceletium tortuosum in the Chick Anxiety-Depression Model," Thesis for the University of Mississippi: 31 pages (2017).

Fujita et al., "Quantification of brain phosphodiesterase 4 in rat with (R)-[11C] Rolipram-PET," NeuroImage, 26: 1201-1210 (2005).

Gericke et al., "Sceletium—A review update," Journal of Ethnopharmacology, 119: 653-663 (2008).

Harvey et al., "Pharmacological actions of the South African medicinal and functional food plant Sceletium tortuosum and its principal alkaloids," Journal of Ethnopharmacology, 137: pp. 1124-1129 (2011).

Hoffman et al., "Ergogenic Effects of 8 Days of Sceletium Tortuosum Supplementation on Mood, Visual Tracking, and Reaction in Recreationally Trained Men and Women," The Journal of Strength and Conditioning Research, 34(9): 2476-2481 (2020).

International Search Report and Written Opinion for Application No. PCT/US18/31505 dated Jul. 23, 2018.

International Search Report and Written Opinion for Application No. PCT/US22/48128 dated Feb. 7, 2023.

Invitation to Pay Additonal Fees for Application No. PCT/US22/48152 dated Jan. 3, 2023.

Invitation to Pay Additonal Fees for Application No. PCT/US22/48206 dated Jan. 3, 2023.

Jeffs et al., "Late stages in the biosynthesis of mesembrine: sceletenone as a precursor to the cis-3a-(3, 4-dimethoxyphenyl) octahydroindole alkaloids", Journal of the Chemical Society, Chemical Communications 2: 60-61 (1977).

Jeffs et al., "Sceletium alkaloids. Structures of five new bases from Sceletium namaquens", The Journal of Organic Chemistry 47(19): 3611-3617 (1982).

Jeffs, et al. 'Sceletium Alkaloids in the Alkaloids', Chapter 1, The Alkaloids, vol. XIX, 1981, Academic Press, Inc., pp. 1-80.

Johson et al., "An evolutionary analysis of cAMP-specific Phosphodiesterase 4 alternative splicing," BMC Evolutionary Biology, 10: Article 247 pp. 1-14 (2010).

Krstenansky., "Mesembrine alkaloids: Review of their occurrence, chemistry, and pharmacology," Journal of Ethnopharmacology, 195: 10-19 (2017).

Loria et al., "Effects of Sceletium tortuosum in rats," Journal of Ethnopharmacology, 155: pp. 731-735 (2014).

Luo et al., "A network pharmacology-based approach to explore the therapeutic potential of Sceletium tortuosum in the treatment of neurodegenerative disorders," PLOS ONE, 17(8): 21 pages (2022).

Manda et al., "Quantification of mesembrine and mesembrenone in mouse plasma using UHPLC-QToF-MS: Application to a pharmacokinetic study," Biomedical Chromatography, 31(3): Article e3815 pp. 1-7 (2017).

Manganyi et al., "A Chewable Cure "Kanna": Biological and Pharmaceutical Properties of Sceletium tortuosum," Molecules, 26: Article 2557 pp. 1-15 (2021).

Maphanga et al., "*Mesembryanthemum tortuosum* L. alkaloids modify anxiety-like bahaviour in a zebrafish model," Journal of Ethnopharmacology, 290: 13 pages (2022).

Martin et al., "Mass spectra of Sceletium alkaloids" Organic Mass Spectrometry, 11(1):1-19 (1976).

Meyer et al., "GC-MS, LC-MSn, LC-high resolution-MSn, and NMR studies on the metabolism and toxicological detection of mesembrine and mesembrenone, the main alkaloids of the legal high "Kanna" isolated from Sceletium tortuosum," Analytical and Bioanalytical Chemistry, 407: 761-778 and Supplementary Information (2015).

Murbach et al., "A toxicological safety assessment of a standardized extract of Sceletium tortuosum (Zembrin) in rats," Food and Chemical Toxicology, 74: pp. 190-199 (2014).

Nell et al., "A Randomized, Double-Blind, Parallel-Group, Placebo-Controlled Trial of Extract Sceletium tortuosum (Zembrin) in Healthy Adults," The Journal of Alternative and Complementary Medicine, 19(11): 898-904 (2013).

Oh-Ishi, et al. 'Synthesis of dl-Mesembrine and Its Trans Isomer', Tetrahedron Letters, 1968, vol. 52, pp. 5445-5448.

Olatunji et al., "Sceletium tortuosum: A review on its phytochemistry, pharmacokinetics, biological and clinical activities," Journal of Ethnopharmacology, 280: Article 114476 pp. 1-15 (2021).

Pansare, et al. 'Stereoselective Synthesis of 3-Aryloctahydroindoles and Application in a Formal Synthesis of (−)-Pancracine', Organic Letters, 2010, vol. 12(3), pp. 556-559.

Patnala et al., "Medicinal use of Sceletium: Characterization of Phytochemical Components of Sceletium Plant Species using HPLC with UV and Electrospray Ionization—Tandem Mass Spectroscopy," J Pharm Pharm Sci, 18(4): 414-423 (2015).

Patnala, S., "Pharmaceutical Analysis and Quality of Complementary Medicines: Sceletium and Associated Products," Sceletium Review Thesis, Rhodes University: 251 pages (2007).

Perez et al., "Evaluating prodrug strategies for esterase-triggered release of alcohols" Chem Med Chem, 8(10): 1662-1667 (2013).

Plenge et al., "The antidepressant drug vilazodone is an allosteric inhibitor of the serotonin transporter," Nature Communications, 12: Article No. 5063 pp. 1-12 (2021).

Pubchem 23088482.

Reay et al., "Sceletium tortuosum (Zembrin®) ameliorates experimentally induced anxiety in healthy volunteers," Human Psychopharmacology: Clinical & Experimental, 35(6): 1-7 (2020).

Reyes-Irisarri et al., "Differential distribution of PDE4B splice variant mRNAs in rat brain and the effects of systemic administration of LPS in their expression," Synapse, 62: 74-79 (2008).

Richter et al., "PDE4 as a target for cognition enhancement," Expert Opin Ther Targets, 17(9): pp. 1011-1027 (2013).

Roscher et al., "Forensic analysis of mesembrine alkaloids in S celetium tortuosum by nonaqueous capillary electrophoresis mass spectrometry", *Electrophoresis* 33(11): 1567-1570 (2012).

Said et al., "Antidepressant potential of Mesembryanthemum cordifolium roots assisted by metabolomic analysis and virtual screening," Natural Product Research: pp. 1-6 (2020).

(56) References Cited

OTHER PUBLICATIONS

Scherman et al., "[3H]Dihydrotetrabenazine, a New In Vitro Monoaminergic Probe for Human Brain," Journal of Neurochemistry, 50(4): 1131-1136 (1988).

Singh, "Utilization of nanotechnology for formulation development, optimization and evaluation of brain targeted drug delivery system," Thesis submitted to Lovely Professional University: 59 pages (2015).

Spina, "PDE4 inhibitors: current status," British Journal of Pharmacology, 155: 308-315 (2008).

Takano et al., "A Nonhuman Primate PET Study: Measurement of Brain PDE4 Occupancy by Roflumilast Using (R)-[11C] Rolipram," Molecular Imaging and Biology, 20: 615-622 (2018).

Terburg et al., "Acute Effects of Sceletium tortuosum (Zembrin), a Dual 5-HT Reuptake and PDE4 Inhibitor, in the Human Amygdala and its Connection to the Hypothalamus," Neuropsychopharmacology, 38: 2708-2716 (2013).

Tibbo et al., "Phosphodiesterase 4B: Master Regulator of Brain Signaling," Cells, 9(5): Article 1254 pp. 1-17 (2020).

Van der Aart et al., "Quantification of human brain PDE4 occupancy by GSK356278: A [11C](R)-rolipram PET study," Journal of Cerebral Blood Flow & Metabolism, 38(11): 2033-2040 (2018).

Viljoen et al., "Formulation of Medicated Chewing Gum Containing Sceletium tortuosum and Process Optimization Utilizing the SeDeM Diagram Expert System," AAPS PharmSciTech, 22: Article No. 102 pp. 1-15 (2021).

Wakabayashi et al., "Monkey, rat, and first in human evaluation of [18F]PF-06445974, a PET radioligand that preferentially labels phosphodiesterase 4B," Journal of Nuclear Medicine, 62(Supplement 1): Abstract 1054 pp. 1-2 (2021).

Walker et al., "In Vivo Evaluation of 11C-DASB for Quantitative SERT Imaging in Rats and Mice," The Journal of Nuclear Medicine, 57(1): 115-121 (2016).

Zhang et al., "Comparison of the Pharmacological Profiles of Selective PDE4B and PDE4D Inhibitors in the Central Nervous System," Scientific Reports, 7: Article No. 40115 pp. 1-10 (2017).

Zhang et al., "The Discovery of a Novel Phosphodiesterase (PDE) 4B-Preferring Radioligand for Positron Emission Tomography (PET) Imaging," Journal of Medicinal Chemistry, 60: 8538-8551 and Supplementary Information (2017).

Zhu et al., "The antidepressant- and anxiolytic-like effects of resveratrol: Involvement of phosphodiesterase-4D inhibition," Neuropharmacology, 153: 20-31 (2019).

Zucker et al., "Characterization of high-affinity [3H]TBZOH binding to the human platelet vesicular monoamine transporter," Life Sciences, 69: 231-2317 (2001).

* cited by examiner

FIG. 3

| Compound ID | Structure | SFC separation method | Notes |
|---|---|---|---|
| COMPOUND 044 | (structure with OMe, OMe groups on phenyl attached to bicyclic system with N-Me and spiro dioxolane) | column: DAICEL CHIRALCEL OJ(250mm*30mm,10um);mobile phase: [0.1%NH3H2O ETOH];B%: 25%-25%,6.55;79min | peak 1 |
| COMPOUND 043 | (structure with OMe, OMe groups on phenyl attached to bicyclic system with N-Me and spiro dioxolane) | column: DAICEL CHIRALCEL OJ(250mm*30mm,10um);mobile phase: [0.1%NH3H2O ETOH];B%: 25%-25%,6.55;79min | peak 2 |

| Compound ID | Structure | SFC separation method | Notes |
|---|---|---|---|
| COMPOUND 045 | 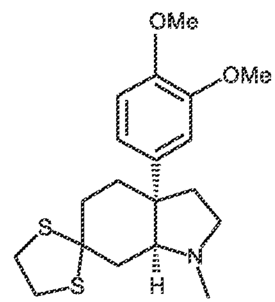 | column: DAICEL CHIRALCEL OJ(250mm*30mm,10um); mobile phase: [0.1%NH3H2O ETOH];B%: 25%-25%,6.55;79min | peak 1 |
| COMPOUND 046 | 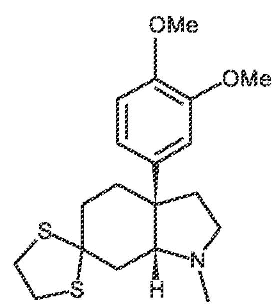 | column: DAICEL CHIRALCEL OJ(250mm*30mm,10um); mobile phase: [0.1%NH3H2O ETOH];B%: 25%-25%,6.55;79min | peak 2 |

FIG. 4

| Compound ID | Structure | Description of purification method |
|---|---|---|
| COMPOUND 013 | (structure: dimethoxyphenyl-substituted bicyclic amine with dioxolane spiro ring) | prep-HPLC (column: Welch Ultimate XB-NH2 250*50*10um;mobile phase: [Hexane-EtOH];B%: 5% - 30%,20min) |
| COMPOUND 014 | (structure: dimethoxyphenyl-substituted bicyclic amine with dithiolane spiro ring) | prep-HPLC (column: Welch Ultimate XB-CN 250*50*10um;mobile phase: [Hexane-EtOH];B%: 10% - 30%,20min) |

FIG. 4 (cont'd)

| COMPOUND 036 | [Structure: bicyclic scaffold with 3,4-dimethoxyphenyl group, N-H pyrrolidine, and nicotinoyl hydrazone substituent] | prep-HPLC (column: Welch Xtimate C18 150*25mm*5um;mobile phase: [water(NH3H2O)-ACN];B%: 10%-40%,8min) |
| --- | --- | --- |
| COMPOUND 037 | [Structure: bicyclic scaffold with 3,4-dimethoxyphenyl group, N-H pyrrolidine, and hydroxyimino (=N-OH) substituent] | pre-HPLC (column: Waters xbridge 150*25mm 10um;mobile phase: [water(NH4HCO3)-ACN];B%: 10%-40%,11min) |

| COMPOUND 038 |  | prep-HPLC(column: Waters xbridge 150*25mm 10um;mobile phase: [water( NH4HCO3)-ACN];B%: 22%-52%,11min) |
| COMPOUND 035 |  | prep-HPLC(column: Waters xbridge 150*25mm 10um;mobile phase: [water( NH4HCO3)-ACN];B%: 22%-52%,11min) |
| COMPOUND 026 |  | prep-HPLC ( column: Welch Xtimate C18 150*25mm*5um;mobile phase: [water(NH3H2O)-ACN];B%: 10%-40%,8min basic condition ) |

FIG. 4(cont'd)

| COMPOUND 006 | 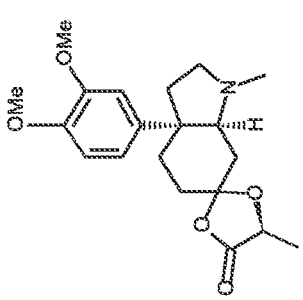 | 1) prep-HPLC (column: Welch Ultimate XB-CN 250*50*10 um;mobile phase: [Neu-ETOH];B%: %-50%,30 min);<br>2) prep-HPLC (column: Phenomenex C18 150*25mm*10um;mobile phase: [water( NH4HCO3)-ACN];B%: 30%-60%,8min);<br>3) prep-HPLC (column: Phenomenex luna C18 150*25mm* 10 um;mobile phase: [water(HCl)-ACN];B%: 8%-38%,10min);<br>4) silica gel column, eluted by EtOH/DCM |
| --- | --- | --- |
| COMPOUND 007 | 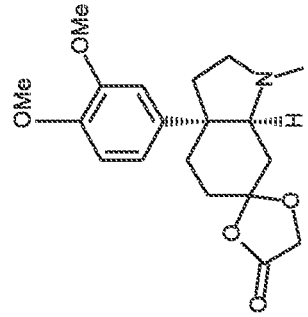 | 1) column: Phenomenex C18 150*25mm*10um;mobile phase: [water( NH4HCO3)-ACN];B%: 20%-50%,8min);<br>2) column: Phenomenex luna C18 150*25 mm * 10 um;mobile phase: [water(HCl)-ACN];B%: 3%-33%, 10 min;<br>3) silica gel column, eluted by EtOH/DCM;<br>4) column: Welch Ultimate XB-CN 250*50*10 um; mobile phase: [Hexane-EtOH];B%: 15%-45%, 25 min; |

DELIVERY OF THERAPEUTIC ALKALOID COMPOUNDS

RELATED APPLICATIONS

This application claims the benefit of priority to U.S. Provisional Patent Application Nos. 63/273,688, filed Oct. 29, 2021; and 63/352,810, filed Jun. 16, 2022.

TECHNICAL FIELD

The present disclosure relates to the field of medicine, including the discovery of novel alkaloid compounds useful for inhibiting the serotonin transporter protein (5-HTT).

BACKGROUND

Plants of the genus *Sceletium* contain indole alkaloids having biological activity useful in treating mental health conditions such as mild to moderate depression. Natural extracts of *Sceletium tortuosum*, an indigenous herb of South Africa also referred to as "kougoed", "channa" or "kanna," can contain the pharmacologically active alkaloids. Mesembrine and mesembrenol are pharmacologically active alkaloids present in *Sceletium tortuosum* extracts used for treatment of anxiety, stress and mental health conditions.

Natural products obtained from plants of the genus *Sceletium* contain varying amounts of (−) mesembrine and (+)/(−) mesembrenone. The structure of mesembrine, also known as 3a-(3,4-dimethoxyphenyl)-octahydro-1-methyl-6H-indol-6-one, has been reported by Popelak et al., Naturwiss.47,156 (1960), and the configuration by P W Jeffs et al., J. Am. Chem. Soc. 91, 3831 (1969). Naturally occurring (−) mesembrine from *Sceletium tortuosum* has been reported as having serotonin (5-HT) uptake inhibitory activity useful in treating mental health conditions such as mild to moderate depression.

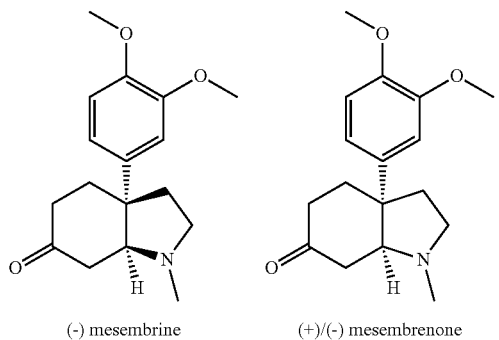 [SMILES: COc1ccc([C@@]23CCC(=O)C[C@@H]2N(C)CC3)cc1OC ; COc1ccc([C@@]23CCC(=O)C[C@@H]2N(C)CC3)cc1OC]

(−) mesembrine          (+)/(−) mesembrenone

An analysis of a standardized commercial extract of *Sceletium tortuosum* was reported in 2011 (obtained as a product under the tradename, Zembrin®) as having 0.35-0.45% total alkaloids, with mesembrenone and mesembrenol comprising ≥60%, and mesembrine contributing <20% (See Harvey et al., "Pharmacological actions of the South African medicinal and functional food plant *Sceletium tortuosum* and its principal alkaloids," Journal of Ethnopharmacology 137 (2011) 1124-11292011 and Murbach et. al., "A toxicological safety assessment of a standardized extract of *Sceletium tortuosum* (Zembrin®) in rats," Food and Chemical Toxicology 74 (2014) 190-199). The extract gave >80% inhibition at serotonin (5-HT) transporter with potency of the isolated alkaloids at the 5-HT transporter reported as shown in Table A below (Harvey et al., 2011). Referring to the data in Table A, concentration-dependent inhibition was found, with mesembrine being the more active compound (i.e., 20 times more potent than mesembrenone and 87 times more active than mesembrenol) in the 5-HT transporter assay. A toxicological safety assessment of this standardized extract was subsequently reported in 2014 (Murbach et al., 2014).

Table A. Summary of analysis of the concentration response curves of alkaloids on binding to the 5-HT transporter (Harvey et al., 2011)

| Compound | 5-HT transporter (SERT) | |
| --- | --- | --- |
|  | $K_i$ (nM) | nH |
| Mesembrine | 1.4 | 1.0 |
| Mesembrenone | 27 | 1.0 |

However, bioactive plant extracts for therapeutic consumption can vary widely both seasonally and between different *Sceletium tortuosum* plants, and fail to provide a sufficiently reproducible and stable phytochemical profile of desired biologically active components. Plants of the genus *Sceletium* and extracts thereof can vary widely in terms of the total alkaloid content, as well as the chemistry and relative concentrations of individual *Sceletium* plant derived alkaloids. In addition, mesembrine is unstable under a variety of conditions that can occur during extraction from plant material, as well as during storage and formulation of the extract. For example, mesembrine has been reported to be unstable under conditions of fermentation, exposure to light, exposure to heat, and in an aqueous medium.

The therapeutic use of mesembrine has been limited by the variability and instability of these compounds content in natural extract products and the instability and pharmacokinetic profile of these compounds as obtained from natural products.

There remains an unmet need for pharmaceutical compositions comprising higher purity, predictable, stable and reproducible forms of therapeutic alkaloid compounds such as mesembrine. In addition, there is a need for oral pharmaceutical compositions providing pure therapeutic alkaloid compositions having desired pharmacokinetic properties upon administration. Finally, there is an unmet need for isolated and stabilized forms of (+) mesembrine, and pharmaceutical compositions comprising markedly different properties than the naturally occurring compositions obtained from plant extracts.

SUMMARY

Described are prodrug compounds that, when administered orally or intravenously to a subject, convert to mesembrine in vivo. Remarkably, the compounds allow for sustained release of mesembrine thereby extending exposure of mesembrine in the brain compared to a subject receiving an equivalent oral or intravenous dose of mesembrine itself. The sustained release and extended brain exposure to mesembrine will address recognized therapeutic shortcomings attributed to the pharmacokinetics of mesembrine. The prodrug compounds provide improved duration of action of mesembrine for enhanced therapeutic benefit.

Described herein are compounds of formula (I):

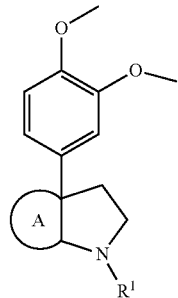

(I)

or a pharmaceutically acceptable salt thereof, wherein
$R^1$ is $C_1$-$C_7$ alkyl or H; and
ring A is

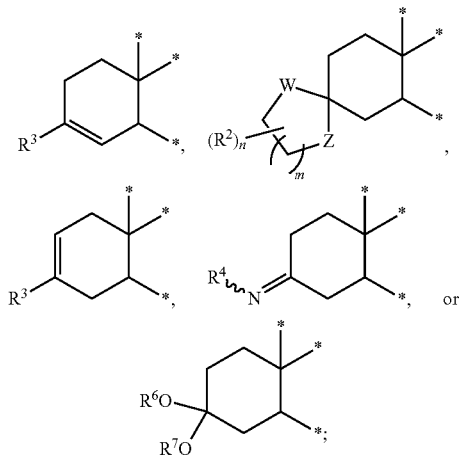

wherein * denotes the attachment points of ring A to the compound of formula (I), and wherein
each of W and Z is independently O, NH, or S;
each $R^2$ is independently $C_1$-$C_3$ alkyl, $C_2$-$C_6$ alkenyl, —COOH, —CONH$_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by —OH, $C_1$-$C_3$ alkyl, or $C_1$-$C_3$ alkanol;
m is 1 or 2;
n is 0, 1, 2, or 3;
$R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, phenoxy or —O(CH$_2$)$_p$OCH$_3$;

p is 2, 3, or 4;
$R^4$ is —OR$^5$ or —N(R$^5$)$_2$;
each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)$C_1$-$C_6$ alkyl, or —C(O)OC$_1$-$C_6$ alkyl; and
each of $R^6$ and $R^7$ is independently $C_1$-$C_3$ alkyl.

In certain embodiments, the compound is of formula (I-1):

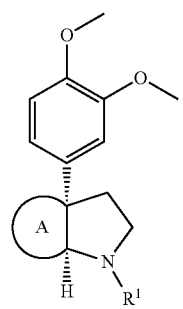

(I-1)

or a pharmaceutically acceptable salt thereof, wherein
$R^1$ is H or $C_1$-$C_7$ alkyl; and
ring A is

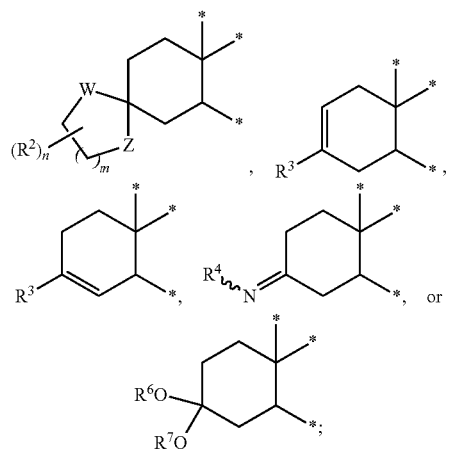

wherein * denotes the attachment points of ring A to the compound of formula (I), and wherein each of W and Z is independently O, NH, or S;

each $R^2$ is independently $C_1$-$C_3$ alkyl, $C_2$-$C_6$ alkenyl, —COOH, —CONH$_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by —OH, $C_1$-$C_3$ alkyl, or $C_1$-$C_3$ alkanol, m is 1 or 2, n is 0, 1, or 2, $R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, or phenoxy;

$R^4$ is —OR$^5$ or —N(R$^5$)$_2$;

each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)$C_1$-$C_6$ alkyl, or —C(O)O$C_1$-$C_6$ alkyl; and each of $R^6$ and $R^7$ is independently $C_1$-$C_3$ alkyl.

In certain embodiments, the compound is of formula (I-1):

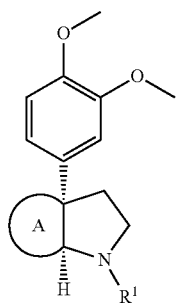

(I-1)

or a pharmaceutically acceptable salt thereof, wherein $R^1$ is $C_1$-$C_7$ alkyl or H; and ring A is

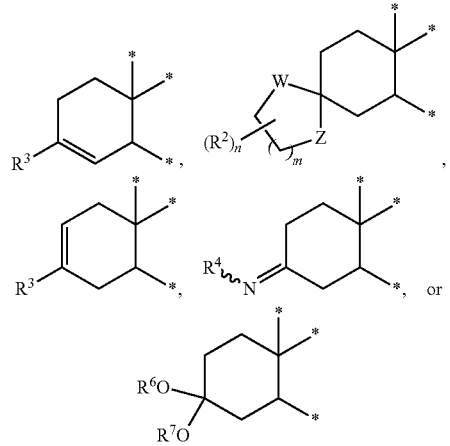

wherein * denotes the attachment points of ring A to the compound of formula (I), and wherein each of W and Z is independently O, NH, or S;

each $R^2$ is independently $C_1$-$C_3$ alkyl, $C_2$-$C_6$ alkenyl, —COOH, —CONH$_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by —OH, $C_1$-$C_3$ alkyl, or $C_1$-$C_3$ alkanol;

m is 1 or 2;

n is 0, 1, or 2;

$R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, or phenoxy or —O(CH$_2$)$_p$OCH$_3$;

p is 2, 3, or 4;

$R^4$ is —OR$^5$ or —N(R$^5$)$_2$;

each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, C(O)

N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)$C_1$-$C_6$ alkyl, or —C(O)O$C_1$-$C_6$ alkyl;

each of $R^6$ and $R^7$ is independently $C_1$-$C_3$ alkyl; and the compound of formula (I-1) has the absolute stereochemistry shown.

In certain embodiments, the compound of formula (I) is a compound of formula (IIa):

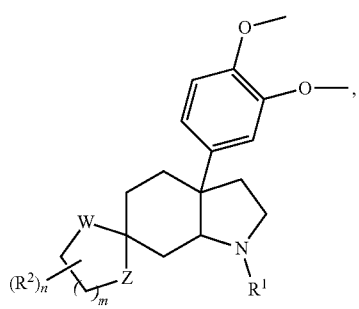

formula (IIa)

or a pharmaceutically acceptable salt thereof, wherein $R^1$, $R^2$, m, n, W, and Z are as defined herein.

In certain embodiments, the compound is of formula (IIa-1):

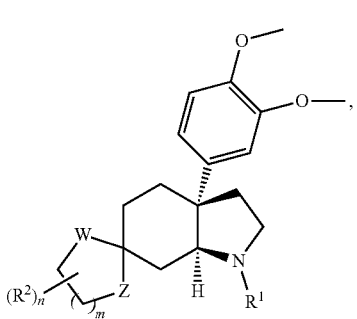

(IIa-1)

or a pharmaceutically acceptable salt thereof, wherein $R^1$, $R^2$, m, n, W, and Z are as defined herein; and the compound of formula (IIa-1) has the absolute stereochemistry shown.

In certain embodiments, the compound of formula (I) is a compound of formula (IIIa):

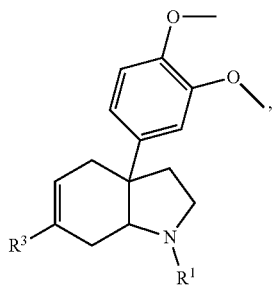

(IIIa)

or a pharmaceutically acceptable salt thereof, wherein $R^1$, and $R^3$ are as defined herein.

In certain embodiments, the compound of formula (I) is a compound of formula (IIIb):

(IIIb)

or a pharmaceutically acceptable salt thereof, wherein $R^1$ and $R^3$ are as defined herein.

In certain embodiments, the compound is of formula (IIIa-1):

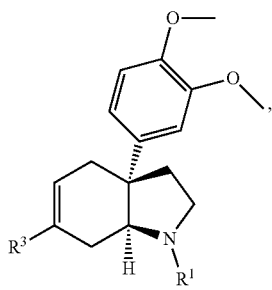

formula (IIIa-1)

or a pharmaceutically acceptable salt thereof, wherein $R^1$ and $R^3$ are as defined herein; and the compound of formula (IIIa-1) has the absolute stereochemistry shown.

In certain embodiments, the compound is of formula (IIIb-1):

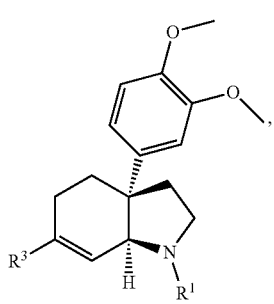

formula (IIIb-1)

or a pharmaceutically acceptable salt thereof, wherein $R^1$ and $R^3$ are as defined herein or a pharmaceutically acceptable salt thereof; and the compound of formula (IIIb-1) has the absolute stereochemistry shown.

In certain embodiments, the compound of formula (I) is a compound of formula (IVa):

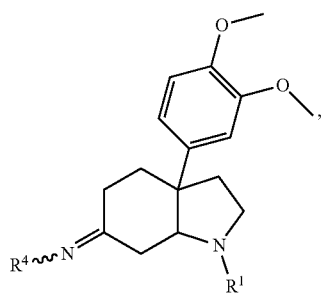

(IVa)

or a pharmaceutically acceptable salt thereof, wherein $R^1$ and $R^4$ are as defined herein.

In certain embodiments, the compound is of formula (IVa-1):

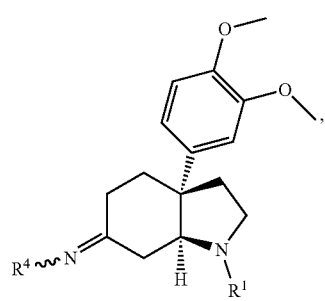

(IVa-1)

or a pharmaceutically acceptable salt thereof, wherein $R^1$ and $R^4$ are as defined herein; and the compound of formula (IVa-1) has the absolute stereochemistry shown.

In certain embodiments, the compound is of formula (IA):

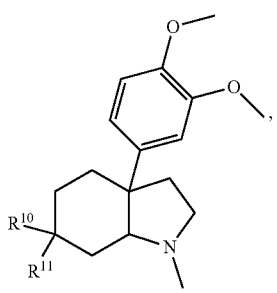

(IA)

or a pharmaceutically acceptable salt thereof, and $R^{10}$ and $R^{11}$ are as defined herein, for example as a biologically labile moiety selected to provide in vivo conversion of a compound of Formula (IA) to mesembrine.

In certain embodiments, the compound is of formula (IB-1) or formula (IB-2):

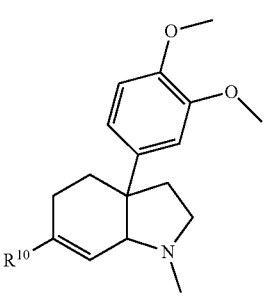

(IB-1)

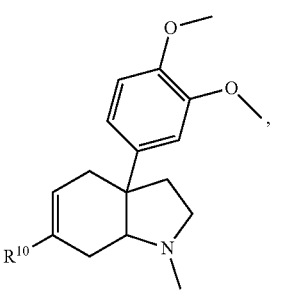

(IB-2)

or a pharmaceutically acceptable salt thereof, wherein $R^{10}$ and $R^{11}$ are as defined herein, for example as a biologically labile moiety selected to provide in vivo conversion of a compound of Formula (IA) to mesembrine.

In certain embodiments, the compound is of formula (V):

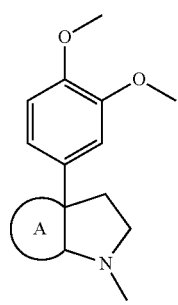

(V)

or a pharmaceutically acceptable salt thereof,
wherein
ring A is

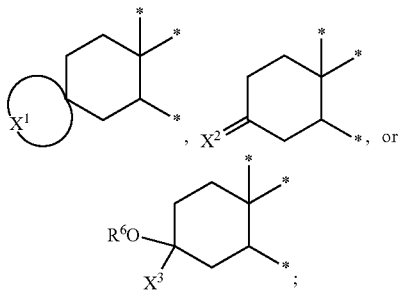

wherein * denotes the attachment points of ring A to the compound of formula (I), and wherein
  $R^6$ is $C_1$-$C_3$ alkyl;
  $X^1$ is >L-$R^{14}$, wherein L is absent or a linker and where > denotes the two single bonds to the cyclohexane ring such that the ring containing $X^1$ forms a $C_3$-$C_6$ alkyl ring, which is optionally substituted by $C_1$-$C_3$ alkanol;
  $X^2$ is =L-$R^{14}$, wherein L is absent or a linker;
  $X^3$ is -L-$R^{14}$, wherein L is absent or a linker; and
  $R^{14}$ comprises a generally recognized as safe (GRAS) compound.

In some embodiments, the compound is of formula (V-1):

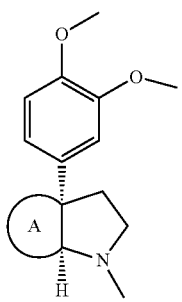

(V-1)

or a pharmaceutically acceptable salt thereof,
wherein
ring A is

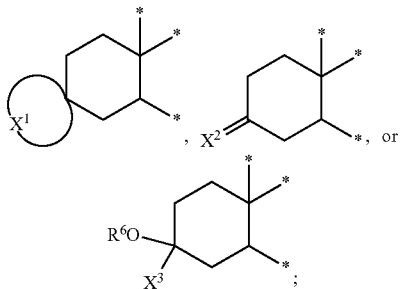

wherein * denotes the attachment points of ring A to the compound of formula (I), and wherein
  $R^6$ is $C_1$-$C_3$ alkyl;
  $X^1$ is >L-$R^{14}$, wherein L is absent or a linker and where > denotes the two single bonds to the cyclohexane ring such that the ring containing $X^1$ forms a $C_3$-$C_6$ alkyl ring, which is optionally substituted by $C_1$-$C_3$ alkanol;
  $X^2$ is =L-$R^{14}$, wherein L is absent or a linker;
  $X^3$ is -L-$R^{14}$, wherein L is absent or a linker;
  $R^{14}$ comprises a generally recognized as safe (GRAS) compound; and
  the compound of formula (V-1) has the absolute stereochemistry shown.

In some embodiments, the compound is selected from the group consisting of:

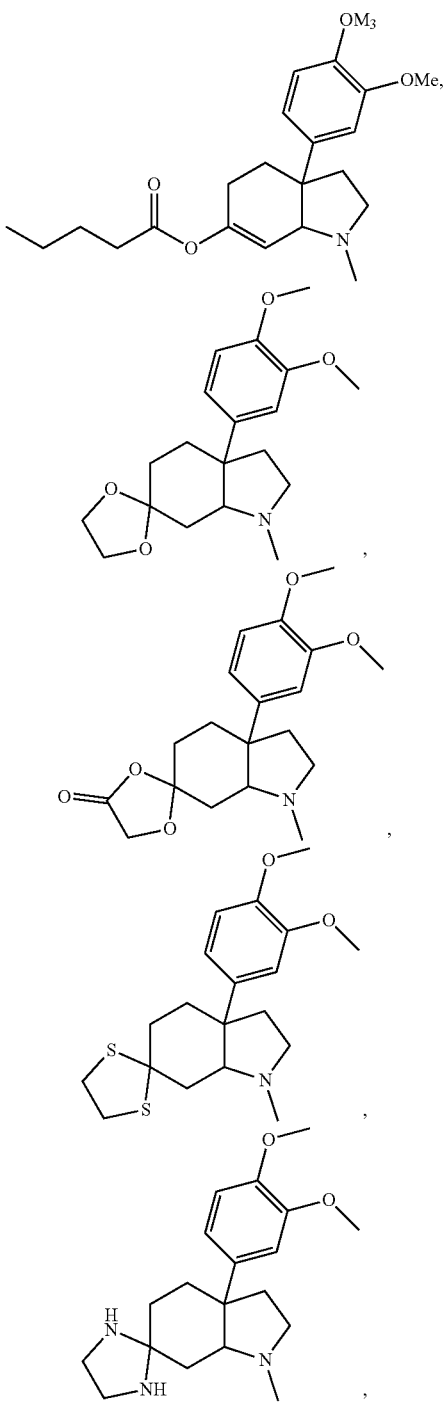

-continued
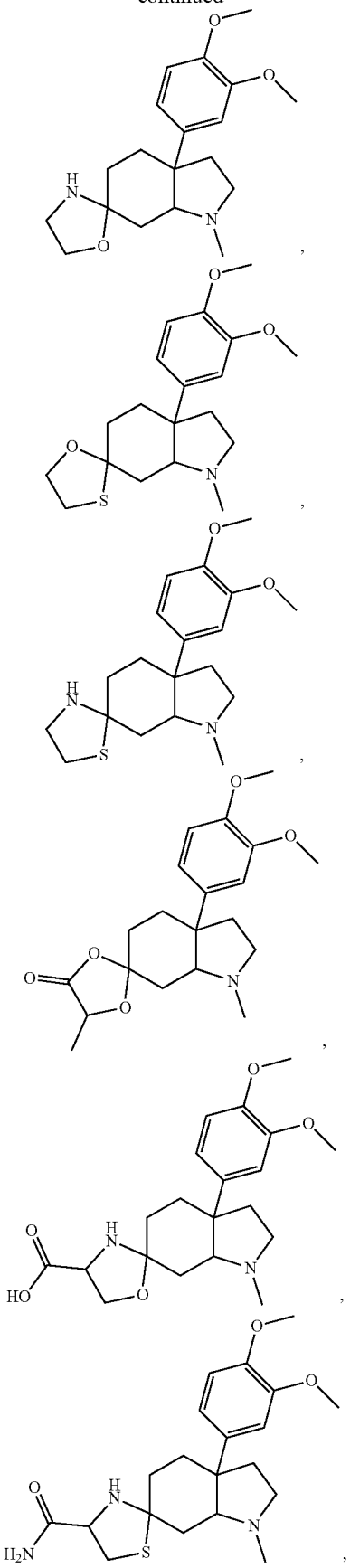
-continued
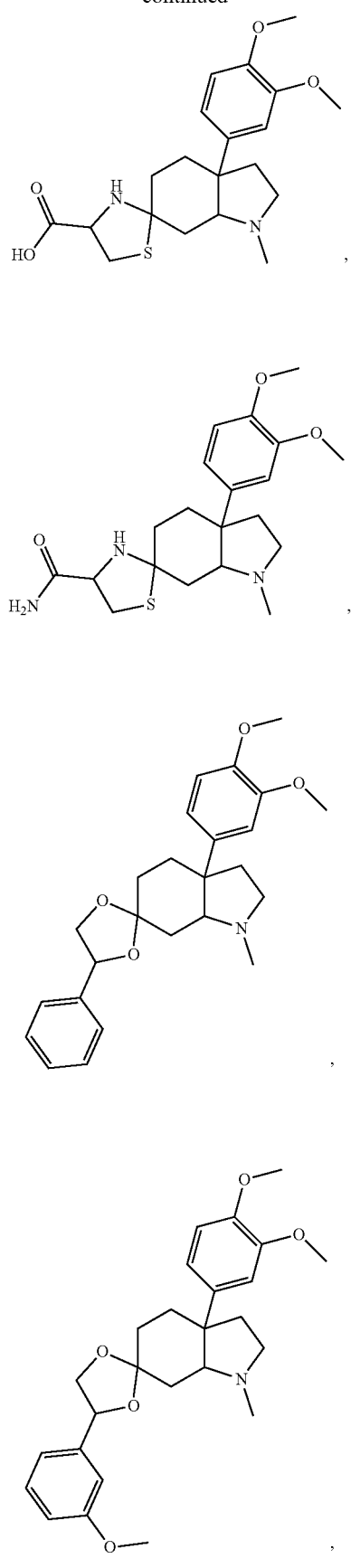

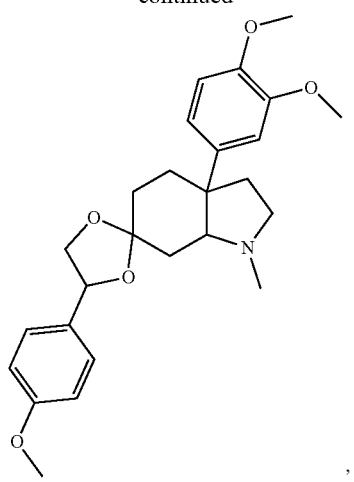
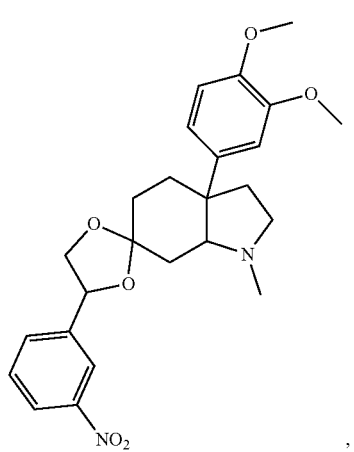
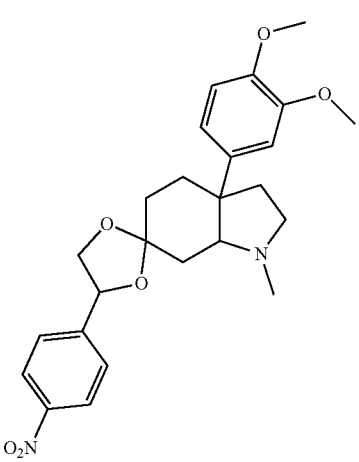
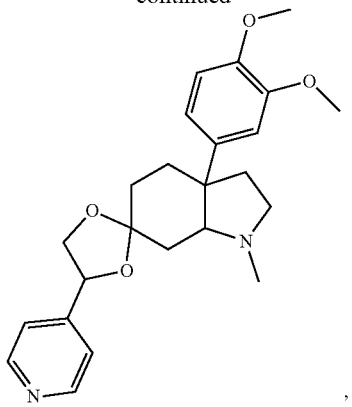
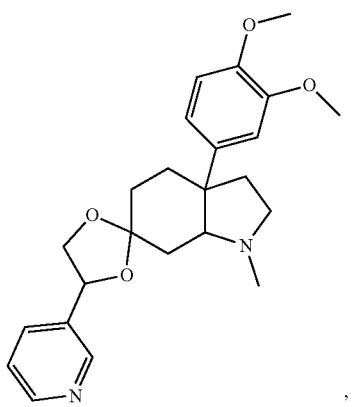
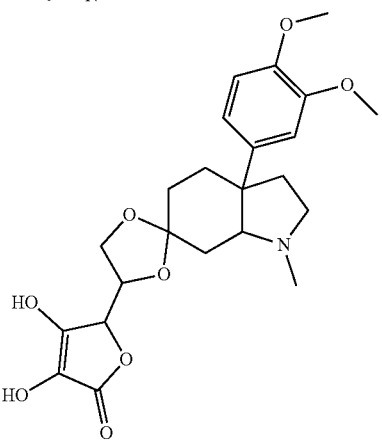
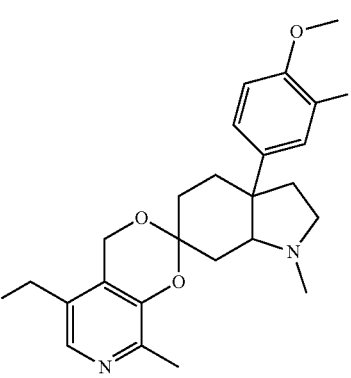

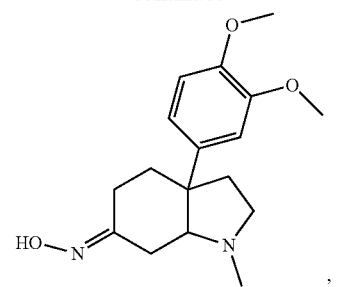,
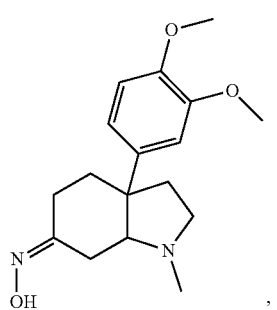,
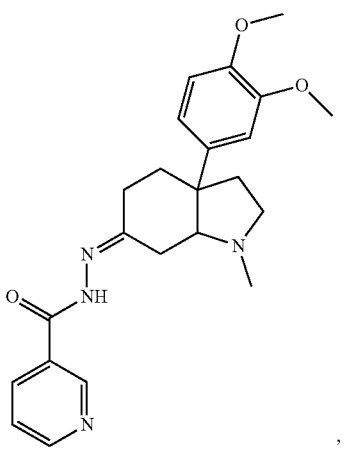,
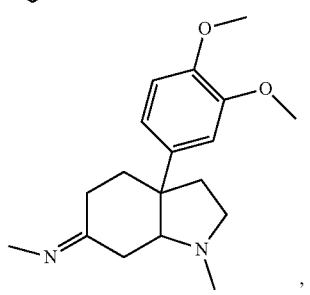,
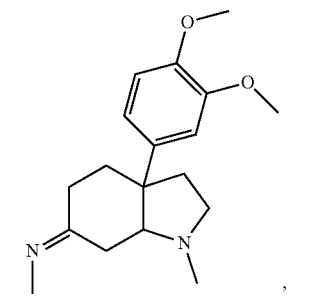,
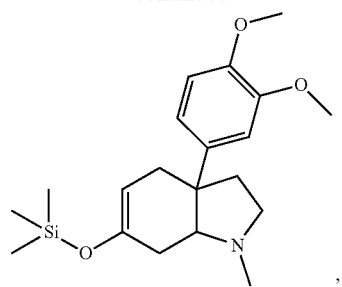,
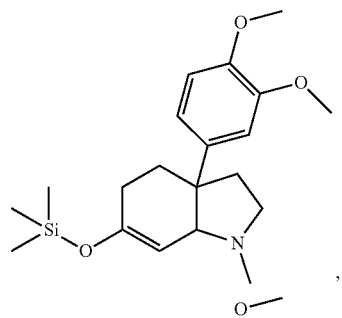,
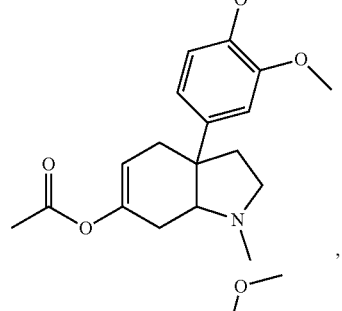,
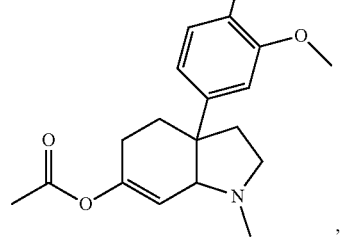,
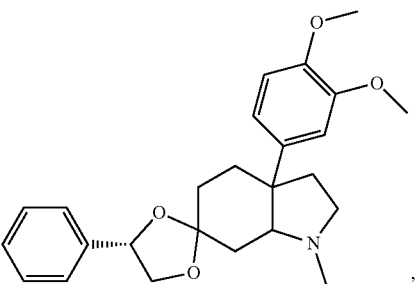,
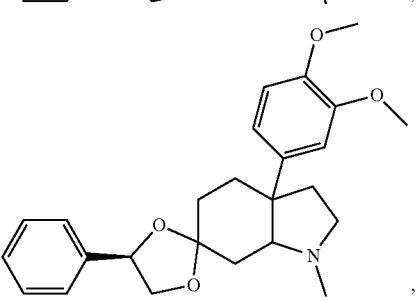,

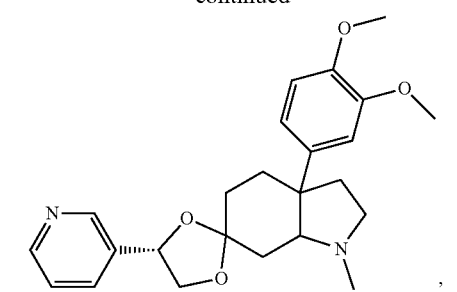,
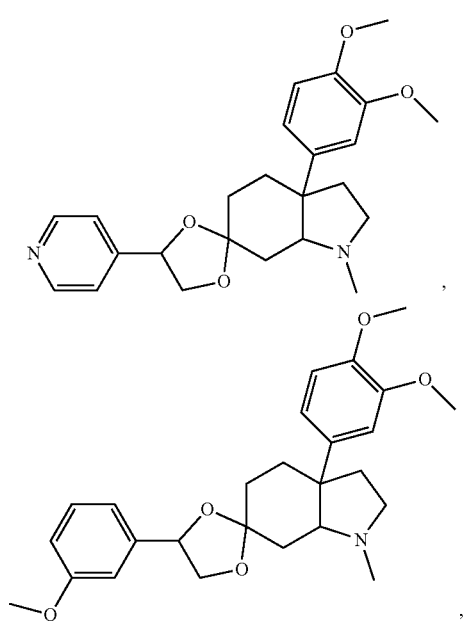,
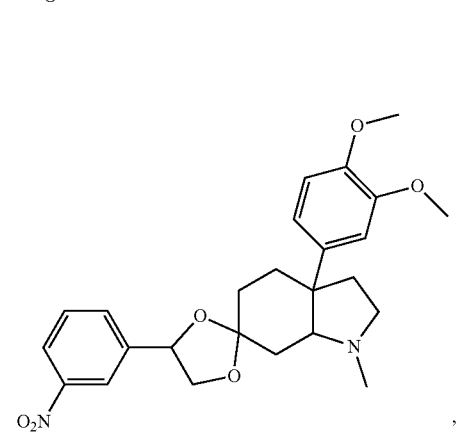,
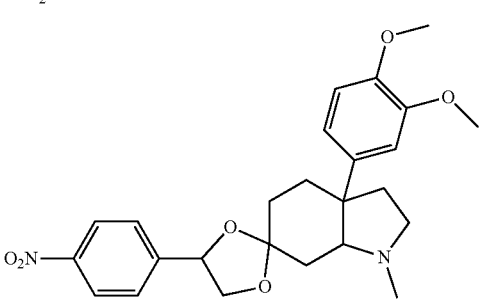,
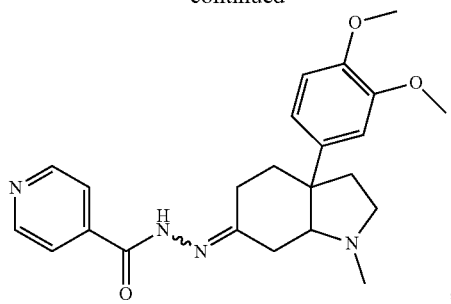,
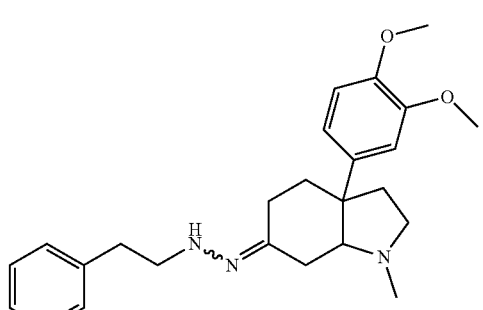,
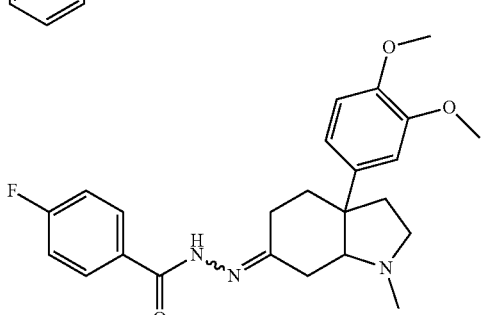,
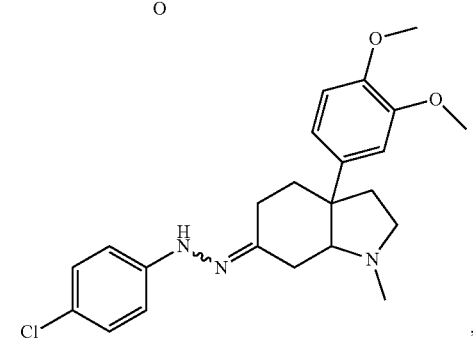,
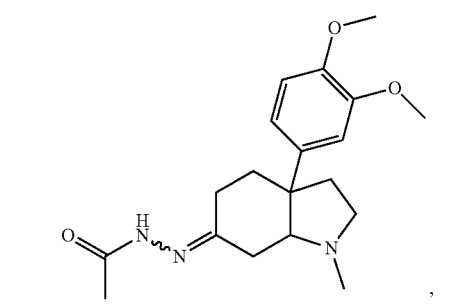, -continued
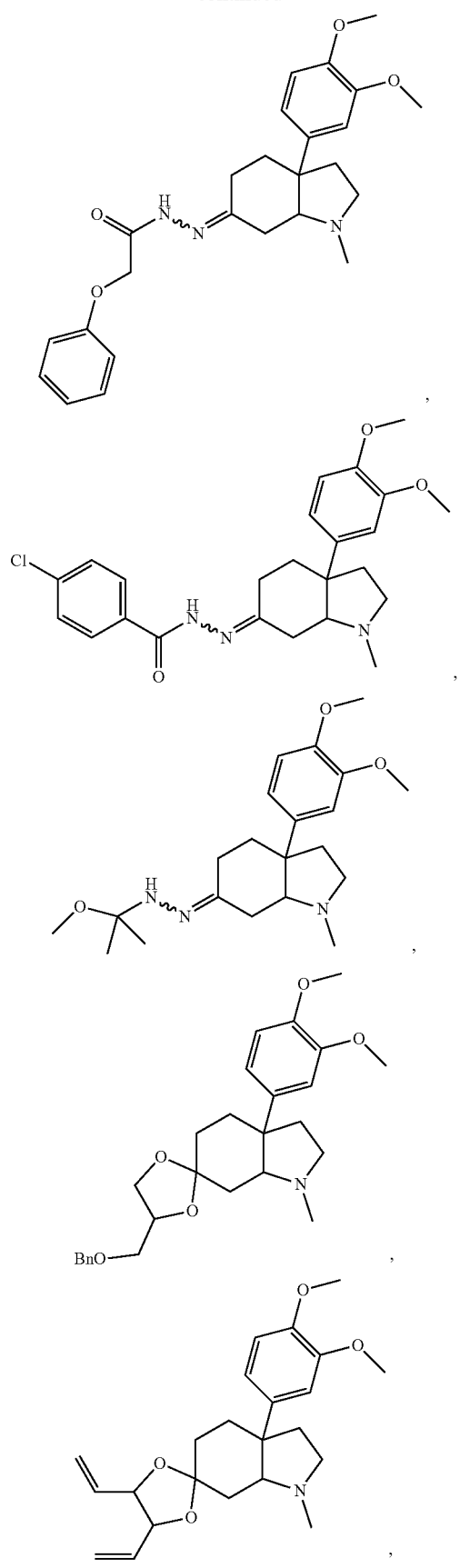
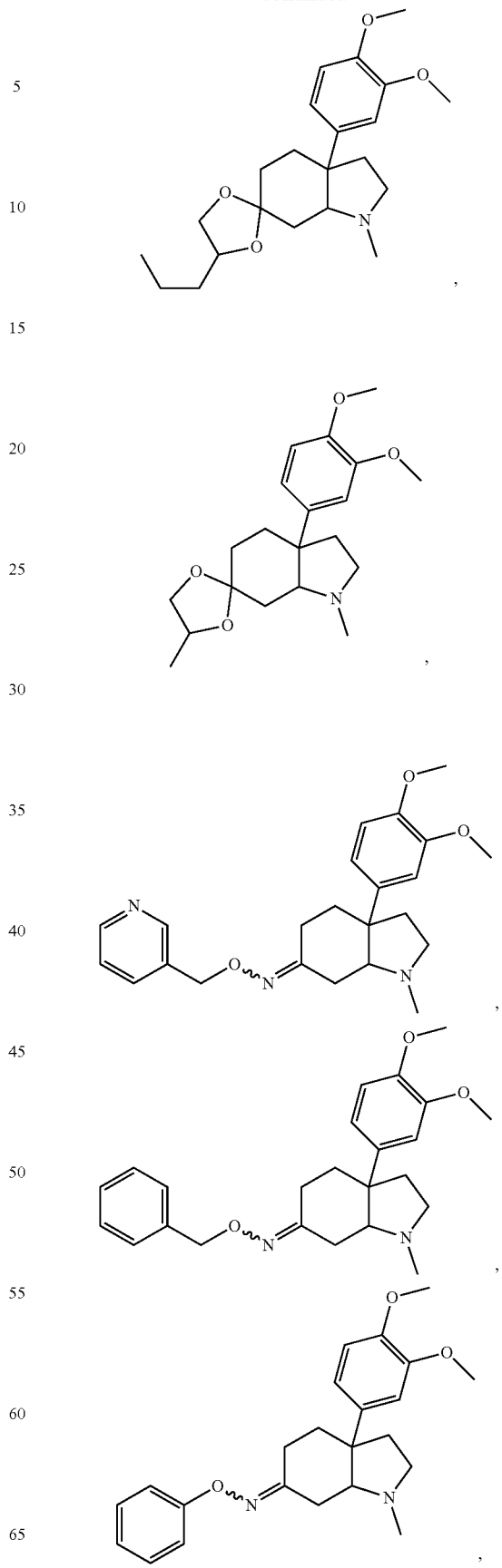

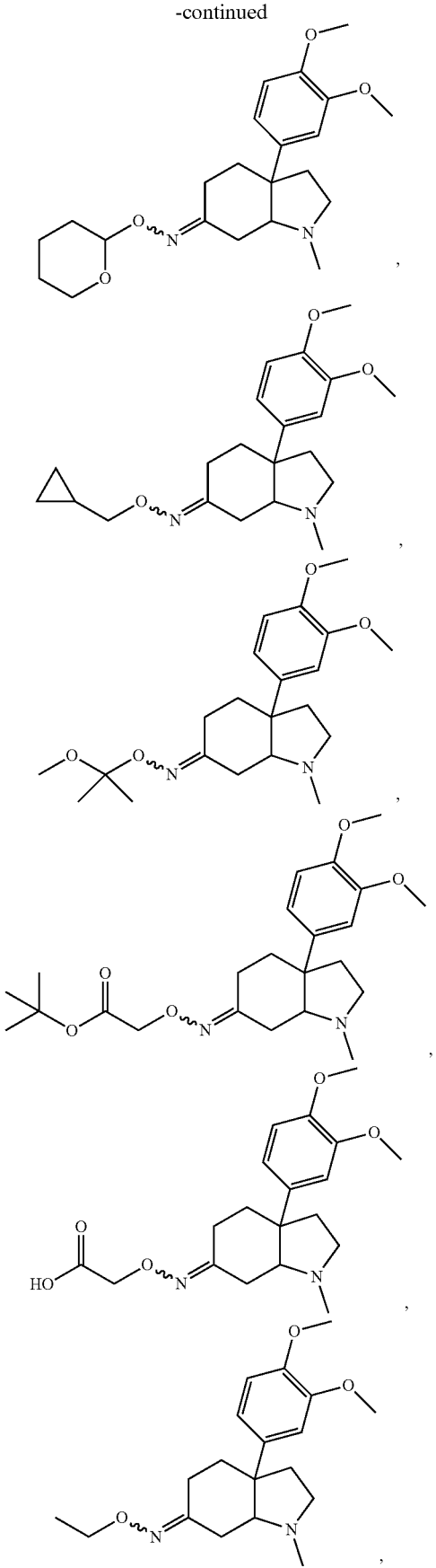
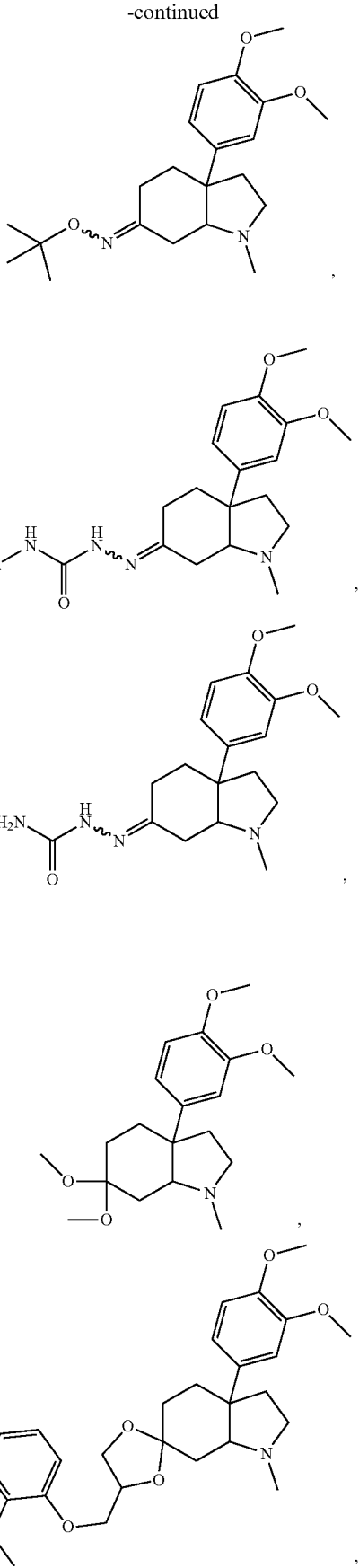

-continued
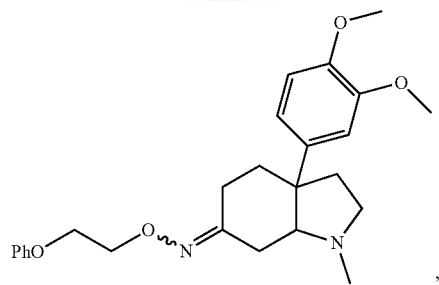
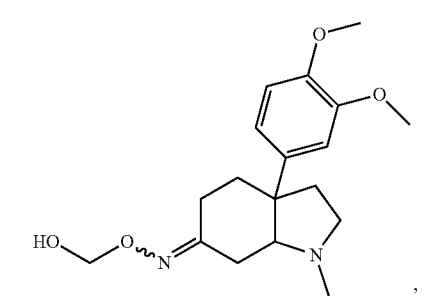
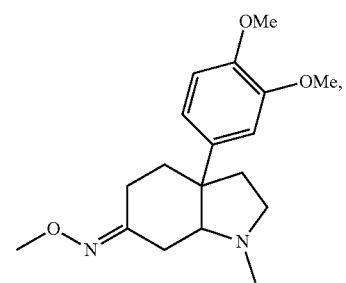
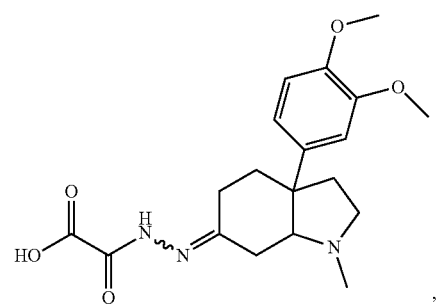
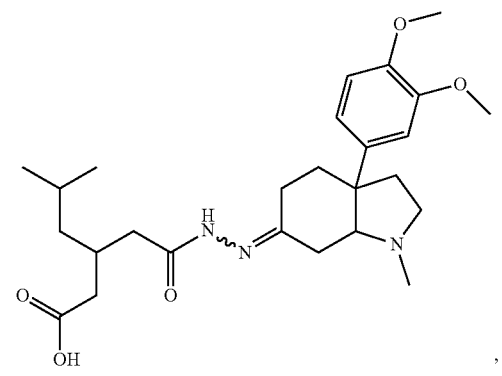
-continued
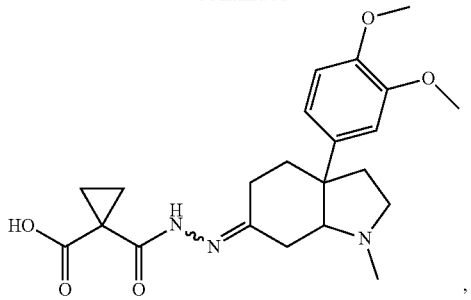
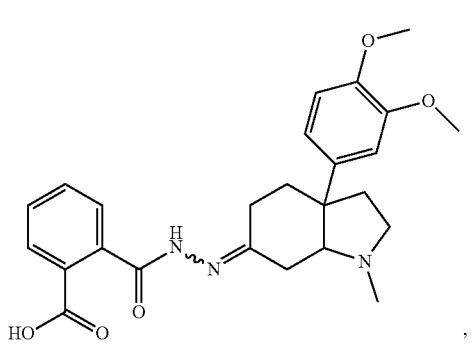
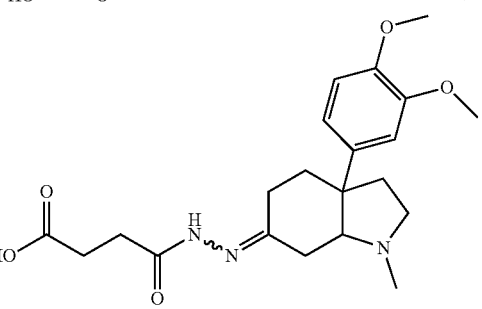
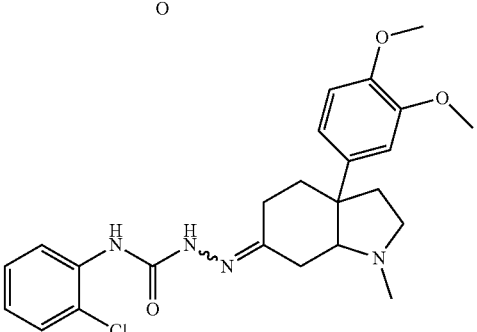
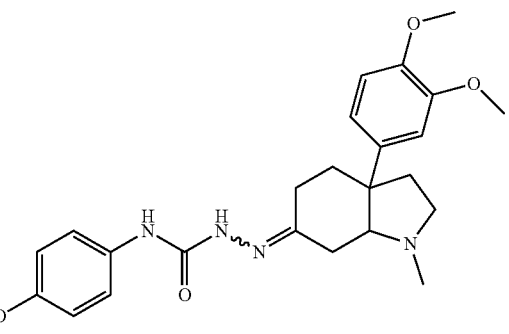

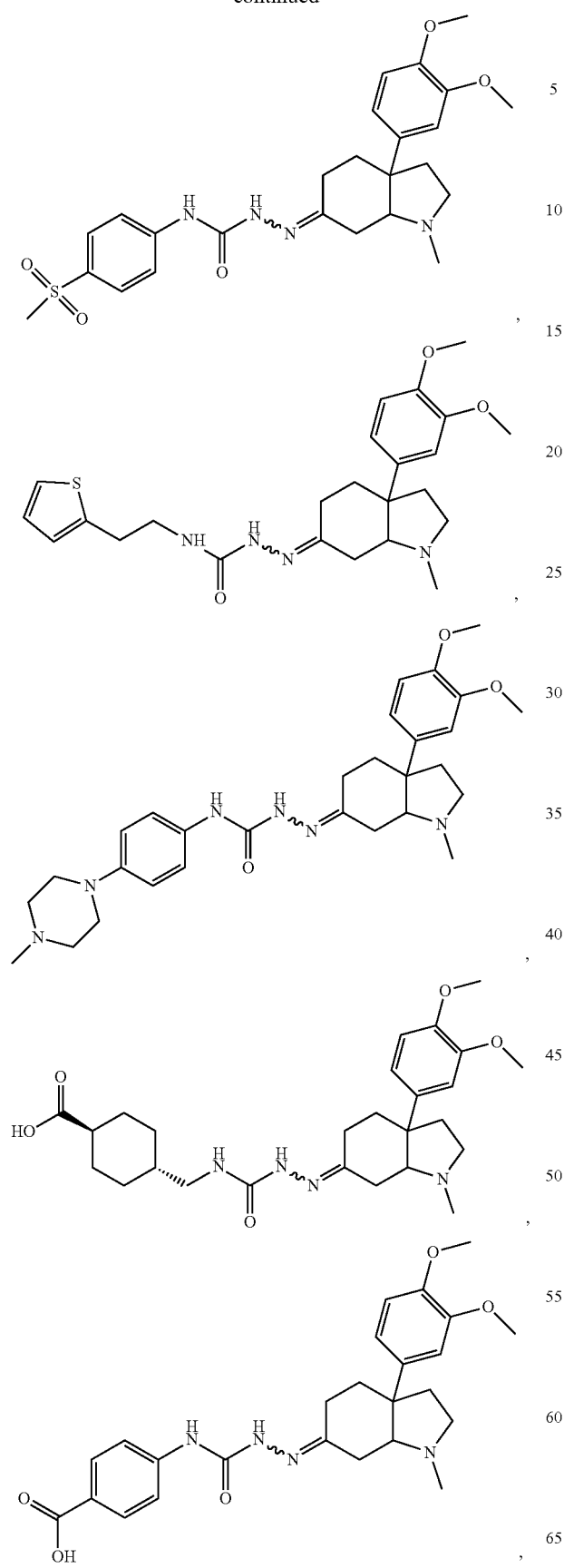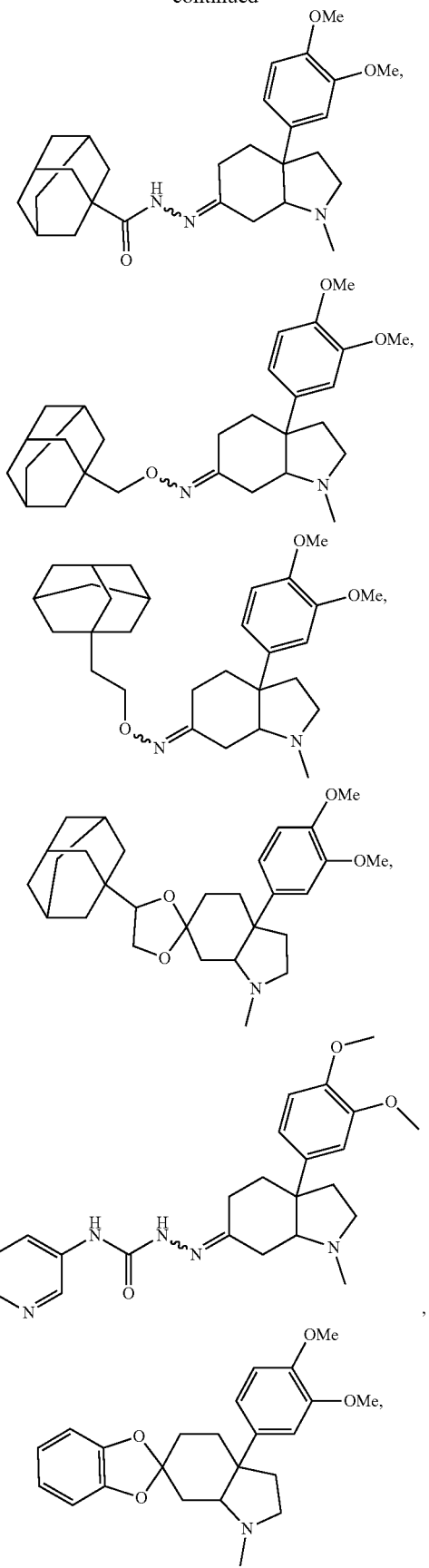

29
-continued
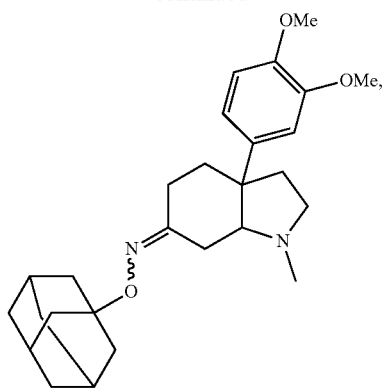
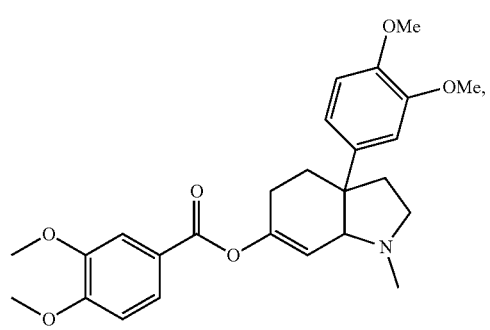
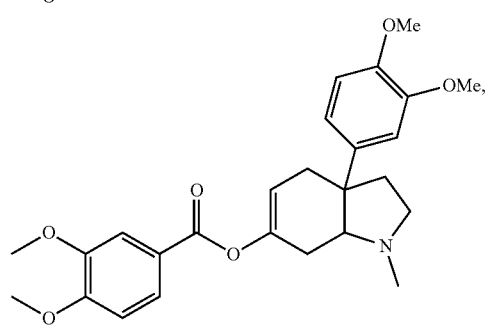
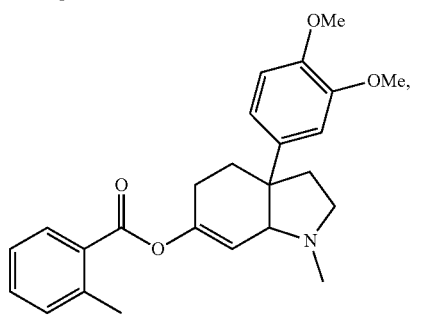
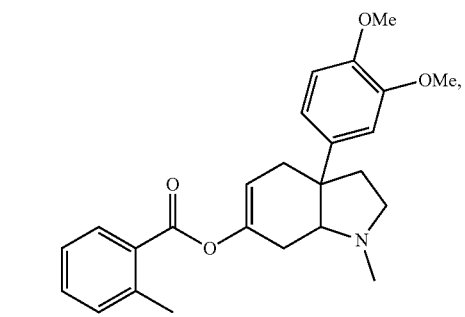
30
-continued
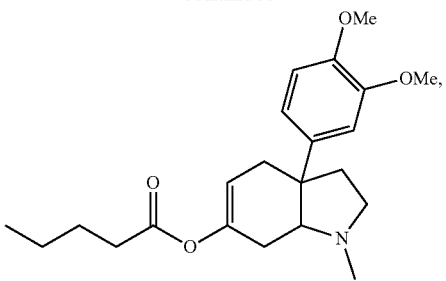
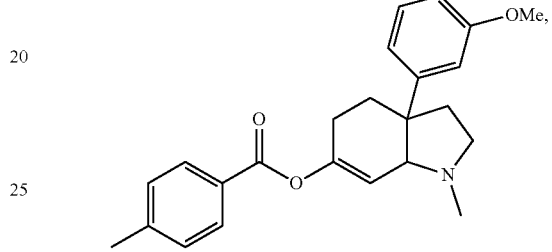
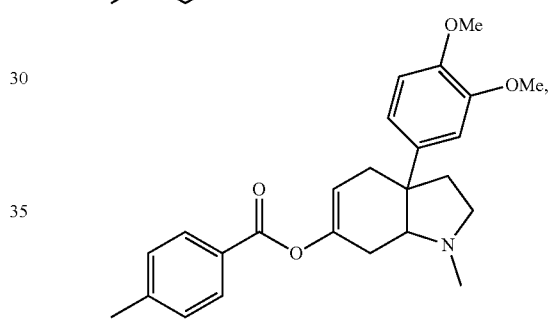
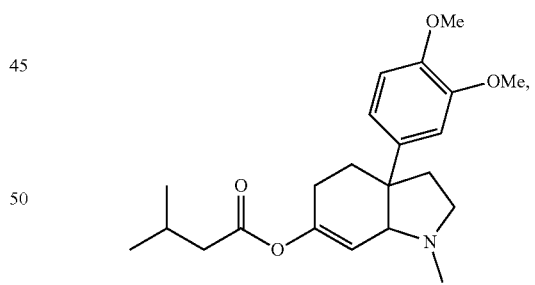
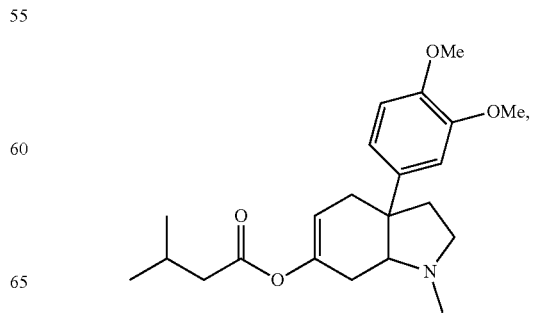

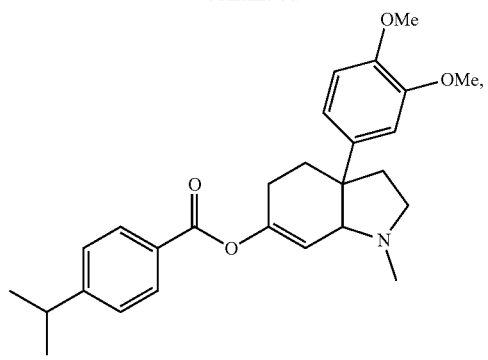
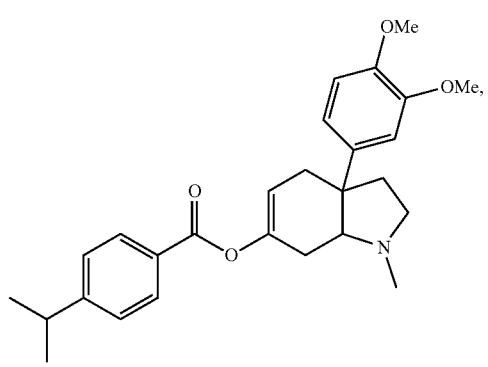
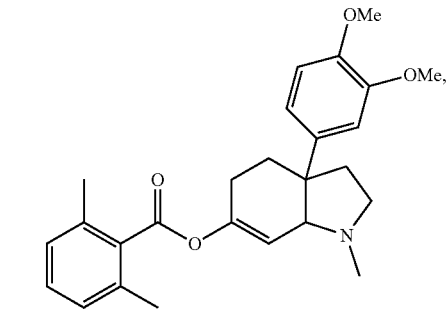
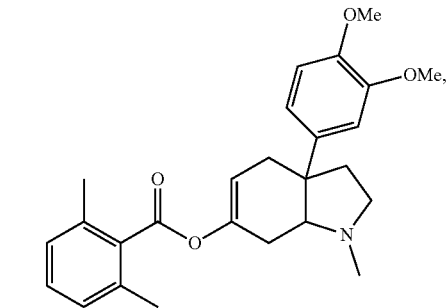
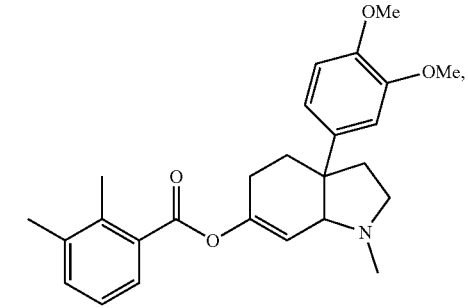
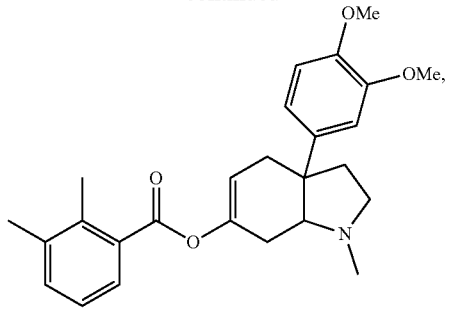
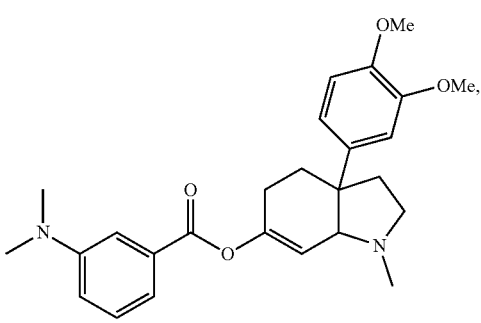
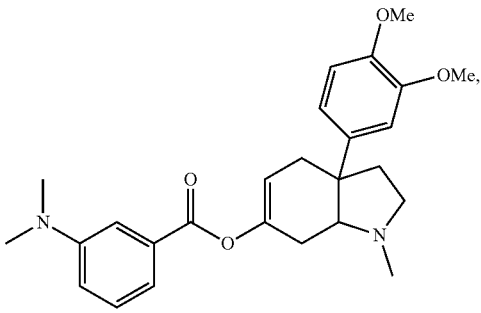
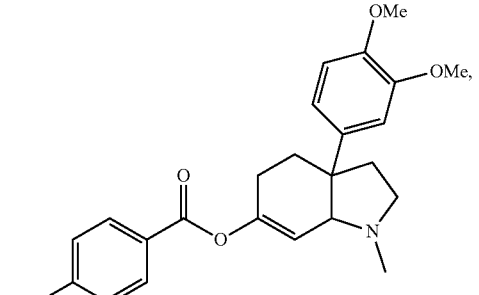
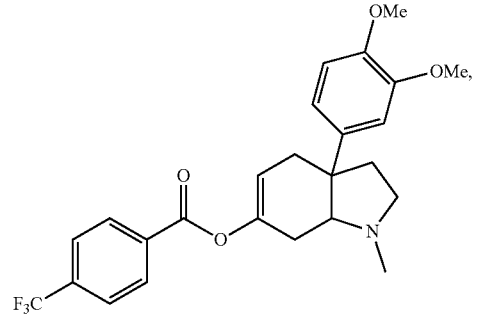

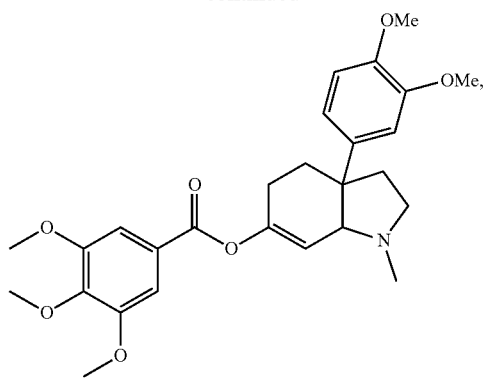
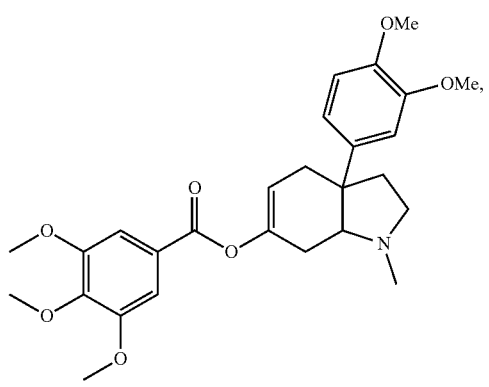
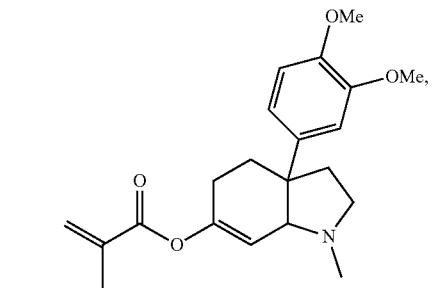
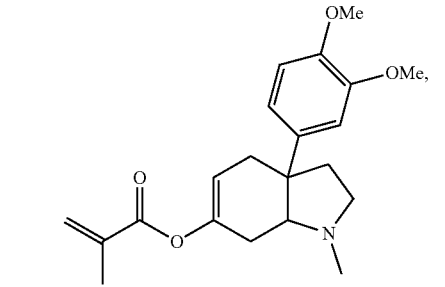
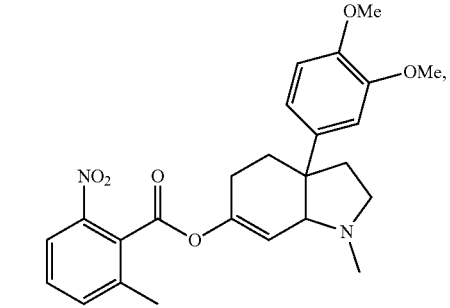
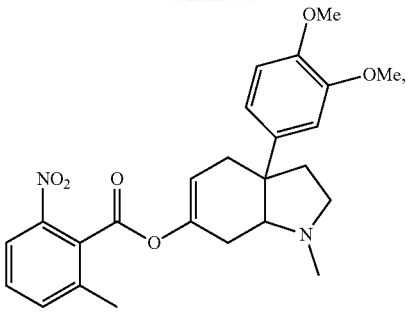
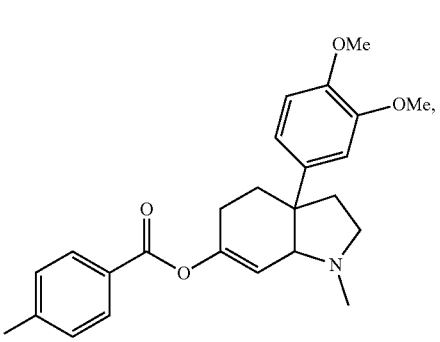
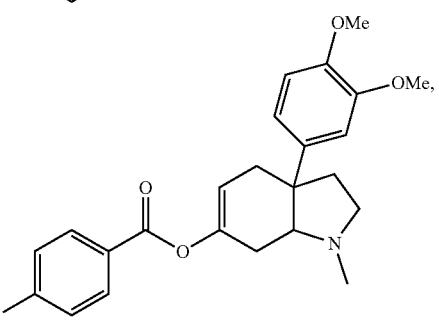
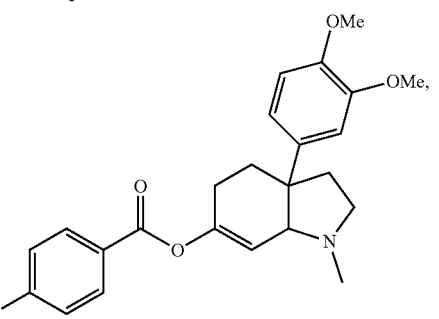
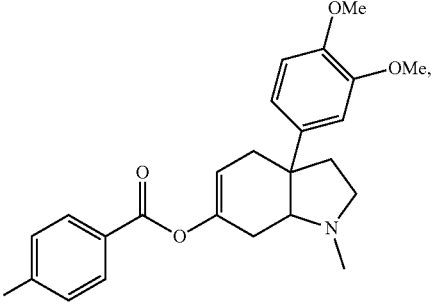

-continued
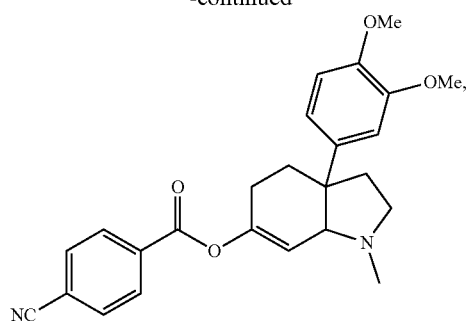
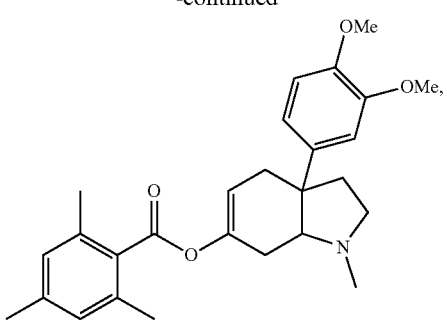
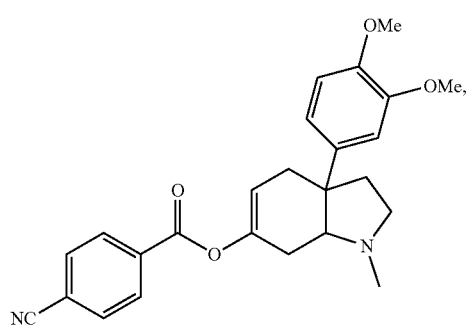
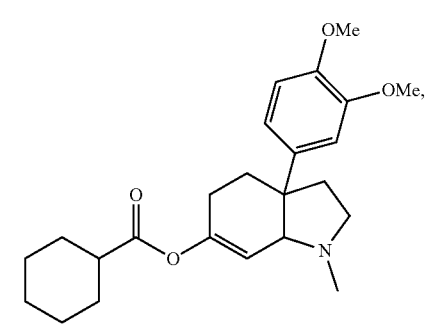
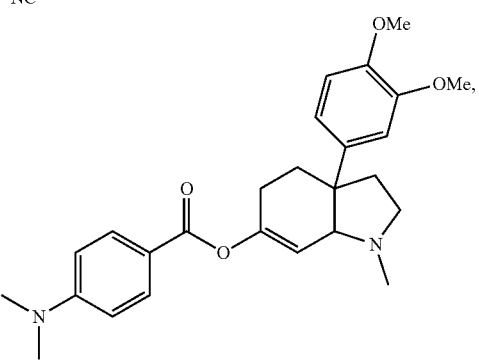
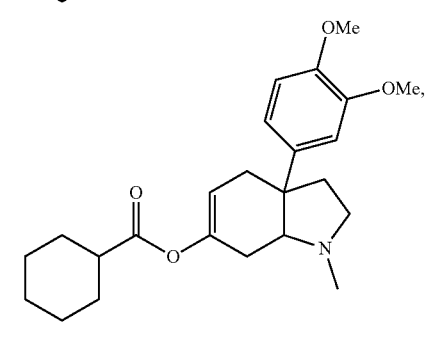
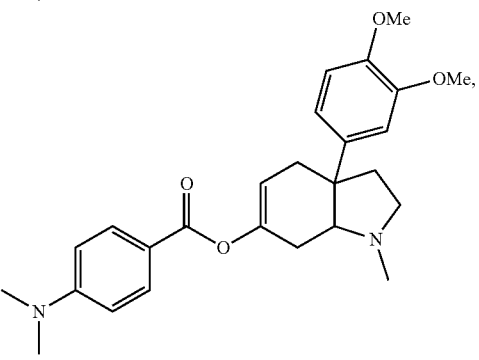
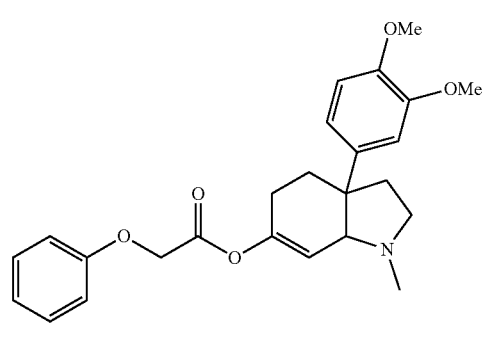
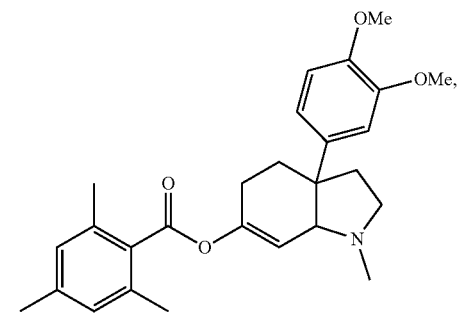
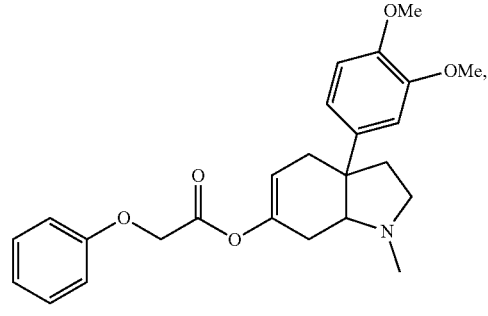

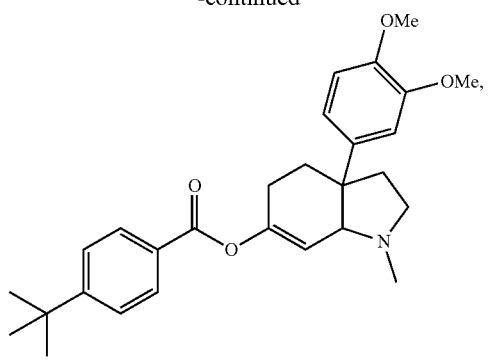
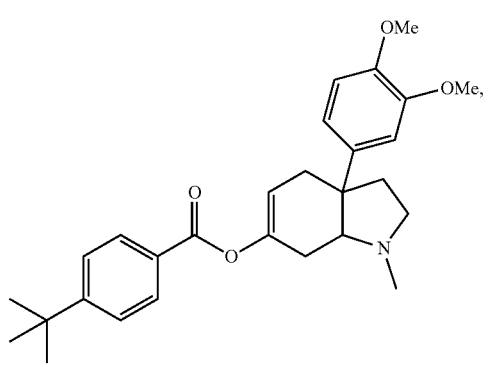
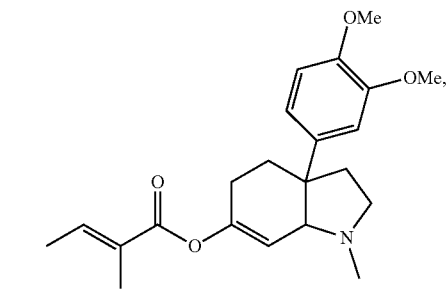
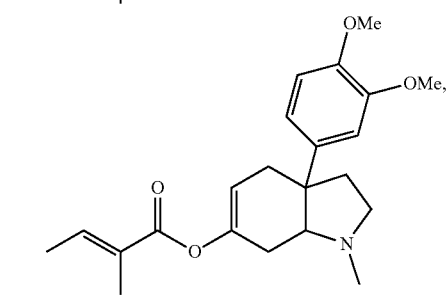
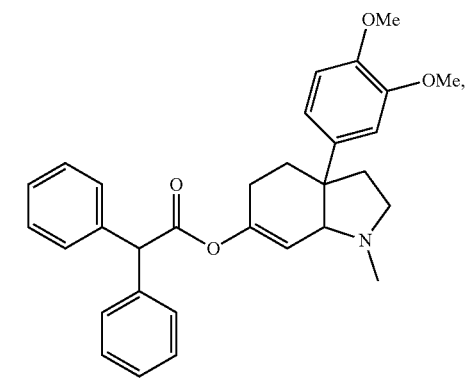
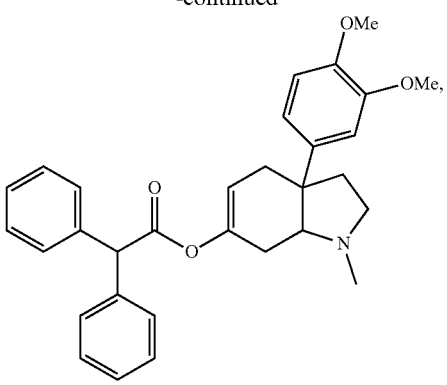
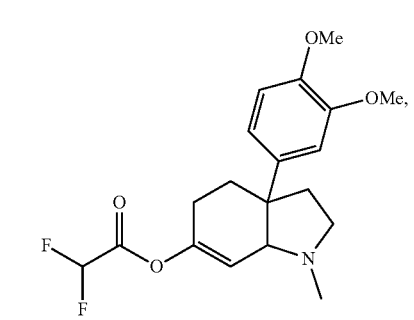
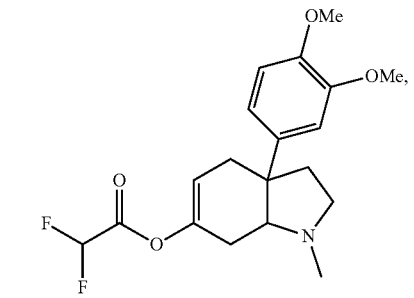
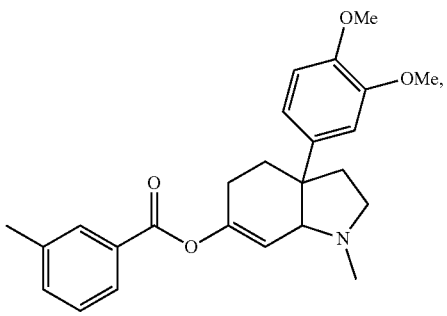
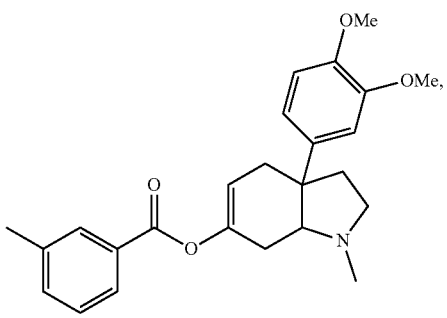

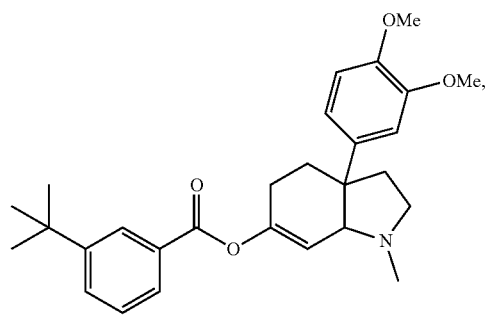
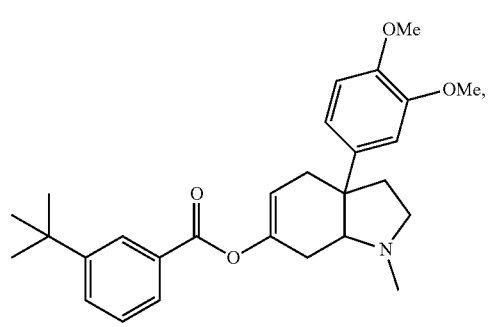
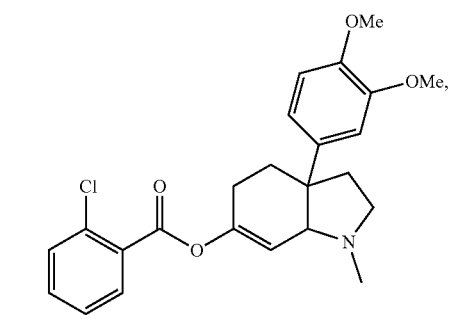
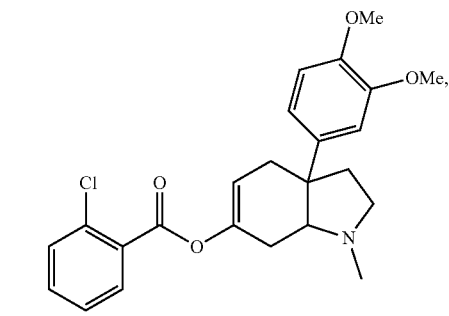
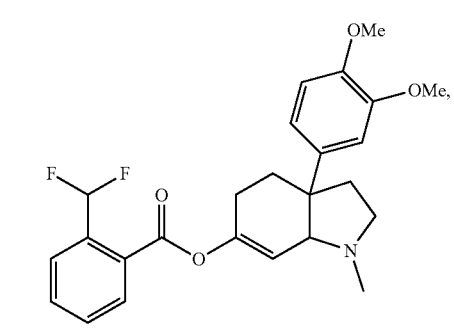
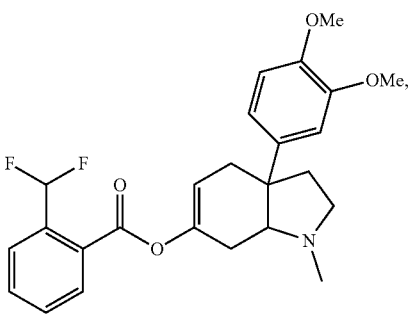
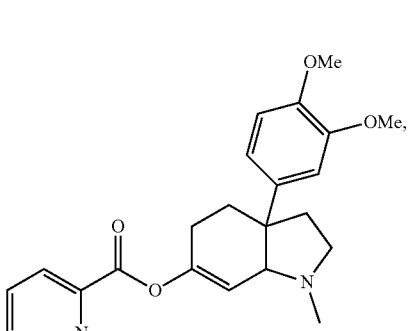
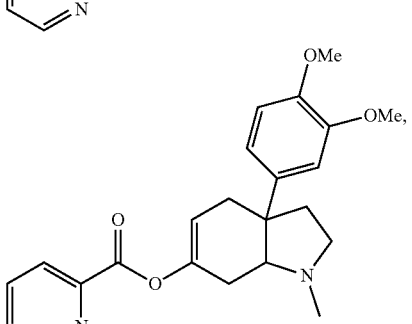
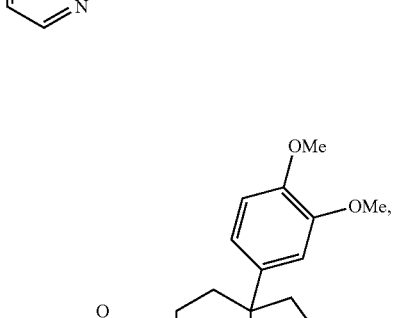
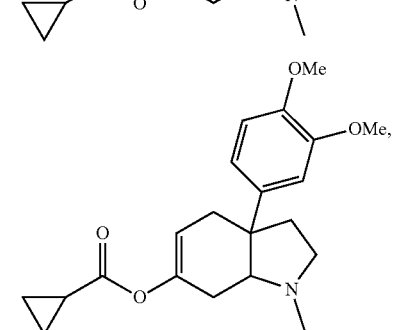

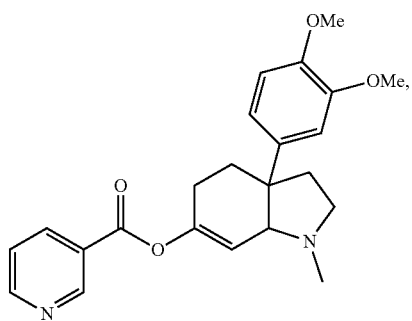
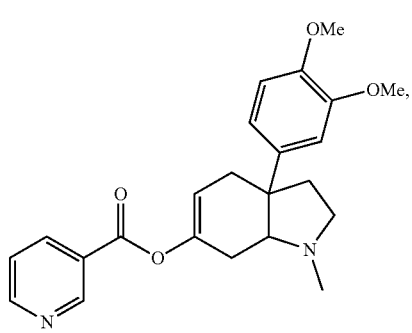
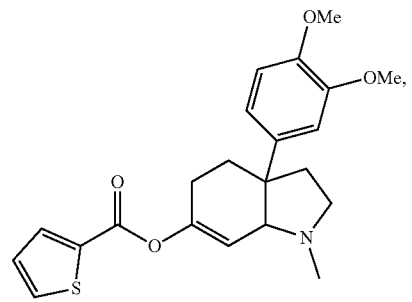

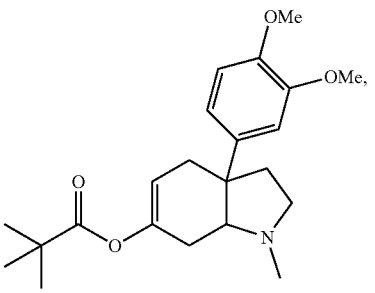
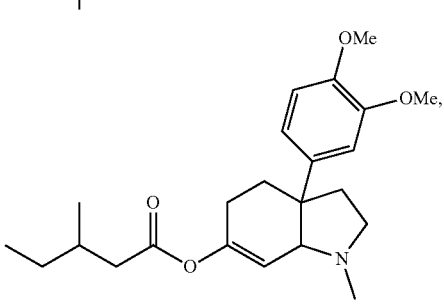
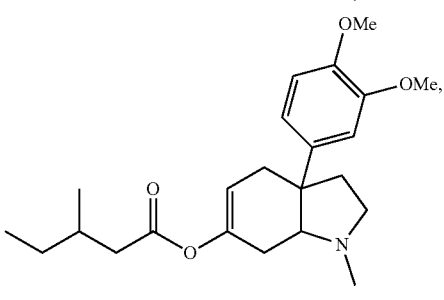
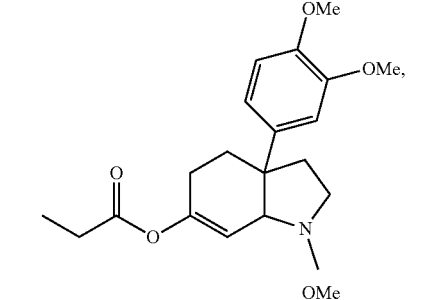
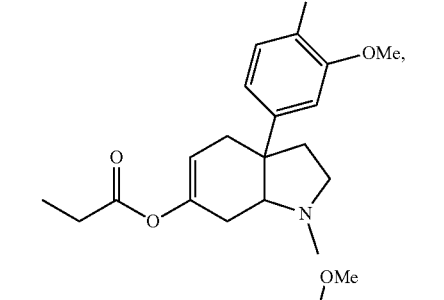
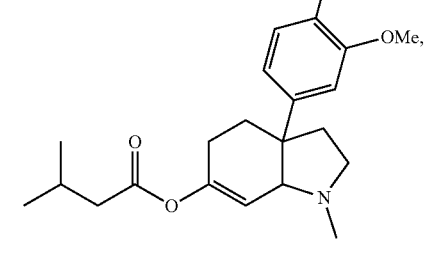

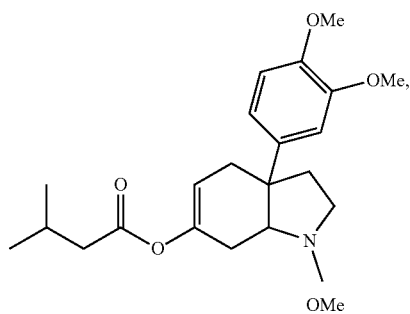
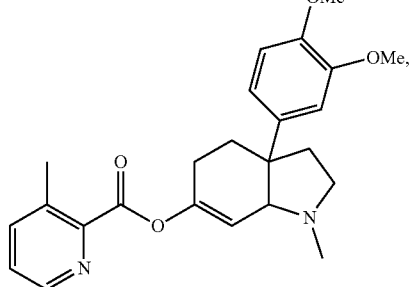
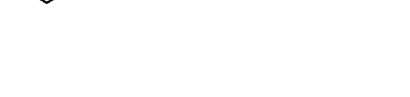
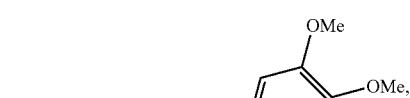
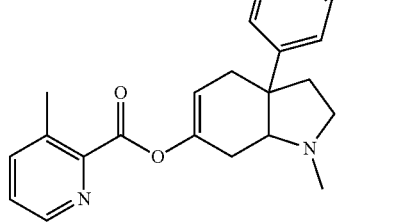
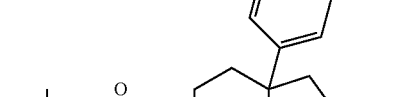
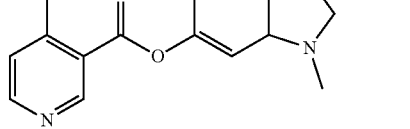
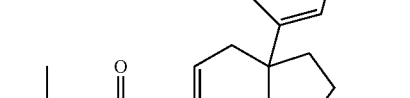
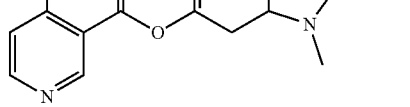
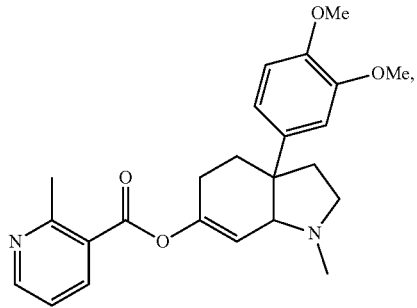
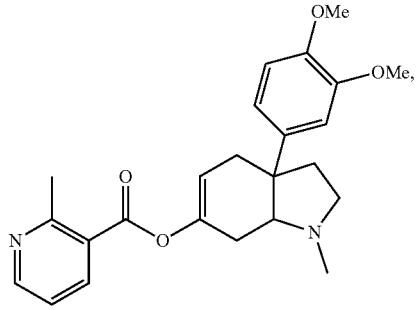
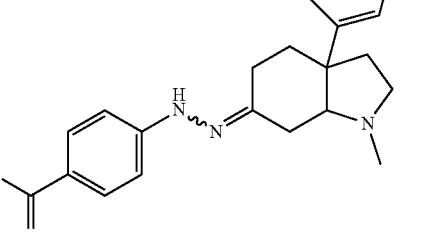
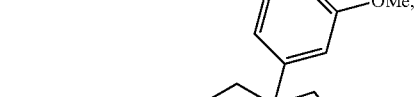
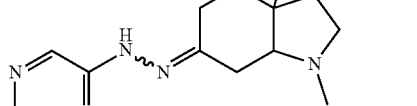
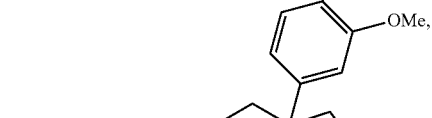
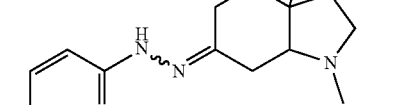

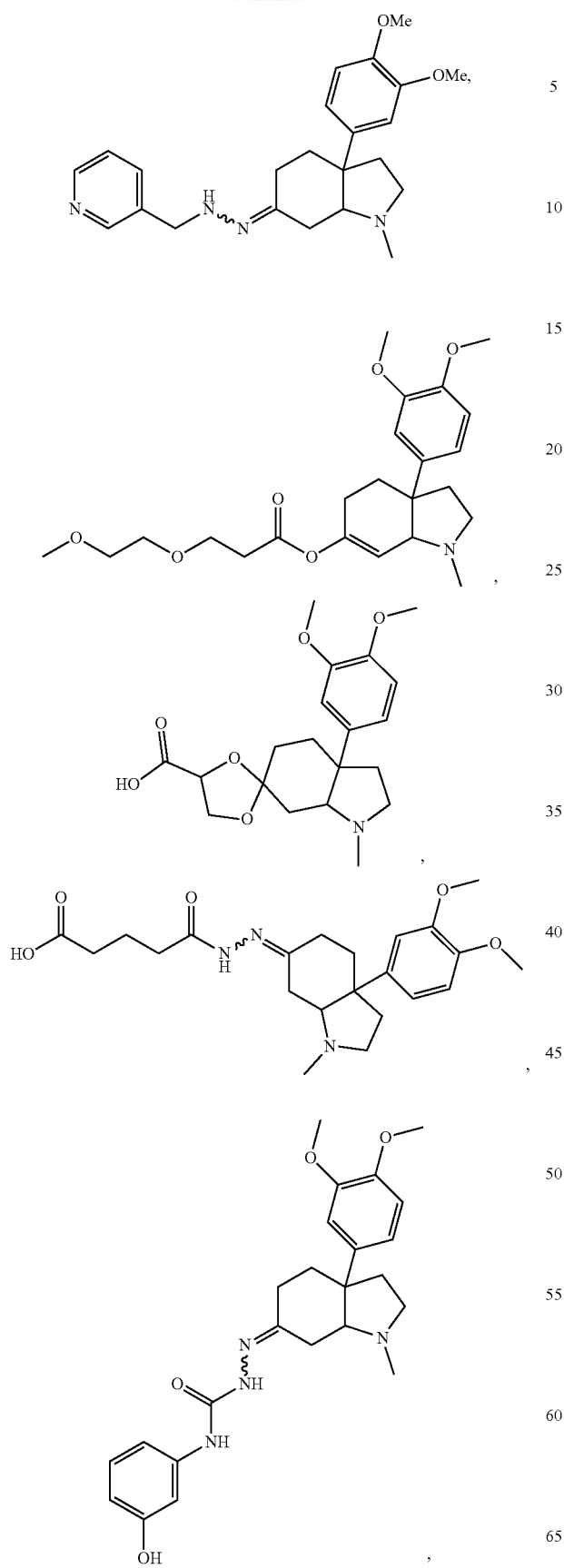
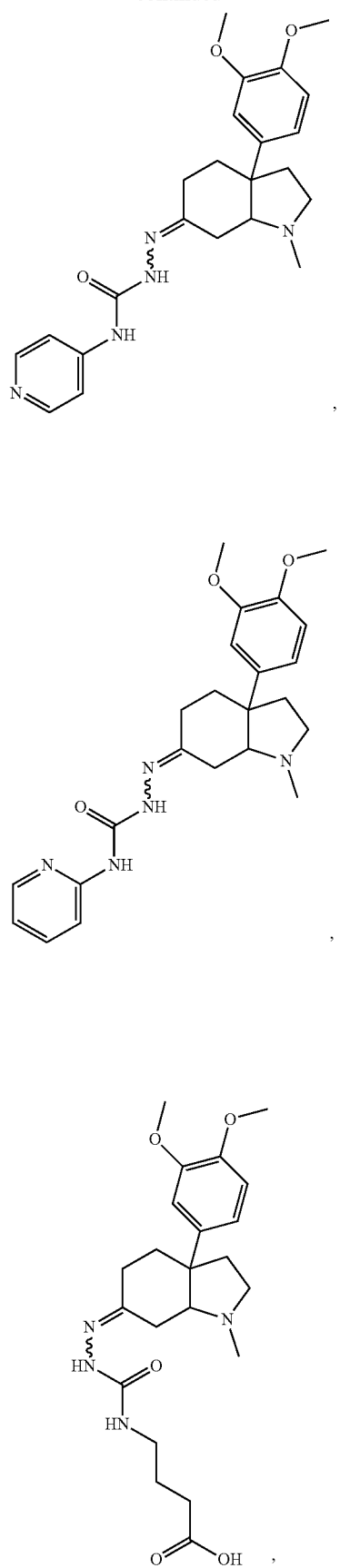

47
-continued
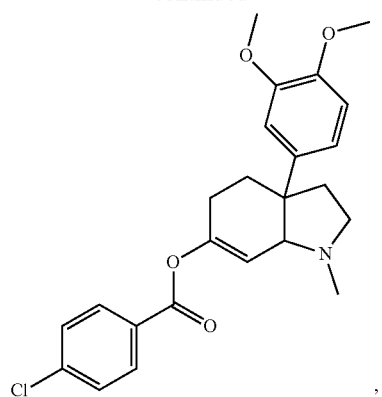
,
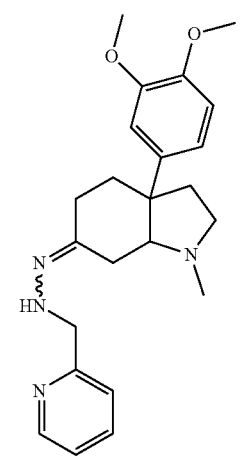
,
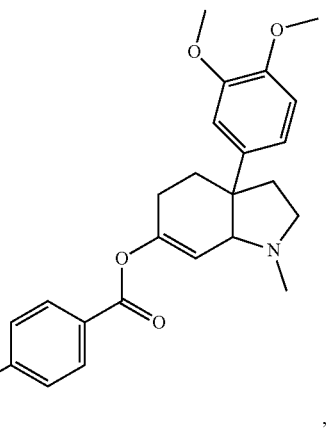
,
48
-continued
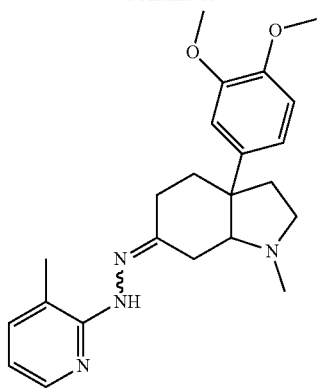
,
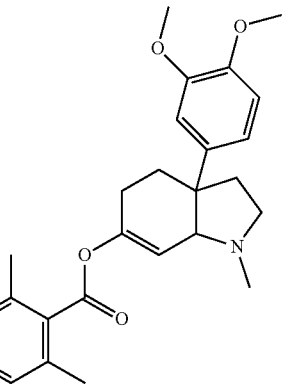
, 49
-continued
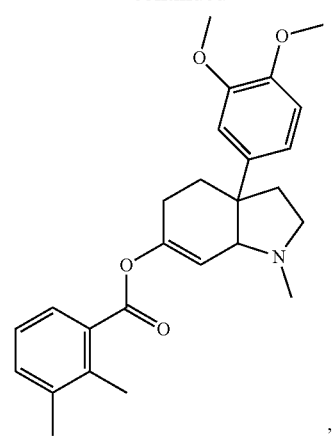
,
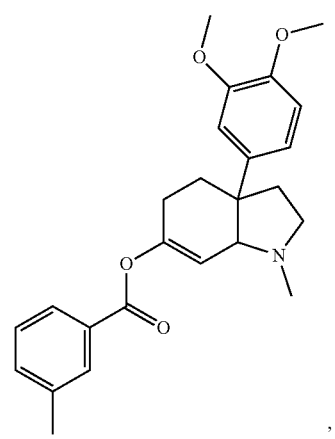
,
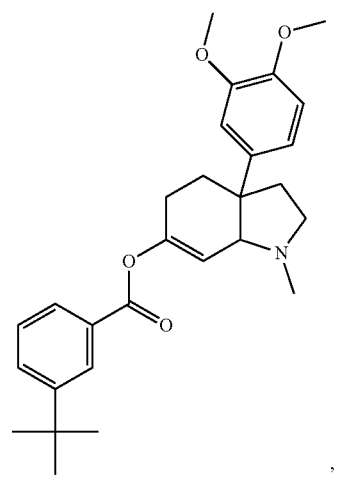
,
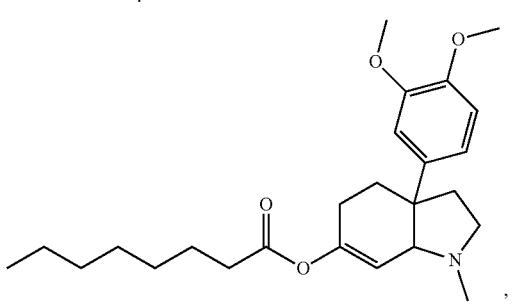
,
50
-continued
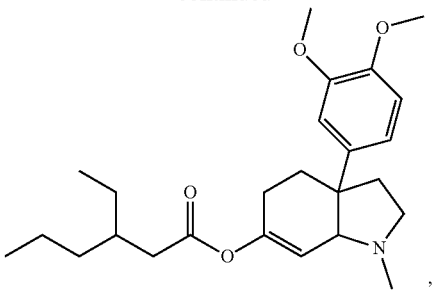
,
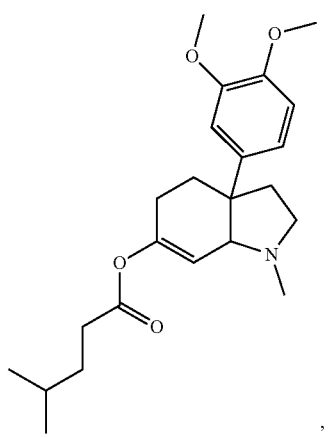
,
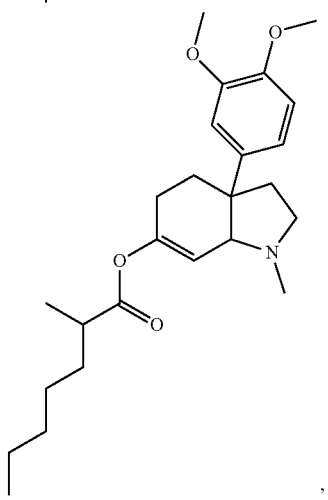
,
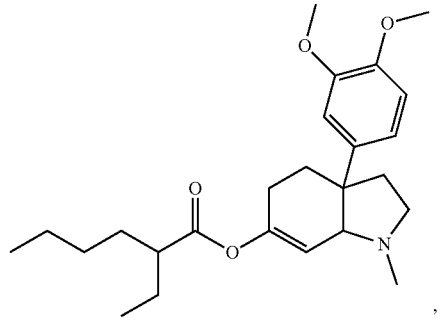
,

51
-continued
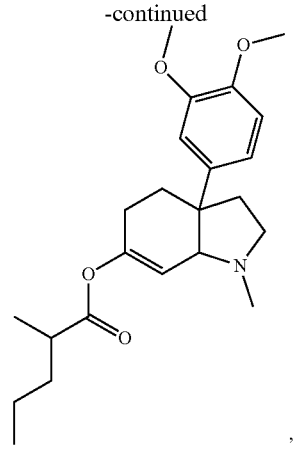
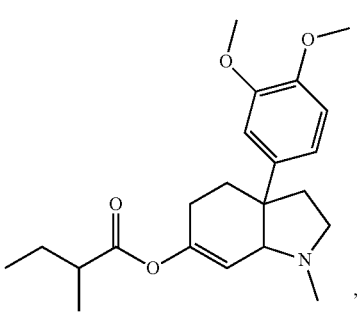
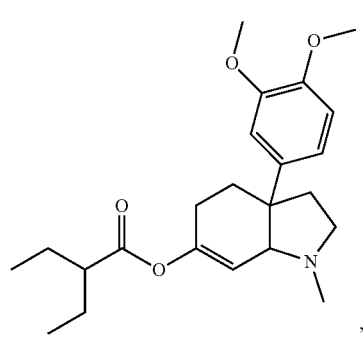
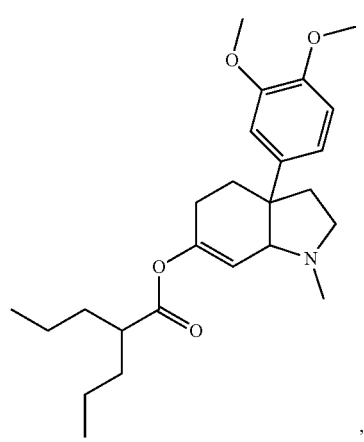
52
-continued
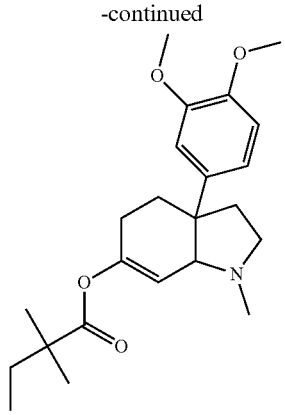
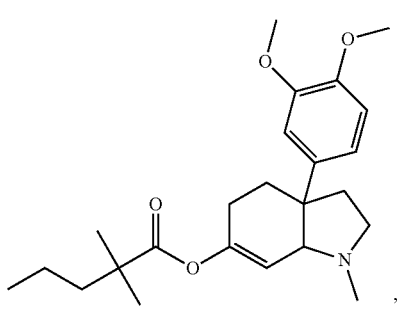
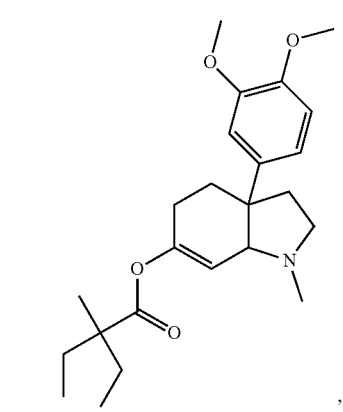
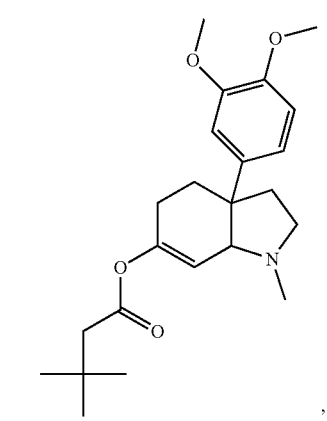
, and

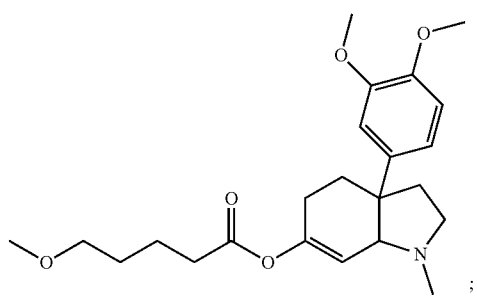
or a pharmaceutically acceptable salt thereof.
In some embodiments, the compound is selected from the group consisting of:
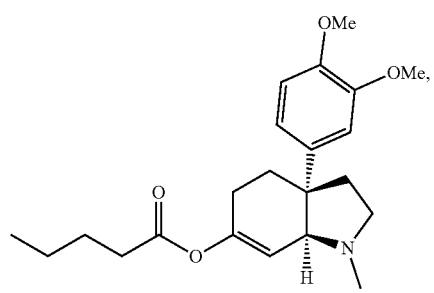
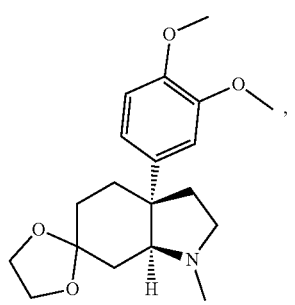
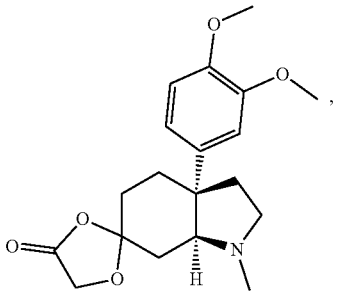
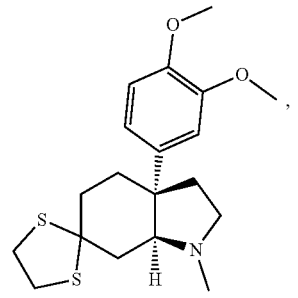
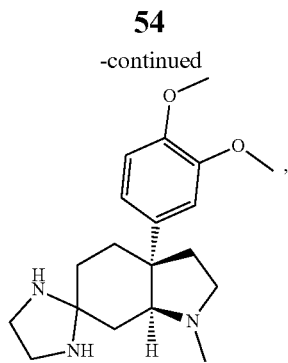
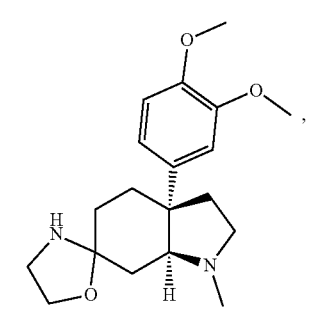
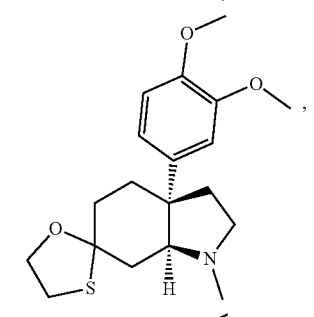
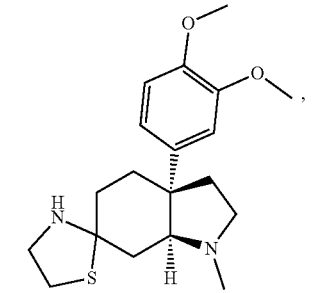
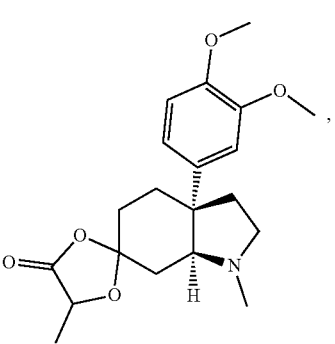

55
-continued
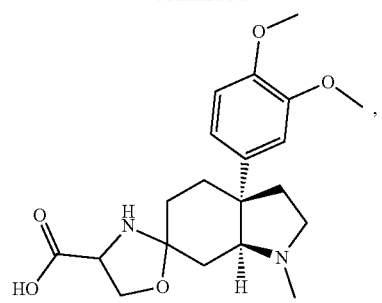
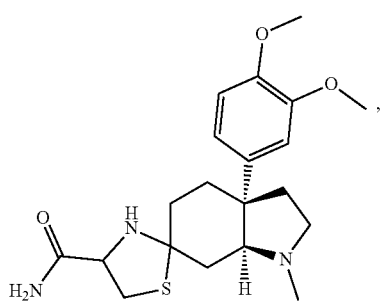
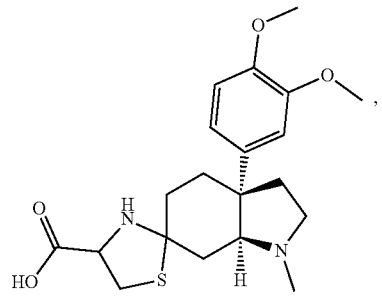
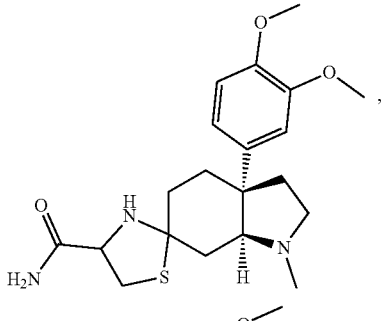
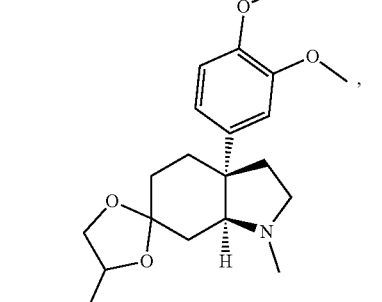
56
-continued
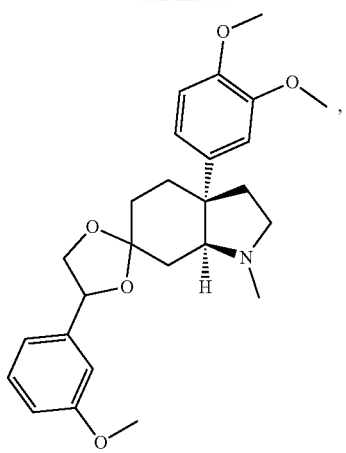
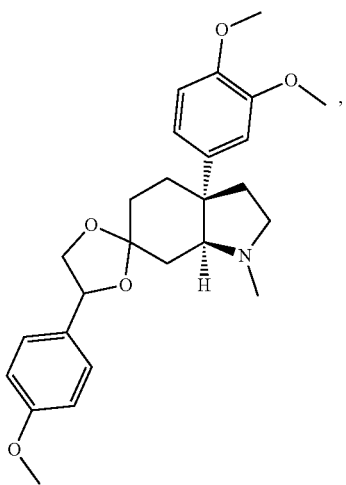
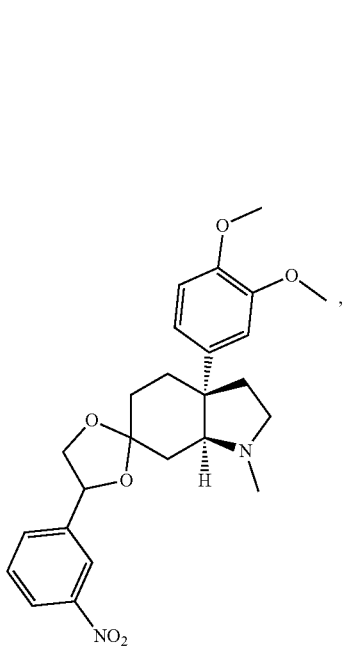

-continued
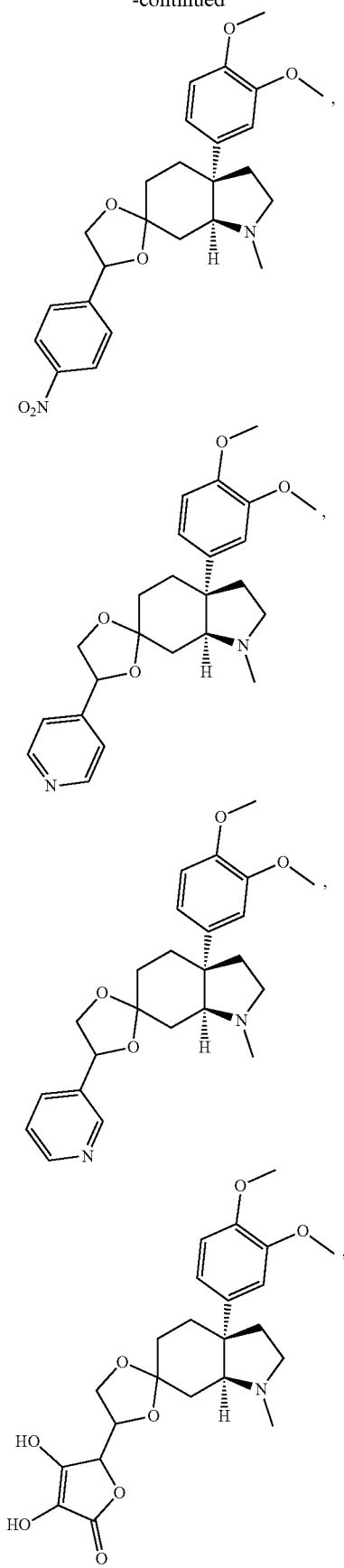
-continued
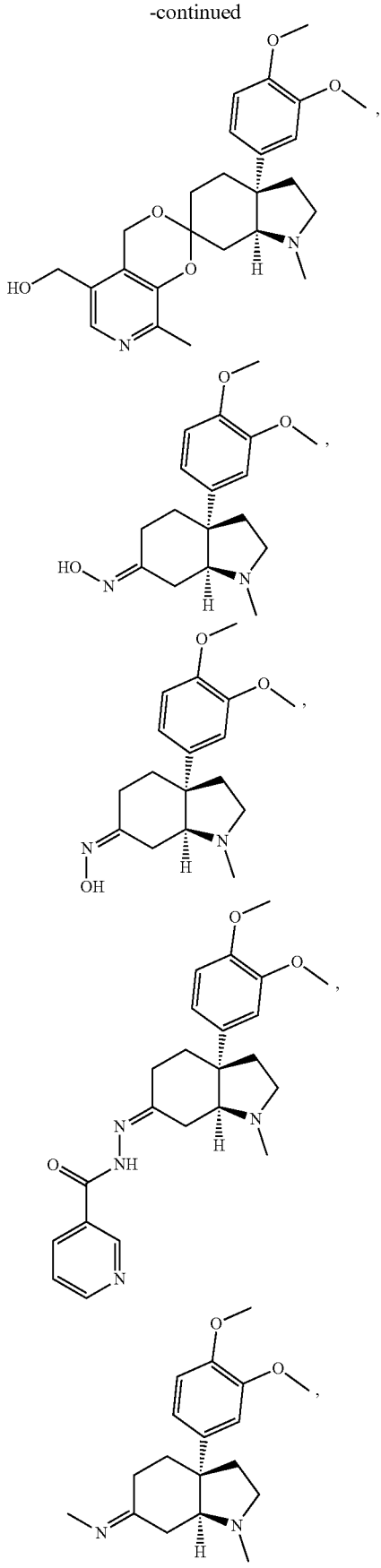

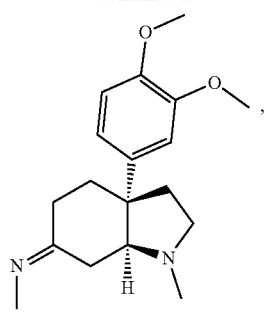
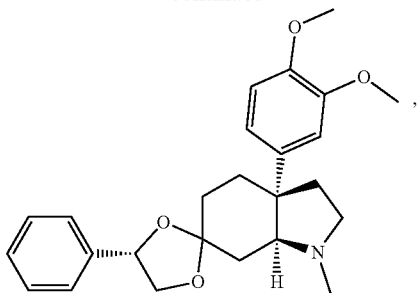
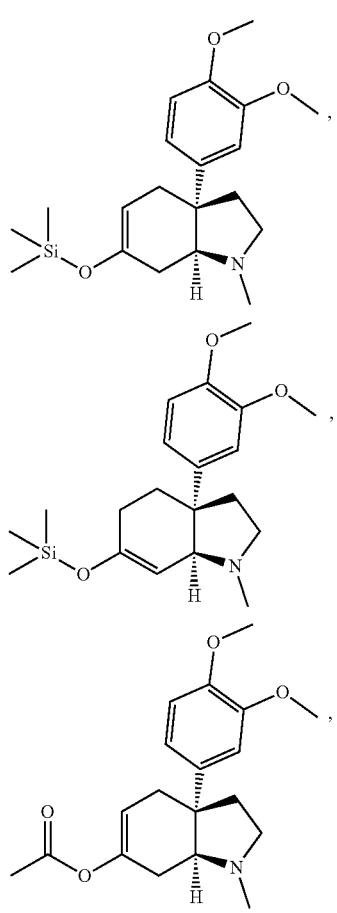
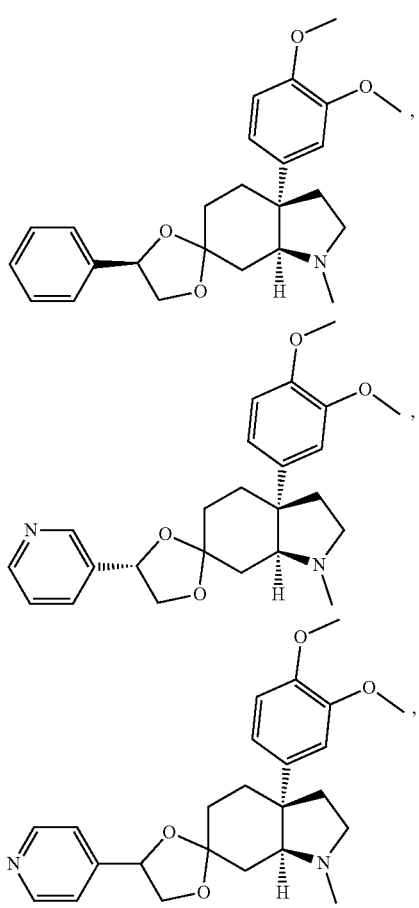
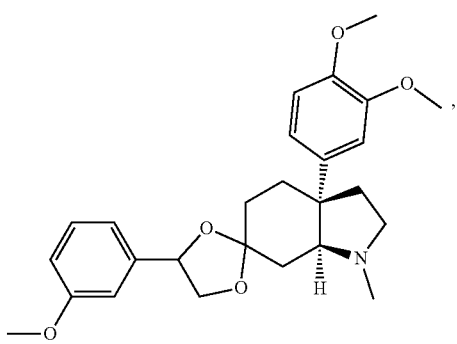

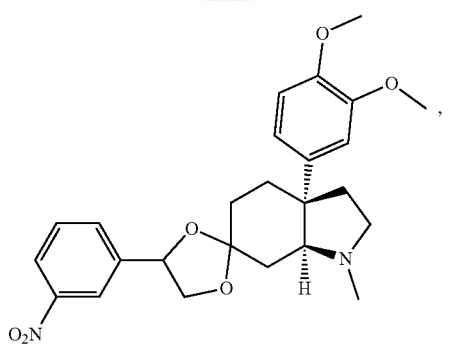
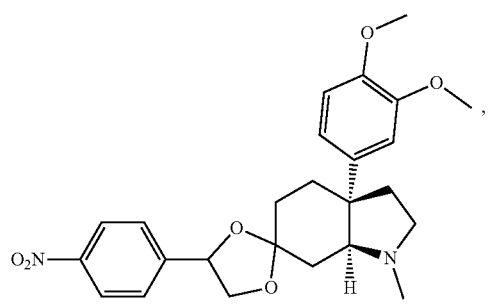
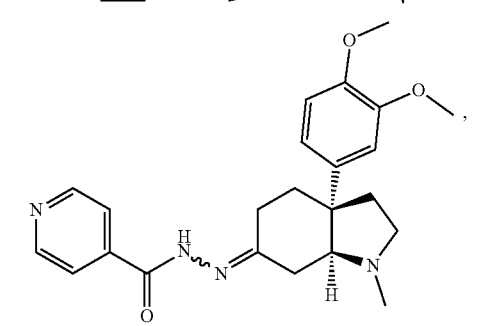
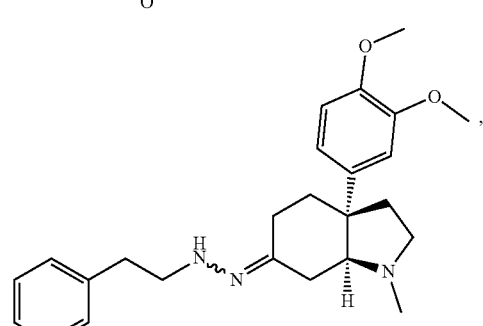
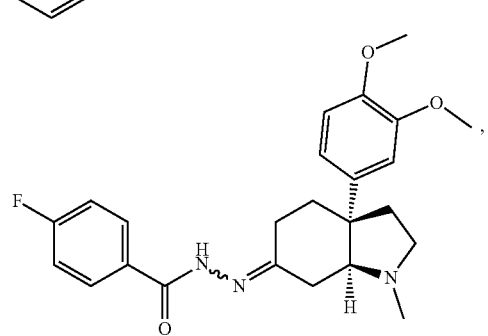
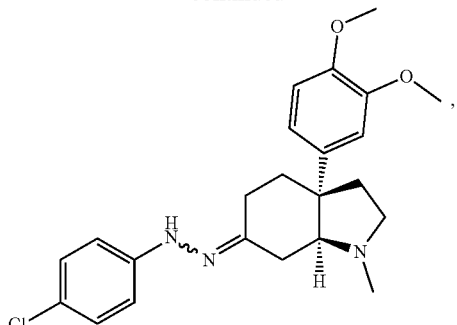
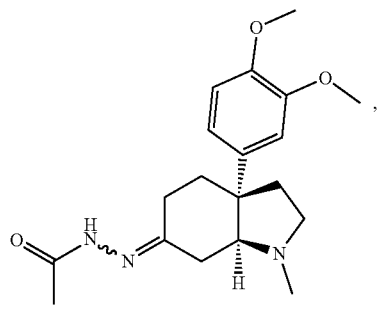
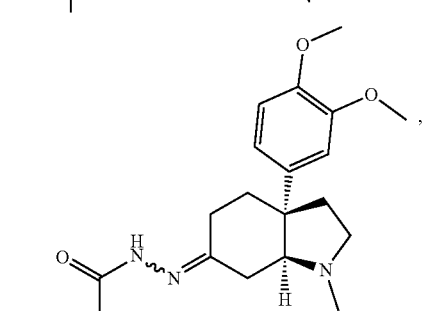
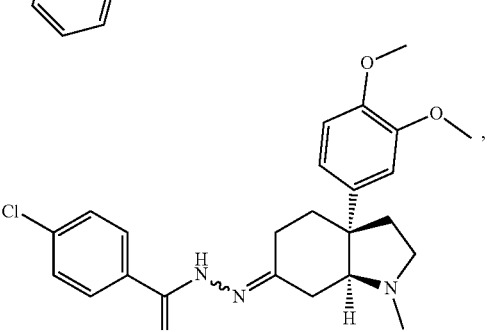
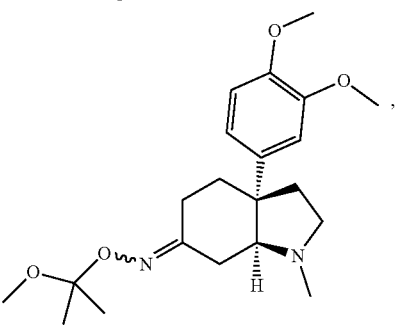

63
-continued
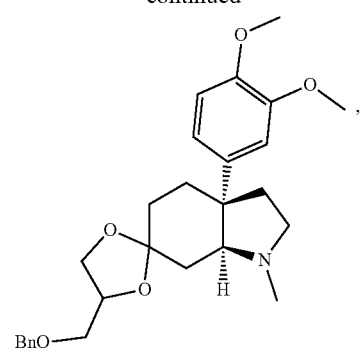
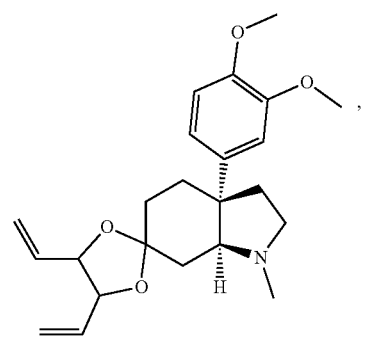
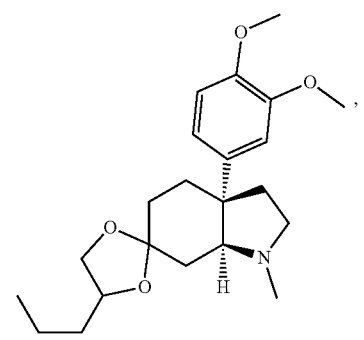
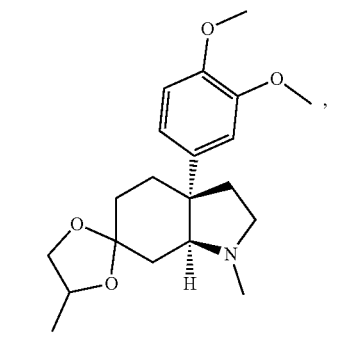
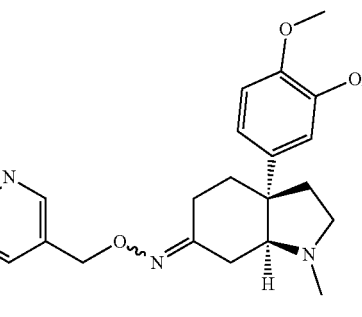
64
-continued
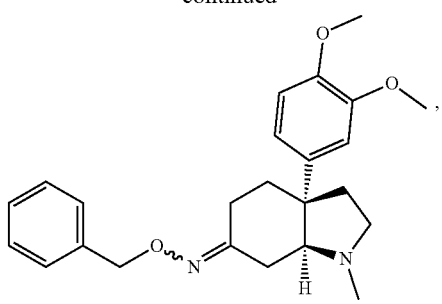
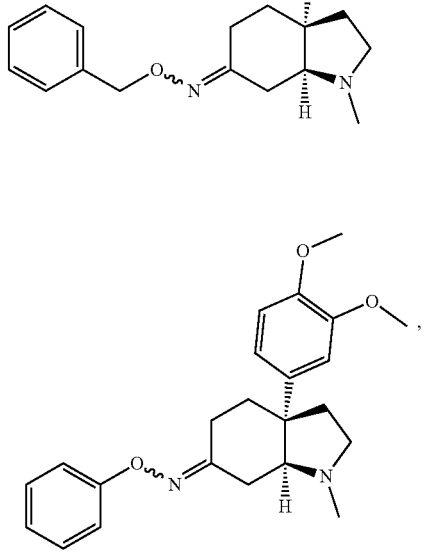
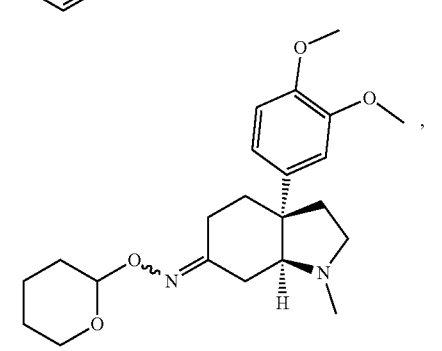
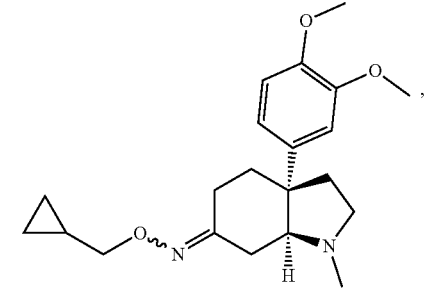
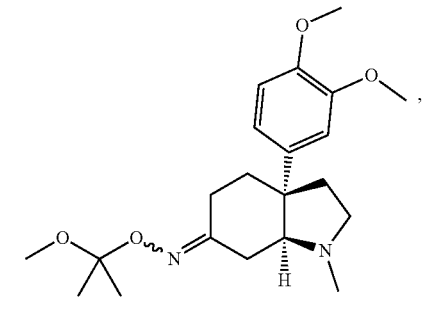

65
-continued
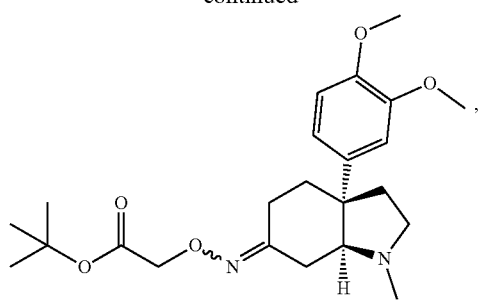
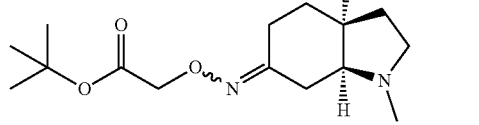
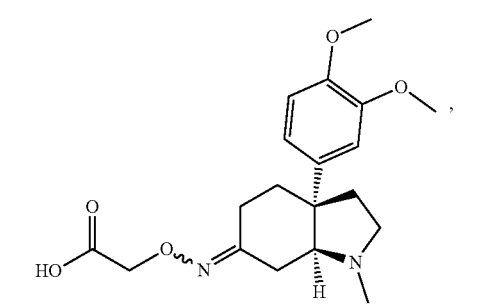
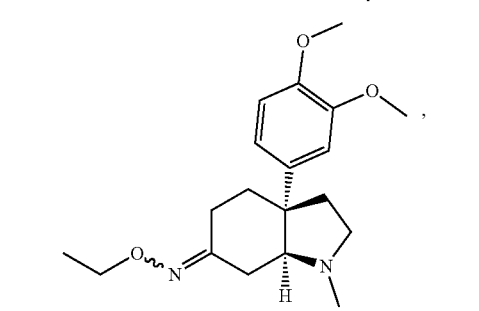
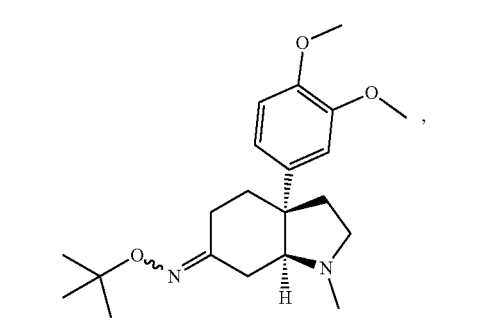
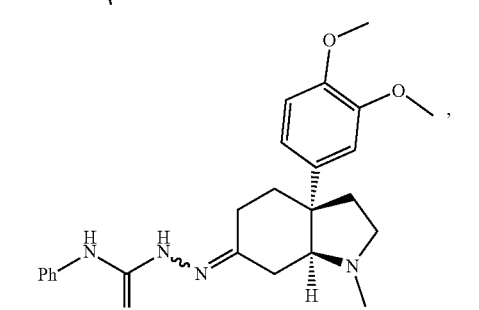
66
-continued
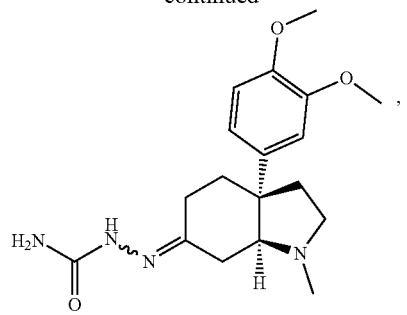
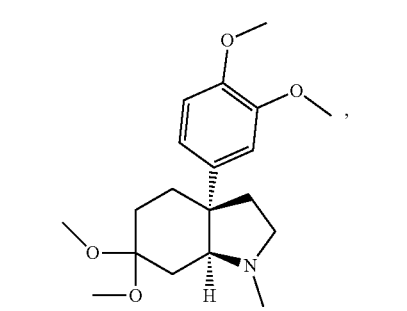
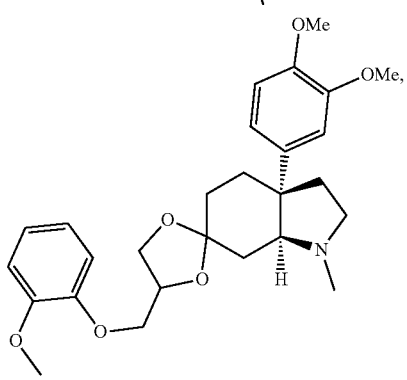
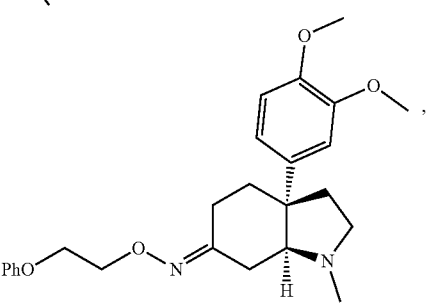
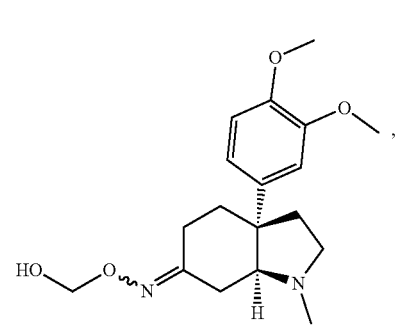

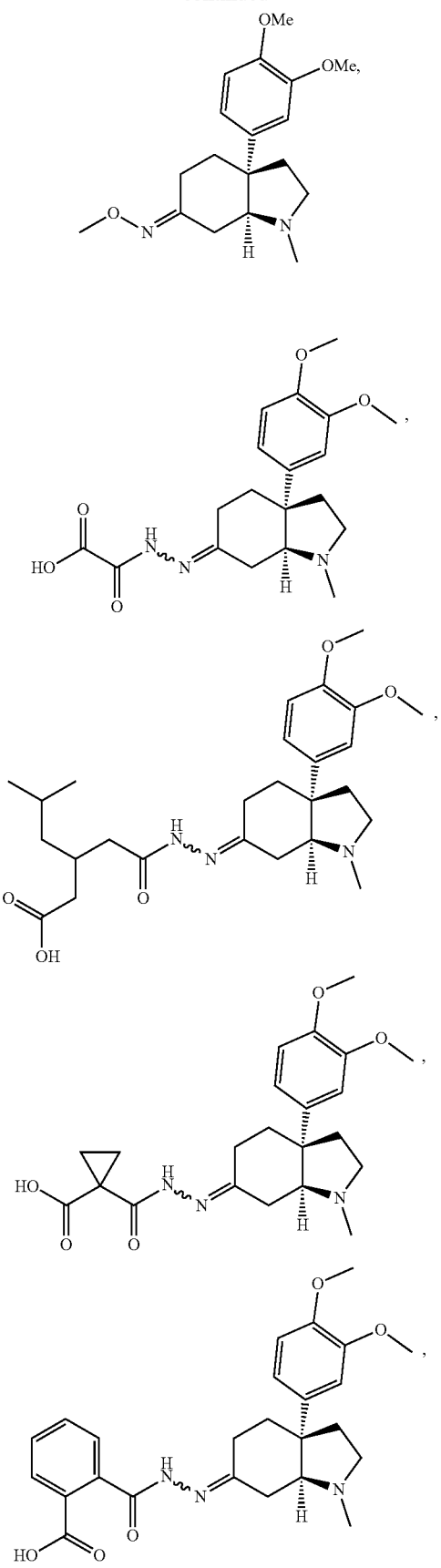
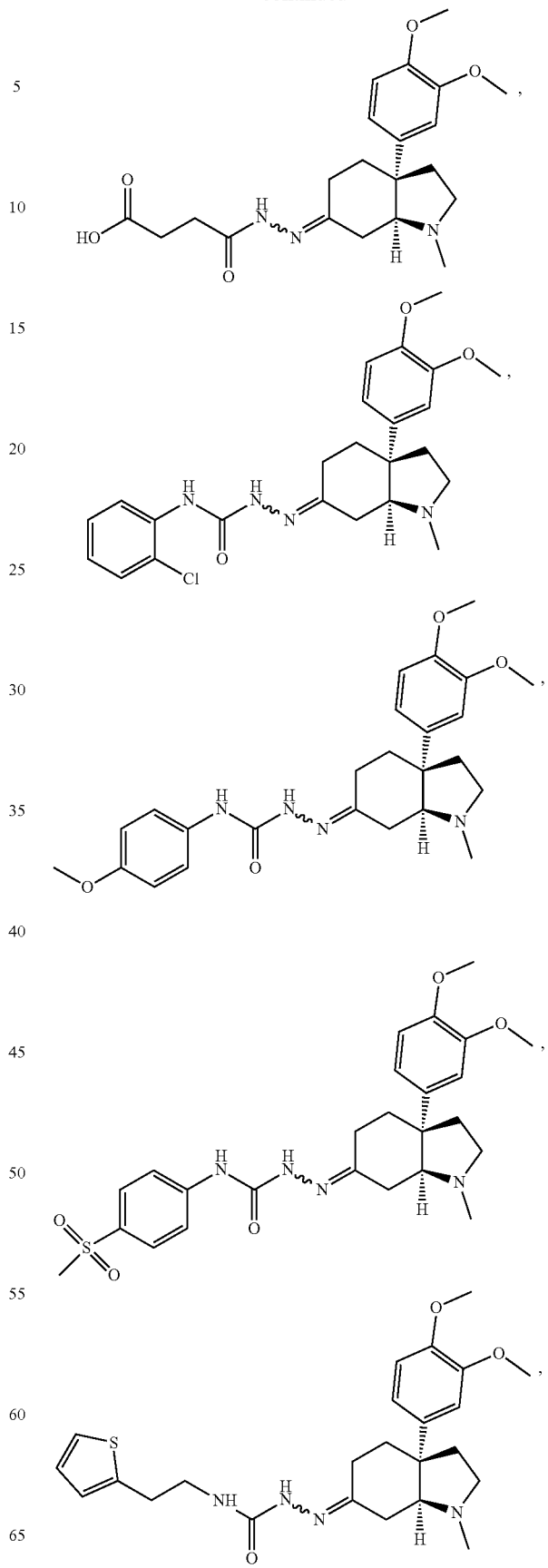

69
-continued
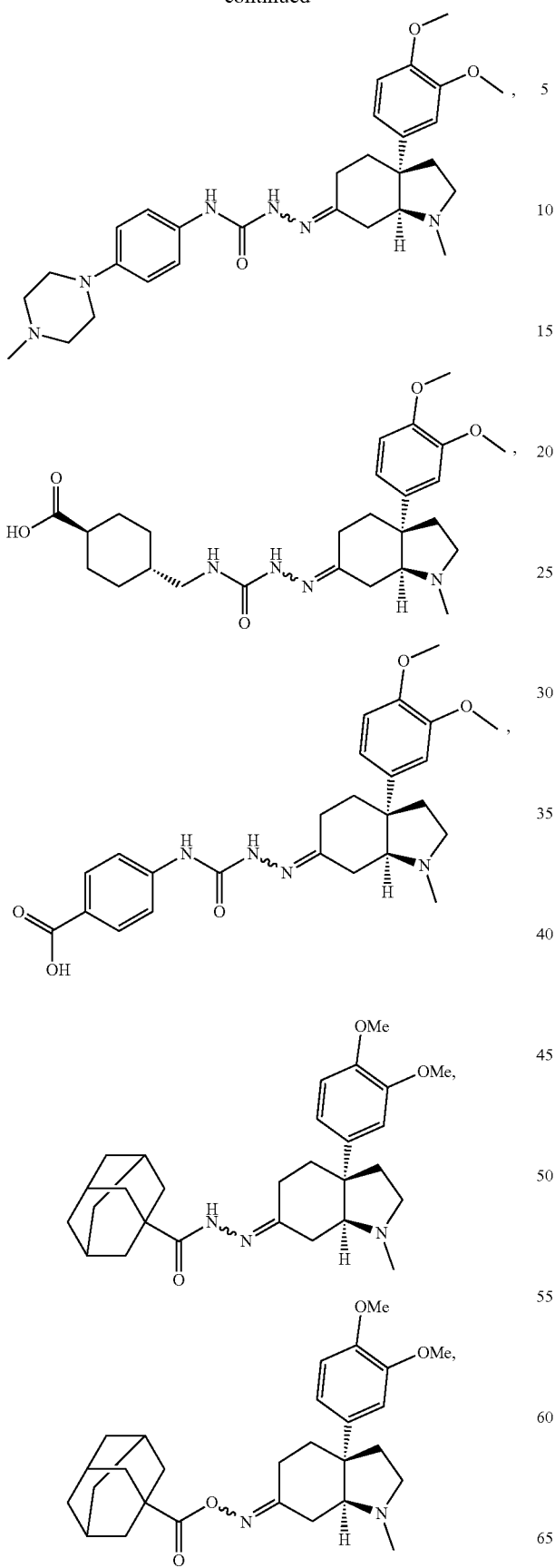
70
-continued
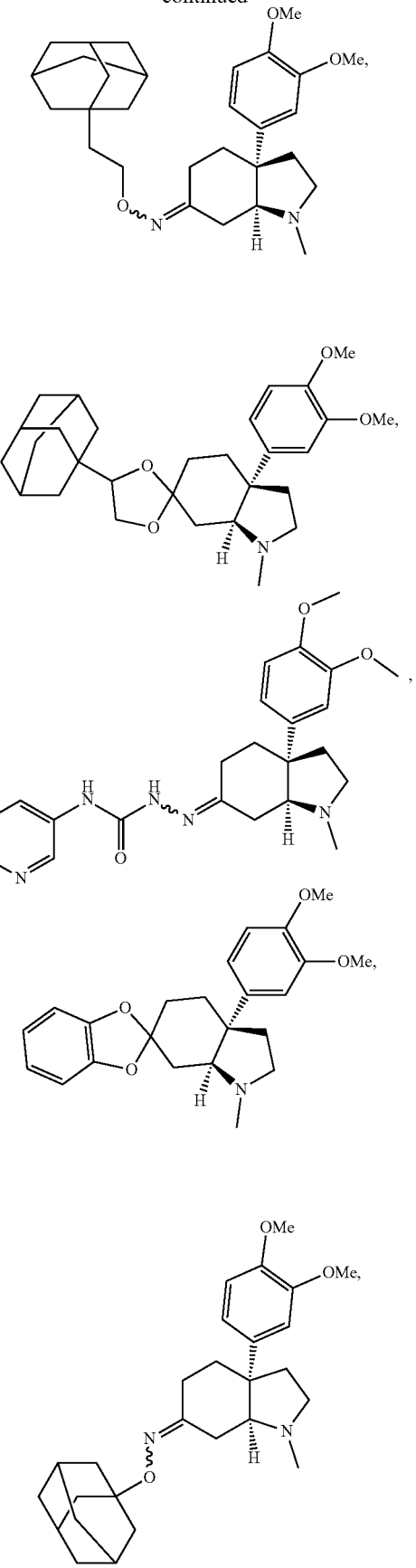

71
-continued
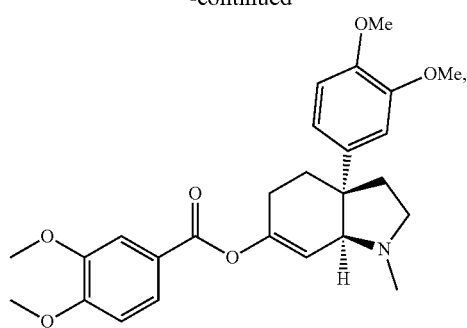
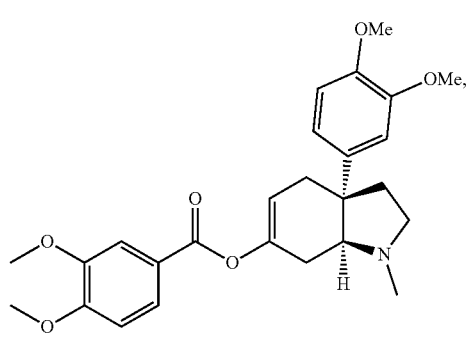
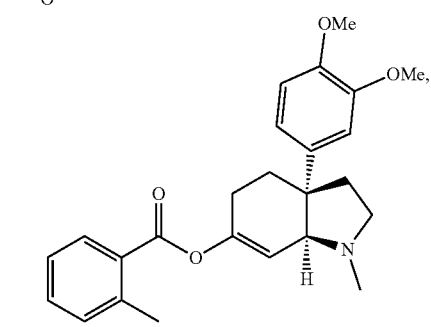
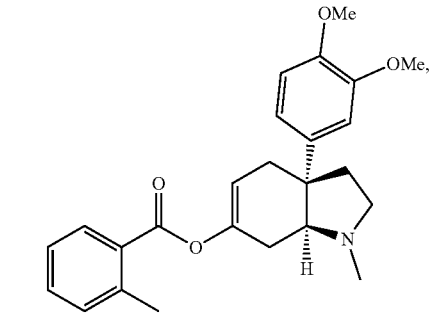
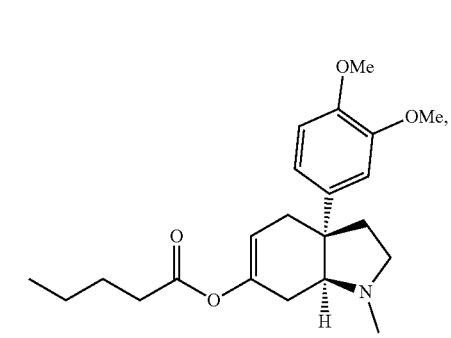
72
-continued
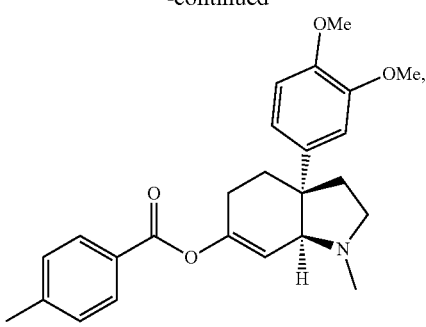
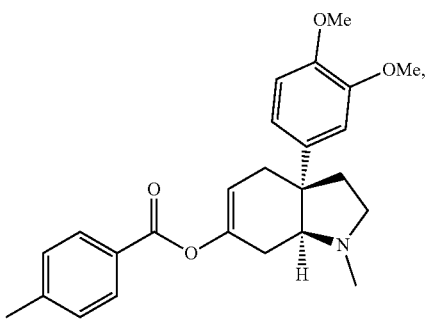
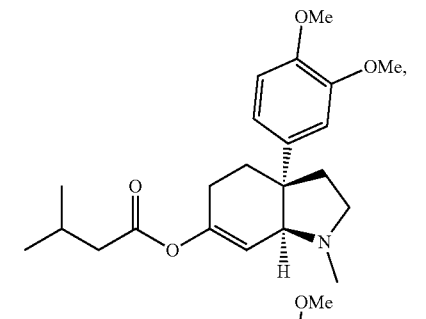
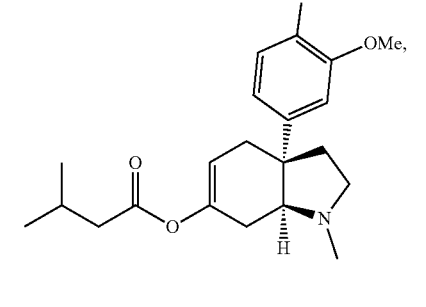
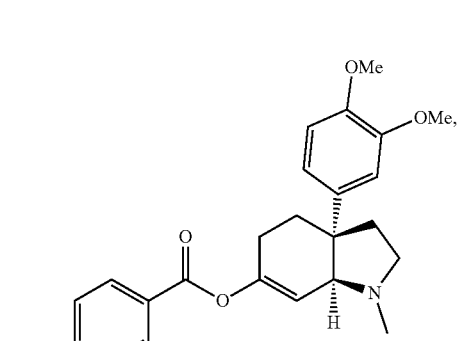

-continued
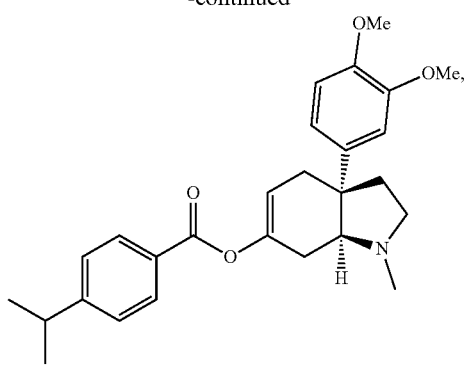
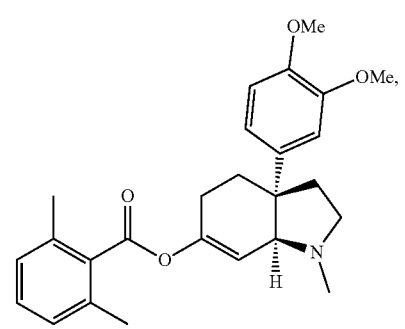
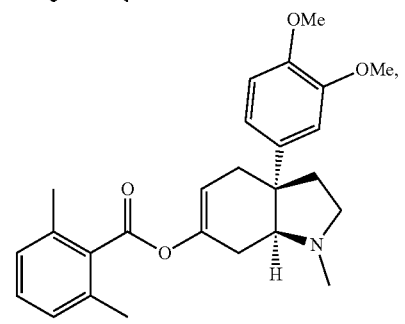
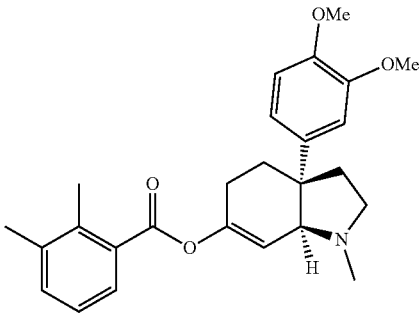
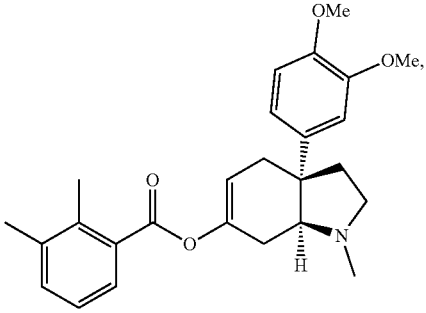
-continued
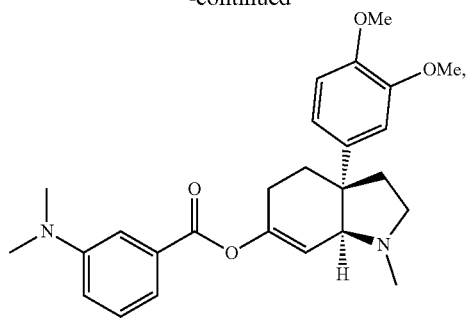
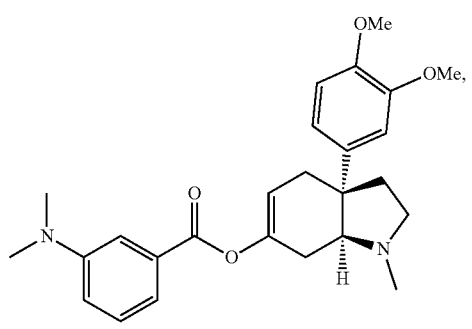
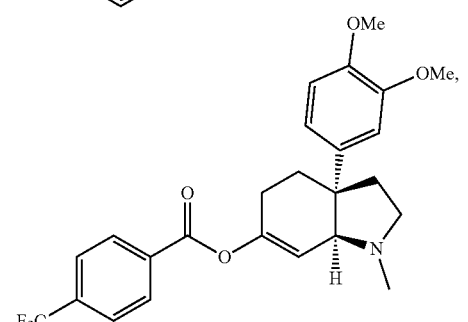
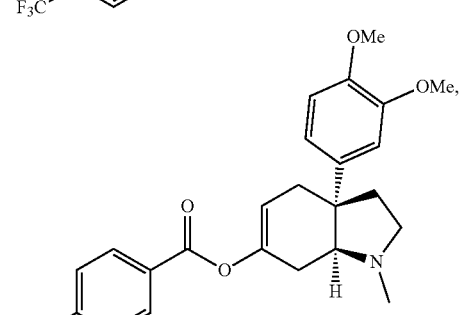
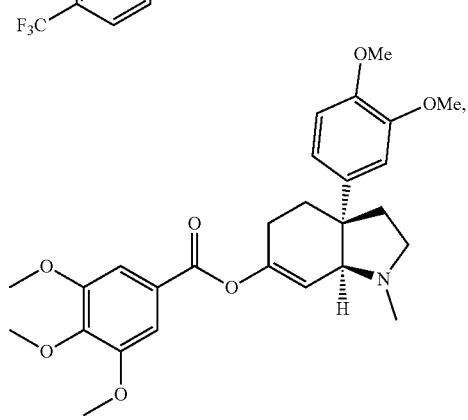

75
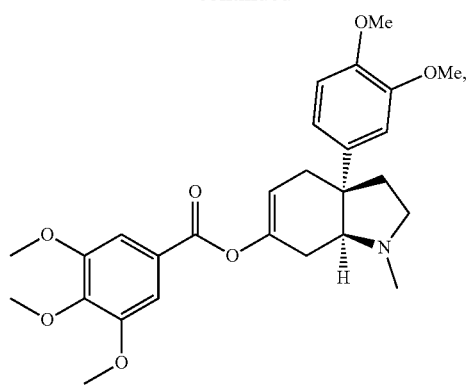
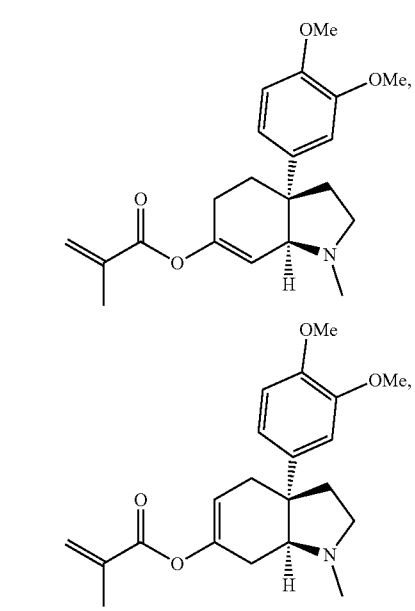
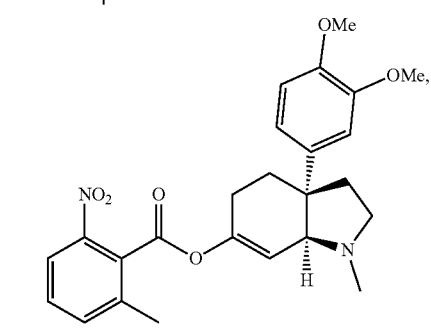
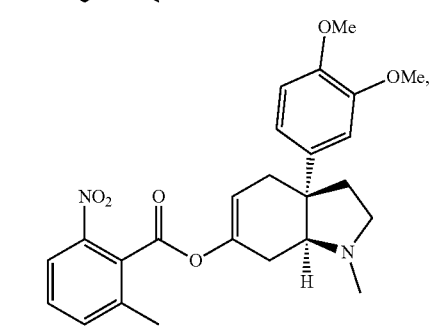
76
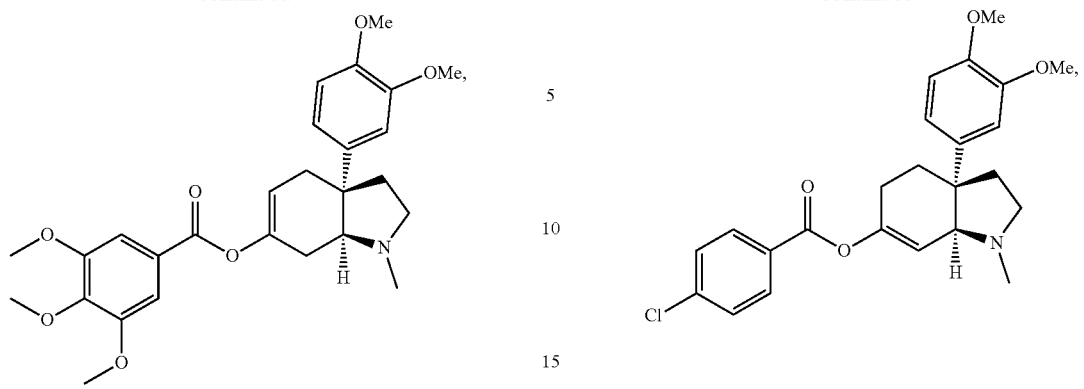
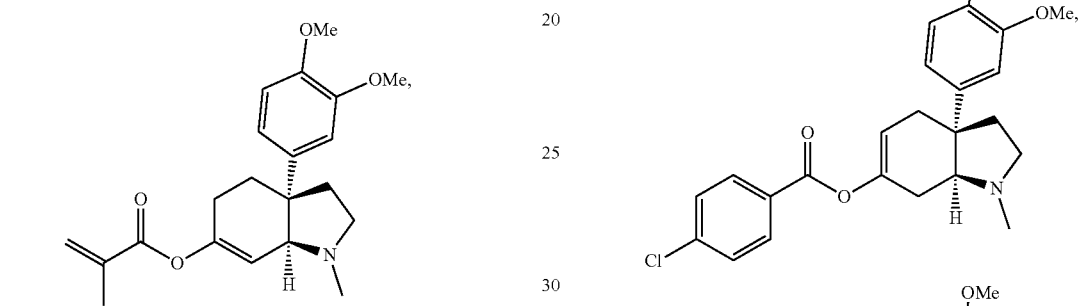
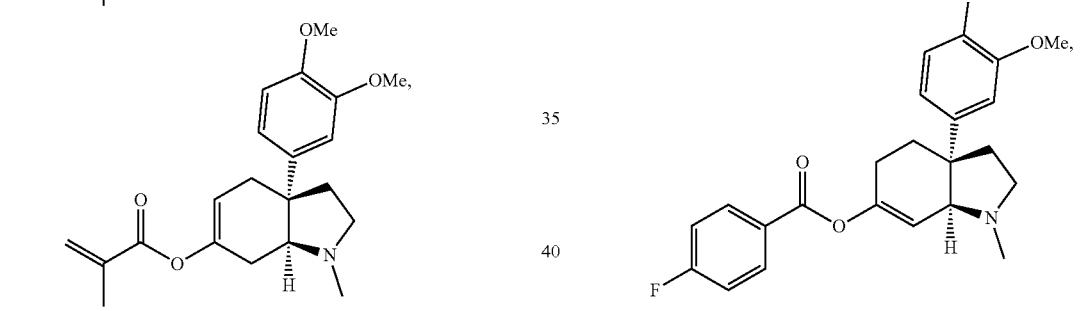
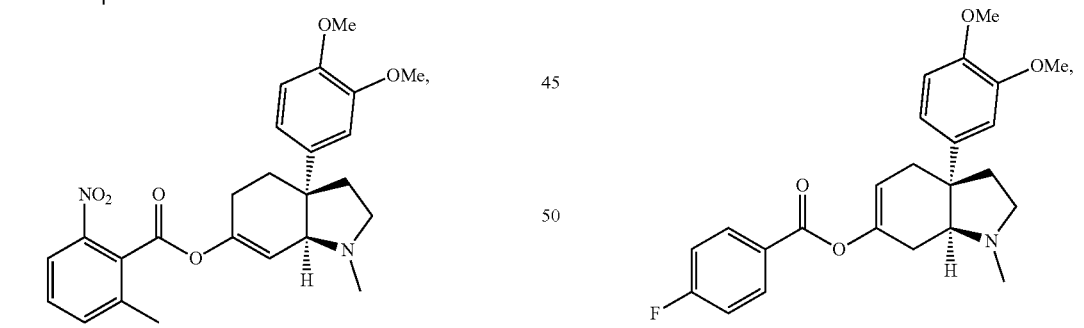
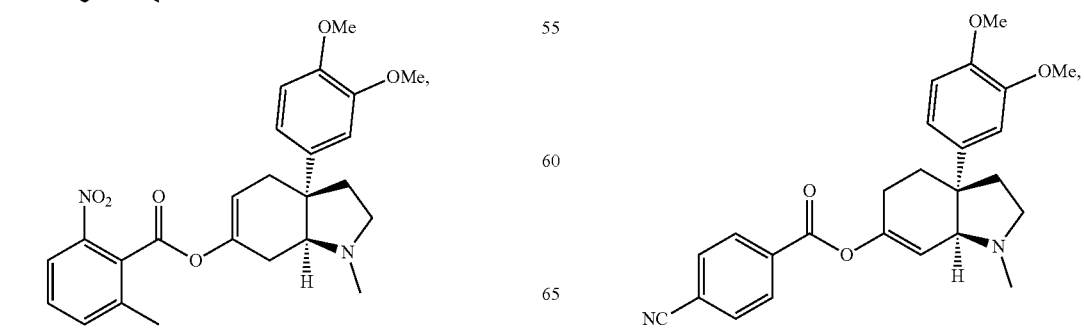

77
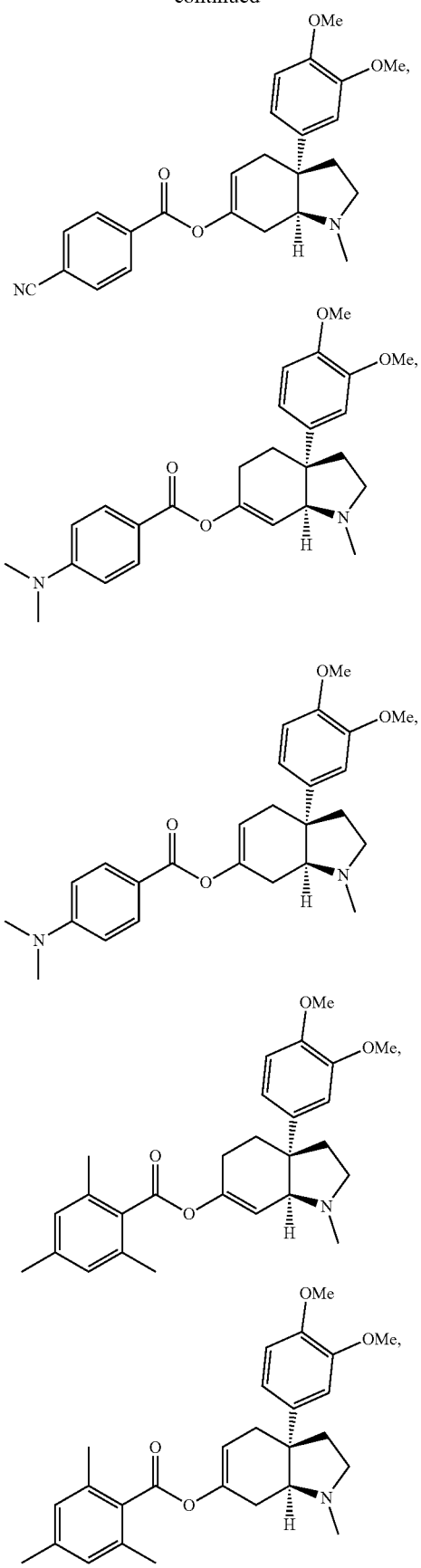
78
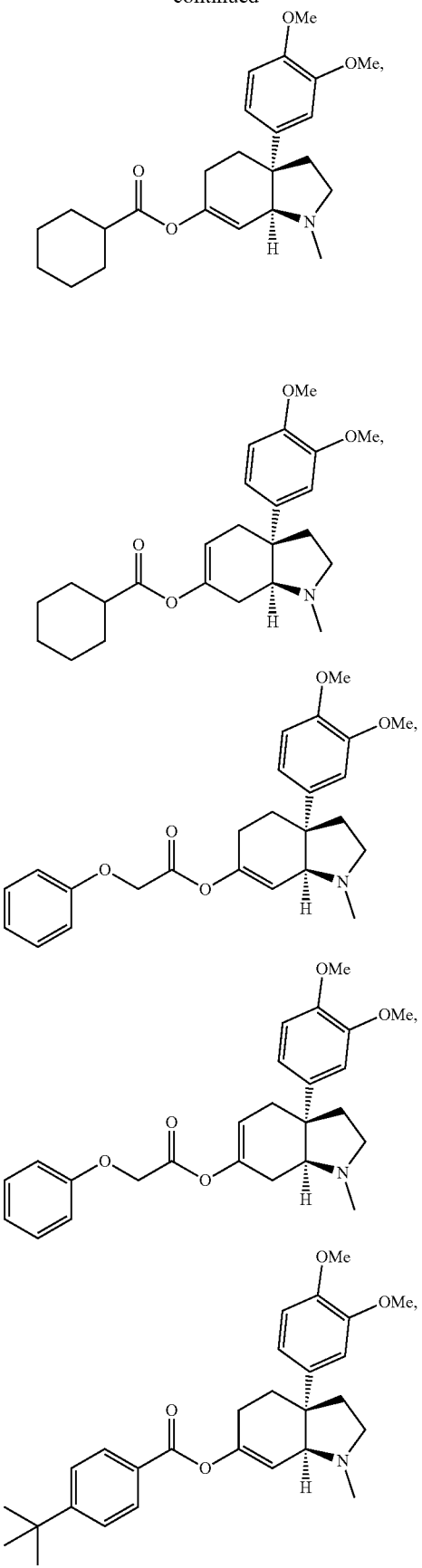

79
-continued
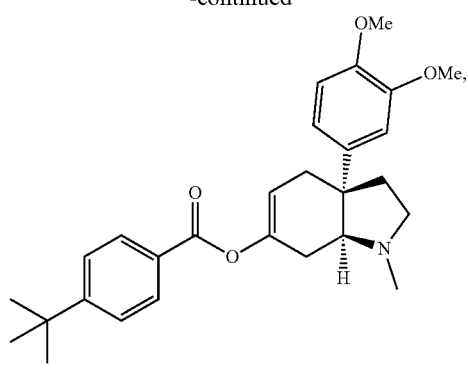
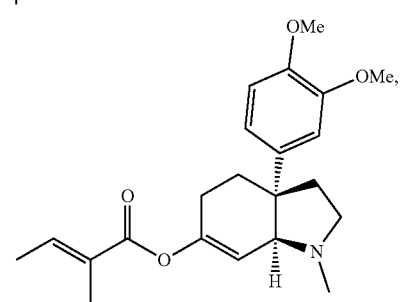
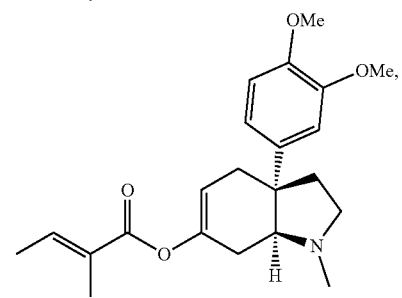
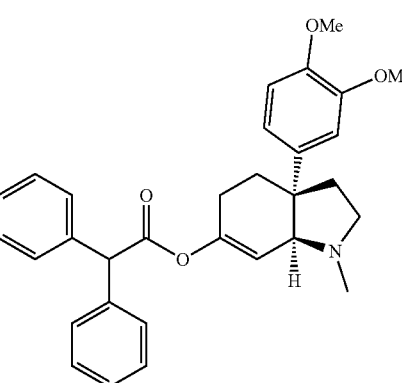
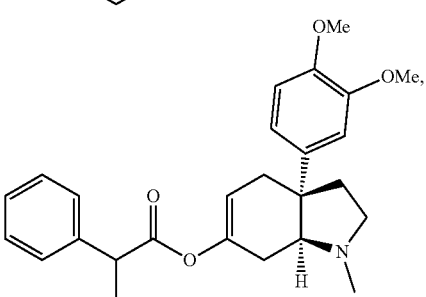
80
-continued
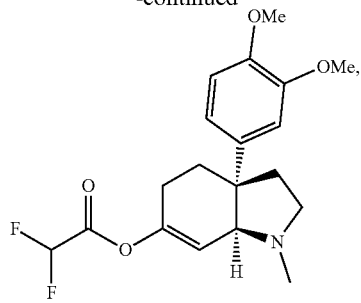
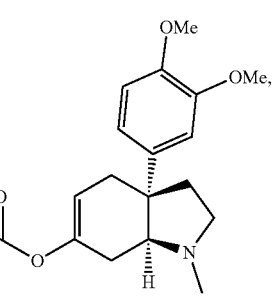
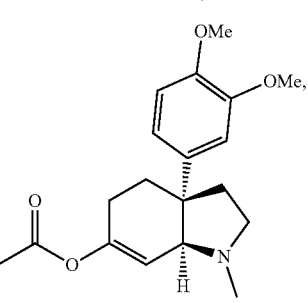
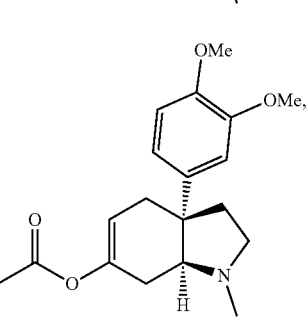
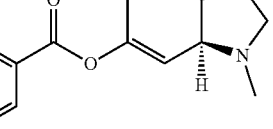

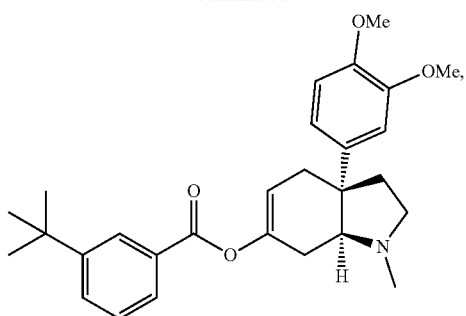
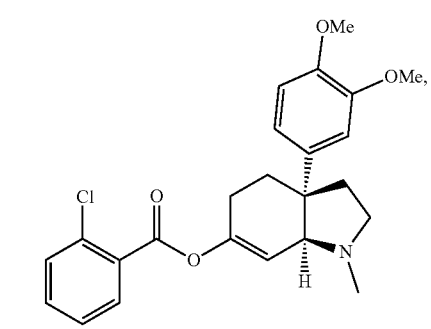

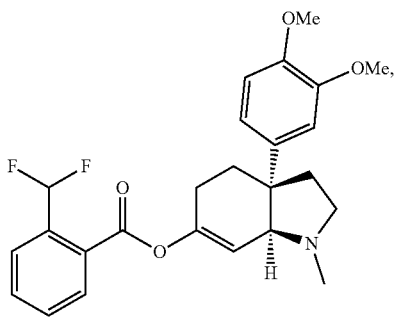
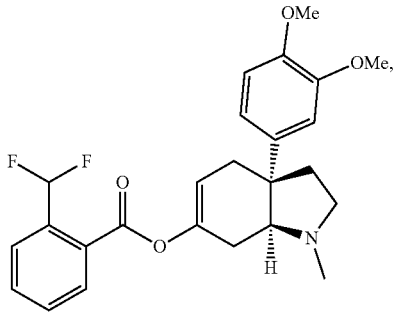
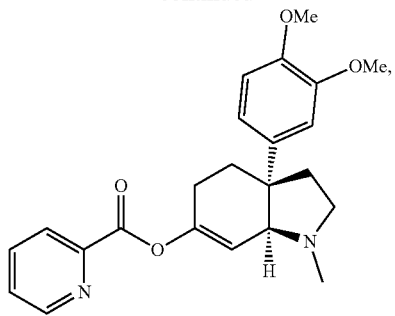
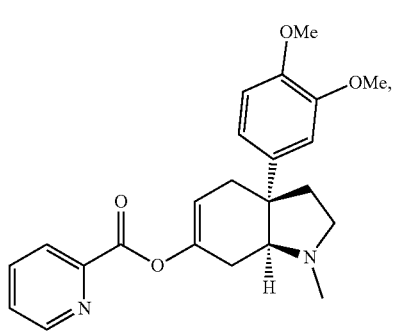
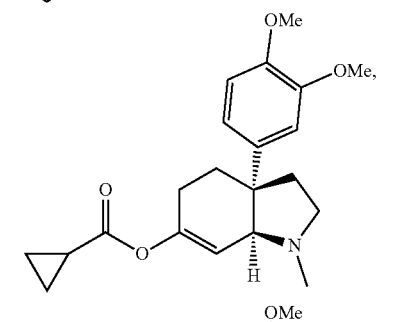
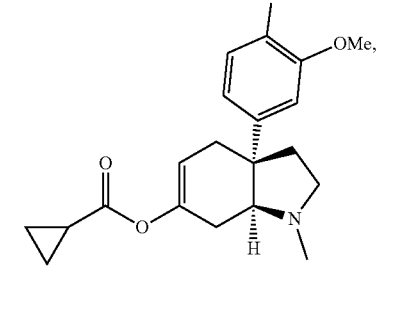
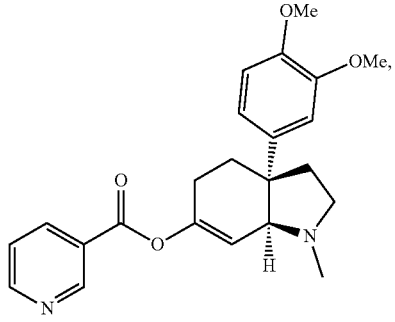

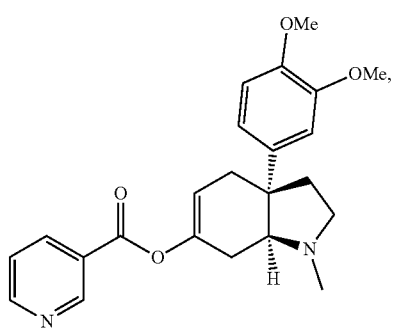
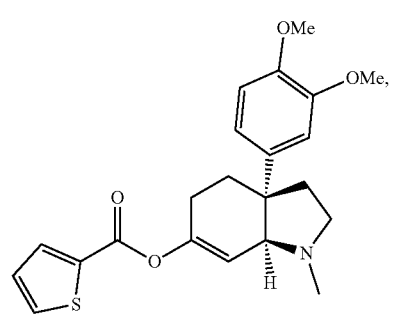
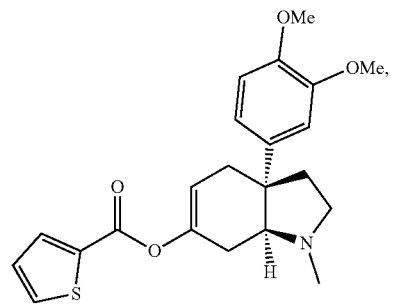
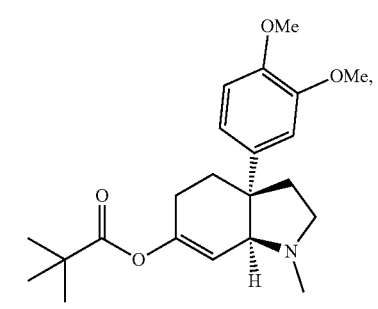
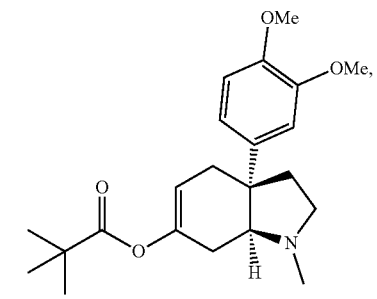
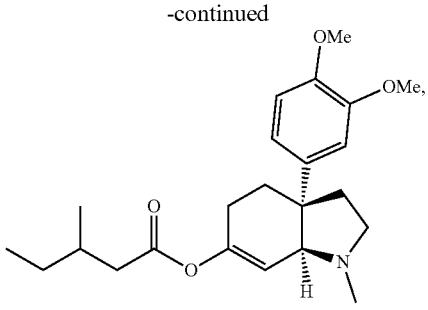
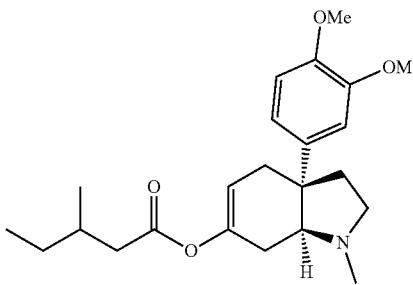
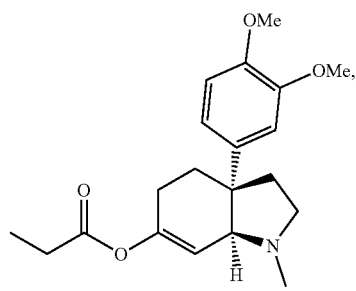
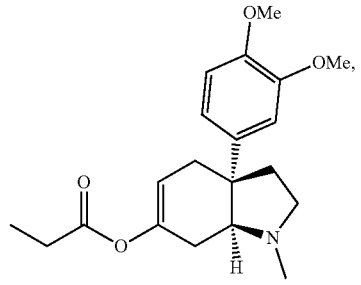
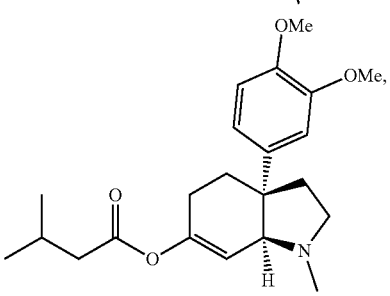
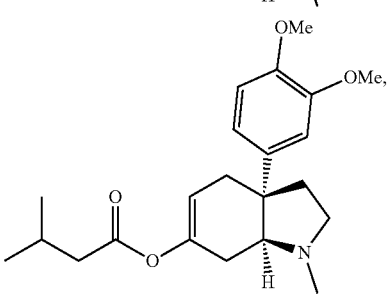

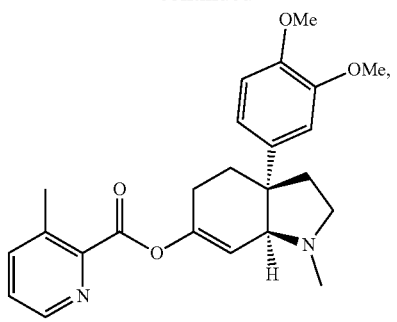
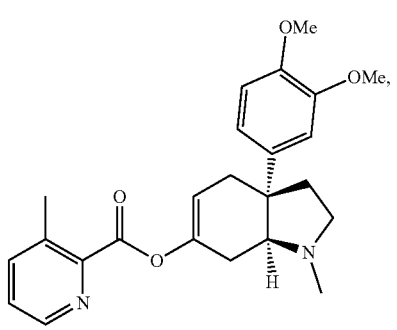
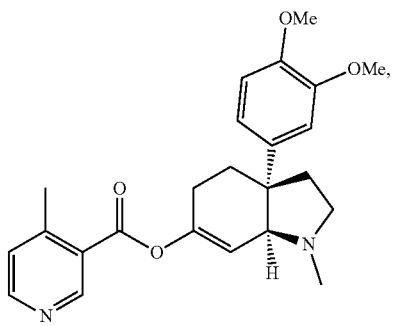
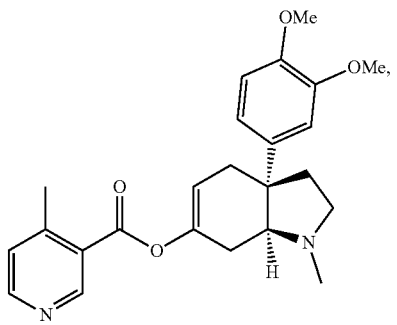
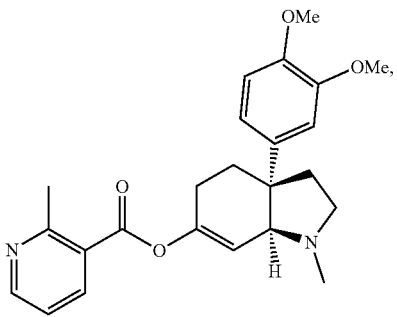
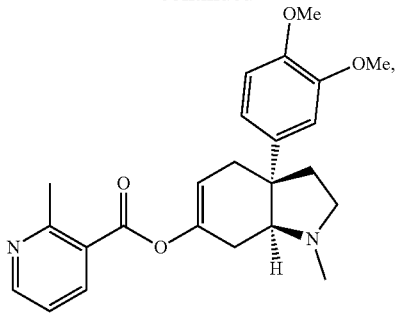
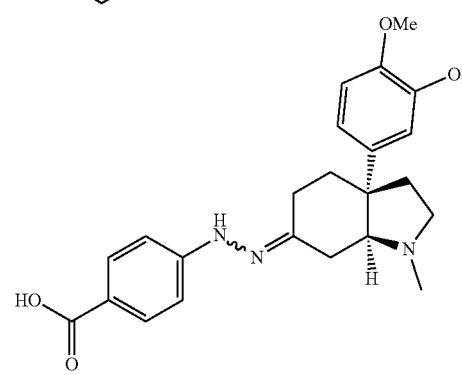
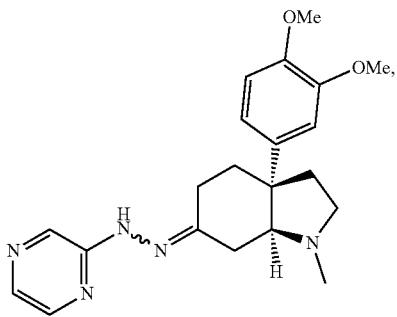
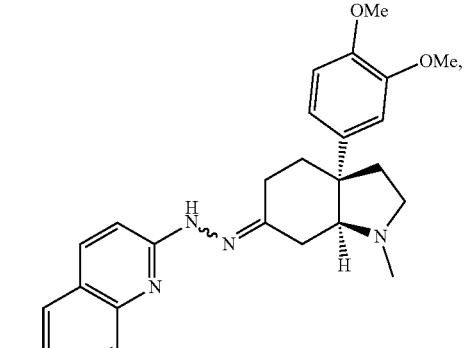
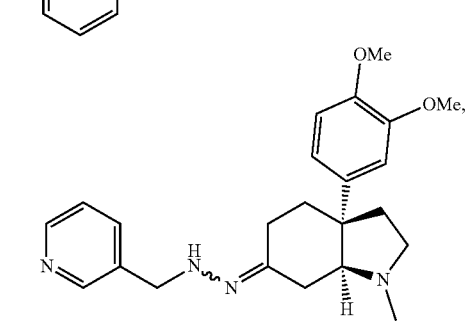

87
-continued
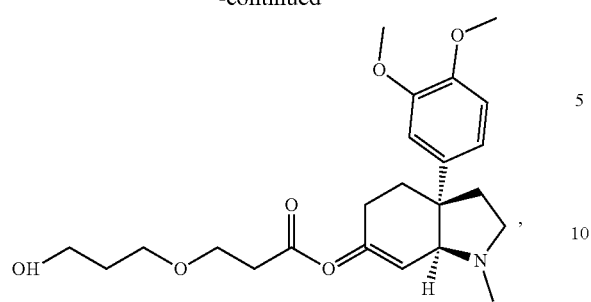
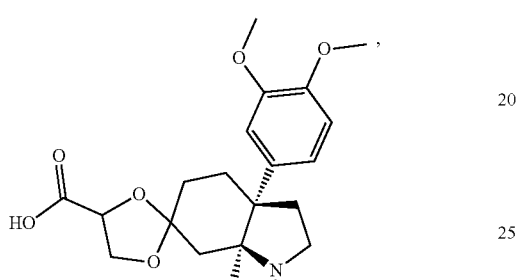
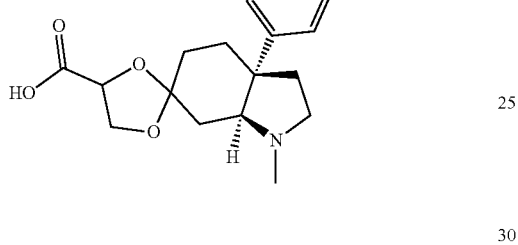

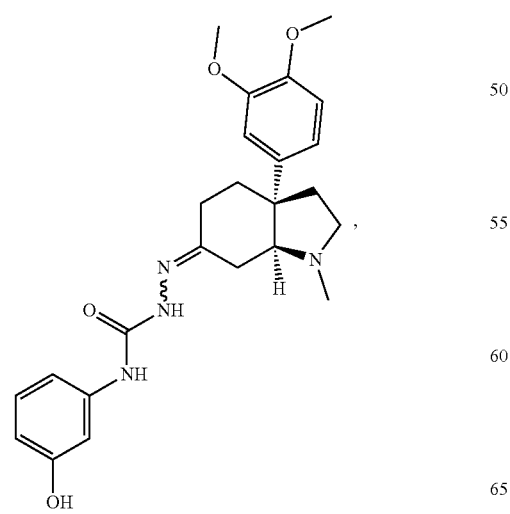
88
-continued
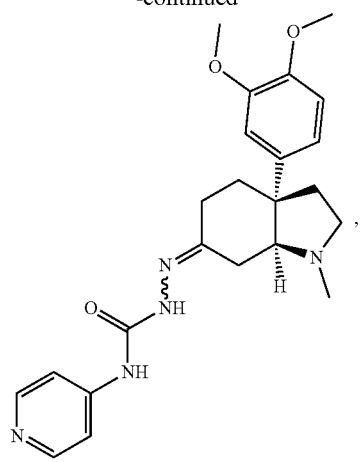
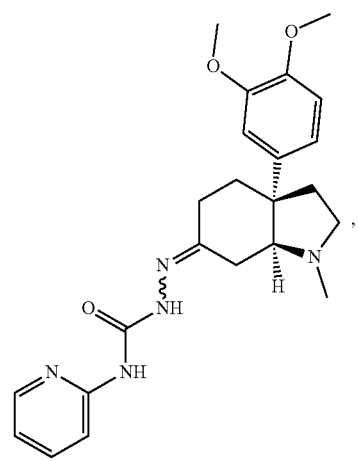
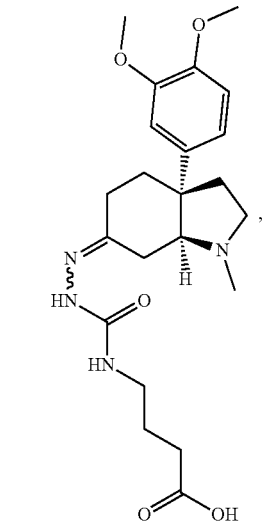

| 89 -continued | 90 -continued |
|---|---|
| 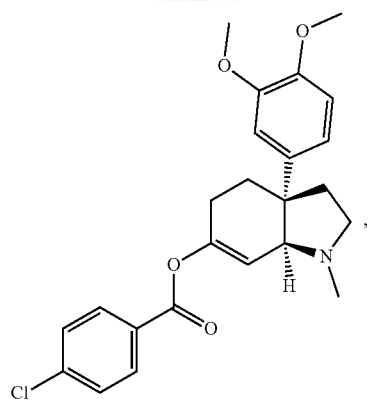 | 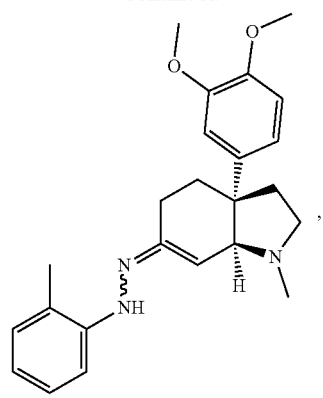 |
| 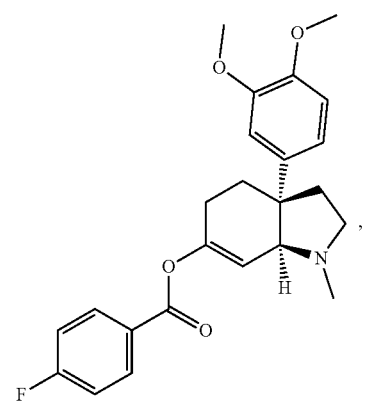 | 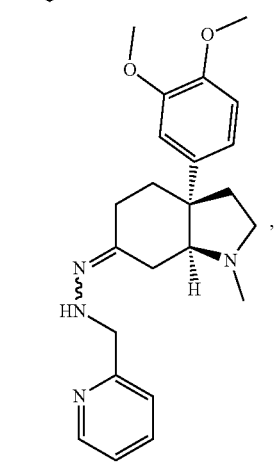 |
| 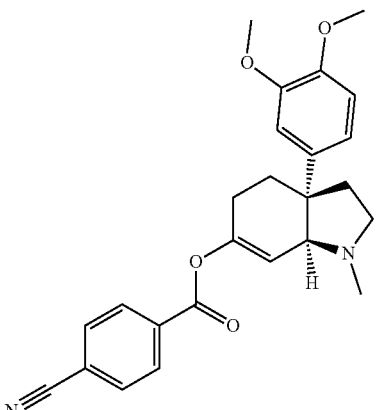 | 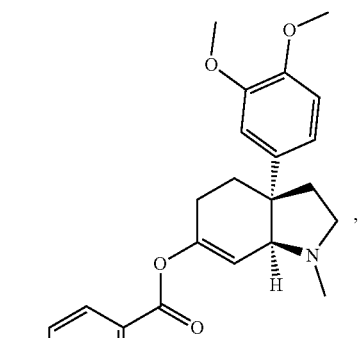 |
| 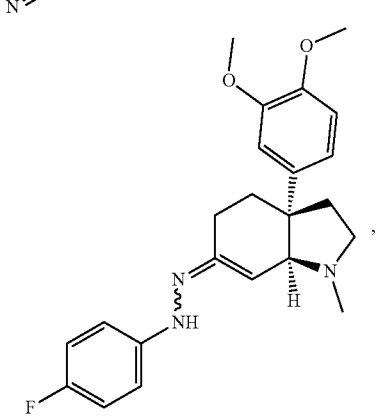 | 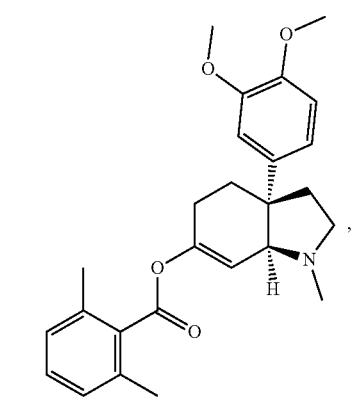 |

91
-continued
92
-continued
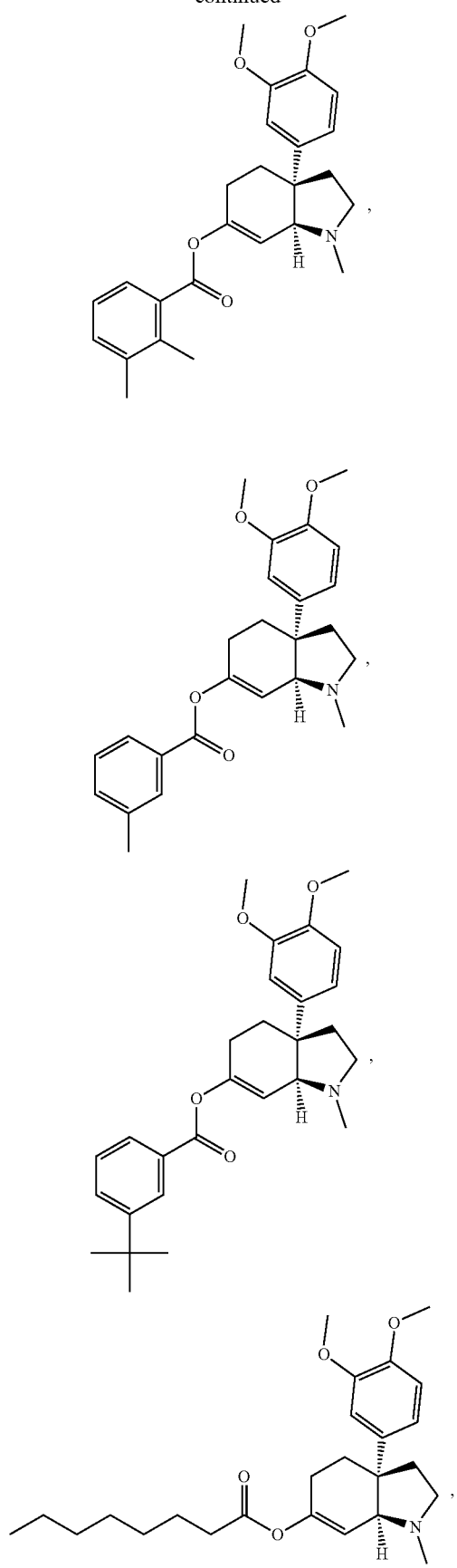
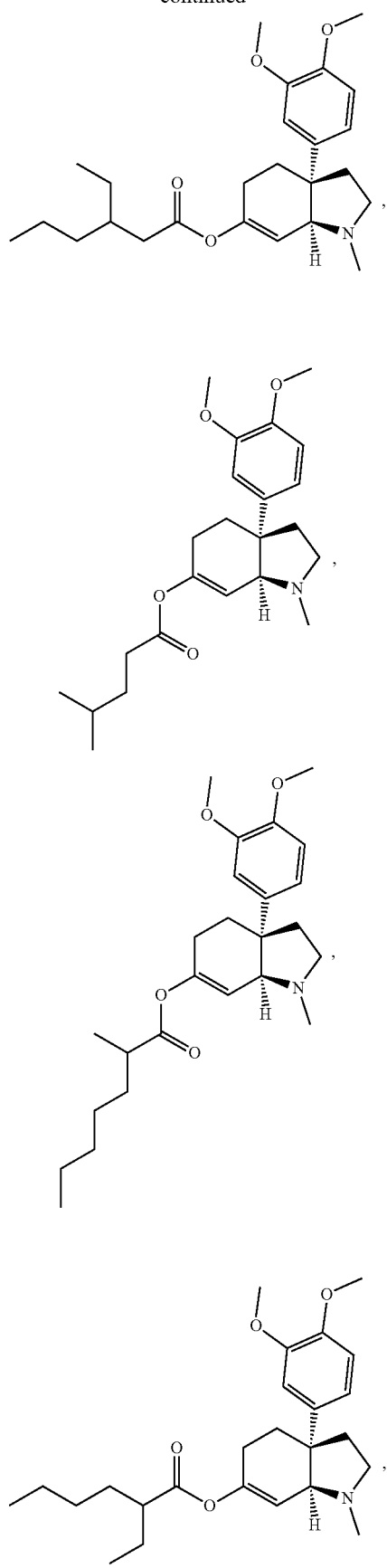

93
-continued
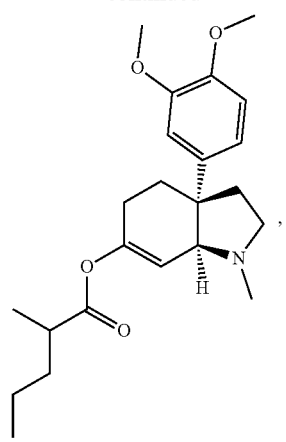
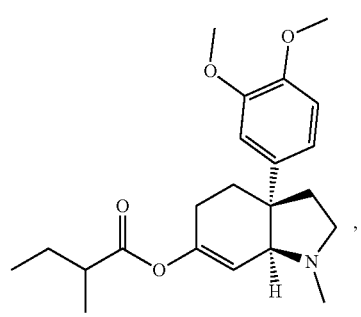
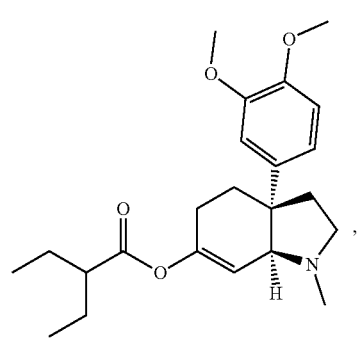
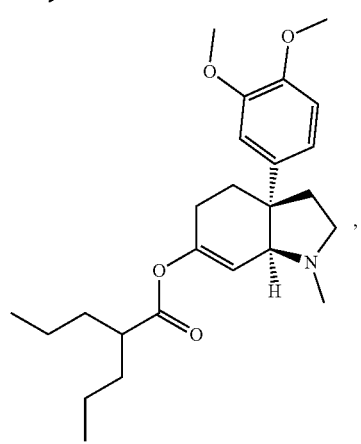
94
-continued
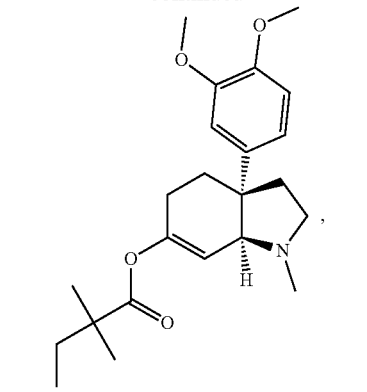
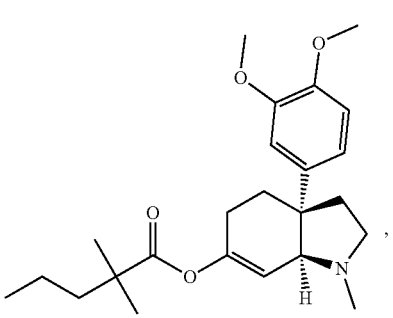
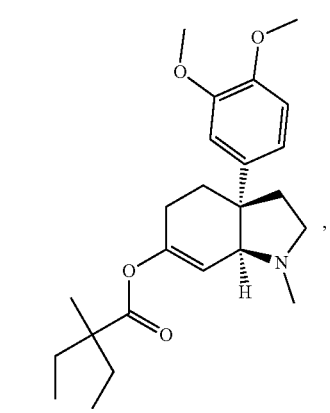
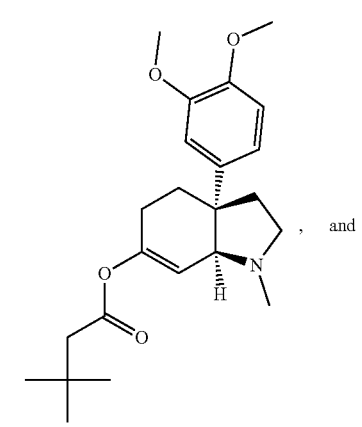, and -continued
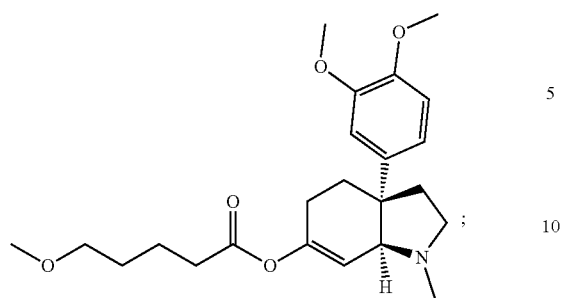
or a pharmaceutically acceptable salt thereof; or a pharmaceutically acceptable salt thereof.
In some embodiments, the compound is selected from the group consisting of:
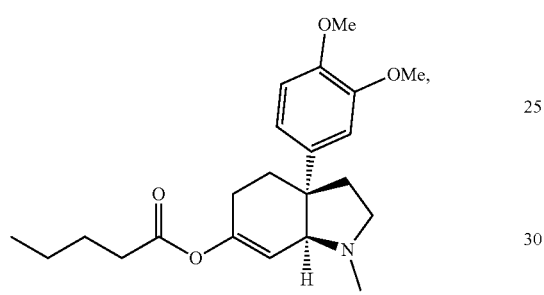
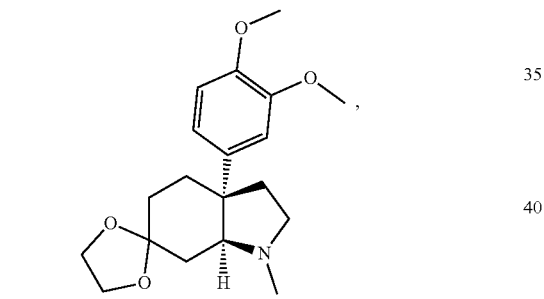
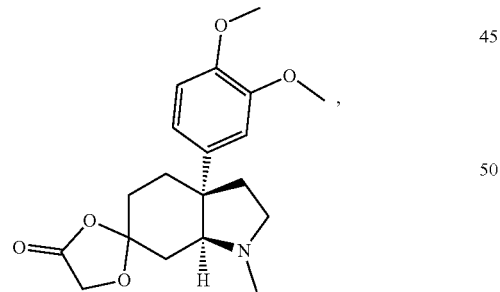
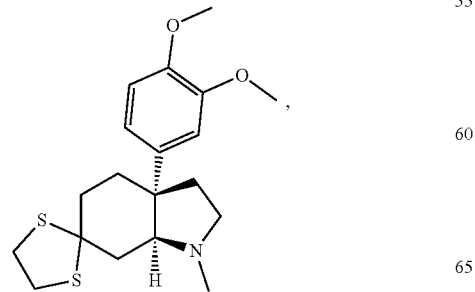
-continued
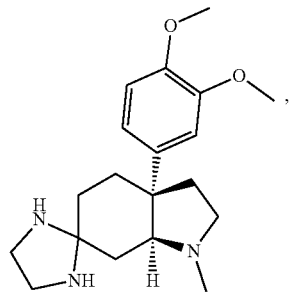
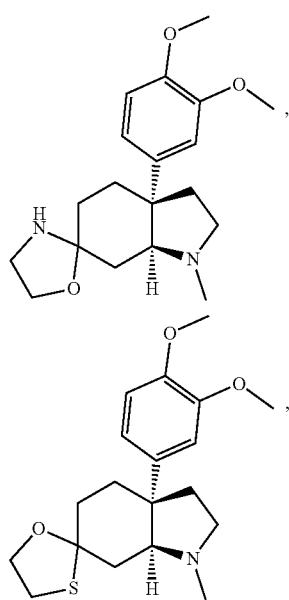
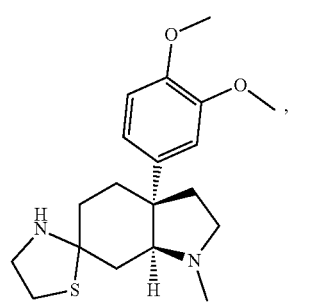
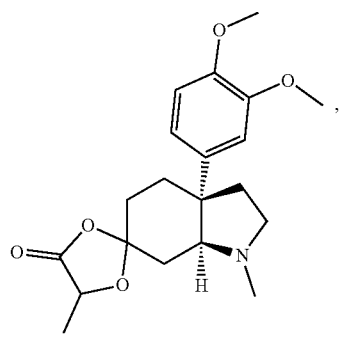

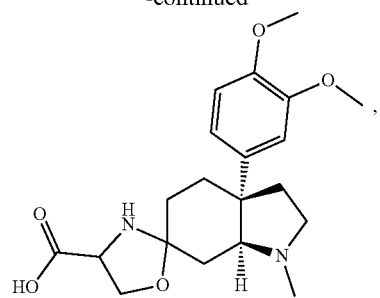
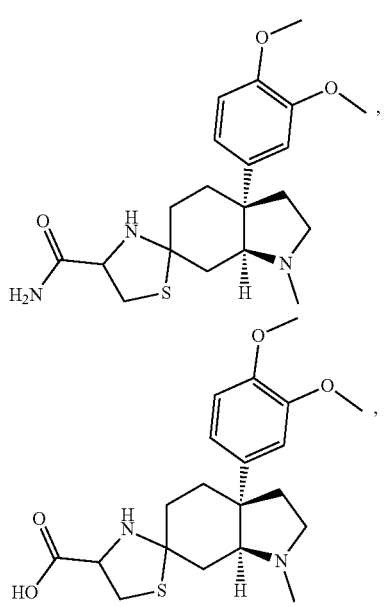
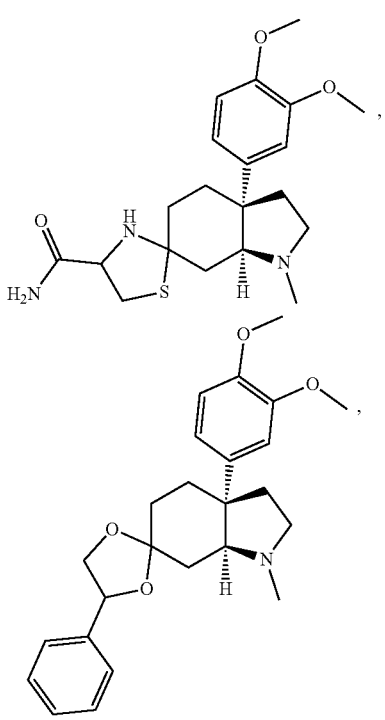
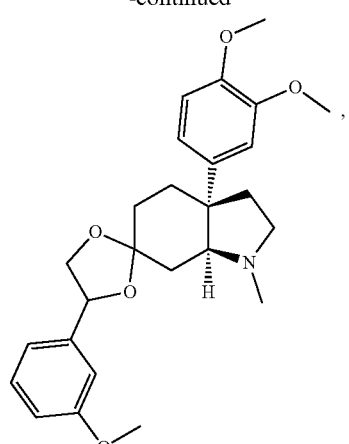
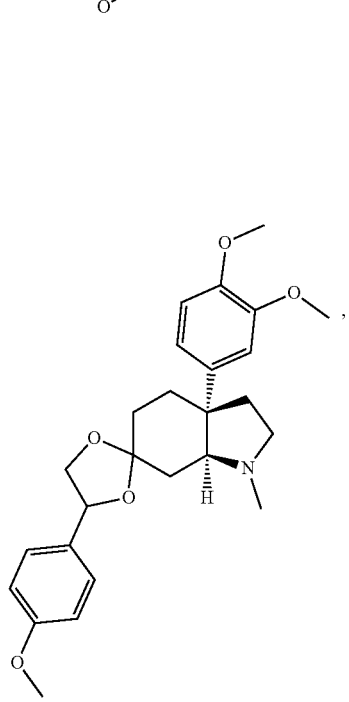
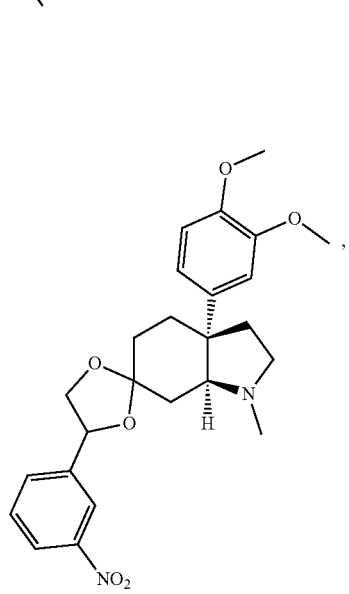

-continued
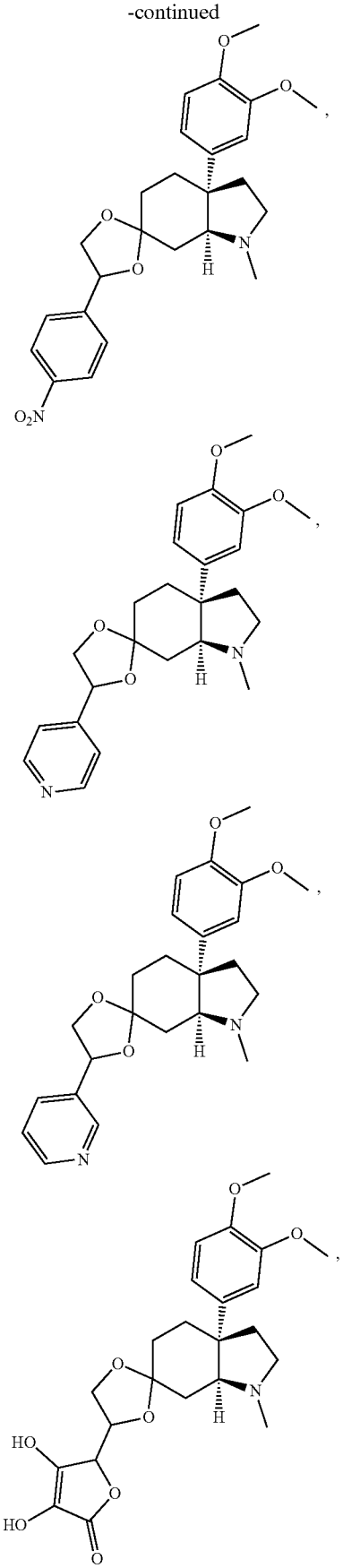
-continued
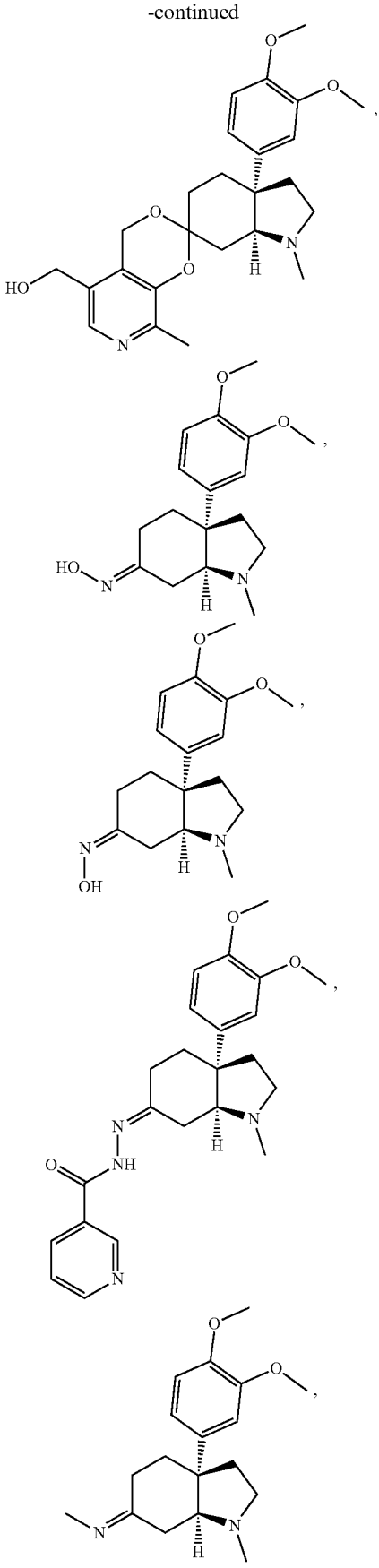

101
-continued
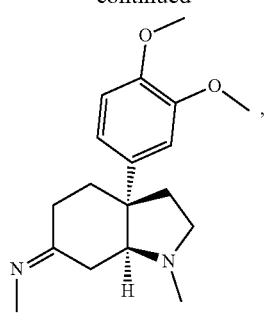
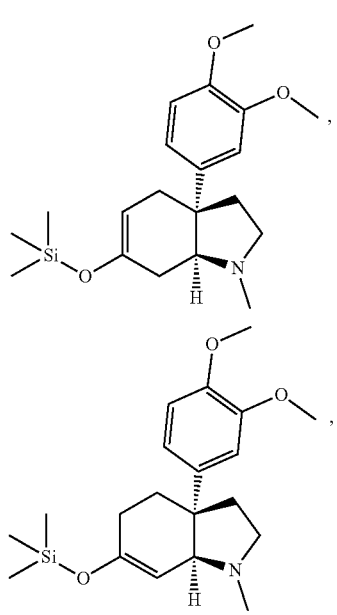
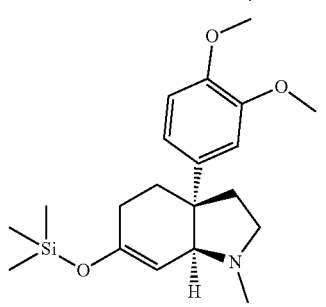
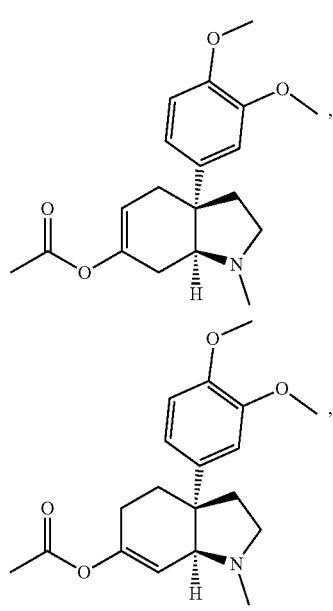
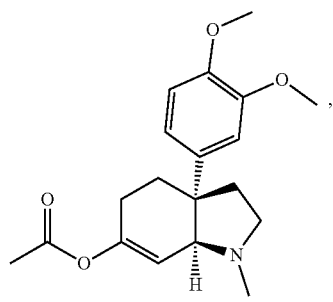
102
-continued
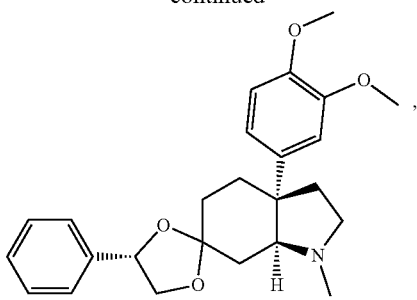
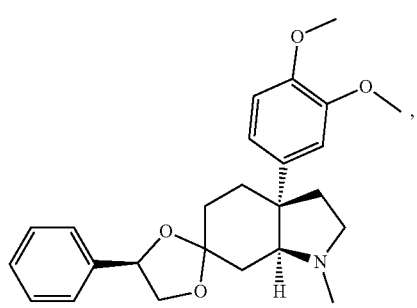
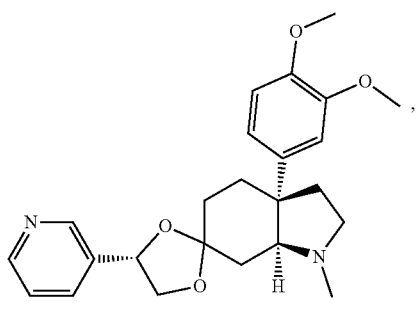
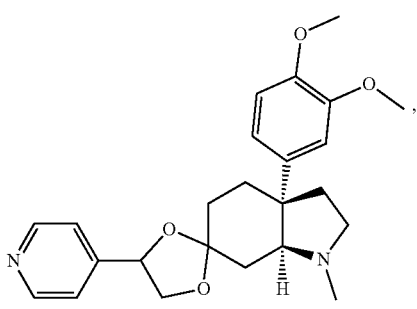
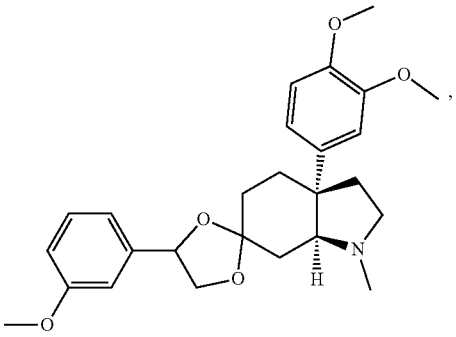

103
-continued
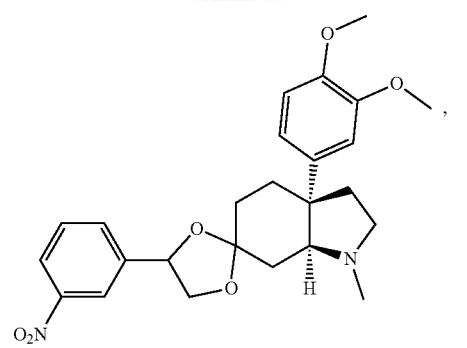
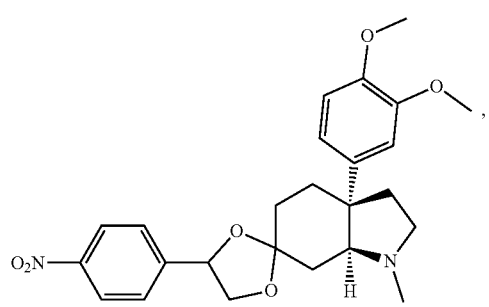
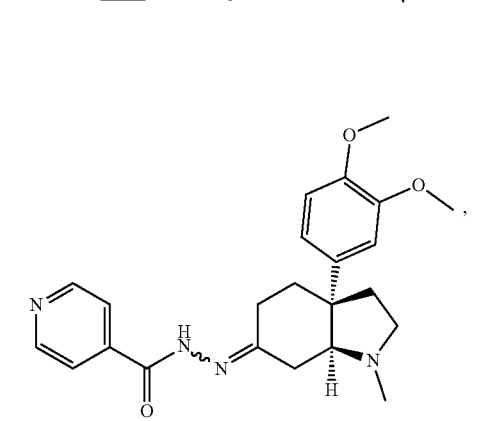
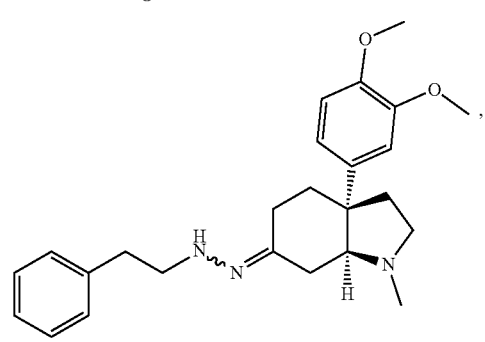
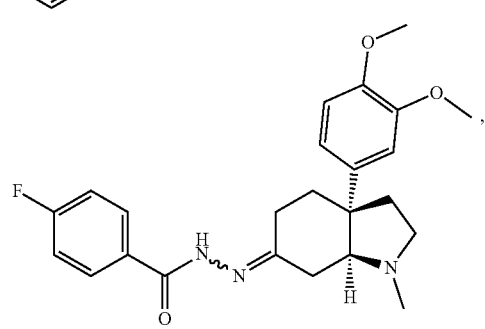
104
-continued
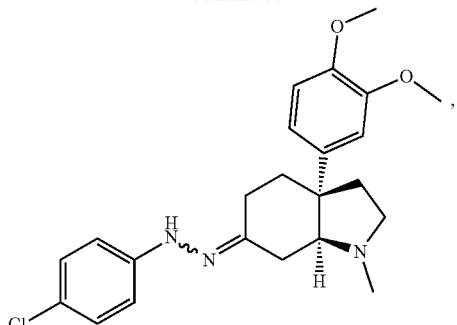
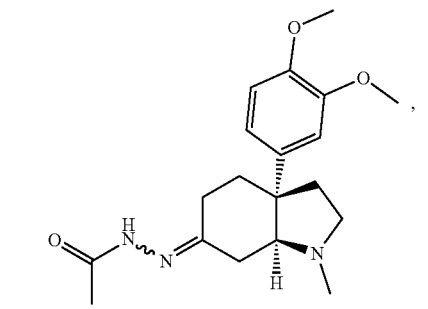
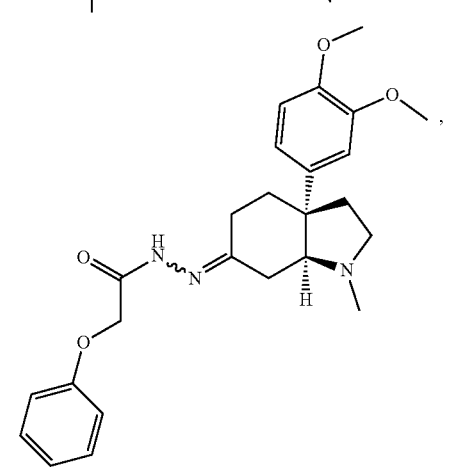
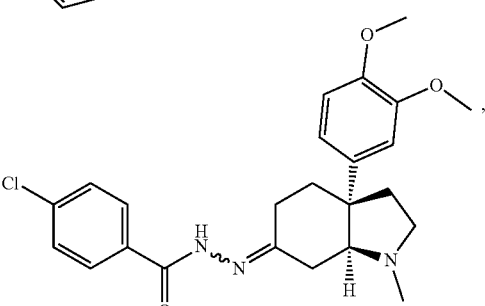
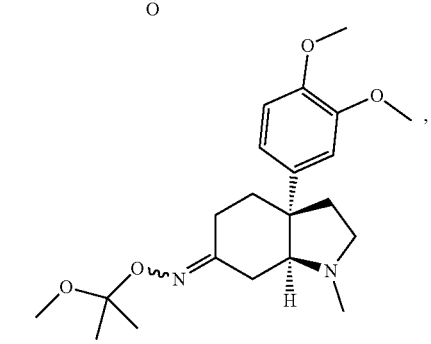

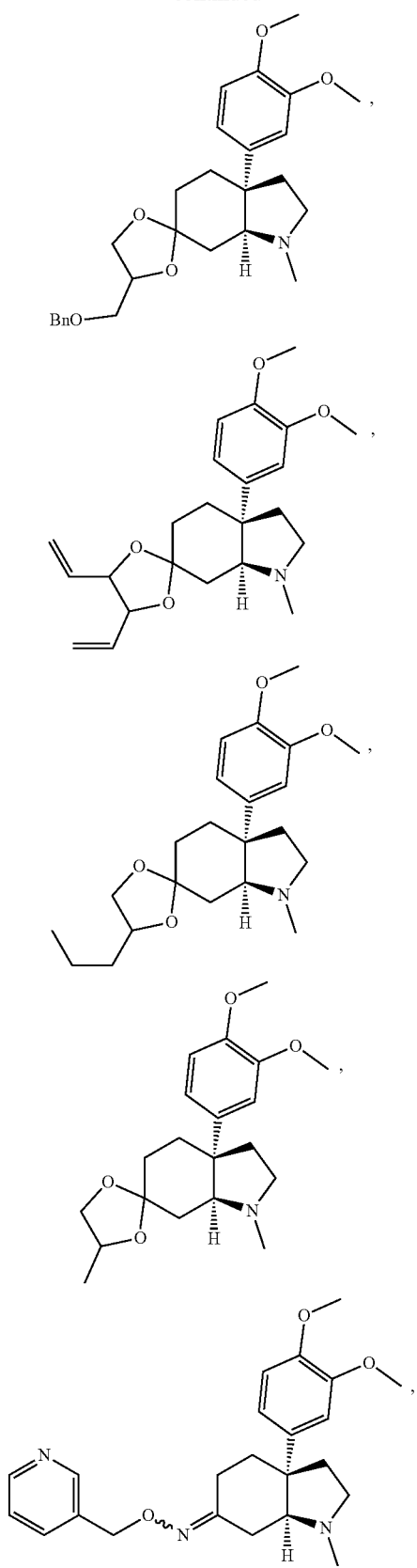
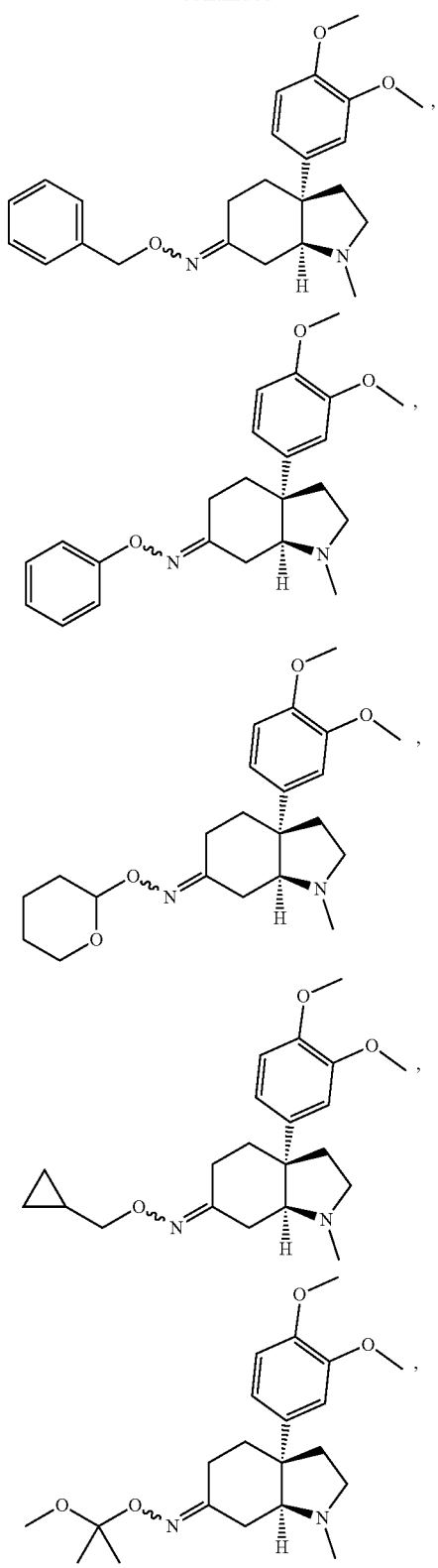

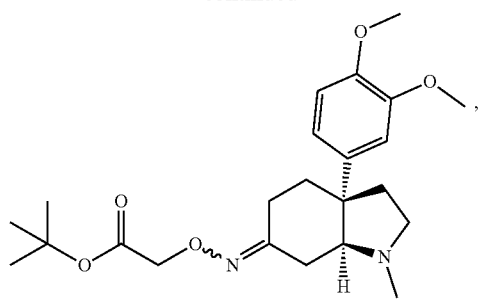
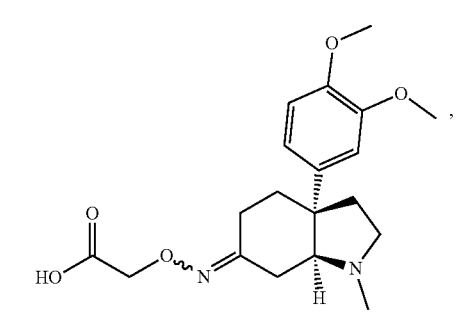
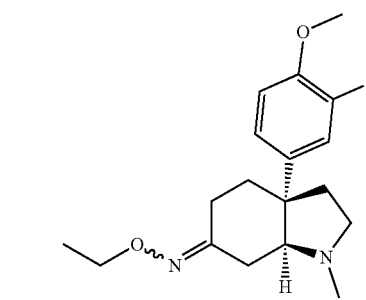
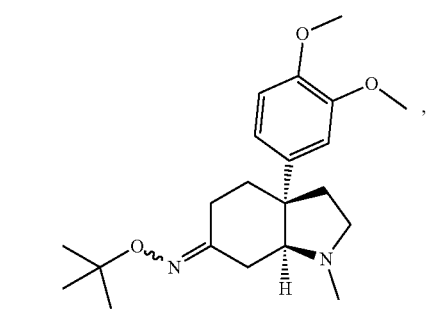
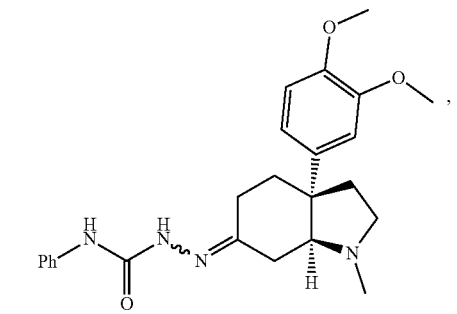
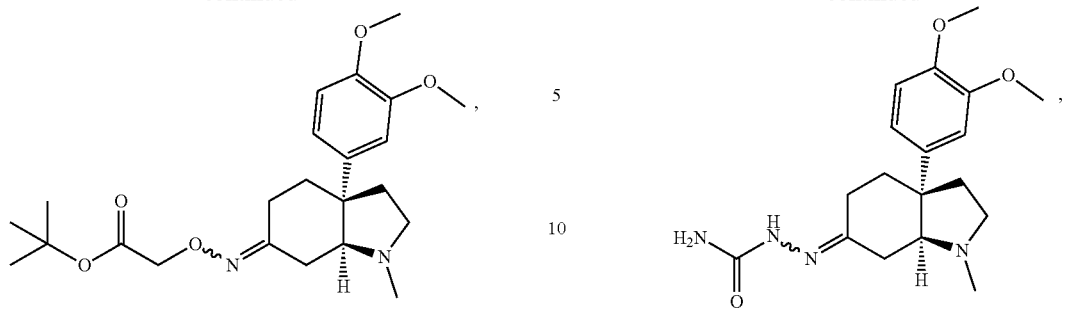
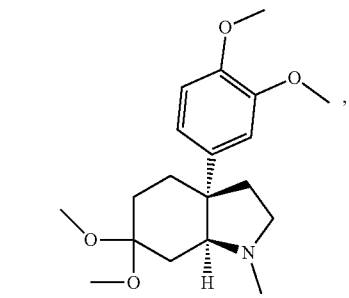
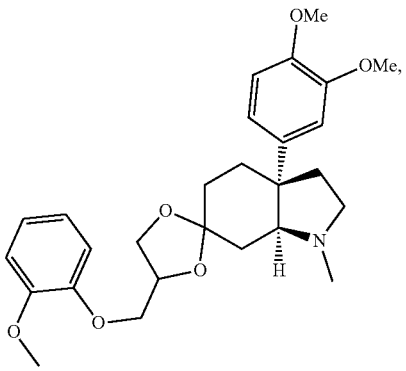
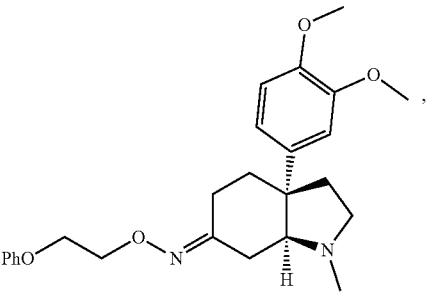
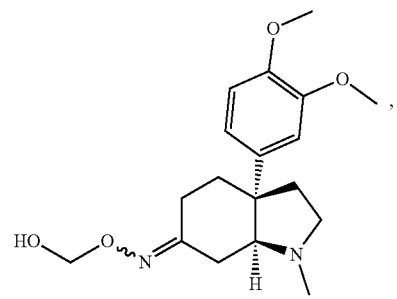

109
-continued
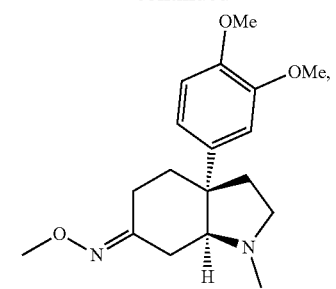
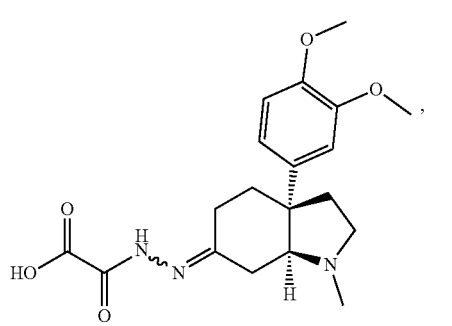
110
-continued
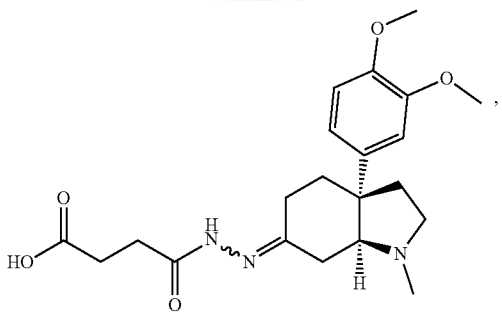
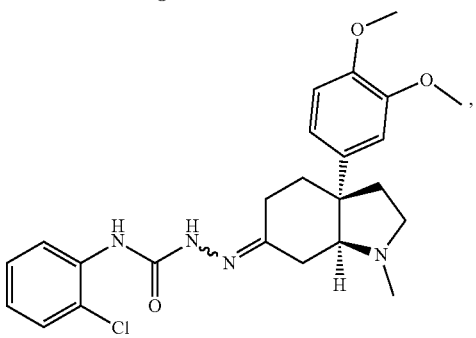
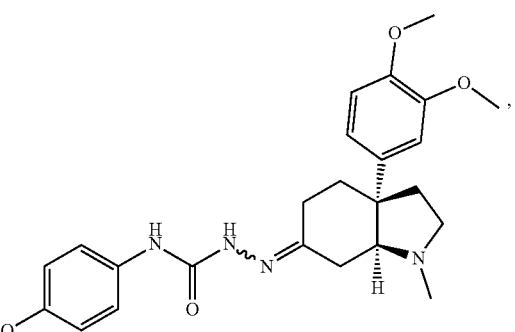
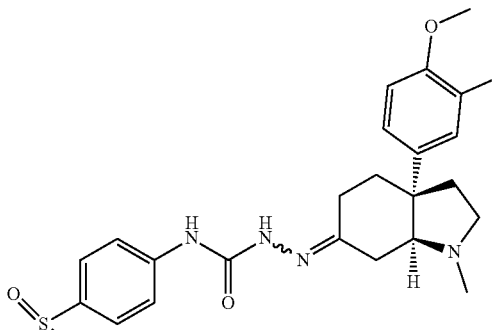
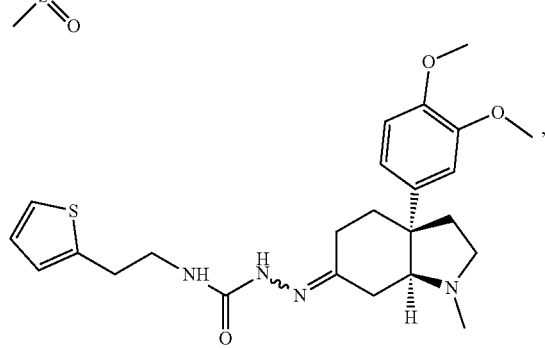

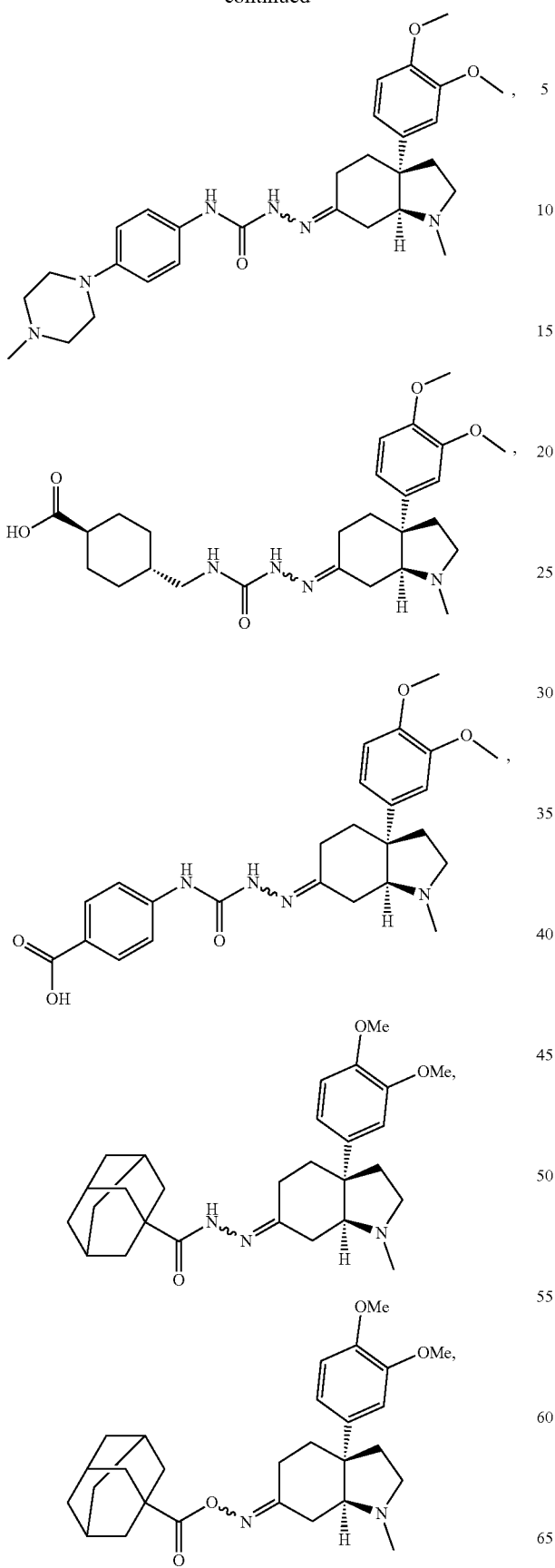
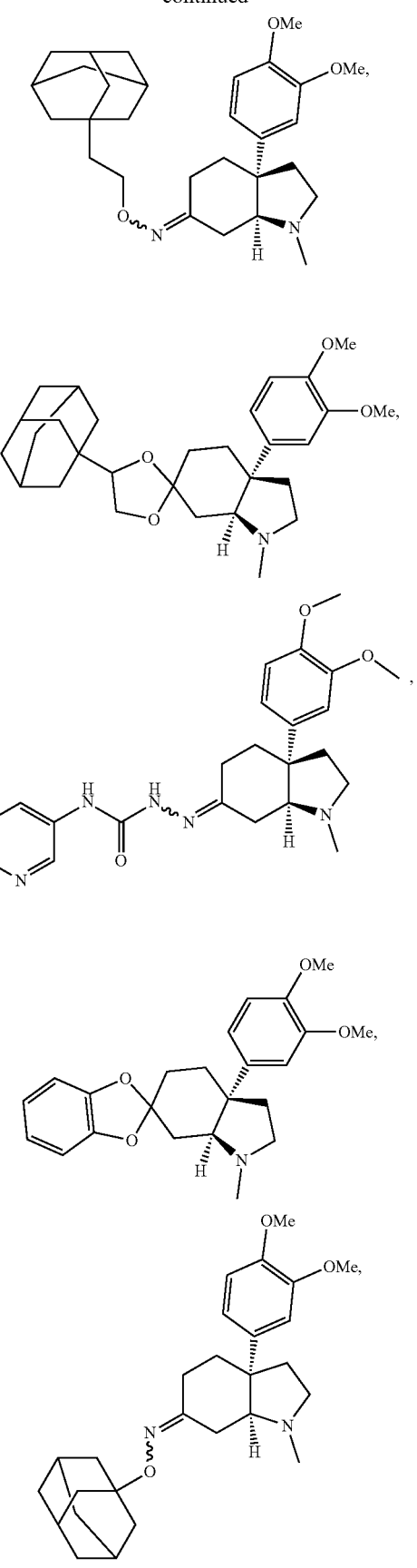

-continued
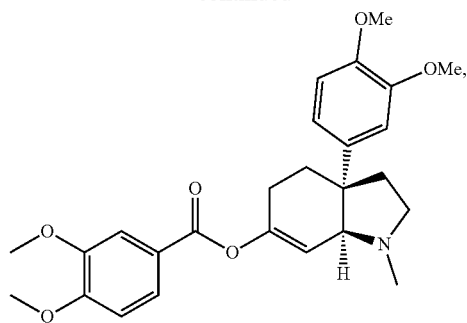
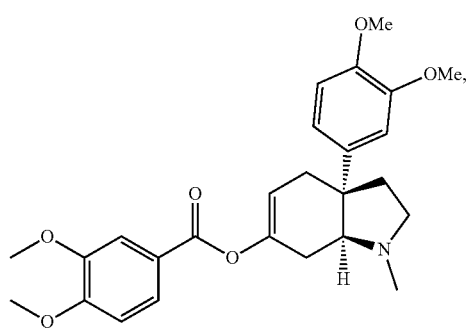
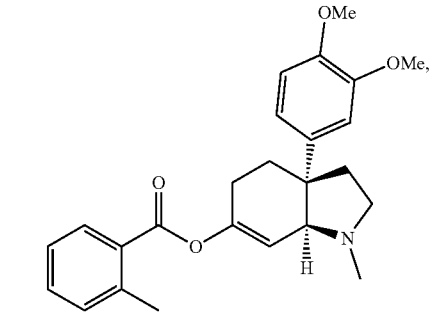
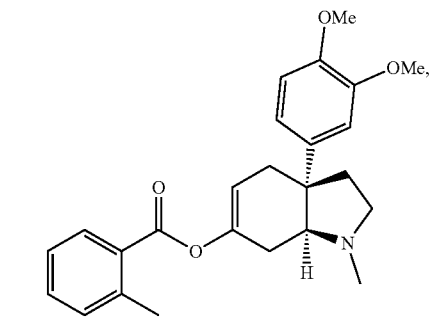
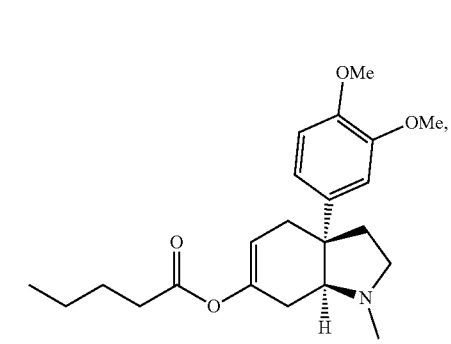
-continued
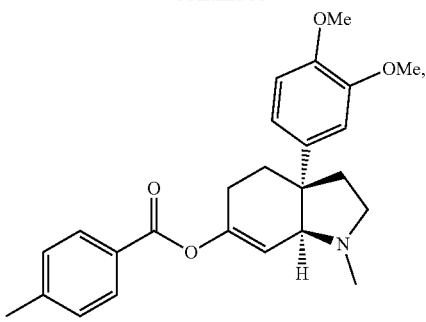
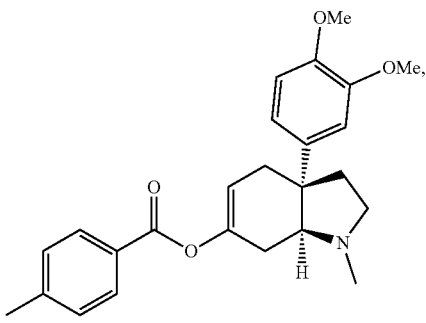
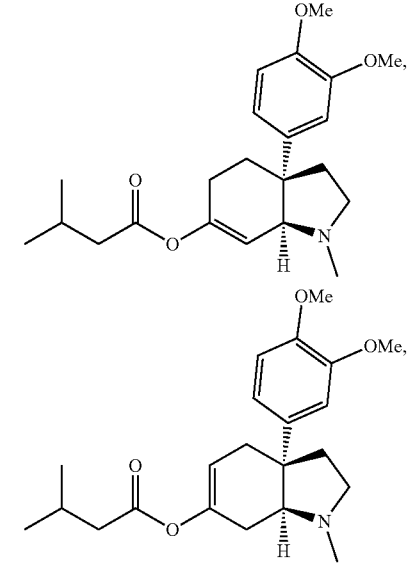
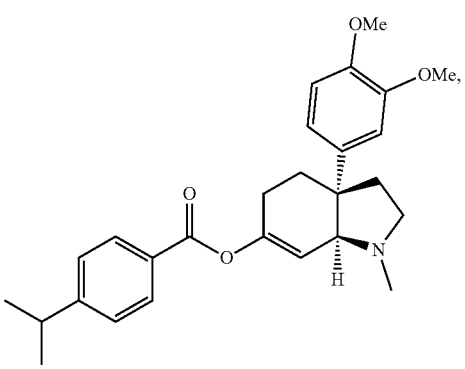

-continued
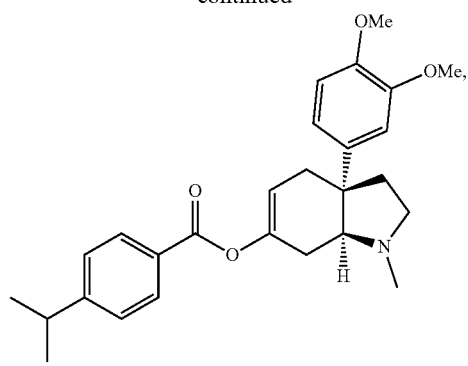
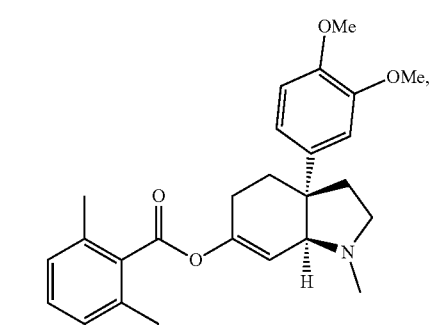
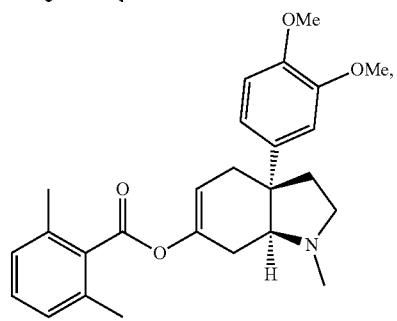
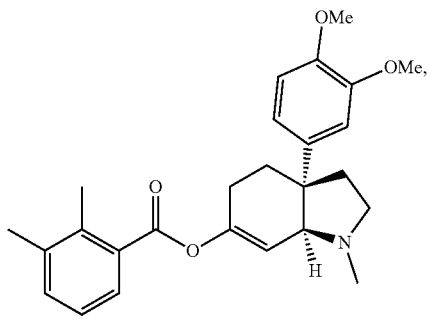
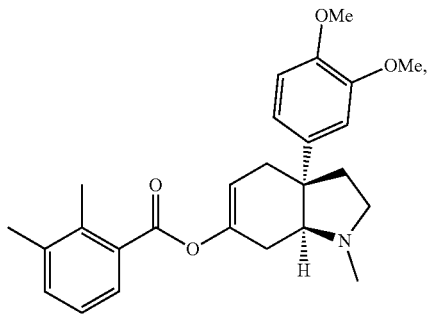
-continued
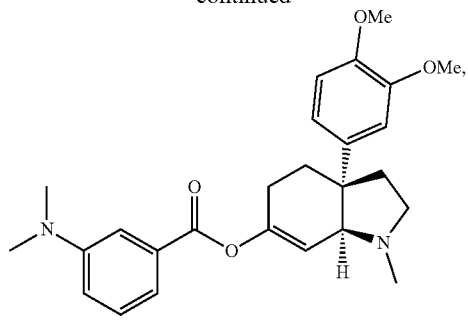
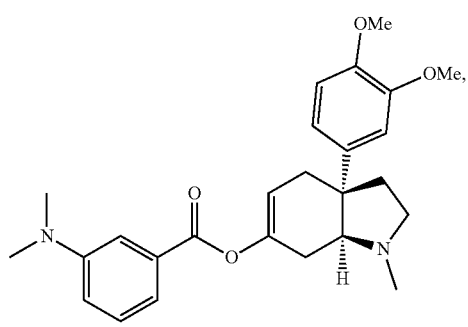
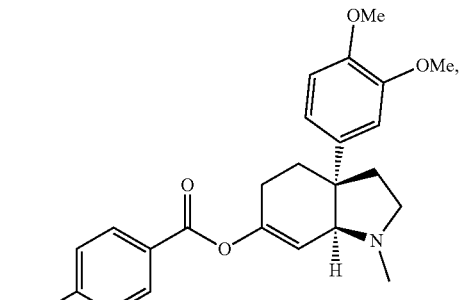
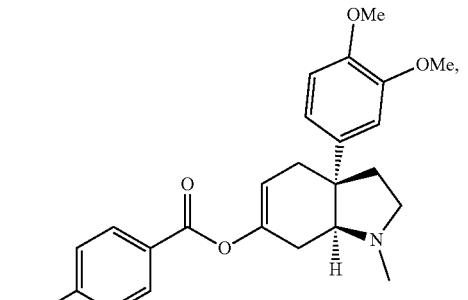
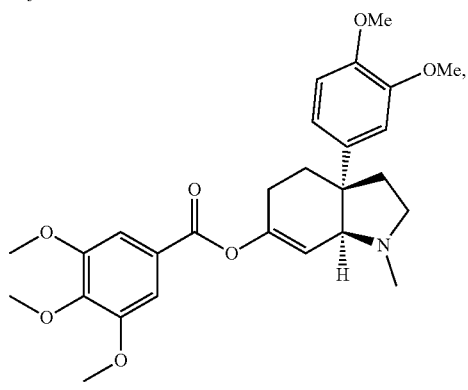

117
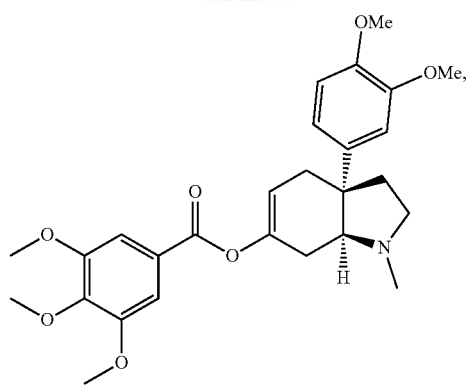
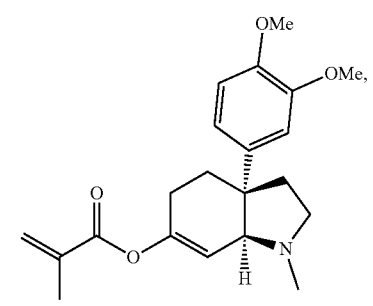
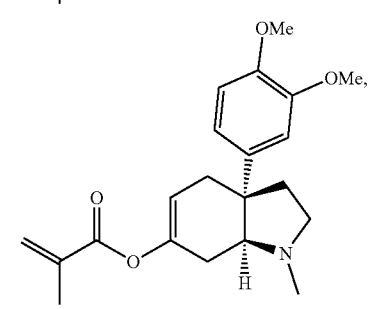
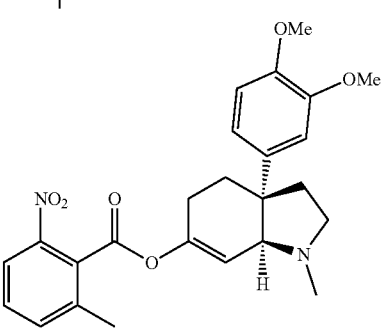
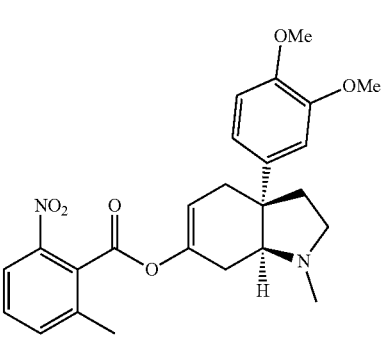
118
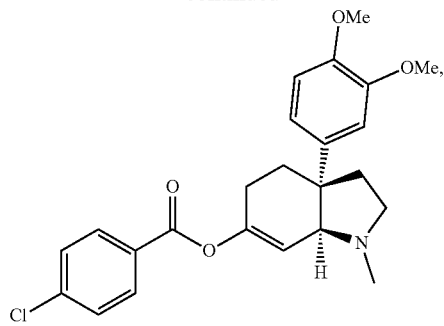
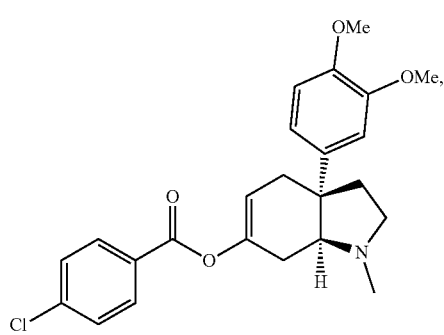
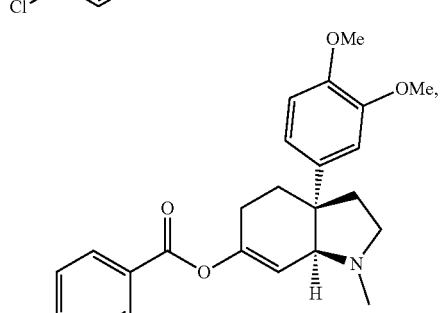
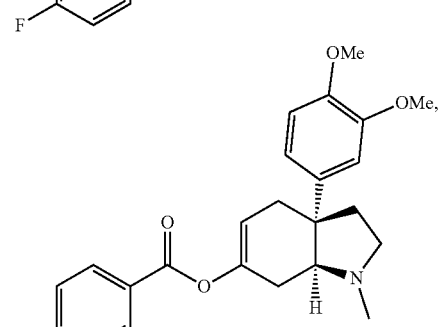
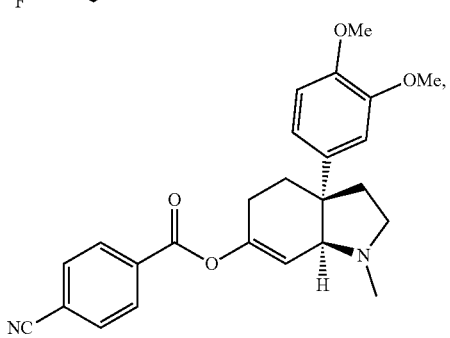

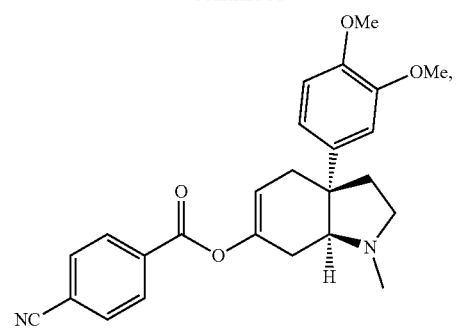
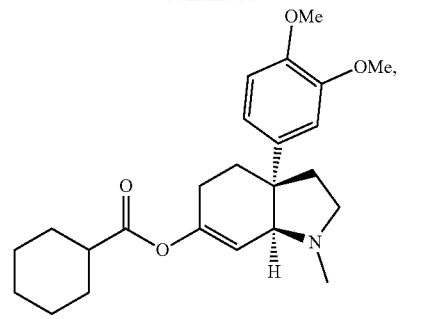
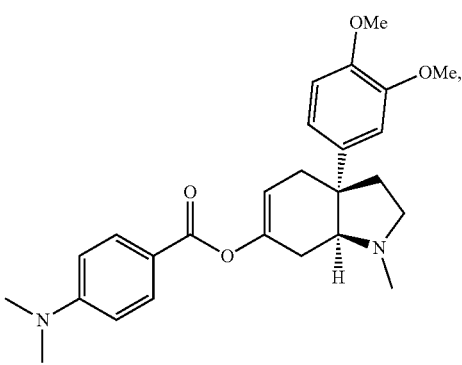
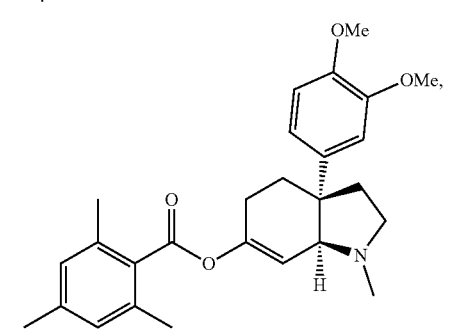
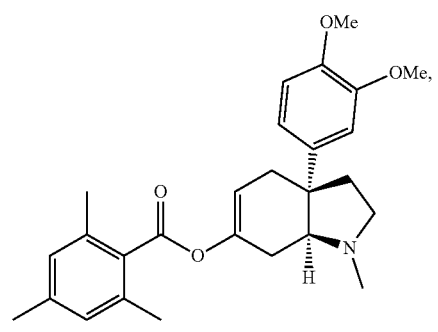
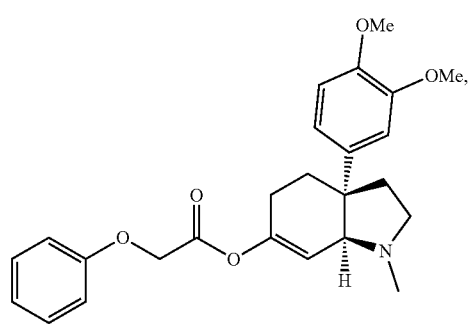
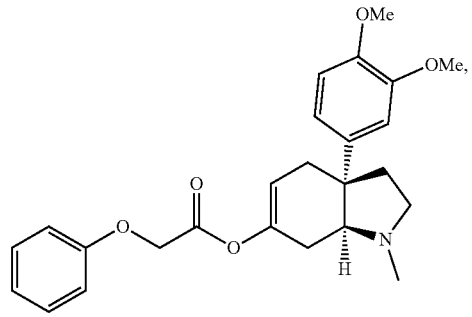
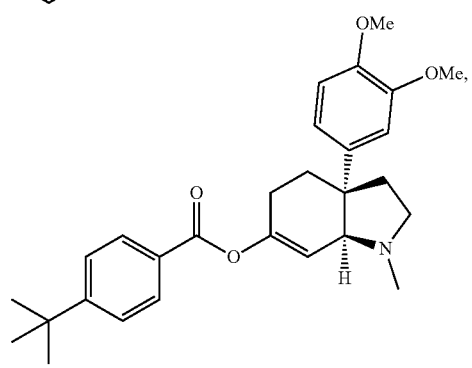

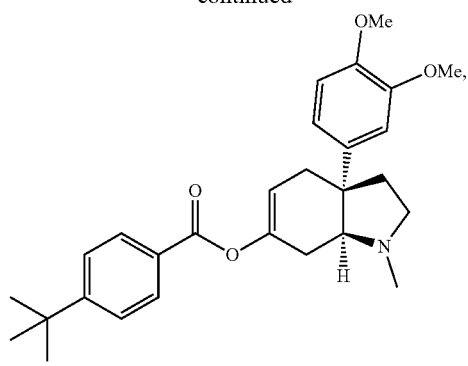
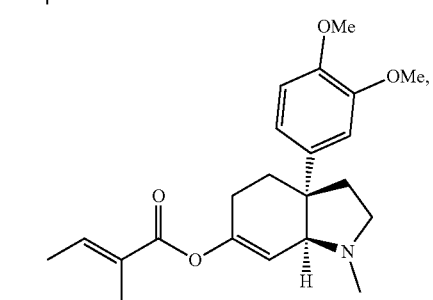
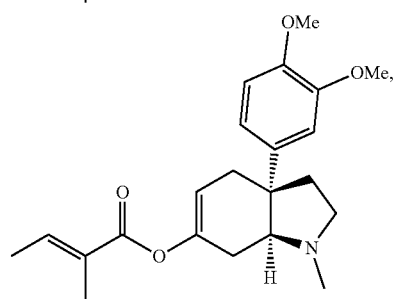
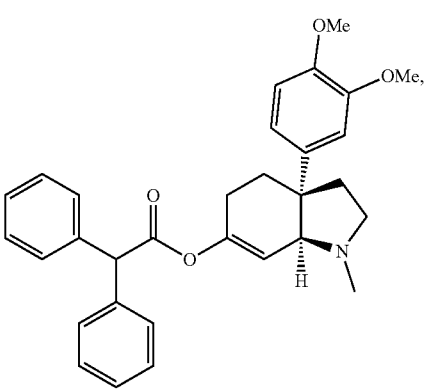
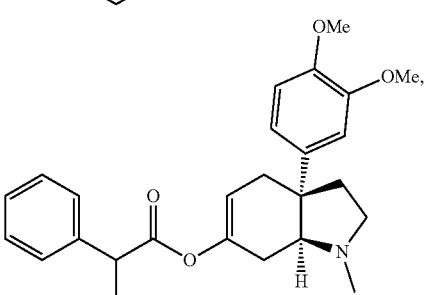
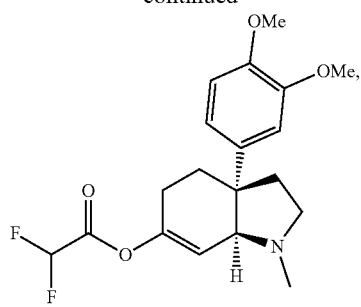
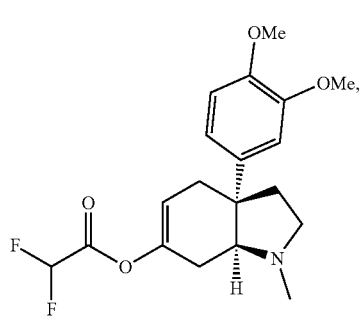
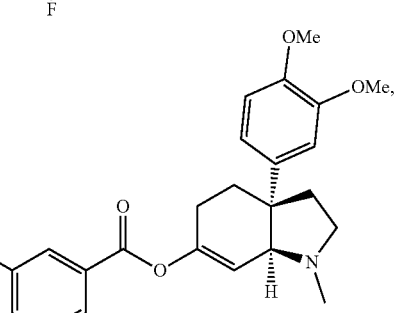
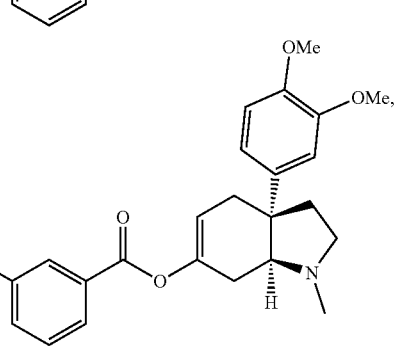
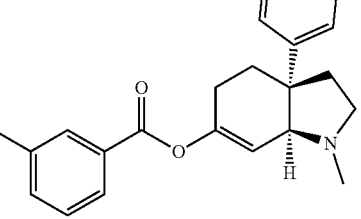

123
-continued
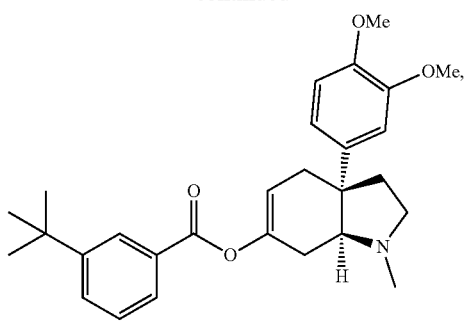
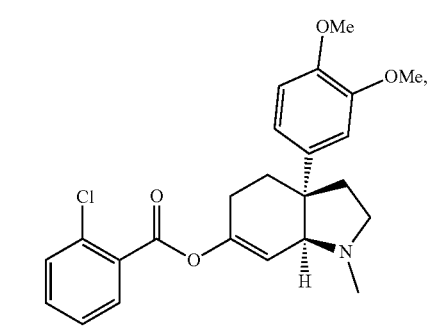
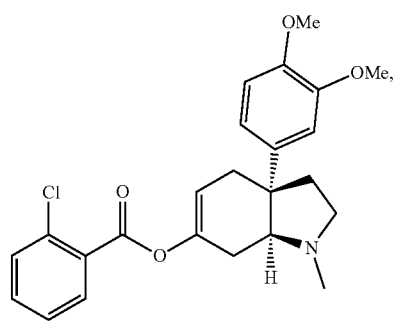
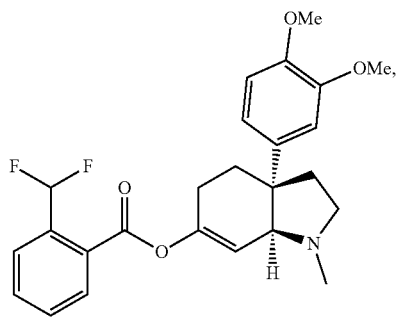
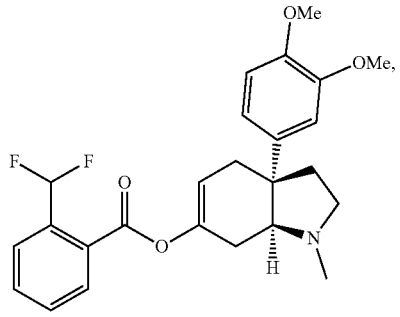
124
-continued
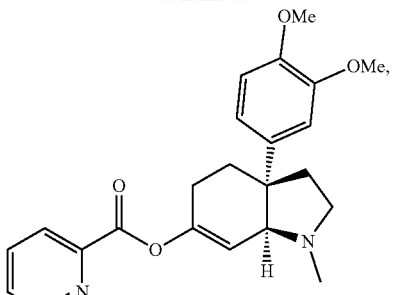
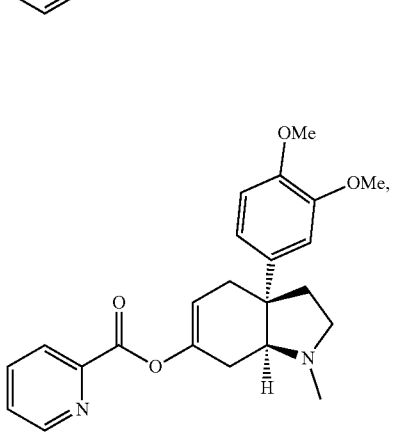
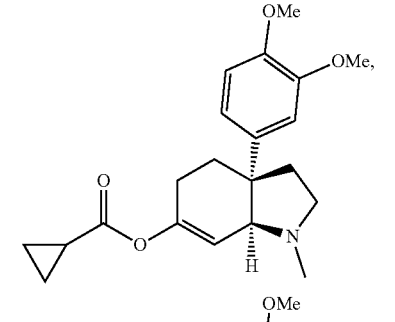
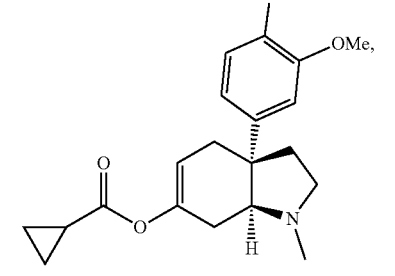
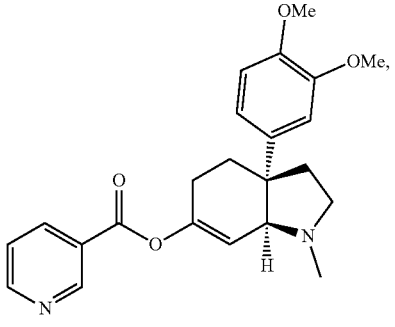

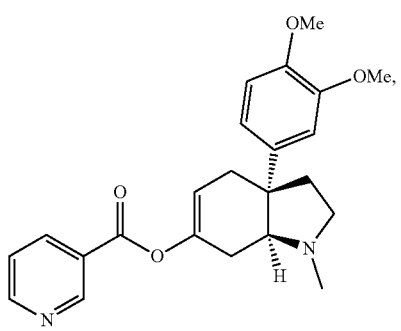
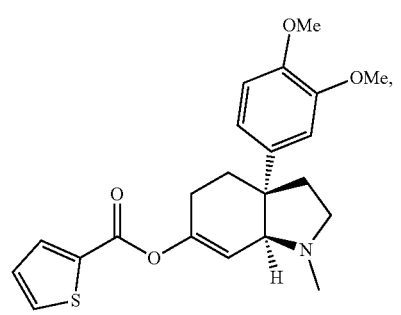
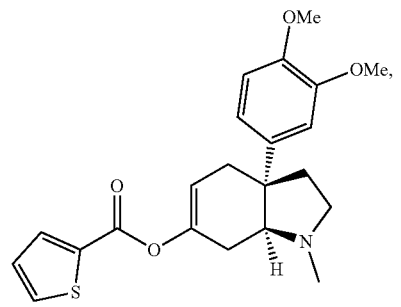
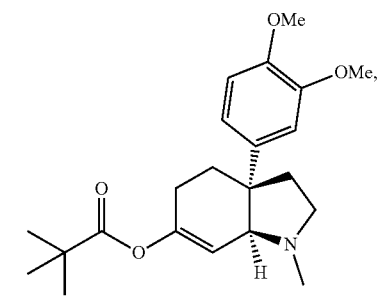
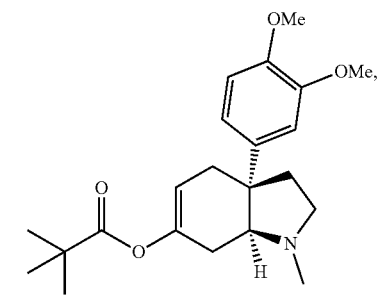
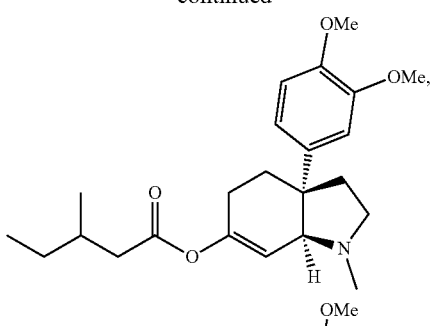
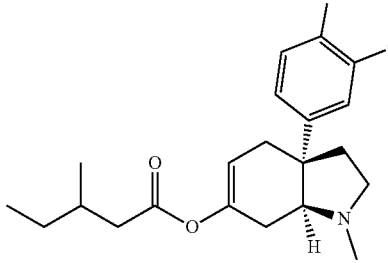
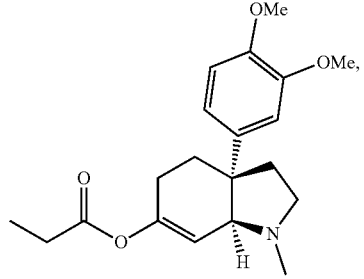
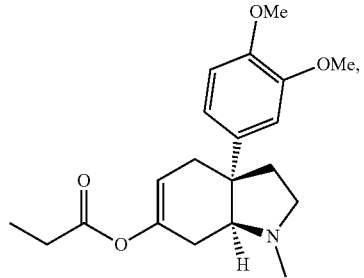
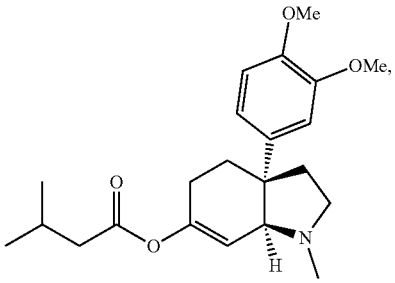
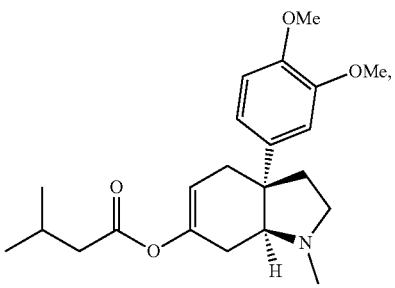

127
-continued
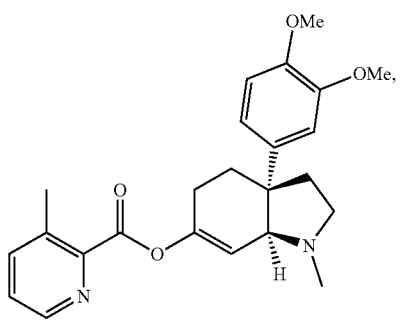
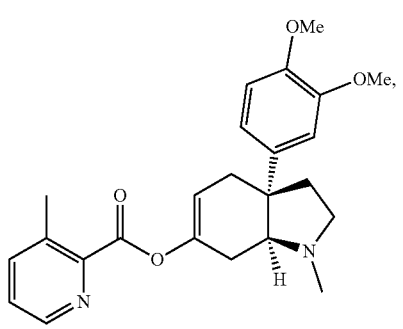
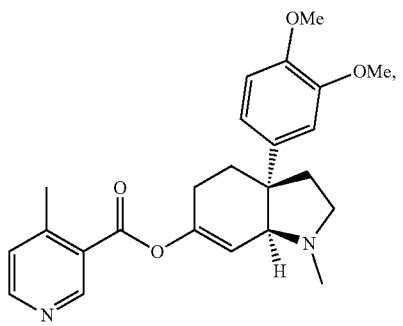
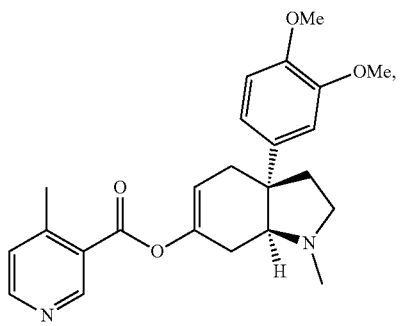
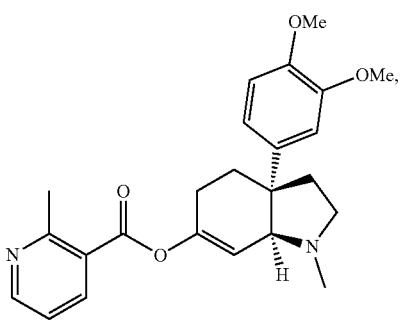
128
-continued
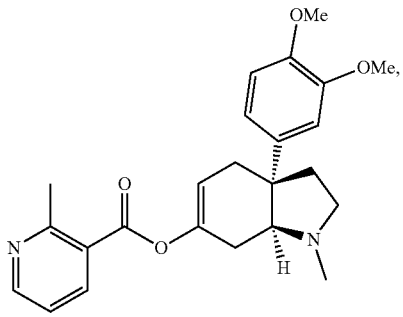
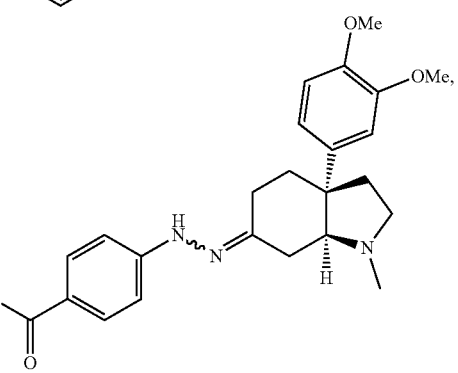
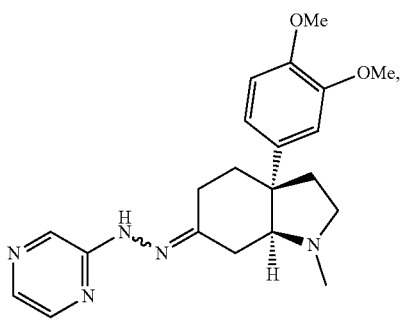
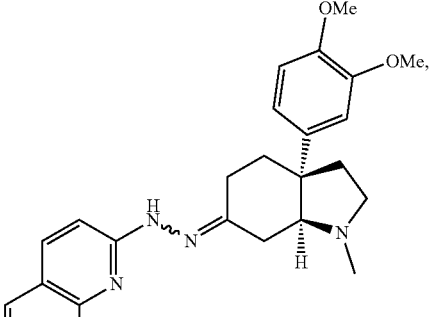
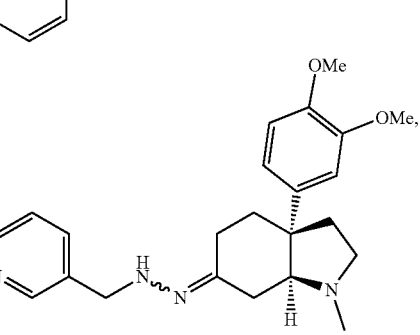

129
-continued
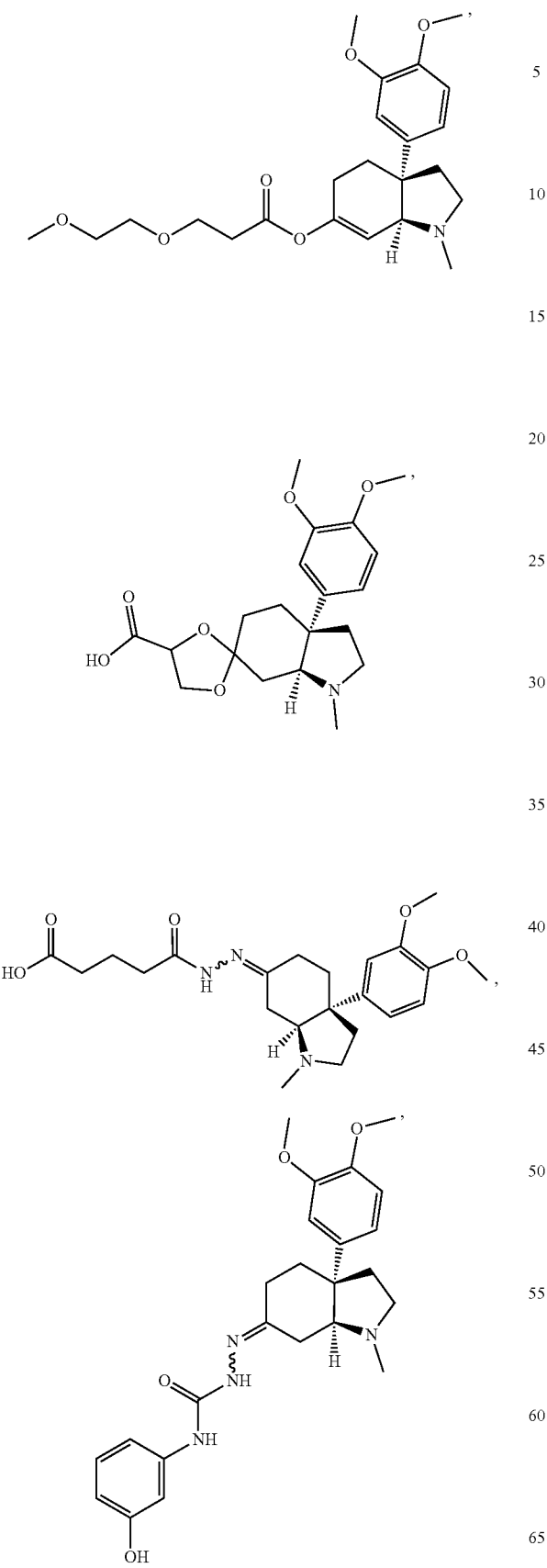
130
-continued
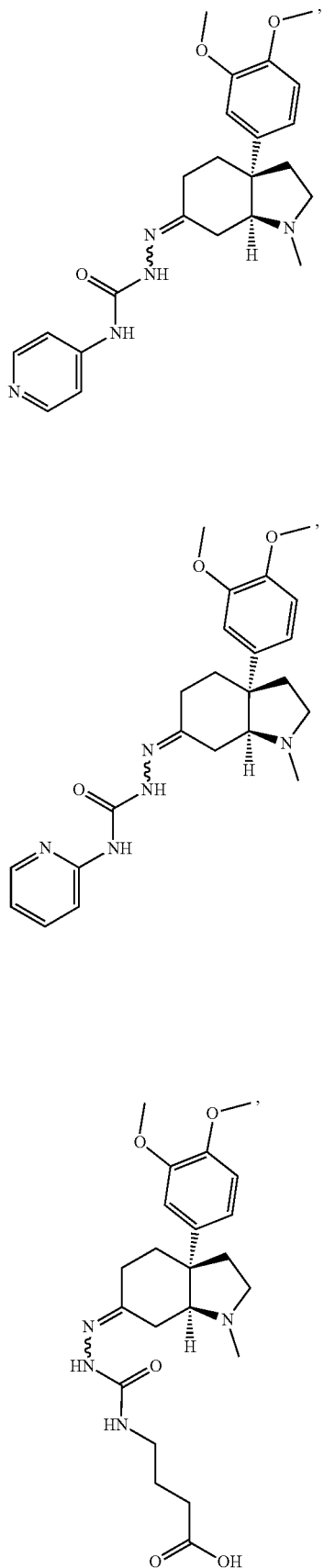

131
-continued
132
-continued
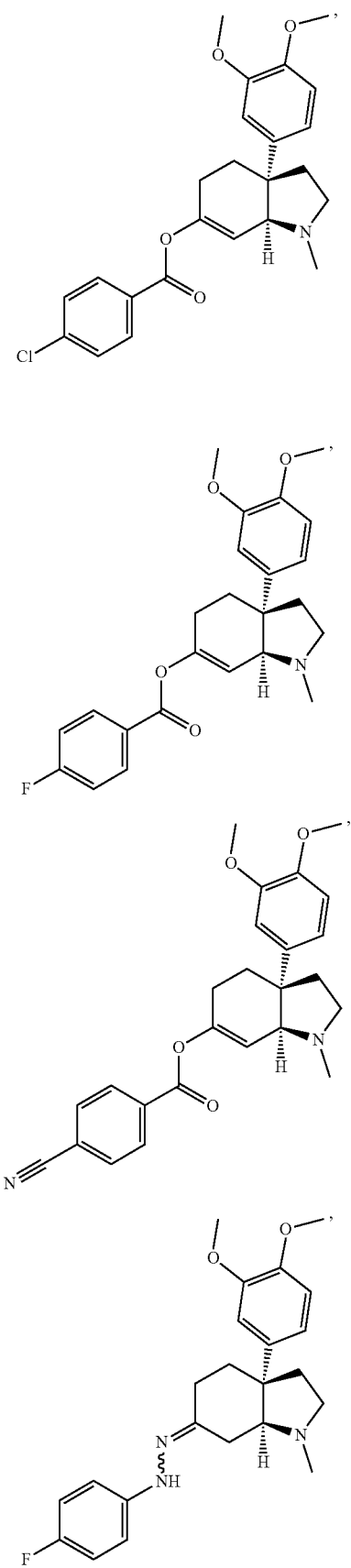
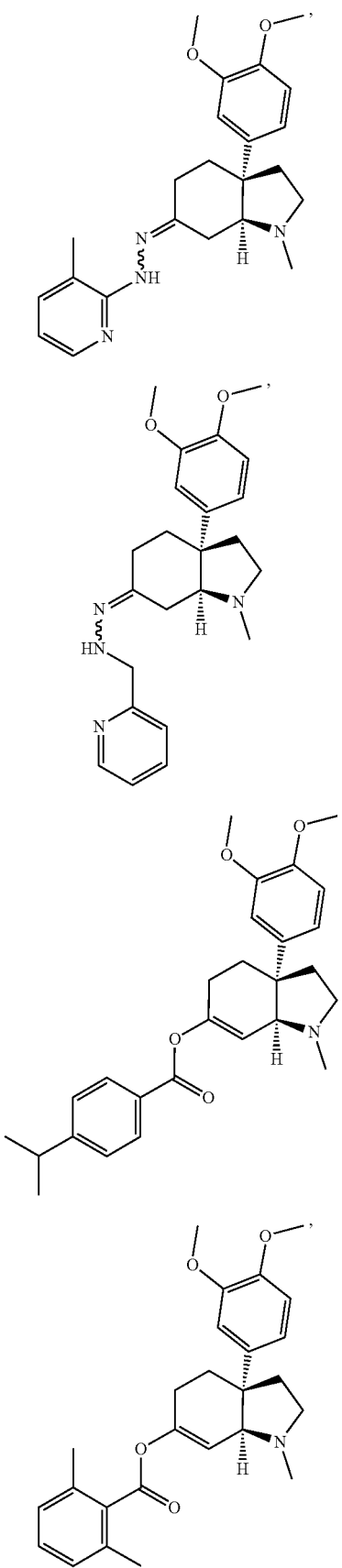

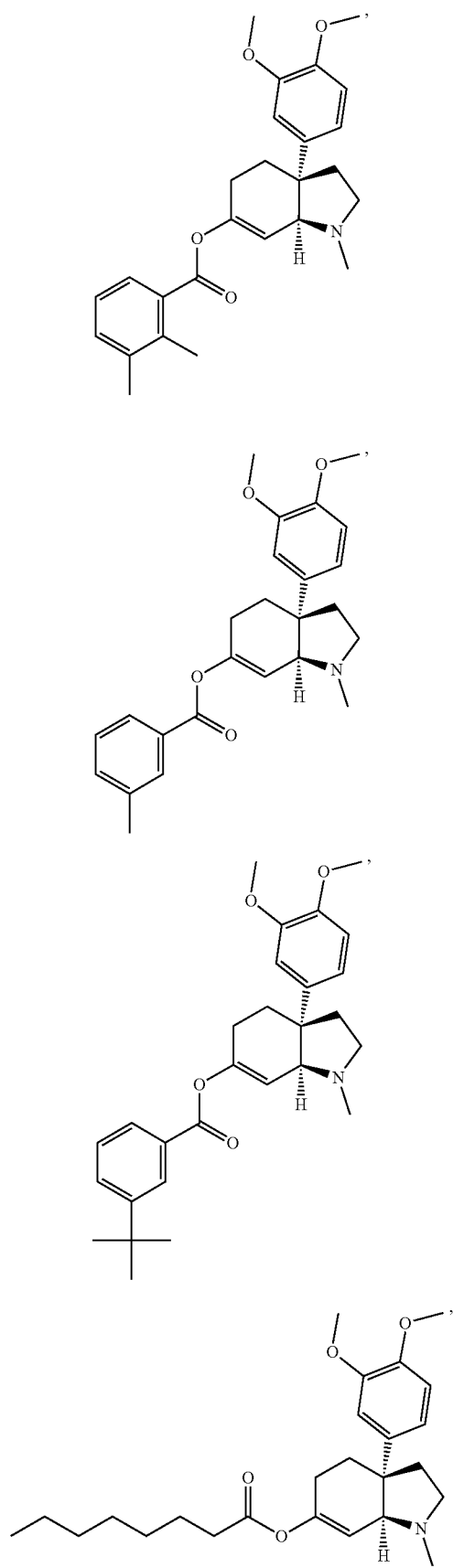

135
-continued
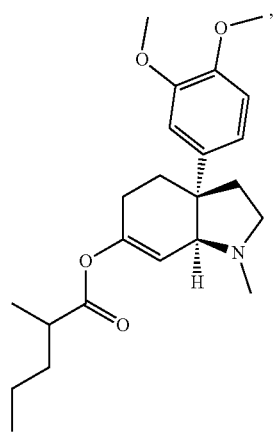
136
-continued
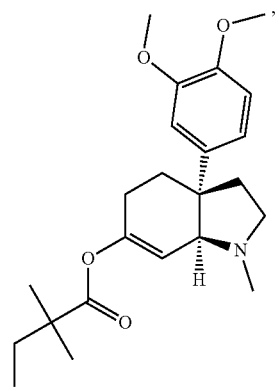
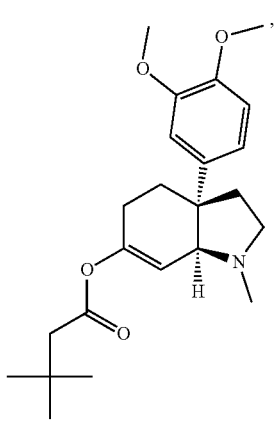

-continued
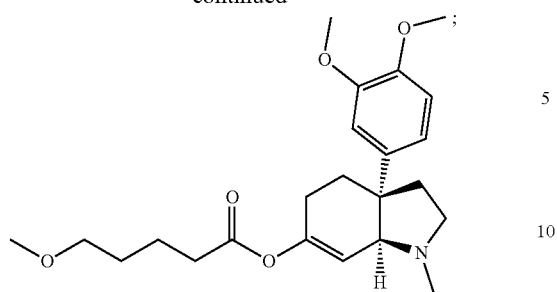
or a pharmaceutically acceptable salt thereof; and the compound has the absolute stereochemistry shown.
In some embodiments, the compound is selected from
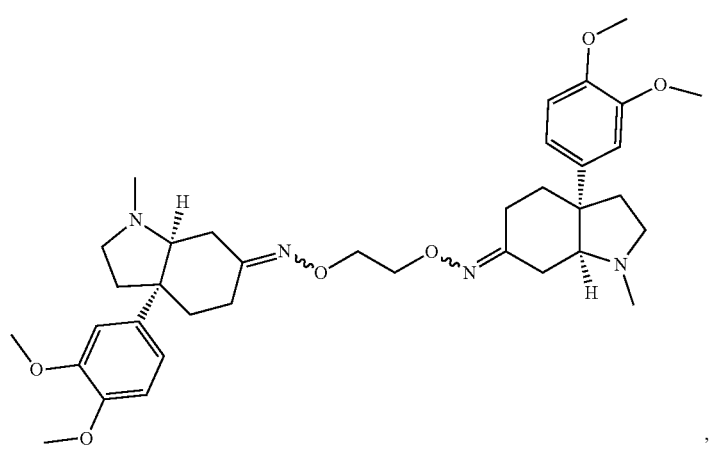
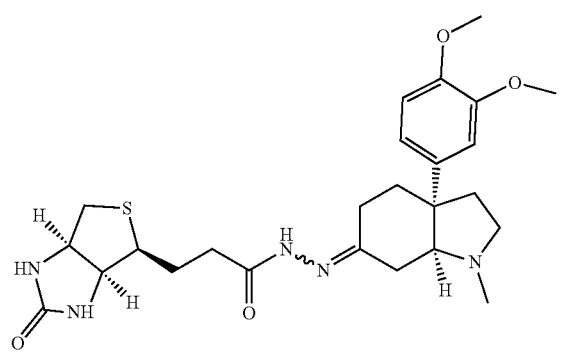
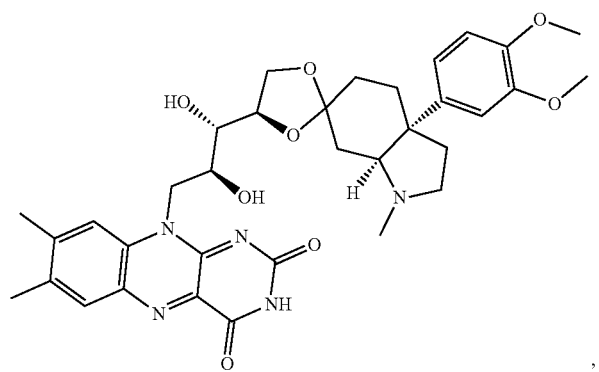

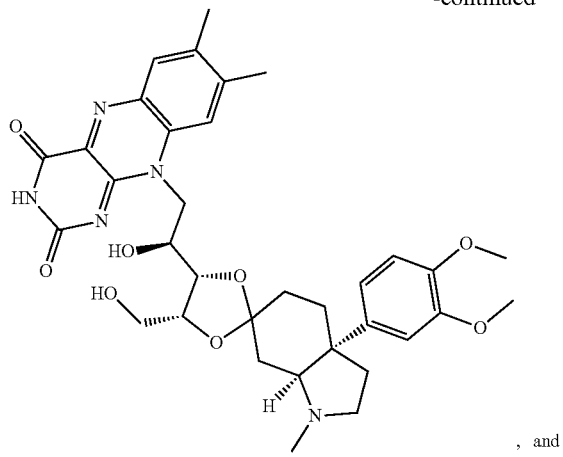

, and

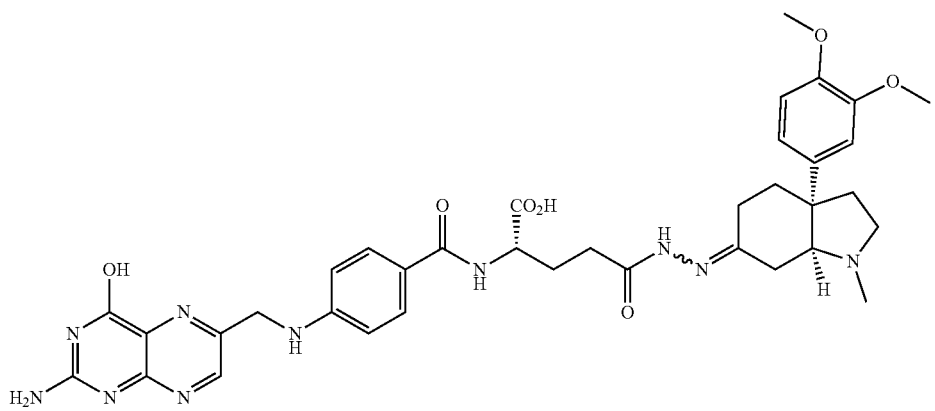

In certain embodiments, the compounds described herein convert to mesembrine as measured by HPLC after 24 hours at a pH of 2 (0.01 M HCl) and a temperature of 37° C. in the Hydrolysis Assay of Example A1.

In certain embodiments, the compounds described herein convert to mesembrine as measured by HPLC in the Hydrolysis Assay of Example A2 in SGF.

The present application relates to compounds that can be converted to mesembrine under conditions encountered within the body, such as upon oral administration. In some embodiments, compounds are provided that hydrolyze to form mesembrine under acidic conditions (e.g., pH 2) at 37° C. In addition, Applicant has discovered compounds useful for isolating stable forms of individual stereoisomers of mesembrine.

The invention is based in part on the discovery of compounds having useful and markedly different from naturally occurring mesembrine, but that can be converted to mesembrine under biologically relevant conditions. Certain compounds provided herein convert to mesembrine under physiologically relevant conditions, using the Hydrolysis Assay of Example A1. In some embodiments, other compounds provided herein can form mesembrine under biologically relevant acidic conditions. For example, in some embodiments, certain compounds provided herein convert to mesembrine at acidic pH and temperatures between room temperature and human body temperature (e.g., Compound 37 converted to mesembrine at acidic pH 2.0 in the Hydrolysis Assay at temperatures of 25 or 37° C., as provided in the data in Example A1). In some embodiments, certain compounds provided herein convert to mesembrine at acidic pH and temperatures above room temperature including at human body temperature (e.g., Compound 13 converted to mesembrine at acidic pH 2.0 in the Hydrolysis Assay at temperatures of 37 and 50° C. but not at 5° C., as provided in the data in Example A1). In contrast, the naturally occurring compound (–) mesembrine (herein "Compound 001") did not further hydrolyze under a variety of biologically relevant conditions ranging from acidic (pH 2.0 in 0.01 M HCl) to neutral buffered conditions (pH 7.4 in 20 mM PBS) from room temperature (25° C.) to elevated temperature (40° C.) (in the Hydrolysis Assay described in Example A1).

In some embodiments, compounds are provided that permit the separation and isolation of stable form of the (+) form of mesembrine separated from the naturally occurring (–) form of mesembrine. In certain embodiments, this disclosure provides compositions comprising (+) mesembrine,

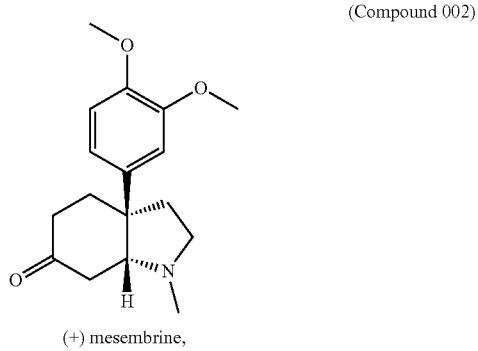 [SMILES: COc1ccc([C@]23CCC(=O)C[C@H]2N(C)CC3)cc1OC]

(Compound 002)

(+) mesembrine, or a pharmaceutically acceptable salt thereof.

In some embodiments, (+) mesembrine compositions can comprise stabilized (+) mesembrine in the absence of levels of (−) mesembrine detectable by HPLC. In some embodiments, mesembrine compositions comprise enriched in (+) mesembrine compared to (−) mesembrine. Scheme 1 provides a method of preparing mesembrenone, followed by conversion to mesembrine.

The Examples provide non-limiting examples of reactions of racemic- and (+) and (−) mesembrine with various reactive compounds to obtain compounds disclosed herein. In some embodiments, compositions can comprise greater than 15% (w/w) mesembrine of the total alkaloid content in composition.

In certain embodiments, the present disclosure provides a method of treating a mental disorder, comprising administering to the subject a compound of the present disclosure.

Numerous embodiments are further provided that can be applied to any aspect of the present invention described herein.

DETAILED DESCRIPTION

Figure 1:
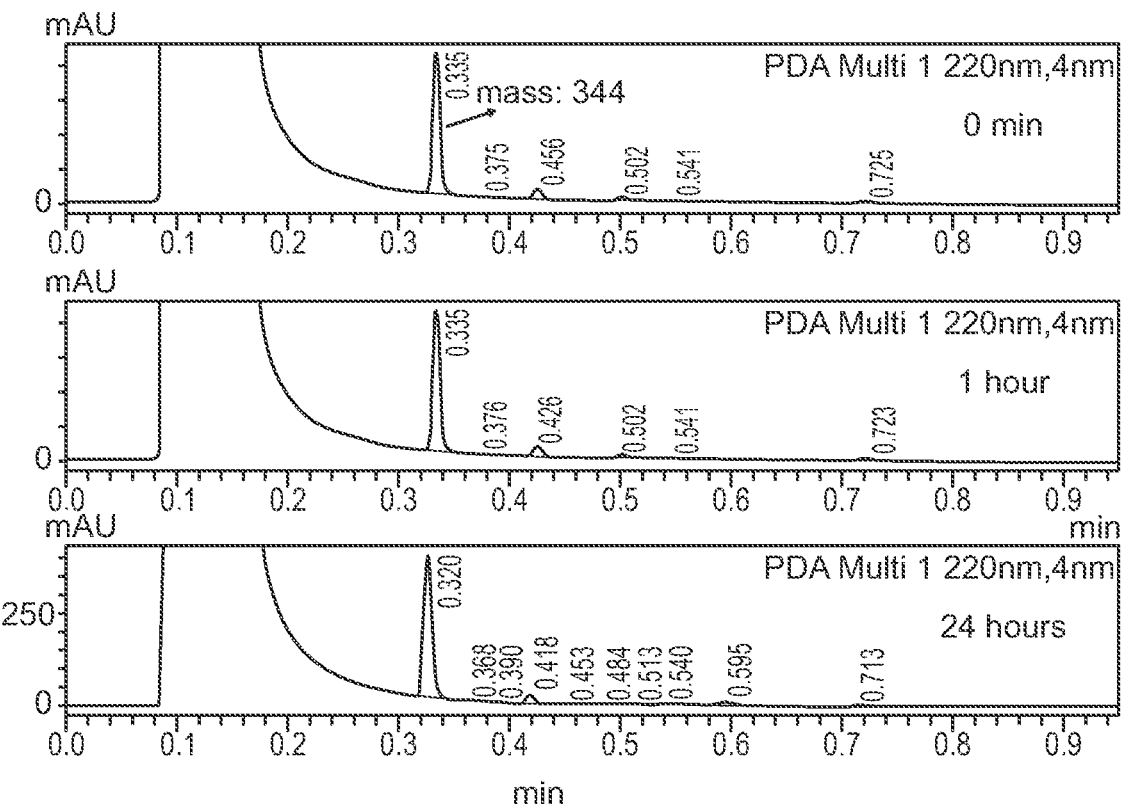
FIG. 1 is a series of LCMS graphs obtained from compound 013 in the acid hydrolysis assay of Example A1.

The present invention is based, at least in part, on mesembrine and analogs thereof. Although (−) mesembrine is bioactive with certain desirable pharmacologic effects, certain other properties are less than ideal for use as a therapeutic. For example, the pharmacokinetics described for (−) mesembrine show rapid metabolism and excretion, which an undesirably low half-life in plasma of less than 2 hours. To take advantage of the desirable properties of (−) mesembrine and improve upon absorption, distribution, metabolism and excretion (ADME) that impact pharmacokinetics (PK), compounds have been developed and described here. At least some of the compounds have the shared properties characterized by one or more of the following: (1) they have a function group manipulation at, or related to, the ketone; (2) the modification to the structure impacts physiochemical properties; (3) they break down in the presence of aqueous acid to form mesembrine (e.g., (−) mesembrine); (4) they are intended to tune the ADME/PK of mesembrine (e.g., (−) mesembrine) in vivo. An in vitro aqueous hydrolysis assay to that may predict parameters associated with absorption and pharmacokinetics in vivo is also described here. As described herein, mesembrine (001) has a rapid onset but short duration of action in vivo. In combination with its poor bioavailability, the short duration of action warrants development of prodrugs forms that address these deficiencies. In certain embodiments, compounds described herein address these deficiencies by hydrolyzing to mesembrine in vivo. Indeed, brain time-concentration plots after administration of prodrugs described herein demonstrate slow but continual release of mesembrine in vivo. In certain embodiments, these effects may be due to the increased lipophilicity and steric bulk of the prodrug.

Exemplarly Compounds of the Invention

In certain embodiments, compounds described herein can form mesembrine (e.g., (−) mesembrine) under biologically relevant conditions. For example, in some embodiments, compounds of disclosed herein (e.g., compounds of Formula (I)) can hydrolyze in highly acidic environments (e.g., pH of about 2 at room temperature or more comparably stringent conditions typically encountered within the alimentary canal of a mammal) at a rate that is advantageous for providing a desired bioabsorption (% F) following oral administration by a mammal and leading to a desired pharmacokinetic profile of mesembrine (e.g., (–) mesembrine) to the mammal.

In some embodiments, a compound according to the present disclosure is a compound of formula (I):

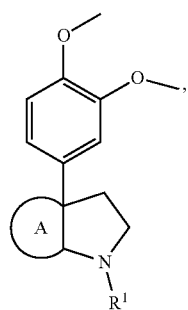

(I)

or a pharmaceutically acceptable salt thereof, wherein
$R^1$ is or $C_1$-$C_7$ alkyl or H; and
ring A is

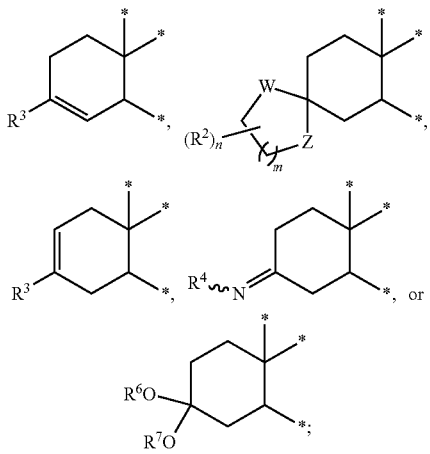

wherein * denotes the attachment points of ring A to the compound of formula (I), and wherein
each of W and Z is independently O, NH, or S;
each $R^2$ is independently $C_1$-$C_3$ alkyl, $C_2$-$C_6$ alkenyl, —COOH, —CONH$_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by —OH, $C_1$-$C_3$ alkyl, or $C_1$-$C_3$ alkanol;
m is 1 or 2;
n is 0, 1, 2, or 3;
$R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, phenoxy or —O(CH$_2$)$_p$ OCH$_3$;
p is 2, 3, or 4;
$R^4$ is —OR$^5$ or —N(R$^5$)$_2$;
each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)$C_1$-$C_6$ alkyl, or —C(O)O$C_1$-$C_6$ alkyl; and
each of $R^6$ and $R^7$ is independently $C_1$-$C_3$ alkyl.

In some embodiments, a compound according to the present disclosure is of formula (I):

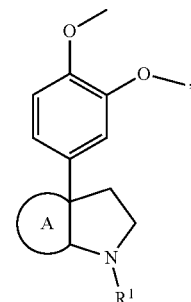

(I)

or a pharmaceutically acceptable salt thereof, wherein
$R^1$ is H or $C_1$-$C_7$ alkyl; and
ring A is

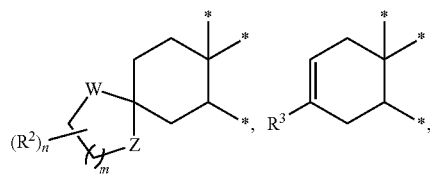

-continued

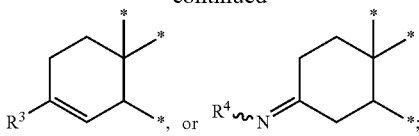

wherein * denotes the attachment points of ring A to the compound of formula (I), and wherein
  each of W and Z is independently O, NH, or S;
  each $R^2$ is independently $C_1$-$C_3$ alkyl, —COOH, —CONH$_2$, phenyl, 5- to 7-membered heterocyclyl, or 5- to 7-membered heteroaryl, wherein each hydrogen atom in phenyl, 5- to 7-membered heterocyclyl and 5- to 7-membered heteroaryl is optionally substituted by —OH, $C_1$-$C_3$ alkyl, $C_1$-$C_3$ alkoxy, $C_1$-$C_3$ alkanol, or —NO$_2$, or two $R^2$s on a single carbon atom combine to form =O; or two adjacent $R^2$s together with the carbon atoms to which they are attached combine to form 5- to 7-membered heteroaryl, wherein each hydrogen atom in 5- to 7-membered heteroaryl is optionally substituted by —OH, $C_1$-$C_3$ alkyl, or $C_1$-$C_3$ alkanol;
  m is 1 or 2;
  n is 0, 1, or 2;
  $R^3$ is —OSi($C_1$-$C_6$ alkyl)$_3$ or —OC(O)$C_1$-$C_6$ alkyl; and
  $R^4$ is OH, $C_1$-$C_6$ alkoxy, or —NHC(O)-5- to 7-membered heteroaryl, wherein each hydrogen atom in 5- to 7-membered heteroaryl is optionally substituted by —OH, $C_1$-$C_3$ alkyl, or $C_1$-$C_3$ alkanol.

In some embodiments, a compound according to the present disclosure is of formula (I):

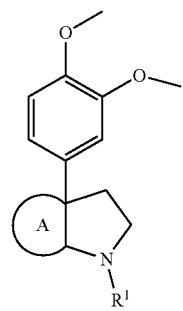

(I)

or a pharmaceutically acceptable salt thereof, wherein
  $R^1$ is H or $C_1$-$C_7$ alkyl; and
  ring A is

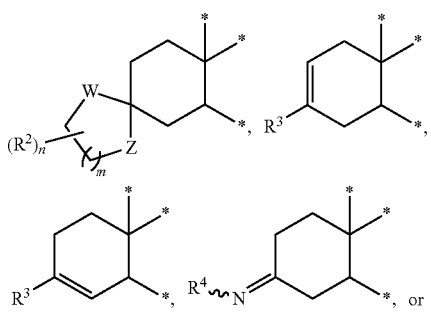

-continued wherein * denotes the attachment points of ring A to the compound of formula (I), and wherein
  each of W and Z is independently O, NH, or S;
  each $R^2$ is independently $C_1$-$C_3$ alkyl, $C_2$-$C_6$ alkenyl, —COOH, —CONH$_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by —OH, $C_1$-$C_3$ alkyl, or $C_1$-$C_3$ alkanol;
  m is 1 or 2;
  n is 0, 1, or 2;
  $R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, or phenoxy;
  $R^4$ is —OR$^5$ or —N(R$^5$)$_2$;
  each R$^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)$C_1$-$C_6$ alkyl, or —C(O)O$C_1$-$C_6$ alkyl; and
  each of R$^6$ and R$^7$ is independently $C_1$-$C_3$ alkyl.

In some embodiments, the compound is of the compound is of formula (I-1):

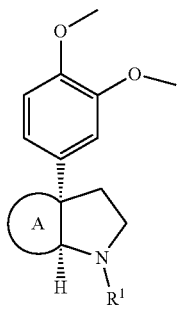

(I-1)

or a pharmaceutically acceptable salt thereof, wherein
$R^1$ is $C_1$-$C_7$ alkyl or H; and
ring A is

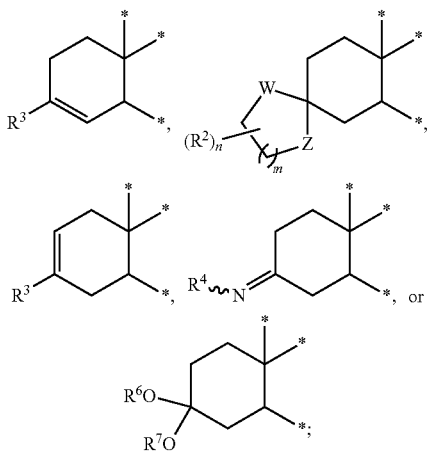

wherein * denotes the attachment points of ring A to the compound of formula (I), and wherein
each of W and Z is independently O, NH, or S;
each $R^2$ is independently $C_1$-$C_3$ alkyl, $C_2$-$C_6$ alkenyl, —COOH, —CONH$_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by —OH, $C_1$-$C_3$ alkyl, or $C_1$-$C_3$ alkanol;
m is 1 or 2;
n is 0, 1, 2, or 3;
$R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, or phenoxy or —O(CH$_2$)$_p$OCH$_3$;
p is 2, 3, or 4;
$R^4$ is —OR$^5$ or —N(R$^5$)$_2$;
each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, C(O)N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)$C_1$-$C_6$ alkyl, or —C(O)O$C_1$-$C_6$ alkyl;
each of $R^6$ and $R^7$ is independently $C_1$-$C_3$ alkyl; and
the compound of formula (I-1) has the absolute stereochemistry shown.

In certain embodiments, the compound is of formula (I-1):

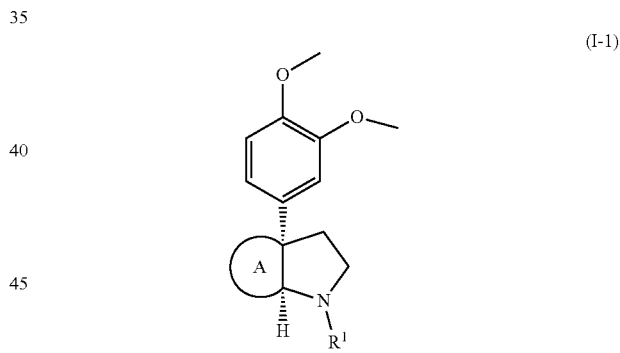

(I-1)

or a pharmaceutically acceptable salt thereof, wherein
$R^1$ is H or $C_1$-$C_7$ alkyl; and
ring A is

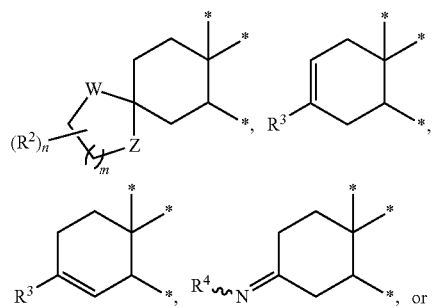

-continued

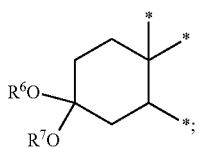

wherein * denotes the attachment points of ring A to the compound of formula (I), and wherein each of W and Z is independently O, NH, or S;

each $R^2$ is independently $C_1$-$C_3$ alkyl, $C_2$-$C_6$ alkenyl, —COOH, —CONH$_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by —OH, $C_1$-$C_3$ alkyl, or $C_1$-$C_3$ alkanol, m is 1 or 2, n is 0, 1, or 2, $R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, or phenoxy;

$R^4$ is —OR$^5$ or —N(R$^5$)$_2$;

each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —C(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)$C_1$-$C_6$ alkyl, or —C(O)OC$_1$-$C_6$ alkyl; and each of $R^6$ and $R^7$ is independently $C_1$-$C_3$ alkyl.

In certain embodiments, the compound is of formula (I-1):

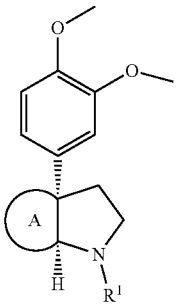

(I-1)

or a pharmaceutically acceptable salt thereof, wherein $R^1$ is H or $C_1$-$C_7$ alkyl; and ring A is

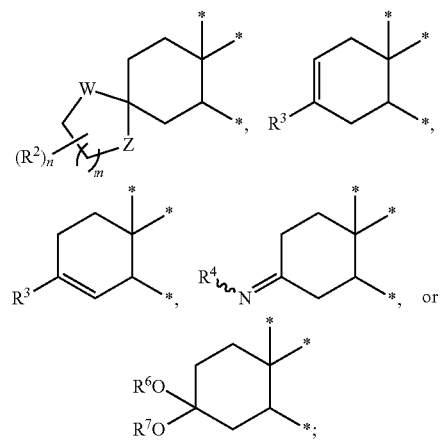

wherein * denotes the attachment points of ring A to the compound of formula (I), and wherein each of W and Z is independently O, NH, or S;

each $R^2$ is independently $C_1$-$C_3$ alkyl, $C_2$-$C_6$ alkenyl, —COOH, —CONH$_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by —OH, $C_1$-$C_3$ alkyl, or $C_1$-$C_3$ alkanol, m is 1 or 2, n is 0, 1, or 2, $R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, or phenoxy;

$R^4$ is $-OR^5$ or $-N(R^5)_2$;

each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, $-C(O)$-5- to 7-membered heteroaryl, $-C(O)-C_1$-$C_8$ alkyl, $-C(O)-C_3$-$C_{10}$ cycloalkyl, $-C(O)$-phenyl, $-C(O)N(H)$-phenyl, $-C(O)N(H)$-5- to 7-membered heteroaryl, $-C(O)N(H)-C_1$-$C_6$ alkyl, $-C(O)C(O)OH$, or $-CONH_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, $-C(O)$-5- to 7-membered heteroaryl, $-C(O)-C_1$-$C_8$ alkyl, $-C(O)-C_3$-$C_{10}$ cycloalkyl, $-C(O)$-phenyl, $-C(O)N(H)$-phenyl, $-C(O)N(H)$-5- to 7-membered heteroaryl, and $-C(O)N(H)-C_1$-$C_6$ alkyl is optionally substituted by halogen, OH, $C_1$-$C_3$ alkyl, $C_3$-$C_{10}$ cycloalkyl optionally substituted by $-COOH$, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, $-COOH$, $-S(O)_2CH_3$, $-C(O)C_1$-$C_6$ alkyl, or $-C(O)OC_1$-$C_6$ alkyl; and each of $R^6$ and $R^7$ is independently $C_1$-$C_3$ alkyl; and the compound of formula (I-1) has the absolute stereochemistry shown.

In some embodiments, ring A is

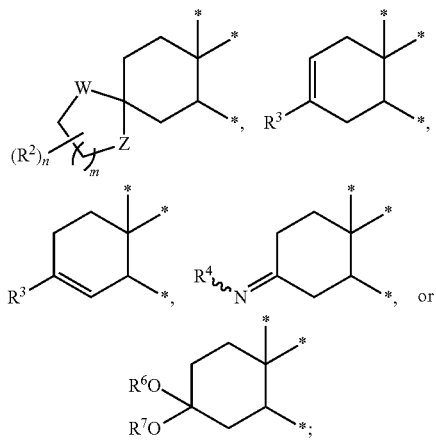

wherein * denotes the attachment points of ring A to the compound of formula (I).

In some embodiments, each of W and Z is independently O, NH, or S. In some embodiments, W is O. In some embodiments, W is NH. In some embodiments, W is S.

In some embodiments, each $R^2$ is independently $C_1$-$C_3$ alkyl, $C_2$-$C_6$ alkenyl, $-COOH$, $-CONH_2$, $C_3$-$C_{10}$ cycloalkyl, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by $-OH$, $C_1$-$C_3$ alkyl, $C_1$-$C_3$ alkoxy, aryloxy, $C_1$-$C_3$ alkanol, or $-NO_2$, wherein each hydrogen atom in $C_1$-$C_3$ alkoxy and aryloxy is optionally substituted by $C_1$-$C_3$ alkoxy or phenyl. In some embodiments, each $R^2$ is independently $C_1$-$C_3$ alkyl, $C_2$-$C_6$ alkenyl, $-COOH$, $-CONH_2$, phenyl, 5- to 7-membered heterocyclyl, or 5- to 7-membered heteroaryl. In some embodiments, each hydrogen atom in $C_1$-$C_3$ alkyl, $C_2$-$C_6$ alkenyl, phenyl, 5- to 7-membered heterocyclyl and 5- to 7-membered heteroaryl is optionally substituted by $-OH$, $C_1$-$C_3$ alkyl, $C_1$-$C_3$ alkoxy, $C_1$-$C_3$ alkanol, or $-NO_2$.

In some embodiments, $R^2$ is $-COOH$, $-CONH_2$, phenyl, 5- to 7-membered heterocyclyl, or 5- to 7-membered heteroaryl, wherein each hydrogen atom in phenyl, 5- to 7-membered heterocyclyl and 5- to 7-membered heteroaryl is optionally substituted by $-OH$, $C_1$-$C_3$ alkyl, $C_1$-$C_3$ alkoxy, aryloxy, $C_1$-$C_3$ alkanol, or $-NO_2$, wherein each hydrogen atom in $C_1$-$C_3$ alkoxy and aryloxy is optionally substituted by $C_1$-$C_3$ alkoxy or phenyl. In some embodiments, $R^2$ is phenyl, wherein each hydrogen atom in phenyl is optionally substituted by $-OH$, $C_1$-$C_3$ alkyl, $C_1$-$C_3$ alkoxy, or $-NO_2$. In some embodiments, $R^2$ is 5- to 7-membered heterocyclyl or 5- to 7-membered heteroaryl, wherein each hydrogen atom in 5- to 7-membered heterocyclyl and 5- to 7-membered heteroaryl is optionally substituted by $-OH$, $C_1$-$C_3$ alkyl, $C_1$-$C_3$ alkoxy, $C_1$-$C_3$ alkanol, or $-NO_2$. In some embodiments, $R^2$ is pyridyl. In some embodiments, $R^2$ is

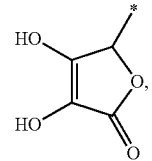

wherein * denotes the point of attachment of $R^2$ the compound. In some embodiments, $R^2$ is $-COOH$ or $-CONH_2$.

In some embodiments, two $R^2$s on a single carbon atom combine to form $=O$.

In some embodiments, two instances of $R^2$ on a single carbon atom combine to form $=O$; or two adjacent $R^2$s together with the carbon atoms to which they are attached combine to form 5- to 7-membered heteroaryl or phenyl, wherein each hydrogen atom in 5- to 7-membered heteroaryl or phenyl is optionally substituted by $-OH$, $C_1$-$C_3$ alkyl, or $C_1$-$C_3$ alkanol, In some embodiments, two adjacent $R^2$s together with the carbon atoms to which they are attached combine to form 5- to 7-membered heteroaryl, wherein each hydrogen atom in 5- to 7-membered heteroaryl is optionally substituted by $-OH$, $C_1$-$C_3$ alkyl, or $C_1$-$C_3$ alkanol. In some embodiments, the two $R^2$s together with the carbon atoms to which they are attached combine to form pyridyl, wherein each hydrogen atom in pyridyl is optionally substituted by $-OH$, $C_1$-$C_3$ alkyl, or $C_1$-$C_3$ alkanol.

In some embodiments, m is 1 or 2.

In some n is 0, 1, or 2. In some embodiments, n is 0. In some embodiments, n is 1. In some embodiments, n is 2.

In some n is 0, 1, 2, or 3. In some embodiments, n is 0. In some embodiments, n is 1. In some embodiments, n is 2. In some embodiments, n is 3.

In some embodiments, $R^3$ is $-OSi(C_1$-$C_6$ alkyl$)_3$ or $-OC(O)C_1$-$C_6$ alkyl. In some embodiments, $R^3$ is $-OSi(C_1$-$C_6$ alkyl$)_3$. In some embodiments, $R^3$ is $-OC(O)C_1$-$C_6$ alkyl (e.g., methyl).

In some embodiments, $R^3$ is $-OSi(C_1$-$C_6$ alkyl$)_3$, $-OC(O)C_1$-$C_6$ alkyl, $-OC(O)C_2$-$C_6$ alkenyl, $-OC(O)C_3$-$C_{10}$ cycloalkyl, $-OC(O)$phenyl, $-OC(O)$-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, $-N(C_1$-$C_3$ alkyl$)_2$, $C_1$-$C_3$ haloalkyl, cyano, phenyl, or phenoxy. In some embodiments, of $R^3$ is $-OC(O)C_1$-$C_6$ alkyl and the $C_1$-$C_6$ alkyl is methyl, ethyl, butyl, isobutyl, tertbutyl, or 2-methylbutyl, wherein each hydrogen atom in methyl, ethyl, butyl, isobutyl, tertbutyl, and 2-methylbutyl is optionally substituted by halogen or phenyl. In some embodiments, $R^3$ is —OC(O)$C_2$-$C_6$ alkenyl (e.g., isopropenyl or butenyl). In some embodiments, is —OC(O)$C_3$-$C_{10}$ cycloalkyl (e.g., cyclopropyl or cyclohexyl). In some embodiments, $R^3$ is —OC(O)phenyl, wherein each hydrogen atom in phenyl is optionally substituted by methyl, isopropyl, tertbutyl, chloro, fluoro, $CF_3$, —$CHF_2$, cyano, —$N(CH_3)_2$, methoxy, or nitro. In some embodiments, —OC(O)-5- to 7-membered heteroaryl, which may be optionally substituted (e.g., pyridyl or thiophenyl, wherein each hydrogen atom in pyridyl or thiophenyl is optionally substituted by methyl).

In some embodiments, $R^3$ is —OC(O)$C_1$-$C_6$ alkyl and the $C_1$-$C_6$ alkyl is ethyl, propyl, butyl, pentyl, or hexyl, wherein each hydrogen atom in methyl, ethyl, propyl, butyl, pentyl, and hexyl is optionally substituted by methyl, ethyl, methoxy or —O(CH$_2$)$_p$OCH$_3$; and p is 2, 3, or 4. In some embodiments, $R^3$ is

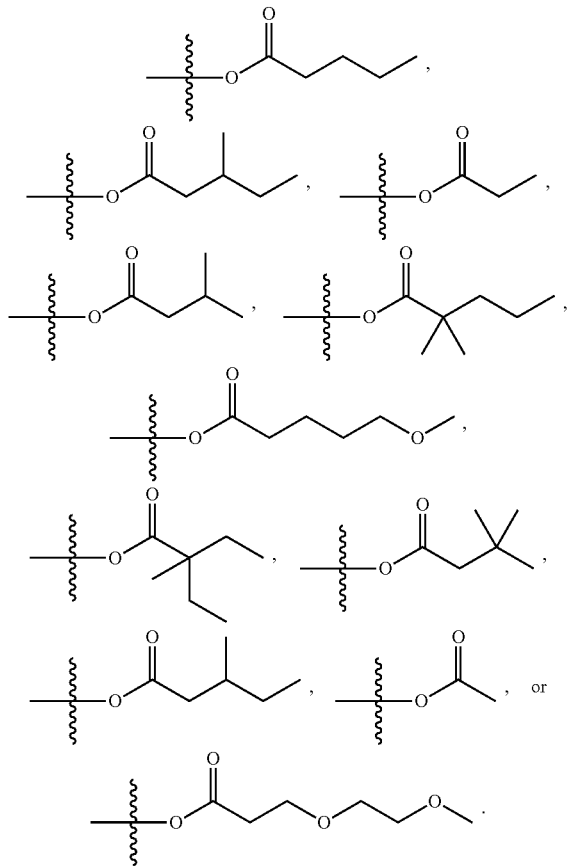

In some embodiments, $R^3$ is —OC(O)$C_3$-$C_{10}$ cycloalkyl (e.g., cyclopropyl or cyclohexyl). In some embodiments, the $C_3$-$C_{10}$ cycloalkyl is cyclohexyl.

In some embodiments, $R^3$ is —OC(O)phenyl, wherein each hydrogen atom in phenyl is optionally substituted by methyl, isopropyl, tertbutyl, chloro, fluoro, $CF_3$, —$CHF_2$, cyano, —$N(CH_3)_2$, -methoxy, or nitro. In some embodiments, $R^3$ is —OC(O)phenyl, wherein each hydrogen atom in phenyl is optionally substituted by methyl. In some embodiments, $R^3$ is —OC(O)phenyl, wherein one hydrogen atom in phenyl is substituted by methyl.

In some embodiments, $R^3$ is —OC(O)-5- to 7-membered heteroaryl, for example pyridyl or thiophenyl, wherein each hydrogen atom in pyridyl or thiophenyl is optionally substituted by methyl. In some embodiments, the 5- to 7-membered heteroaryl is pyridyl wherein each hydrogen atom in pyridyl is optionally substituted by methyl. In some embodiments, the 5- to 7-membered heteroaryl is unsubstituted pyridyl.

In some embodiments, $R^3$ is —OC(O)$C_1$-$C_6$ alkyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_3$-$C_{10}$ cycloalkyl, phenyl, and 5- to 7-membered heteroaryl is optionally substituted by $C_1$-$C_6$ alkyl, $C_1$-$C_3$ alkoxy, or —O(CH$_2$)$_p$OCH$_3$; and p is 2, 3, or 4. In some embodiments, the $C_1$-$C_6$ alkyl is unsubstituted or is substituted by methoxy. In some embodiments, the $C_3$-$C_{10}$ cycloalkyl is unsubstituted cyclohexyl. In some embodiments, phenyl is monosubstituted, for example by methyl. In some embodiments, the 5- to 7-membered heteroaryl is unsubstituted pyridyl.

In some embodiments, $R^3$ is —OC(O)$C_1$-$C_6$ alkyl, —OC(O)$C_2$-$C_6$ alkenyl, —OC(O)$C_3$-$C_{10}$ cycloalkyl, —OC(O)phenyl, or —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, or —O(CH$_2$)$_p$OCH$_3$; and p is 2, 3, or 4.

In some embodiments, $R^4$ is OH, $C_1$-$C_6$ alkoxy, or —NHC(O)-5- to 7-membered heteroaryl. In some embodiments, each hydrogen atom in 5- to 7-membered heteroaryl is optionally substituted by —OH, $C_1$-$C_3$ alkyl, or $C_1$-$C_3$ alkanol.

In some embodiments, $R^4$ is —$OR^5$ or —$N(R^5)_2$.

In some embodiments, $R^4$ is $OR^5$ wherein $R^5$ is H, $C_1$-$C_6$ alkyl, $C_3$-$C_{10}$ cycloalkyl, $C_3$-$C_6$ heterocycloalkyl or phenyl, wherein each hydrogen atom in $C_1$-$C_6$ alkyl, $C_3$-$C_6$ heterocycloalkyl and phenyl is optionally substituted with —OH, $C_1$-$C_6$ alkoxy, 5- to 7-membered heteroaryl, phenyl, phenoxy, $C_3$-$C_6$ cycloalkyl, —C(O)O$C_1$-$C_6$ alkyl, $C_3$-$C_{10}$ cycloalkyl, or —COOH.

In some embodiments, $R^4$ is —$N(R^5)_2$ wherein each $R^5$ is independently H (preferably one is H), —$C_1$-$C_6$ alkyl, —C(O)-5- to 7-membered heteroaryl, —C(O)-phenyl, phenyl, —C(O)—$C_1$-$C_3$ alkyl, —(O)—$C_3$-$C_{10}$ cycloalkyl, —C(O)N(H)-phenyl, —C(O)N(H)-pyridyl, —C(O)COOH, or —CONH$_2$, wherein each hydrogen atom in —$C_1$-$C_6$ alkyl, —C(O)-5- to 7-membered heteroaryl, —C(O)-phenyl, phenyl, —(O)—$C_1$-$C_3$ alkyl, and —C(O)N(H)-phenyl, is optionally substituted by halogen, aryloxy, carboxylate, phenyl, —S(O)$_2$CH$_3$, $C_1$-$C_3$ alkoxy, $C_3$-$C_6$ cycloalkyl optionally substituted by carboxylate, or 5- to 7-membered heterocyclyl optionally substituted by methyl.

In some embodiments, $R^4$ is —$N(R^5)_2$ and one $R^5$ is H and the other $R^5$ is —C(O)N(H)-phenyl optionally substituted by —COOH.

In some embodiments, each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —(O)—$C_1$-$C_8$ alkyl, —(O)—$C_3$-$C_{10}$ cycloalkyl, —C(O)-phenyl, —C(O)N(H)-phenyl, —C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —(O)—$C_1$-$C_8$ alkyl, —(O)—$C_3$-$C_{10}$ cycloalkyl, —C(O)-phenyl, —C(O)N(H)-phenyl, —C(O)N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)C$_1$-C$_6$ alkyl, or —C(O)OC$_1$-C$_6$ alkyl. In some embodiments, each $R^5$ is H, $C_1$-$C_6$ alkyl, $C_3$-$C_6$ heterocycloalkyl, $C_1$-$C_6$ alkoxy, phenyl, —C(O)-5- to 7-membered heteroaryl, —C(O)—$C_1$-$C_3$ alkyl, —C(O)-phenyl, —C(O)N(H)-phenyl, or —CONH$_2$. In some embodiments, each hydrogen atom in $C_1$-$C_6$ alkyl, $C_1$-$C_6$ alkoxy phenyl, and 5- to 7-membered heteroaryl is optionally substituted by halogen, OH, $C_1$-$C_3$ alkyl, $C_3$-$C_6$ cycloalkyl, phenyl, 5- to 7-membered heteroaryl aryloxy (e.g., phenoxy), $C_1$-$C_6$ alkoxy, $C_1$-$C_3$ alkanol, —COOH, —C(O)C$_1$-C$_6$ alkyl, or —C(O)OC$_1$-C$_6$ alkyl. In some embodiments, $R^5$ is 5- to 10-membered heteroaryl

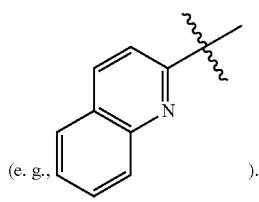

(e. g., ).

In some embodiments, each of $R^6$ and $R^7$ is independently $C_1$-$C_3$ alkyl, for example methyl.

In some embodiments, $R^1$ is H or $C_1$-$C_7$ alkyl. In some embodiments, $R^1$ is $C_1$-$C_3$ alkyl. In some embodiments, $R^1$ is methyl.

In some embodiments, the compound is of formula (V)

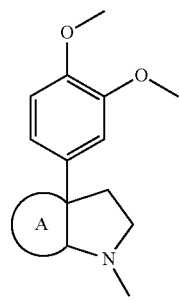

(V)

or a pharmaceutically acceptable salt thereof,
wherein
ring A is

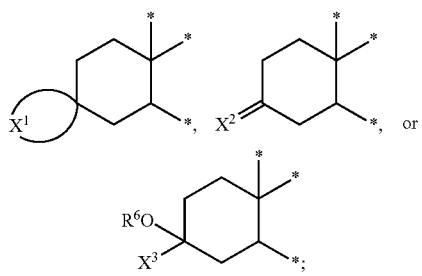

wherein * denotes the attachment points of ring A to the compound of formula (I), and wherein $R^6$ is $C_1$-$C_3$ alkyl;
$X^1$ is >L-R$^{14}$, wherein L is absent or a linker and where >denotes the two single bonds to the cyclohexane ring such that the ring containing $X^1$ forms a $C_3$-$C_6$ alkyl ring, which is optionally substituted by $C_1$-$C_3$ alkanol;
$X^2$ is =L-R$^{14}$, wherein L is absent or a linker;
$X^3$ is -L-R$^{14}$, wherein L is absent or a linker; and
$R^{14}$ comprises a generally recognized as safe (GRAS) compound.

In some embodiments, the compound is of formula (V-1)

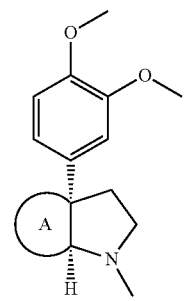

(V-1)

or a pharmaceutically acceptable salt thereof,
wherein
ring A is

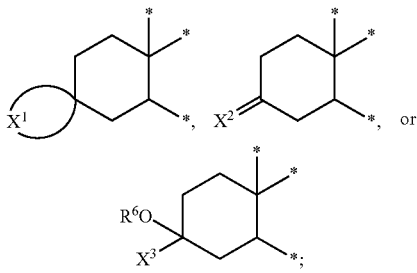

wherein * denotes the attachment points of ring A to the compound of formula (I), and wherein
$R^6$ is $C_1$-$C_3$ alkyl;
$X^1$ is >L-R$^{14}$, wherein L is absent or a linker and where >denotes the two single bonds to the cyclohexane ring such that the ring containing $X^1$ forms a $C_3$-$C_6$ alkyl ring, which is optionally substituted by $C_1$-$C_3$ alkanol;
$X^2$ is =L-R$^{14}$, wherein L is absent or a linker;
$X^3$ is -L-R$^{14}$, wherein L is absent or a linker;
$R^{14}$ comprises a generally recognized as safe (GRAS) compound; and
the compound of formula (V-1) has the absolute stereochemistry shown.

In some embodiments, the L in >L-R$^{14}$ can be absent such that the $R^{14}$ moiety forms two single bonds to the ring structure. In some embodiments, the L in >L- can cooperate with the carbon to which the two single bonds are attached to form a 3-7 membered heterocycle (e.g.,

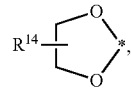

wherein the * denotes the carbon of the cyclohexyl ring).

In some embodiments, the L in =L-R$^{14}$ can be such that the R$^{14}$ moiety forms a double bond to the ring structure (e.g., =R$^{14}$). In some embodiments, =L-R$^{14}$ is =N—R$^{14}$, =N—NH—R$^{14}$, =N—O—R$^{14}$, =N—OC$_1$-C$_6$ alkyl-R$^{14}$, or =N—OC$_1$-C$_6$ alkyl-O—N=R$^{14}$.

In some embodiments, the L in -L-R$^{14}$ can be such that the R$^{14}$ moiety forms a single bond to the ring structure (e.g., —R$^{14}$). In some embodiments, -L-R$^{14}$ is —O—R$^{14}$.

In some embodiments, R$^{14}$ comprises a GRAS moiety. In some embodiments, R$^{14}$ is selected from

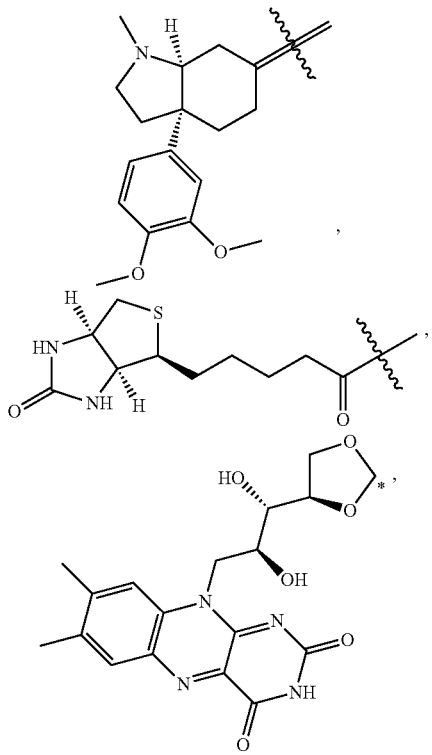

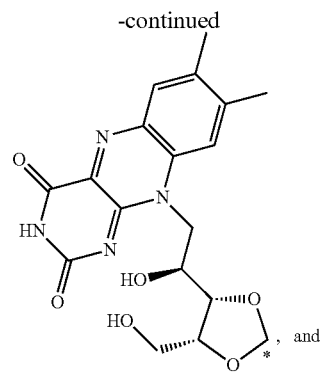, and

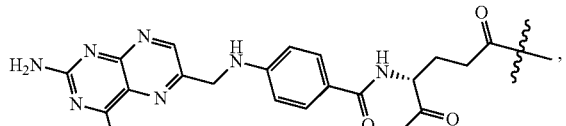

where the * denotes the carbon of the cyclohexyl ring when L is absent.

In some embodiments, the compounds of Formula (I) can be obtained by reacting mesembrine with a compound designated as Generally Recognized as Safe (GRAS) by the U.S. Food and Drug Administration (FDA) (G) under sections 201(s) and 409 of the U.S. federal Food, Drug and Cosmetics Act (FDCA), and under the corresponding implementing regulations in 21 CFR 170.3 and 21 CFR 170.30. For example, compounds that convert to mesembrine can be obtained by reaction of either compound with lactic acid, glycolic acid, ascorbic acid (vitamin C), and pyridoxine (vitamin B6) derivatives. Table 2 provides examples of compounds that can be reacted to obtain compounds of Formula (I) by the reaction: Compound M+Compound R→Compound C.

TABLE 2

| Reactant M | Reactant R | Product Compound C |
|---|---|---|

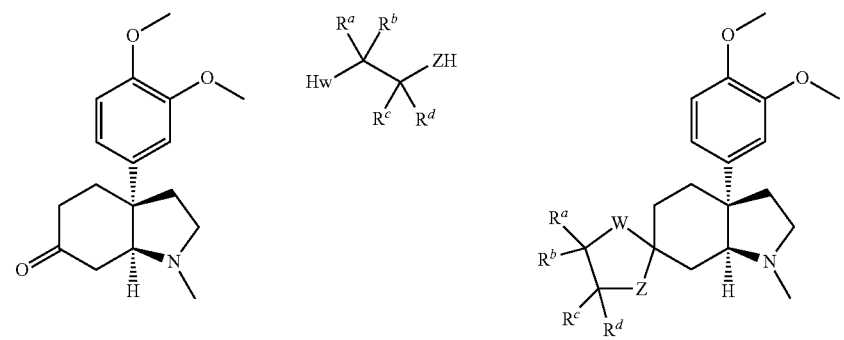

TABLE 2-continued
| Reactant M | Reactant R | Product Compound C |
|---|---|---|
| 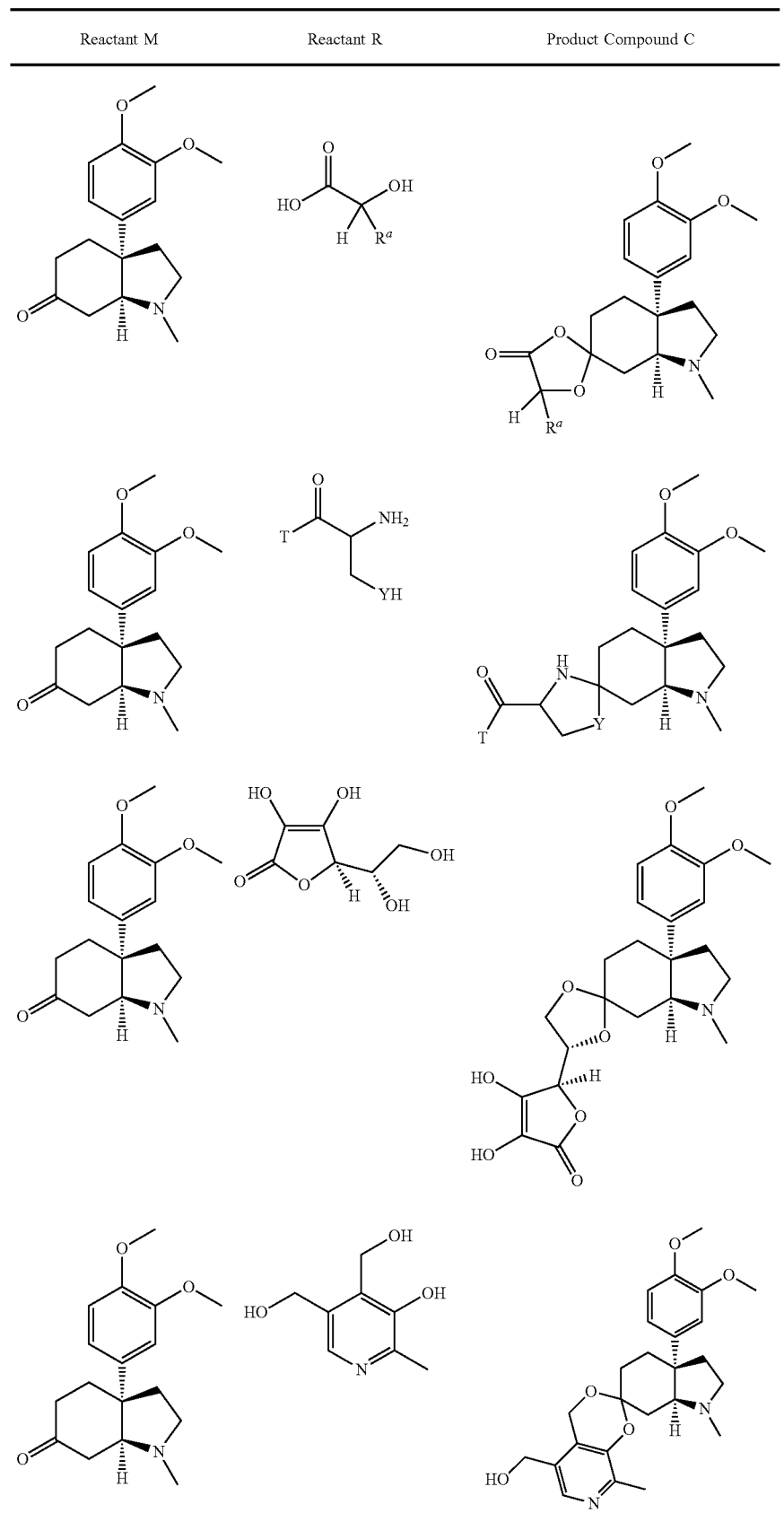 | | |

TABLE 2-continued

| Reactant M | Reactant R | Product Compound C |
|---|---|---|
| | $(R^8)_2O$ or $R^8$—X | |

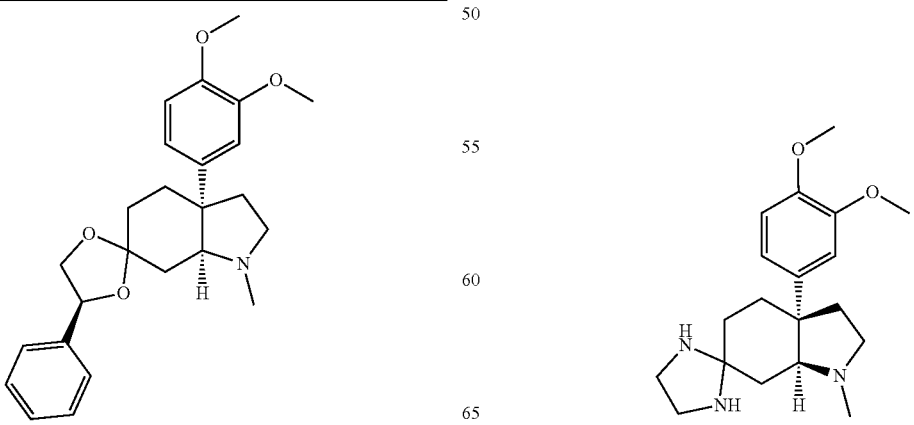

Unless otherwise indicated in the tables of compounds herein, the abbreviation RAC or rac indicates a racemic mixture, and DIAST indicates a specific diastereomer. In illustrative embodiments, although a compound may be depicted with ▲ or ⋯ bonds, such a depiction may be denoting relative stereochemistry based on elution peaks from a chiral separation.

Compounds of Formula (I) including compounds of Formula (IIa) can be prepared as described with respect to exemplary compounds in the examples below. In general, treatment of a ketone, such as mesembrine, with an appropriate diol or dithiane, and an acid catalyst, such as p-toluenesulfonic acid or methanesulfonic acid, in a solvent, such as toluene, at an elevated temperature is a method to prepare compounds of Formula (IIa).

TABLE 1

Exemplary Compounds of Formula IIa

TABLE 1-continued

Exemplary Compounds of Formula IIa

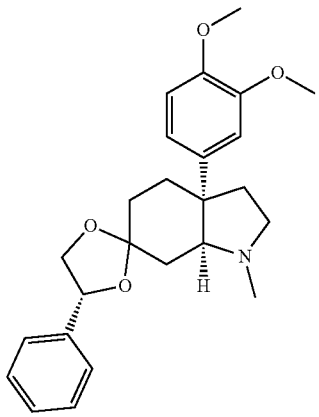 [SMILES: COc1ccc([C@]23CCN(C)[C@H]2CC2(CC3)OC[C@@H](c3ccccc3)O2)cc1OC]

TABLE 1-continued

Exemplary Compounds of Formula IIa

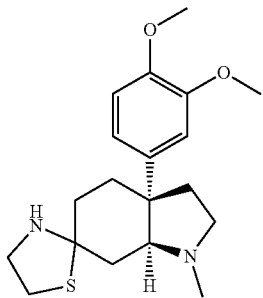 [SMILES: COc1ccc([C@]23CCN(C)[C@H]2CC2(CC3)NCCS2)cc1OC]

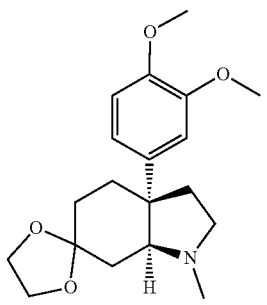 [SMILES: COc1ccc([C@]23CCN(C)[C@H]2CC2(CC3)OCCO2)cc1OC]

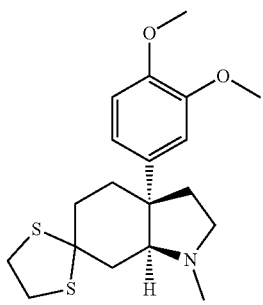 [SMILES: COc1ccc([C@]23CCN(C)[C@H]2CC2(CC3)SCCS2)cc1OC]

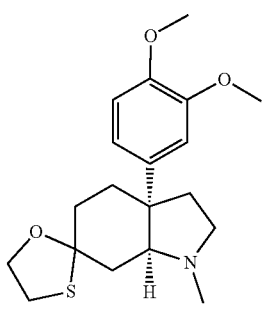 [SMILES: COc1ccc([C@]23CCN(C)[C@H]2CC2(CC3)OCCS2)cc1OC]

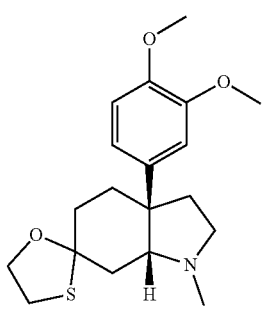

In some embodiments, the compound of formula (I) is a compound of formula (IX):

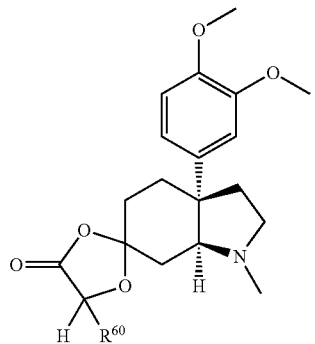

(IX)

or a pharmaceutically acceptable salt thereof, and $R_{60}$ is hydrogen or methyl.

In some embodiments, a compound of formula (I) can convert to mesembrine (e.g., (−) mesembrine) upon oral administration to a mammal and upon hydrolysis in sufficiently acidic conditions (e.g., pH 2 at 37 degrees C.), where $R_{60}$ is defined with respect to Formula (IX) above.

Compounds of Formula (IX) can be prepared as described with respect to compounds in the examples below. In general treatment of a ketone, such as mesembrine, with an appropriate alpha-hydroxy carboxylic acid, with a Lewis acid, such as boron trifluoride etherate, in a solvent, such as dichloromethane, is a method to prepare compounds of Formula (IX). For example, a compound of formula (IX) where $R_{60}$ is methyl can be obtained by reacting mesembrine with lactic acid (e.g., with TsOH, toluene). In some embodiments, the compound can be a lactate or glycolate derivative of mesembrine. $R_{60}$ in Scheme 2 is as defined above with respect to Formula (I-B).

Table 2 provides non-limiting examples of certain compounds of Formula (IX).

TABLE 2

Exemplary Compounds of Formula IX

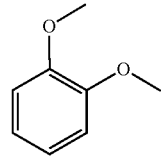


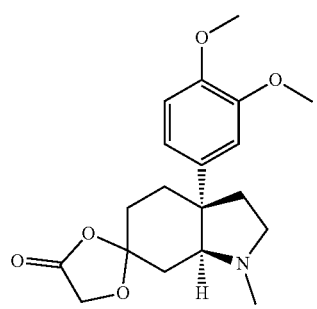 [SMILES: COc1ccc([C@]23CCN(C)[C@H]2CC2(CC3)OCC(=O)O2)cc1OC]

In some embodiments, the compound of Formula (I) is a compound of Formula (X) or a pharmaceutically acceptable salt thereof:

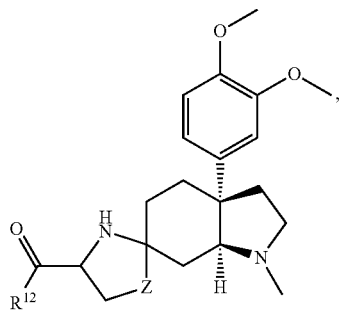

(X)

wherein Z is S or O; and $R_{12}$ is hydroxyl or amino.

In some embodiments, a compound of Formula (X) can convert to mesembrine (e.g., (−) mesembrine) upon oral administration to a mammal and upon hydrolysis in sufficiently acidic conditions (e.g., pH 2 at 37° C.), where Z, and Ru are as defined with respect to Formula (X) above.

Compounds of Formula (X) can be prepared as described with respect to exemplary compounds in the examples below. In general, treatment of a ketone, such as mesembrine, with an appropriate alpha-amino carboxylic acid or alpha-amino amide, in a solvent, such as ethanol, at an elevated temperature is a method to prepare compounds of Formula (X).

Table 3 provides non-limiting examples of certain compounds of Formula (X).

TABLE 3

Exemplary Compounds of Formula X

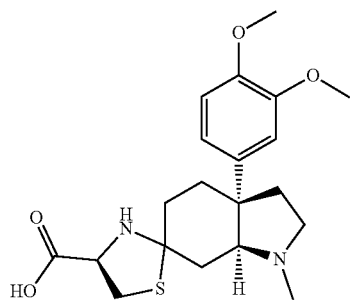

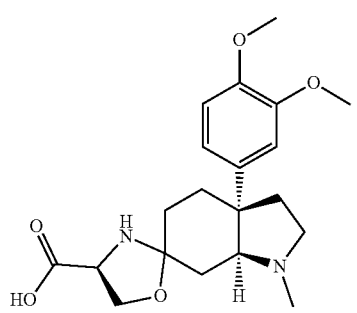

TABLE 3-continued

Exemplary Compounds of Formula X

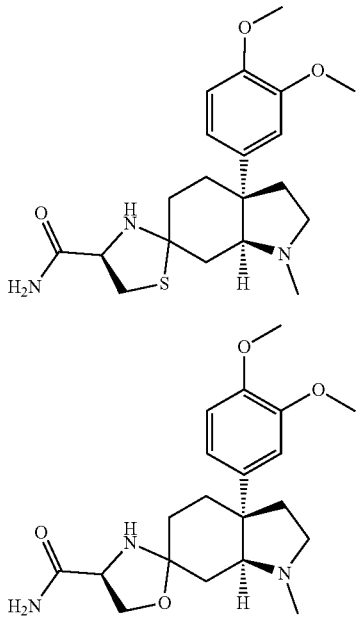

In some embodiments, the compound of Formula (I) is a compound of Formula (XI) or a pharmaceutically acceptable salt thereof:

XI

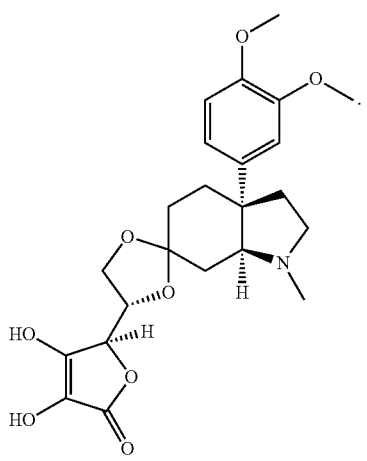

In some embodiments, a compound of Formula (XI) can convert to mesembrine (e.g., (−) mesembrine) upon oral administration to a mammal and upon hydrolysis in sufficiently acidic conditions (e.g., pH 2 at 37° C.). In some embodiments, the compound can be an ascorbate derivative of mesembrine.

Compounds of Formula (XI) can be prepared as described with respect to compounds in the examples below. In general, treatment of a ketone such as mesembrine, with a naturally occurring diol, such as ascorbic acid, with an acid catalyst in a solvent, such as toluene, is a method to prepare compounds of Formula (XI). In some embodiments, mesembrine can be reacted with ascorbic acid (e.g., TsOH, acetone) to obtain a compound of Formula (XI).

Table 4 provides non-limiting examples of certain compounds of Formula (XI).

TABLE 4

Exemplary Compounds of Formula XI

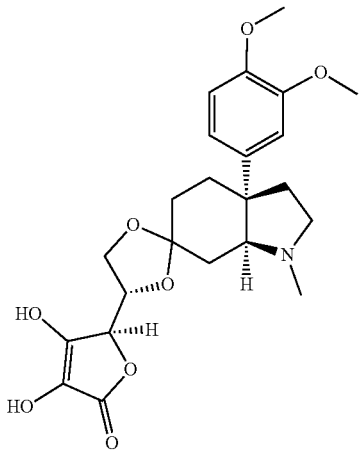

In some embodiments, the compound of Formula (I) is a compound of Formula (XII) or a pharmaceutically acceptable salt thereof:

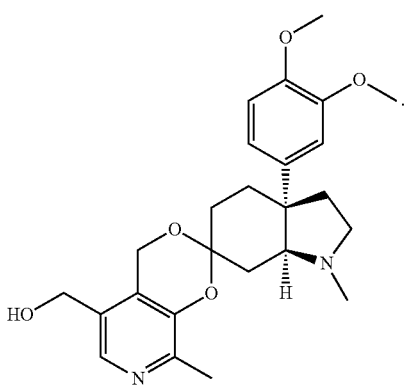

XII

In some embodiments, a compound of Formula (XII) can be a compound of Formula (XII-1) that converts to mesembrine (e.g., (−) mesembrine) upon oral administration to a mammal and upon hydrolysis in sufficiently acidic conditions (e.g., pH 2 at 37° C.).

Compounds of Formula (XII) can be prepared as described with respect to exemplary compounds in the examples below. In general treatment of a ketone such as mesembrine with a compound such as pyridoxine or an analog thereof (e.g., a vitamin B6 analog), with an acid catalyst in a solvent is a method to prepare compounds of Formula (XII).

Table 5 provides non-limiting examples of certain compounds of Formula (XII).

TABLE 5

Exemplary Compounds of Formula XII

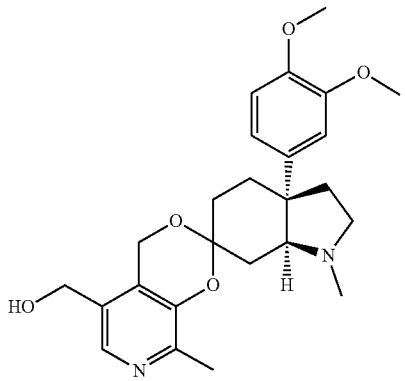 [SMILES: COc1ccc([C@]23CCN(C)[C@H]2CC2(CC3)OCc3c(CO)cnc(C)c3O2)cc1OC]

In some embodiments, a compound of Formula (I) can be a compound of Formula (XIII) or a pharmaceutically acceptable salt thereof:

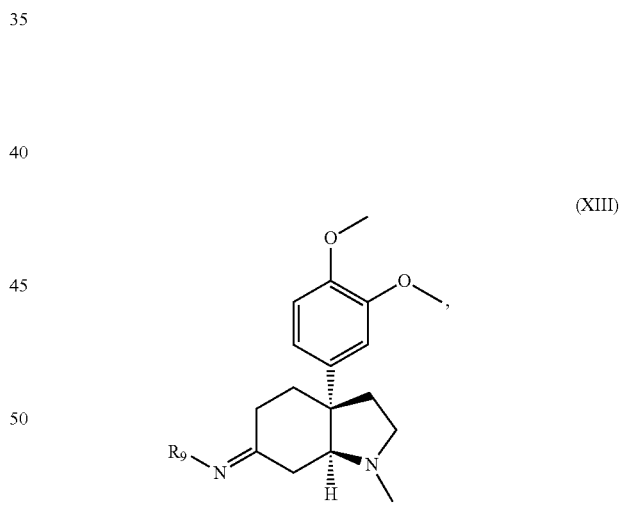

(XIII)

wherein $R_9$ is hydroxyl, methoxy, or —NH—C(O)-6-member nitrogen-containing heteroaryl. In some embodiments, the 6-member nitrogen-containing heteroaryl is pyridine.

In some embodiments, a compound of Formula (XIII) can convert to mesembrine (e.g., (−) mesembrine) under acidic conditions, such as upon oral administration to a mammal. For example, a compound of Formula (XIII) can convert to mesembrine (e.g., (−) mesembrine) due to the reaction by enzyme, gastric acid and the like under the physiological conditions in the body of a mammal.

Table 6 provides non-limiting examples of certain compounds of Formula (XIII)

TABLE 6

Exemplary Compounds of Formula (XIII).

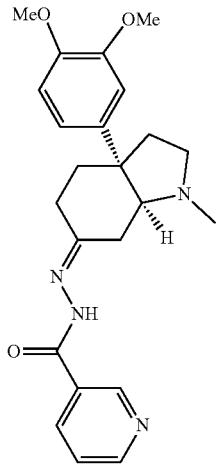 [SMILES: COc1ccc([C@@]23CC/C(=N/NC(=O)c4cccnc4)C[C@@H]2N(C)CC3)cc1OC]

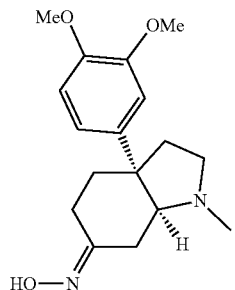 [SMILES: COc1ccc([C@@]23CC/C(=N\O)C[C@@H]2N(C)CC3)cc1OC]

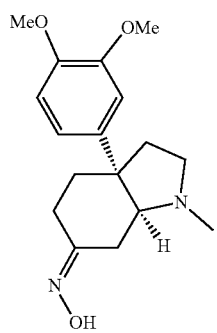 [SMILES: COc1ccc([C@@]23CC/C(=N/O)C[C@@H]2N(C)CC3)cc1OC]

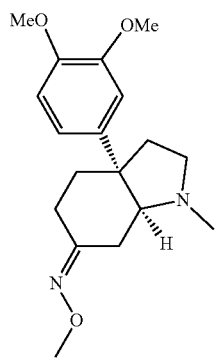 [SMILES: CO/N=C1/CC[C@@]2(c3ccc(OC)c(OC)c3)CCN(C)[C@H]2C1]

TABLE 6-continued

Exemplary Compounds of Formula (XIII).

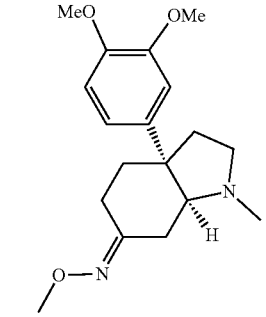

In certain embodiments, the invention relates to a compound of Formula (XIV), or a pharmaceutically acceptable salt thereof, as defined above. In some embodiments, a compound of Formula (XIV) can be a compound of Formula (XIV-1) or Formula (XIV-2), or a pharmaceutically acceptable salt thereof:

Formula (XIV-1)

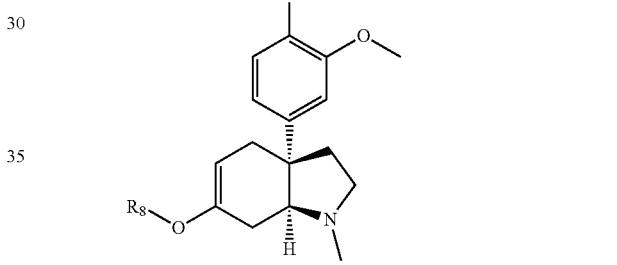

Formula (XIV-2)

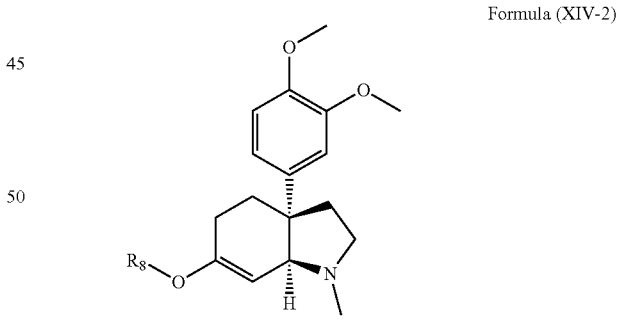

wherein $R_8$ is —Si(CH$_3$)$_3$ or —(O)—CH$_3$.

Compounds of Formula (XIV) including compounds of Formula (XIV-1) and Formula (XIV 2) can be prepared as described with respect to exemplary compounds in the examples below. In general, treating a ketone, such as mesembrine, with an appropriate base, such as potassium tert-butoxide, and an acid anhydride, in a solvent, such as THF, is a method to prepare compounds of Formula (XIV).

Table 8 provides non-limiting examples of certain compounds of Formula (XIV).

TABLE 8

Exemplary Compounds of Formula (XIV).

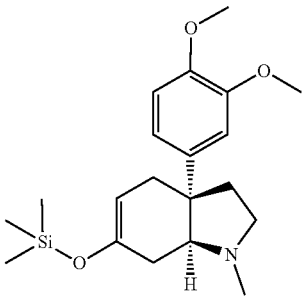

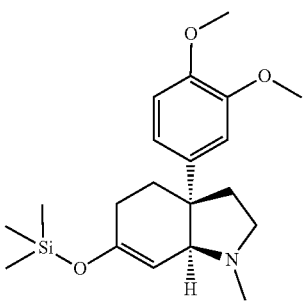

In some embodiments, the compound is a compound of Formula (XV) or a pharmaceutically acceptable salt thereof

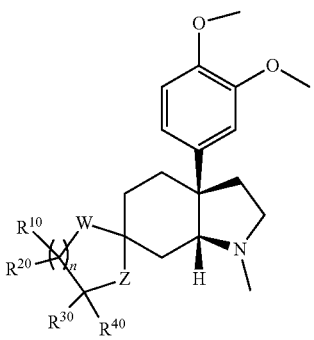

Formula XV wherein n is 0 or 1;

W and Z are each independently $CH_2$, O, S or NH, provided that at least one of W or Z is O, S or NH; and $R_{10}$, $R_{20}$, $R_{30}$ and $R_{40}$ are each hydrogen.

In some embodiments, W and Z in Formula (XV) are each O. In some embodiments, W and Z in Formula (XV) are each S. In some embodiments, W and Z in Formula (XV) are each NH. In some embodiments, W is NH and Z is S in Formula (XV). In some embodiments, W is O and Z is S in Formula (XV). In some embodiments, W is $CH_2$ and Z is O in Formula (XV). In some embodiments, W is $CH_2$ and Z is NH in Formula (XV).

In some embodiments, a compound of Formula (XV) can be a compound of Formula (XV-1):

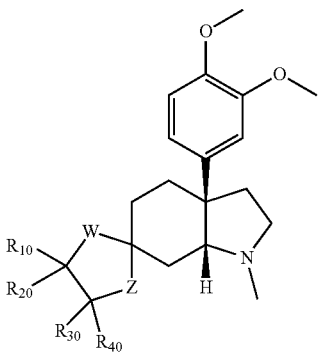

(XV-1)

Compounds of Formula (XV) including compounds of Formula (XV-1) can be prepared as described with respect to exemplary compounds in the examples below.

Table 9 provides non-limiting examples of certain compounds of Formula (XV).

TABLE 9

Exemplary Compounds of Formula XV

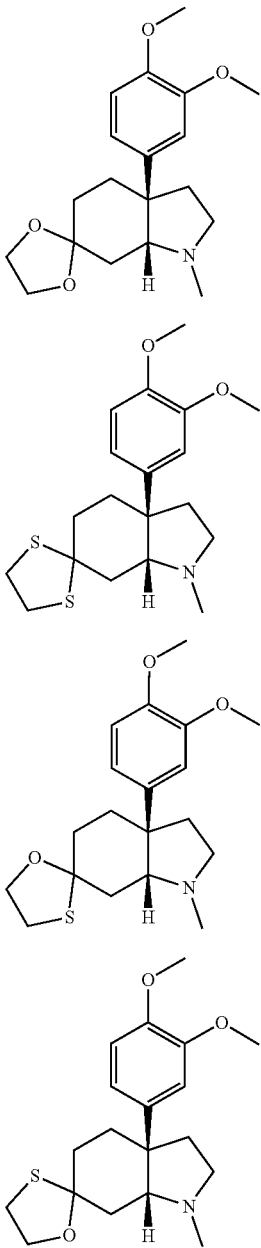

A total synthesis of (±)-mesembrine has also been reported (Jeffs P. *Sceletium* alkaloids. In: Jeffs P. The Alkaloids: Chemistry and Physiology. Vol 19. New York, NY: Academic Press; 1981:1-80). Mesembrine alkaloids have been synthesized in a manner similar to that of Amaryllidaceae alkaloids (e.g., Roe C, Sandoe E J, Stephenson G R, Anson C E. Stereoselectivity in the organoiron-mediated synthesis of (±)-mesembrine. Tetrahedron Lett. 2008; 49(4): 650-653; and Shamma M, Rodriguez H R. The synthesis of (+)-mesembrine. Tetrahedron. 1968; 24(22):6583-6589.5714008).

In some embodiments, compositions can comprise greater than 15% (w/w) mesembrine of the total alkaloid content in composition. In some embodiments, compositions can comprise greater than 50% (w/w) mesembrine of the total alkaloid content in composition. In some embodiments, compositions can comprise greater than 90% (w/w) mesembrine of the total alkaloid content in composition. In some embodiments, compositions can comprise greater than 99% (w/w) mesembrine of the total alkaloid content in composition.

In some embodiments, compositions can comprise greater than 15% (w/w) of mesembrine (e.g., (−) mesembrine) of the total alkaloid content in composition. In some embodiments, compositions can comprise greater than 50% (w/w) mesembrine (e.g., (−) mesembrine) of the total alkaloid content in composition. In some embodiments, compositions can comprise greater than 90% (w/w) mesembrine (e.g., (−) mesembrine) of the total alkaloid content in composition. In some embodiments, compositions can comprise greater than 99% (w/w) mesembrine (e.g., (−) mesembrine) of the total alkaloid content in composition.

In some embodiments, many prodrugs of mesembrine (e.g., (−) mesembrine) are disclosed herein. Illustratively, converting mesembrine to a prodrug can be performed by modifying the ketone on the fused ring. In some embodiments, the modification can be take the form of a protecting group. Illustrative ketone protecting groups are known in the art as described in Greene's Protective Groups in Organic Synthesis, fourth edition, the disclosure of which is hereby incorporated by reference. Illustrative ketone protecting groups include acyclic ketals, cyclic ketals, chiral ketals, dithio ketals, cyclic dithio ketals, monothiol ketals, cyclic monothiol ketals, cyanohydrins, hydrazones, oximes, pyrrole carbinols, O-silylimdazoyl aminals, cyclic aminals, and benzothiazoles. Ketones may also be protected by protecting the enolate, for example by trimethylsilyl enol ethers, and enamines, In some embodiments, a method of isolating stable forms of (+) mesembrenone and (−) mesembrenone is provided. In illustrative embodiments, the method minimizes racemization of mesembrenone. In some embodiments, stereoisomer analogs of (+) mesembrenone and (−) mesembrenone can be formed. The (+)/(−) mesembrenone analogs can then be separated. The (+) analog is then be converted to (+) mesembrine. The (−) analog is then converted to (−) mesembrine. The conversion can be performed by hydrolysis, preferably in the presence of an acid.

In illustrative embodiments, a method of extending the pharmacokinetic properties of mesembrine is described. In illustrative embodiments, the pharmacokinetic properties of mesembrine is extended by forming a prodrug, for example by modifying the ketone on the fused ring.

In some embodiments, compounds of Formula (I-1) can form mesembrine (e.g., (−) mesembrine) under biologically relevant conditions, including compounds of formula (I-1), formula (IIa-1), formula (IIIc-1), and formula (IVa-1). In certain embodiments, methods of administering a therapeutic alkaloid compound comprise the oral administration of a compound of formula (I-1), formula (IIa-1), formula (IIIc-1), and formula (IVa-1). In certain embodiments, methods of administering a therapeutically effective amount of mesembrine can comprise the step of administering a compound of formula (IIa-1).

In some embodiments, methods of treating a patient suffering from a disease comprise administering to a patient a composition comprising a compound disclosed herein for the treatment or prevention of a mental health disorder. In some embodiments, methods of treating a patient suffering from a disease comprise administering to a patient a composition comprising a compound disclosed herein for the treatment or prevention of a diagnosed condition selected from anxiety and depression. In some embodiments, a method comprises the administration to a patient in need thereof of a therapeutically effective amount of a compound of Formula (I) for the treatment of depression. In some embodiments, a method comprises the administration to a patient in need thereof of a therapeutically effective amount of a compound of Formula (I) for the treatment of a condition selected from the group consisting of: anxiety associated with depression, anxiety with depression, mixed anxiety and depressive disorder. In some embodiments, a method comprises the administration to a patient in need thereof of a therapeutically effective amount of a compound of Formula (I) for the treatment of anxiety and hysteria or anxiety and depression.

In some embodiments, the compound disclosed herein is administered to the patient in a unit dose. In some embodiments, the compound disclosed herein is prescribed to a patient in an oral unit dose for such as a capsule or tablet once or more times per day. In some embodiments, a compound disclosed herein is administered to a patient for the treatment of a disease or condition for which mesembrine is safe and effective for treatment. In some embodiments, a method comprises the administration to a patient in need thereof of a therapeutically effective amount of a compound of Formula (I) for the treatment of anxiety. In some embodiments, a method comprises the administration to a patient in need thereof of a therapeutically effective amount of a compound of Formula (I) for the treatment of a disease selected from the group consisting of mild to moderate depression and major depressive episodes. In some embodiments, a method comprises the administration to a patient in need thereof of a therapeutically effective amount of a compound of Formula (I) for the treatment of a disease selected from the group consisting of psychological and psychiatric disorders where anxiety is present. In some embodiments, a method comprises the administration to a patient in need thereof of a therapeutically effective amount of a compound of Formula (I) for the treatment of major depressive episodes. In some embodiments, a method comprises the administration to a patient in need thereof of a therapeutically effective amount of a compound of Formula (I) for the treatment of a disease selected from the group consisting of alcohol and drug dependence, bulimia nervosa, and obsessive-compulsive disorders. In some embodiments, an amount of from 20 micrograms to 2 milligrams of a compound of Formula (I) is orally administered to a patient to treat the patient in need thereof with a therapeutic compound selected from the group consisting of (−) mesembrine, (+) mesembrine, and (−)/(+) mesembrine,. In some embodiments, an amount of from 20 micrograms to 2 milligrams of a compound of Formula (I) is orally administered to a patient to treat the patient in need thereof with (−) mesembrine.

Pharmaceutical Compositions

In certain embodiments, the present application is directed to a pharmaceutical composition comprising an active pharmaceutical ingredient. In certain embodiments, the pharmaceutical composition comprises a compound as disclosed herein as the active pharmaceutical ingredient (API) and a pharmaceutically acceptable carrier comprising one or more excipients. In some embodiments, the pharmaceutical composition optionally further comprises an additional therapeutic compound (i.e., agent) with the pharmaceutically acceptable carrier. The pharmaceutical composition can be a medicament.

Pharmaceutically acceptable carriers include those known in the art. The choice of a pharmaceutically acceptable carrier can depend, for example, on the desired route of administration of the composition. A pharmaceutical composition (preparation) can be administered to a subject by any of a number of routes of administration including, for example, parenteral administration (e.g. intravenously, subcutaneously, or intramuscularly), oral administration (for example, tablets, and capsules); absorption through the oral mucosa (e.g., sublingually) or transdermally (for example as a patch applied to the skin) or topically (for example, as a cream, ointment or spray applied to the skin).

In some embodiments, pharmaceutical compositions comprising compounds of Formula (I) or pharmaceutically acceptable salts thereof can be formulated for oral administration. For example, a compound provided herein can be combined with suitable compendial excipients to form an oral unit dosage form, such as a capsule or tablet, containing a target dose of a compound of Formula (I). The drug product can be prepared by first manufacturing the compound of Formula (I) as an active pharmaceutical ingredient (API), followed by roller compaction/milling with intragranular excipients and blending with extra granular excipients. A Drug Product can contain the selected compound of Formula (I) as the API and excipient components in a tablet in a desired dosage strength of a compound of Formula (1). The blended material can be compressed to form tablets and then film coated. The excipients can be selected from materials appropriate for inclusion in a pharmaceutical composition for an intended purpose and route of delivery including providing a desired manufacturing and stability properties and/or desired in vivo characteristics or other properties to the pharmaceutical composition. In some embodiments, the pharmaceutical composition can include a compound of Formula (I) as the API in combination with a filler (e.g., a form of microcrystalline cellulose), a dry binder or disintegrant (e.g., a cross-linked polymer), a glidant (e.g., colloidal silicon dioxide) and/or a lubricant (e.g., magnesium stearate). In some embodiments, the pharmaceutical composition can comprise a material such as an extended release or disintegrant involved in carrying or transporting the API pharmaceutical agent from one organ, or portion of the body, to another organ, or portion of the body of a subject, including materials to desirable control the absorption of the API in the intestine.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

To prepare solid dosage forms for oral administration, the active ingredient is mixed with one or more pharmaceutically acceptable carriers, such as sodium citrate or dicalcium phosphate, and/or any of the following: (1) fillers or extenders, (2) binders, (3) humectants, (4) disintegrating agents, (5) solution retarding agents, (6) absorption accelerators, (7) wetting agents, (8) absorbents, (9) lubricants, (10) complexing agents, and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using suitable excipients. The pharmaceutical compositions according to the present invention may contain conventional pharmaceutical carriers and/or auxiliary agents. In some embodiments, he pharmaceutical compositions according to the present invention may contain conventional carrier agents including a binder, a lubricant and/or a glidant selected from those products and materials generally used in pharmaceutical industry for preparation of pharmaceutical compositions for an intended route of administration.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

Liquid dosage forms useful for oral administration include pharmaceutically acceptable carriers and the active ingredient provided as a solid form for reconstitution prior to administration or as a liquid (e.g., solutions, suspensions, or emulsions). In addition to the active ingredient, a liquid dosage forms may contain inert diluents commonly used in the art. For example, formulations of pharmaceutically acceptable compositions for injection can include aqueous solutions such as water or physiologically buffered saline or other solvents or vehicles suitable for the intended route of administration. In some embodiments, the pharmaceutical composition is formulated for parenteral administration.

The therapeutically effective amount of a pharmaceutical composition can be determined by human clinical trials to determine the safe and effective dose for a patient with a relevant diagnosis. It is generally understood that the effective amount of the compound may vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the pharmaceutical composition at a dose and dose interval determined to be safe and effective for the patient.

The present disclosure includes the use of pharmaceutically acceptable salts of compounds of the invention in the compositions and methods of the present invention. Pharmaceutically-acceptable salts include, for example, acid-addition salts and base-addition salts. The acid that is added to a compound to form an acid-addition salt can be an organic acid or an inorganic acid. A base that is added to a compound to form a base-addition salt can be an organic base or an inorganic base. In some embodiments, a pharmaceutically-acceptable salt is a metal salt, in some embodiments, a pharmaceutically-acceptable salt is an ammonium salt. For example, a pharmaceutically acceptable acid addition salt can exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups, $C_1$-$C_{10}$ branched-chain alkyl groups, cycloalkyl (alicyclic) groups, alkyl-substituted cycloalkyl groups, and cycloalkyl-substituted alkyl groups. Preferably, the "alkyl" group refers to $C_1$-$C_7$ straight-chain alkyl groups or $C_1$-$C_7$ branched-chain alkyl groups. Most preferably, the "alkyl" group refers to $C_1$-$C_3$ straight-chain alkyl groups or $C_1$-$C_3$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "haloalkyl" refers to an alkyl group substituted with at least one hydrogen atom on a carbon replaced by a halogen. Illustrative halogens include fluoro, chloro, bromo, and iodo.

Illustrative haloalkyl groups include trifluoromethyl and 2,2,2-trifluoroethyl, etc.

The term "alkoxyalkyl" refers to an alkyl group substituted with an alkoxy group and may be represented by the general formula alkyl-O-alkyl.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. Coalkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

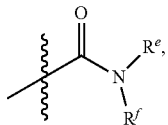

wherein $R^e$ and $R^f$ each independently represent a hydrogen or hydrocarbyl group, or $R^e$ and $R^f$ taken together with the N atom to which they are attached complete a heterocycle having from 4 to 8 atoms in the ring structure.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Preferably, the "alkoxy" group refers to $C_1$-$C_7$ straight-chain alkoxy groups or $C_1$-$C_7$ branched-chain alkoxy groups. Representative alkoxy groups include methoxy, ethoxy, propoxy, tert-butoxy and the like.

The term "aryloxy" refers to an aryl group having an oxygen attached thereto. Preferably, the "aryloxy" group refers to $C_6$-$C_{10}$ aryloxy groups or 5-7-membered heteroaryloxy groups. Representative aryloxy groups include phenoxy ($C_6H_5$—O—) and the like.

The terms "amine" and "amino" are art-recognized and refer to both unsubstituted and substituted amines and salts thereof, e.g., a moiety that can be represented by

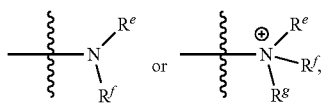

wherein $R^e$, $R^f$, and $R^g$, each independently represent a hydrogen or a hydrocarbyl group, or $R^e$ and $R^f$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring, for example a phenyl. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

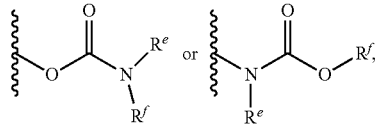

wherein $R^e$ and $R^f$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —C(O)O$R^9$ wherein $R^9$ represents a hydrocarbyl group.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains six or fewer carbon atoms, preferably four or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

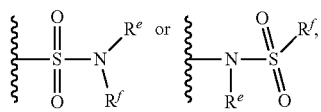

wherein $R^e$ and $R^f$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^e$ or —SC(O)R$^e$ wherein R$^e$ represents a hydrocarbyl.

The term "thioether", as used herein, is equivalent to an ether, wherein the oxygen is replaced with a sulfur.

The term "urea" is art-recognized and may be represented by the general formula

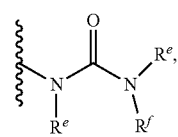

wherein $R^e$ and $R^f$ independently represent hydrogen or a hydrocarbyl.

The term "modulate" as used herein includes the inhibition or suppression of a function or activity (such as cell proliferation) as well as the enhancement of a function or activity.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. The mono- or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form mesembrine. Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs include using ester or phosphoramidate as biologically labile or cleavable (protecting) groups. The prodrugs of this disclosure are metabolized to produce mesembrine. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

Alternative Embodiments

In some embodiments, compounds described herein are compounds of formula (I):

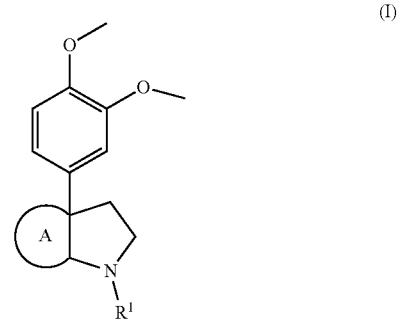

(I)

or a pharmaceutically acceptable salt thereof, wherein
R¹ is H or $C_1$-$C_7$ alkyl; and
ring A is

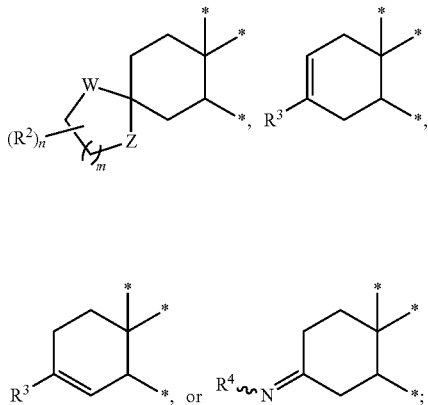

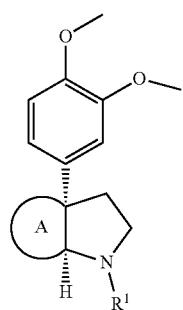

wherein * denotes the attachment points of ring A to the compound of formula (I), and wherein each of W and Z is independently O, NH, or S;

each $R^2$ is independently $C_1$-$C_3$ alkyl, —COOH, —CONH₂, phenyl, 5- to 7-membered heterocyclyl, or 5- to 7-membered heteroaryl, wherein each hydrogen atom in phenyl, 5- to 7-membered heterocyclyl and 5- to 7-membered heteroaryl is optionally substituted by —OH, $C_1$-$C_3$ alkyl, $C_1$-$C_3$ alkoxy, $C_1$-$C_3$ alkanol, or —NO₂, or two $R^4$s on a single carbon atom combine to form =O; or two adjacent $R^4$s together with the carbon atoms to which they are attached combine to form 5- to 7-membered heteroaryl, wherein each hydrogen atom in 5- to 7-membered heteroaryl is optionally substituted by —OH, $C_1$-$C_3$ alkyl, or $C_1$-$C_3$ alkanol, m is 1 or 2, n is 0, 1, or 2, $R^3$ is —OSi($C_1$-$C_6$ alkyl)3 or —OC(O)$C_1$-$C_6$ alkyl; and $R^4$ is OH, $C_1$-$C_6$ alkoxy, or —NHC(O)-5- to 7-membered heteroaryl, wherein each hydrogen atom in 5- to 7-membered heteroaryl is optionally substituted by —OH, $C_1$-$C_3$ alkyl, or $C_1$-$C_3$ alkanol.

In certain embodiments, the compound is of formula (I-1):

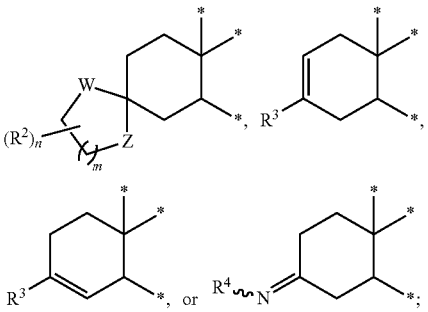

or a pharmaceutically acceptable salt thereof, wherein
R¹ is H or $C_1$-$C_7$ alkyl: and
ring A is wherein * denotes the attachment points of ring A to the compound of formula (I), and wherein each of W and Z is independently O, NH, or S;

each $R^2$ is independently $C_1$-$C_3$ alkyl, —COOH, —CONH₂, phenyl, 5- to 7-membered heterocyclyl, or 5- to 7-membered heteroaryl, wherein each hydrogen atom in phenyl, 5- to 7-membered heterocyclyl and 5- to 7-membered heteroaryl is optionally substituted by —OH, $C_1$-$C_3$ alkyl, $C_1$-$C_3$ alkoxy, $C_1$-$C_3$ alkanol, or —NO₂, or two $R^4$s on a single carbon atom combine to form =O; or two adjacent $R^4$s together with the carbon atoms to which they are attached combine to form 5- to 7-membered heteroaryl, wherein each hydrogen atom in 5- to 7-membered heteroaryl is optionally substituted by —OH, $C_1$-$C_3$ alkyl, or $C_1$-$C_3$ alkanol, m is 1 or 2, n is 0, 1, or 2, $R^3$ is —OSi($C_1$-$C_6$ alkyl)₃ or —OC(O)$C_1$-$C_6$ alkyl; and $R^4$ is OH, $C_1$-$C_6$ alkoxy, or —NHC(O)-5- to 7-membered heteroaryl, wherein each hydrogen atom in 5- to 7-membered heteroaryl is optionally substituted by —OH, $C_1$-$C_3$ alkyl, or $C_1$-$C_3$ alkanol; and the compound of formula (I-1) has the absolute stereochemistry shown.

In certain embodiments, the compound of formula (I) is a compound of formula (IIa):

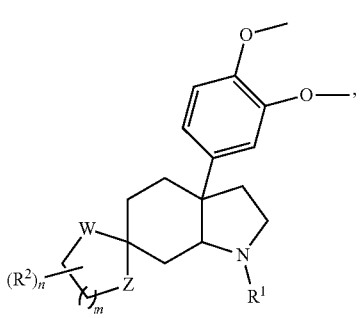

formula (IIa)

or a pharmaceutically acceptable salt thereof, wherein R¹, $R^2$, m, n, W, and Z are as defined herein.

In certain embodiments, the compound is of formula (IIa-1):

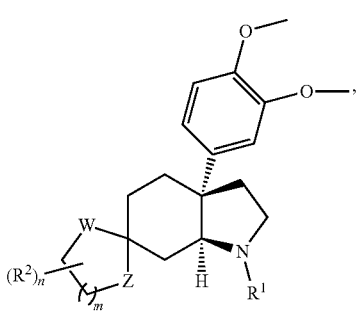
(IIa-1)

or a pharmaceutically acceptable salt thereof, wherein $R^1$, $R^2$, m, n, W, and Z are as defined herein; and the compound of formula (IIa-1) has the absolute stereochemistry shown.

In certain embodiments, the compound of formula (I) is a compound of formula (IIIa):

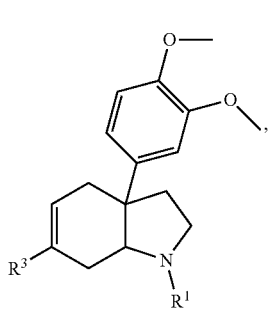
(IIIa)

or a pharmaceutically acceptable salt thereof, wherein $R^1$, and $R^3$ are as defined herein.

In certain embodiments, the compound of formula (I) is a compound of formula (IIIb):

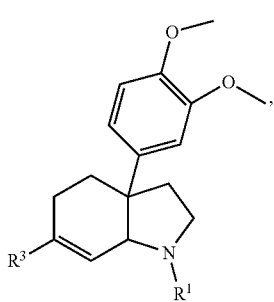
(IIIb)

or a pharmaceutically acceptable salt thereof, wherein $R^1$ and $R^3$ are as defined herein.

In certain embodiments, the compound is of formula (IIIc-1):

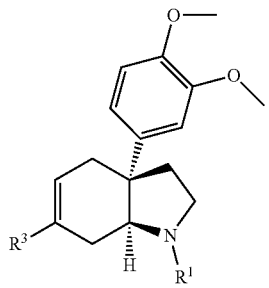

formula (IIIa-1) or a pharmaceutically acceptable salt thereof, wherein $R^1$ and $R^3$ are as defined herein; and the compound of formula (IIIc-1) has the absolute stereochemistry shown.

In certain embodiments, the compound is of formula (IIIb-1):

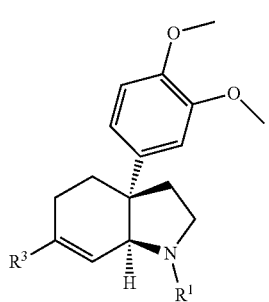

formula (IIIb-1) or a pharmaceutically acceptable salt thereof, wherein $R^1$ and $R^3$ are as defined herein or a pharmaceutically acceptable salt thereof.

In certain embodiments, the compound is of formula (IIIb-1):

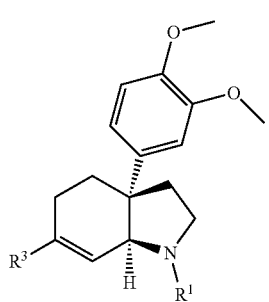

formula (IIIb-1) or a pharmaceutically acceptable salt thereof, wherein $R^1$ and $R^3$ are as defined herein or a pharmaceutically acceptable salt thereof; and the compound of formula (IIIb-1) has the absolute stereochemistry shown.

In certain embodiments, the compound of formula (I) is a compound of formula (IVa):

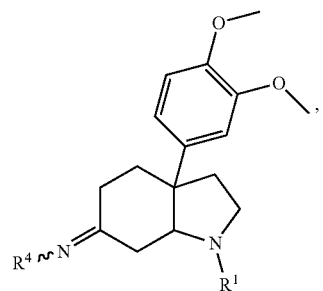

(IVa)

or a pharmaceutically acceptable salt thereof, wherein $R^1$ and $R^4$ are as defined herein.

In certain embodiments, the compound is of formula (IVa-1):

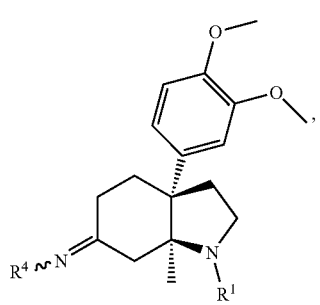

(IVa-1)

or a pharmaceutically acceptable salt thereof, wherein $R^1$ and $R^4$ are as defined herein; and the compound of formula (IVa-1) has the absolute stereochemistry shown.

In certain embodiments, the compound is of formula (IA):

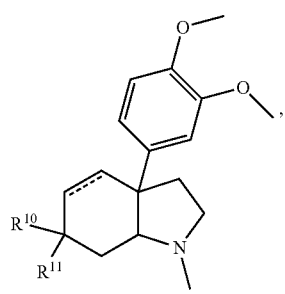

(IA)

or a pharmaceutically acceptable salt thereof, wherein the dashed bond is absent or present, and $R^{10}$ and $R^{11}$ are as defined herein, for example as a biologically labile moiety selected to provide in vivo conversion of a compound of Formula (IA) to mesembrine.

In certain embodiments, the compound is of formula (IB-1)

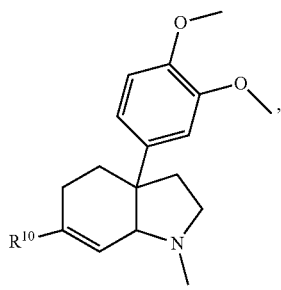

(IB-1)

or formula (IB-2)

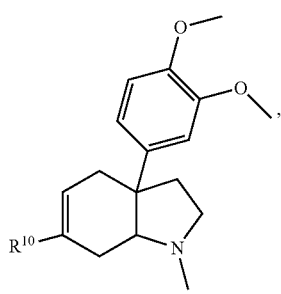

(IB-2)

or a pharmaceutically acceptable salt thereof, wherein $R^{10}$ and $R^{11}$ are as defined herein, for example as a biologically labile moiety selected to provide in vivo conversion of a compound of Formula (IA) to mesembrine.

In some embodiments, the compound is selected from the group consisting of:

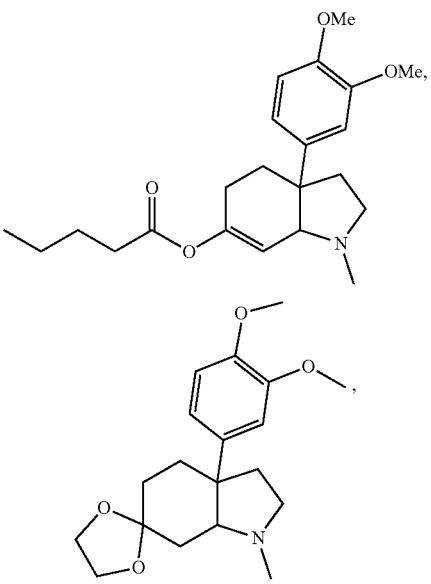

193
-continued
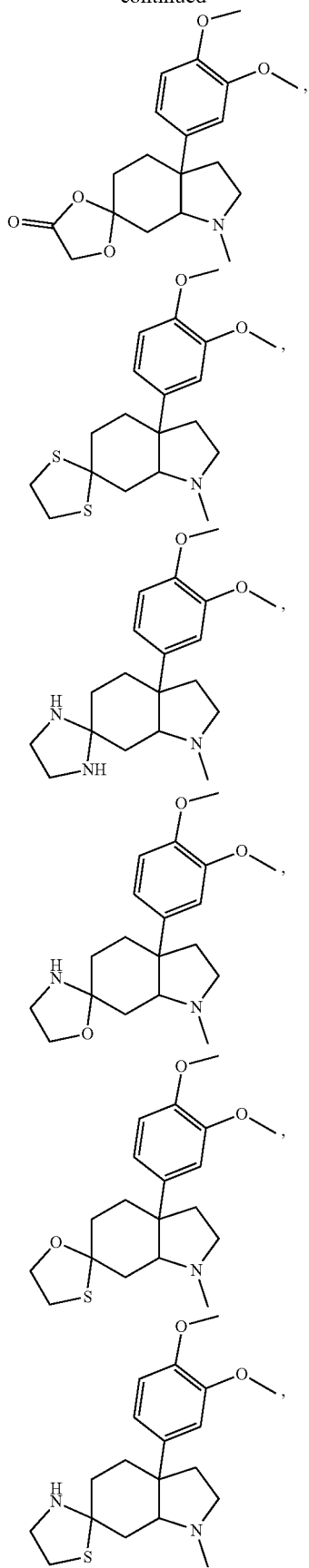
194
-continued
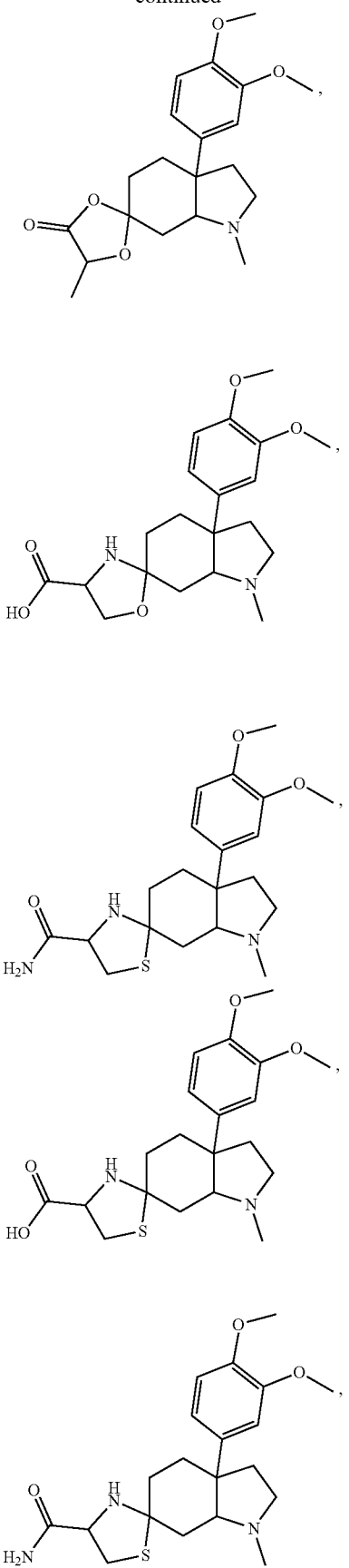

195
-continued
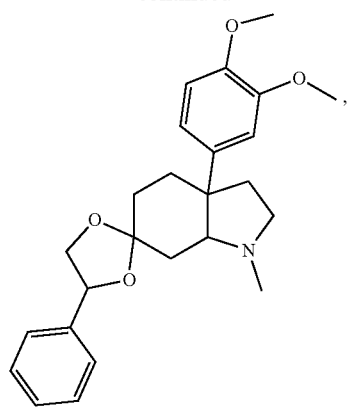
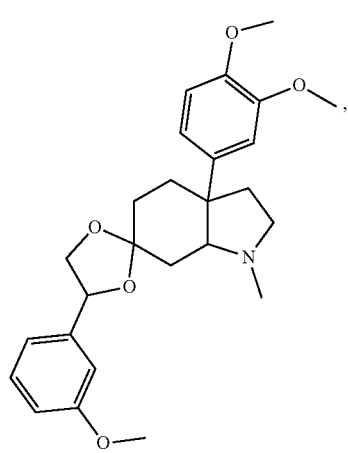
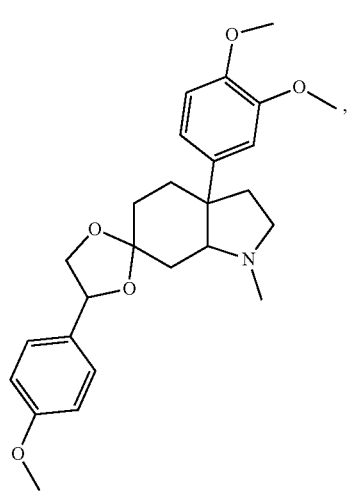
196
-continued
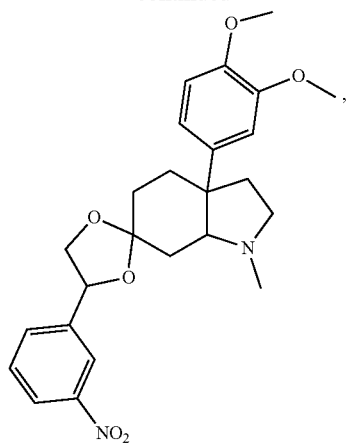
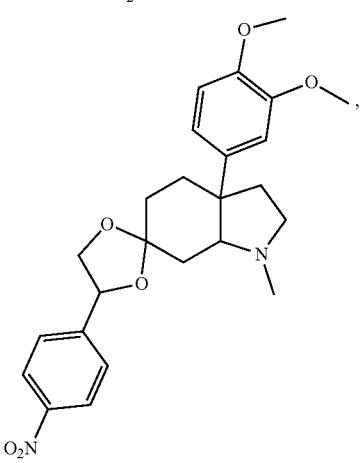
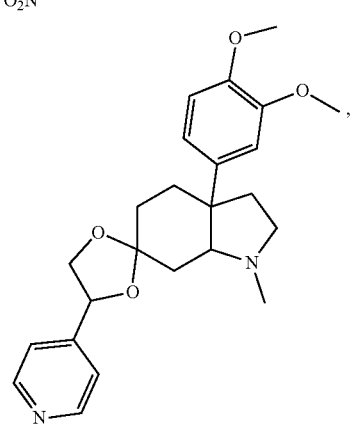
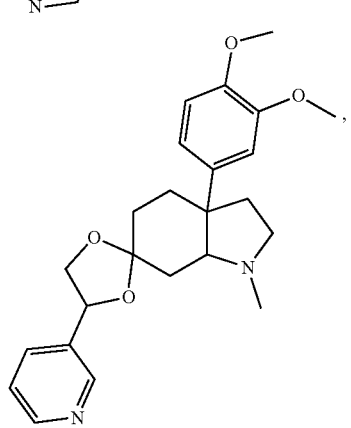

197
-continued
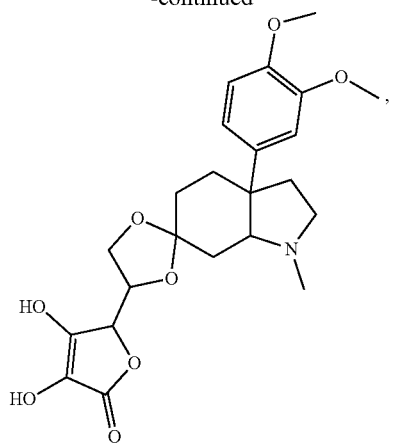
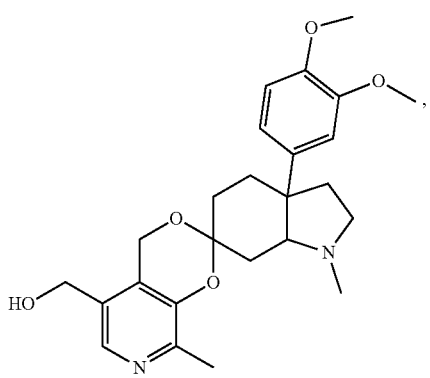
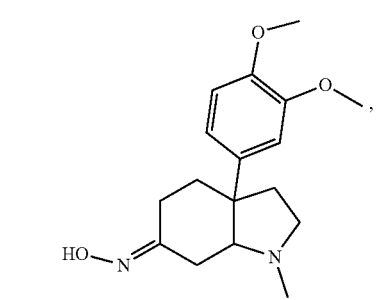
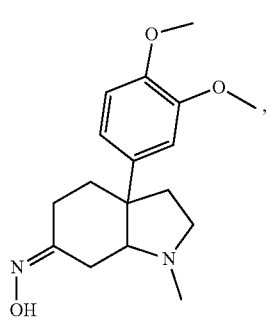
198
-continued
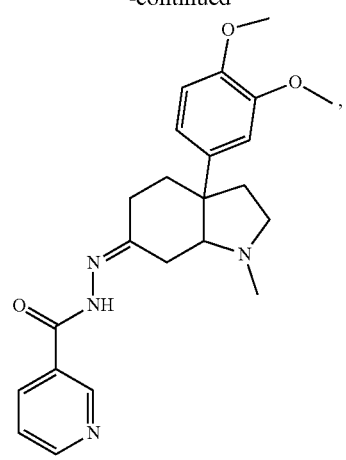
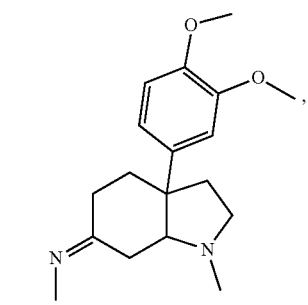
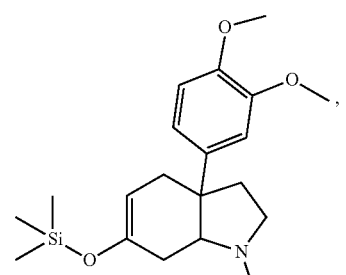
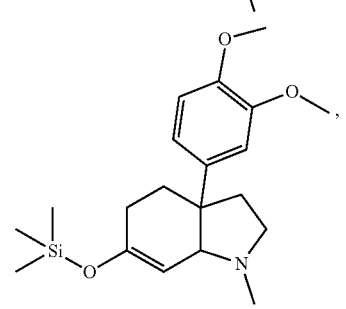

199
-continued
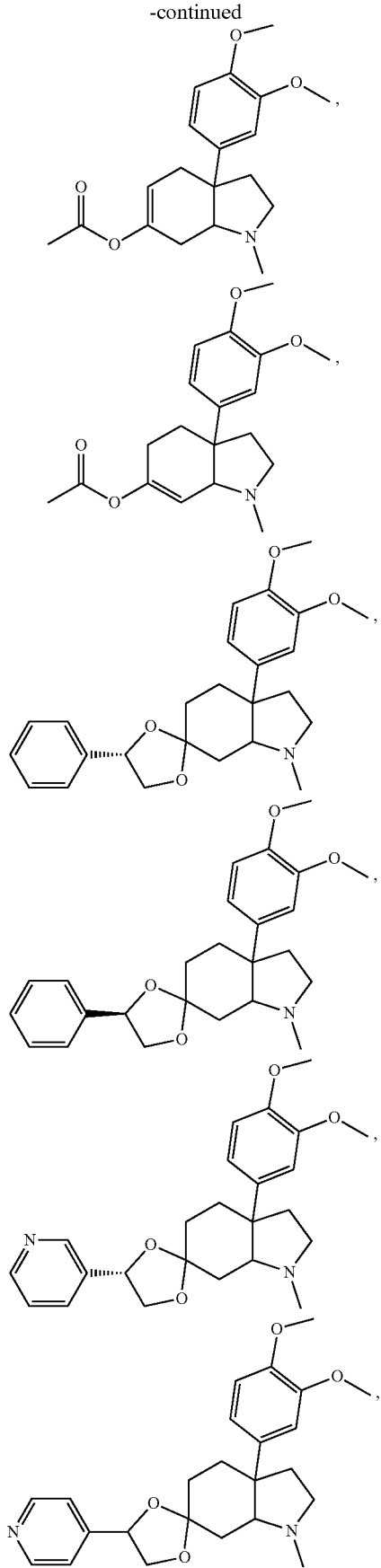
200
-continued
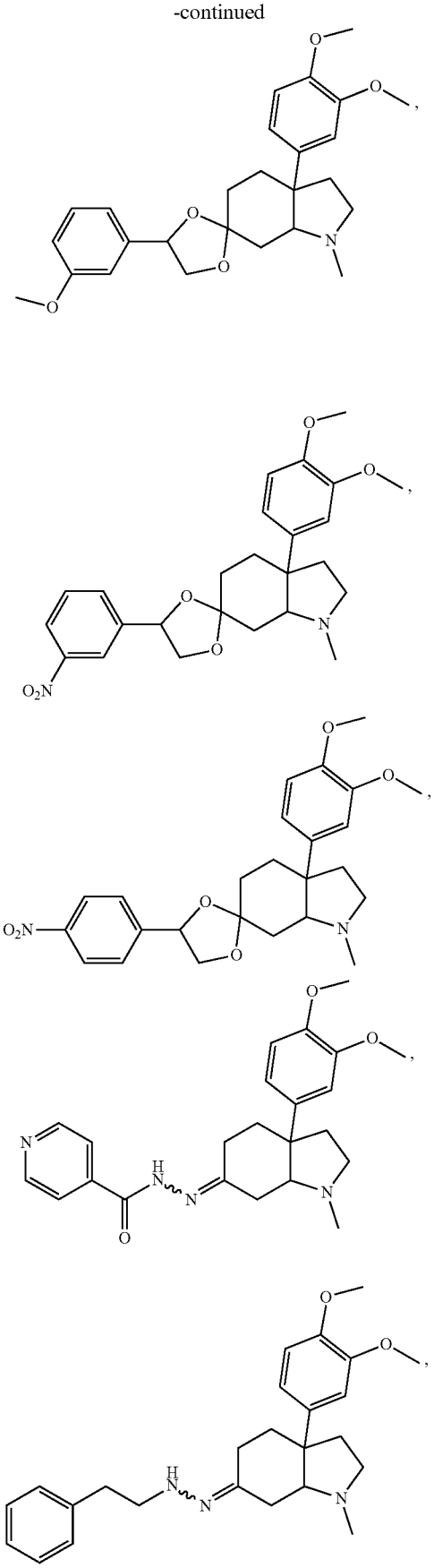

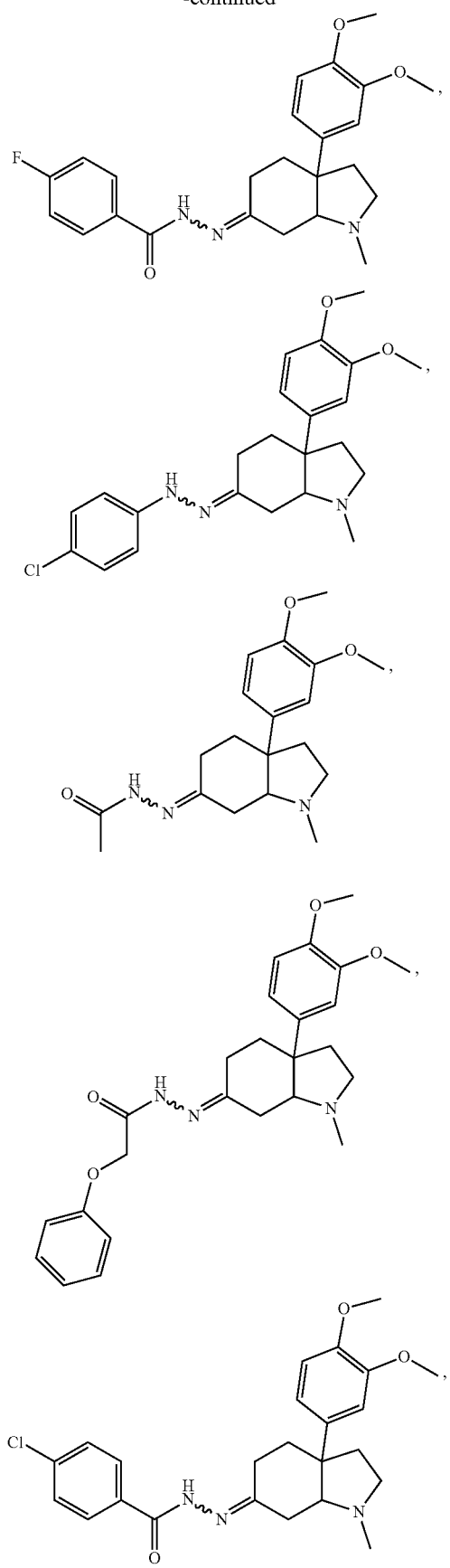
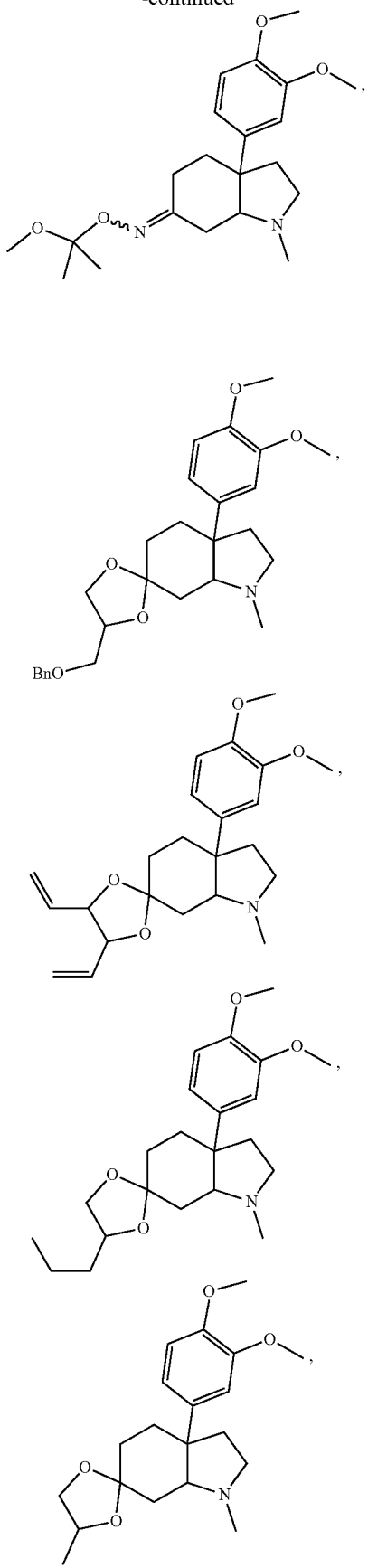

203
-continued
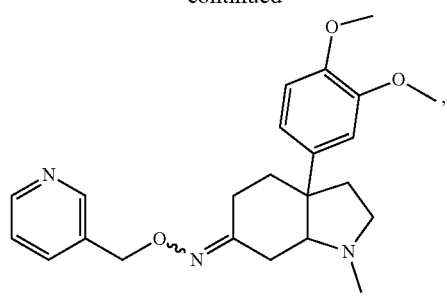
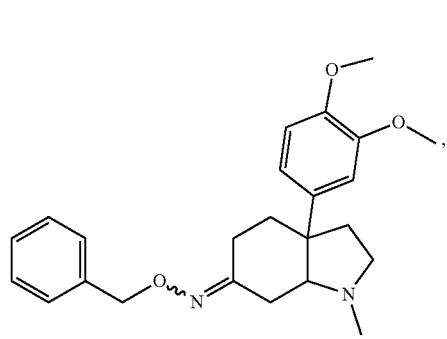
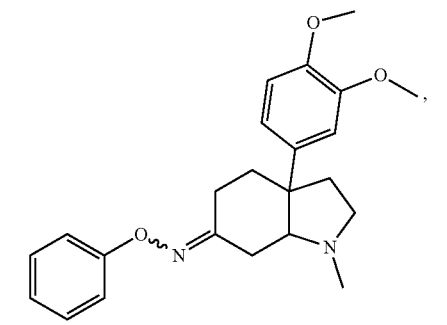
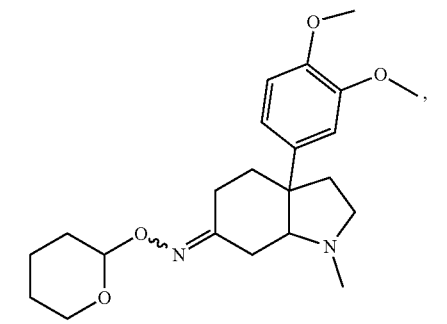
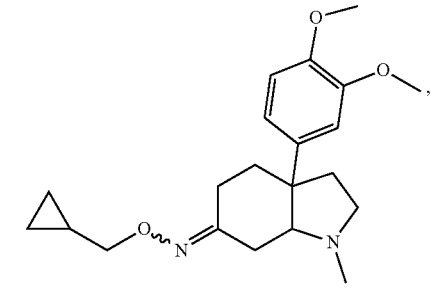
204
-continued
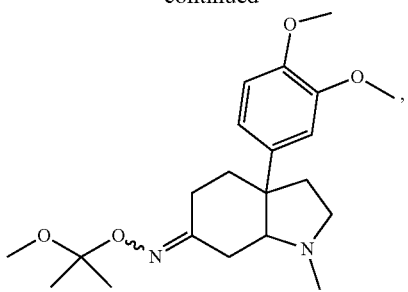
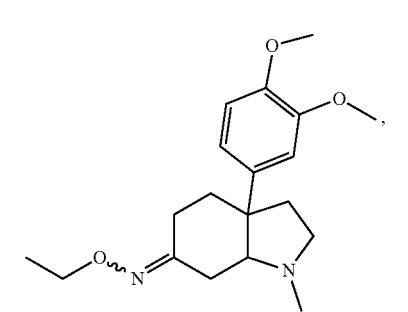
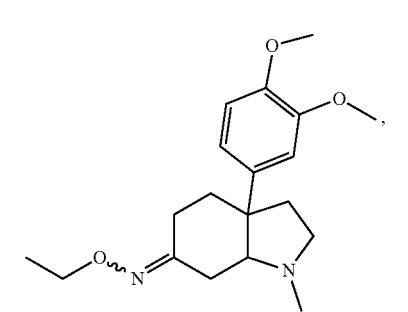
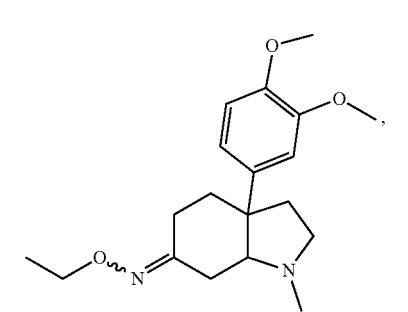
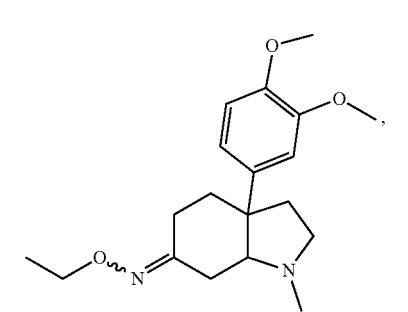

205
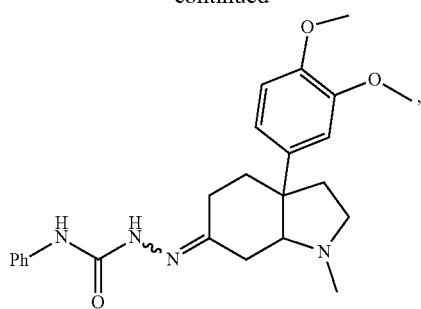
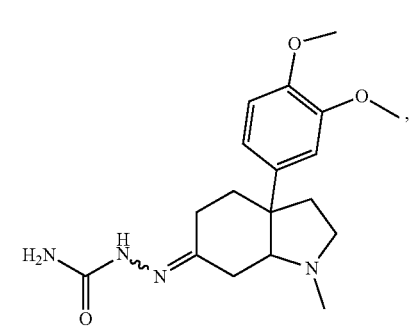
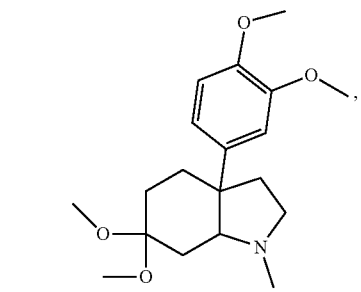
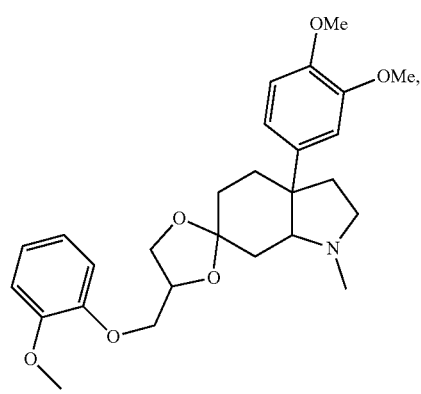
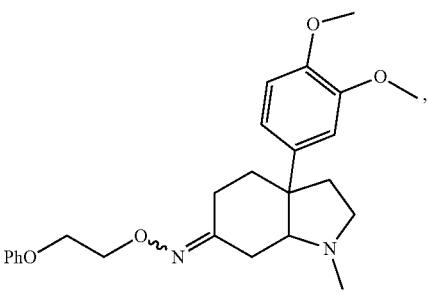
206
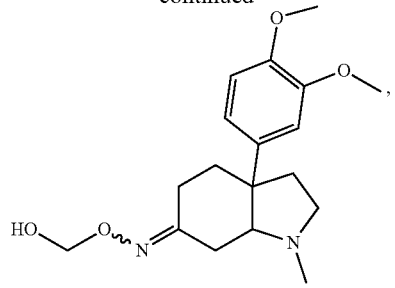
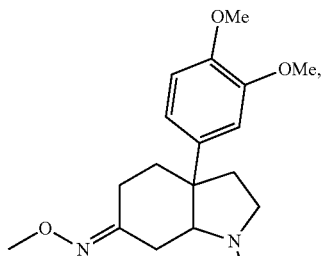
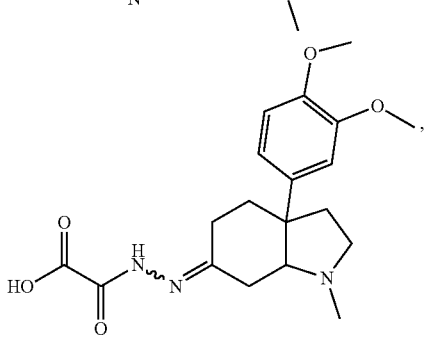
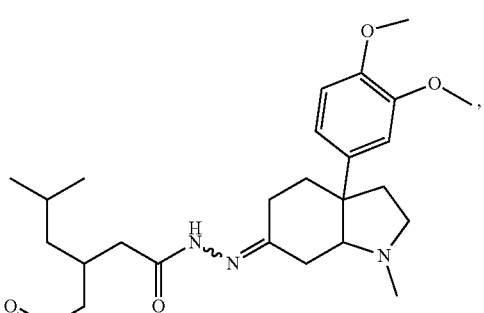
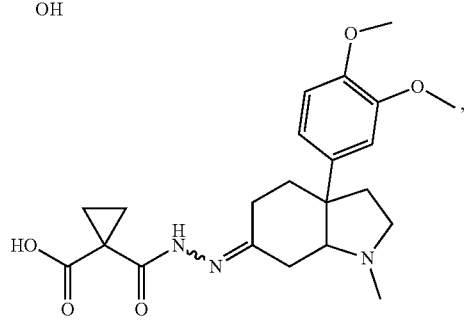

207
-continued
208
-continued
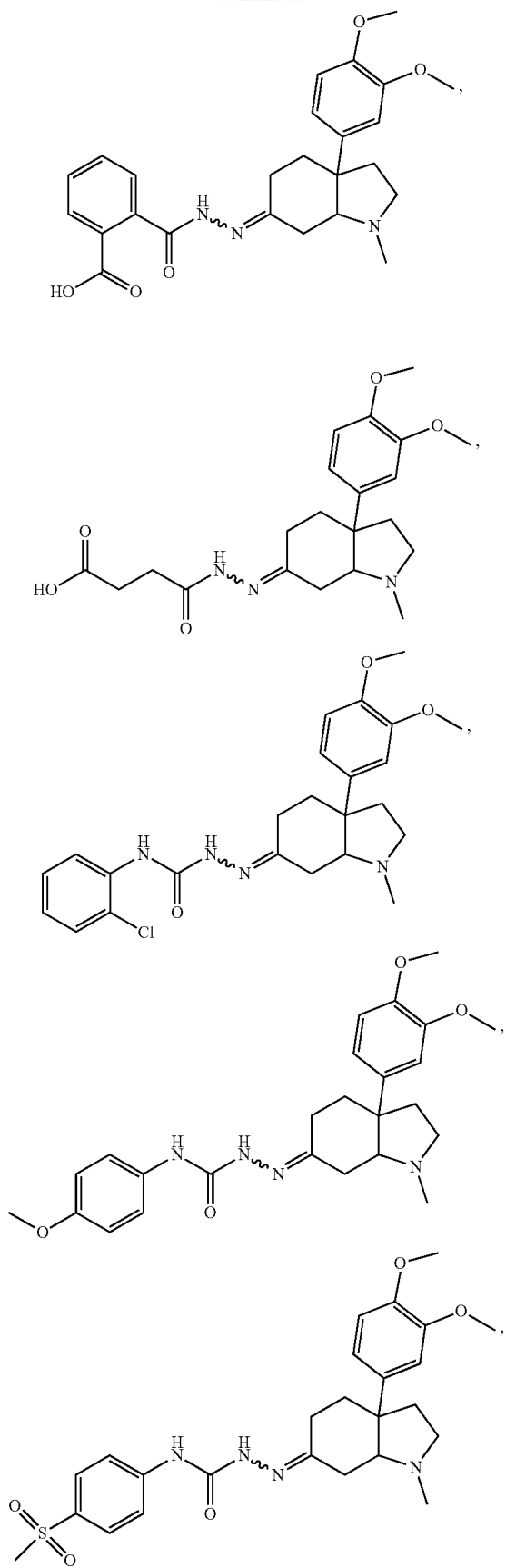
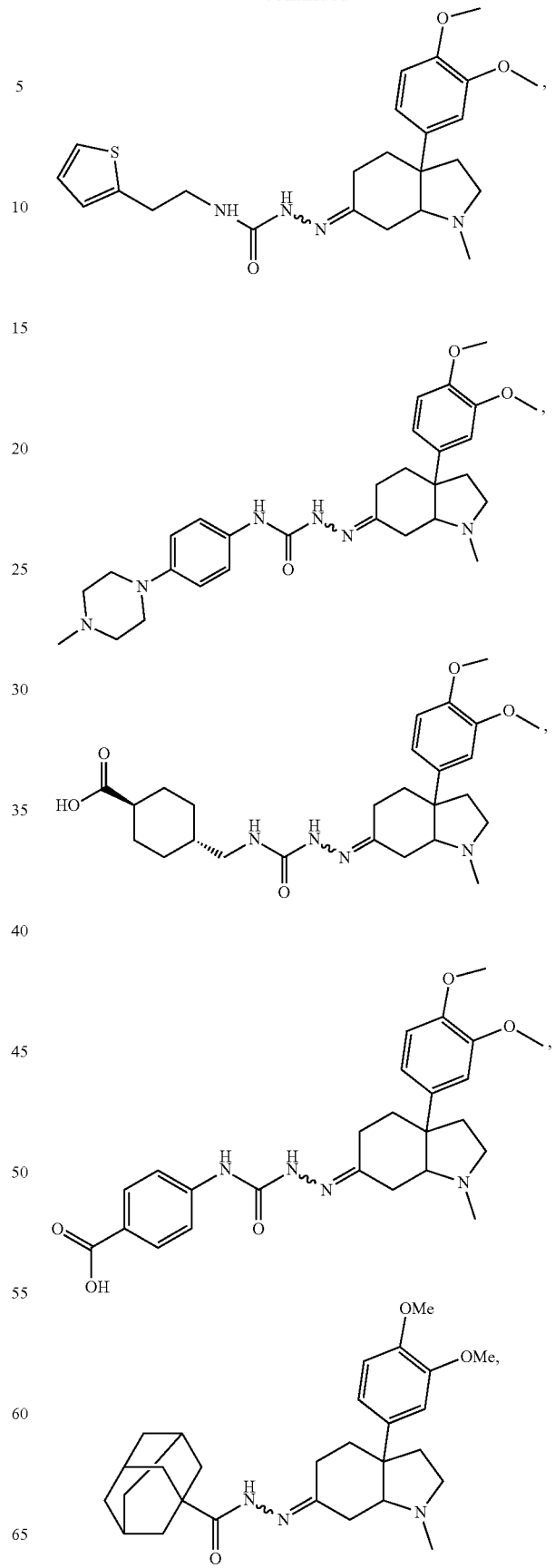

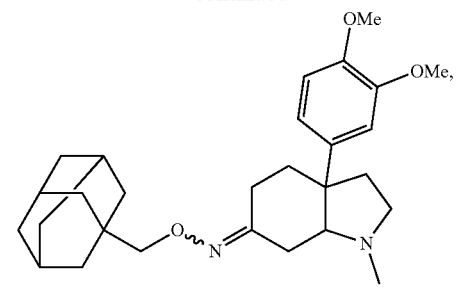
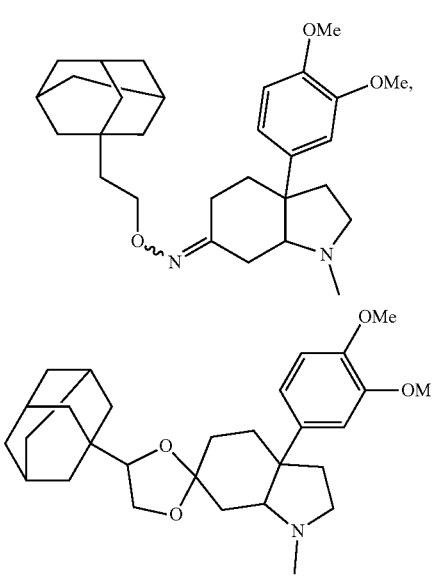
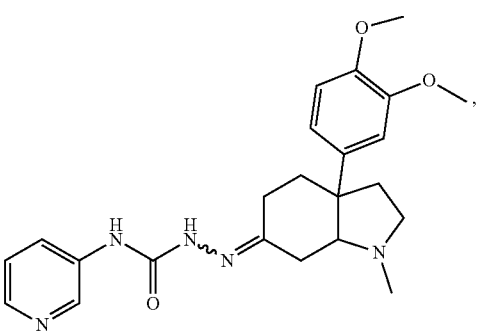
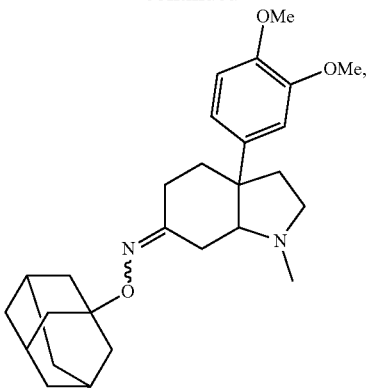
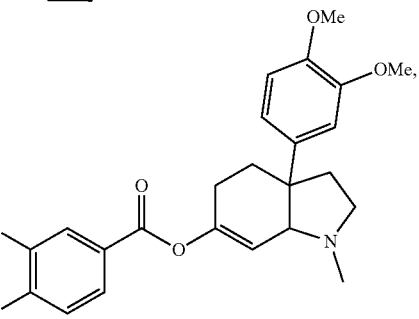
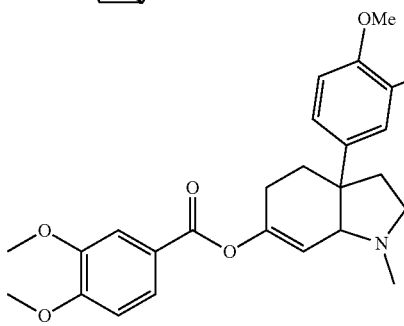
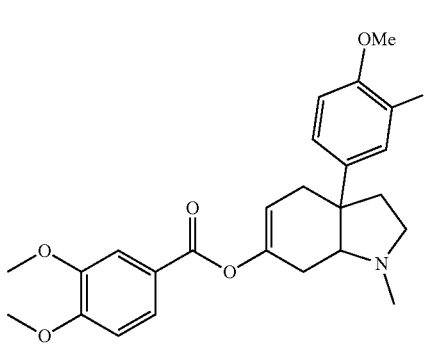

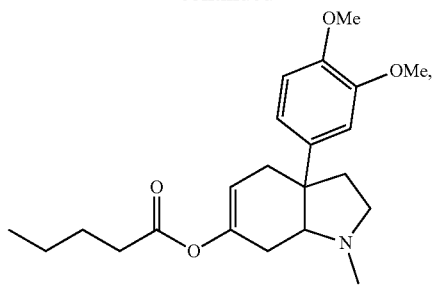
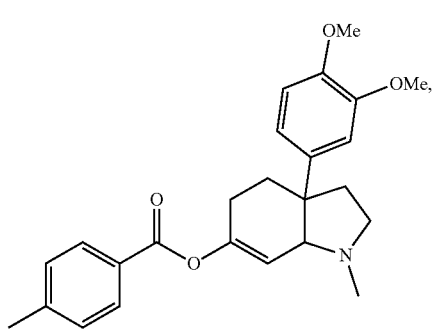
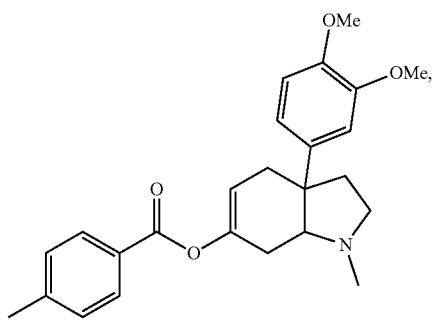
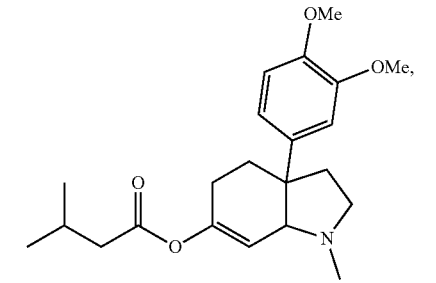
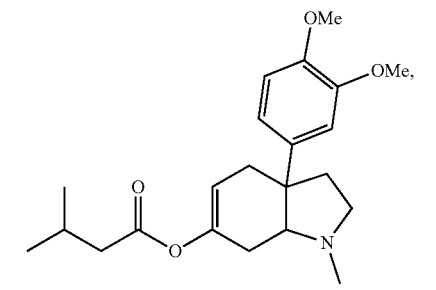
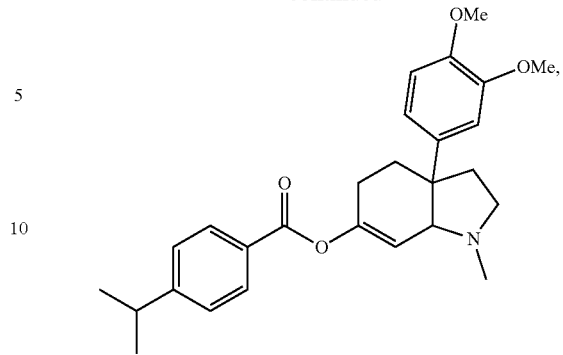
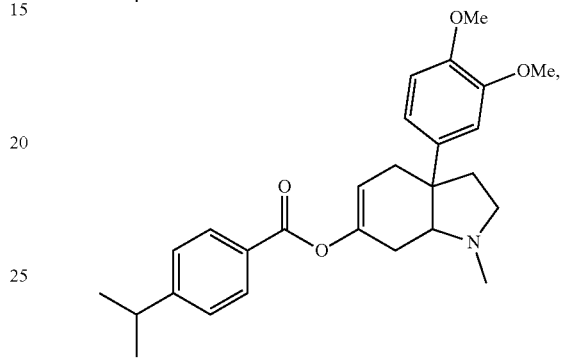
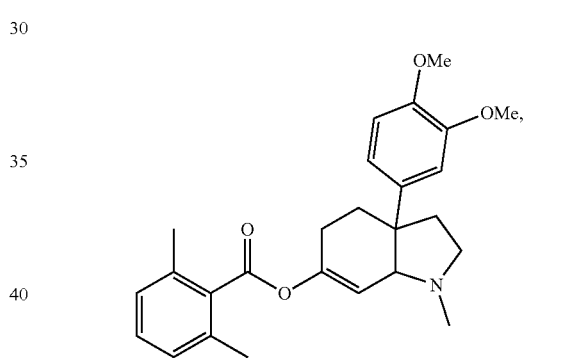
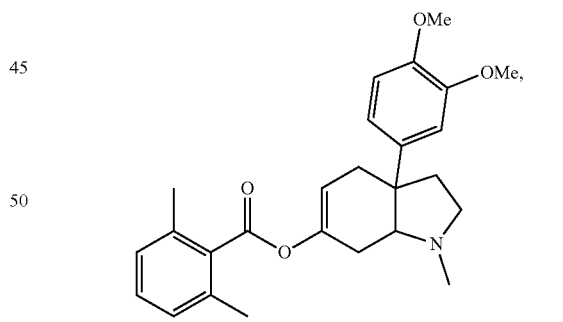
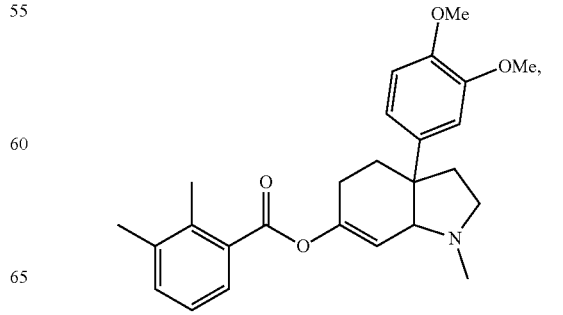

213
-continued
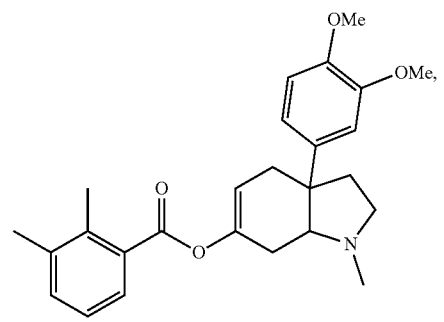
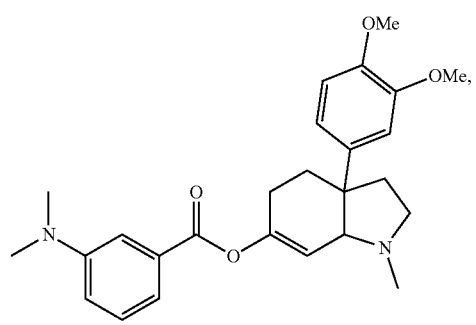
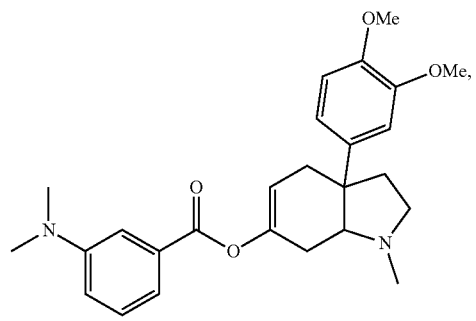
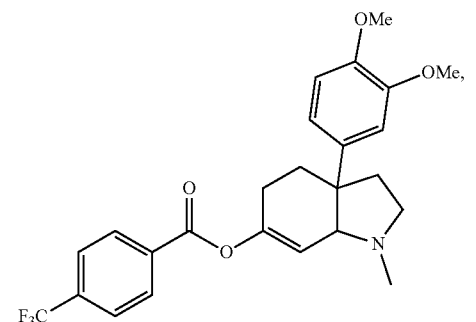
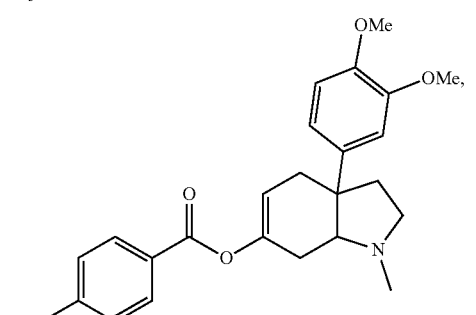
214
-continued
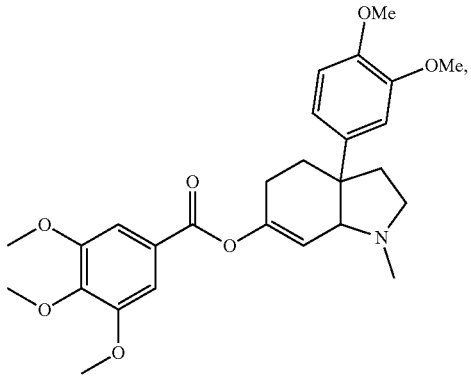
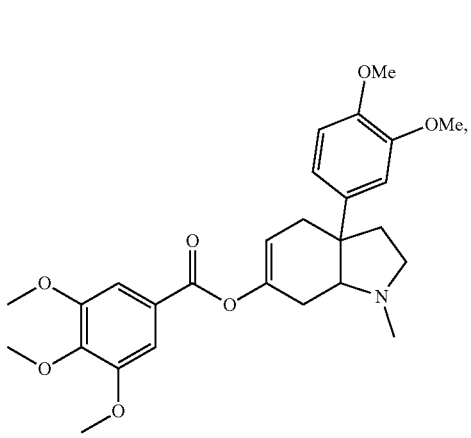
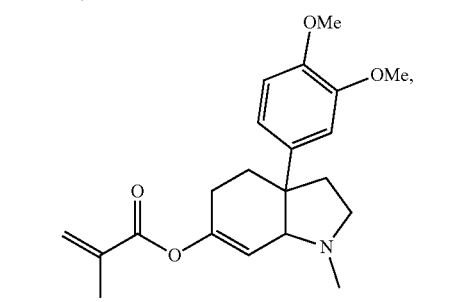
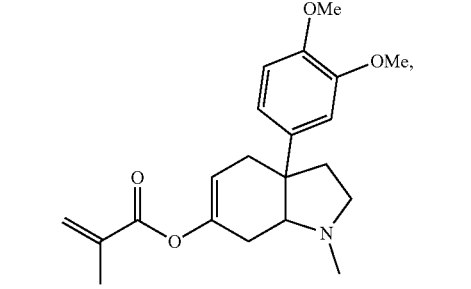
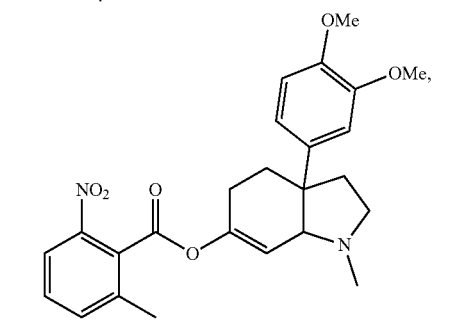

215
-continued
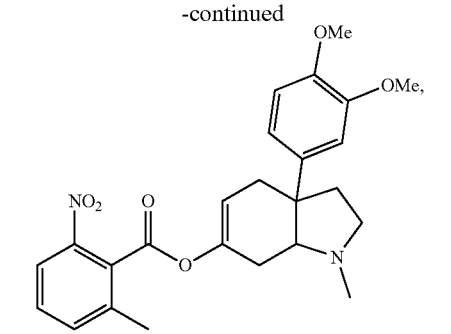
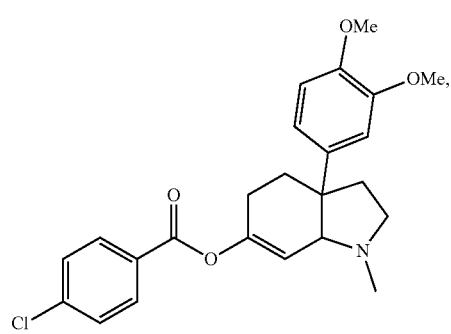
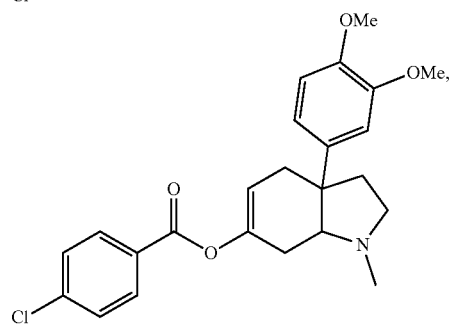
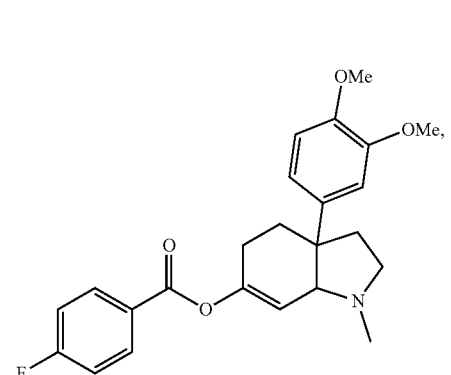
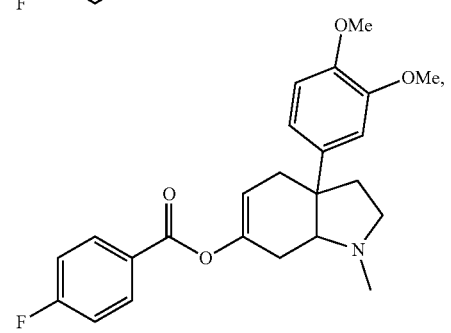
216
-continued
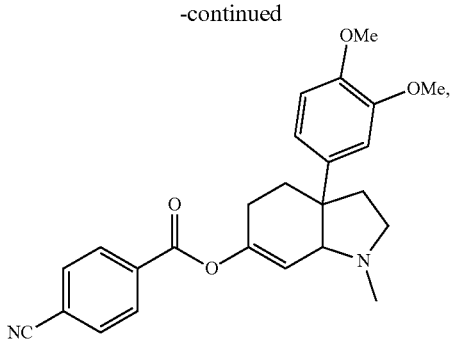
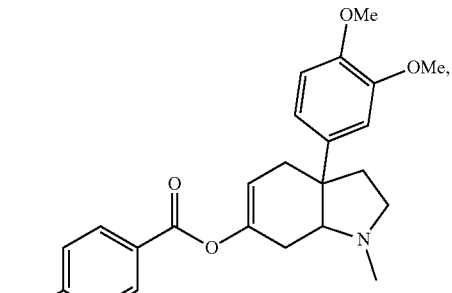
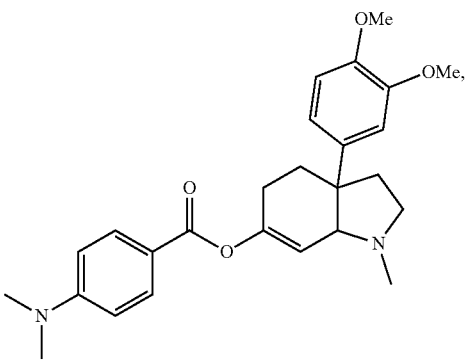
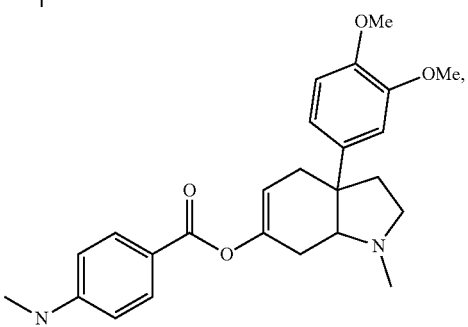
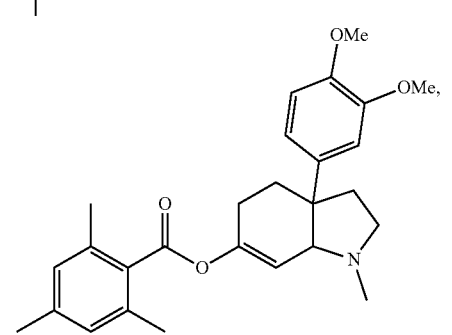

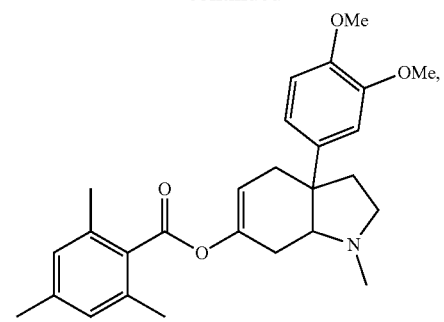
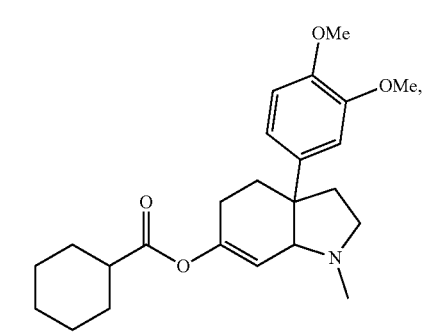
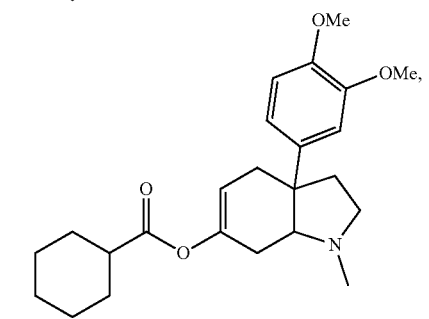
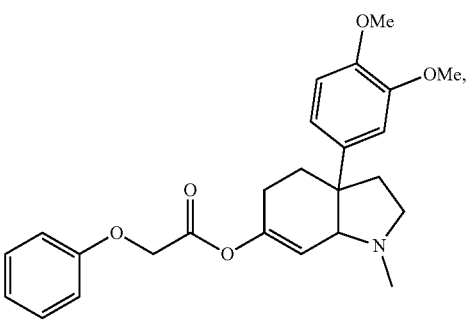
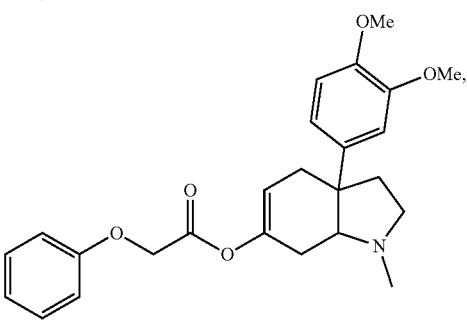
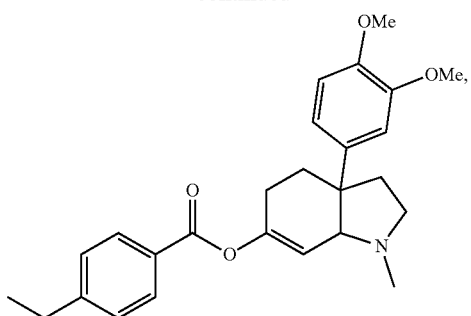
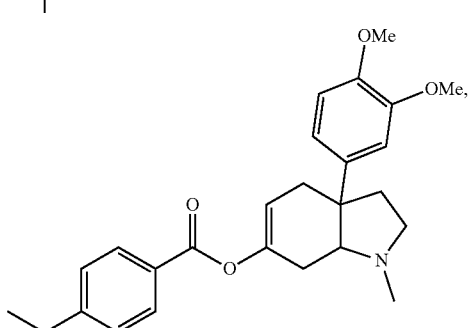
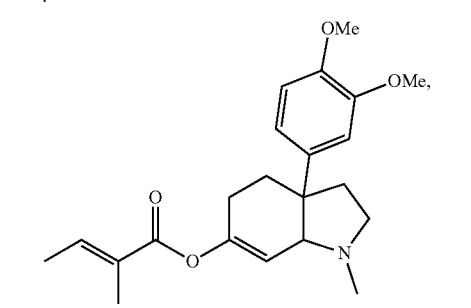
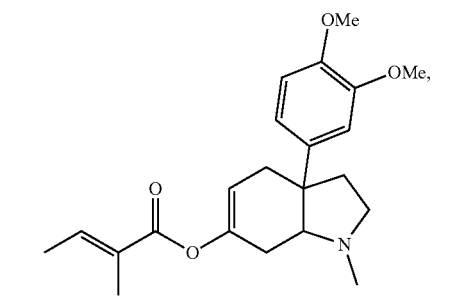
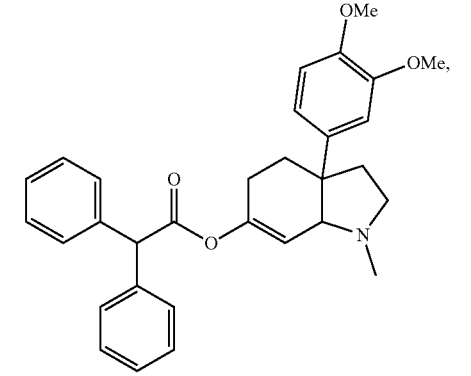

219
-continued
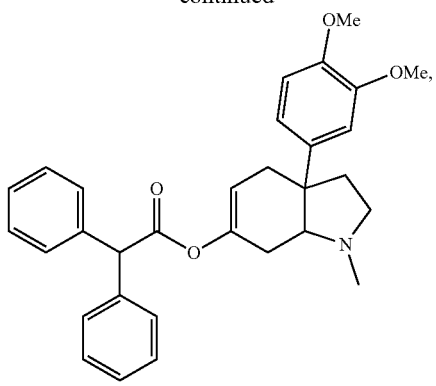
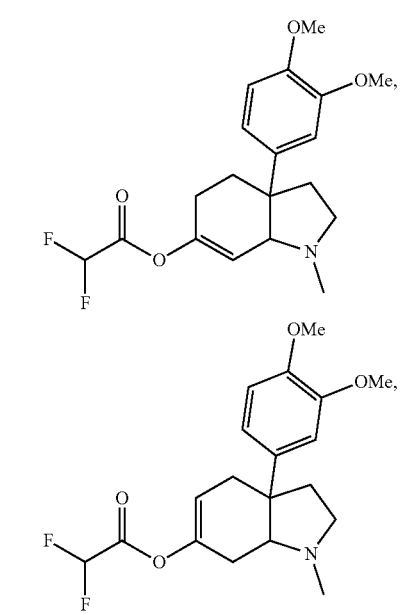

220
-continued
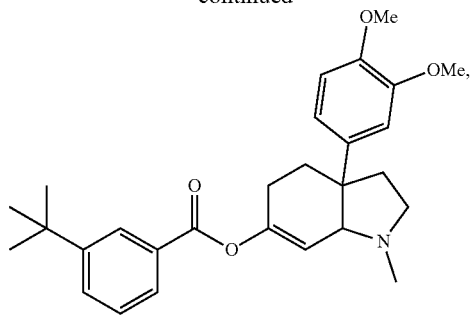
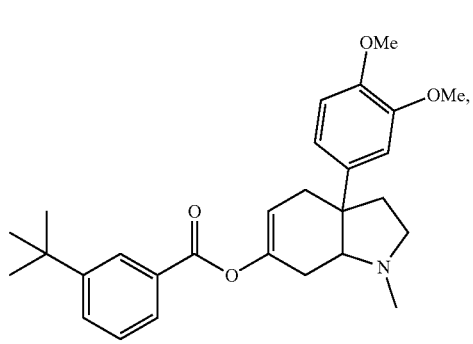
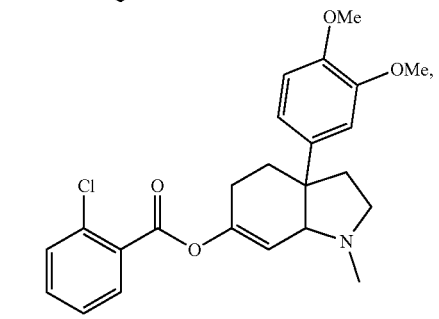
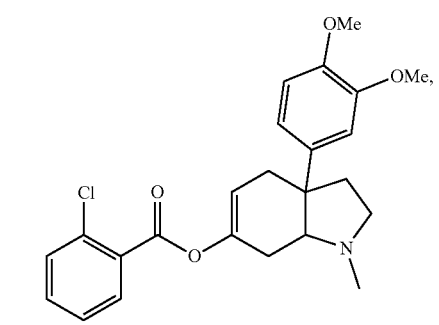
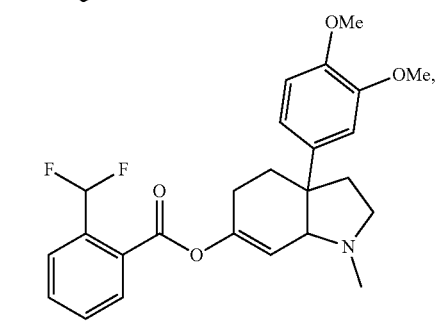

-continued
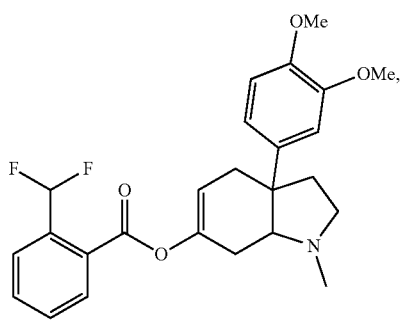
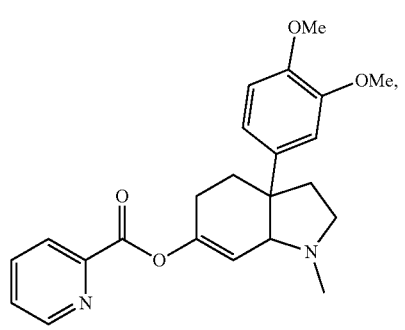
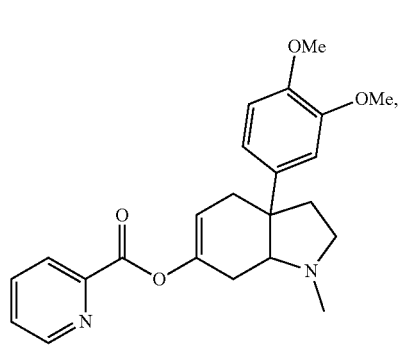
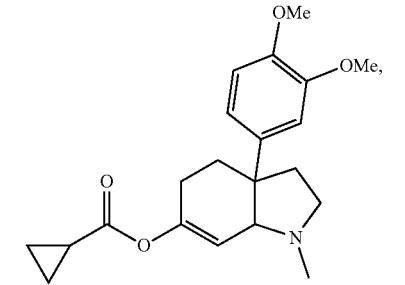
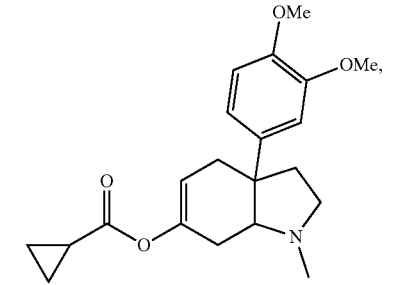
-continued
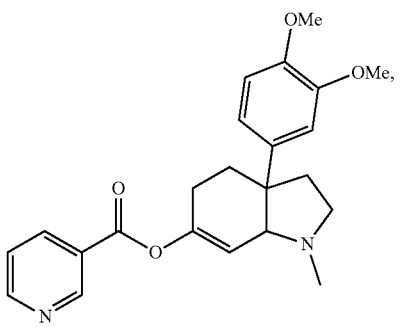
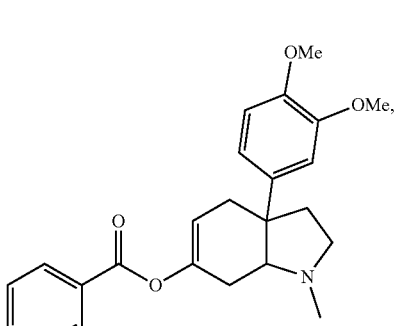
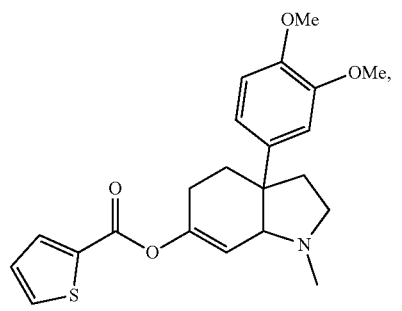
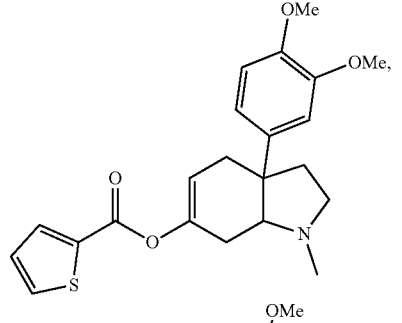
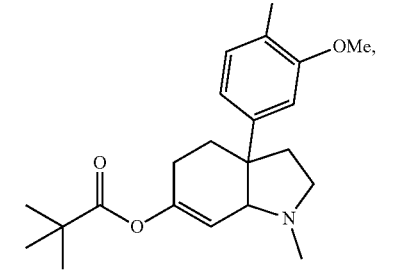

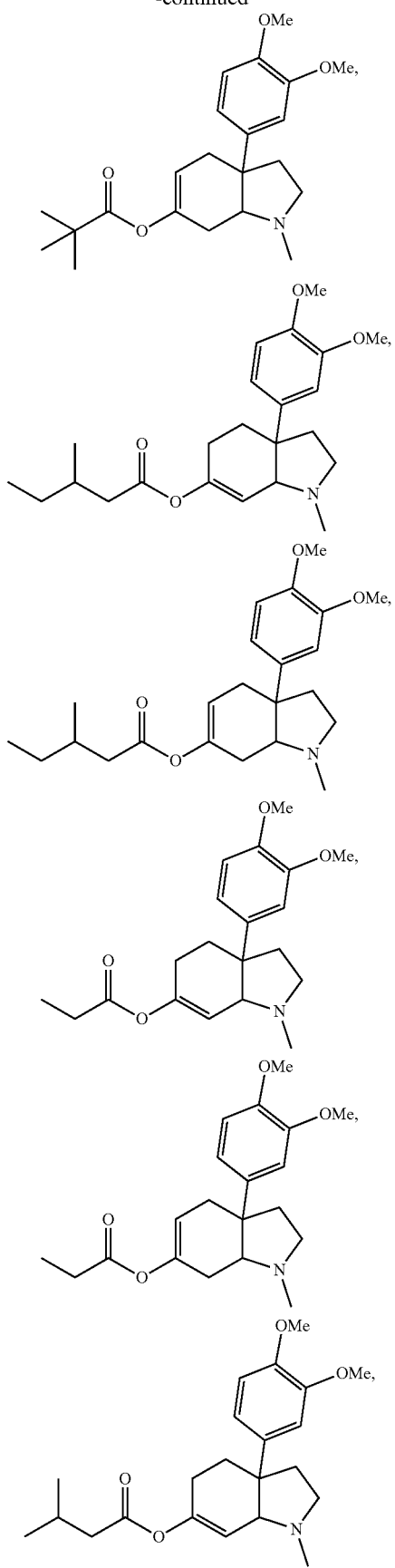
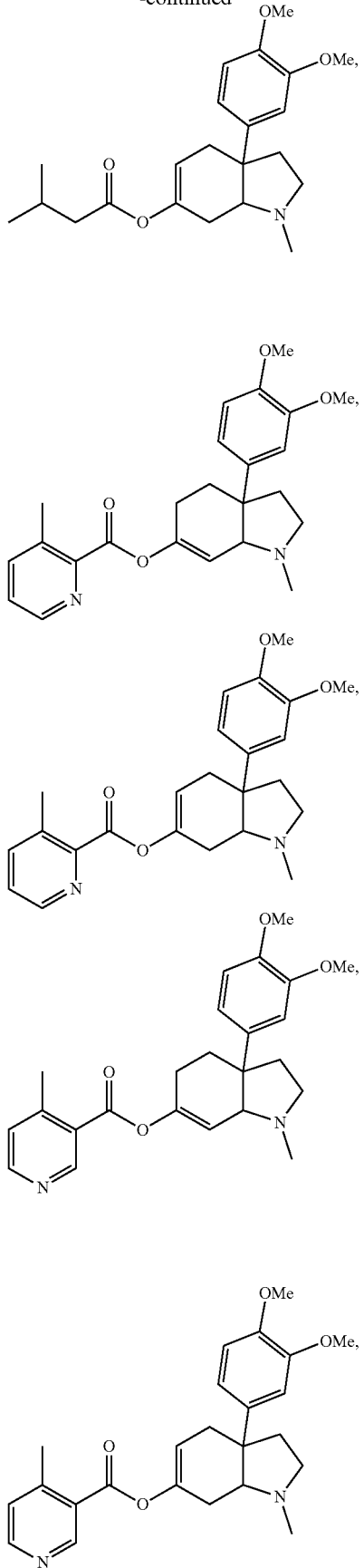

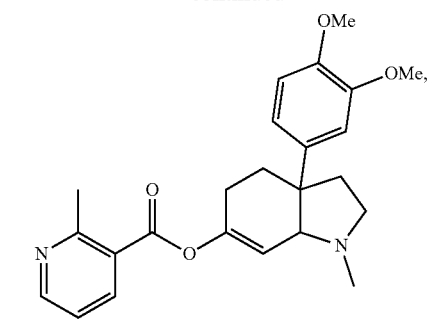
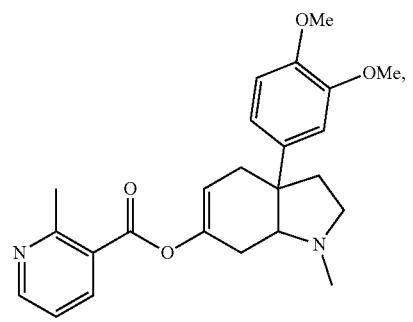
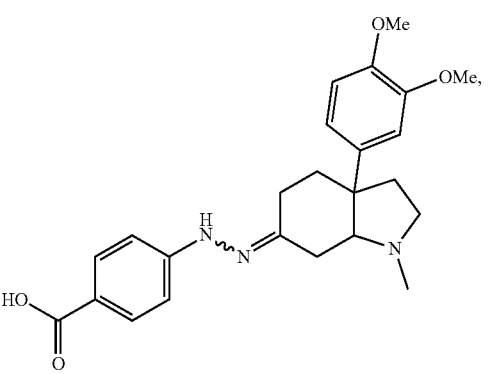
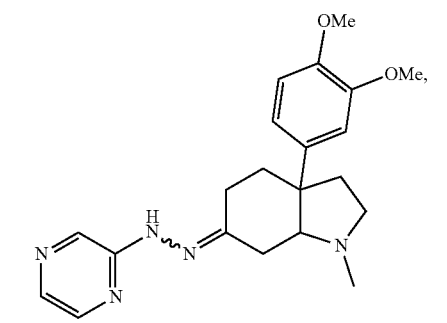
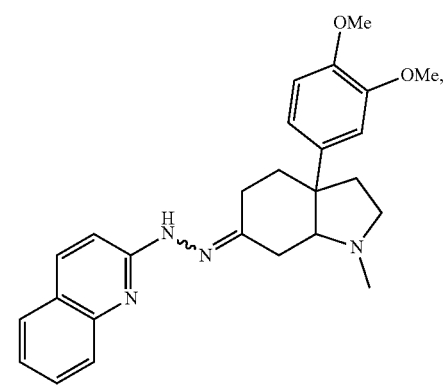
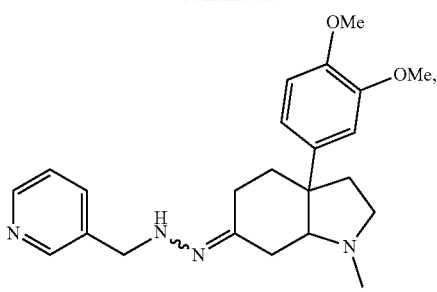
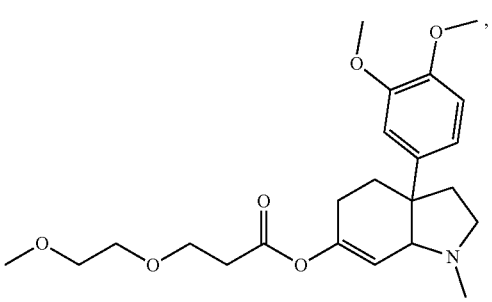
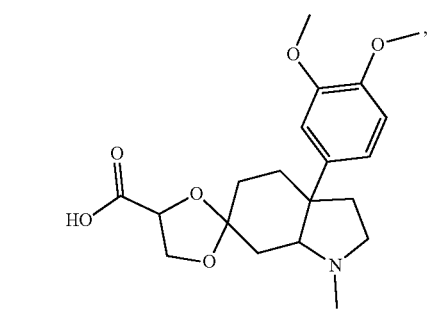
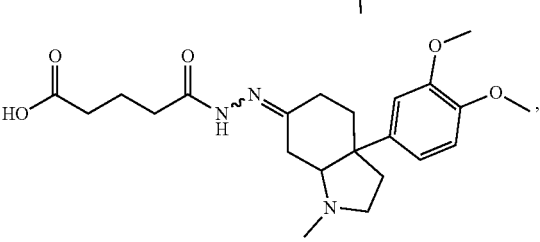
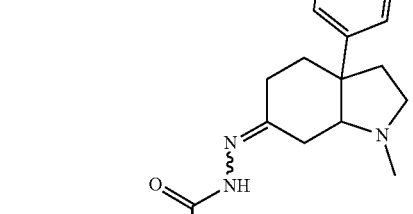
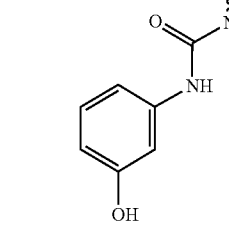

227
-continued
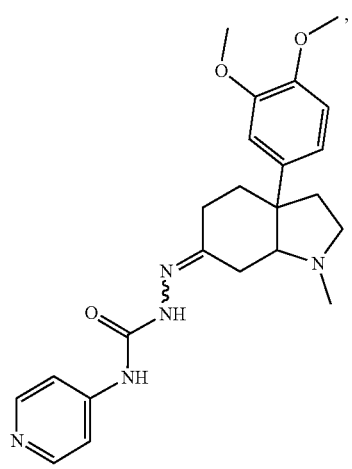
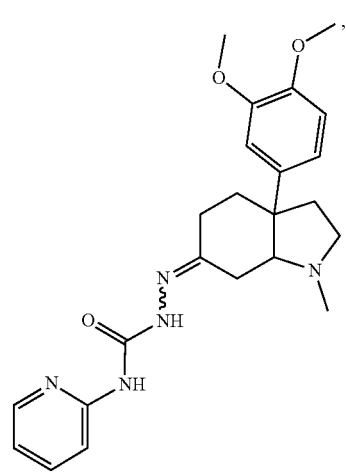
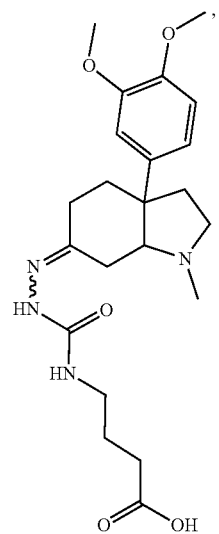
228
-continued
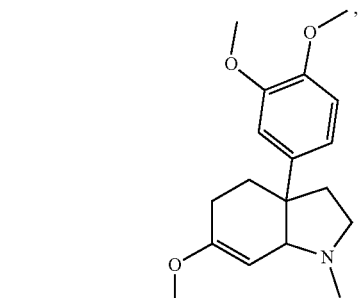
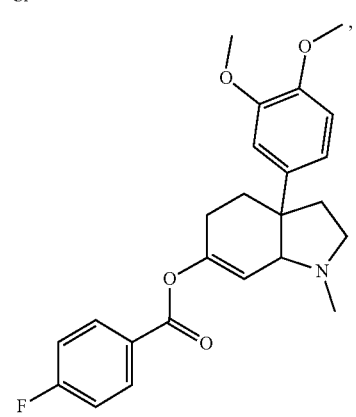
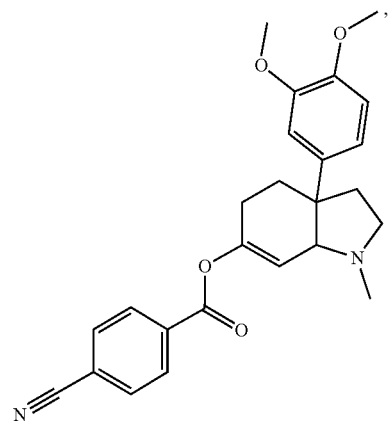
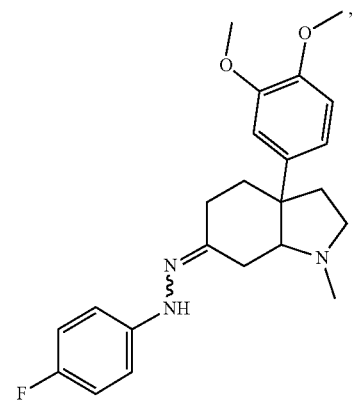

229
-continued
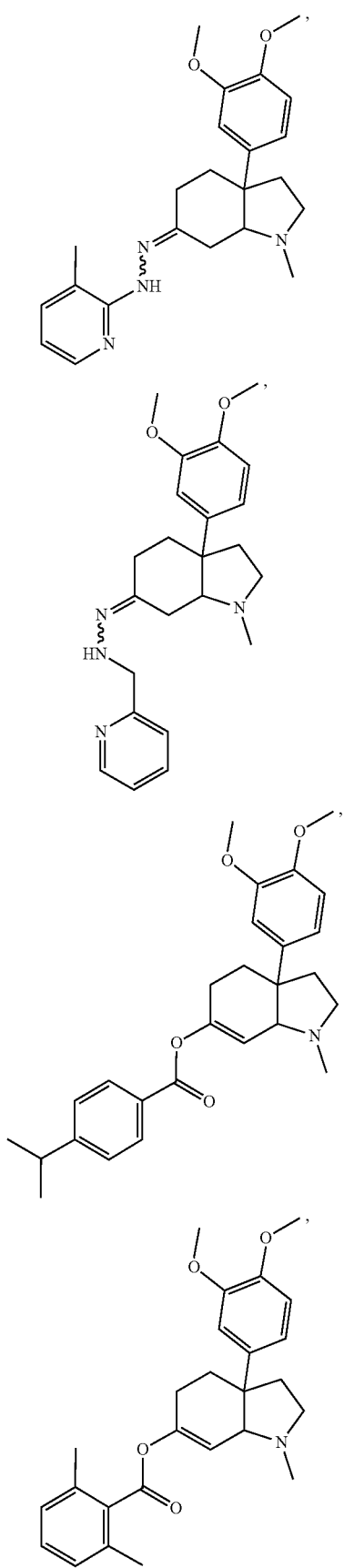 [SMILES: COc1ccc(C23CCC(=NNc4ncccc4C)CC2N(C)CC3)cc1OC ; COc1ccc(C23CCC(=NNCc4ccccn4)CC2N(C)CC3)cc1OC ; COc1ccc(C23CCC(OC(=O)c4ccc(C(C)C)cc4)=CC2N(C)CC3)cc1OC ; COc1ccc(C23CCC(OC(=O)c4c(C)cccc4C)=CC2N(C)CC3)cc1OC]
230
-continued
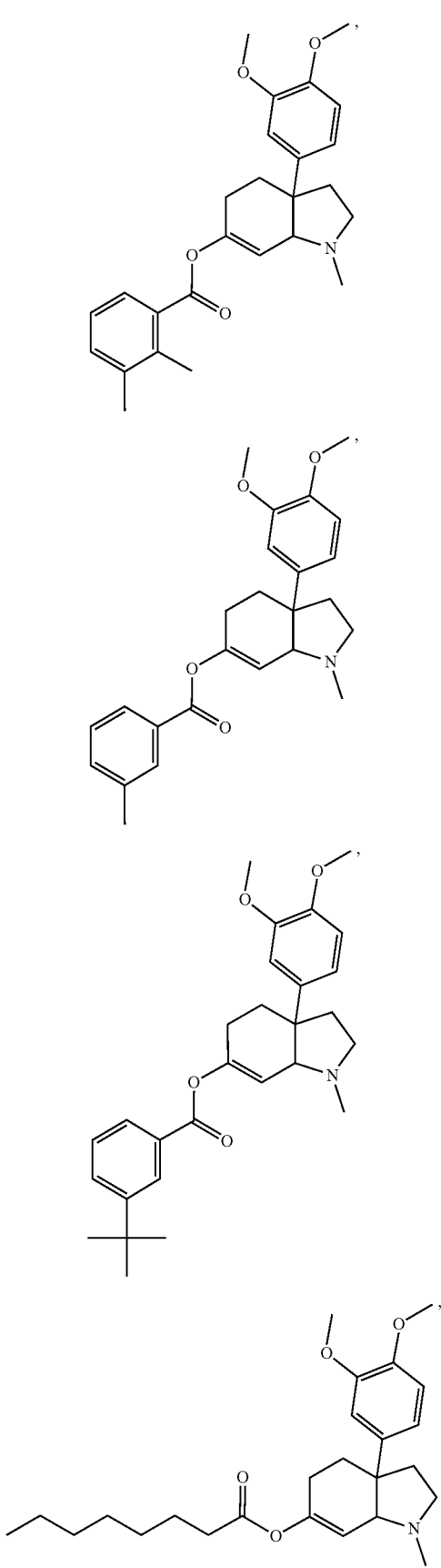

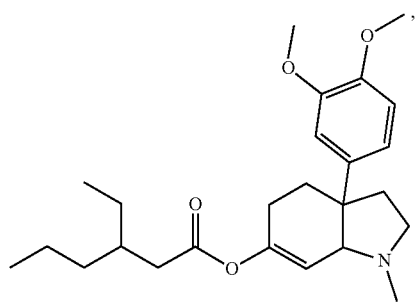
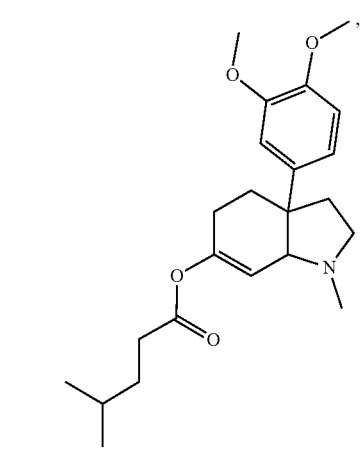
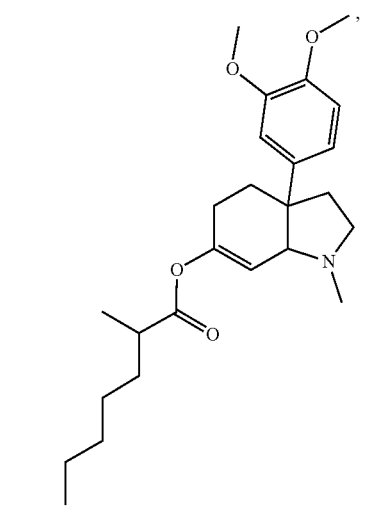
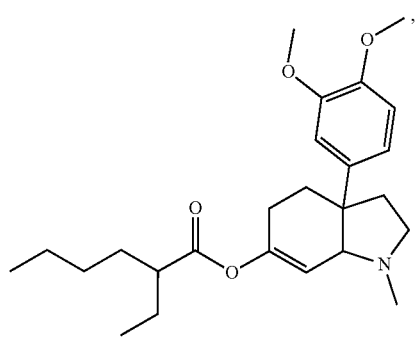
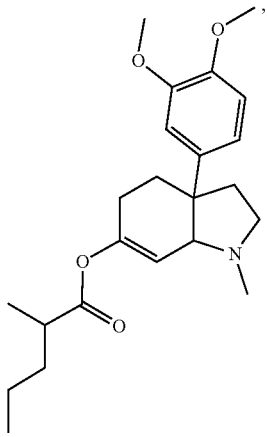
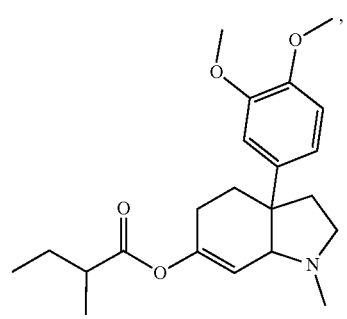
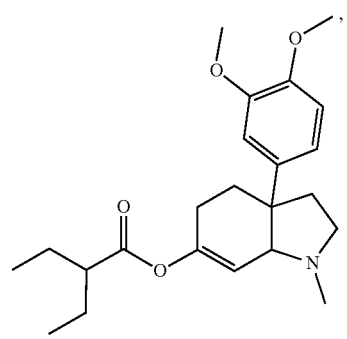
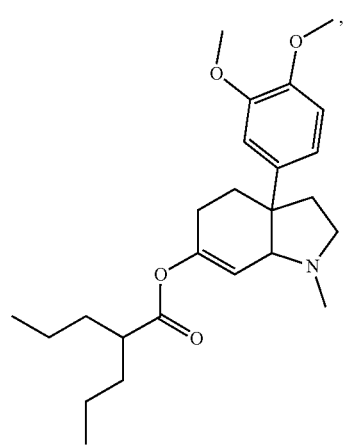

233
-continued
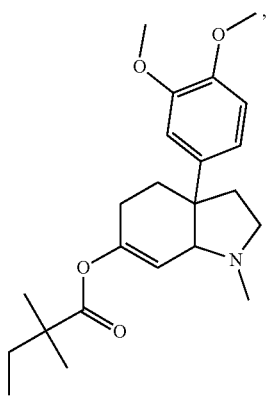
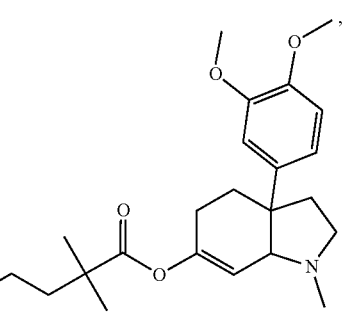
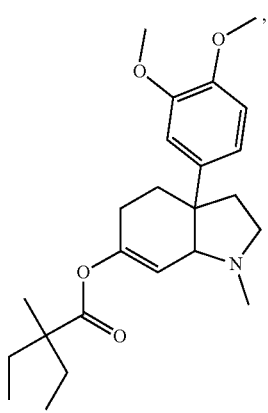
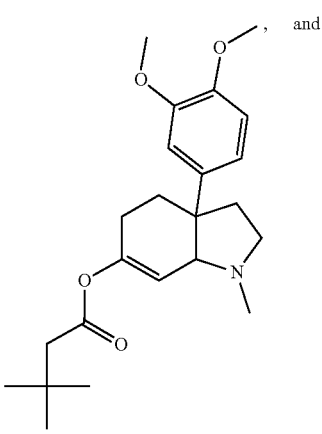
234
-continued
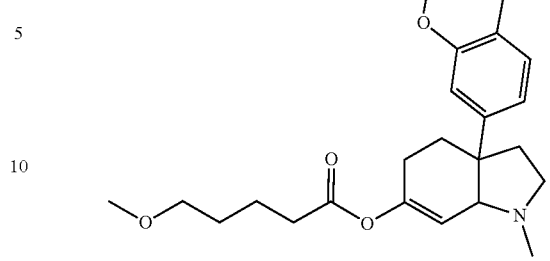
or a pharmaceutically acceptable salt thereof.
In some embodiments, the compound is selected from the group consisting of:
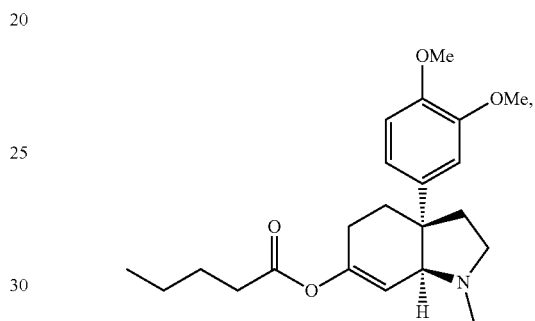
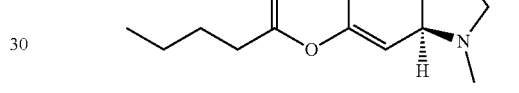
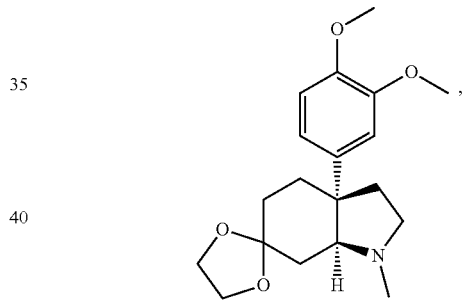
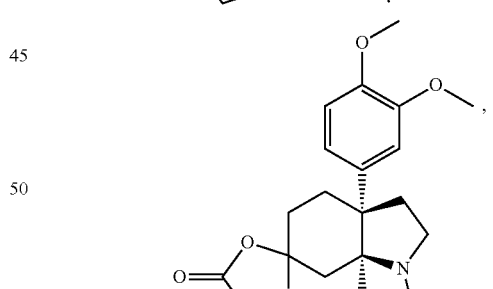
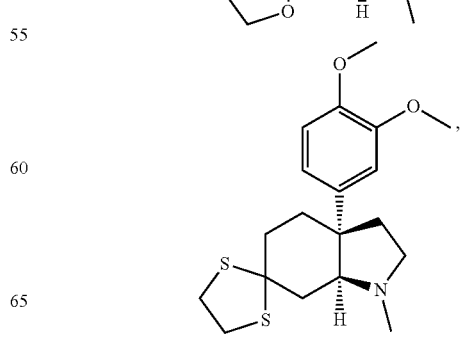

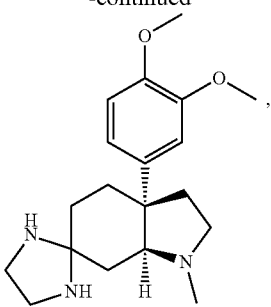
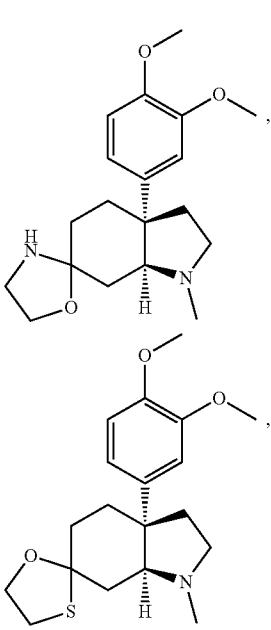
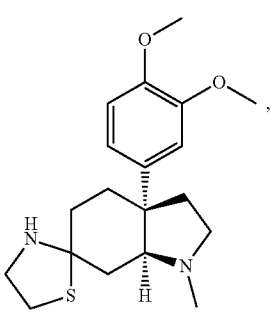
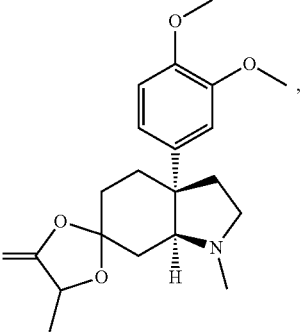
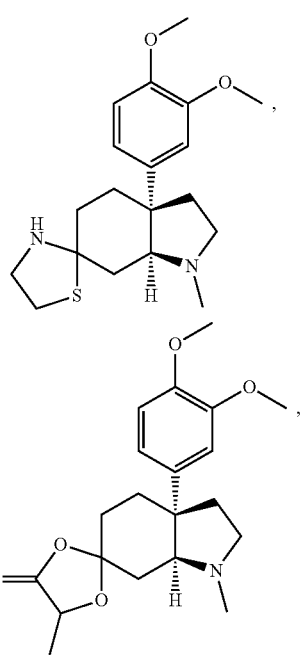
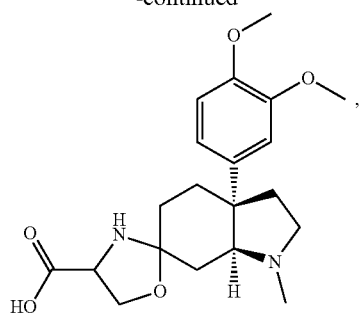
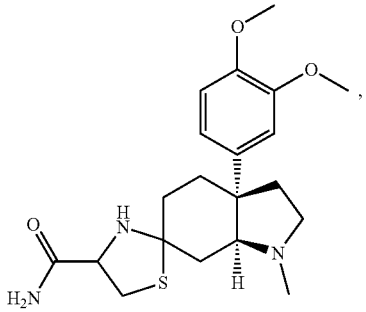
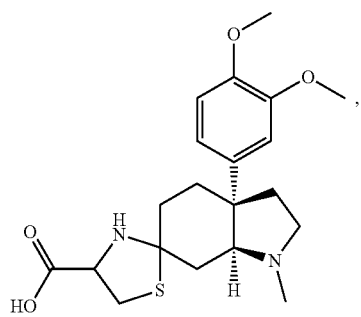
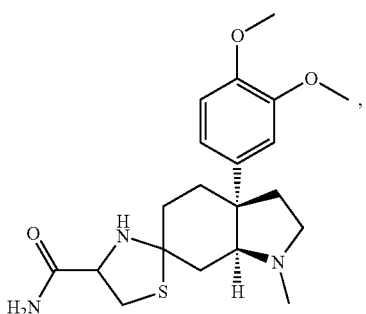
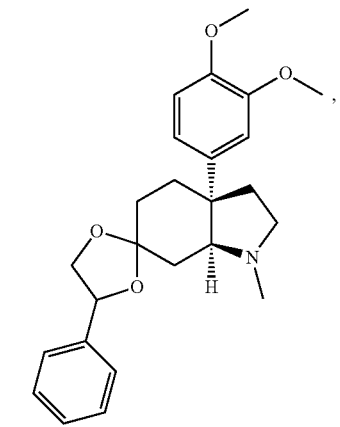

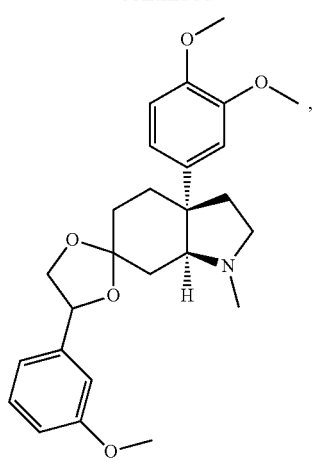
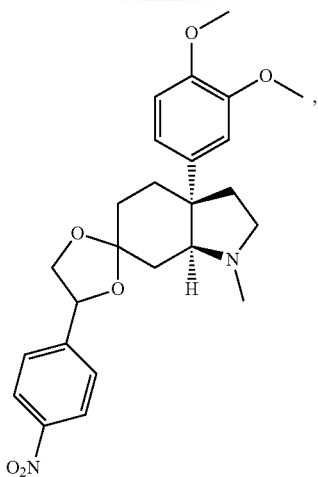
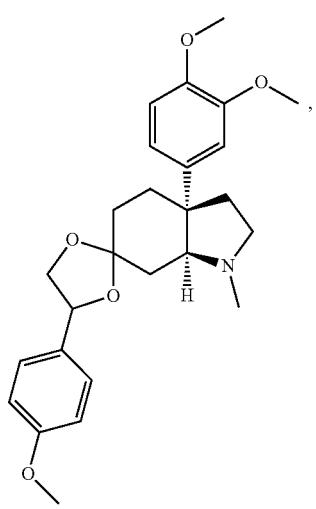
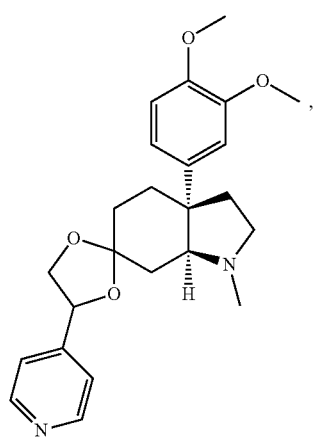
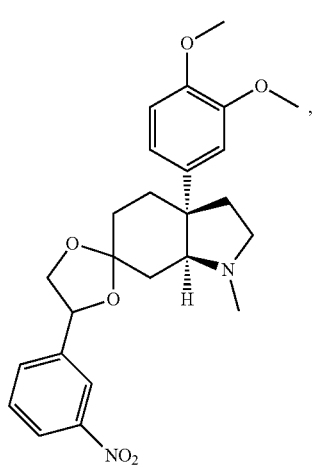
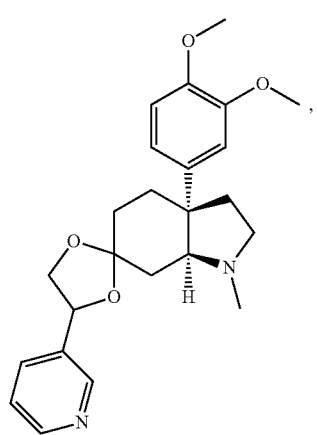

239
-continued
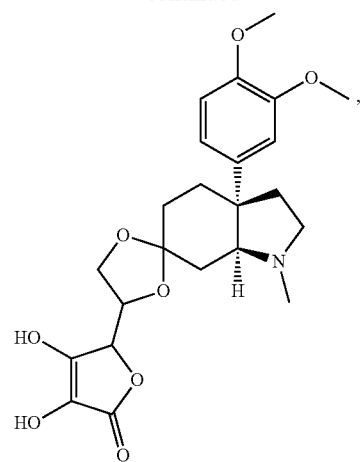
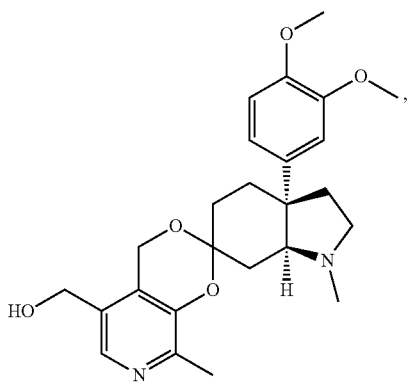
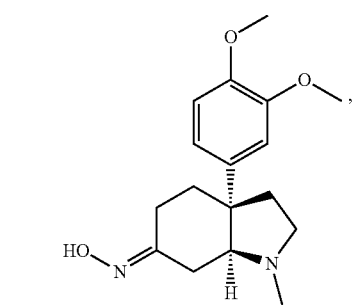
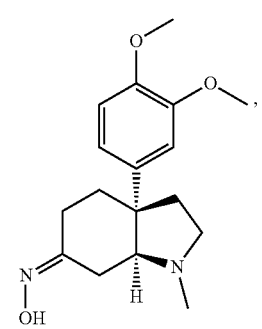
240
-continued
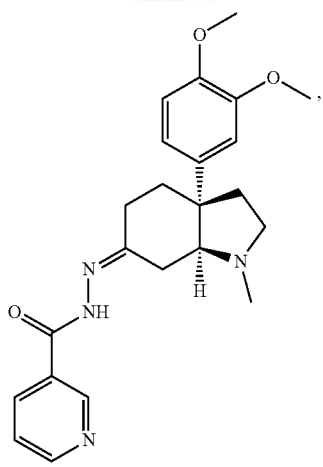
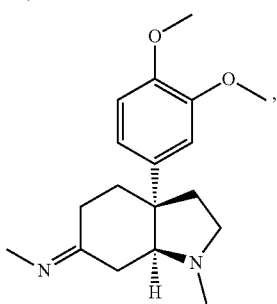
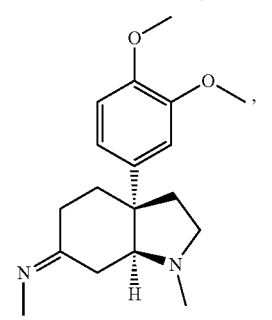
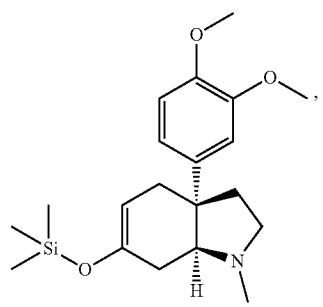
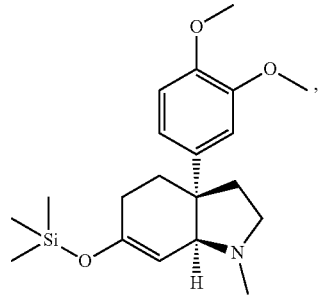

241
-continued
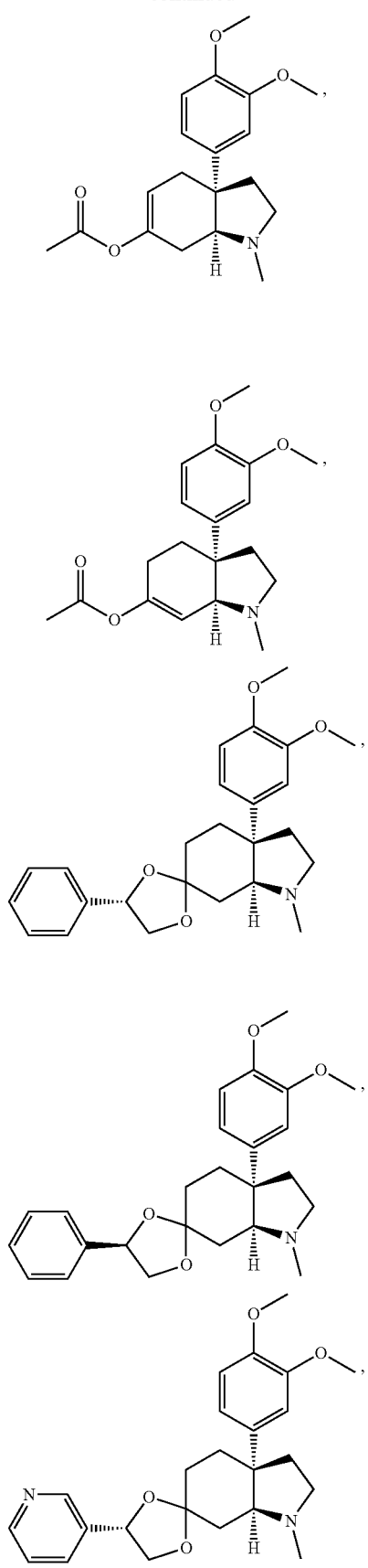
242
-continued
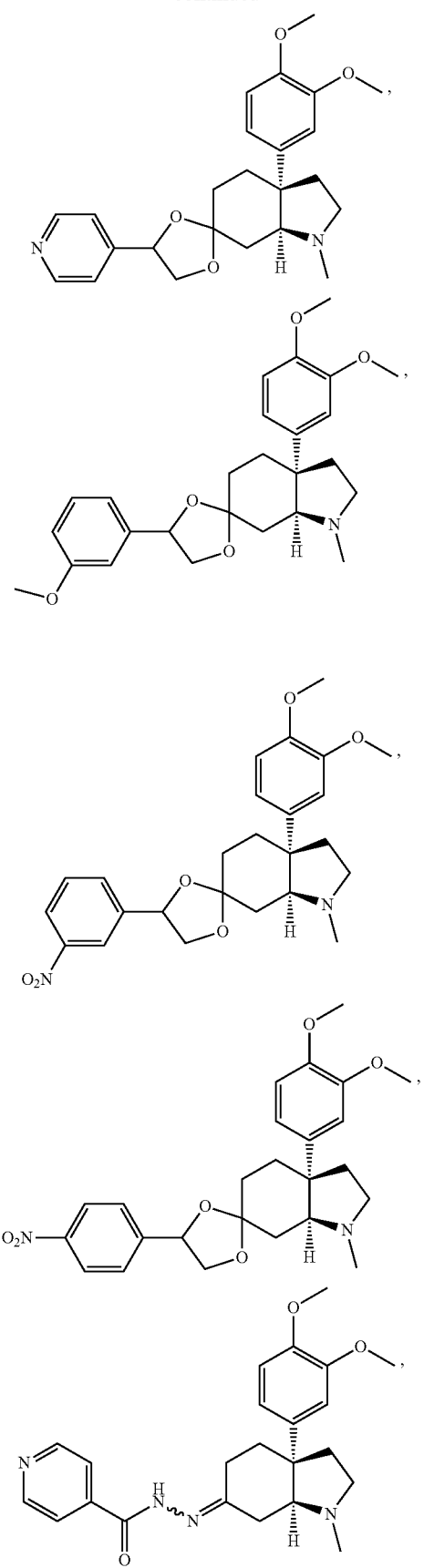

243
-continued
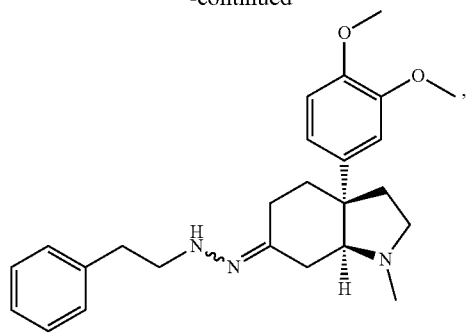
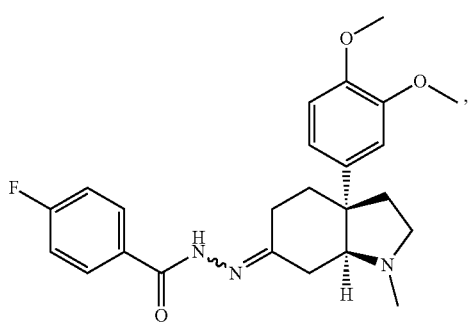
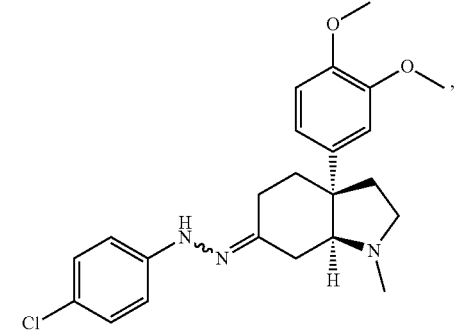
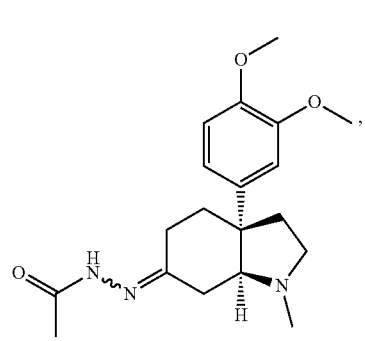
244
-continued
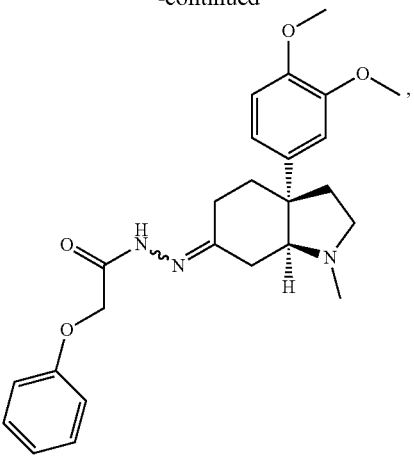
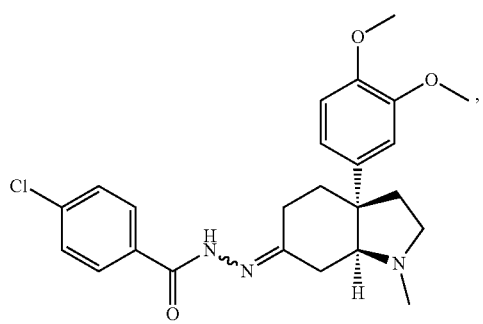
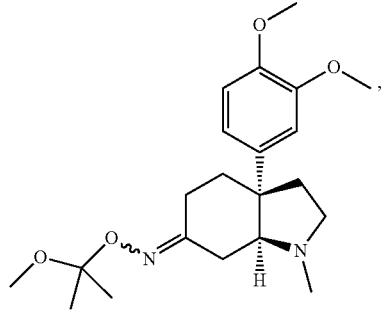
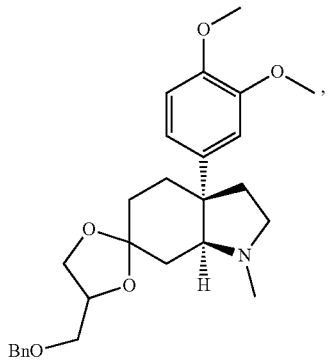

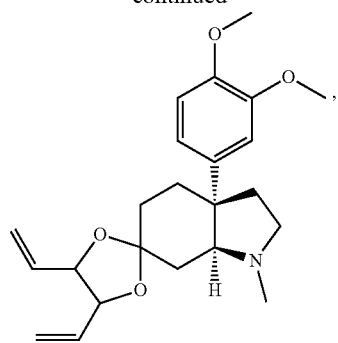
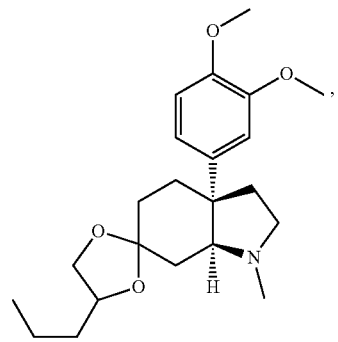

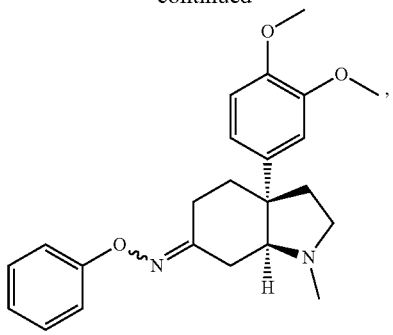
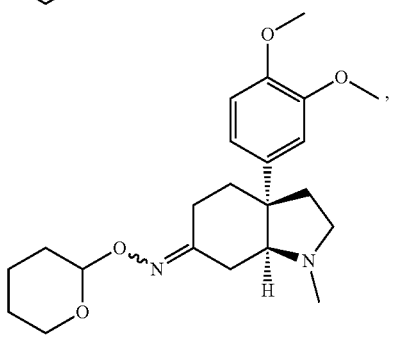

247
-continued
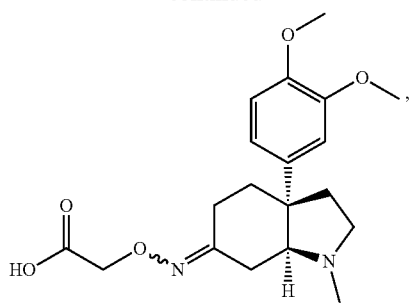
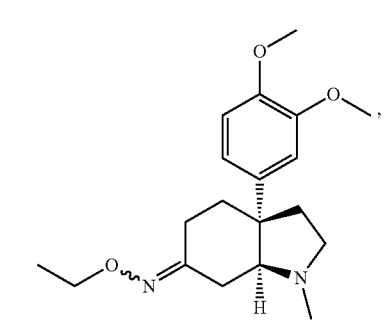
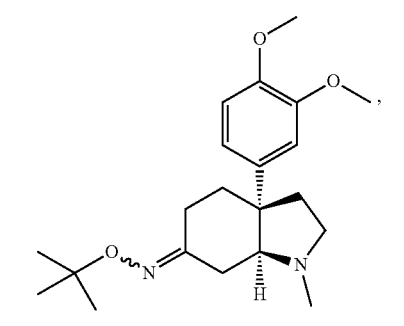
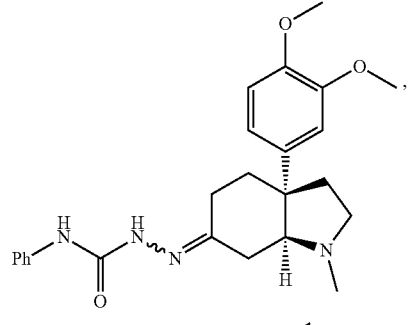
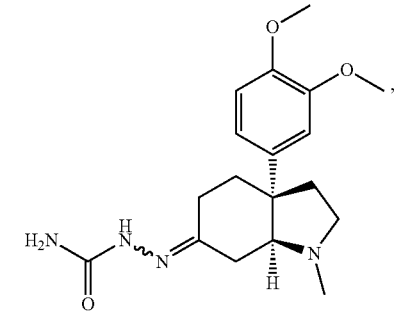
248
-continued
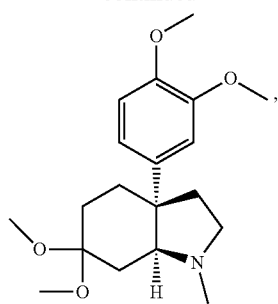
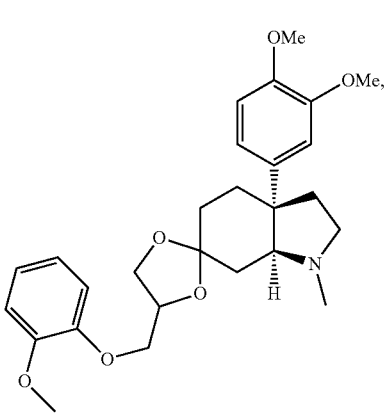
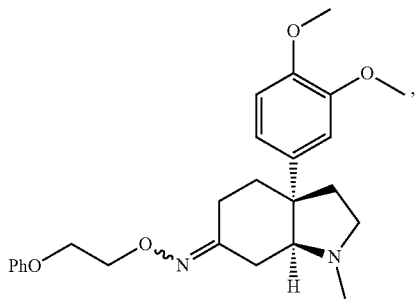
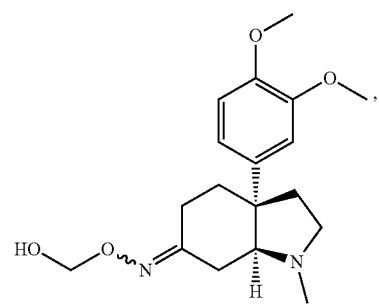
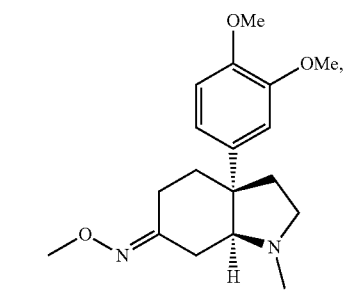

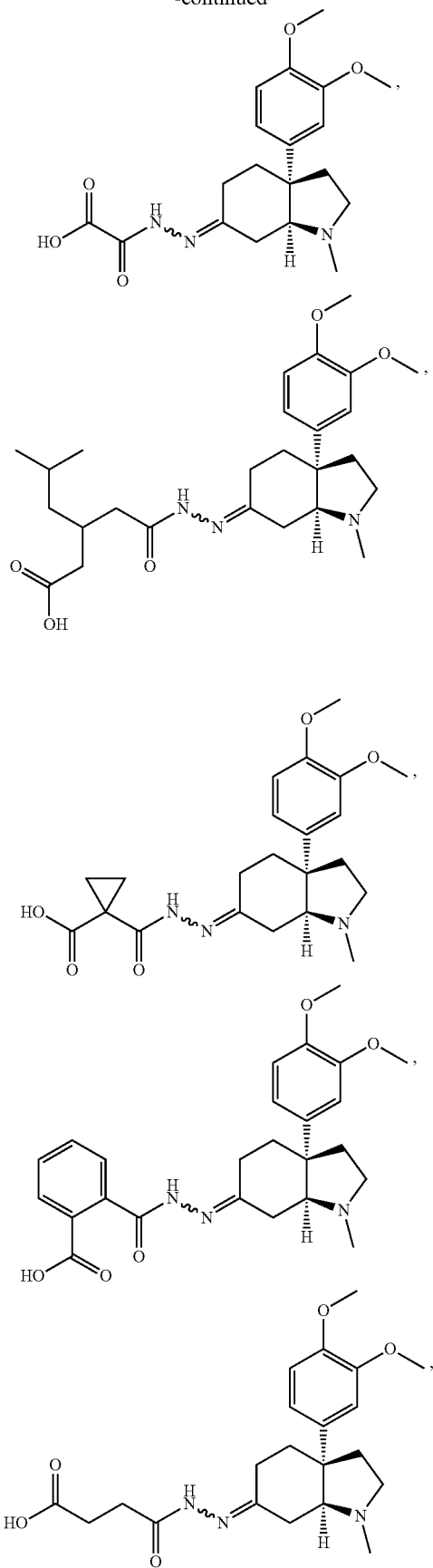
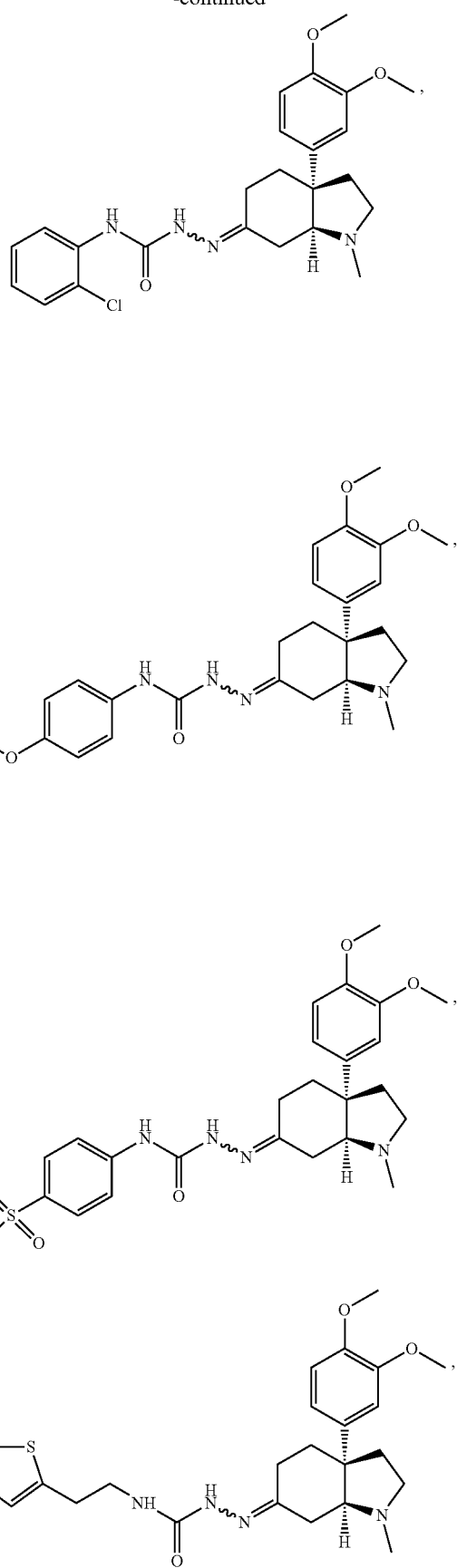

251
-continued
252
-continued
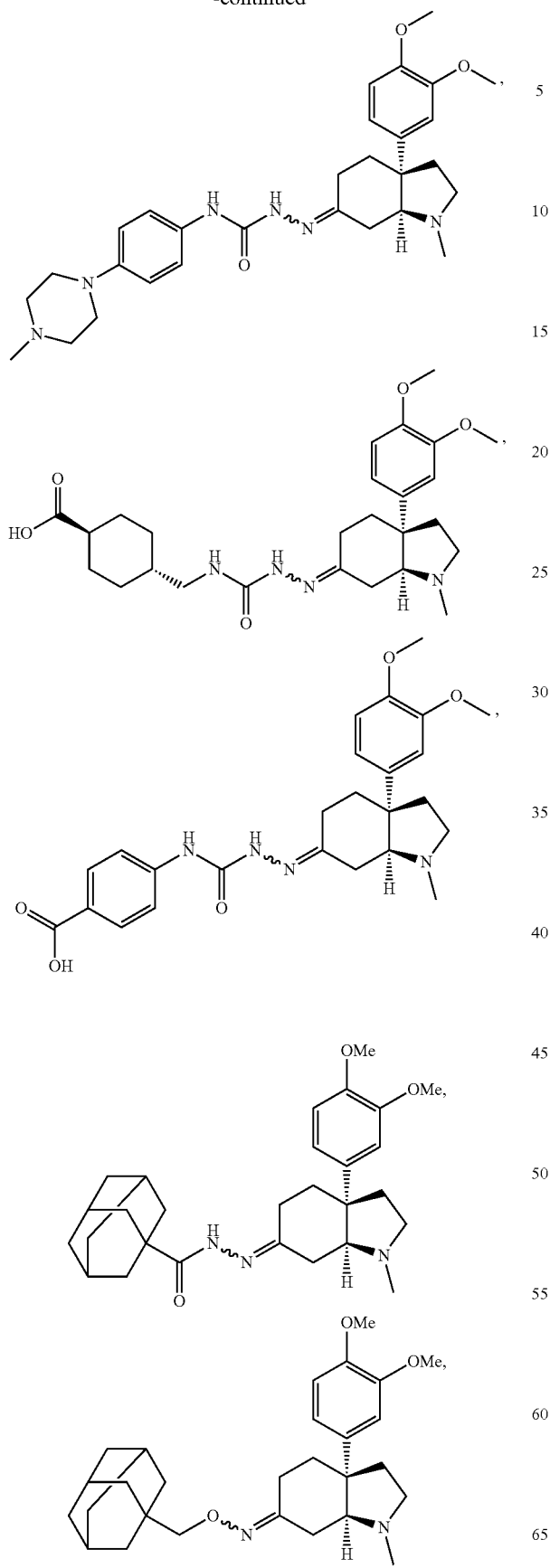
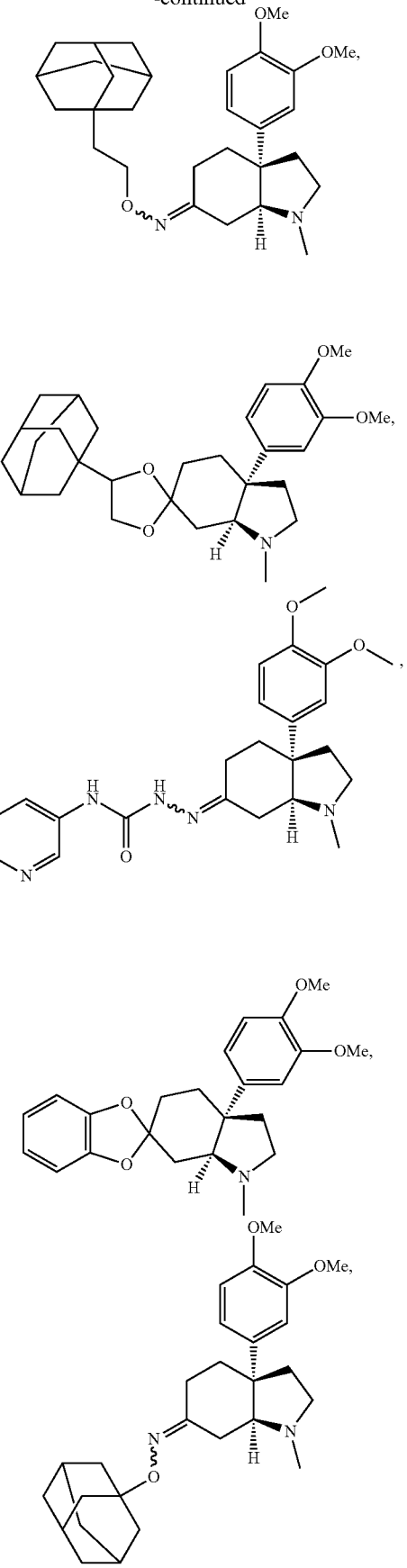

253
-continued
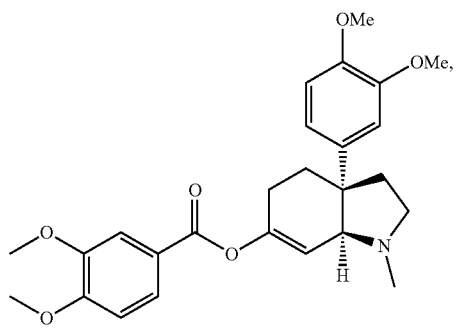
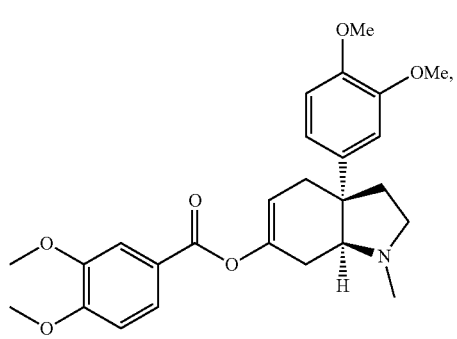
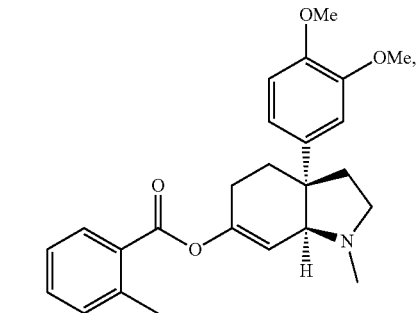
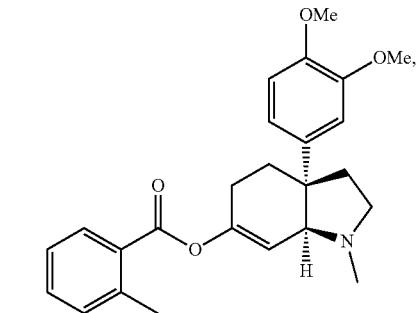
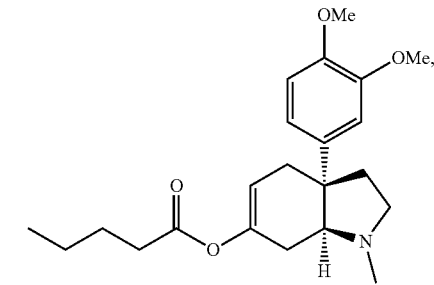
254
-continued
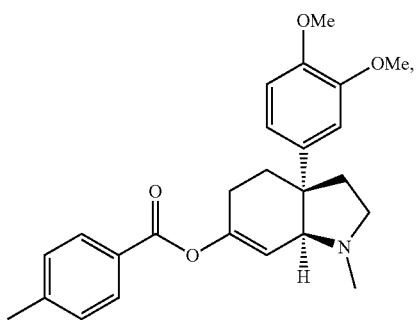
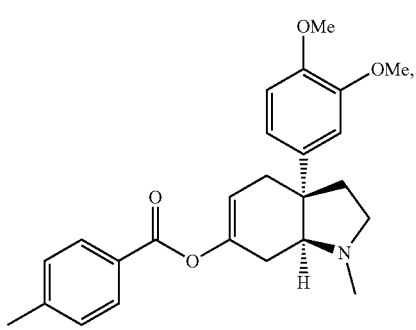
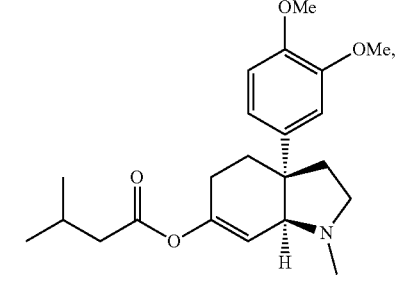
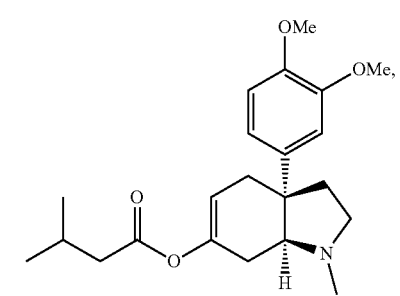
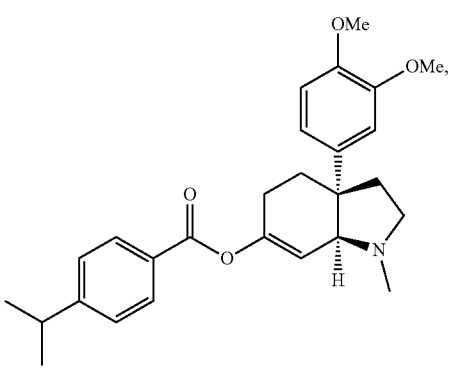

255
-continued
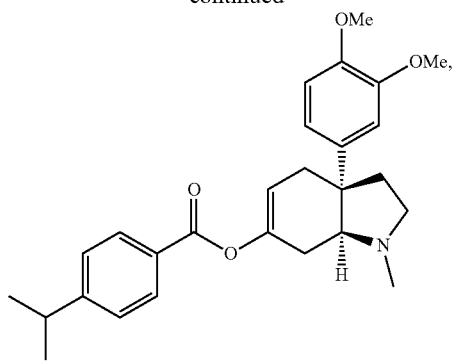
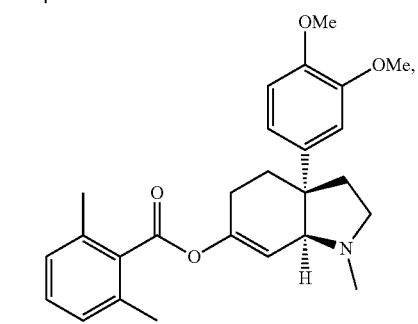
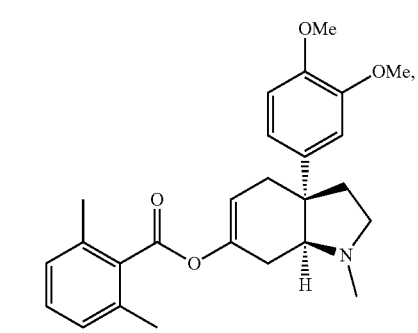
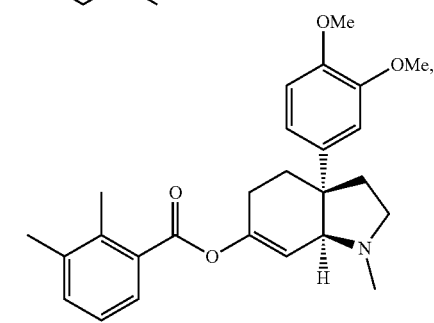
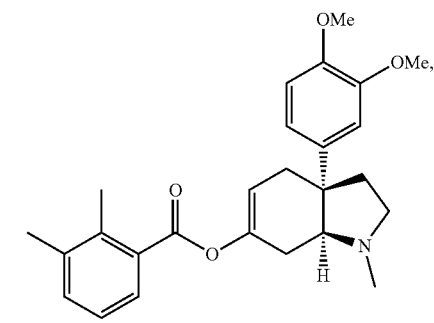
256
-continued
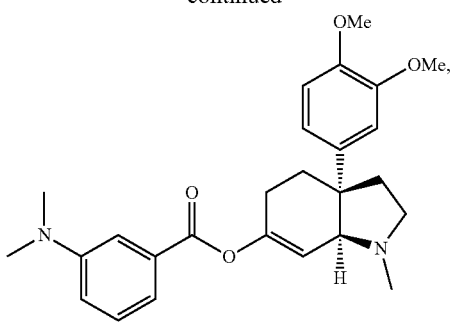
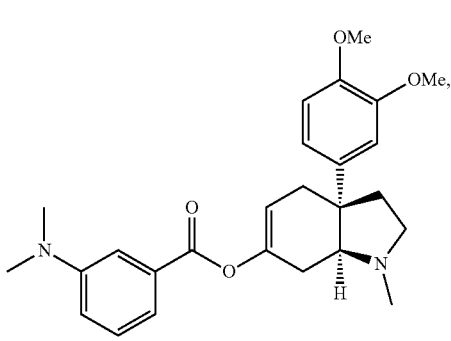
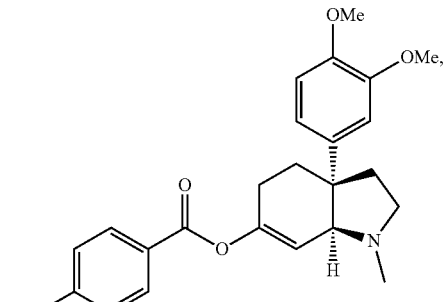
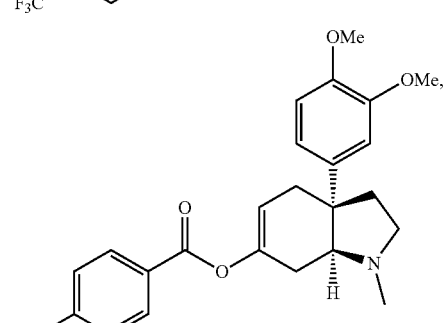
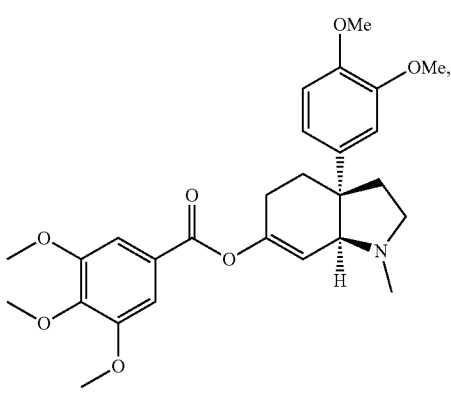

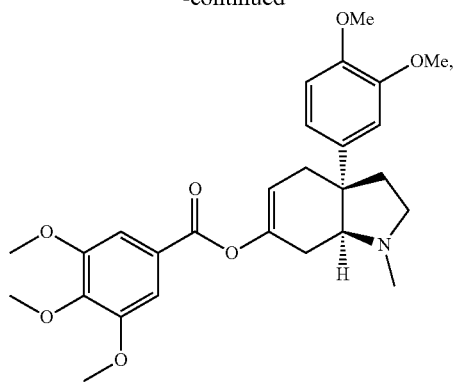
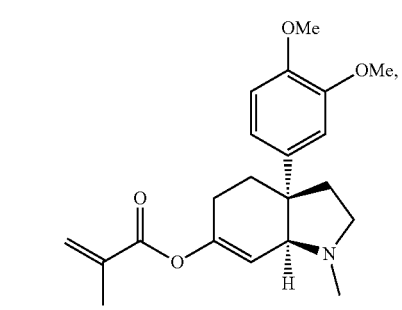
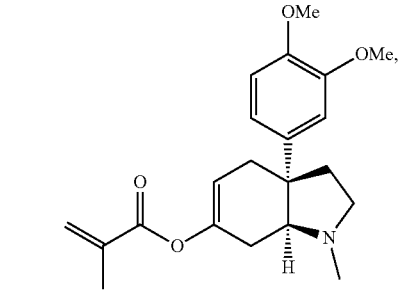
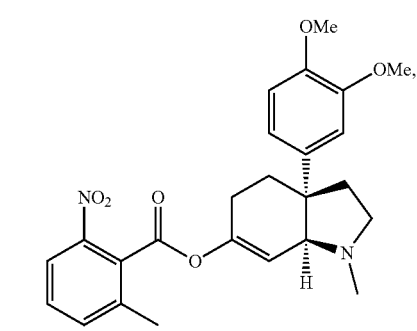
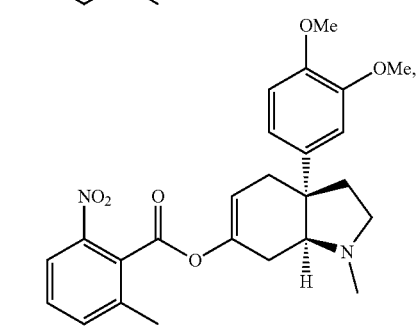
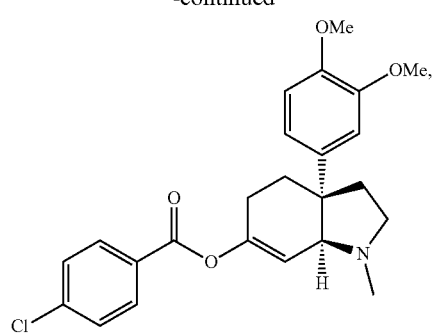
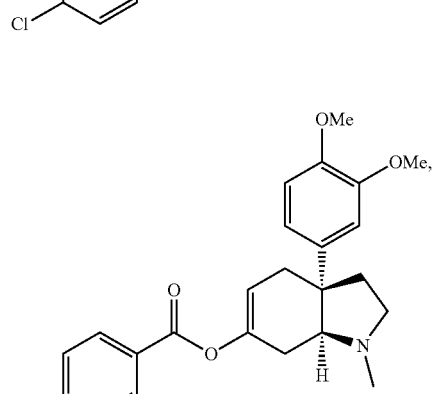
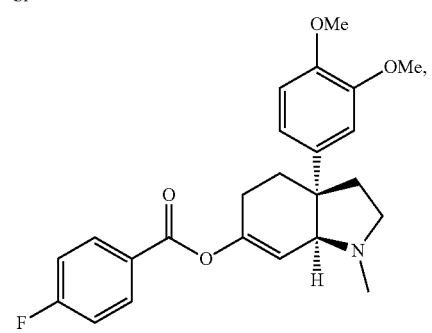
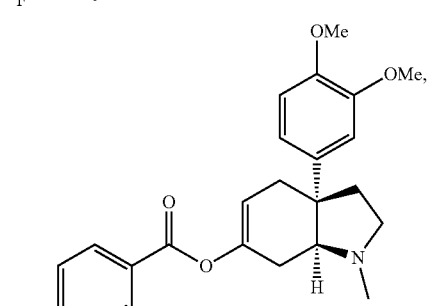
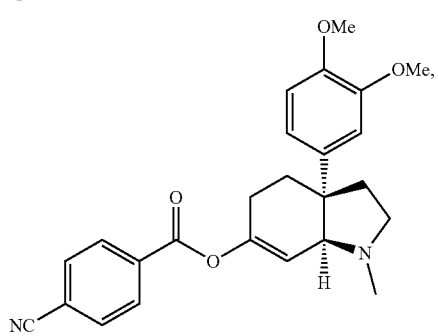

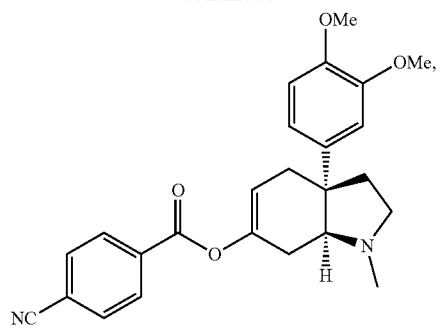
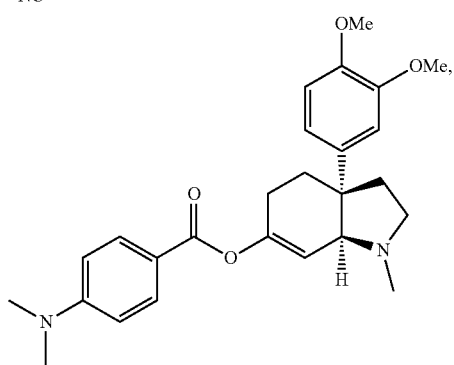
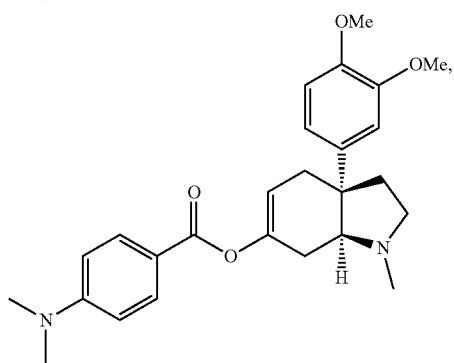
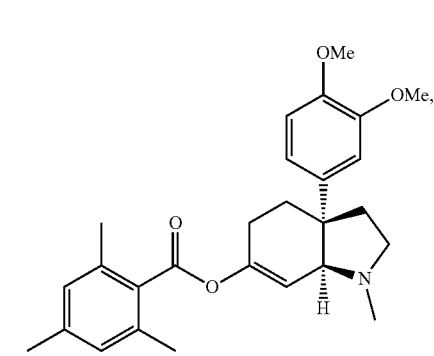
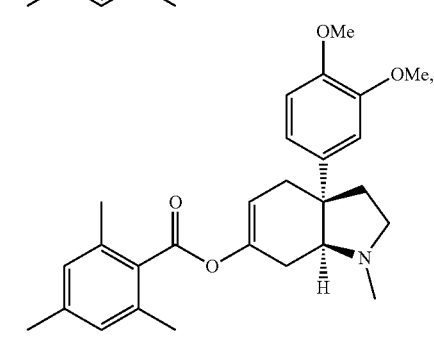
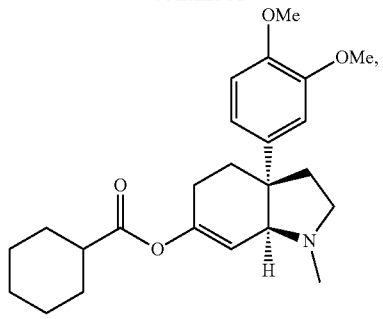
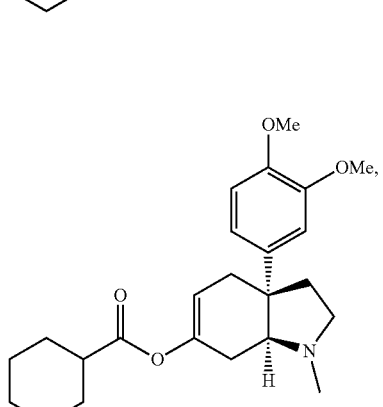
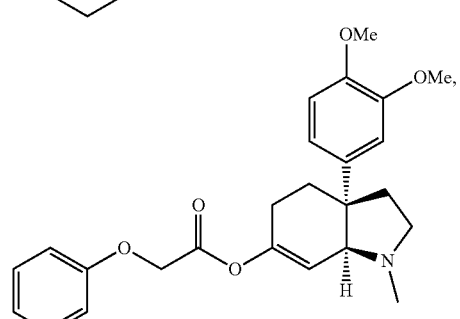
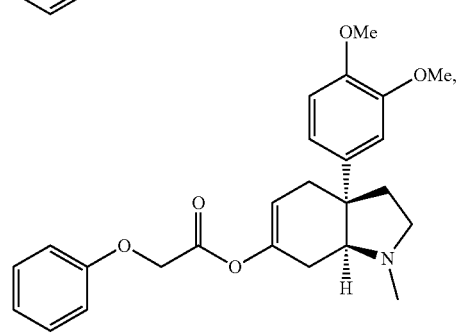
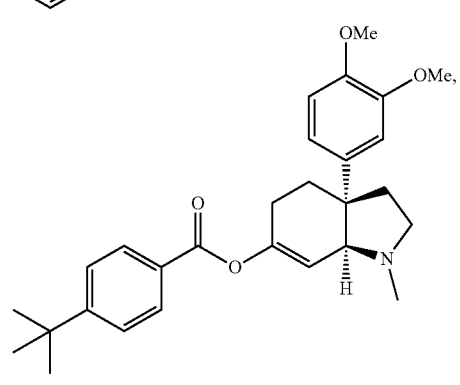

-continued
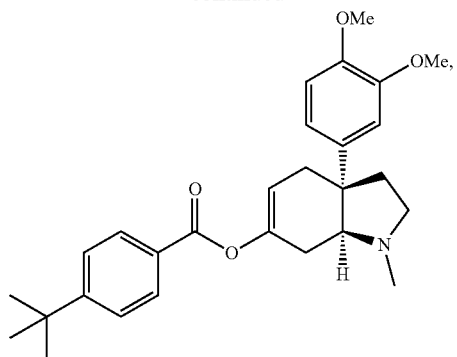
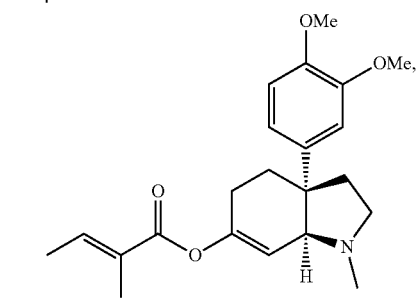
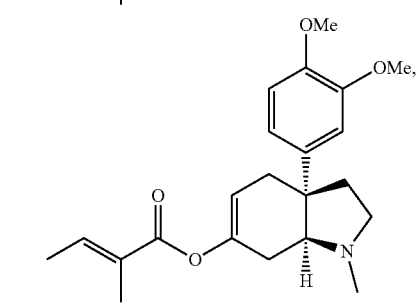
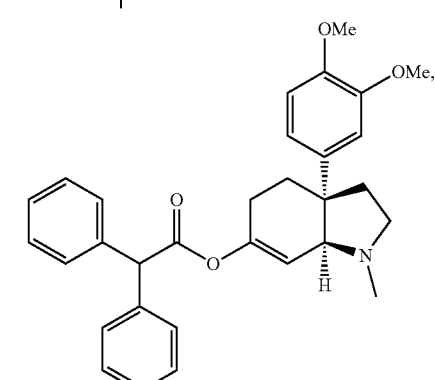
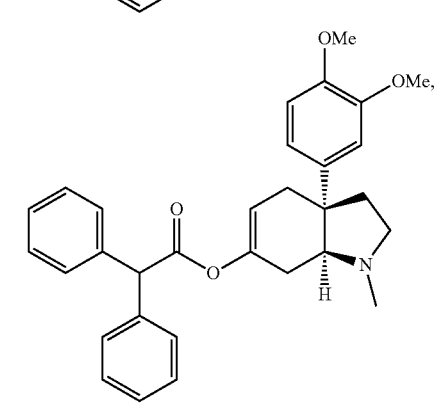
-continued
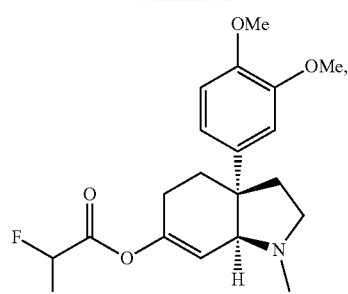
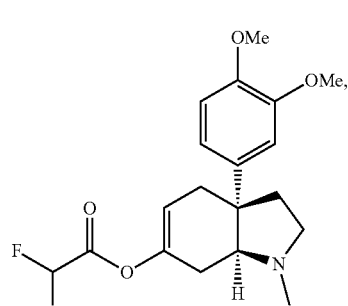
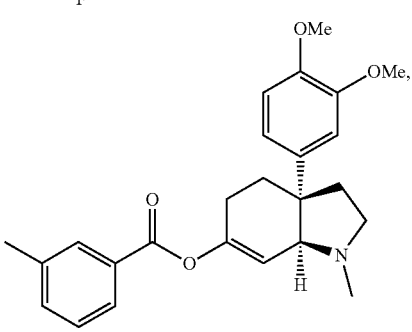
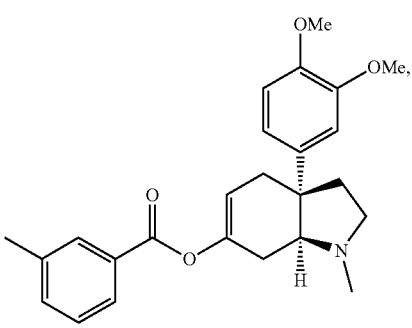
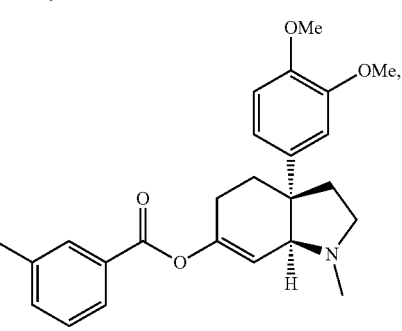

263
-continued
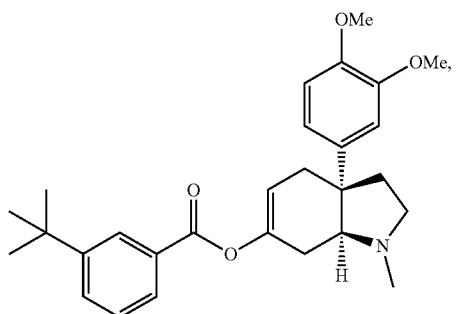
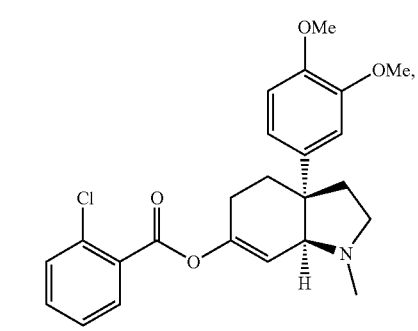
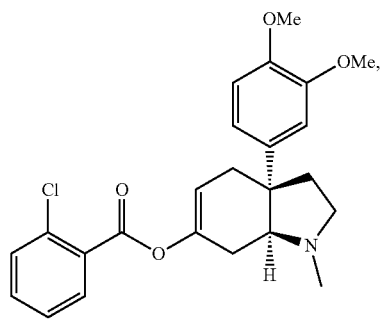
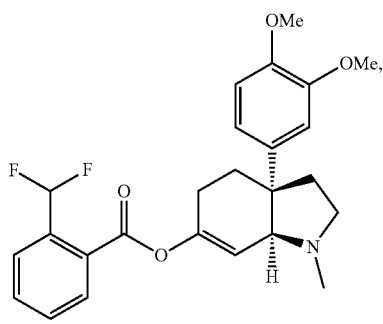
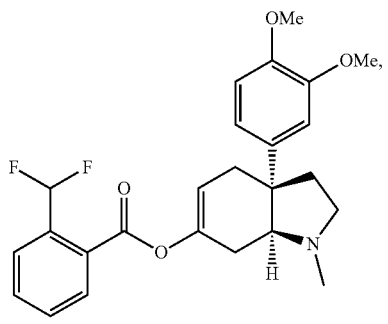
264
-continued
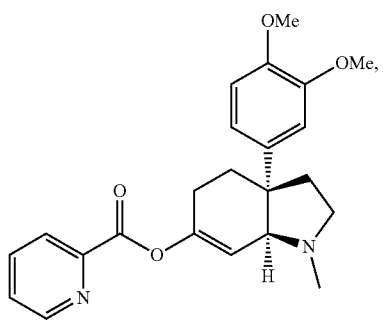
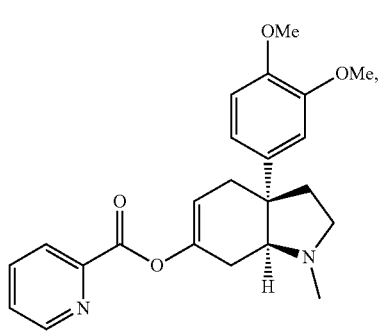
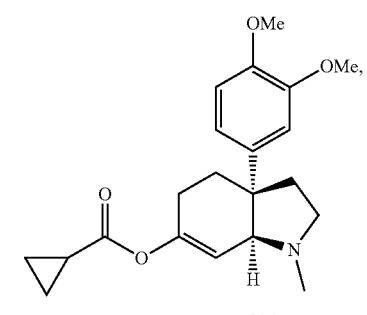
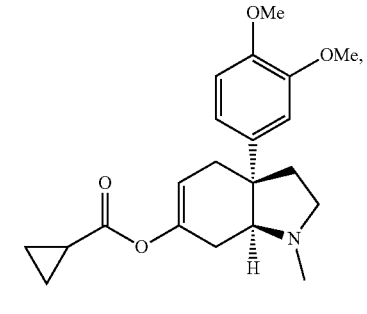
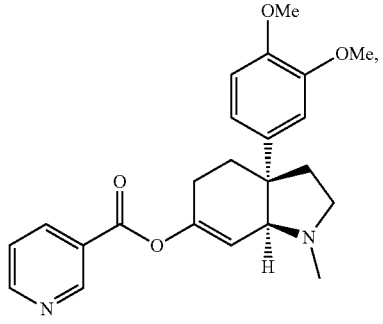

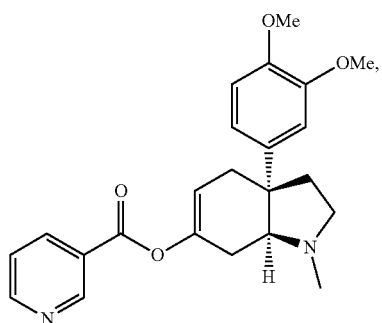
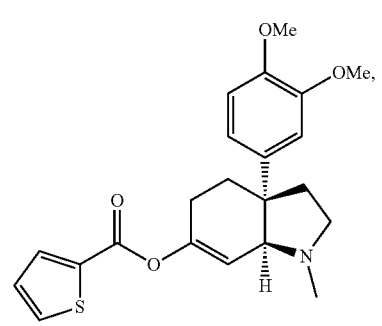
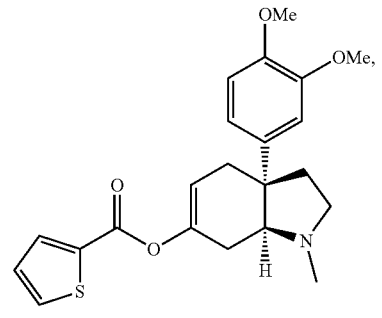
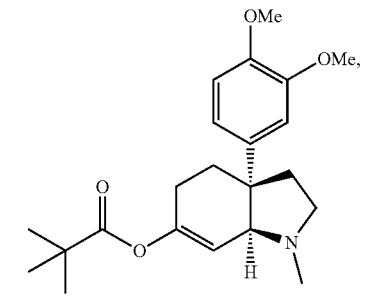
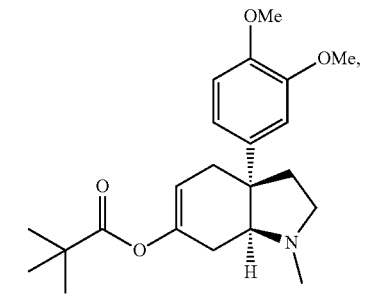
-continued
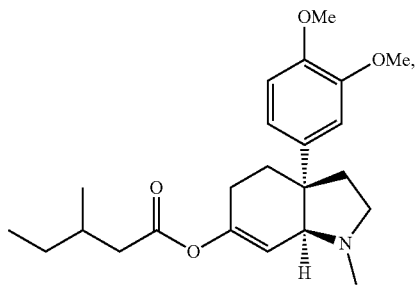
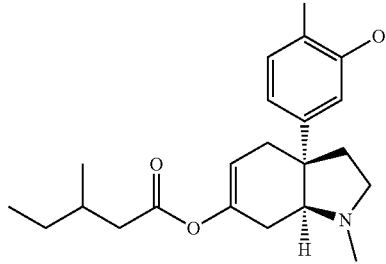
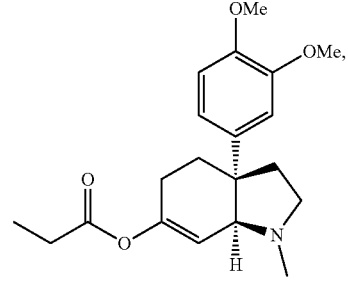
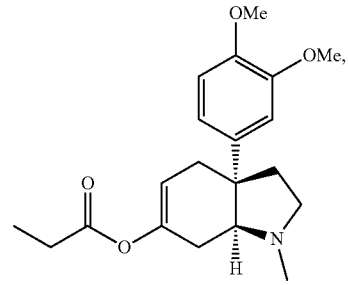
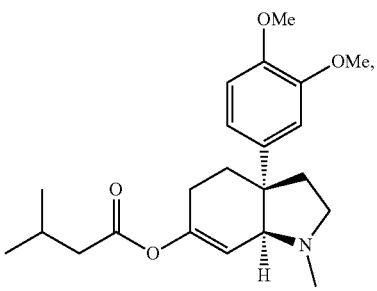
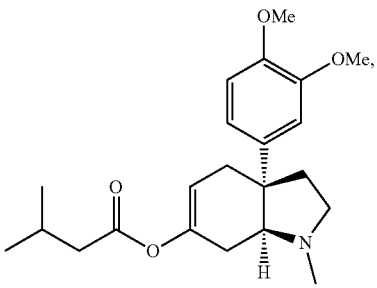

267
-continued
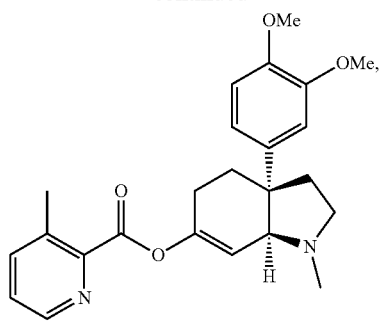
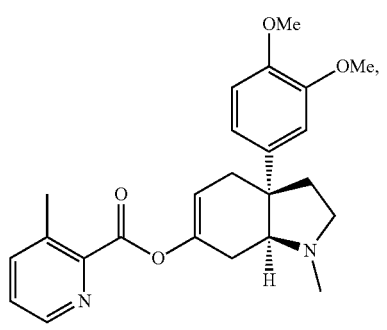
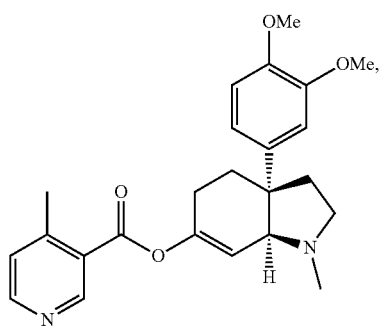 [SMILES: COc1ccc([C@@]23CCC(OC(=O)c4cccnc4)=C[C@@H]2N(C)CC3)cc1OC]
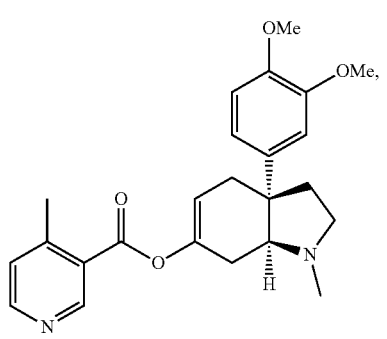
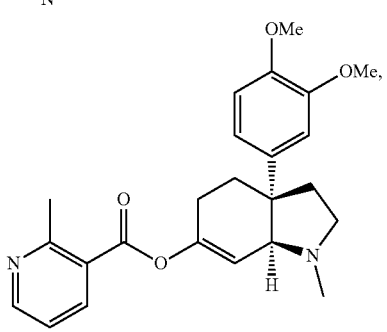
268
-continued
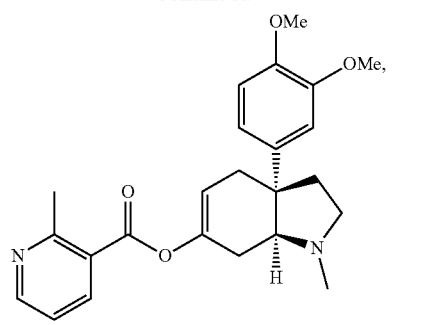
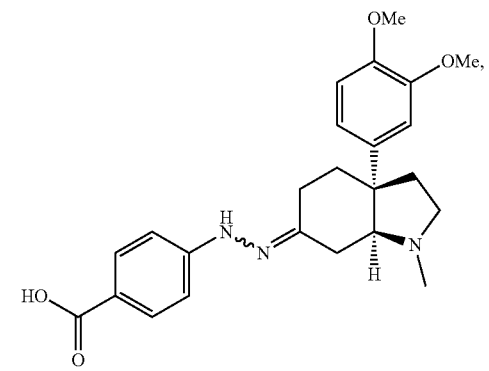
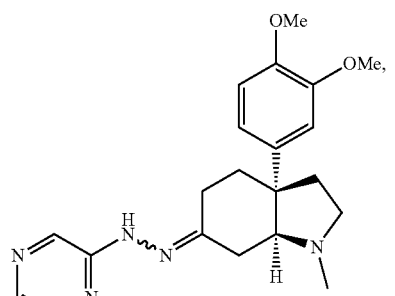
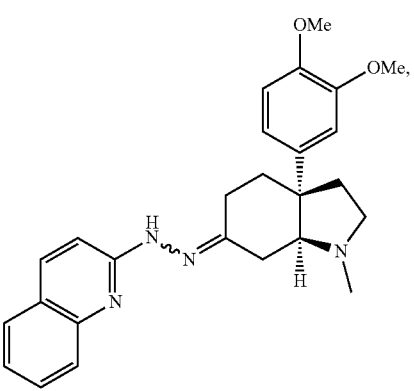
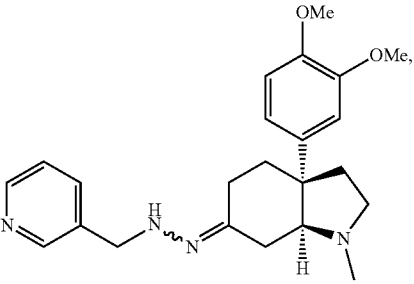

269
-continued
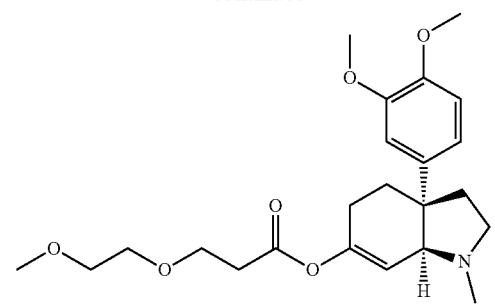
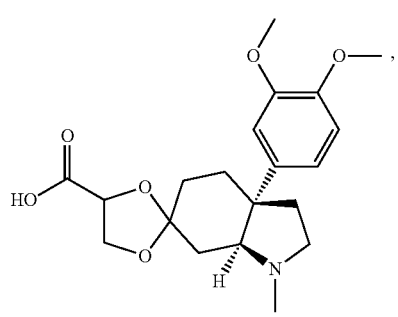
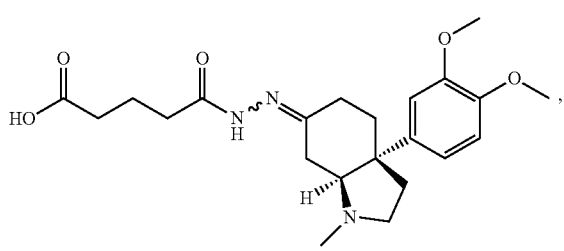
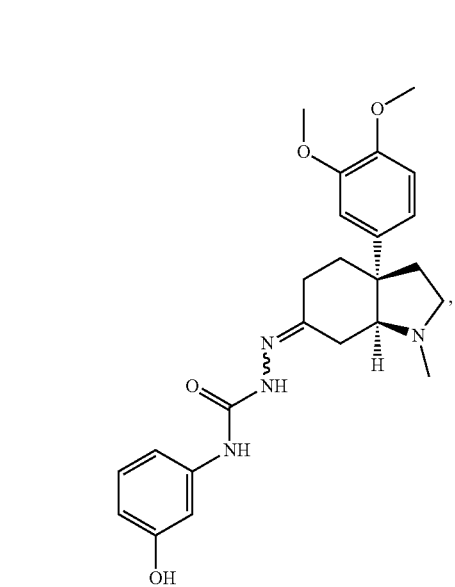
270
-continued
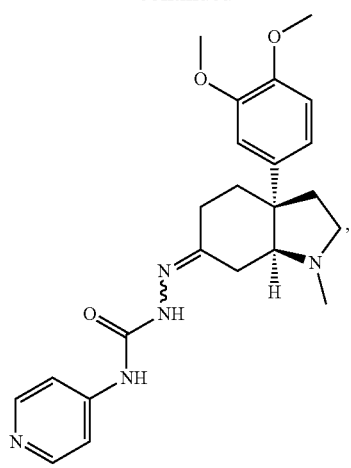
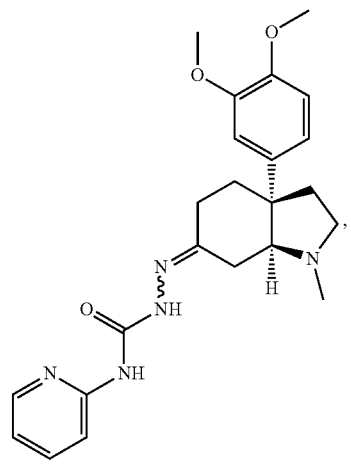

271
-continued
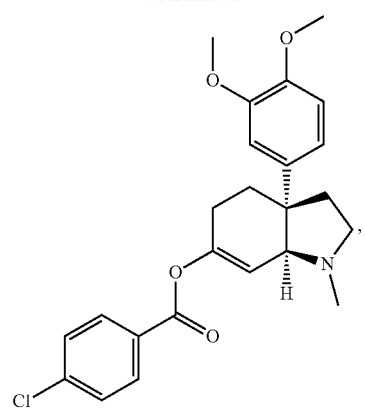
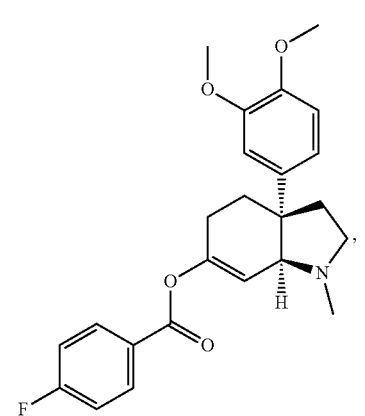
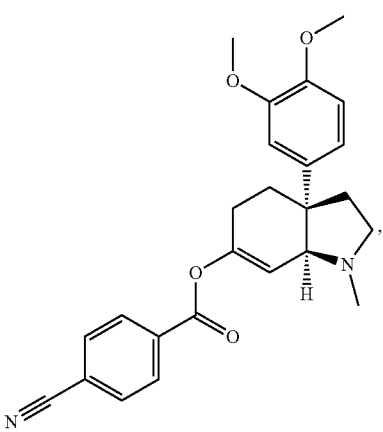
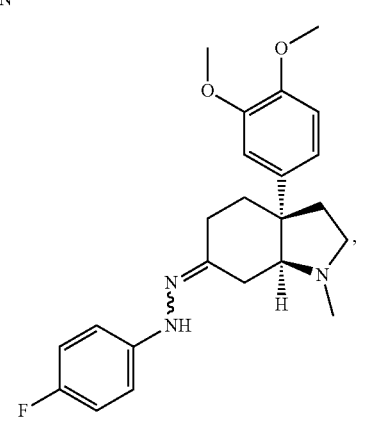
272
-continued
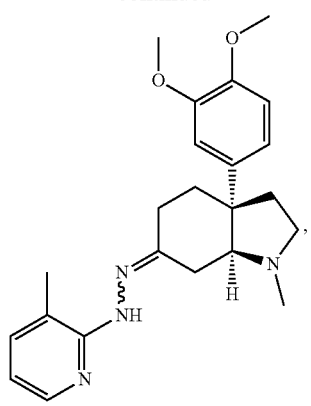
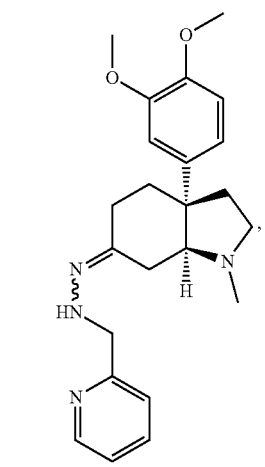
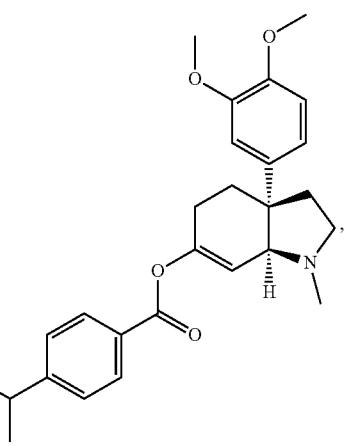
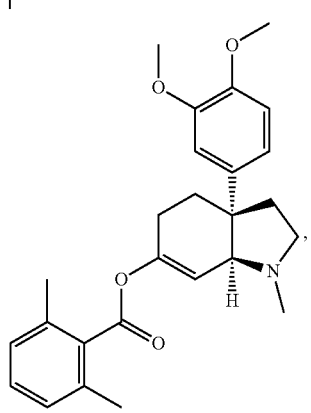

273
-continued
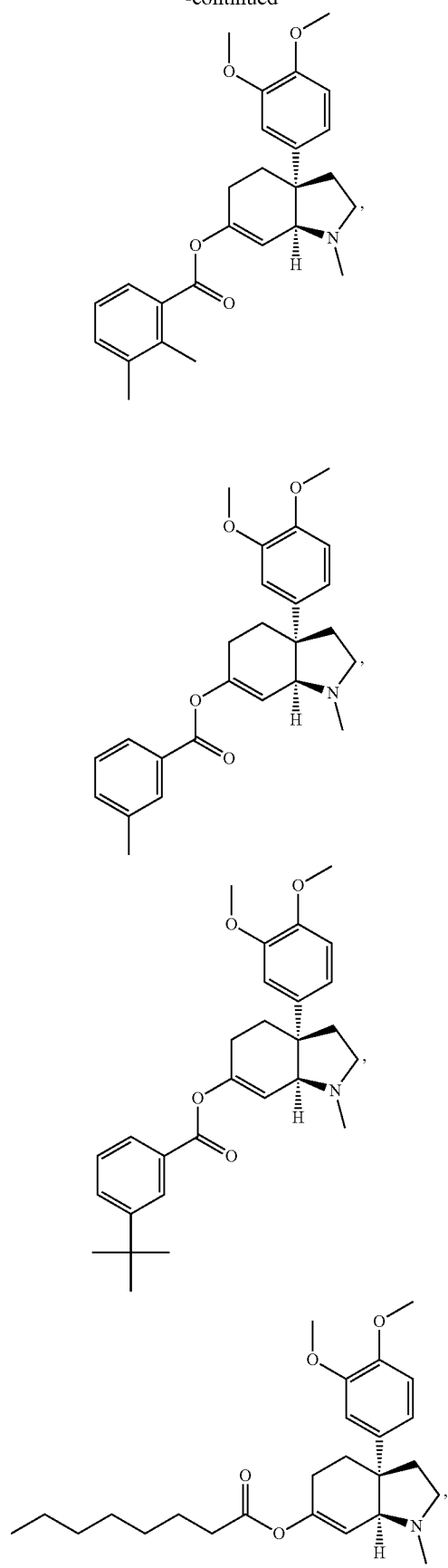
274
-continued
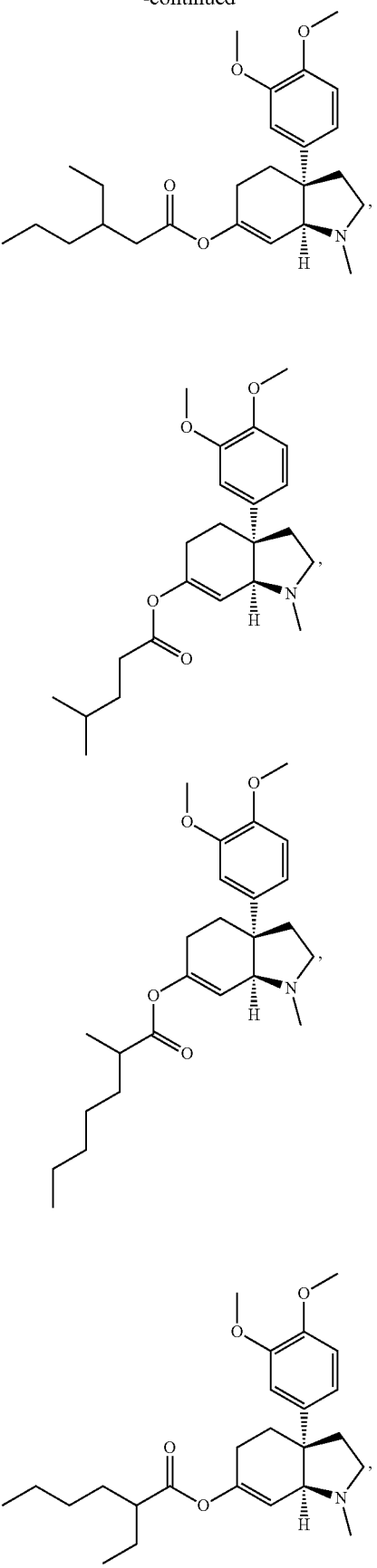

275
-continued
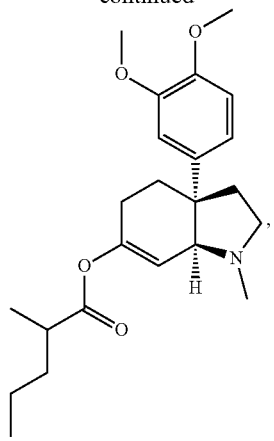
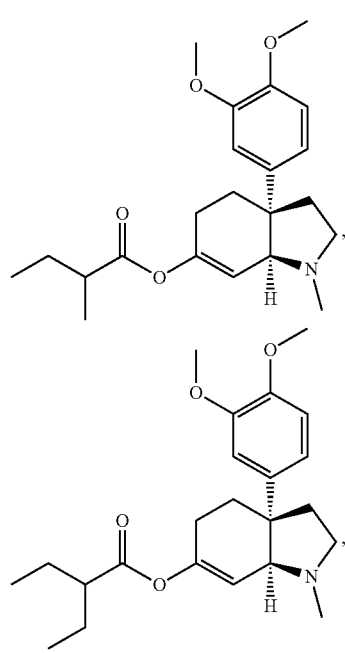
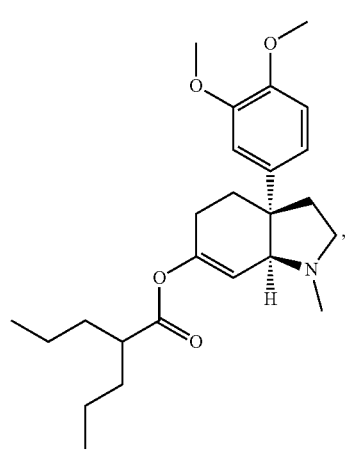
276
-continued
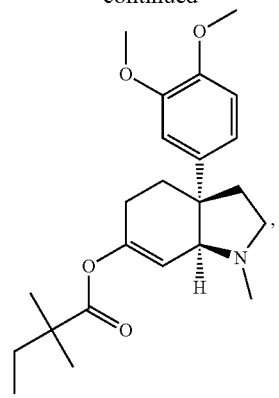
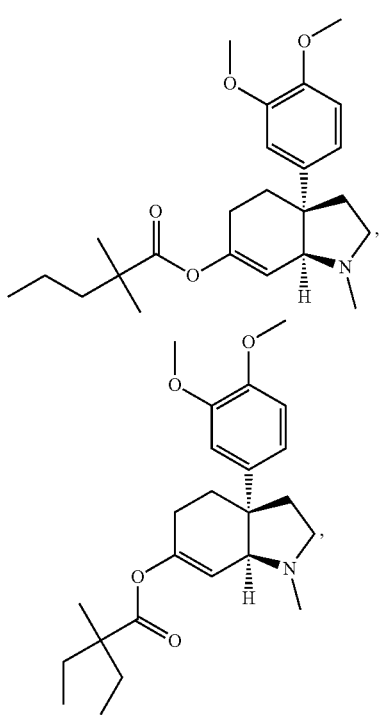
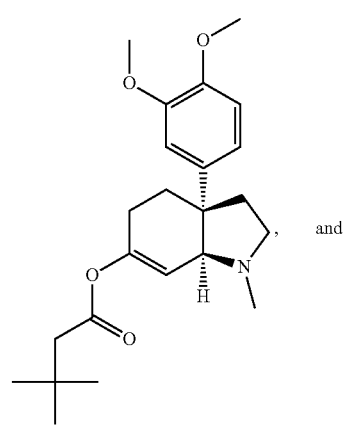
and -continued
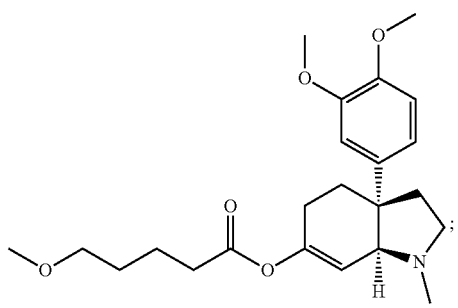 [SMILES: COCCCCC(=O)OC1=C[C@@H]2N(C)CC[C@]2(c2ccc(OC)c(OC)c2)CC1]
or a pharmaceutically acceptable salt thereof.
In some embodiments, the compound is selected from the group consisting of:
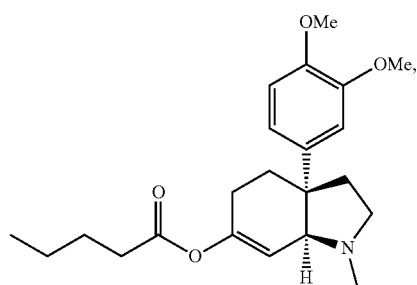
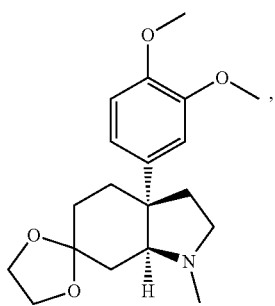
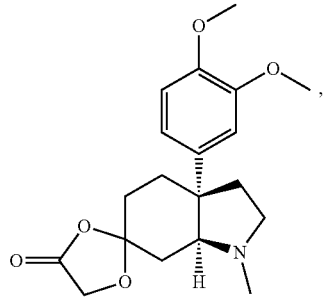
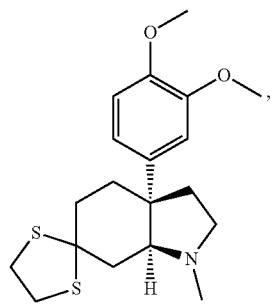
-continued
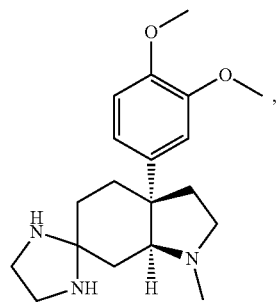
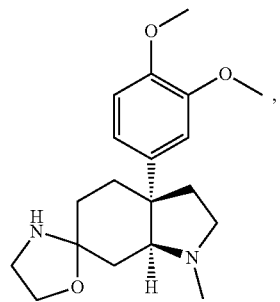
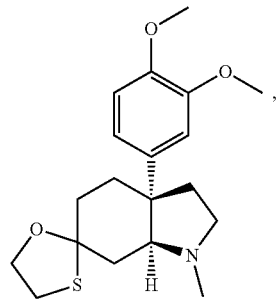
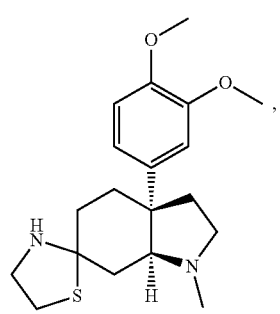
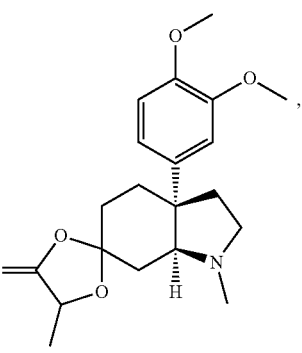

279
-continued
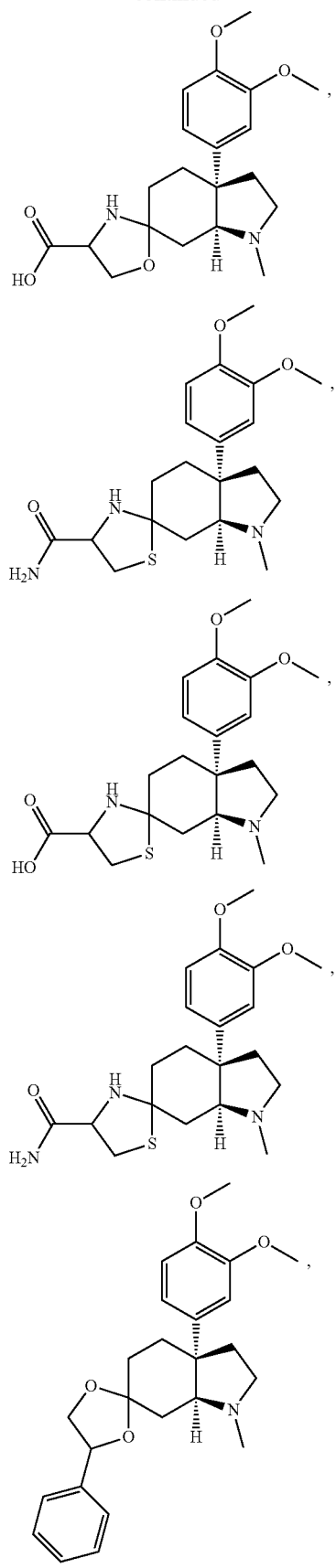
280
-continued
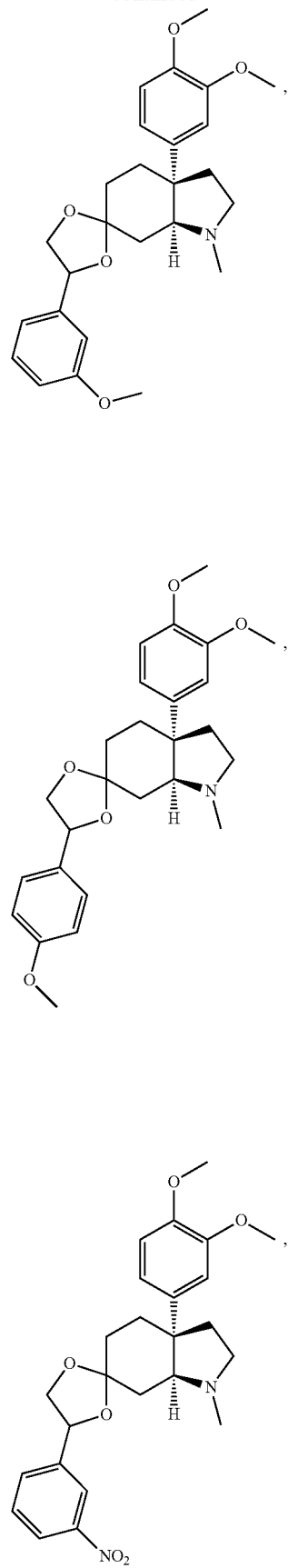

281
-continued
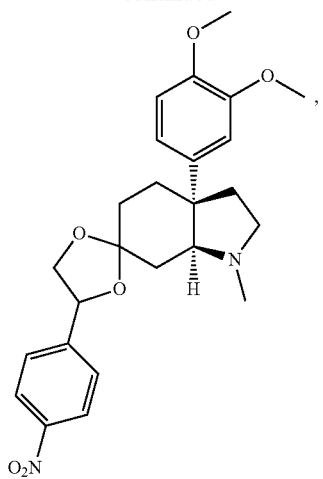
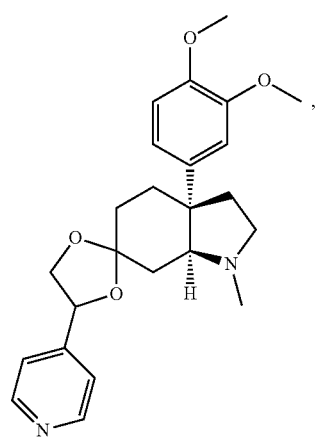
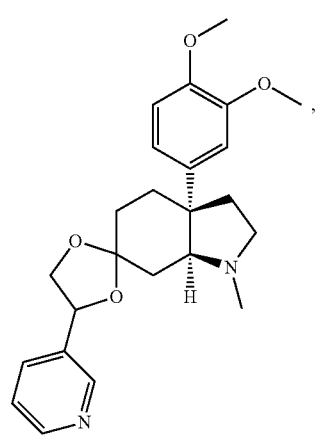
282
-continued
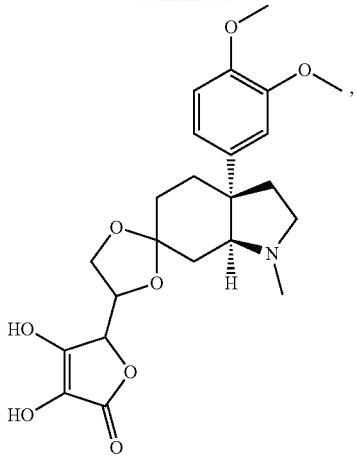
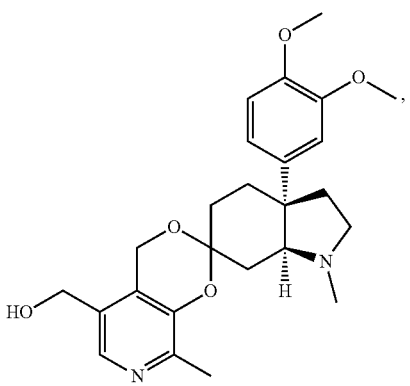
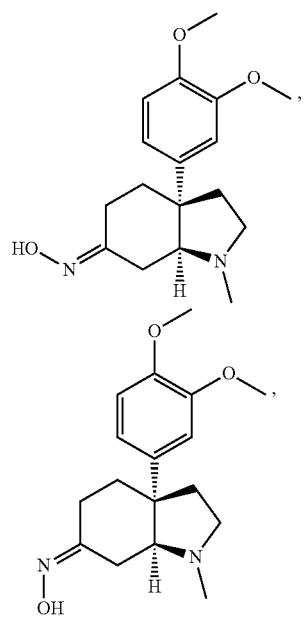

283
-continued
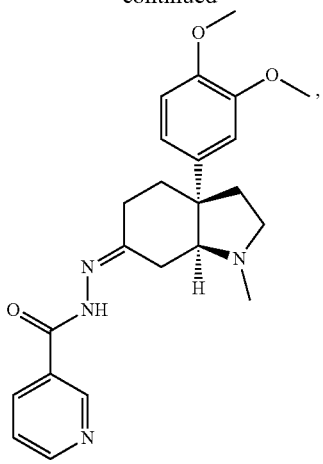
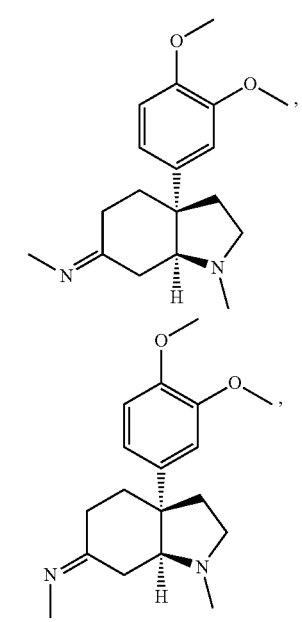
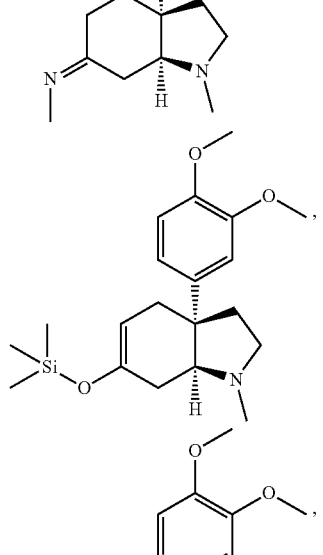
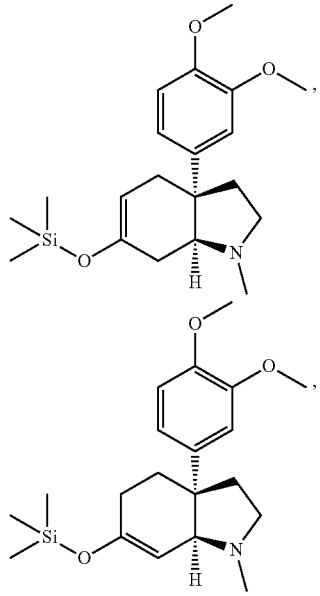
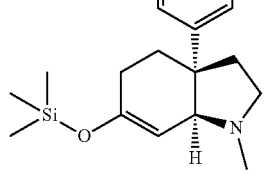
284
-continued
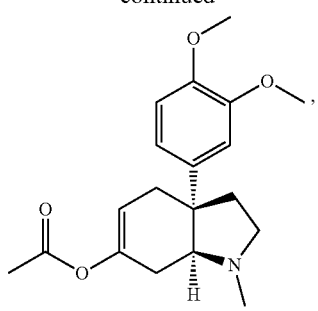
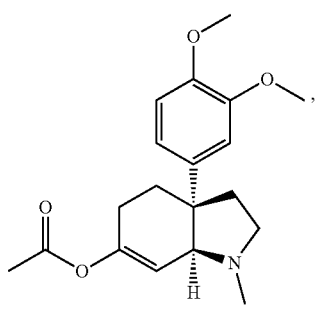
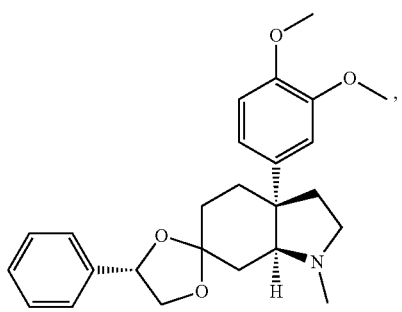
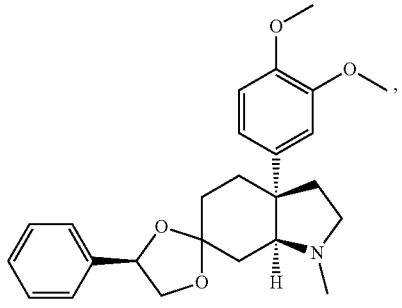
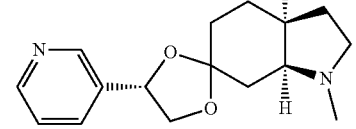

285
-continued
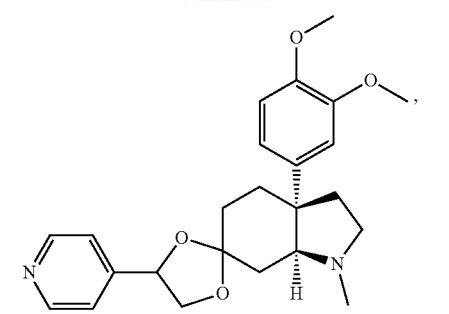
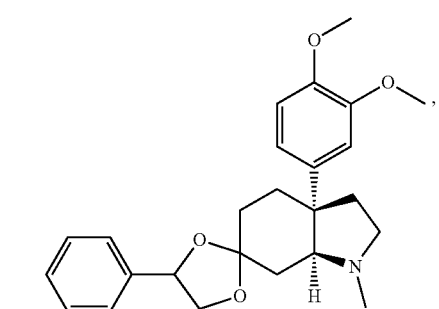
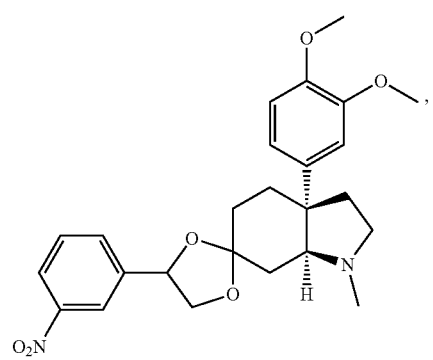
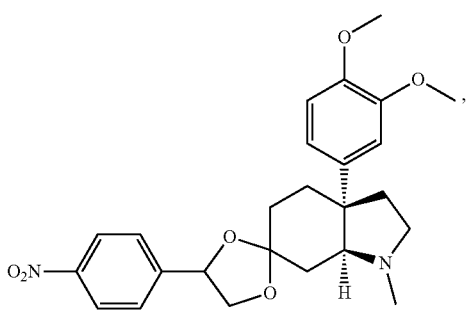
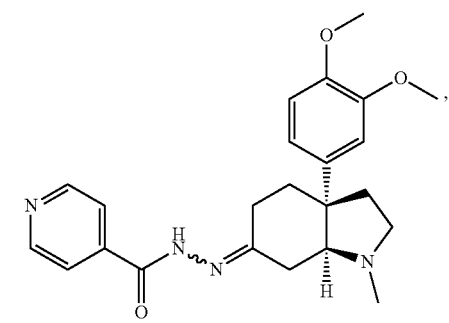
286
-continued
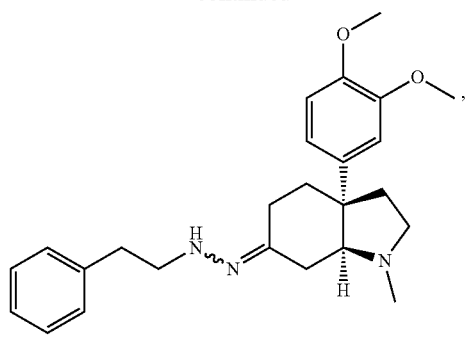
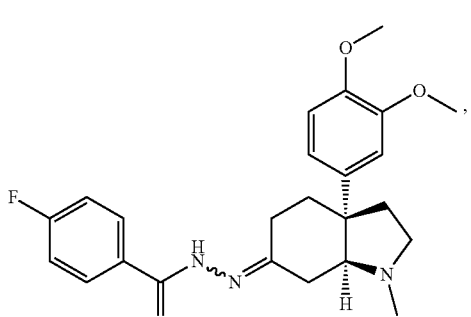
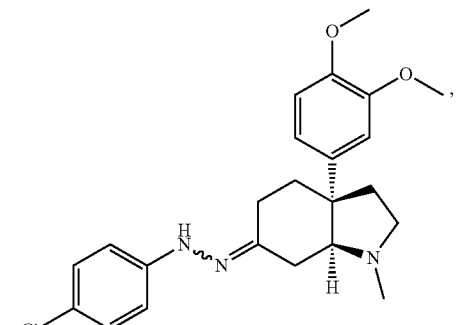
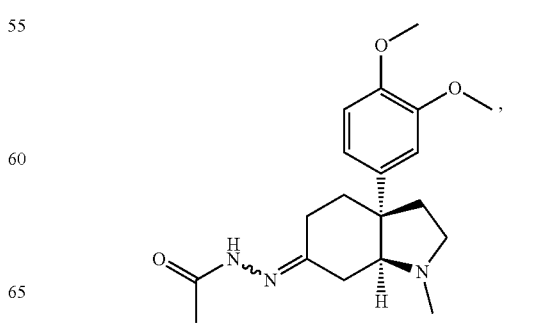

287
-continued
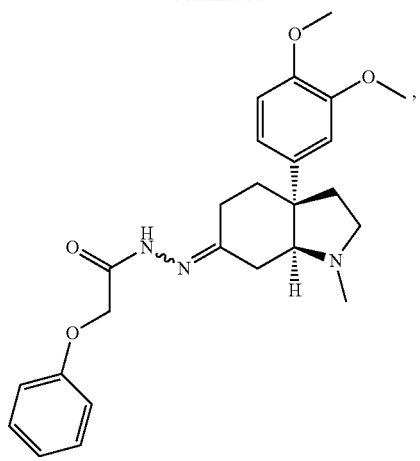
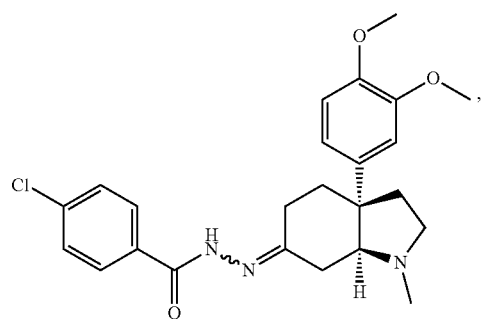
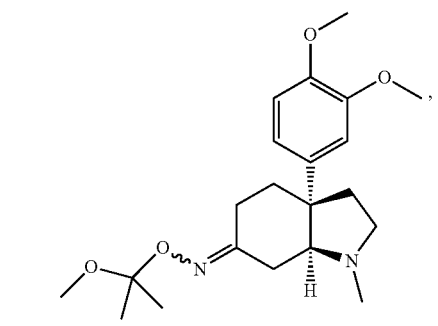
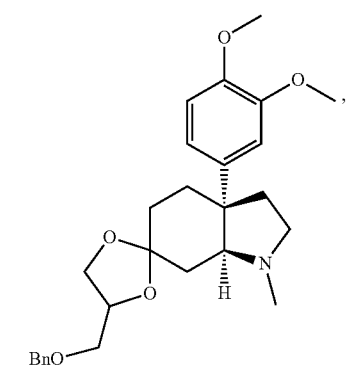
288
-continued
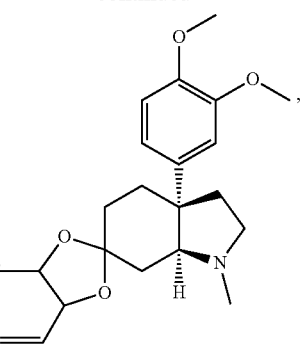
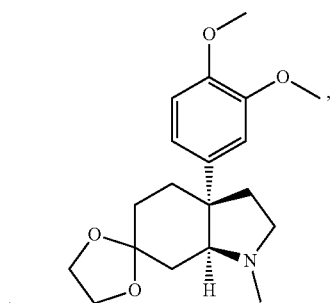
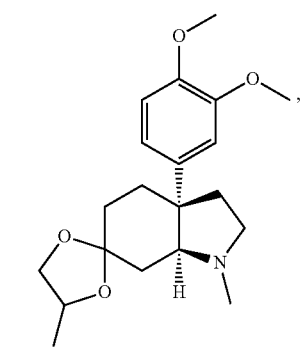

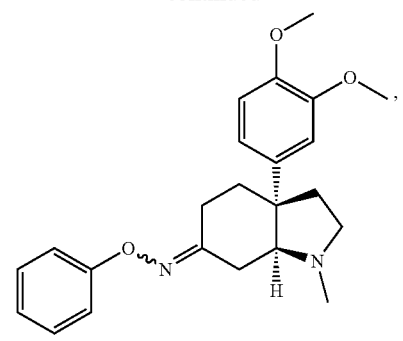
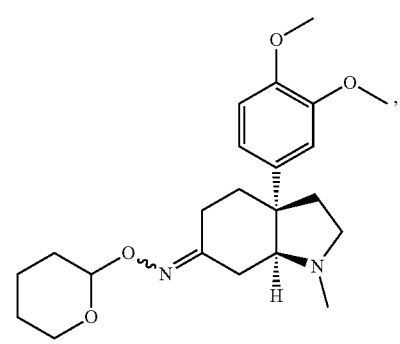
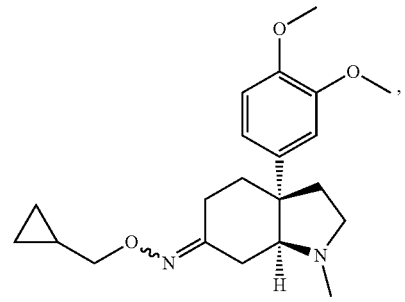
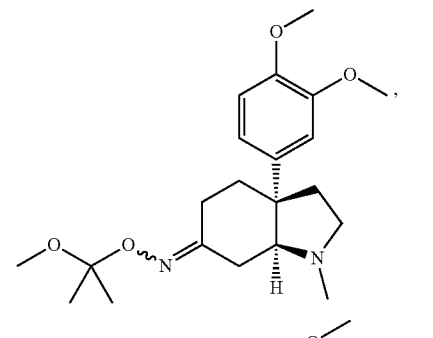
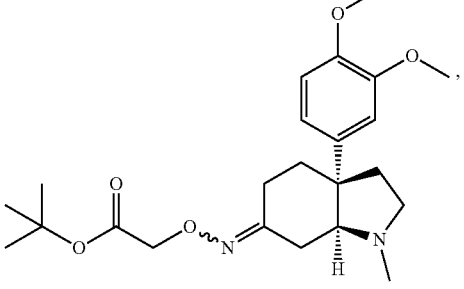
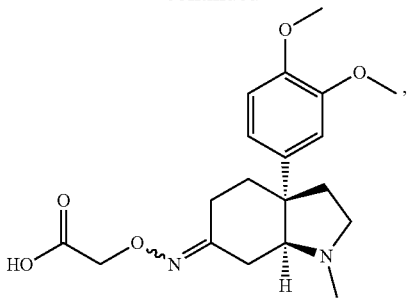
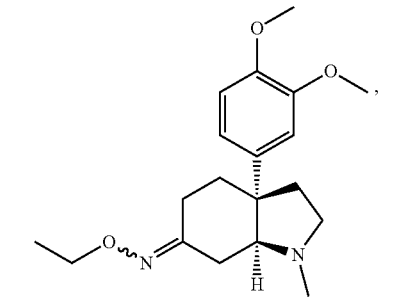
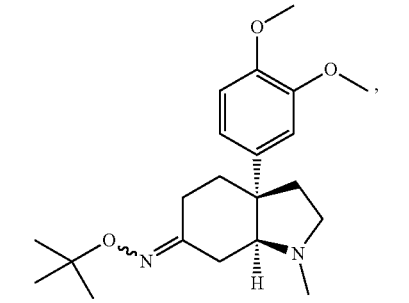
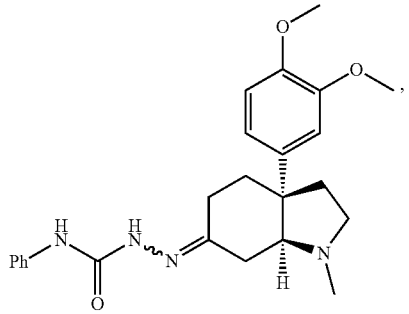
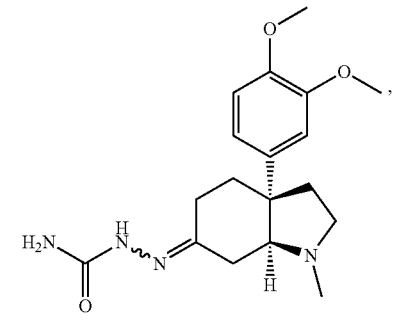

291
-continued
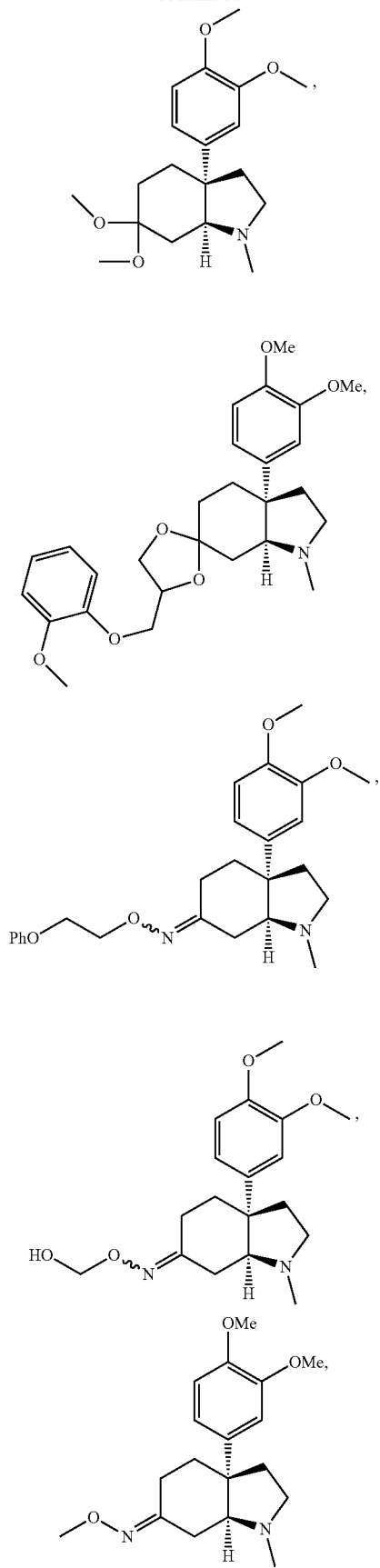
292
-continued
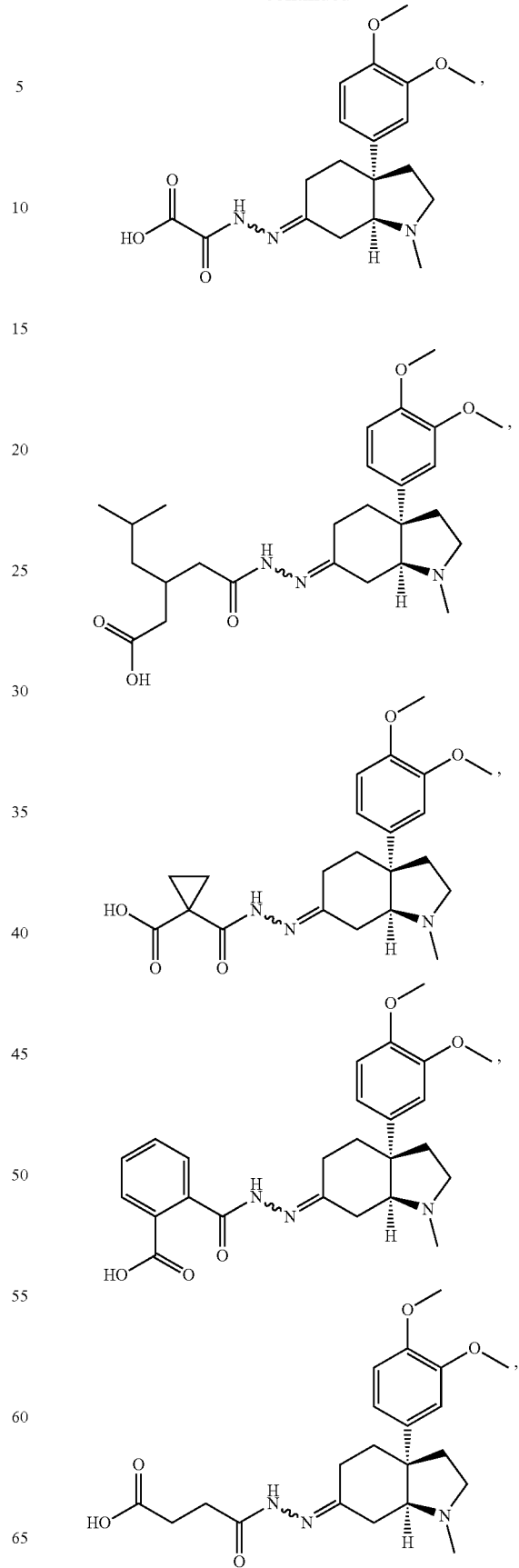

293
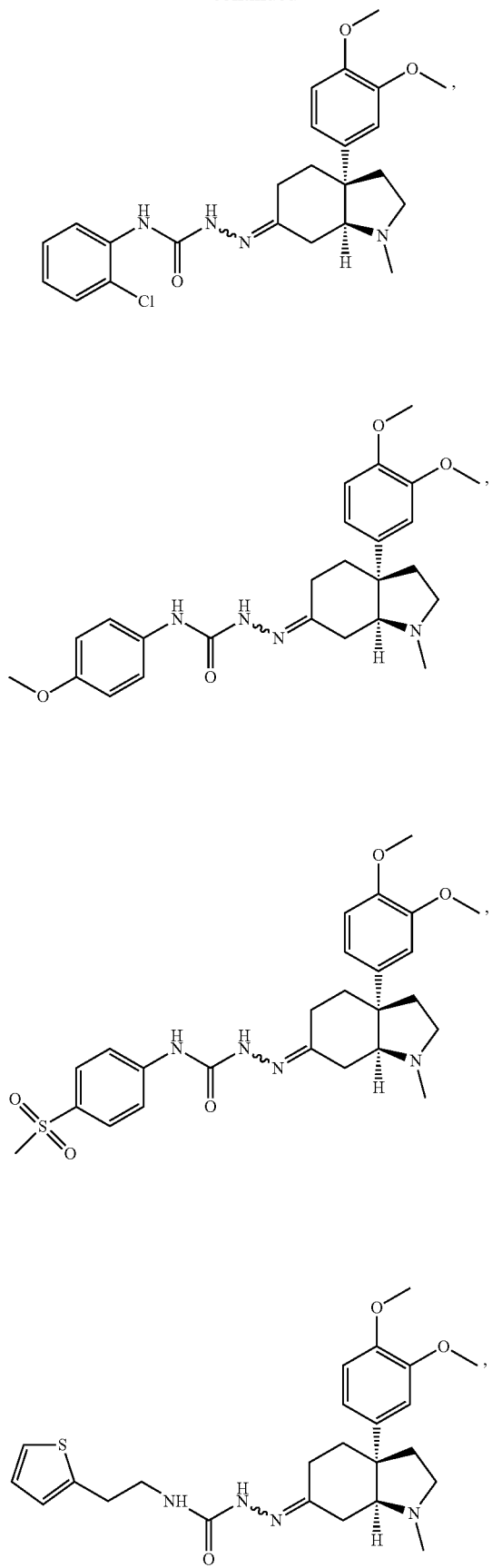
294
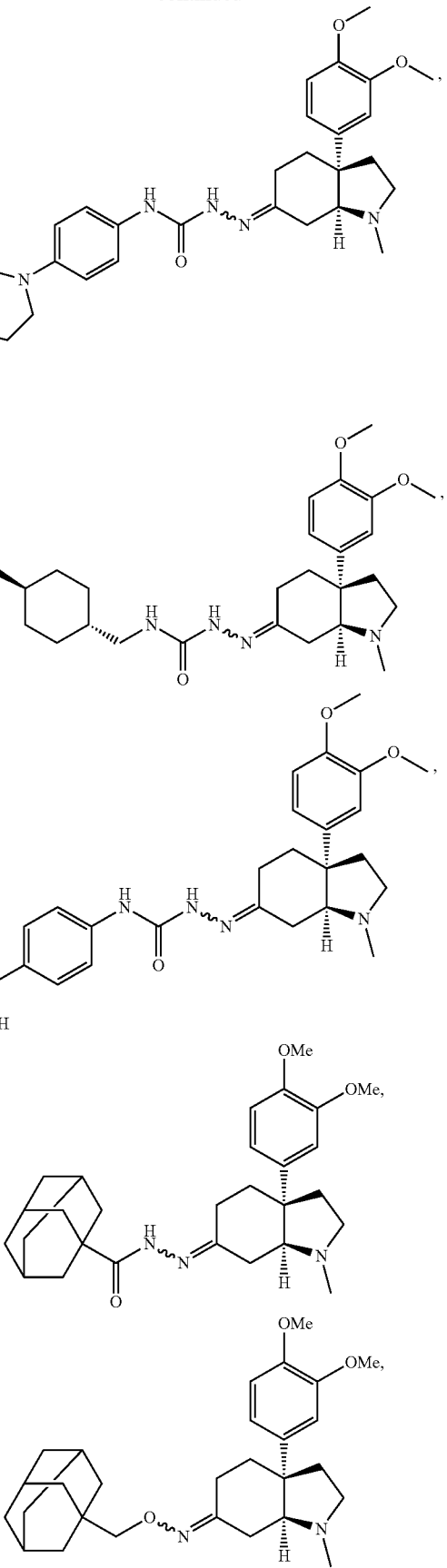

295
-continued
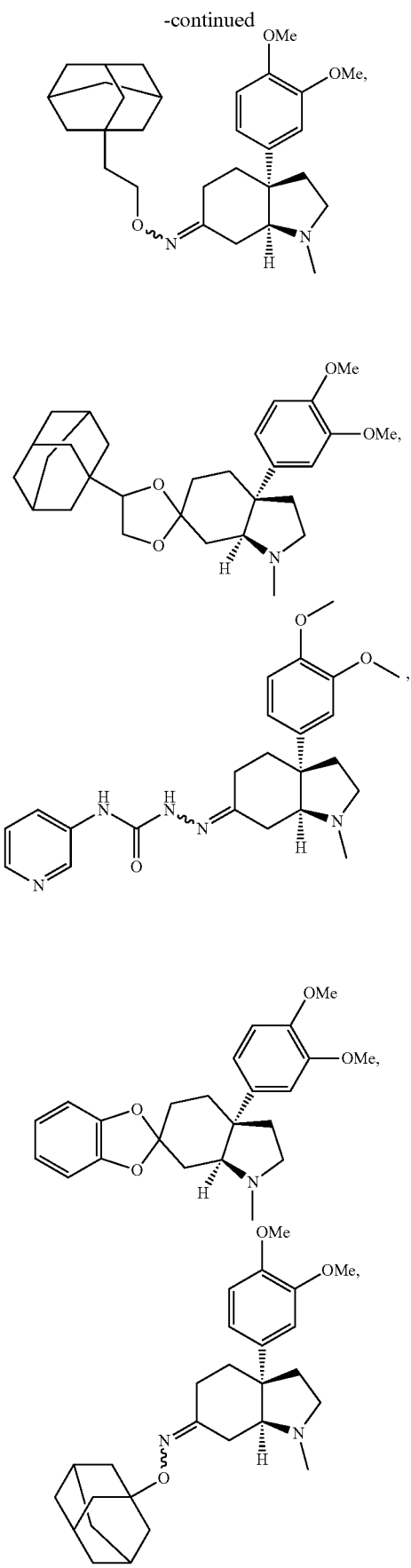
296
-continued
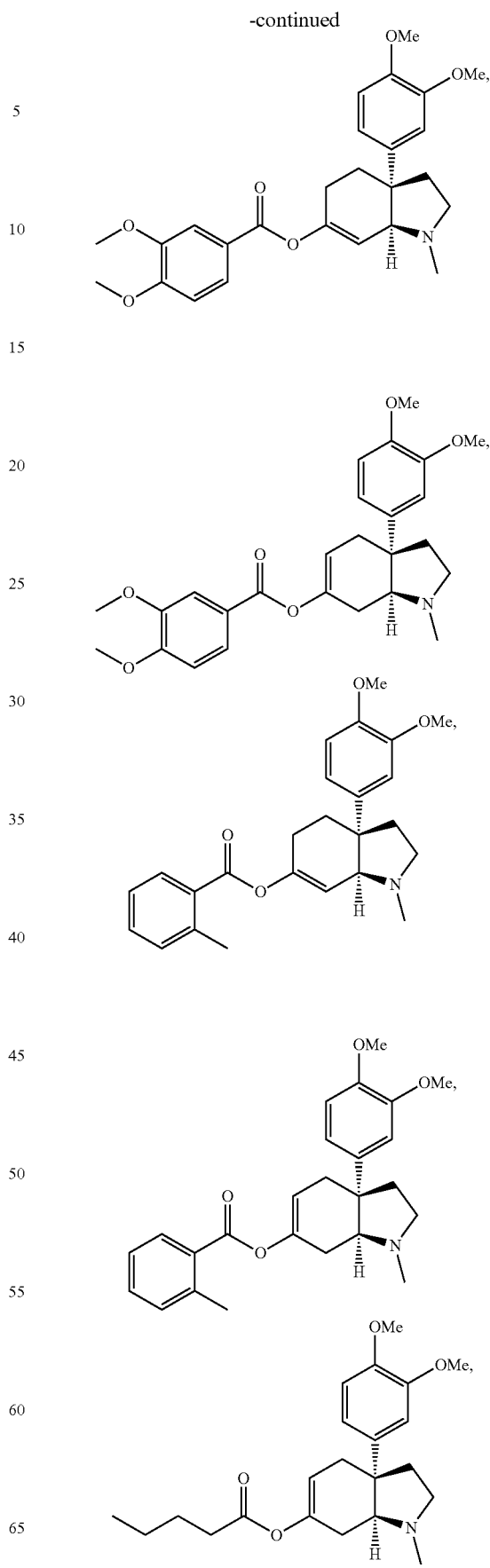

297
-continued
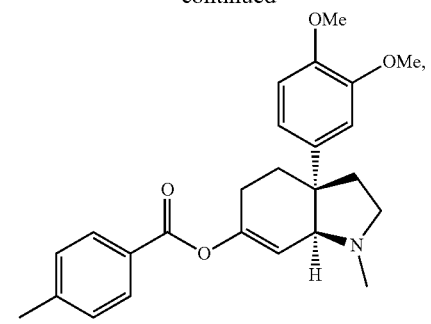
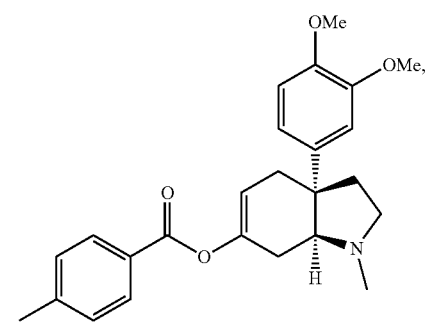
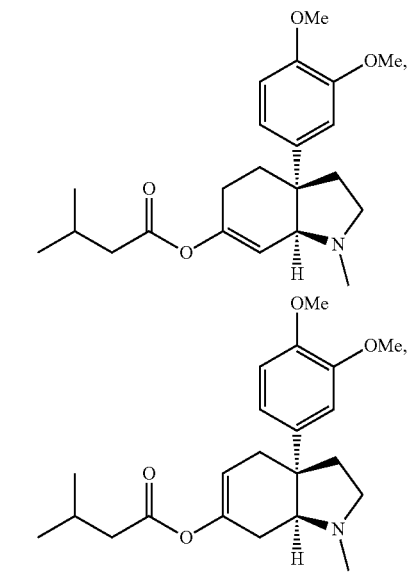
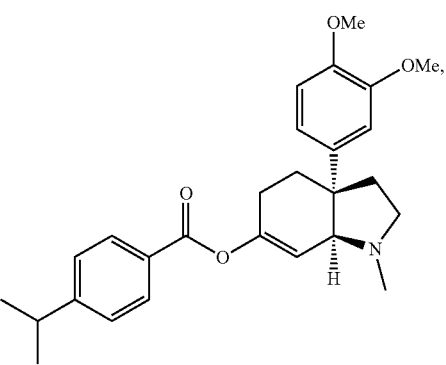
298
-continued
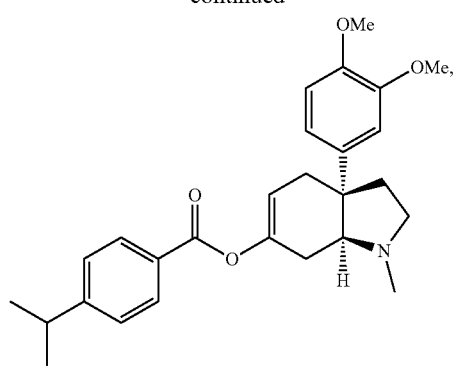
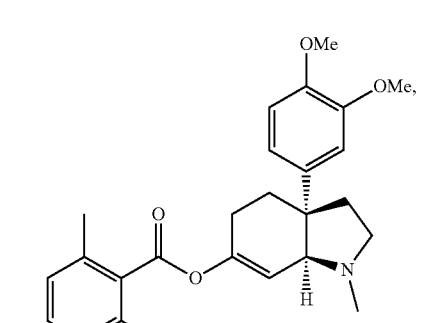
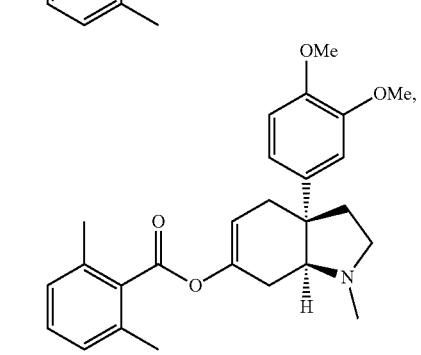
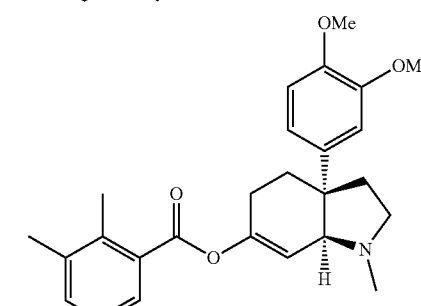
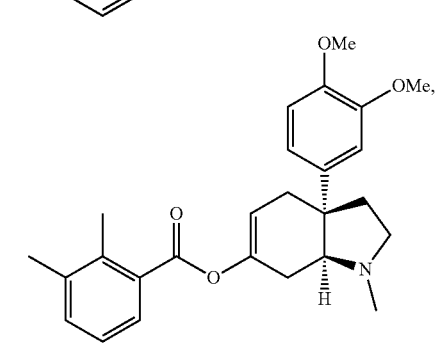

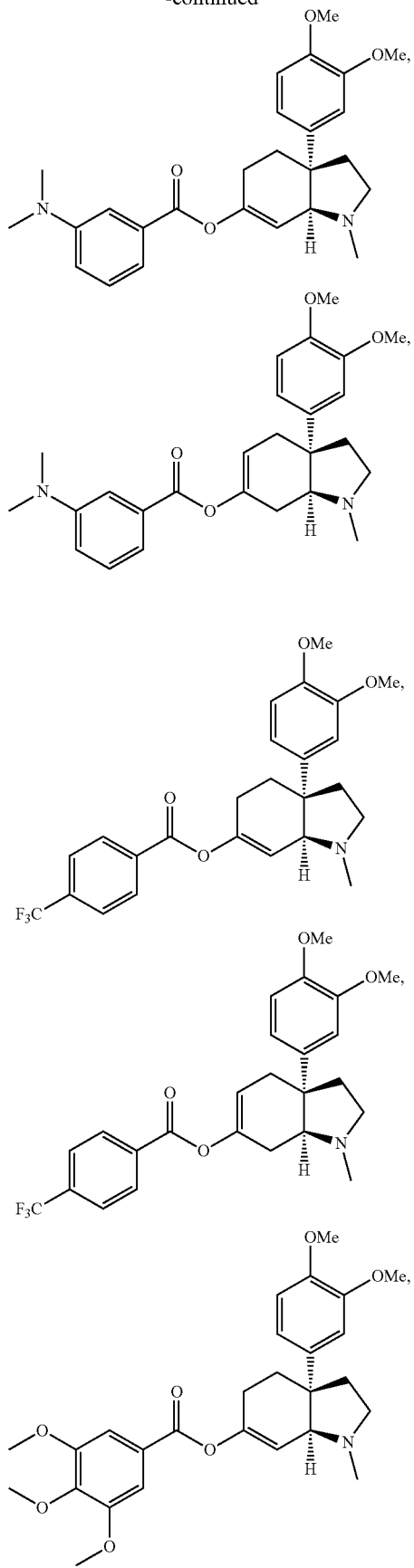
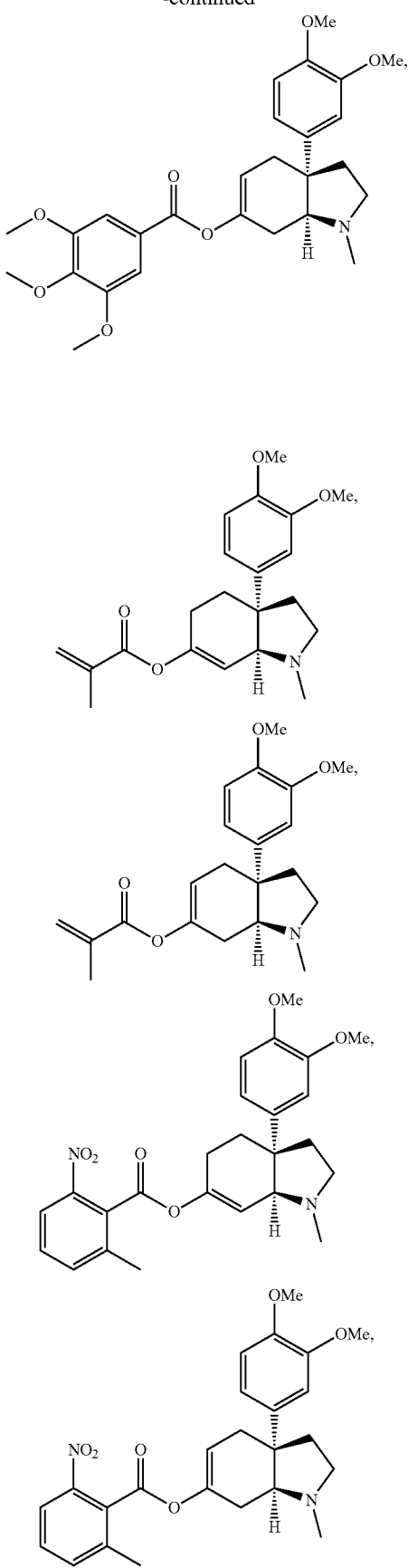

-continued
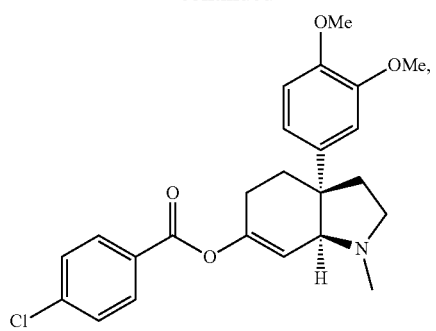
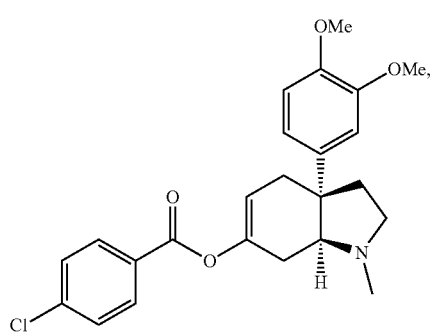
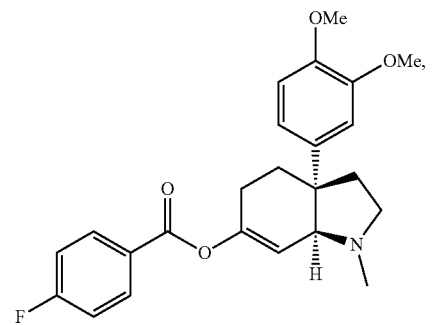
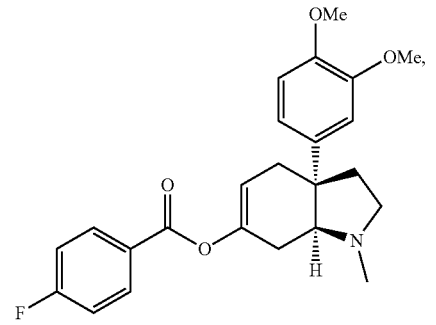
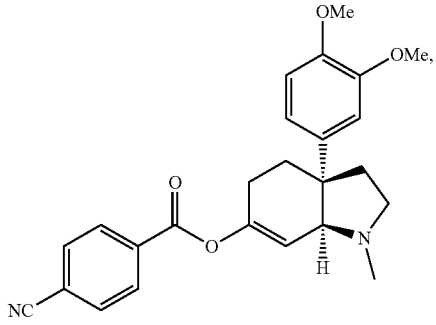
-continued
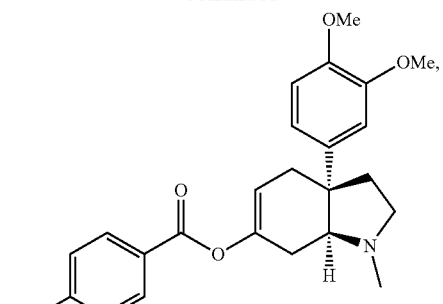
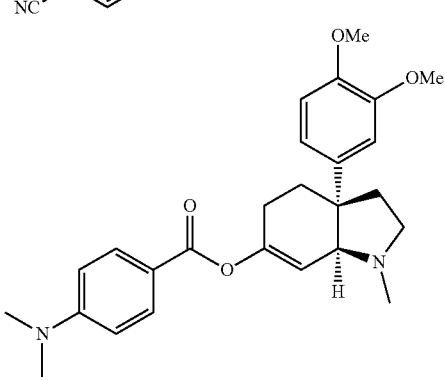
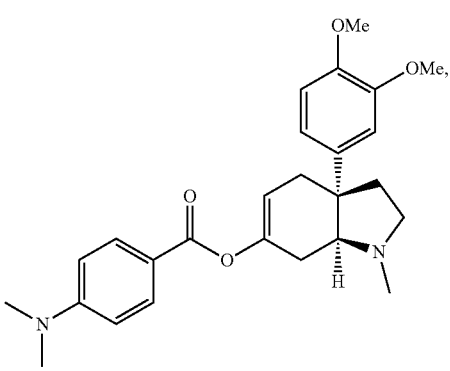
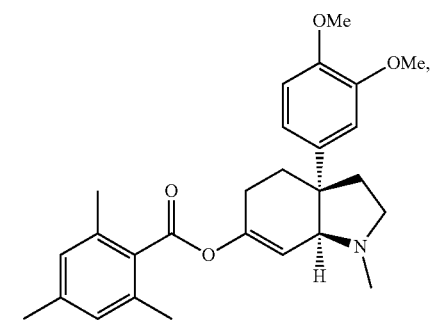
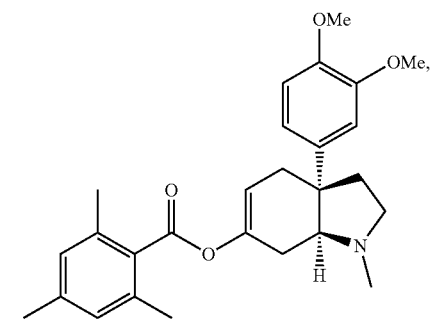

303
-continued
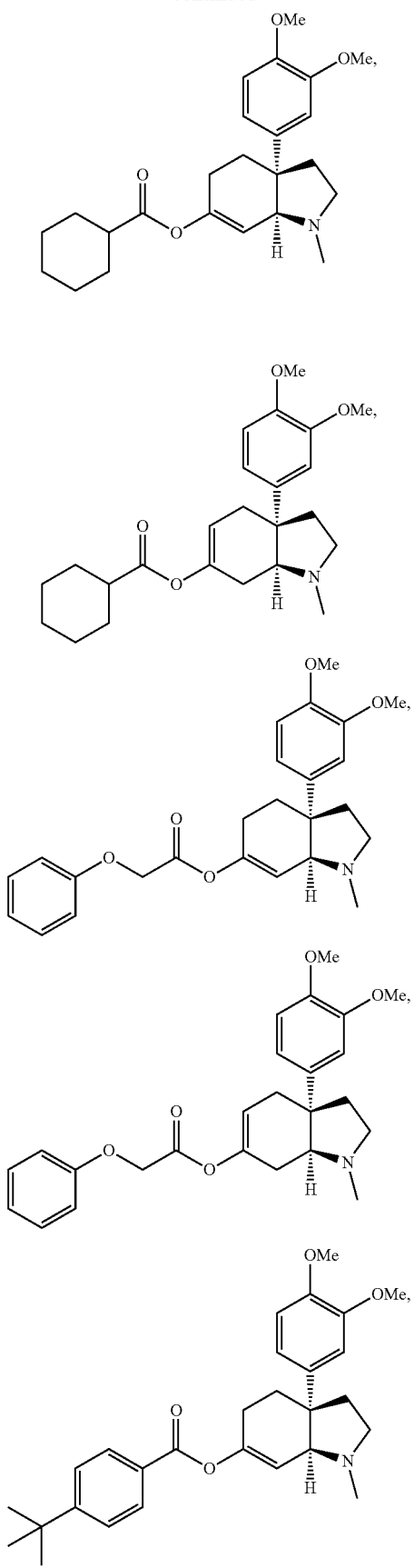
304
-continued
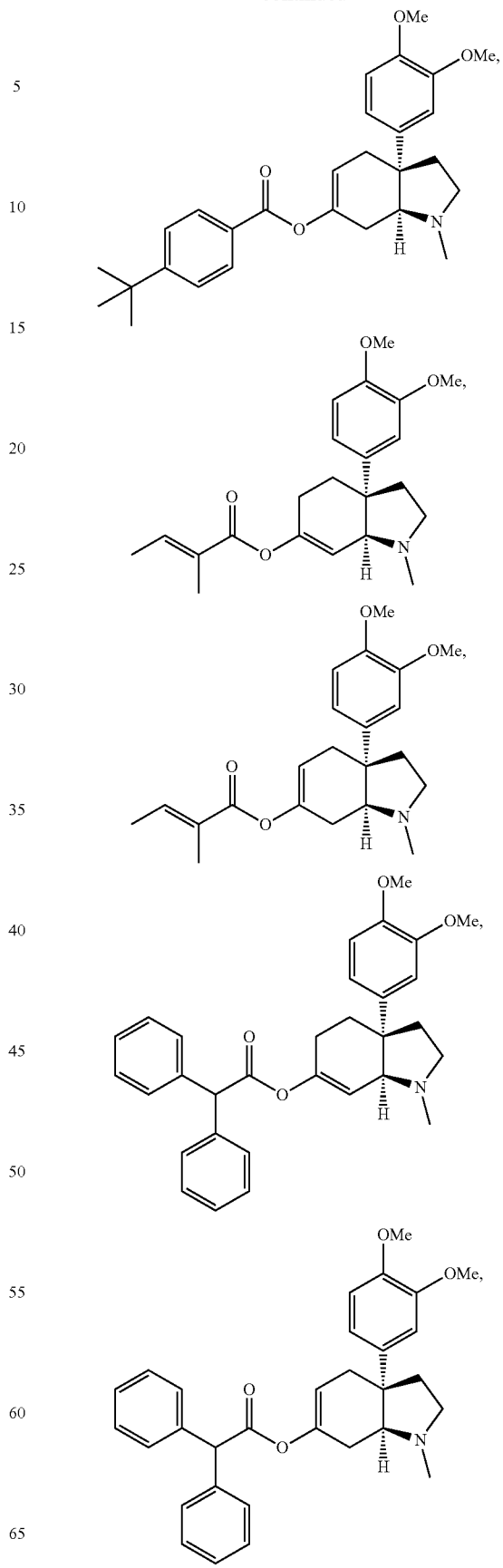

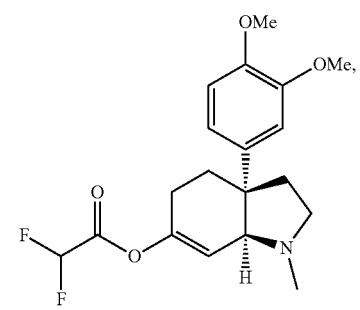
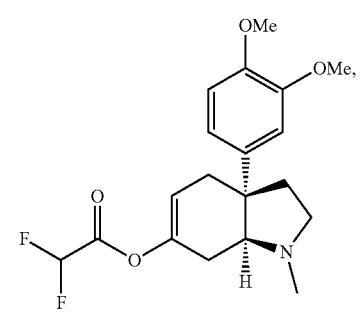
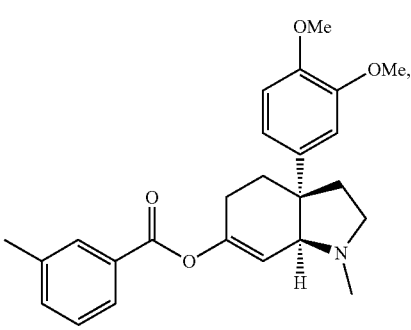
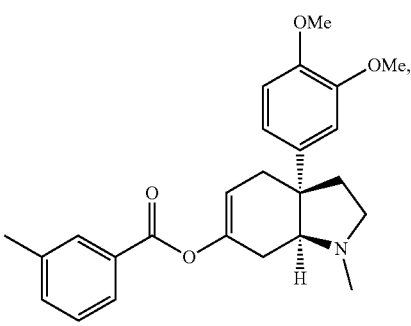
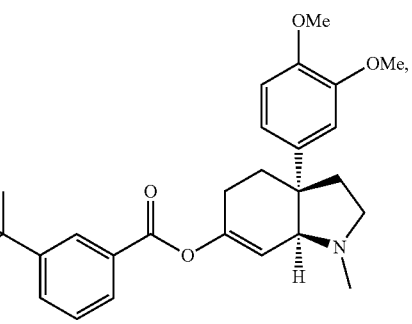
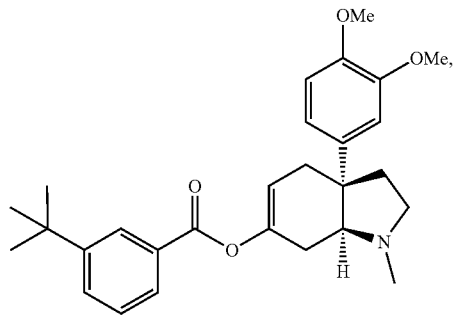
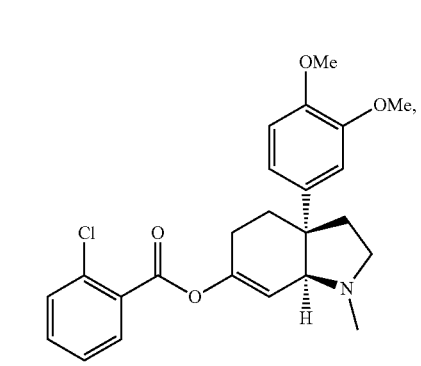
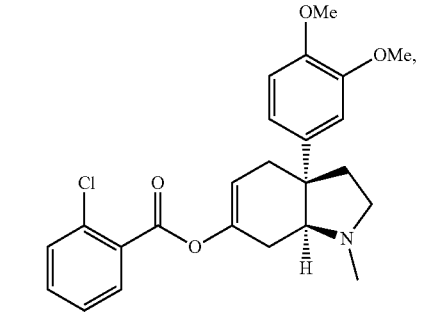
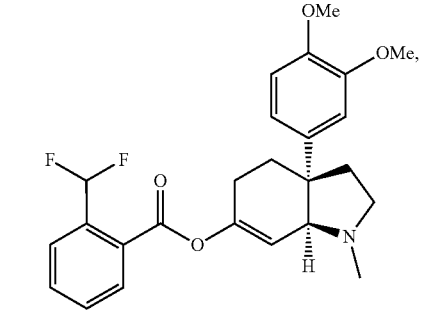
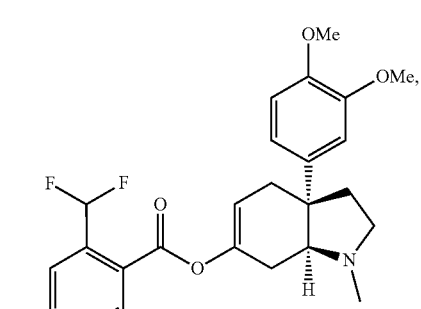

307
-continued
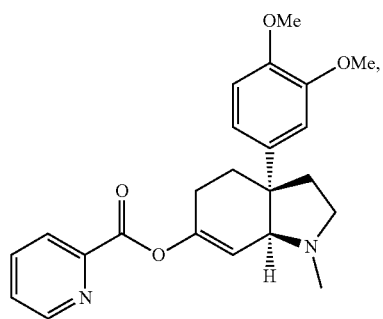
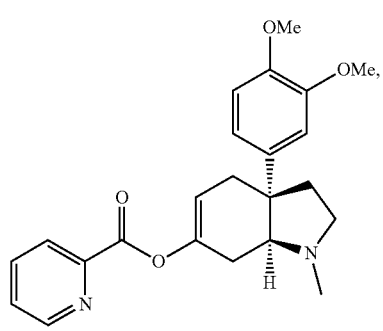
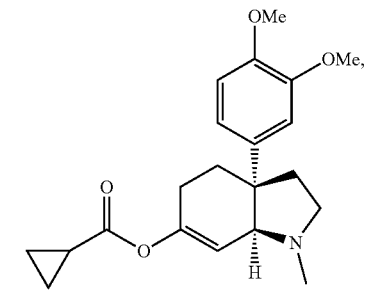
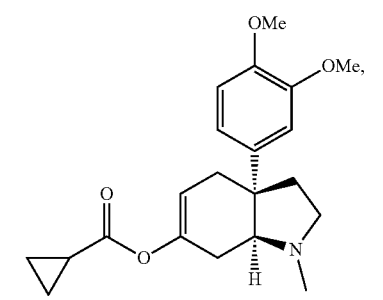
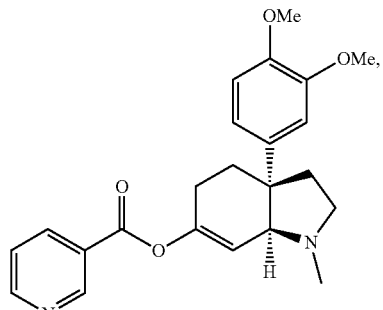
308
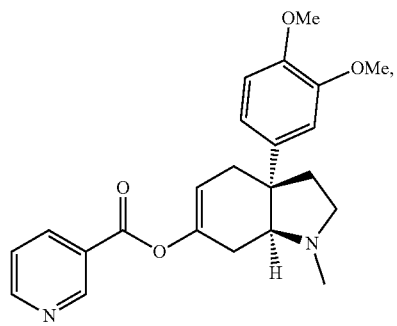
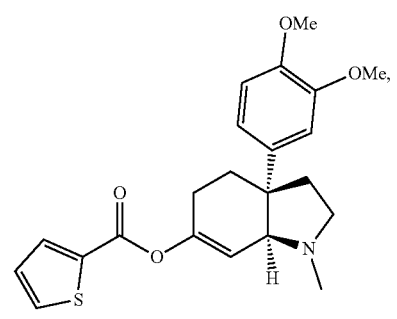
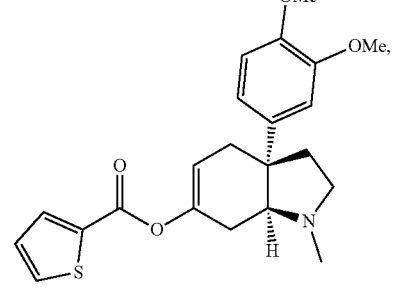
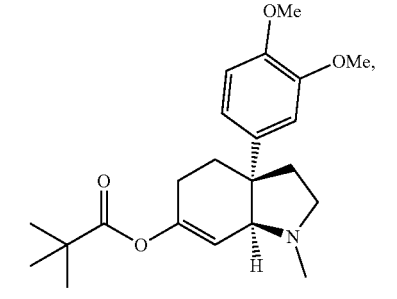
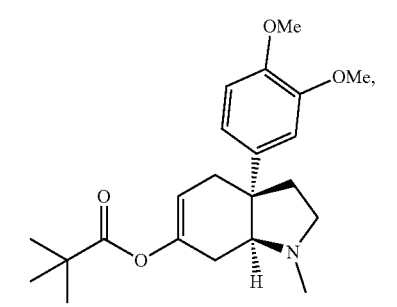

309
-continued
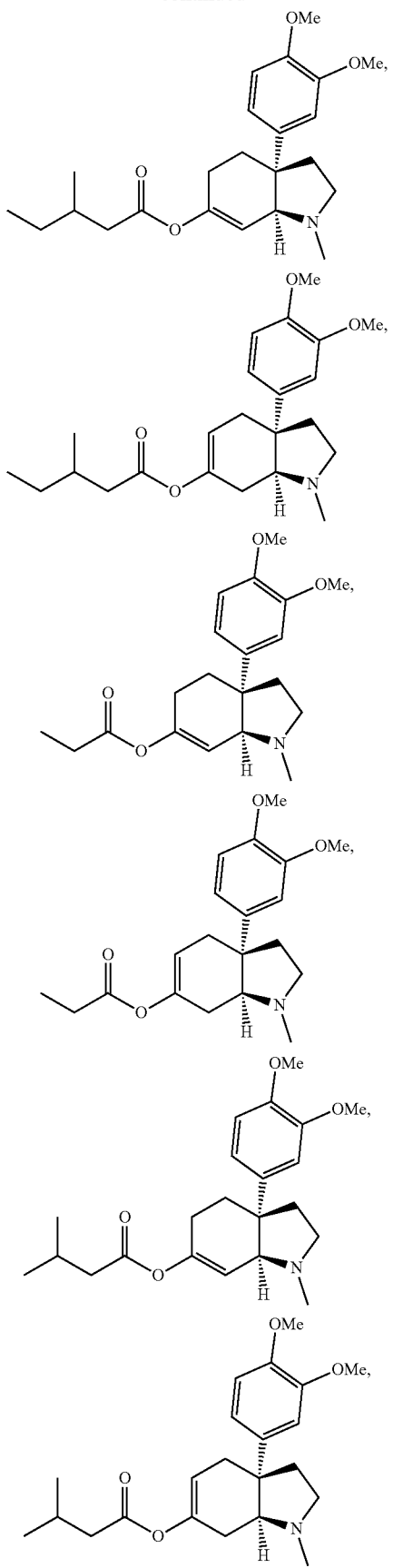
310
-continued
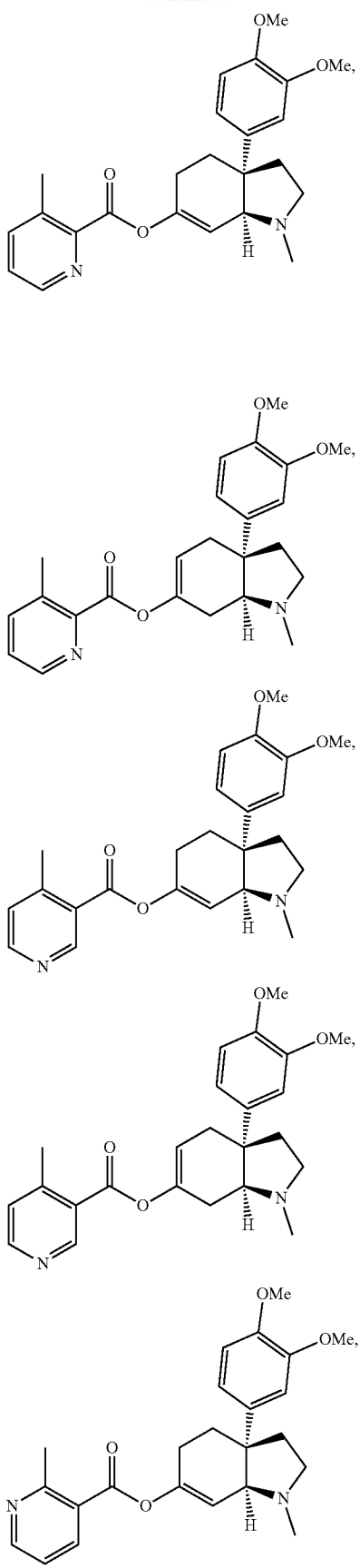

-continued
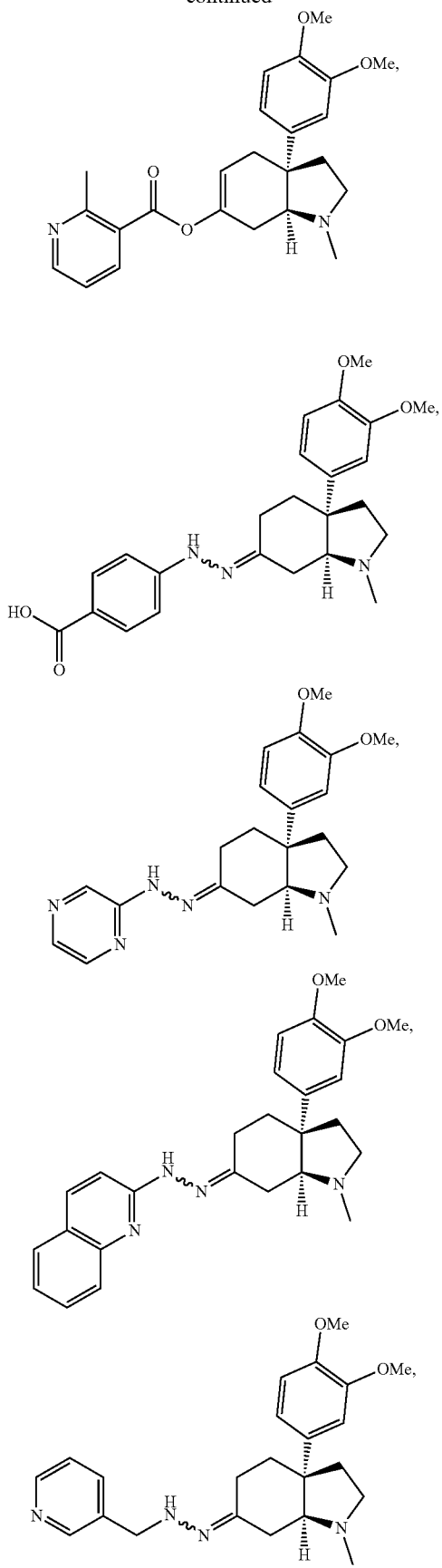
-continued
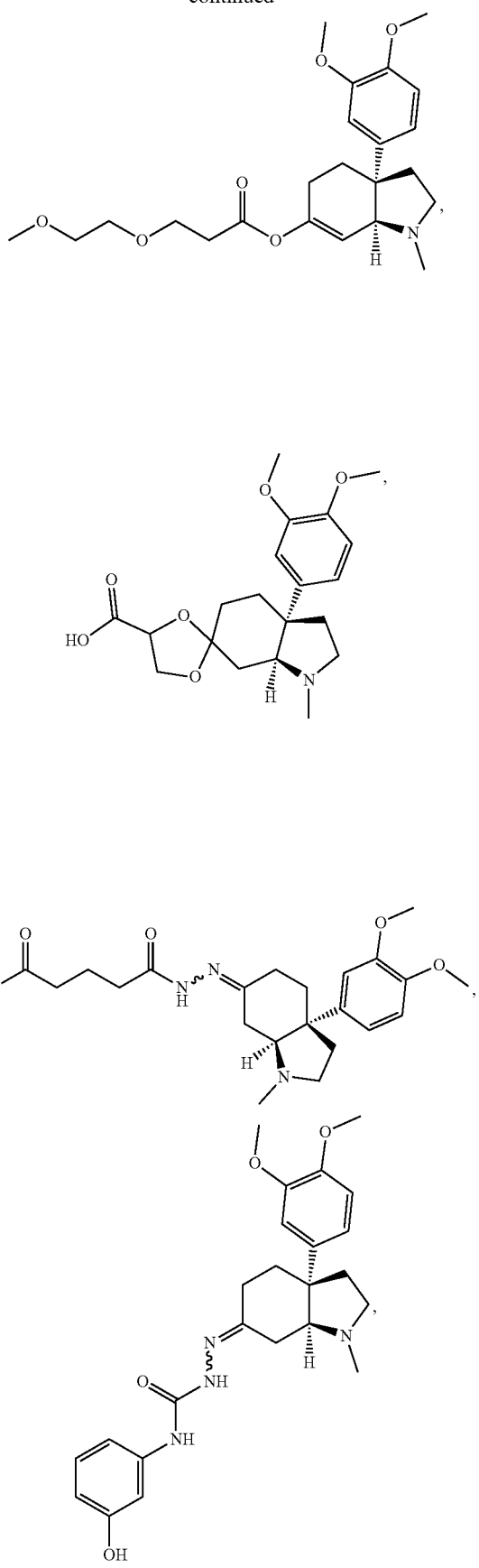

313
-continued
314
-continued
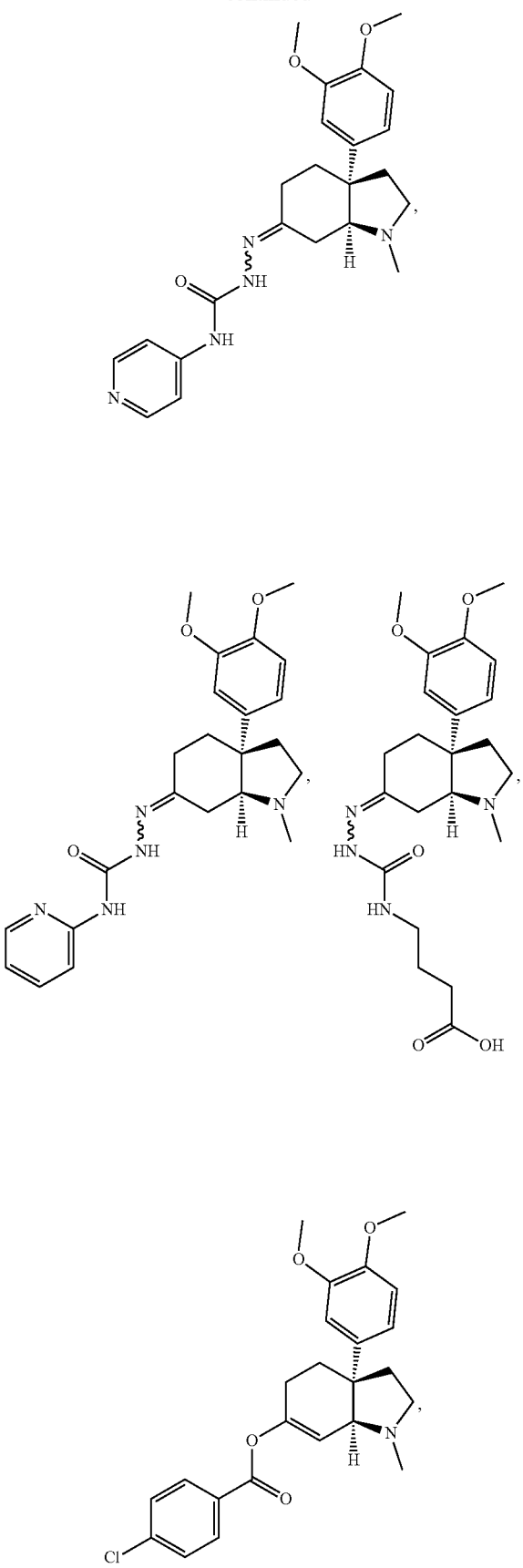
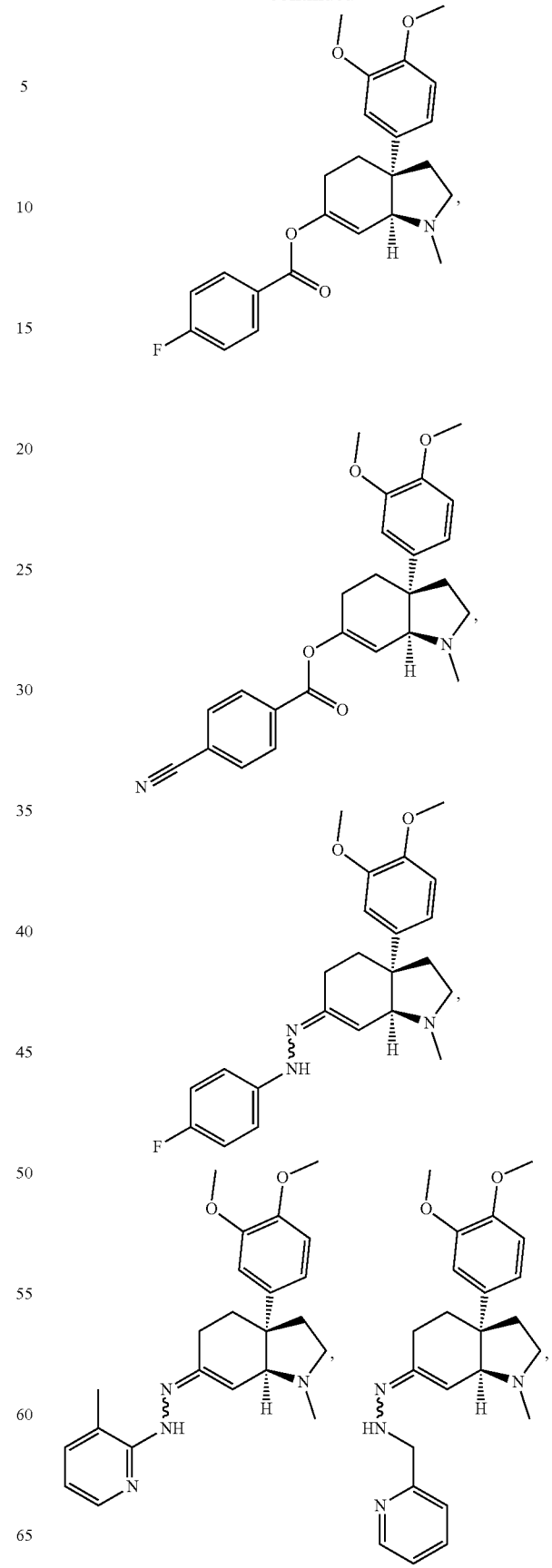

315
-continued
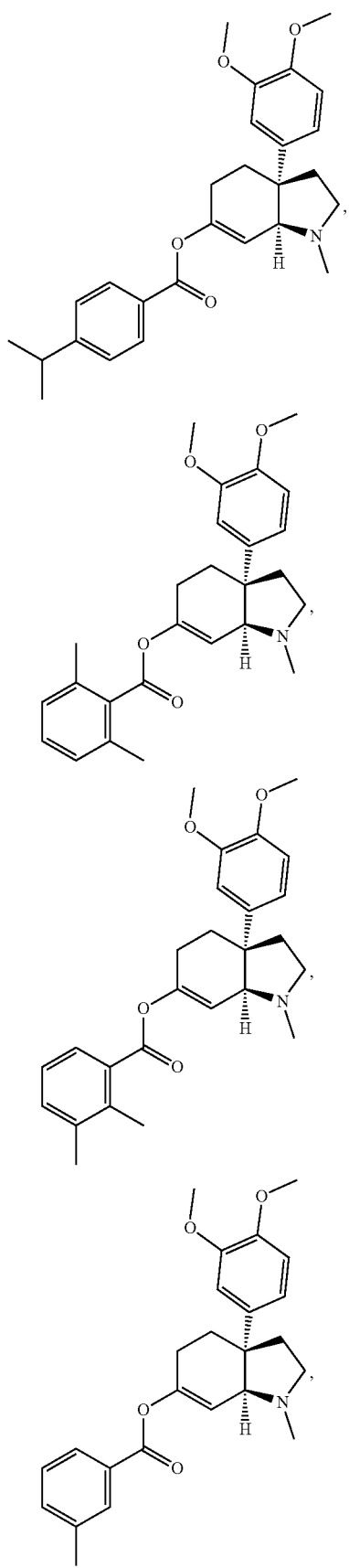
316
-continued
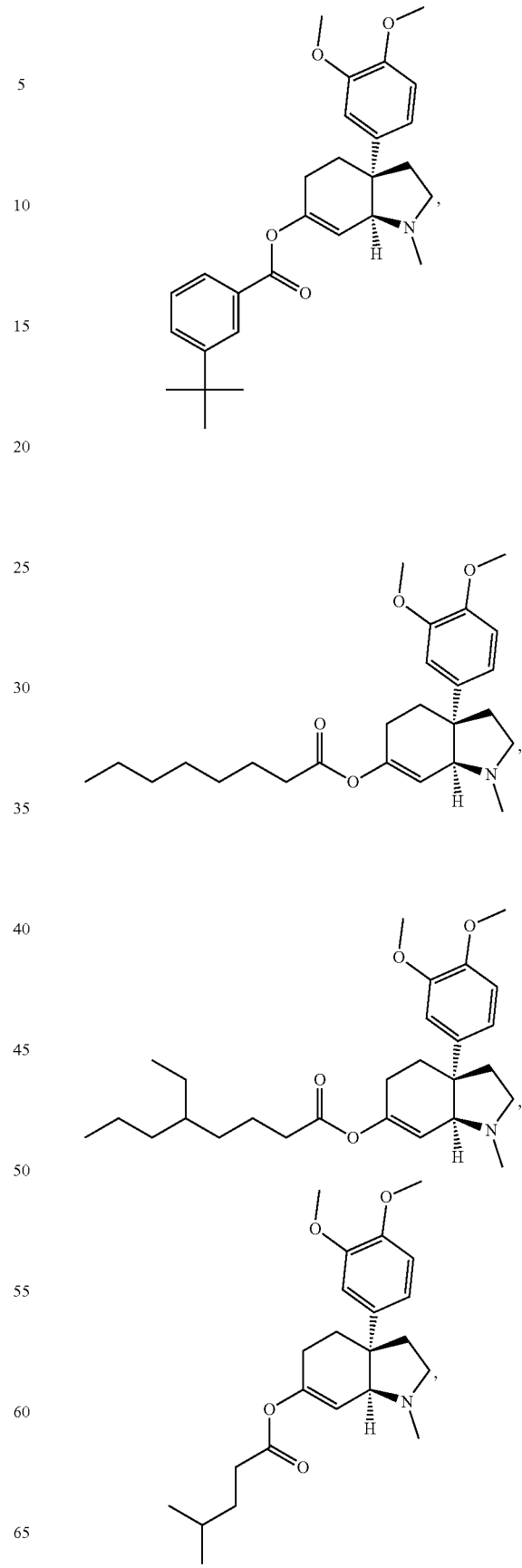

317
-continued
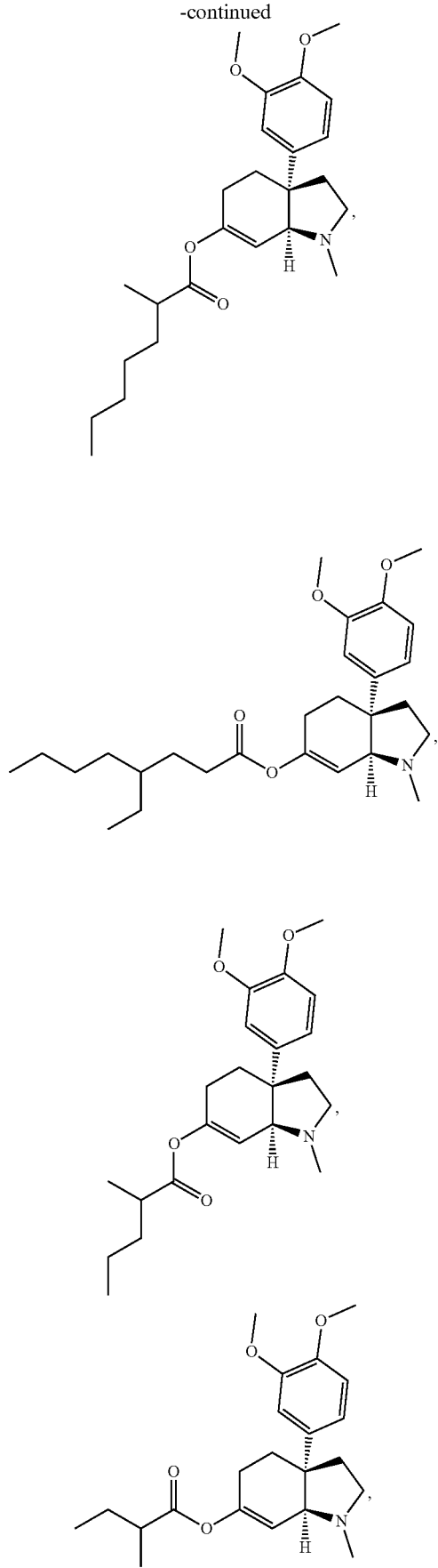
318
-continued
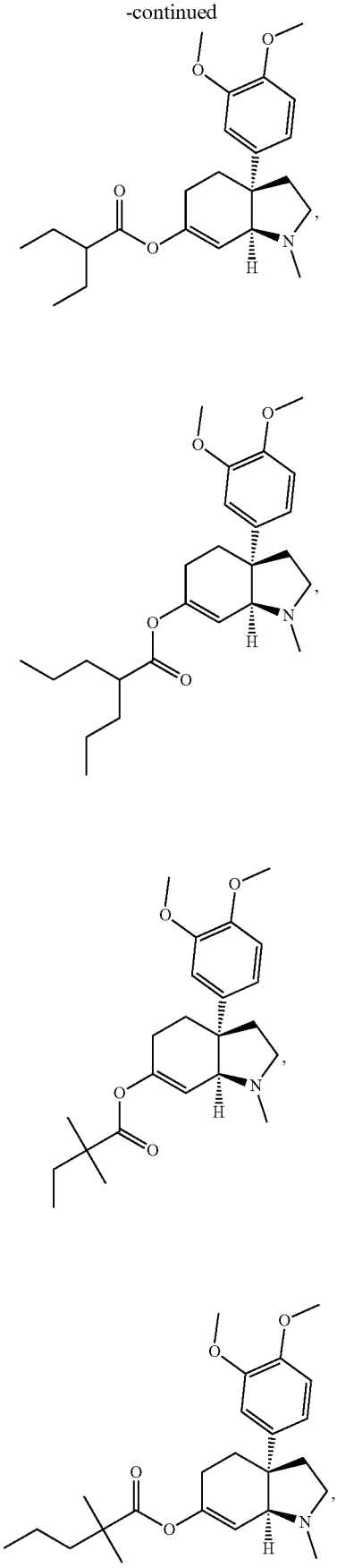

319
-continued
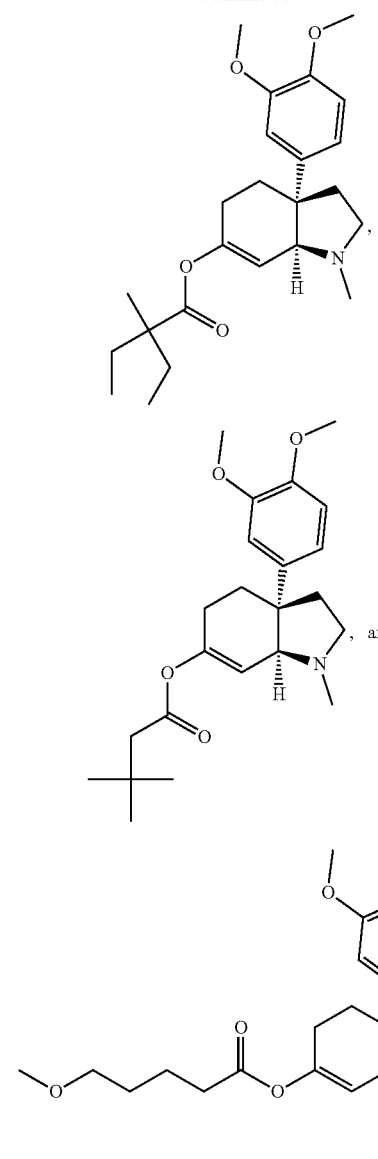
or a pharmaceutically acceptable salt thereof; or a pharmaceutically acceptable salt thereof; wherein the compound has the absolute stereochemistry shown.
In some embodiments, the compound is selected from the group consisting of:
320
-continued
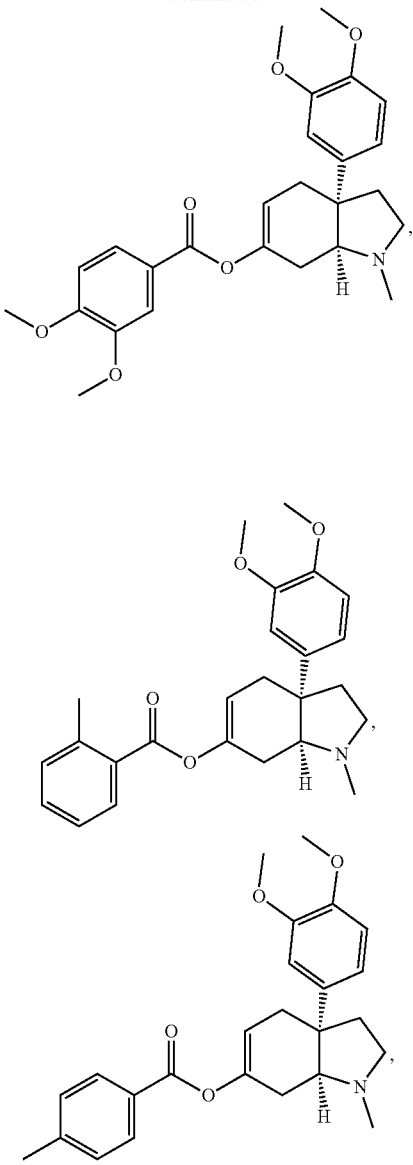
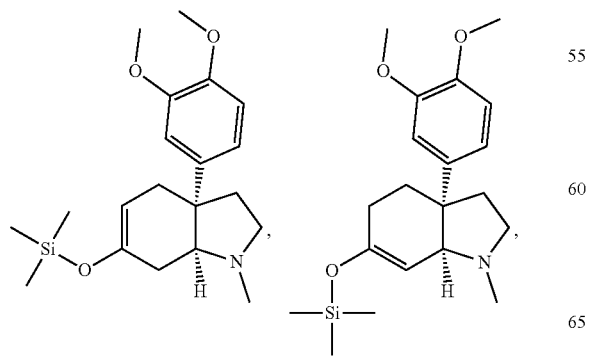
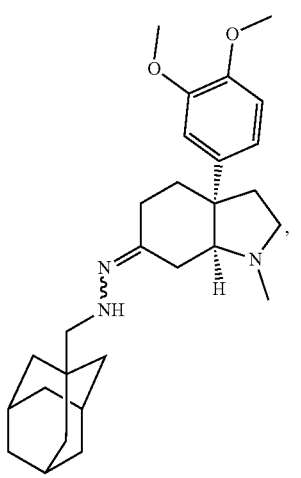

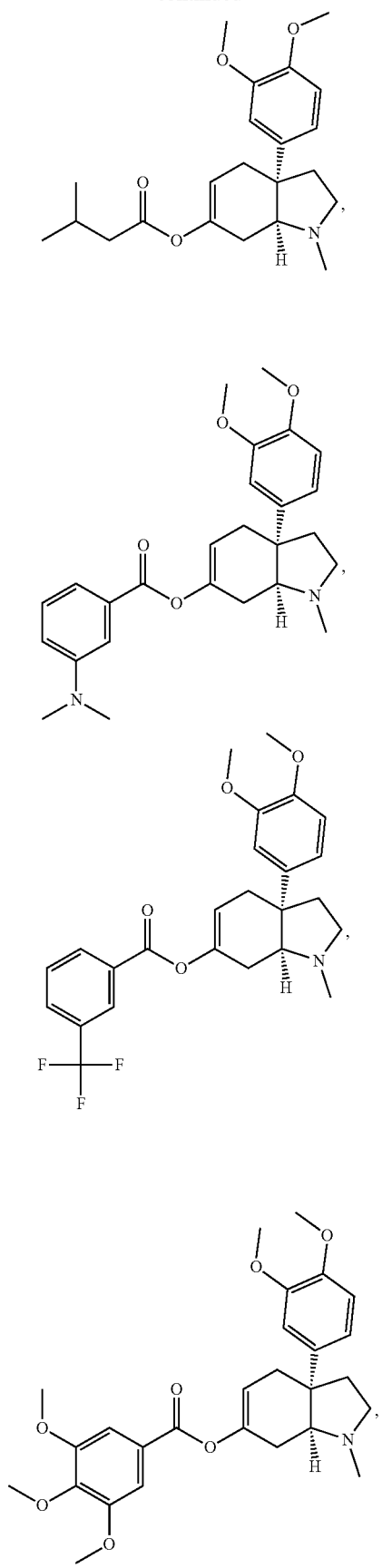
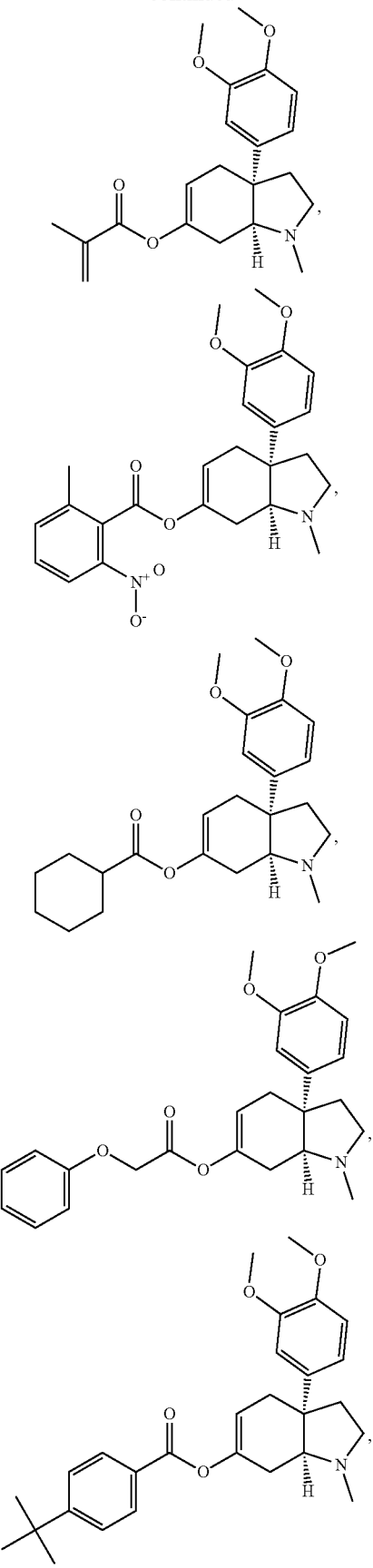

323
-continued
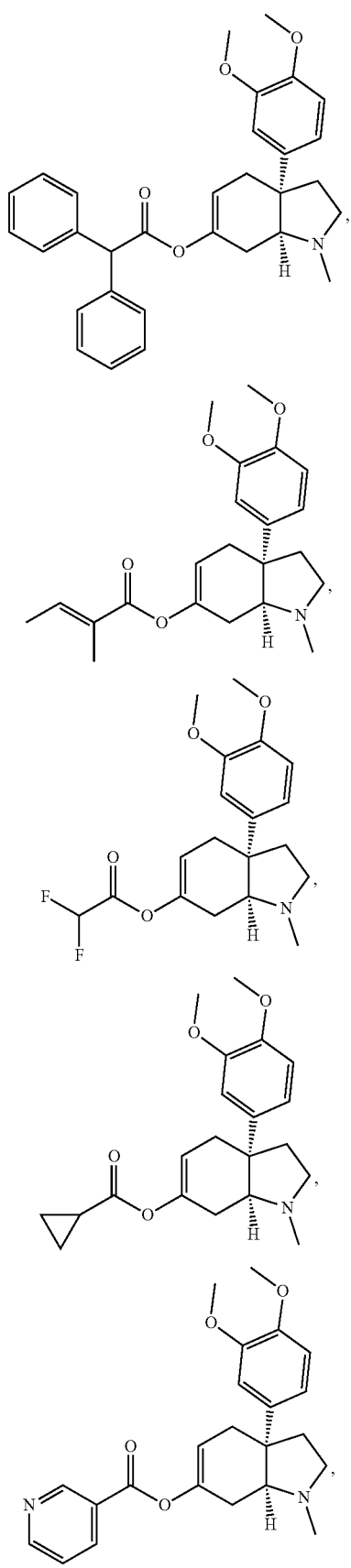
324
-continued
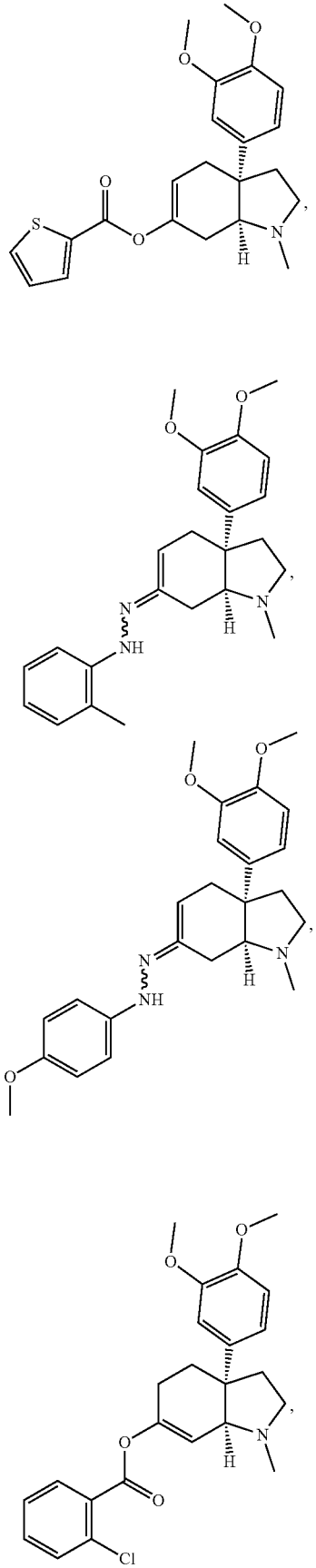

325
-continued
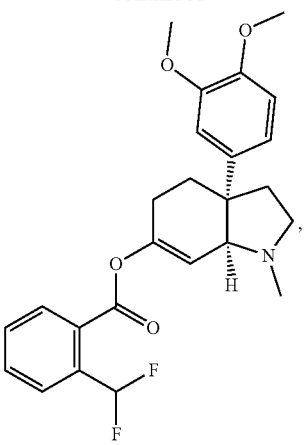
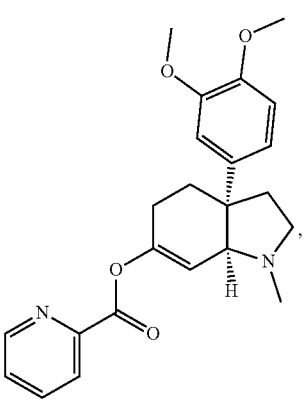
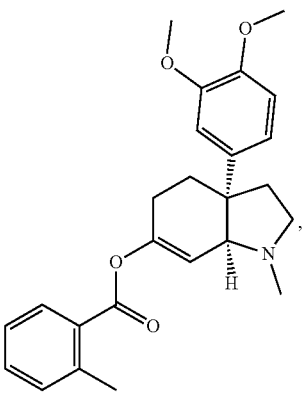
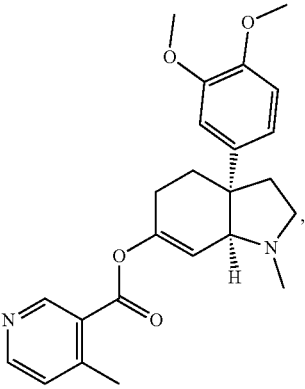
326
-continued
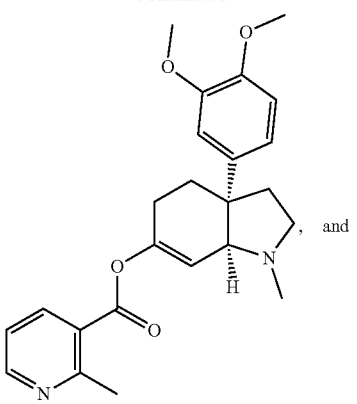, and
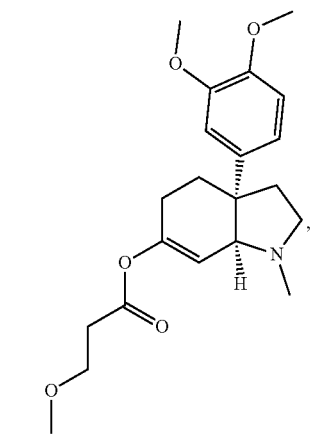
or a pharmaceutically acceptable salt thereof.
In some embodiments, the compound is selected from the group consisting of:
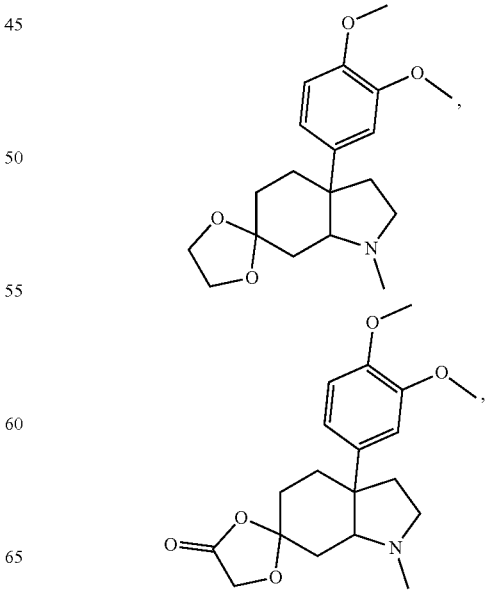

327
-continued
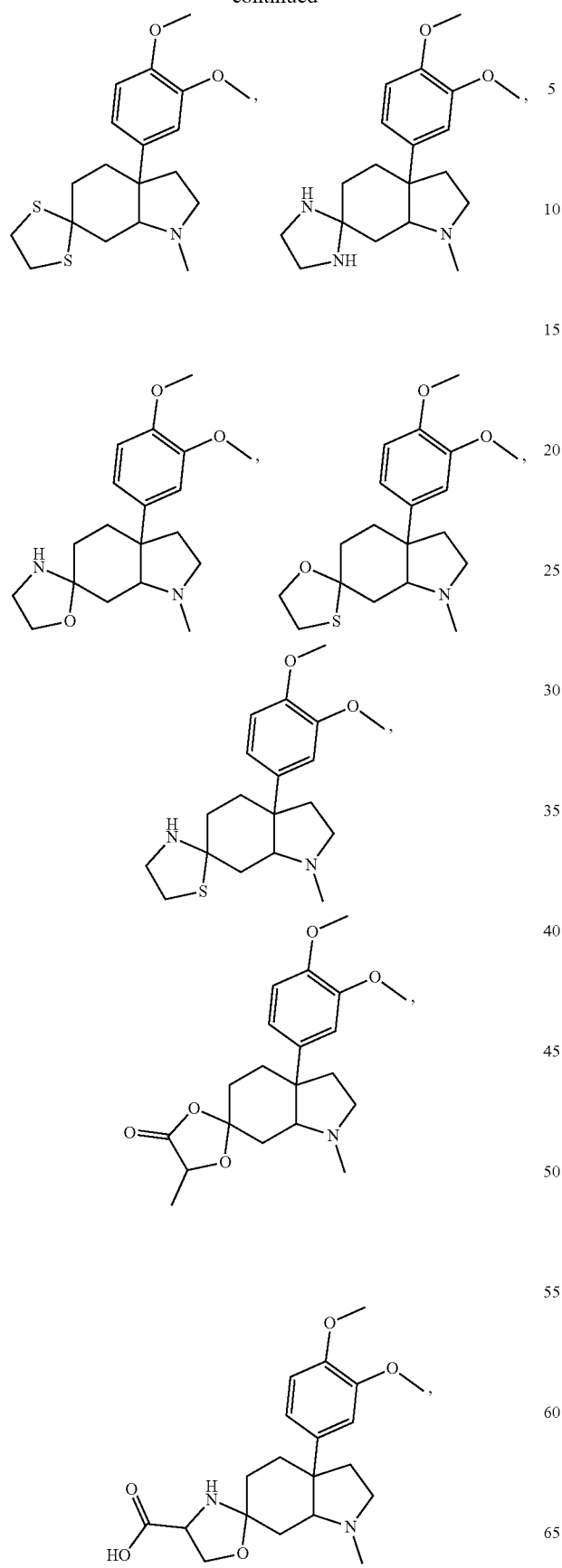
328
-continued
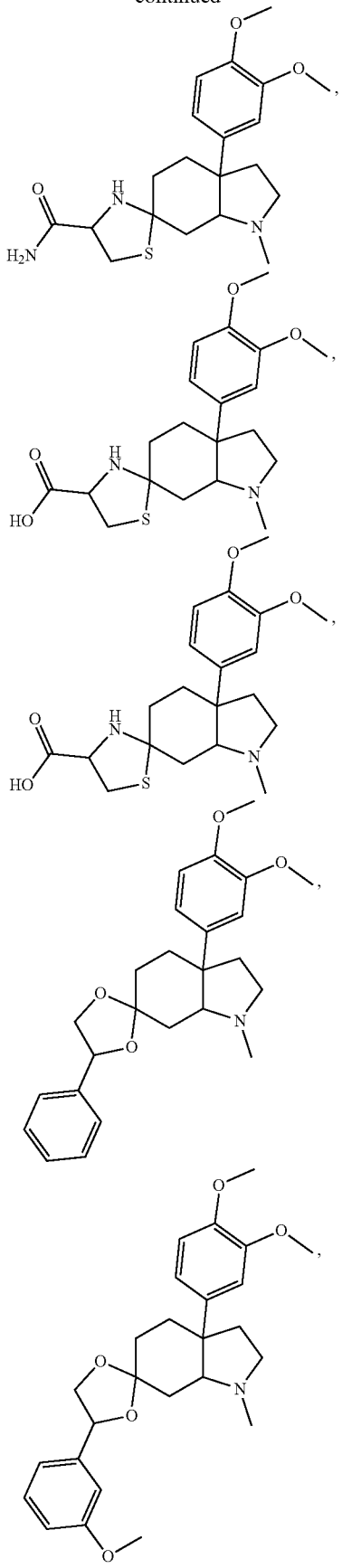

329
-continued
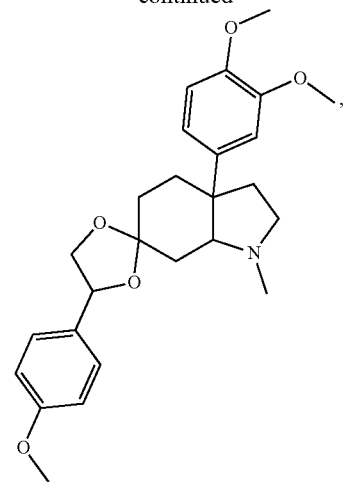
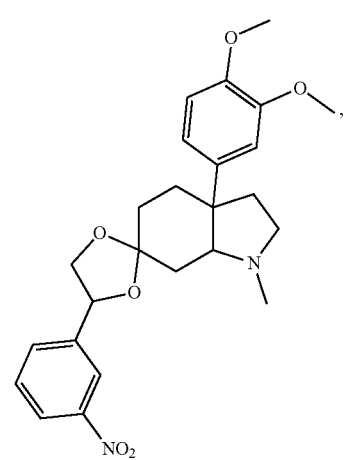
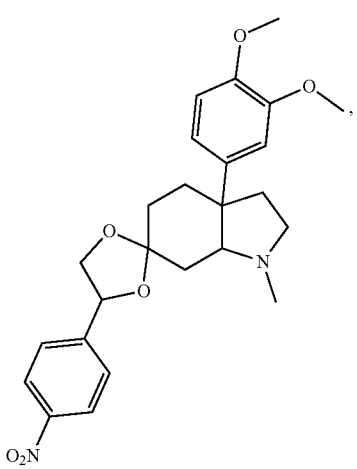
330
-continued
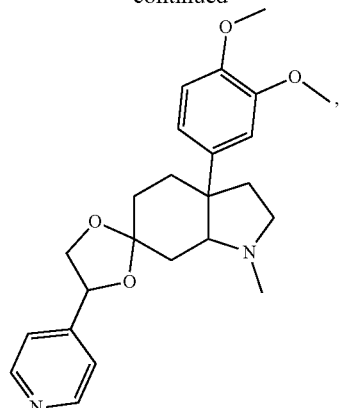
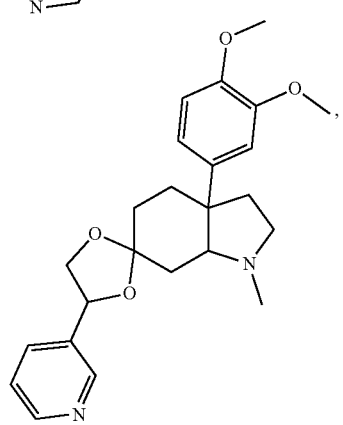
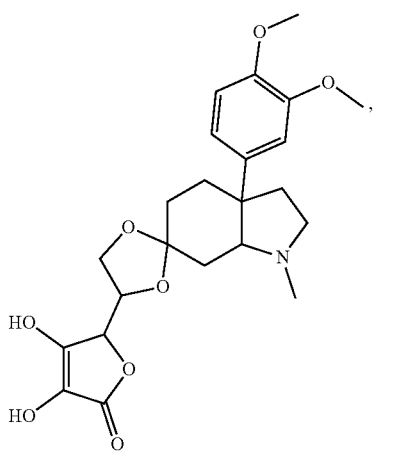
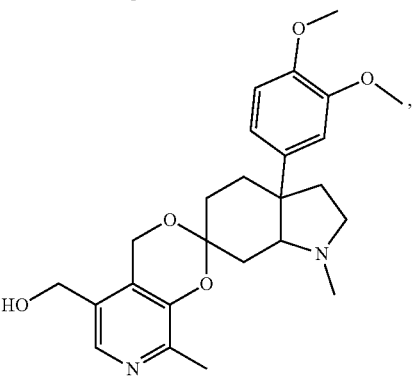

331
-continued
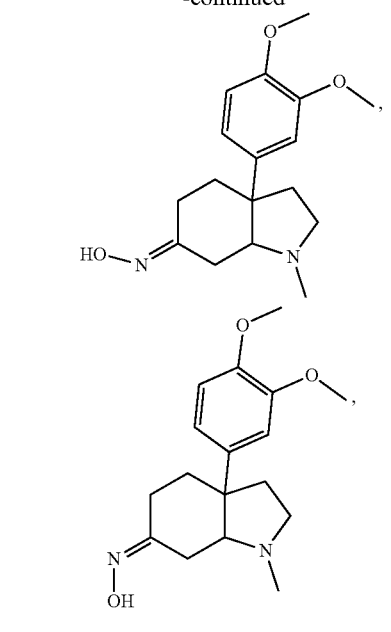
332
-continued
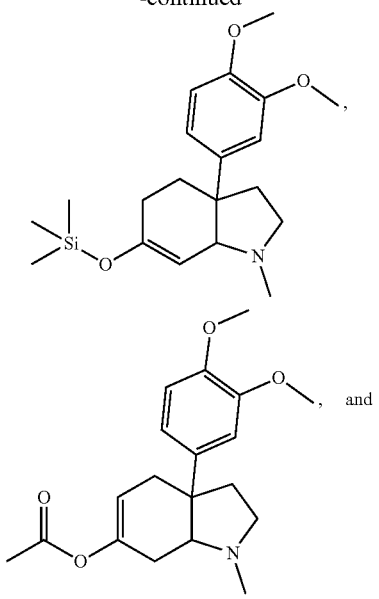
or a pharmaceutically acceptable salt thereof.
In some embodiments, the compound is selected from the group consisting of:
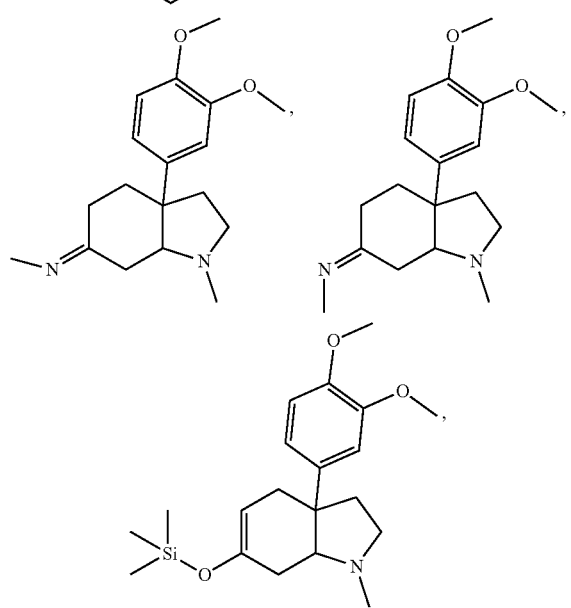
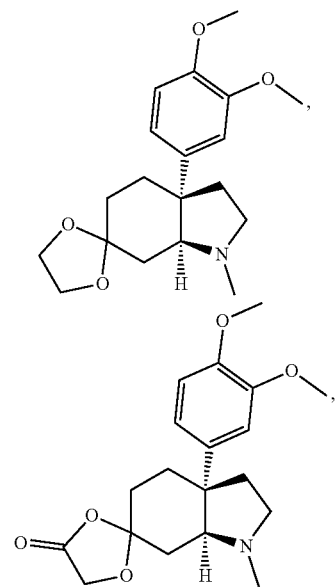

333
-continued
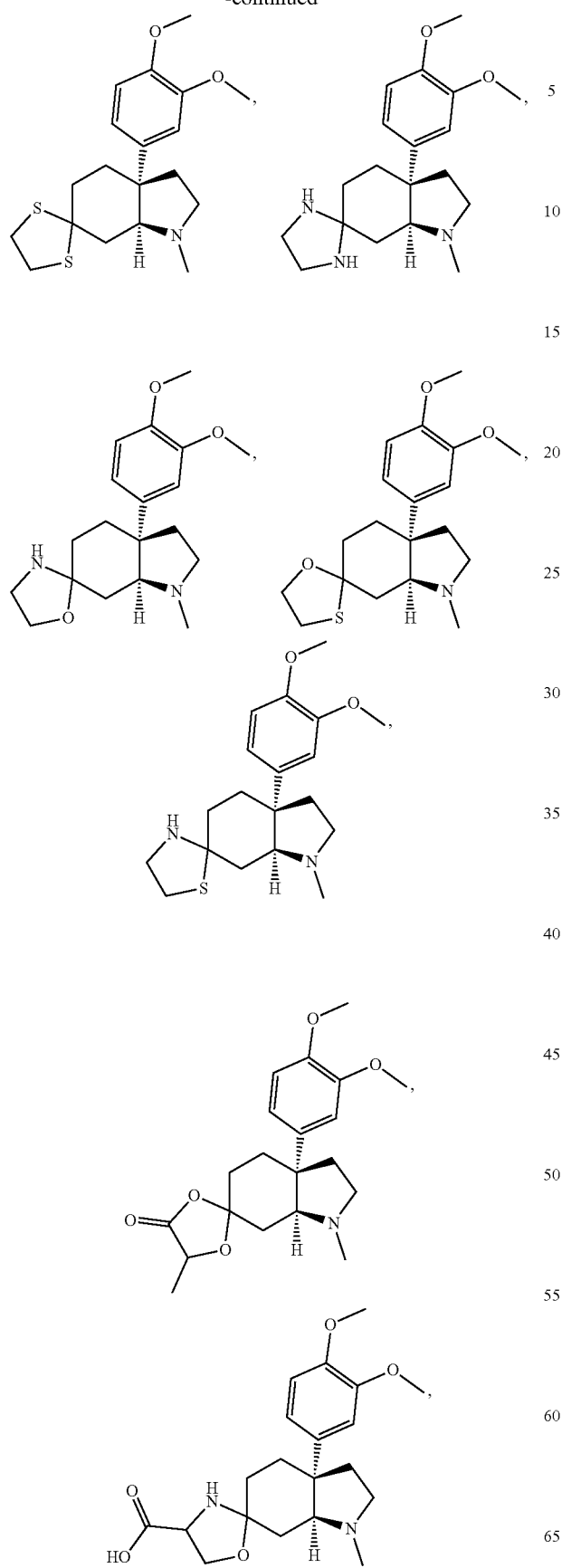
334
-continued
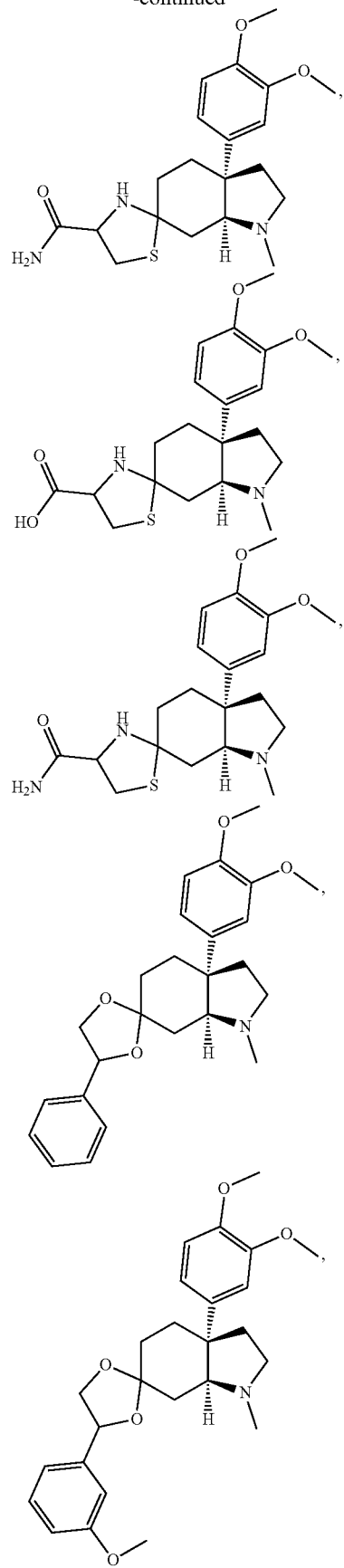

335
-continued
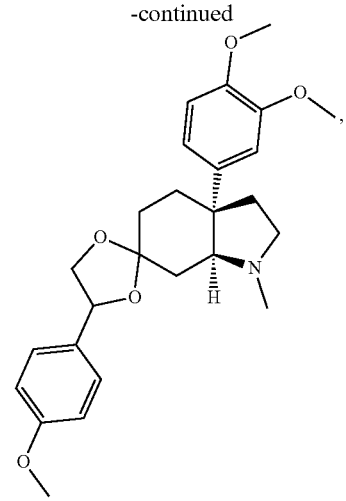
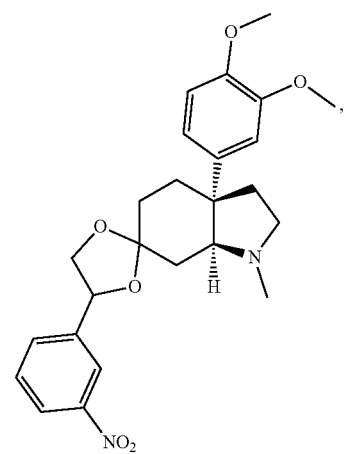
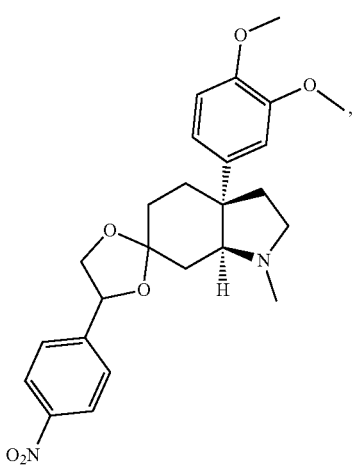
336
-continued
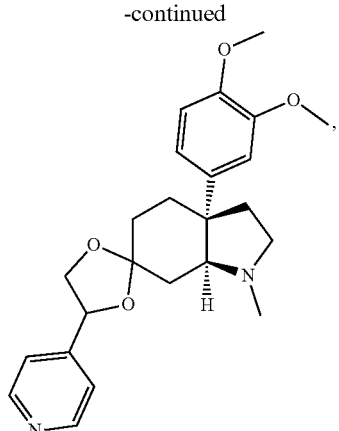
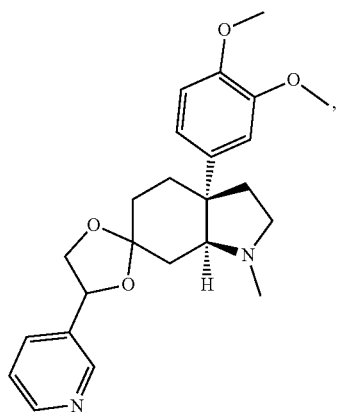
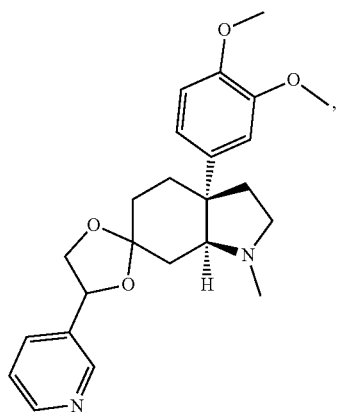
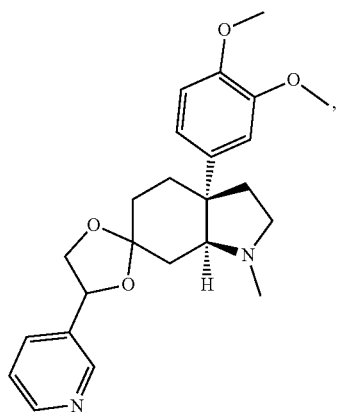

337
-continued

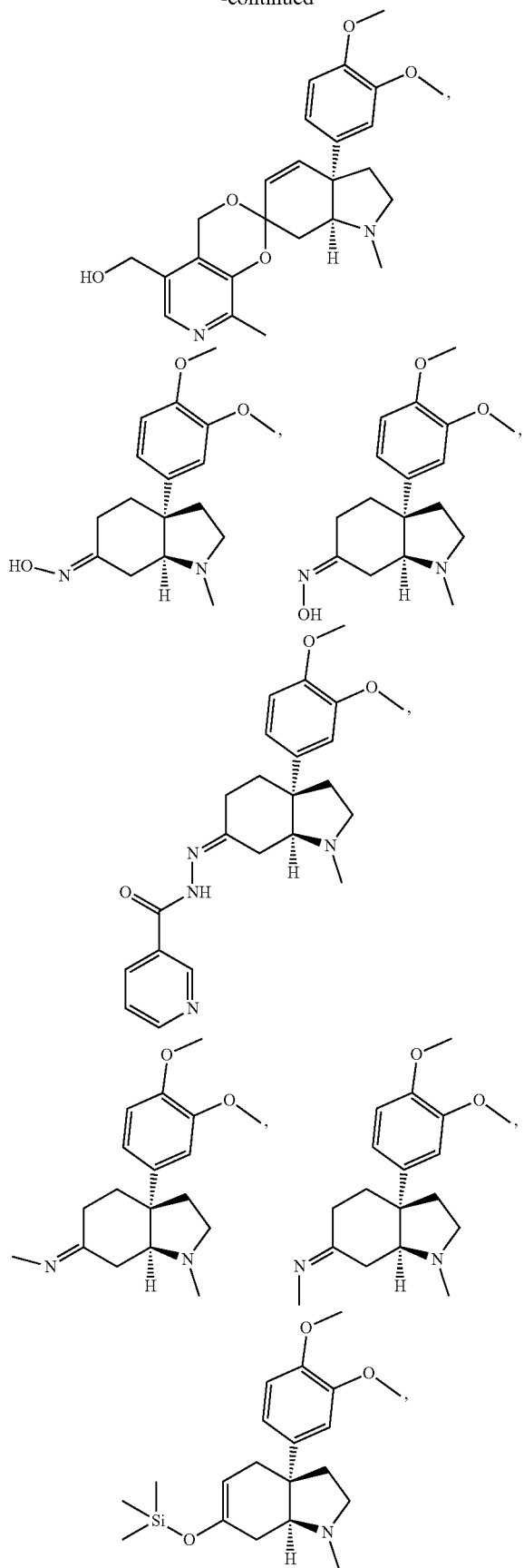

338
-continued

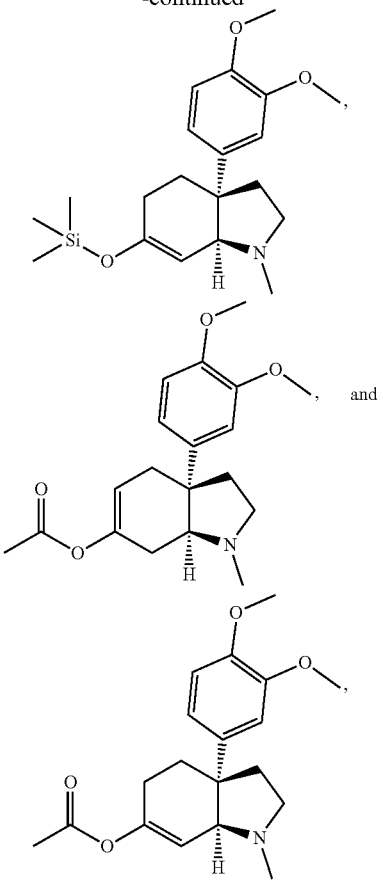

or a pharmaceutically acceptable salt thereof; and the compound has the absolute stereochemistry shown.

In certain embodiments, compounds described herein can form mesembrine (e.g., (−) mesembrine) under biologically relevant conditions. For example, in some embodiments, compounds of disclosed herein (e.g., compounds of Formula (I)) can hydrolyze in highly acidic environments (e.g., pH of about 2 at room temperature or more comparably stringent conditions typically encountered within the alimentary canal of a mammal) at a rate that is advantageous for providing a desired bioabsorption (% F) following oral administration by a mammal and leading to a desired pharmacokinetic profile of mesembrine (e.g., (−) mesembrine) to the mammal.

In some embodiments, a compound according to the present disclosure is of formula (I):

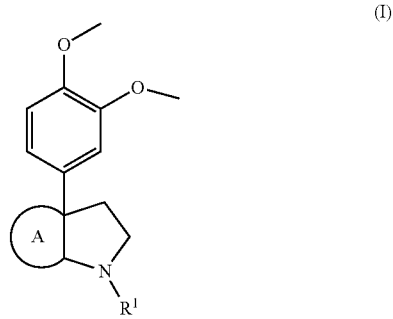

(I)

or a pharmaceutically acceptable salt thereof.

In some embodiments, ring A is

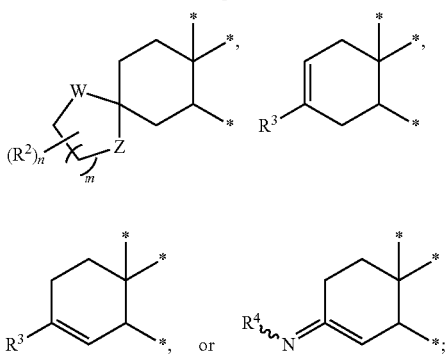

wherein * denotes the attachment points of ring A to the compound of formula (I).

In some embodiments, each of W and Z is independently O, NH, or S. In some embodiments, W is O. In some embodiments, W is NH. In some embodiments, W is S.

In some embodiments, each $R^2$ is independently $C_1$-$C_3$ alkyl, —COOH, —CONH$_2$, phenyl, 5- to 7-membered heterocyclyl, or 5- to 7-membered heteroaryl. In some embodiments, each hydrogen atom in phenyl, 5- to 7-membered heterocyclyl and 5- to 7-membered heteroaryl is optionally substituted by —OH, $C_1$-$C_3$ alkyl, $C_1$-$C_3$ alkoxy, $C_1$-$C_3$ alkanol, or —NO$_2$. In some embodiments, $R^2$ is —COOH, —CONH$_2$, phenyl, 5- to 7-membered heterocyclyl, or 5- to 7-membered heteroaryl, wherein each hydrogen atom in phenyl, 5- to 7-membered heterocyclyl and 5- to 7-membered heteroaryl is optionally substituted by —OH, $C_1$-$C_3$ alkyl, $C_1$-$C_3$ alkoxy, $C_1$-$C_3$ alkanol, or —NO$_2$. In some embodiments, $R^2$ is phenyl, wherein each hydrogen atom in phenyl is optionally substituted by —OH, $C_1$-$C_3$ alkyl, $C_1$-$C_3$ alkoxy, or —NO$_2$. In some embodiments, $R^2$ is 5- to 7-membered heterocyclyl or 5- to 7-membered heteroaryl, wherein each hydrogen atom in 5- to 7-membered heterocyclyl and 5- to 7-membered heteroaryl is optionally substituted by —OH, $C_1$-$C_3$ alkyl, $C_1$-$C_3$ alkoxy, $C_1$-$C_3$ alkanol, or —NO$_2$. In some embodiments, $R^2$ is pyridyl. In some embodiments, $R^2$ is

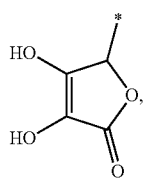

wherein * denotes the point of attachment of $R^2$ the compound. In some embodiments, $R^2$ is —COOH or —CONH$_2$.

In some embodiments, two $R^2$s on a single carbon atom combine to form =O.

In some embodiments, two adjacent $R^2$s together with the carbon atoms to which they are attached combine to form 5- to 7-membered heteroaryl, wherein each hydrogen atom in 5- to 7-membered heteroaryl is optionally substituted by —OH, $C_1$-$C_3$ alkyl, or $C_1$-$C_3$ alkanol. In some embodiments, the two $R^2$s together with the carbon atoms to which they are attached combine to form pyridyl, wherein each hydrogen atom in pyridyl is optionally substituted by —OH, $C_1$-$C_3$ alkyl, or $C_1$-$C_3$ alkanol.

In some embodiments, m is 1 or 2.

In some n is 0, 1, or 2. In some embodiments, n is 0. In some embodiments, n is 1. In some embodiments, n is 2.

In some embodiments, $R^3$ is —OSi($C_1$-$C_6$ alkyl)$_3$ or —OC(O)$C_1$-$C_6$ alkyl. In some embodiments, $R^3$ is —OSi($C_1$-$C_6$ alkyl)$_3$. In some embodiments, $R^3$ is —OC(O)$C_1$-$C_6$ alkyl (e.g., —OC(O)CH$_3$).

In some embodiments, $R^4$ is OH, $C_1$-$C_6$ alkoxy, or —NHC(O)-5- to 7-membered heteroaryl. In some embodiments, each hydrogen atom in 5- to 7-membered heteroaryl is optionally substituted by —OH, $C_1$-$C_3$ alkyl, or $C_1$-$C_3$ alkanol.

In some embodiments, $R^1$ is H or $C_1$-$C_7$ alkyl. In some embodiments, $R^1$ is $C_1$-$C_3$ alkyl. In some embodiments, $R^1$ is methyl.

In some embodiments, the compounds of Formula (I) can be obtained by reacting mesembrine or with a compound designated as Generally Recognized as Safe (GRAS) by the U.S. Food and Drug Administration (FDA) (G) under sections 201(s) and 409 of the U.S. federal Food, Drug and Cosmetics Act (FDCA), and under the corresponding implementing regulations in 21 CFR 170.3 and 21 CFR 170.30. For example, novel compounds that convert to mesembrine can be obtained by reaction of either compound with lactic acid, glycolic acid, ascorbic acid (vitamin C), and pyridoxine (vitamin B6) derivatives. Table provides examples of compounds that can be reacted to obtain compounds of Formula (I) by the reaction: Compound M+Compound R→Compound C.

| Reactant M | Reactant R | Product Compound C |
|---|---|---|
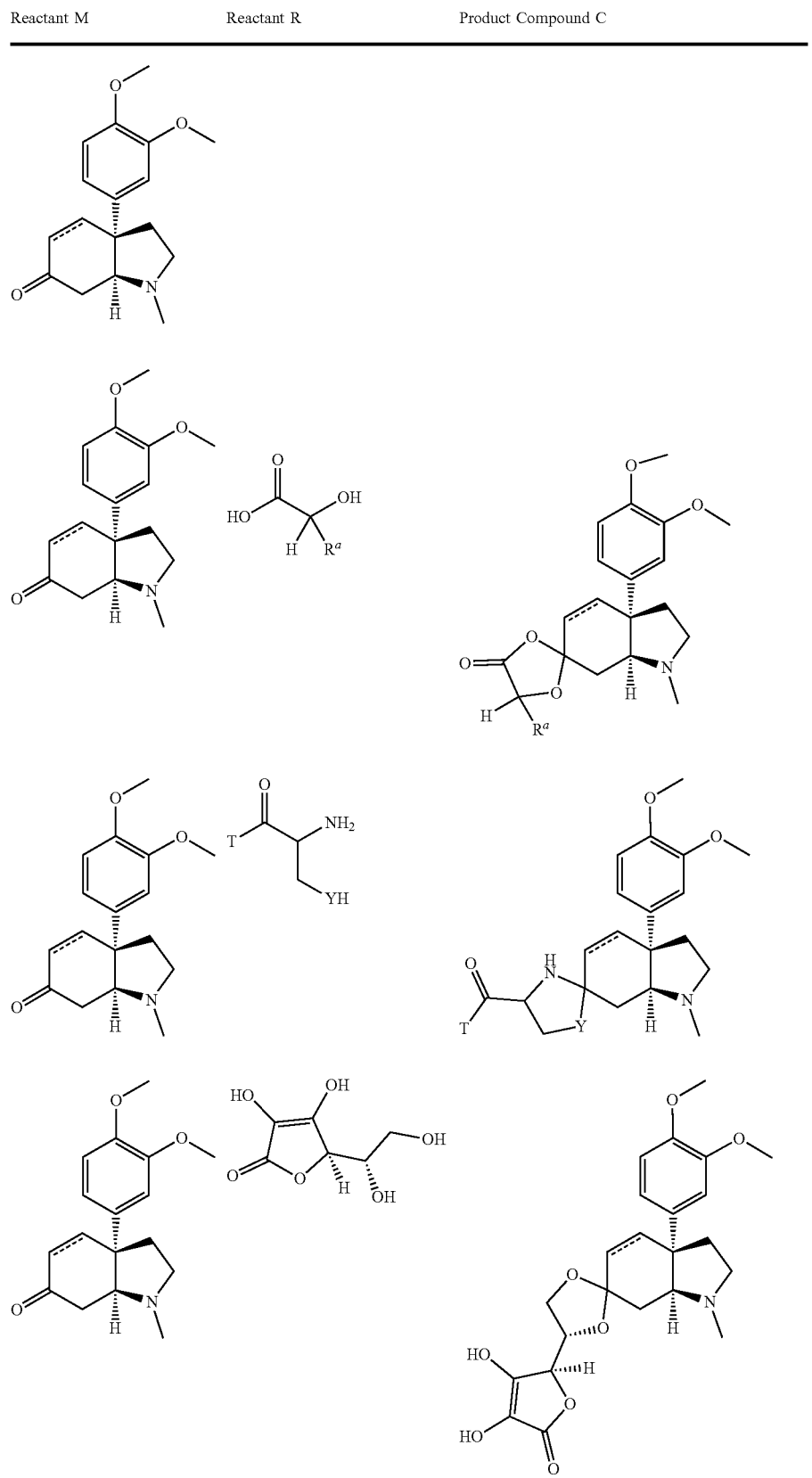

| Reactant M | Reactant R | Product Compound C |
|---|---|---|

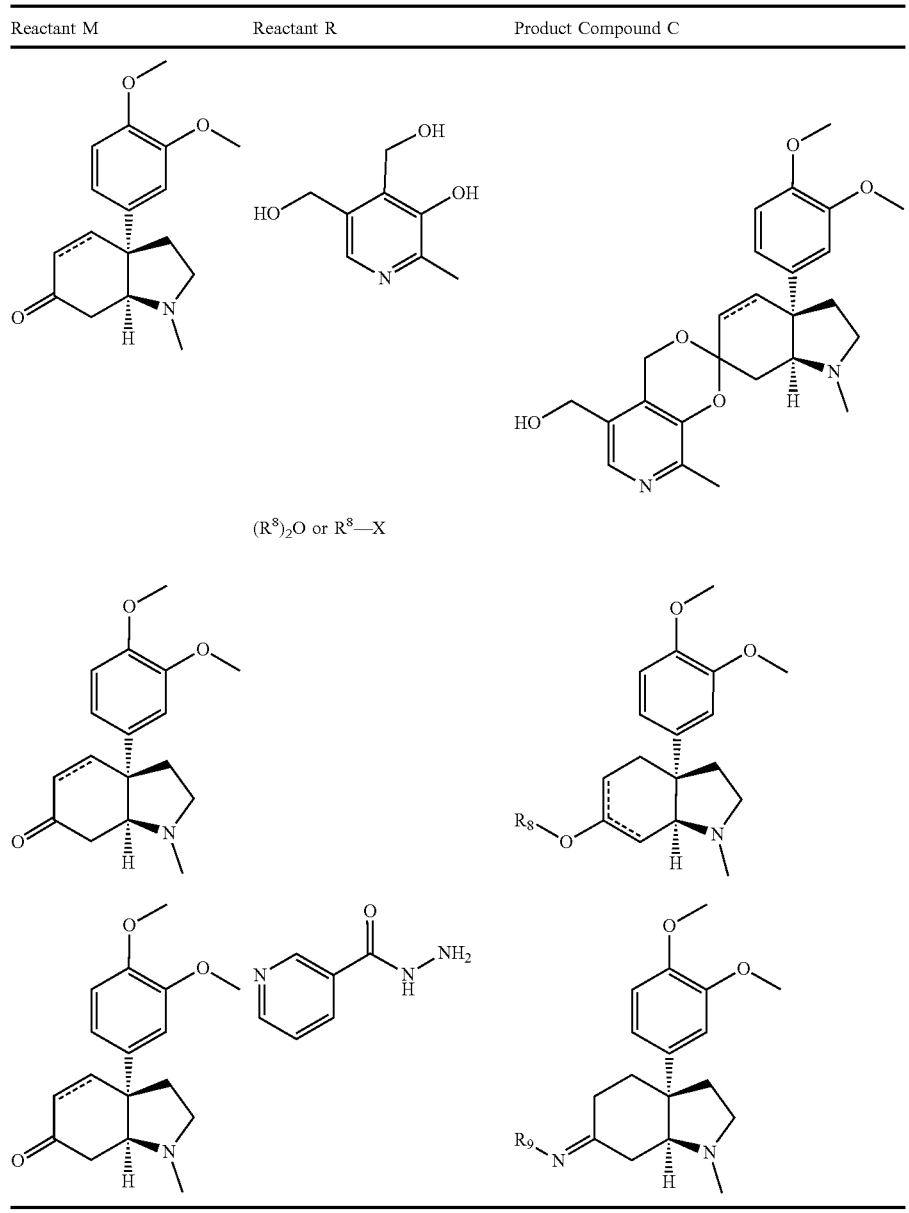

Wherein the dashed bond is present or absent.

Unless otherwise indicated in the tables of compounds herein, the abbreviation RAC or rac indicates a racemic mixture, and DIAST indicates a specific diastereomer. In illustrative embodiments, although a compound may be depicted with ▰ or ▱ bonds, such a depiction may be denoting relative stereochemistry based on elution peaks from a chiral separation.

Compounds of Formula (I) including compounds of Formula (IIa) and Formula (IIb) can be prepared as described with respect to exemplary compounds in the examples below. In general, treatment of a ketone, such as mesembrine, with an appropriate diol or dithiane, and an acid catalyst, such as p-toluenesulfonic acid or methanesulfonic acid, in a solvent, such as toluene, at an elevated temperature is a method to prepare compounds of Formula (IIa-IIb).

TABLE 1

Exemplary Compounds of Formula IIa-IIb

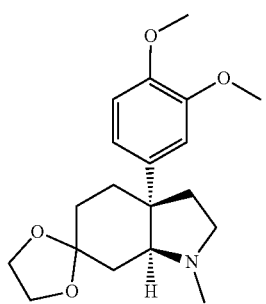 [SMILES: COc1ccc([C@]23CCN(C)[C@H]2CC2(CC3)OCCO2)cc1OC]

TABLE 1-continued
Exemplary Compounds of Formula IIa-IIb
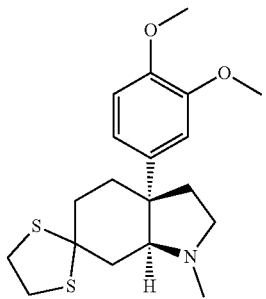 [SMILES: COc1ccc([C@]23CCN(C)[C@H]2CC2(CC3)SCCS2)cc1OC]
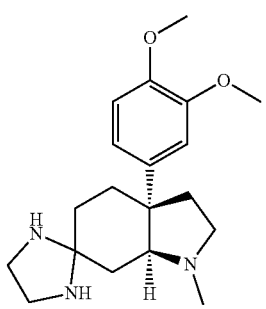 [SMILES: COc1ccc([C@]23CCN(C)[C@H]2CC2(CC3)NCCN2)cc1OC]
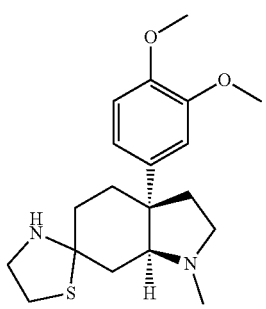 [SMILES: COc1ccc([C@]23CCN(C)[C@H]2CC2(CC3)NCCS2)cc1OC]
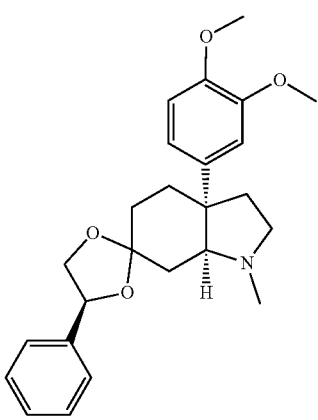 [SMILES: COc1ccc([C@]23CCN(C)[C@H]2CC2(CC3)OC[C@H](c3ccccc3)O2)cc1OC]
TABLE 1-continued
Exemplary Compounds of Formula IIa-IIb
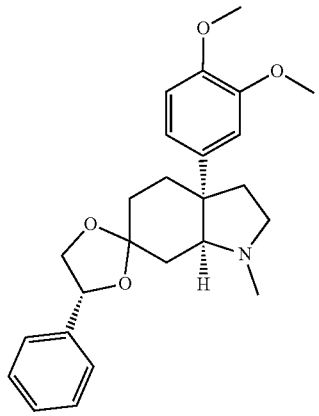 [SMILES: COc1ccc([C@]23CCN(C)[C@H]2CC2(CC3)OC[C@@H](c3ccccc3)O2)cc1OC]
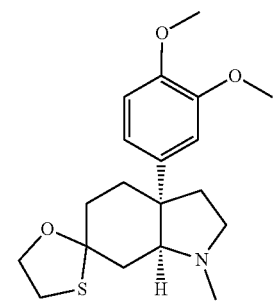 [SMILES: COc1ccc([C@]23CCN(C)[C@H]2CC2(CC3)OCCS2)cc1OC]
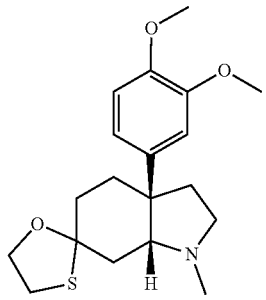 [SMILES: COc1ccc([C@@]23CCN(C)[C@@H]2CC2(CC3)OCCS2)cc1OC]
In some embodiments, the compound of formula (I) is a compound of formula (IX):
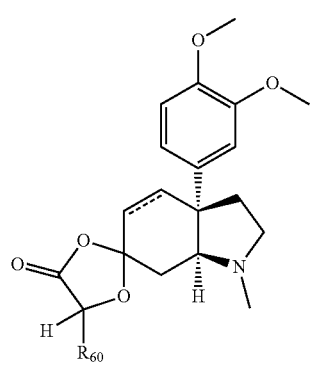
(IX)
or a pharmaceutically acceptable salt thereof, wherein the dashed bond is absent or present, and $R_{60}$ is hydrogen or methyl.

In some embodiments, a compound of formula (I) can be a compound of Formula (IX-1) that converts to mesembrine (e.g., (−) mesembrine) upon oral administration to a mammal and upon hydrolysis in sufficiently acidic conditions (e.g., pH 2 at 37 degrees C.), where $R_{60}$ is defined with respect to Formula (IX) above.

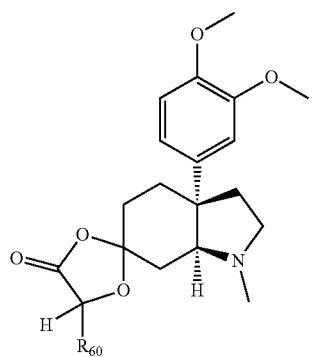

Formula (IX-1)

Compounds of Formula (IX) including compounds of Formula (IX-1) can be prepared as described with respect to compounds in the examples below. In general treatment of a ketone, such as mesembrine, with an appropriate alpha-hydroxy carboxylic acid, with a Lewis acid, such as boron trifluoride etherate, in a solvent, such as dichloromethane, is a method to prepare compounds of Formula (IX). For example, a compound of formula (IX-1) where $R_{60}$ is methyl can be obtained by reacting mesembrine with lactic acid (e.g., with TsOH, toluene). In some embodiments, the compound can be a lactate or glycolate derivative of mesembrine. $R_{60}$ in Scheme 2 is as defined above with respect to Formula (I-B).

Table provides non-limiting examples of certain compounds of Formula (IX).

TABLE

Exemplary Compounds of Formula IX

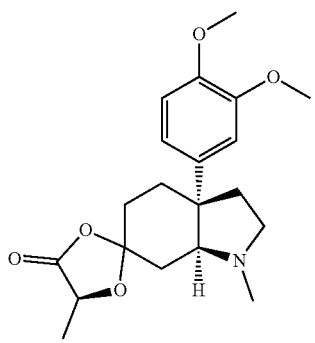

TABLE-continued

Exemplary Compounds of Formula IX

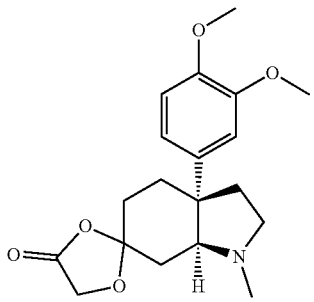 [SMILES: COc1ccc([C@]23CCN(C)[C@H]2CC2(CC3)OCC(=O)O2)cc1OC]

In some embodiments, the compound of Formula (I) is a compound of Formula (X) or a pharmaceutically acceptable salt thereof:

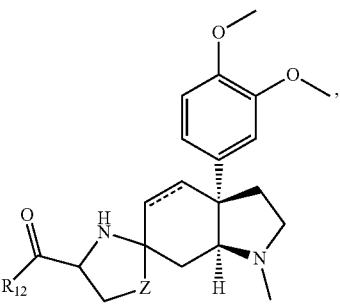

(X)

wherein the dashed bond is absent or present, Z is S or O; and $R_{12}$ is hydroxyl or amino.

In some embodiments, a compound of Formula (X) can be a compound of Formula (X-1) that converts to mesembrine (e.g., (−) mesembrine) upon oral administration to a mammal and upon hydrolysis in sufficiently acidic conditions (e.g., pH 2 at 37° C.), where Z, and $R_{12}$ are as defined with respect to Formula (X) above.

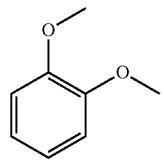
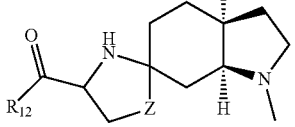

(X-1)

Compounds of Formula (X) including compounds of Formula (X-1) can be prepared as described with respect to exemplary compounds in the examples below. In general, treatment of a ketone, such as mesembrine, with an appropriate alpha-amino carboxylic acid or alpha-amino amide, in a solvent, such as ethanol, at an elevated temperature is a method to prepare compounds of Formula (X).

Table provides non-limiting examples of certain compounds of Formula (X).

TABLE

Exemplary Compounds of Formula X

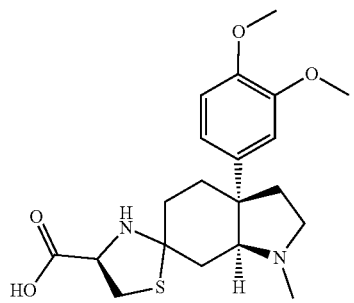

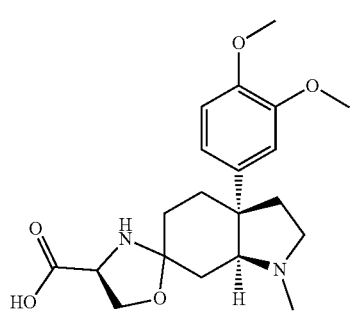

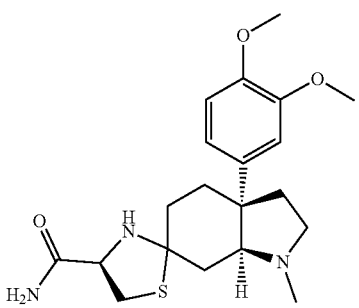

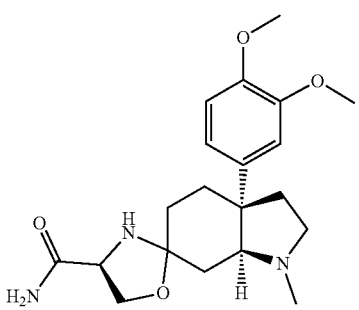

In some embodiments, the compound of Formula (I) is a compound of Formula (XI) or a pharmaceutically acceptable salt thereof:

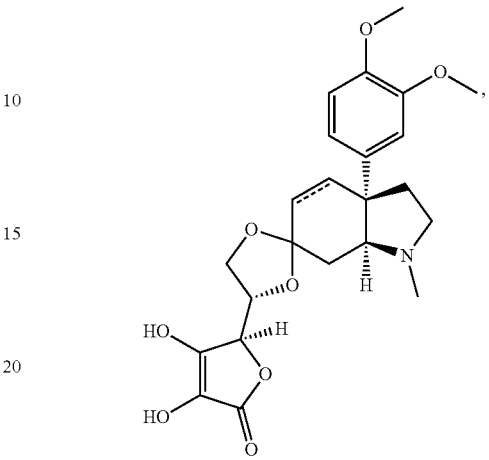

XI wherein the dashed bond is absent or present.

In some embodiments, a compound of Formula (XI) can be a compound of Formula (XI-1) that converts to mesembrine (e.g., (−) mesembrine) upon oral administration to a mammal and upon hydrolysis in sufficiently acidic conditions (e.g., pH 2 at 37° C.).

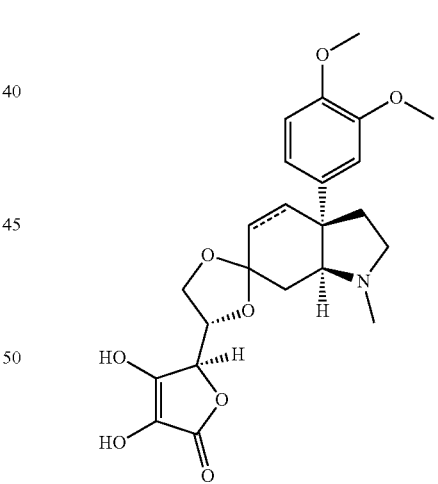

Formula (XI-1)

Compounds of Formula (XI) including compounds of Formula (XI-1) and Formula (XI-2) can be prepared as described with respect to compounds in the examples below. In general, treatment of a ketone such as mesembrine, with a naturally occurring diol, such as ascorbic acid, with an acid catalyst in a solvent, such as toluene, is a method to prepare compounds of Formula (XI). In some embodiments, mesembrine can be reacted with ascorbic acid (e.g., TsOH, acetone) to obtain a compound of Formula (XI-1).

Table provides non-limiting examples of certain compounds of Formula (XI).

TABLE

Exemplary Compounds of Formula XI

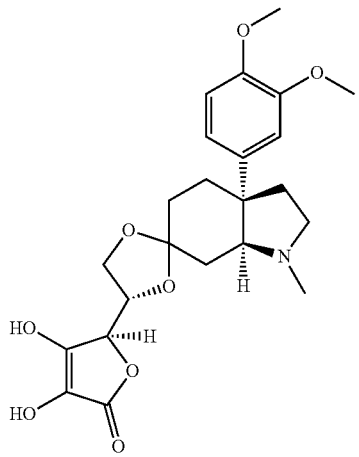

In some embodiments, the compound of Formula (I) is a compound of Formula (XII) or a pharmaceutically acceptable salt thereof:

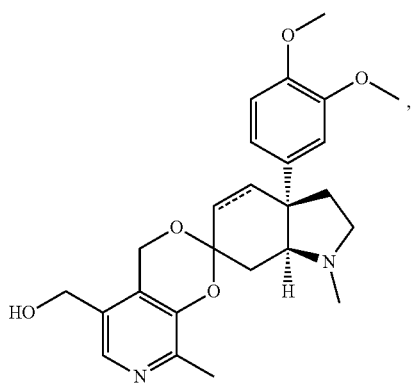

Formula (XII)

wherein the dashed bond is absent or present.

In some embodiments, a compound of Formula (XII) can be a compound of Formula (XII-1) that converts to mesembrine (e.g., (−) mesembrine) upon oral administration to a mammal and upon hydrolysis in sufficiently acidic conditions (e.g., pH 2 at 37° C.).

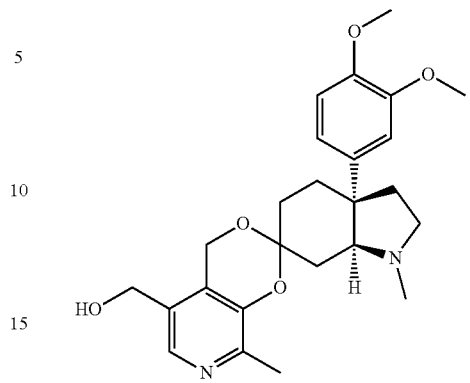

Formula (XII-1)

Compounds of Formula (XII) including compounds of Formula (XII-1) can be prepared as described with respect to exemplary compounds in the examples below. In general treatment of a ketone such as mesembrine, with a compound such as pyridoxine or an analog thereof (e.g., a vitamin B6 analog), with an acid catalyst in a solvent is a method to prepare compounds of Formula (XII).

Table 5 provides non-limiting examples of certain compounds of Formula (XII).

TABLE

Exemplary Compounds of Formula XII

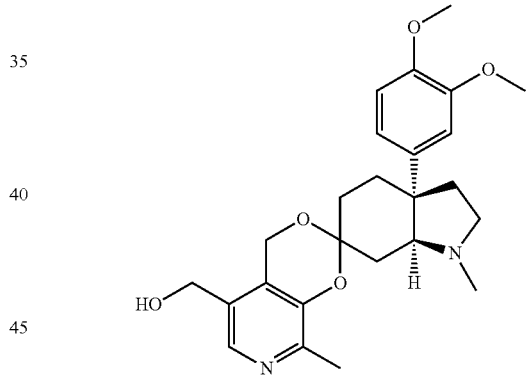

In some embodiments, a compound of Formula (I) can be a compound of Formula (XIII) or a pharmaceutically acceptable salt thereof:

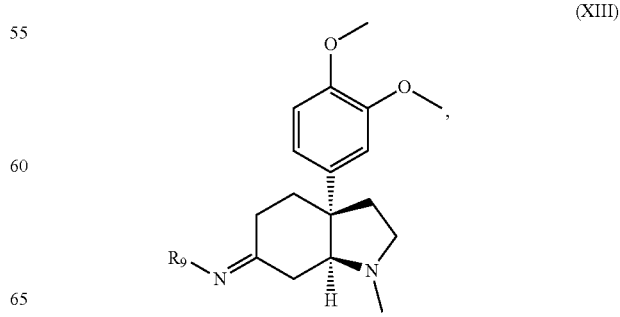

(XIII)

wherein R_9 is hydroxyl, methoxy, or —NH—C(O)-6-member nitrogen-containing heteroaryl. In some embodiments, the 6-member nitrogen-containing heteroaryl is pyridine.

In some embodiments, a compound of Formula (XIII) can convert to mesembrine (e.g., (−) mesembrine) under acidic conditions, such as upon oral administration to a mammal. For example, a compound of Formula (XIII) can convert to mesembrine (e.g., (−) mesembrine) due to the reaction by enzyme, gastric acid and the like under the physiological conditions in the body of a mammal.

Table 6 provides non-limiting examples of certain compounds of Formula (XIII)

TABLE 6

Exemplary Compounds of Formula (XIII).

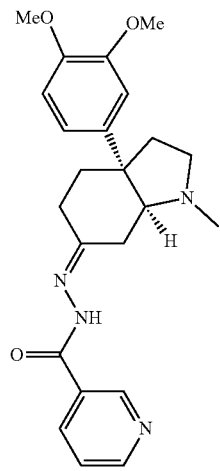 [SMILES: COc1ccc([C@@]23CC/C(=N/NC(=O)c4cccnc4)C[C@@H]2N(C)CC3)cc1OC]

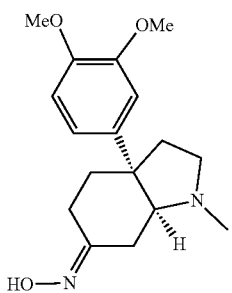 [SMILES: COc1ccc([C@@]23CC/C(=N\O)C[C@@H]2N(C)CC3)cc1OC]

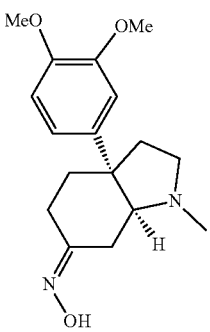

TABLE 6-continued

Exemplary Compounds of Formula (XIII).

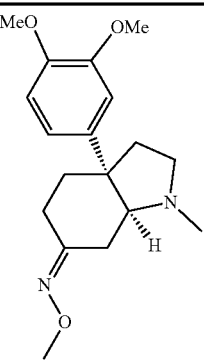

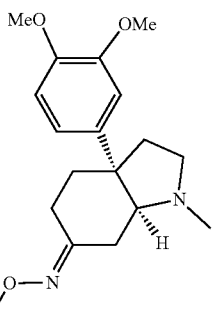

In certain embodiments, the invention relates to a compound of Formula (XIV), or a pharmaceutically acceptable salt thereof, as defined above. In some embodiments, a compound of Formula (XIV) can be a compound of Formula (XIV-1) or Formula (XIV-2), or a pharmaceutically acceptable salt thereof:

(XIV-1)

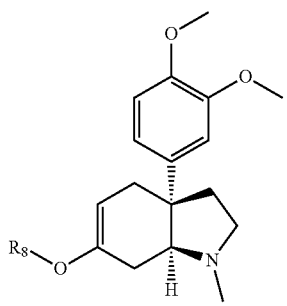

(XIV-2)

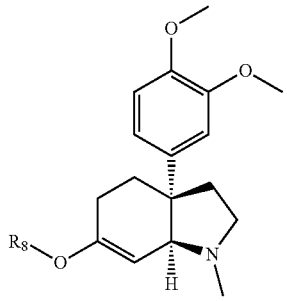

wherein R_8 is —Si(CH_3)_3 or —(O)—CH_3.

Compounds of Formula (XIV) including compounds of Formula (XIV-1) and Formula (XIV 2) can be prepared as described with respect to exemplary compounds in the examples below. In general, treating a ketone, such as mesembrine, with an appropriate base, such as potassium tert-butoxide, and an acid anhydride, in a solvent, such as THF, is a method to prepare compounds of Formula (XIV).

Table 8 provides non-limiting examples of certain compounds of Formula (XIV).

TABLE 8

Exemplary Compounds of Formula (XIV).

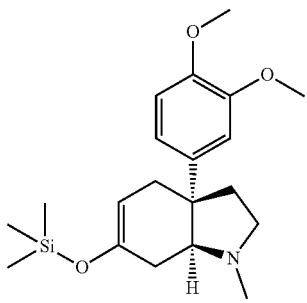

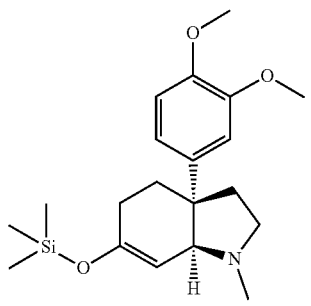

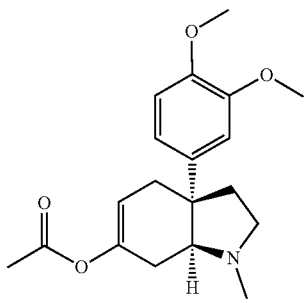 [SMILES: COc1ccc([C@@]23CC=C(OC(C)=O)C[C@@H]2N(C)CC3)cc1OC]

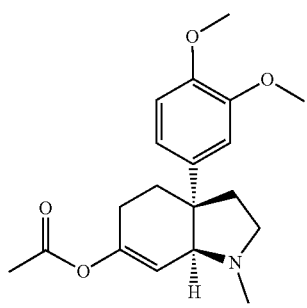 [SMILES: COc1ccc([C@@]23CCC(OC(C)=O)=C[C@@H]2N(C)CC3)cc1OC]

In some embodiments, the compound is a compound of Formula (XV) or a pharmaceutically acceptable salt thereof:

Formula XV

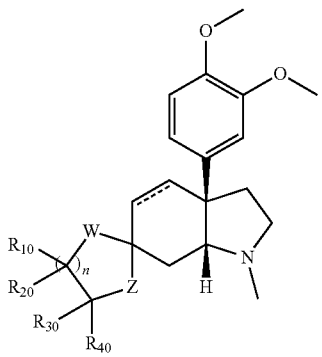

wherein the dashed bond is absent or present;

n is 0 or 1,

W and Z are each independently $CH_2$, O, S or NH, provided that at least one of W or Z is O, S or NH; and $R_{10}$, $R_{20}$, $R_{30}$ and $R_{40}$ are each hydrogen.

In some embodiments, W and Z in Formula (XV) are each O. In some embodiments, W and Z in Formula (XV) are each S. In some embodiments, W and Z in Formula (XV) are each NH. In some embodiments, W is NH and Z is S in Formula (XV). In some embodiments, W is O and Z is S in Formula (XV). In some embodiments, W is $CH_2$ and Z is O in Formula (XV). In some embodiments, W is $CH_2$ and Z is NH in Formula (XV).

In some embodiments, a compound of Formula (XV) can be a compound of Formula (XV-1):

(XV-1)

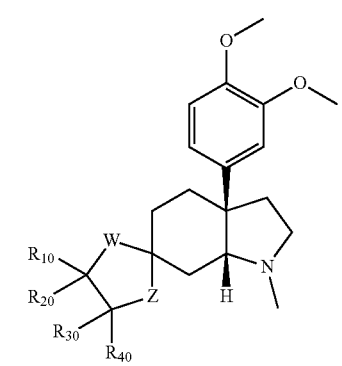

Compounds of Formula (XV) including compounds of Formula (XV-1) and Formula (XV-2) can be prepared as described with respect to exemplary compounds in the examples below.

Table 9 provides non-limiting examples of certain compounds of Formula (I-A).

TABLE 9

Exemplary Compounds of Formula XV

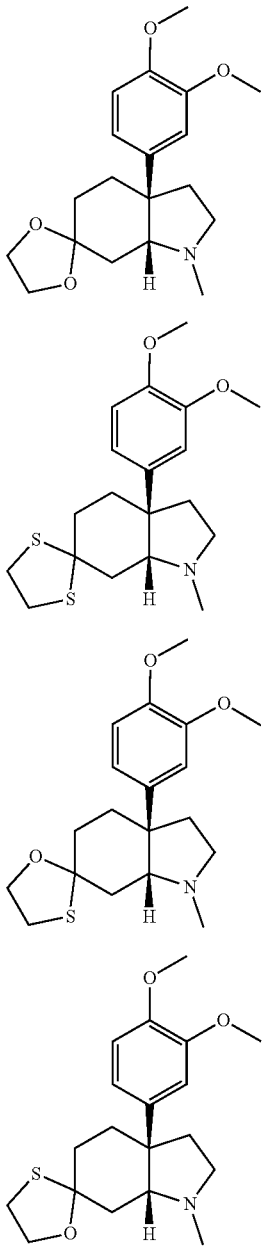

A total synthesis of (±)-mesembrine has also been reported (Jeffs P. *Sceletium* alkaloids. In: Jeffs P. The Alkaloids: Chemistry and Physiology. Vol 19. New York, NY: Academic Press; 1981:1-80). Mesembrine alkaloids have been synthesized in a manner similar to that of Amaryllidaceae alkaloids (e.g., Roe C, Sandoe E J, Stephenson G R, Anson C E. Stereoselectivity in the organoiron-mediated synthesis of (±)-mesembrine. Tetrahedron Lett. 2008; 49(4): 650-653; and Shamma M, Rodriguez H R. The synthesis of (+)-mesembrine. Tetrahedron. 1968; 24(22):6583-6589.5714008).

In some embodiments, compositions can comprise greater than 15% (w/w) mesembrine of the total alkaloid content in composition. In some embodiments, compositions can comprise greater than 50% (w/w) mesembrine of the total alkaloid content in composition. In some embodiments, compositions can comprise greater than 90% (w/w) mesembrine of the total alkaloid content in composition. In some embodiments, compositions can comprise greater than 99% (w/w) mesembrine of the total alkaloid content in composition.

In some embodiments, compositions can comprise greater than 15% (w/w) of mesembrine (e.g., (−) mesembrine) of the total alkaloid content in composition. In some embodiments, compositions can comprise greater than 50% (w/w) mesembrine (e.g., (−) mesembrine) of the total alkaloid content in composition. In some embodiments, compositions can comprise greater than 90% (w/w) mesembrine (e.g., (−) mesembrine) of the total alkaloid content in composition. In some embodiments, compositions can comprise greater than 99% (w/w) mesembrine (e.g., (−) mesembrine) of the total alkaloid content in composition.

In some embodiments, many prodrugs of mesembrine (e.g., (−) mesembrine) are disclosed herein. Illustratively, converting mesembrine to a prodrug can be performed by modifying the ketone on the fused ring. In some embodiments, the modification can be take the form of a protecting group. Illustrative ketone protecting groups are known in the art as described in Greene's Protective Groups in Organic Synthesis, fourth edition, the disclosure of which is hereby incorporated by reference. Illustrative ketone protecting groups include acyclic ketals, cyclic ketals, chiral ketals, dithio ketals, cyclic dithio ketals, monothiol ketals, cyclic monothiol ketals, cyanohydrins, hydrazones, oximes, pyrrole carbinols, O-silylimdazoyl aminals, cyclic aminals, and benzothiazoles. Ketones may also be protected by protecting the enolate, for example by trimethylsilyl enol ethers, and enamines, In some embodiments, a method of isolating stable forms of (+) mesembrenone and (−) mesembrenone is provided. In illustrative embodiments, the method minimizes racemization of mesembrenone. In some embodiments, stereoisomer analogs of (+) mesembrenone and (−) mesembrenone can be formed. The (+)/(−) mesembrenone analogs can then be separated. The (+) analog can then be converted to (+) mesembrenone. The (−) analog can then be converted to (−) mesembrenone. The conversion can be performed by hydrolysis, preferably in the presence of an acid.

In illustrative embodiments, a method of extending the pharmacokinetic properties of mesembrine is described. In illustrative embodiments, the pharmacokinetic properties of mesembrine is extended by forming a prodrug, for example by modifying the ketone on the fused ring.

In some embodiments, compounds of Formula (I-1) can form mesembrine (e.g., (−) mesembrine) under biologically relevant conditions, including compounds of formula (I-1), formula (IIa-1), formula (IIIc-1), and formula (IVa-1). In certain embodiments, methods of administering a therapeutic alkaloid compound comprise the oral administration of a compound of formula (I-1), formula (IIa-1), formula (IIIc-1), and formula (IVa-1). In certain embodiments, methods of administering a therapeutically effective amount of mesembrine can comprise the step of administering a compound of formula (IIa-1).

In some embodiments, a compound according to the present disclosure is a compound of formula (I):

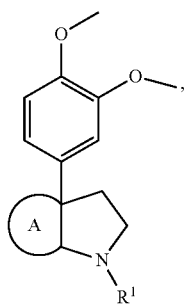

or a pharmaceutically acceptable salt thereof,
wherein
$R^1$ is $C_1$-$C_7$ alkyl; and
ring A is

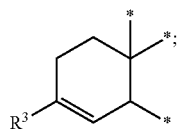

wherein * denotes the attachment points of ring A to the compound of formula (I), and wherein $R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, phenoxy or —O(CH$_2$)$_p$ OCH$_3$; and p is 2, 3, or 4.

In some embodiments, a compound according to the present disclosure is a compound of formula (I):

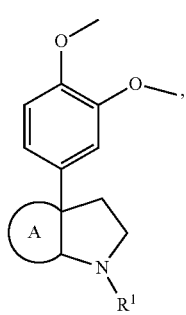

(I)

or a pharmaceutically acceptable salt thereof,
wherein
$R^1$ is $C_1$-$C_7$ alkyl; and
ring A is

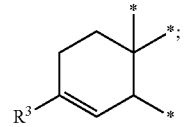

wherein * denotes the attachment points of ring A to the compound of formula (I), and wherein $R^3$ is —OC(O)$C_1$-$C_6$ alkyl, —OC(O)$C_3$-$C_{10}$ cycloalkyl, —OC(O)phenyl, wherein each hydrogen atom in $C_1$-$C_6$ alkyl, $C_3$-$C_{10}$ cycloalkyl, and phenyl, is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, phenoxy or —O(CH$_2$)$_p$OCH$_3$; and p is 2, 3, or 4.

In some embodiments, a compound according to the present disclosure is a compound of formula (I):

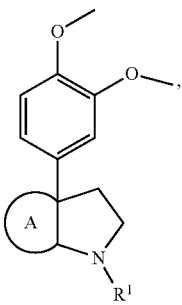

(I)

or a pharmaceutically acceptable salt thereof,
wherein
$R^1$ is methyl; and
ring A is

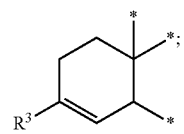

wherein * denotes the attachment points of ring A to the compound of formula (I), and wherein $R^3$ is —OC(O)$C_1$-$C_6$ alkyl, —OC(O)$C_3$-$C_{10}$ cycloalkyl, —OC(O)phenyl, wherein each hydrogen atom in $C_1$-$C_6$ alkyl, $C_3$-$C_{10}$ cycloalkyl, and phenyl, is optionally substituted by halogen, $C_1$-$C_6$ alkyl, $C_1$-$C_3$ alkoxy, $C_1$-$C_3$ haloalkyl, or —O(CH$_2$)$_p$OCH$_3$; and p is 2, 3, or 4.

In some embodiments, a compound according to the present disclosure is a compound of formula (I):

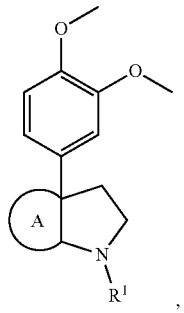 (I)

or a pharmaceutically acceptable salt thereof, wherein
R¹ is methyl; and
ring A is

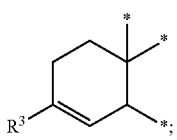

wherein * denotes the attachment points of ring A to the compound of formula (I), and wherein
R³ is —OC(O)C₁-C₆ alkyl.

In some embodiments, a compound according to the present disclosure is a compound of formula (I):

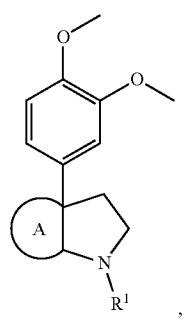 (I)

or a pharmaceutically acceptable salt thereof, wherein
R¹ is methyl; and
ring A is

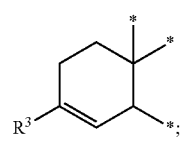

wherein * denotes the attachment points of ring A to the compound of formula (I), and wherein
R³ is —OC(O)phenyl, wherein each hydrogen atom in phenyl is optionally substituted by halogen, C₁-C₆ alkyl, C₁-C₃ alkoxy, nitro, —N(C₁-C₃ alkyl)₂, C₁-C₃ haloalkyl, cyano, phenyl, phenoxy or —O(CH₂)ₚOCH₃; and
p is 2, 3, or 4.

In some embodiments, a compound according to the present disclosure is a compound of formula (I):

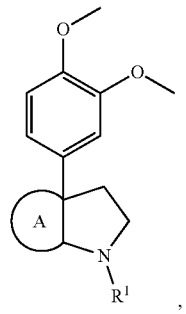 (I)

or a pharmaceutically acceptable salt thereof, wherein
R¹ is methyl; and
ring A is

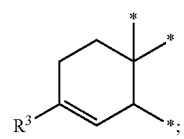

wherein * denotes the attachment points of ring A to the compound of formula (I), and wherein
R³ is —OC(O)phenyl, wherein each hydrogen atom in phenyl is optionally substituted by C₁-C₆ alkyl.

In some embodiments, a compound according to the present disclosure is a compound of formula (I):

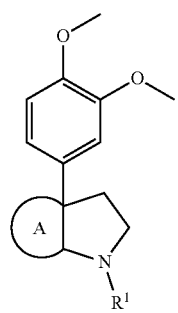 (I)

or a pharmaceutically acceptable salt thereof, wherein
R¹ is or C₁-C₇ alkyl; and
ring A is

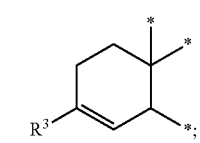

wherein * denotes the attachment points of ring A to the compound of formula (I), and wherein R³ is —OC(O)phenyl, wherein each hydrogen atom in phenyl is optionally substituted by methyl.

In some embodiments, a compound according to the present disclosure is a compound of formula (I):

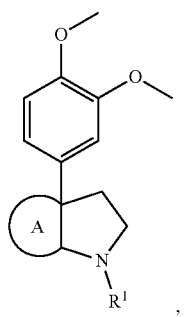

(I)

or a pharmaceutically acceptable salt thereof, wherein
R¹ is methyl; and
ring A is

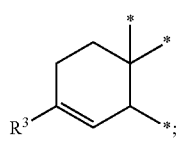

wherein * denotes the attachment points of ring A to the compound of formula (I), and wherein R³ is —OC(O)C₃-C₁₀ cycloalkyl, wherein C₃-C₁₀ cycloalkyl is optionally substituted by halogen, C₁-C₆ alkyl, C₁-C₃ alkoxy, nitro, —N(C₁-C₃ alkyl)₂, C₁-C₃ haloalkyl, cyano, phenyl, phenoxy or —O(CH₂)ₚOCH₃; and p is 2, 3, or 4.

In some embodiments, a compound according to the present disclosure is a compound of formula (I):

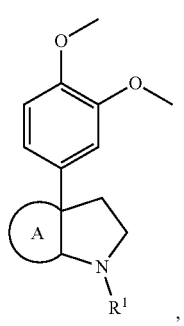

(I)

or a pharmaceutically acceptable salt thereof, wherein
R¹ is methyl; and
ring A is

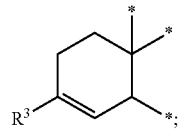

wherein * denotes the attachment points of ring A to the compound of formula (I), and wherein R³ is —OC(O)C₆ cycloalkyl, wherein C₆ cycloalkyl is optionally substituted by halogen, C₁-C₆ alkyl, C₁-C₃ alkoxy, nitro, —N(C₁-C₃ alkyl)₂, C₁-C₃ haloalkyl, cyano, phenyl, phenoxy or —O(CH₂)ₚOCH₃; and p is 2, 3, or 4.

In some embodiments, a compound according to the present disclosure is a compound of formula (I):

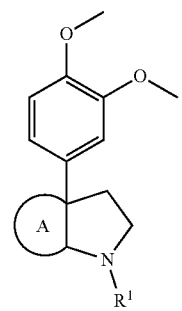

(I)

or a pharmaceutically acceptable salt thereof, wherein
R¹ is methyl; and
ring A is

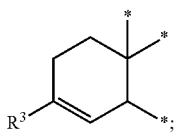

wherein * denotes the attachment points of ring A to the compound of formula (I), and wherein R³ is —OC(O)C₆ cycloalkyl.

In some embodiments, a compound according to the present disclosure is a compound of formula (IIIb-2):

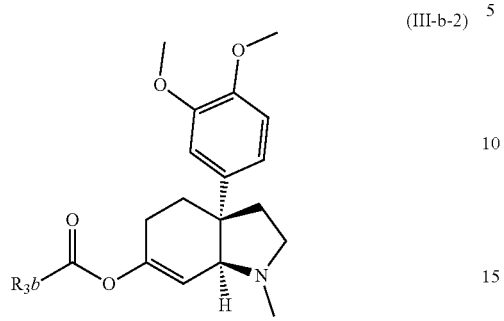
(III-b-2)

or a pharmaceutically acceptable salt thereof, wherein
$R_{3b}$ is $C_1$-$C_6$ alkyl, $C_3$-$C_6$ cycloalkyl, phenyl, or 5- to 7-membered heteroaryl, wherein each hydrogen atom in $C_1$-$C_6$ alkyl, $C_3$-$C_6$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, phenoxy or —O(CH$_2$)$_p$OCH$_3$; and
p is 2, 3, or 4.

In some embodiments, a compound according to the present disclosure is a compound of formula (IIIb-2):

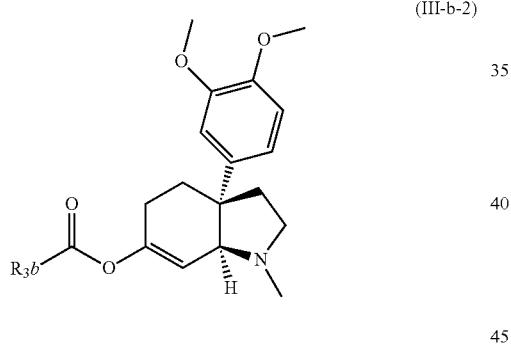
(III-b-2)

or a pharmaceutically acceptable salt thereof, wherein $R_{3b}$ is $C_1$-$C_6$ alkyl optionally substituted with methoxy.

In some embodiments, a compound according to the present disclosure is a compound of formula (IIIb-2):

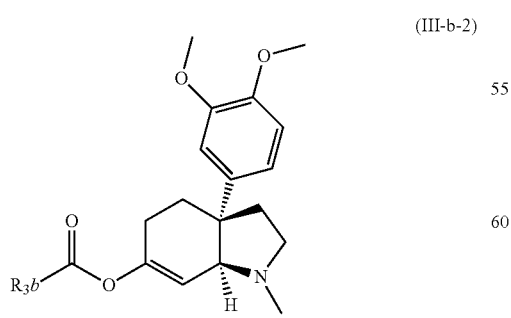
(III-b-2)

or a pharmaceutically acceptable salt thereof, wherein $R_{3b}$ is $C_1$-$C_6$ alkyl.

In some embodiments, a compound according to the present disclosure is a compound of formula (IIIb-2):

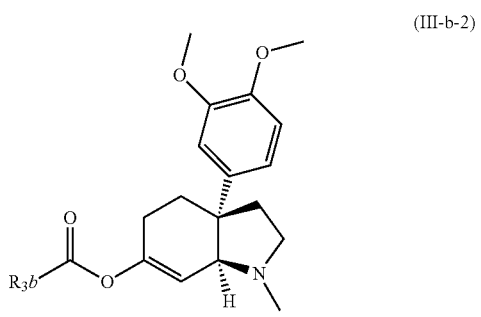
(III-b-2)

or a pharmaceutically acceptable salt thereof, wherein $R_{3b}$ is $C_3$-$C_6$ cycloalkyl.

In some embodiments, a compound according to the present disclosure is a compound of formula (IIIb-2):

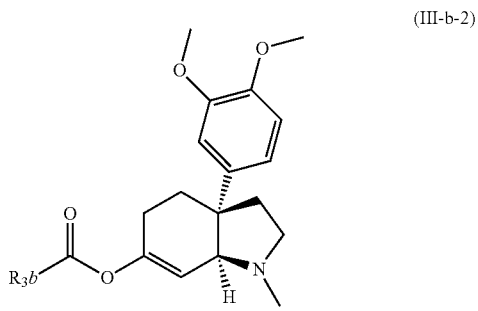
(III-b-2)

or a pharmaceutically acceptable salt thereof, wherein $R_{3b}$ is phenyl, optionally substituted by $C_1$-$C_6$ alkyl.

In some embodiments, a compound according to the present disclosure is a compound of formula (IIIb-2):

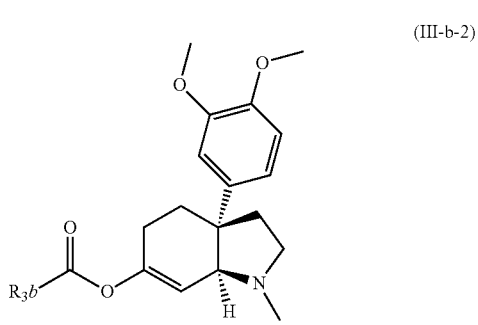
(III-b-2)

or a pharmaceutically acceptable salt thereof, wherein $R_{3b}$ is phenyl, optionally substituted by methyl.

In certain embodiments, the compound is of formula (I):

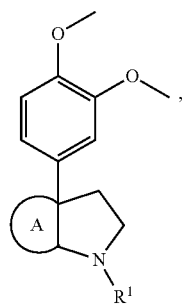
(I)

or a pharmaceutically acceptable salt thereof, wherein
$R^1$ is $C_1$-$C_7$ alkyl or H; and
ring A is

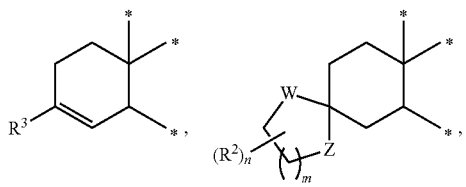

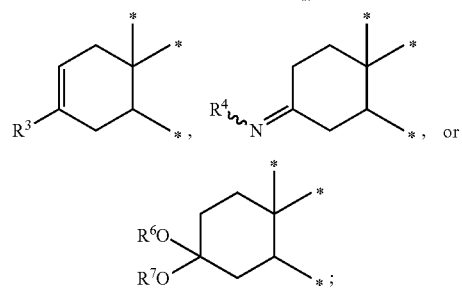

, or

;

wherein * denotes the attachment points of ring A to the compound of formula (I), and wherein
each of W and Z is independently O, NH, or S;
each $R^2$ is independently $C_1$-$C_3$ alkyl, $C_2$-$C_6$ alkenyl, —COOH, —CONH$_2$, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$, wherein each hydrogen atom in $C_1$-$C_3$ alkoxy and aryloxy is optionally substituted by $C_1$-$C_3$ alkoxy or phenyl; or two $R^2$s on a single carbon atom combine to form =O; or two adjacent $R^2$s together with the carbon atoms to which they are attached combine to form 5- to 7-membered heteroaryl, wherein each hydrogen atom in 5- to 7-membered heteroaryl is optionally substituted by —OH, $C_1$-$C_3$ alkyl, or $C_1$-$C_3$ alkanol
m is 1 or 2,
n is 0, 1, 2, 3 or 4;
$R^3$ is —OSi($C_1$-$C_6$ alkyl)$_3$, —OC(O)$C_1$-$C_6$ alkyl, —OC(O)$C_2$-$C_6$ alkenyl, —OC(O)$C_3$-$C_{10}$ cycloalkyl, —OC(O)phenyl, —OC(O)-5- to 7-membered heteroaryl, wherein each hydrogen atom in $C_1$-$C_6$ alkyl, $C_2$-$C_6$ alkenyl, $C_3$-$C_{10}$ cycloalkyl, phenyl, and 5- to 7-membered heteroaryl is optionally substituted by halogen, $C_1$-$C_6$ alkyl, $C_1$-$C_3$ alkoxy, nitro, —N($C_1$-$C_3$ alkyl)$_2$, $C_1$-$C_3$ haloalkyl, cyano, phenyl, or phenoxy;
$R^4$ is —OR$^5$ or —N(R$^5$)$_2$;
each $R^5$ is H, $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —(O)—$C_1$-$C_8$ alkyl, —C(O)—$C_3$-$C_{10}$ cycloalkyl, —C(O)-phenyl, —C(O)N(H)-phenyl, —C(O)N(H)-5- to 7-membered heteroaryl, —C(O)N(H)—$C_1$-$C_6$ alkyl, —C(O)C(O)OH, or —CONH$_2$, wherein each hydrogen atom in $C_1$-$C_6$ alkyl, $C_3$-$C_6$ heterocycloalkyl, $C_3$-$C_{10}$ cycloalkyl, $C_1$-$C_6$ alkoxy, phenyl, 5- to 10-membered heteroaryl, —C(O)-5- to 7-membered heteroaryl, —(O)—$C_1$-$C_8$ alkyl, —(O)—$C_3$-$C_{10}$ cycloalkyl, —C(O)-phenyl, —C(O)N(H)-phenyl, —C(O)N(H)-5- to 7-membered heteroaryl, and —C(O)N(H)—$C_1$-$C_6$ alkyl is optionally substituted by halogen, OH, $C_1$-$C_3$ alkyl, $C_3$-$C_{10}$ cycloalkyl optionally substituted by —COOH, phenyl, 5- to 7-membered heteroaryl, aryloxy, $C_1$-$C_6$ alkoxy, $C_1$-$C_3$ alkanol, $C_3$-$C_6$ heterocycloalkyl optionally substituted with methyl, —COOH, —S(O)$_2$CH$_3$, —C(O)$C_1$-$C_6$ alkyl, or —C(O)O$C_1$-$C_6$ alkyl; and
each of $R^6$ and $R^7$ is independently $C_1$-$C_3$ alkyl.

In certain embodiments, the compound is of formula (I):

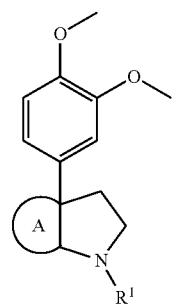
(I)

or a pharmaceutically acceptable salt thereof, wherein
$R^1$ is methyl; and
ring A is

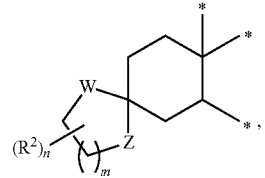
, wherein * denotes the attachment points of ring A to the compound of formula (I), and wherein
each of W and Z is independently O, NH, or S;
each $R^2$ is independently $C_1$-$C_3$ alkyl, —COOH, —CONH$_2$, phenyl, 5- to 7-membered heterocyclyl, or 5- to 7-membered heteroaryl, wherein each hydrogen atom in $C_1$-$C_3$ alkyl, $C_2$-$C_6$ alkenyl, phenyl, 5- to 7-membered heterocyclyl and 5- to 7-membered heteroaryl is optionally substituted by —OH, $C_1$-$C_3$ alkyl, $C_1$-$C_3$ alkoxy, aryloxy, $C_1$-$C_3$ alkanol, or —NO$_2$; or two $R^2$s on a single carbon atom combine to form =O; or two adjacent $R^2$s together with the carbon atoms to which they are attached combine to form 5- to 7-membered heteroaryl, wherein each hydrogen atom in 5- to 7-membered heteroaryl is optionally substituted by —OH, $C_1$-$C_3$ alkyl, or $C_1$-$C_3$ alkanol;
m is 1 or 2; and
n is 0, 1, 2, 3 or 4.

In certain embodiments, the compound is of formula (I):

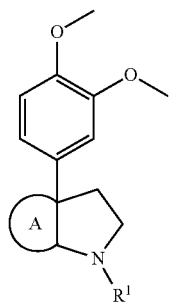
(I)

or a pharmaceutically acceptable salt thereof, wherein
$R^1$ is methyl; and
ring A is

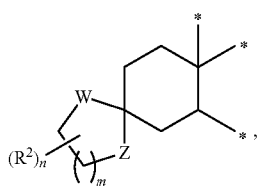

wherein * denotes the attachment points of ring A to the compound of formula (I), and wherein
each of W and Z is independently O, NH, or S;
m is 1 or 2;
n is 0; or n is 1 and $R^2$ is $C_1$-$C_3$ alkyl, —COOH, —CONH$_2$, phenyl, or a 6-membered heterocyclyl comprising at least one nitrogen heteroatom; or n is 2, 3 or 4 and two $R^2$s on a single carbon atom combine to form =O and the remaining $R^2$ (if present) is $C_1$-$C_3$ alkyl;
wherein each hydrogen atom in phenyl or 6-membered heteroaryl in $R^2$ is optionally substituted by —OH, $C_1$-$C_3$ alkyl, $C_1$-$C_3$ alkoxy, or —NO$_2$; and
m is 1.

In certain embodiments, the compound is of formula (I):

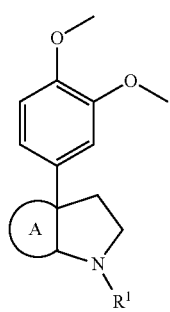
(I)

or a pharmaceutically acceptable salt thereof, wherein
$R^1$ is methyl; and
ring A is

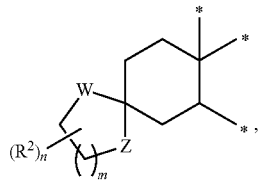

wherein * denotes the attachment points of ring A to the compound of formula (I), and wherein
each of W and Z is independently O, NH, or S;
m is 1; and
n is 0; or n is 1 and $R^2$ is methyl, —COOH, —CONH$_2$, phenyl, or a 6-membered heterocyclyl comprising at least one nitrogen heteroatom; or n is 2, 3 or 4 with two $R^2$s on a single carbon atom combine to form =O and the remaining $R^2$ (if present) is methyl, wherein each hydrogen atom in phenyl or 6-membered heteroaryl in $R^2$ is optionally substituted by —OH, methyl, methoxy, or —NO$_2$.

In certain embodiments, the compound is of formula (I):

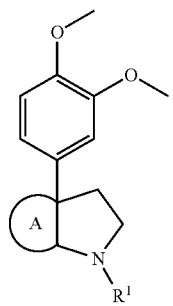
(I)

or a pharmaceutically acceptable salt thereof, wherein
$R^1$ is methyl; and
ring A is

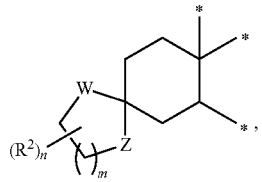

wherein * denotes the attachment points of ring A to the compound of formula (I), and wherein
  each of W and Z is independently O, NH, or S;
  m is 1; and
  n is 1 and R² is

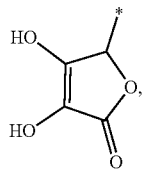

wherein * denotes the point of attachment of R² the compound.

In certain embodiments, the compound is of formula (I):

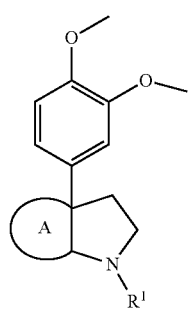

(I)

or a pharmaceutically acceptable salt thereof, wherein
  R¹ is methyl; and
  ring A is

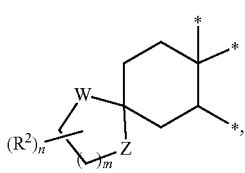

wherein * denotes the attachment points of ring A to the compound of formula (I), and wherein
  each of W and Z is independently O, NH, or S;
  m is 1; and
  n is 2, 3 or 4; and
  two adjacent R²s together with the carbon atoms to which they are attached combine to form 5- to 7-membered heteroaryl comprising a nitrogen heteroatom, wherein each hydrogen atom in 5- to 7-membered heteroaryl is optionally substituted by —OH, $C_1$-$C_3$ alkyl, or $C_1$-$C_3$ alkanol.

In certain embodiments, the compound is of formula (I):

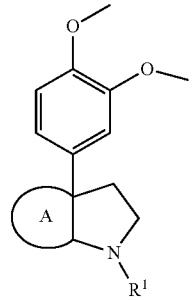

(I)

or a pharmaceutically acceptable salt thereof, wherein
  R¹ is methyl; and
  ring A is

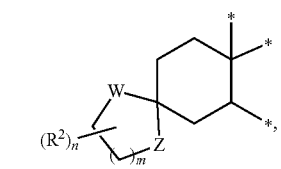

wherein * denotes the attachment points of ring A to the compound of formula (I), and wherein
  each of W and Z is independently O, NH, or S;
  m is 1; and
  n is 2, 3 or 4; and
  two adjacent $R^e$s together with the carbon atoms to which they are attached combine to form 6-membered heteroaryl comprising a nitrogen heteroatom, wherein each hydrogen atom in 6-membered heteroaryl is optionally substituted by —OH, $C_1$-$C_3$ alkyl, or $C_1$-$C_3$ alkanol.

In certain embodiments, the compound is of formula (I):

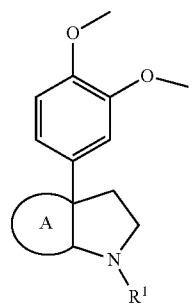

(I)

or a pharmaceutically acceptable salt thereof, wherein
  R¹ is methyl; and
  ring A is

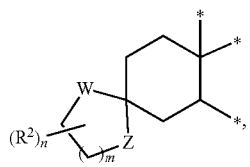

wherein * denotes the attachment points of ring A to the compound of formula (I), and wherein each of W and Z is independently O, NH, or S;
m is 1; and
n is 0.

In certain embodiments, the compound is of formula (I):

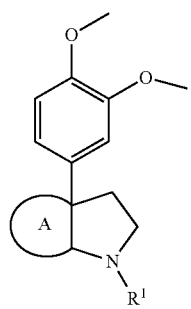
(I)

or a pharmaceutically acceptable salt thereof, wherein
R¹ is methyl; and
ring A is

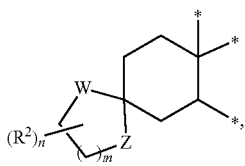

wherein * denotes the attachment points of ring A to the compound of formula (I), and wherein each of W and Z is independently O, NH, or S;
m is 1; and
n is 1 and R² is methyl, —COOH, or —CONH₂.

In certain embodiments, the compound is of formula (I):

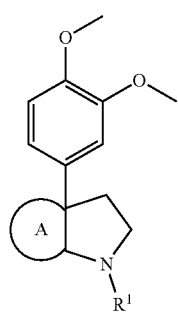
(I)

or a pharmaceutically acceptable salt thereof, wherein
R¹ is methyl; and
ring A is

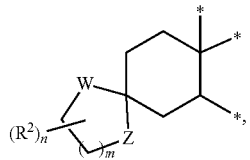

wherein * denotes the attachment points of ring A to the compound of formula (I), and wherein each of W and Z is independently O, NH, or S;
m is 1; and
n is 1 and R² is phenyl or a 6-membered heterocyclyl comprising at least one nitrogen heteroatom, wherein each hydrogen atom in phenyl or 6-membered heteroaryl in R² is optionally substituted by —OH, methyl, methoxy, or —NO₂.

In certain embodiments, the compound is of formula (I):

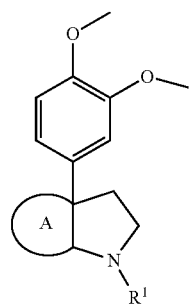
(I)

or a pharmaceutically acceptable salt thereof, wherein
R¹ is methyl; and
ring A is

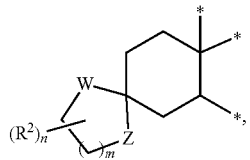

wherein * denotes the attachment points of ring A to the compound of formula (I), and wherein each of W and Z is independently O, NH, or S;
m is 1; and
n is 2 or 3 with two R²s on a single carbon atom combine to form =O and the remaining R² (if present) is methyl;
wherein each hydrogen atom in phenyl or 6-membered heteroaryl in R² is optionally substituted by —OH, methyl, methoxy, or —NO₂.

375

In certain embodiments, the compound is of formula (I):

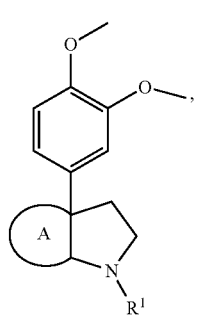
(I)

or a pharmaceutically acceptable salt thereof, wherein
R$^1$ is methyl; and
ring A is

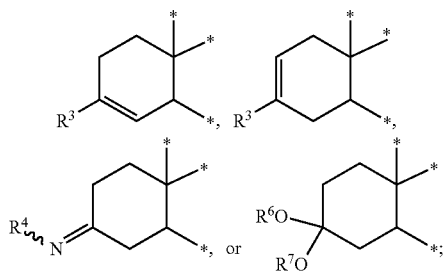

wherein * denotes the attachment points of ring A to the compound of formula (I), and wherein R$^3$ is —OSi(C$_1$-C$_6$ alkyl)$_3$, —OC(O)C$_1$-C$_6$ alkyl, —OC(O)C$_2$-C$_6$ alkenyl, —OC(O)C$_3$-C$_{10}$ cycloalkyl, —OC(O)phenyl, —OC(O)-5- to 7-membered heteroaryl, wherein each hydrogen atom in C$_1$-C$_6$ alkyl, C$_2$-C$_6$ alkenyl, C$_3$-C$_{10}$ cycloalkyl, phenyl, and 5- to 7-membered heteroaryl is optionally substituted by halogen, C$_1$-C$_6$ alkyl, C$_1$-C$_3$ alkoxy, nitro, —N(C$_1$-C$_3$ alkyl)$_2$, C$_1$-C$_3$ haloalkyl, cyano, phenyl, or phenoxy;

R$^4$ is —OR$^5$ or —N(R$^5$)$_2$;

each R$^5$ is H, C$_1$-C$_6$ alkyl, C$_3$-C$_6$ heterocycloalkyl, C$_3$-C$_{10}$ cycloalkyl, C$_1$-C$_6$ alkoxy, phenyl, 5- to 10-membered heteroaryl, —C(O)-5- to 7-membered heteroaryl, —(O)—C$_1$-C$_8$ alkyl, —C(O)—C$_3$-C$_{10}$ cycloalkyl, —C(O)-phenyl, —C(O)N(H)-phenyl, —C(O)N(H)-5- to 7-membered heteroaryl, —C(O)N(H)—C$_1$-C$_6$ alkyl, —C(O)C(O)OH, or —CONH$_2$, wherein each hydrogen atom in C$_1$-C$_6$ alkyl, C$_3$-C$_6$ heterocycloalkyl, C$_3$-C$_{10}$ cycloalkyl, C$_1$-C$_6$ alkoxy, phenyl, 5- to 10-membered heteroaryl, —C(O)-5- to 7-membered heteroaryl, —(O)—C$_1$-C$_8$ alkyl, —(O)—C$_3$-C$_{10}$ cycloalkyl, —C(O)-phenyl, —C(O)N(H)-phenyl, —C(O)N(H)-5- to 7-membered heteroaryl, and —C(O)N(H)—C$_1$-C$_6$ alkyl is optionally substituted by halogen, OH, C$_1$-C$_3$ alkyl, C$_3$-C$_{10}$ cycloalkyl optionally substituted by —COOH, phenyl, 5- to 7-membered heteroaryl, aryloxy, C$_1$-C$_6$ alkoxy, C$_1$-C$_3$ alkanol, C$_3$-C$_6$ heterocycloalkyl optionally substituted with methyl, —COOH, —S(O)$_2$CH$_3$, —C(O)C$_1$-C$_6$ alkyl, or —C(O)OC$_1$-C$_6$ alkyl; and each of R$^6$ and R$^7$ is independently C$_1$-C$_3$ alkyl.

376

In certain embodiments, the compound is of formula (I):

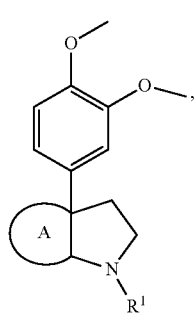
(I)

or a pharmaceutically acceptable salt thereof, wherein
R$^1$ is methyl; and
ring A is

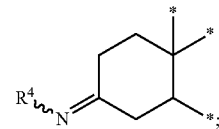

wherein * denotes the attachment points of ring A to the compound of formula (I), and wherein R$^4$ is —OR$^5$ or —N(R$^5$)$_2$; and each R$^5$ is H, C$_1$-C$_6$ alkyl, C$_3$-C$_6$ heterocycloalkyl, C$_3$-C$_{10}$ cycloalkyl, C$_1$-C$_6$ alkoxy, phenyl, 5- to 10-membered heteroaryl, —C(O)-5- to 7-membered heteroaryl, —(O)—C$_1$-C$_8$ alkyl, —C(O)—C$_3$-C$_{10}$ cycloalkyl, —C(O)-phenyl, —C(O)N(H)-phenyl, —C(O)N(H)-5- to 7-membered heteroaryl, —C(O)N(H)—C$_1$-C$_6$ alkyl, —C(O)C(O)OH, or —CONH$_2$, wherein each hydrogen atom in C$_1$-C$_6$ alkyl, C$_3$-C$_6$ heterocycloalkyl, C$_3$-C$_{10}$ cycloalkyl, C$_1$-C$_6$ alkoxy, phenyl, 5- to 10-membered heteroaryl, —C(O)-5- to 7-membered heteroaryl, —(O)—C$_1$-C$_8$ alkyl, —(O)—C$_3$-C$_{10}$ cycloalkyl, —C(O)-phenyl, —C(O)N(H)-phenyl, —C(O)N(H)-5- to 7-membered heteroaryl, and —C(O)N(H)—C$_1$-C$_6$ alkyl is optionally substituted by halogen, OH, C$_1$-C$_3$ alkyl, C$_3$-C$_{10}$ cycloalkyl optionally substituted by —COOH, phenyl, 5- to 7-membered heteroaryl, aryloxy, C$_1$-C$_6$ alkoxy, C$_1$-C$_3$ alkanol, C$_3$-C$_6$ heterocycloalkyl optionally substituted with methyl, —COOH, —S(O)$_2$CH$_3$, —C(O)C$_1$-C$_6$ alkyl, or —C(O)OC$_1$-C$_6$ alkyl.

In certain embodiments, the compound is of formula (I):

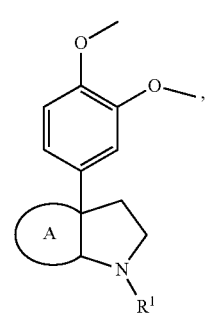
(I)

or a pharmaceutically acceptable salt thereof, wherein
R$^1$ is methyl; and
ring A is

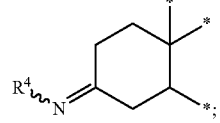

wherein * denotes the attachment points of ring A to the compound of formula (I), and wherein
R$^4$ is —OR$^5$ or —N(R$^5$)$_2$; and
each R$^5$ is H, C$_1$-C$_6$ alkyl, C$_3$-C$_6$ heterocycloalkyl, C$_3$-C$_{10}$ cycloalkyl, C$_1$-C$_6$ alkoxy, phenyl, 5- to 10-membered heteroaryl, —C(O)-5- to 7-membered heteroaryl, —(O)—C$_1$-C$_8$ alkyl, —C(O)—C$_3$-C$_{10}$ cycloalkyl, —C(O)-phenyl, —C(O)N(H)-phenyl, —C(O)N(H)-5- to 7-membered heteroaryl, —C(O)N(H)—C$_1$-C$_6$ alkyl, —C(O)C(O)OH, or —CONH$_2$, wherein each hydrogen atom in C$_1$-C$_6$ alkyl, C$_3$-C$_6$ heterocycloalkyl, C$_3$-C$_{10}$ cycloalkyl, C$_1$-C$_6$ alkoxy, phenyl, 5- to 10-membered heteroaryl, —C(O)-5- to 7-membered heteroaryl, —(O)—C$_1$-C$_8$ alkyl, —(O)—C$_3$-C$_{10}$ cycloalkyl, —C(O)-phenyl, —C(O)N(H)-phenyl, —C(O)N(H)-5- to 7-membered heteroaryl, and —C(O)N(H)—C$_1$-C$_6$ alkyl is optionally substituted by halogen, OH, C$_1$-C$_3$ alkyl, C$_3$-C$_{10}$ cycloalkyl optionally substituted by —COOH, phenyl, 5- to 7-membered heteroaryl, aryloxy, C$_1$-C$_6$ alkoxy, C$_1$-C$_3$ alkanol, C$_3$-C$_6$ heterocycloalkyl optionally substituted with methyl, —COOH, —S(O)$_2$CH$_3$, —C(O)C$_1$-C$_6$ alkyl, or —C(O)OC$_1$-C$_6$ alkyl.

In certain embodiments, the compound is of formula (I):

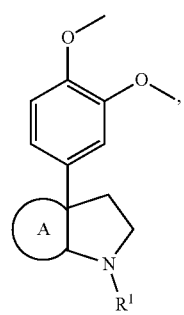

(I)

or a pharmaceutically acceptable salt thereof, wherein
R$^1$ is methyl; and
ring A is

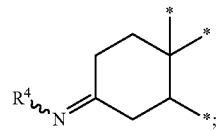

wherein * denotes the attachment points of ring A to the compound of formula (I), and
each of R$^6$ and R$^7$ is independently C$_1$-C$_3$ alkyl.

In certain embodiments, the compound is of formula (V):

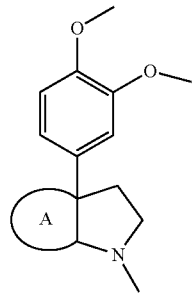

(V)

or a pharmaceutically acceptable salt thereof,
wherein
ring A is wherein * denotes the attachment points of ring A to the compound of formula (I), and wherein
each of W and Z is independently O, NH, or S;
R$^6$ is C$_1$-C$_3$ alkyl;
X$^1$ is >L-R$^{14}$, wherein L is absent or a linker and where >denotes the two single bonds to the cyclohexane ring such that the ring containing X$^1$ forms a C$_3$-C$_6$ alkyl ring, which is optionally substituted by C$_1$-C$_3$ alkanol;
X$^2$ is =L-R$^{14}$, wherein L is absent or a linker;
X$^3$ is -L-R$^{14}$, wherein L is absent or a linker; and
R$^{14}$ comprises a generally recognized as safe (GRAS) compound.

In certain embodiments, the compound is of formula (V):

(V)

or a pharmaceutically acceptable salt thereof,
wherein
ring A is

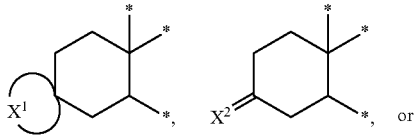

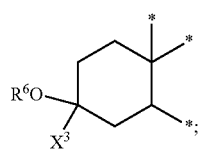

wherein * denotes the attachment points of ring A to the compound of formula (I), and wherein $R^6$ is $C_1$-$C_3$ alkyl;

$X^1$ is >L-$R^{14}$, wherein L is absent or a linker and where > denotes the two single bonds to the cyclohexane ring such that the ring containing $X^1$ forms a $C_3$-$C_6$ alkyl ring, which is optionally substituted by $C_1$-$C_3$ alkanol;

$X^2$ is =L-$R^{14}$, wherein L is absent or a linker;

$X^3$ is -L-$R^{14}$, wherein L is absent or a linker; and wherein —L-$R^{14}$ is selected from

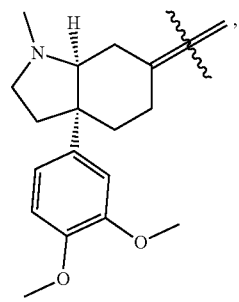

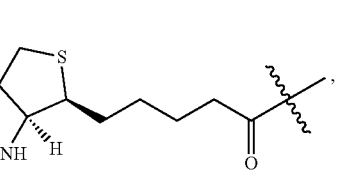

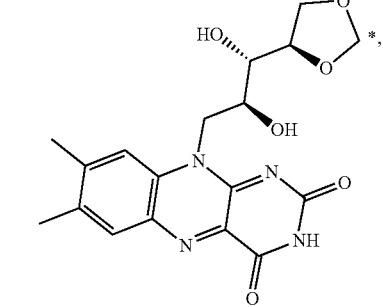

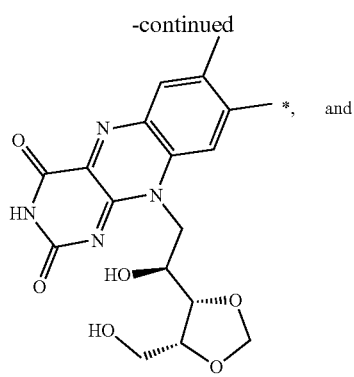

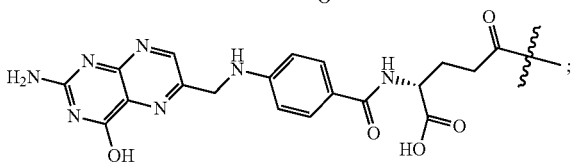

and
the * denotes the carbon of the cyclohexyl ring when L is absent.

In certain embodiments, the compound is of formula (V):

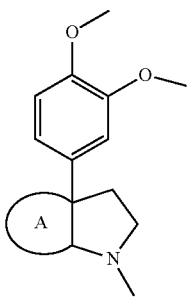

(V)

or a pharmaceutically acceptable salt thereof,
wherein
ring A is

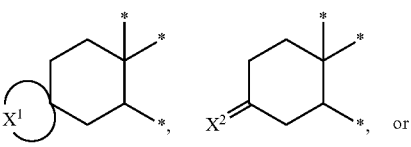

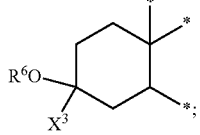

wherein * denotes the attachment points of ring A to the compound of formula (I), and wherein $R^6$ is $C_1$-$C_3$ alkyl;

$X^1$ is >L-$R^{14}$, wherein L is absent or a linker and where > denotes the two single bonds to the cyclohexane ring such that the ring containing $X^1$ forms a $C_3$-$C_6$ alkyl ring, which is optionally substituted by $C_1$-$C_3$ alkanol;

$X^2$ is =L-$R^{14}$, wherein L is absent or a linker;

$X^3$ is -L-$R^{14}$, wherein L is absent or a linker; and wherein —L-R¹⁴ is selected from

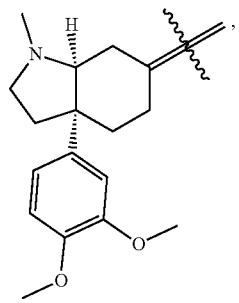

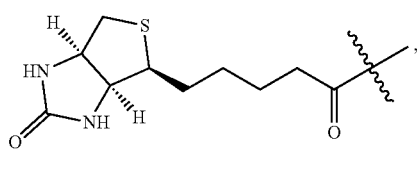

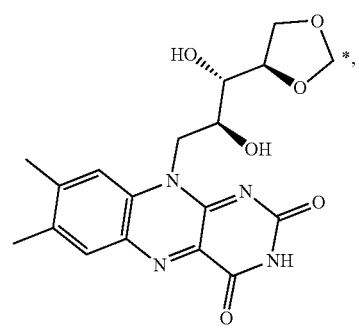

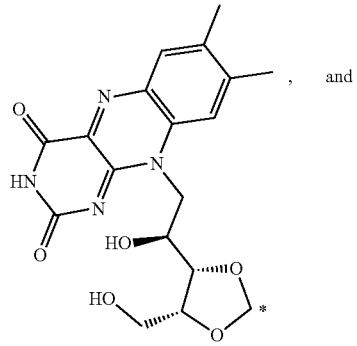

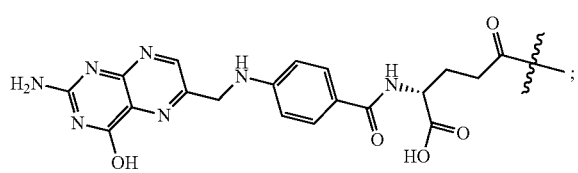

and
the * denotes the carbon of the cyclohexyl ring when L is absent.

In certain embodiments, the compound is of formula (V):

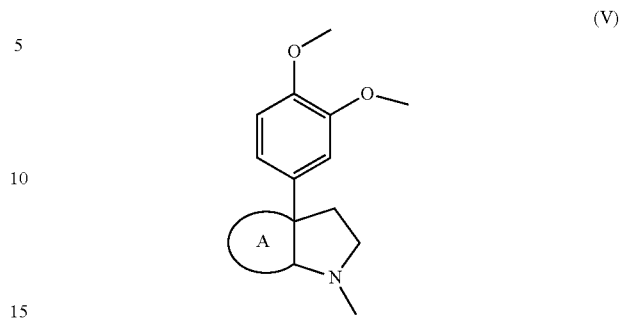

(V)

or a pharmaceutically acceptable salt thereof,
wherein
ring A is

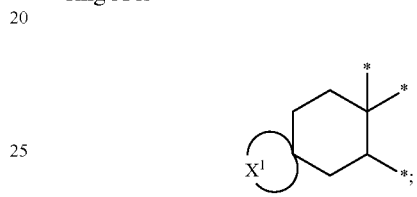

wherein * denotes the attachment points of ring A to the compound of formula (I), and wherein
$X^1$ is >L-R¹⁴, wherein L is absent or a linker and where > denotes the two single bonds to the cyclohexane ring such that the ring containing $X^1$ forms a $C_3$-$C_6$ alkyl ring, which is optionally substituted by $C_1$-$C_3$ alkanol.

EXAMPLES

LC/MS spectra were obtained using Agilent 1200\G1956A or SHIMADZU LCMS-2020. Standard LC/MS conditions were as follows (running time 1.55 minutes):

Acidic condition: Mobile Phase A: 0.0375% TFA in water (v/v). Mobile Phase B: 0.01875% TFA in acetonitrile (v/v); Column: Kinetex EVO C18 30*2.1 mm, 5 μm.

Basic condition: Mobile Phase A: 0.025% $NH_3·H_2O$ in water (v/v). Mobile Phase B: Acetonitrile; Column: Kinetex EVO C18 2.1×30 mm, 5 μm.

|  |  | 5-95AB_0.8 min |  |  |
| --- | --- | --- | --- | --- |
| Instrument |  | SHIMADZU LCMS-2020; |  |  |
| Software |  | LabSolution Version 5.97SP1 |  |  |
| HPLC | Column | Kinetex ® EVO C18 2.1 × 30 mm 5 um |  |  |
|  | Mobile Phase | A: 0.0375% TFA in water (v/v) |  |  |
|  |  | B: 0.01875% TFA in Acetonitrile (v/v) |  |  |
|  | Gradient | Time (min) | B (%) | Flow(mL/min) |
|  |  | 0.00 | 5.0 | 2.0 |
|  |  | 0.60 | 95.0 | 2.0 |
|  |  | 0.78 | 95.0 | 2.0 |
|  |  | 0.79 | 5.0 | 2.0 |
|  |  | 0.80 | 5.0 | 2.0 |
|  | Column Temp | 50° C. |  |  |
|  | Detector | PDA (220 nm & 254 nm) |  |  |
| MS | Ionization source | ESI |  |  |
|  | Drying Gas | N2 |  |  |
|  | Drying Gas Flow | 15 (L/min) |  |  |
|  | DL Voltage | 120 (v) |  |  |
|  | Qarray DC Voltage | 20 (V) |  |  |
|  | MS Polarity | Positive |  |  |

383
-continued

| 5-95AB_0.8 min | |
|---|---|
| MS Mode | Scan |
| Mass range | 100-1000 |

Table of Abbreviations

| | |
|---|---|
| Ac | Acetyl |
| Et | Ethyl |
| Me | Methyl |
| Ms | Methanesulfonyl |
| Ts | p-Toluenesulfonyl |
| Tol | toluene |
| HPLC | High Performance Liquid Chromatography |
| DMSO | Dimethyl sulfoxide |
| LC-MS | Liquid chromatography - mass spectrometry |
| NMR | Nuclear magnetic resonance |
| m | multiplet |
| d | Doublet |
| s | singlet |
| t | triplet |
| SFC | Supercritical fluid chromatography |
| IPA | isopropanol |
| ESI | Electrospray ionization |
| EtOAC | Ethyl acetate |
| t-buOK | Potassium tertbutoxide |
| ACN | acetonitrile |
| MS | Molecular sieves |
| DCM | dichloromethane |
| TMS | trimethylsilyl |
| Bu | Butyl |
| DCC | N,N'-Dicyclohexylcarbodiimide |
| DMAP | 4-dimethylaminopyridine |
| EDCI | 1-ethyl-3-(3-dimethylaminopropyl)carbodiimide |
| hr | hours |
| min | minutes |
| PE | petroleum Ether |
| Bn | Benzyl |
| BOC | tert-Butyloxycarbonyl |
| CDI | Carbonyldiimidazole |
| DEAD | Diethyl azodicarboxylate |
| NMO | N-Methylmorpholine N-oxide |
| Ph | Phenyl |
| TEA | Triethylamine |
| THF | Tetrahydrofuran |
| TFA | Trifluoroacetic Acid |

Summary of Mesembrine Compound Designations

| Compound | Racemic | (−) enantiomer | (+) enantiomer |
|---|---|---|---|
| Mesembrine | Compound 022 | Compound 001 | Compound 002 |

Figure 3:
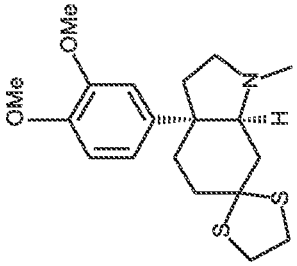
FIG. 3 is a table of SFC separation methods used to separate certain compounds.
Figure 3:
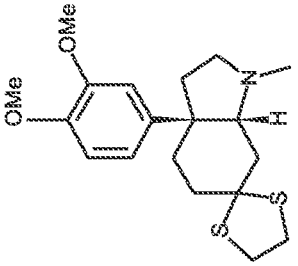
Figure 4:
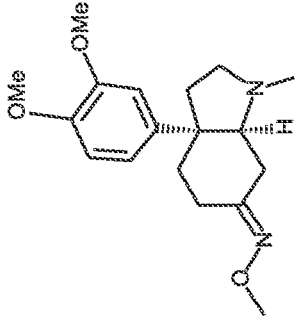
FIG. 4 is a table describing purification methods used to separate certain compounds.
Figure 4:
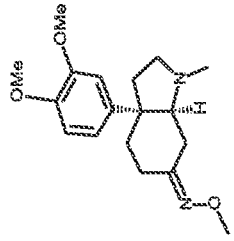
Figure 4:
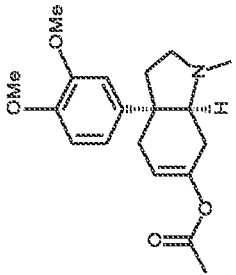

The synthesis of certain exemplary compounds is described below. In addition to the synthetic methods provided in the Examples, FIG. 3 is a table of SFC separation methods used to separate certain compounds, and FIG. 4 is a table describing purification methods used to separate certain compounds.

Example 1

Synthesis of Compound 013, Including Compounds 043 and 044

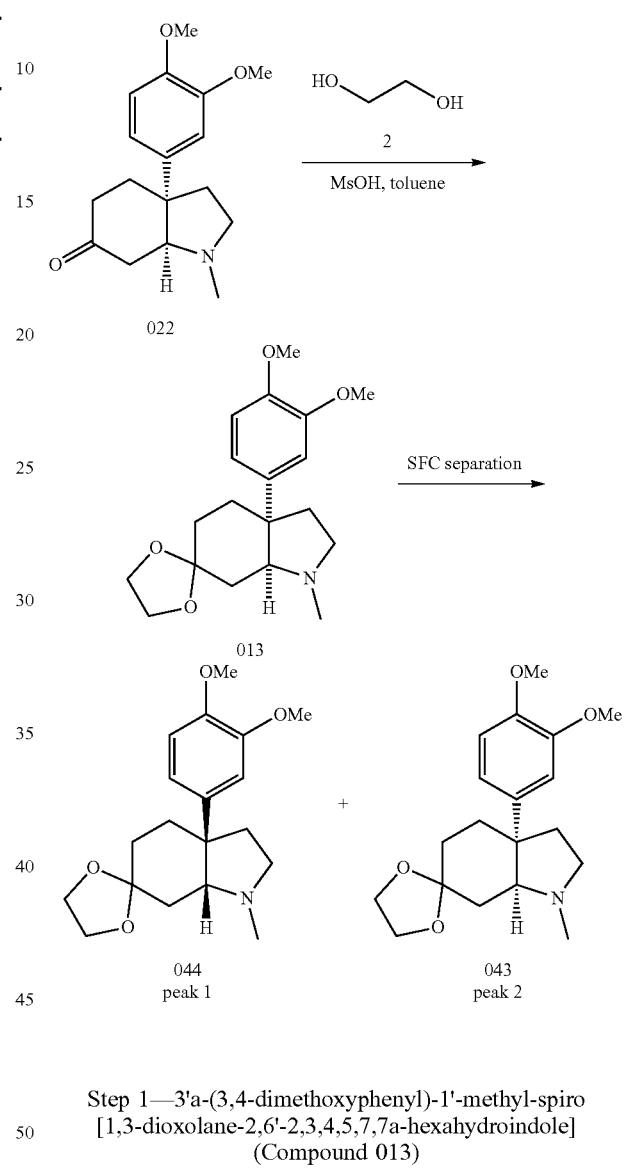

Step 1—3'a-(3,4-dimethoxyphenyl)-1'-methyl-spiro[1,3-dioxolane-2,6'-2,3,4,5,7,7a-hexahydroindole] (Compound 013)

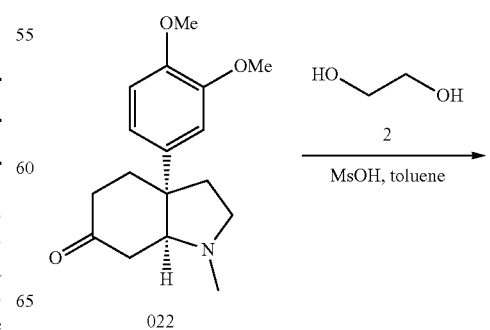

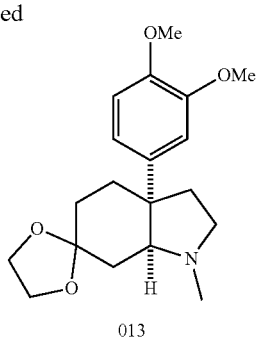

013

To a solution of 3a-(3,4-dimethoxyphenyl)-1-methyl-2,3,4,5,7,7a-hexahydroindol-6-one (500 mg, 1.73 mmol) and ethylene glycol (2.50 g, 40.2 mmol, 2.25 mL) in Tol. (20 mL) was added MsOH (112 mg, 1.17 mmol). The mixture was stirred at 130° C. for 16 hours under N$_2$ atmosphere. On completion, the reaction mixture was concentrated in vacuo to give the residue. The residue was purified by prep-HPLC (neutral condition: column: Welch Ultimate XB—NH$_2$ 250*50*10 um; mobile phase: [Hexane-EtOH]; B %: 5%-15%, 15 min) to give 3'a-(3,4-dimethoxyphenyl)-1'-methyl-spiro[1,3-dioxolane-2,6'-2,3,4,5,7,7a-hexahydroindole] (120 mg) as a yellow oil. LC-MS (ESI$^+$) m/z 334.3 (M+H)$^+$. $^1$H NMR (400 MHz, DMSO-d$_6$) δ 6.99-6.68 (m, 3H), 3.94-3.69 (m, 10H), 2.95 (dt, J=3.2, 8.8 Hz, 1H), 2.74 (t, J=4.0 Hz, 1H), 2.28-2.16 (m, 3H), 2.08 (s, 2H), 1.98-1.80 (m, 3H), 1.79-1.71 (m, 2H), 1.60-1.45 (m, 1H), 1.33-1.15 (m, 1H).

Step 2—Isolation of Compounds 044 & 043

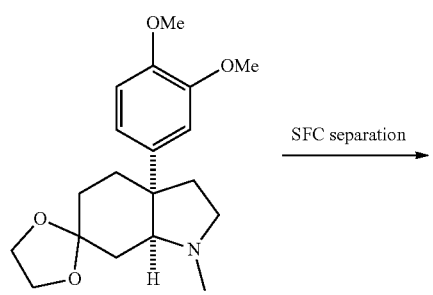

044 peak 1

043 peak 2

3'a-(3,4-dimethoxyphenyl)-1'-methyl-spiro[1,3-dioxolane-2,6'-2,3,4,5,7,7a-hexahydroindole] (120 mg) was separated by SFC (column: DAICEL CHIRALPAK IC(250 mm*30 mm, 10 um); mobile phase: [0.1% NH$_3$H$_2$O IPA]; B %: 40%-40%, 3.2; 50 min) to give 044 (58.1 mg) as a yellow oil and 043 (53.5 mg) as a yellow oil.

COMPOUND 044: LC-MS (ESI$^+$) m/z 334.2 (M+H)$^+$; $^1$H NMR (400 MHz, CDCL$_3$) δ 6.87-6.79 (m, 2H), 6.76-6.70 (m, 1H), 4.02-3.87 (m, 2H), 3.85-3.74 (m, 8H), 3.20 (dt, J=2.8, 9.2 Hz, 1H), 2.63 (s, 1H), 2.30 (s, 3H), 2.24-2.11 (m, 2H), 2.01-1.89 (m, 3H), 1.88-1.81 (m, 2H), 1.79-1.74 (m, 1H), 1.33 (dt, J=3.2, 13.2 Hz, 1H).

COMPOUND 043: LC-MS (ESI$^+$) m/z 334.2 (M+H)$^+$; $^1$H NMR (400 MHz, CDCl$_3$) δ 6.86-6.79 (m, 2H), 6.77-6.70 (m, 1H), 4.00-3.87 (m, 2H), 3.85-3.75 (m, 8H), 3.24-3.15 (m, 1H), 2.64 (s, 1H), 2.30 (s, 3H), 2.23-2.12 (m, 2H), 2.02-1.85 (m, 3H), 1.88-1.69 (m, 3H), 1.38-1.28 (m, 1H).

Example 2

Synthesis of Compound 014, Including Compounds 045 and 046

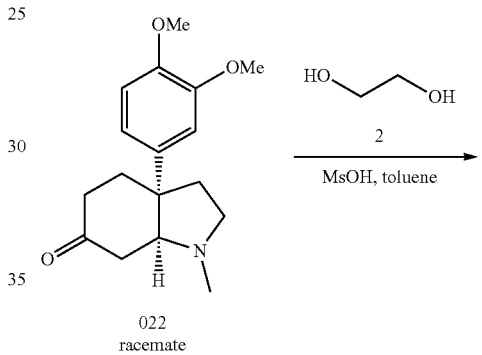

022 racemate

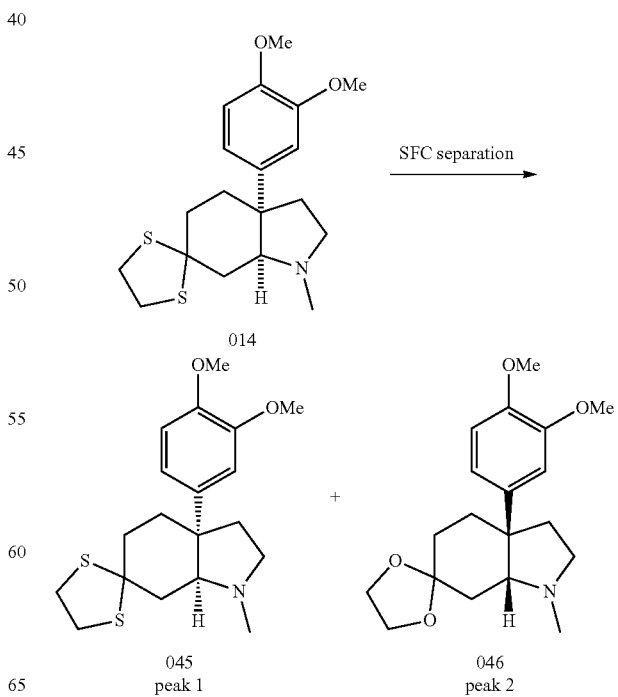

014

045 peak 1

046 peak 2

Step 1—(7'aS)-3'a-(3,4-dimethoxyphenyl)-1'-methyl-spiro[1,3-dithiolane-2,6'-2,3,4,5,7,7a-hexahydroindole] (014)

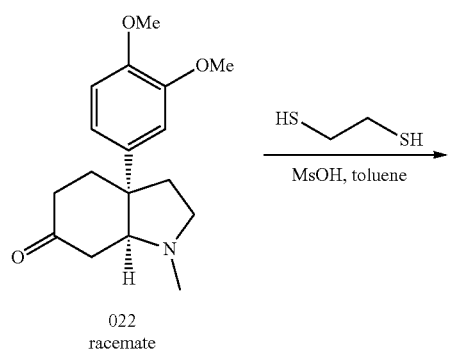

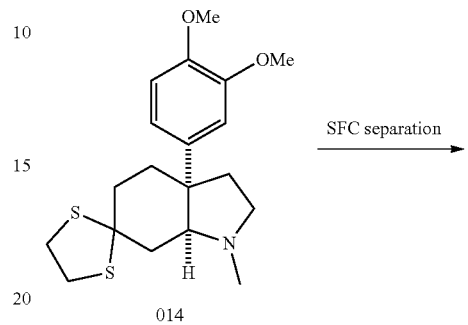

A mixture of (3aS,7aS)-3a-(3,4-dimethoxyphenyl)-1-methyl-2,3,4,5,7,7a-hexahydroindol-6-one (200 mg, 691 umol, 022), ethane-1,2-dithiol (1.63 g, 17.2 mmol, 1.45 mL) and MsOH (13.2 mg, 138 umol) in toluene (10 mL) was heated to reflux at 120° C. and remove water by Dean-Stark trap. On completion, the reaction mixture was concentrated under reduced pressure to remove toluene (10 mL). The residue was diluted with saturated sodium bicarbonate solution 20 mL to adjust pH to 7, and extracted with EtOAc (10 mL×3). The combined organic layers were washed with brine (5 mL×3), dried over anhydrous sodium sulfate, filtered and concentrated under reduced pressure to give a residue. The residue was purified by prep-HPLC (column: Welch Ultimate XB—NH2 250*50*10 um; mobile phase: [Hexane-EtOH]; B %: 10%-15%, 20 min) to give the title compound (80 mg) as a white solid. $^1$H NMR (400 MHz, CDCl$_3$) δ 6.97-6.86 (m, 2H), 6.86-6.74 (m, 1H), 3.90 (d, J=6.0 Hz, 6H), 3.38-3.15 (m, 5H), 2.79 (s, 1H), 2.52-2.31 (m, 7H), 2.04-1.89 (m, 3H), 1.88-1.73 (m, 2H). LC-MS (ESI$^+$) m/z 366.0 (M+H)

Step 2—(3'aS,7'aS)-3'a-(3,4-dimethoxyphenyl)-1'-methyl-spiro[1,3-dithiolane-2,6'-2,3,4,5,7,7a-hexahydroindole] (045 & 046)

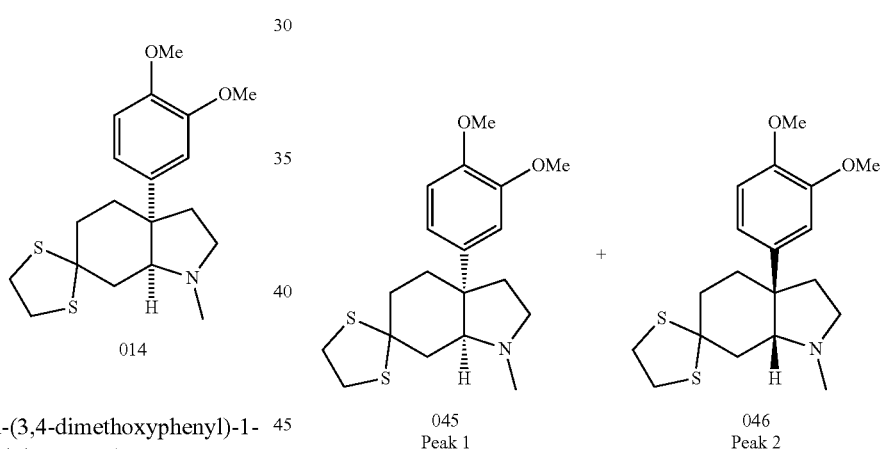

045
Peak 1

046
Peak 2

The racemic compound (80 mg) was separated by SFC (column: DAICEL CHIRALCEL OJ(250 mm*30 mm,10 um); mobile phase: [0.1%NH$_3$H$_2$O EtOH]; B %: 25%-25%, 6.55; 79 min) to give (3'aS,7'aS)-3'a-(3,4-dimethoxyphenyl)-1'-methyl-spiro[1,3-dithiolane-2,6'-2,3,4,5,7,7a-hexahydroindole] (20.0 mg, peak 1) as a yellow gum and (3'aR,7'aR)-3'a-(3,4-dimethoxyphenyl)-1'-methyl-spiro[1,3-dithiolane-2,6'-2,3,4,5,7,7a-hexahydroindole] (20 mg, peak 2) as a yellow gum.

045: LC-MS (ESI$^+$) m/z 366.5 (M+H)$^+$. $^1$H NMR (400 MHz, CDCL$_3$) δ 6.97-6.86 (m, 2H), 6.83 (d, J=8.4 Hz, 1H), 3.90 (d, J=5.6 Hz, 6H), 3.43-3.16 (m, 5H), 2.79 (s, 1H), 2.50-2.32 (m, 7H), 2.03-1.74 (m, 5H).

046: LC-MS (ESI$^+$) m/z 366.6 (M+H)$^+$. $^1$H NMR (400 MHz, CDCL$_3$) δ 6.93-6.87 (m, 2H), 6.85-6.81 (m, 1H), 3.90 (d, J=5.6 Hz, 6H), 3.35-3.16 (m, 5H), 2.79 (s, 1H), 2.51-2.33 (m, 7H), 2.04-1.73 (m, 5H)

Example 3

Prophetic Synthesis of Compound 27

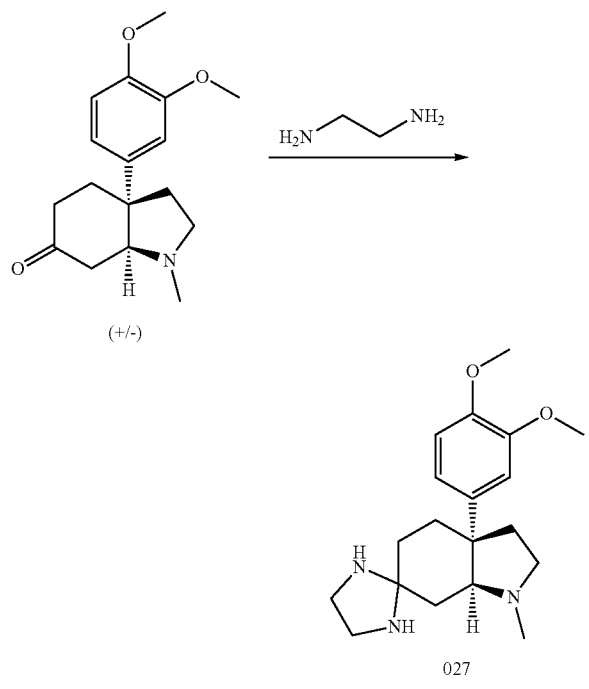

Example 4

Prophetic Synthesis of Compound 28

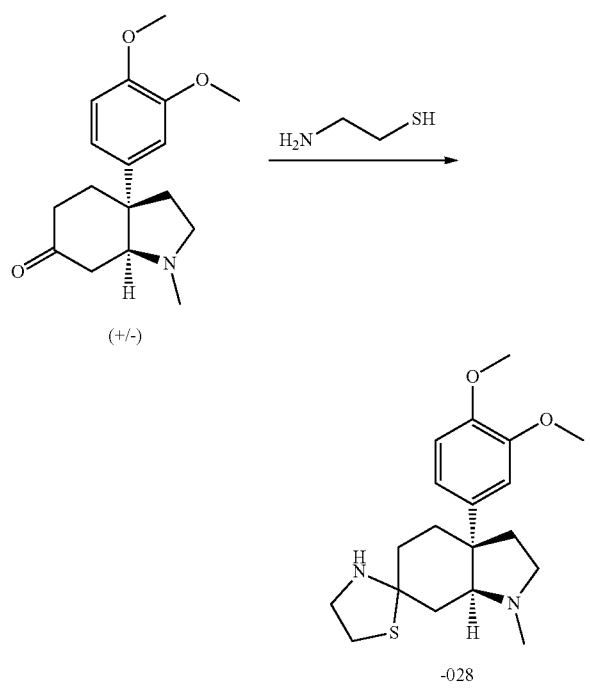

Example 5

Synthesis of Compounds 69 1 (3'aS,7'aS)-3'a -(3,4-dimethoxyphenyl)-1'-methyl-spiro[1,3-oxathiolane-2,6'-2,3,4,5,7,7a -hexahydroindole] (069)

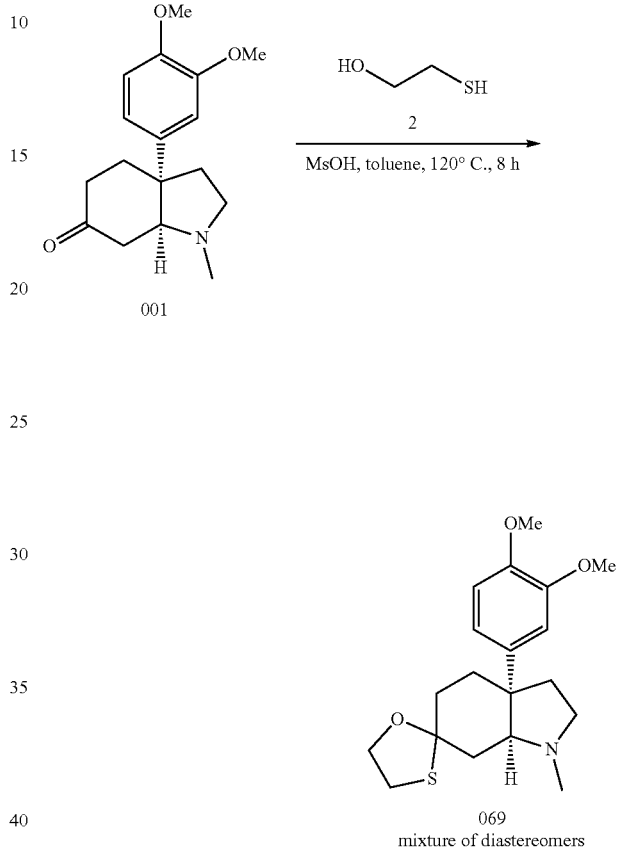

To a solution of (3aS,7aS)-3a-(3,4-dimethoxyphenyl)-1-methyl-2,3,4,5,7,7a-hexahydroindol one (100 mg, 345 umol, from 001), 2-sulfanylethanol (675 mg, 8.64 mmol, 602 uL) in toluene (4 mL) was added MsOH (9.96 mg, 103 umol, 7.38 uL). The mixture was stirred at 120° C. for 8 hours. On completion, the reaction mixture was concentrated in vacuo to give a residue. The reaction mixture was quenched by adding into a cold saturated aqueous NaClO solution (3 mL). The aqueous layer was extracted with ethyl acetate (5 mL×2). The organic layer was separated, dried over anhydrous $Na_2SO_4$, filtered and concentrated under reduced pressure to give the residue. The residue was purified by prep-HPLC (column: Welch Xtimate $C_{18\ 150*25}$ mm*5 um; mobile phase: [water (ammonia hydroxide v/v)-ACN]; B %: 20%-50%, 10 min) to give the title compound (10.1 mg, 9.8% yield) as yellow oil.

LC-MS (ESI+) m/z 350.4 (M+H)+.

$^1$H NMR (400 MHz, $CDCl_3$) δ 6.97-6.77 (m, 3H), 4.22-4.05 (m, 1H), 4.03-3.94 (m, 1H), 3.93-3.84 (m, 6H), 3.35-3.21 (m, 1H), 3.09-2.92 (m, 2H), 2.80 (d, J=1.0 Hz, 1H), 2.68-2.45 (m, 1H), 2.39 (s, 3H), 2.34-2.29 (m, 2H), 2.26-2.18 (m, 1H), 2.09-1.99 (m, 1H), 1.97-1.87 (m, 1H), 1.86-1.75 (m, 1H), 1.60 (s, 1H), 1.35-1.23 (m, 1H).

Example 6

Synthesis of (3'aR,7'aR)-3'a-(3,4-dimethoxyphenyl)-1'-methyl-spiro[1,3-oxathiolane-2,6'-2,3,4,5,7,7a-hexahydroindole] (070)

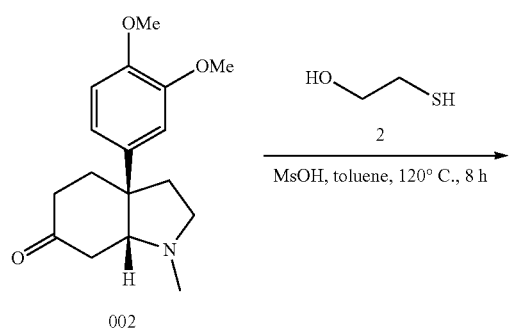

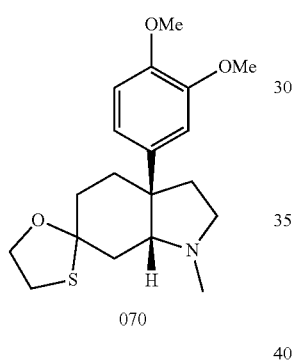

To a solution of (3aR,7aR)-3a-(3,4-dimethoxyphenyl)-1-methyl-2,3,4,5,7,7a-hexahydroindol-6-one (300 mg, 1.04 mmol, from 002), 2-sulfanylethanol (2.03 g, 25.9 mmol, 1.81 mL) in toluene (2 mL) was added MsOH (29.8 mg, 311 umol, 22.1 uL). The mixture was stirred at 120° C. for 8 hours. On completion, the reaction mixture was concentrated in vacuo to give a residue. The reaction mixture was quenched by adding into a cold saturated aqueous NaClO solution (3 mL). The aqueous layer was extracted with ethylacetate (5 mL×2). The organic layer was separated, dried over anhydrous $Na_2SO_4$, filtered and concentrated under reduced pressure to give the residue. The residue was purified by prep-HPLC (column: Welch Xtimate $C_{18}$ 150*25 mm*5 um; mobile phase: [water ($NH_3H_2O$)-ACN]; B %: 41%-71%, 8 min) to give the title compound (12.8 mg, 11% yield) as yellow gum.

LC-MS (ESI+) m/z 350.3 (M+H)+.

$^1$H NMR (400 MHz, $CDCL^3$) δ 6.92-6.86 (m, 2H), 6.85-6.81 (m, 1H), 4.36-4.25 (m, 1H), 4.22-4.10 (m, 1H), 3.89 (d, J=6.4 Hz, 6H), 3.23 (t, J=7.2 Hz, 1H), 3.10-2.94 (m, 2H), 2.66 (d, J=2.0 Hz, 1H), 2.37 (s, 3H), 2.35-2.18 (m, 3H), 2.14-2.05 (m, 1H), 2.04-1.92 (m, 2H), 1.91-1.77 (m, 1H), 1.37-1.26 (m, 2H).

Example 7

Prophetic Synthesis of Compound 6

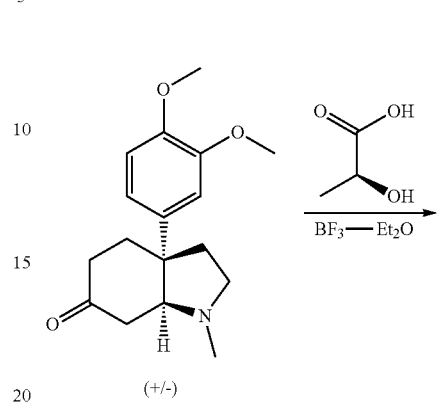

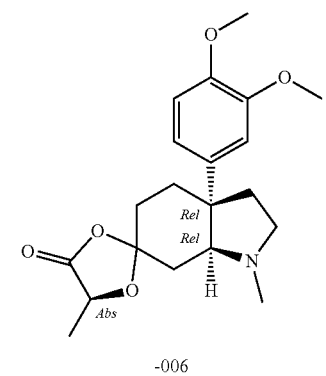

-006

Example 8

Prophetic Synthesis of Compound 7

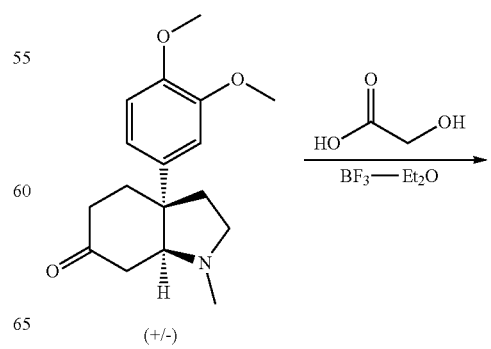

393
-continued
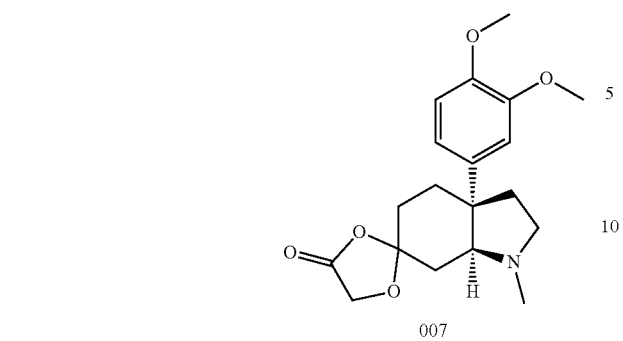
007
Example 9
Prophetic Synthesis of Compound 29
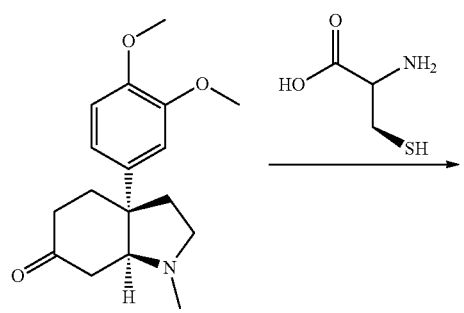
(+/−)
394
Example 10
Prophetic Synthesis of Compound 32
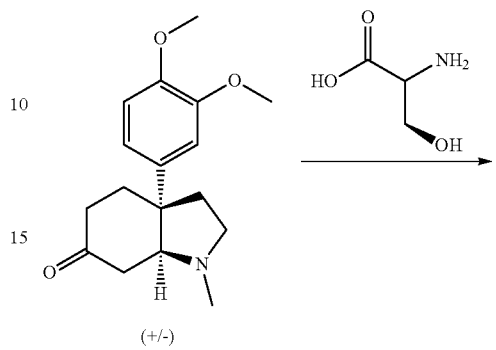
(+/−)
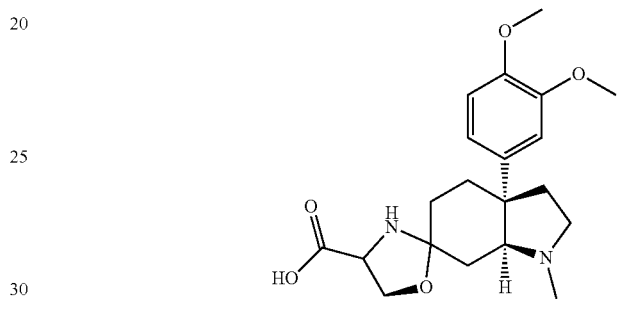
032
Example 11
Prophetic Synthesis of Compound 33
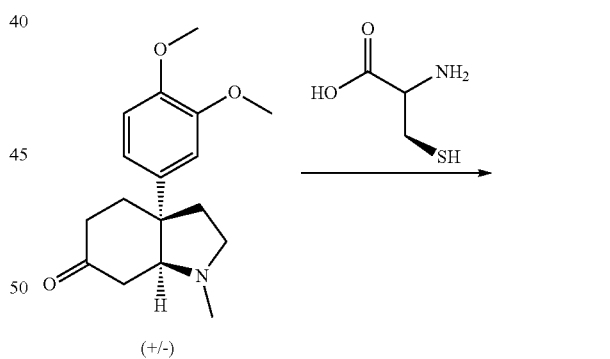
(+/−)
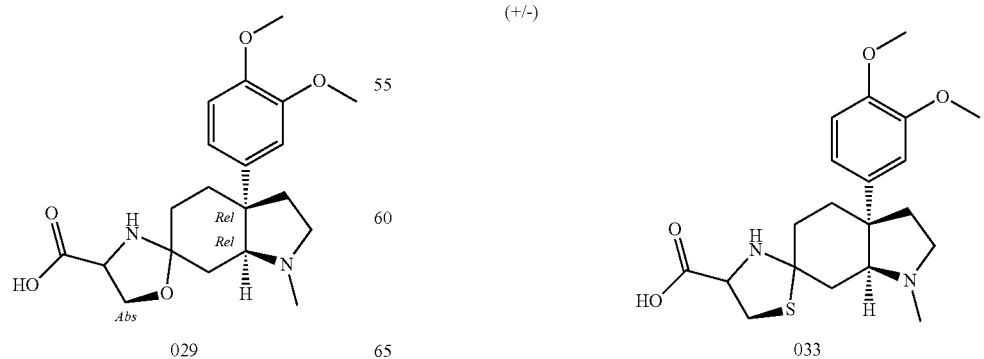
029
033

Example 12
Prophetic Synthesis of Compound 34
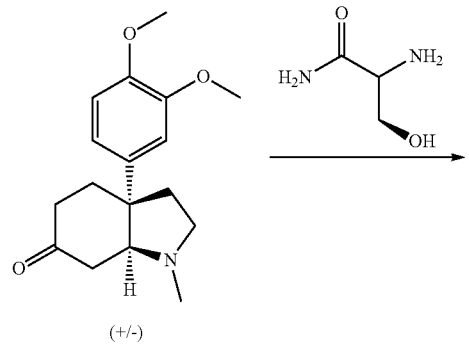
Example 13
Prophetic Synthesis of Compound 5
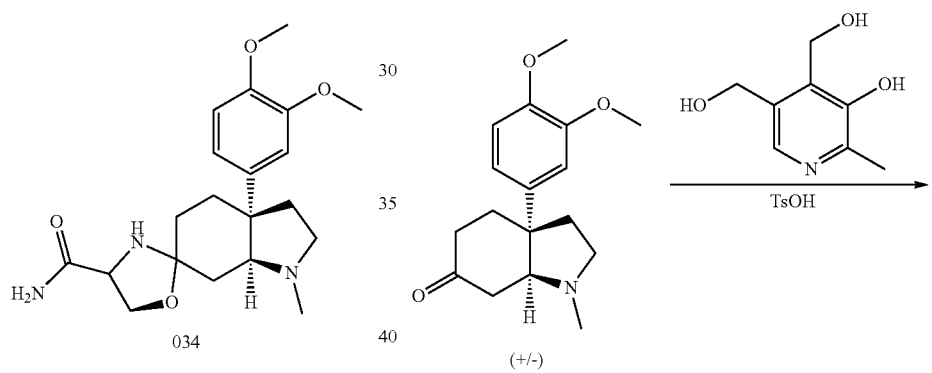
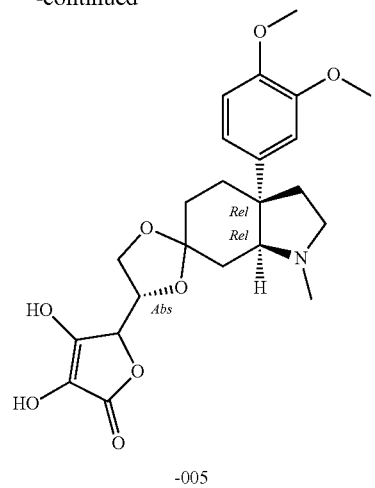
Example 14
Prophetic Synthesis of 008
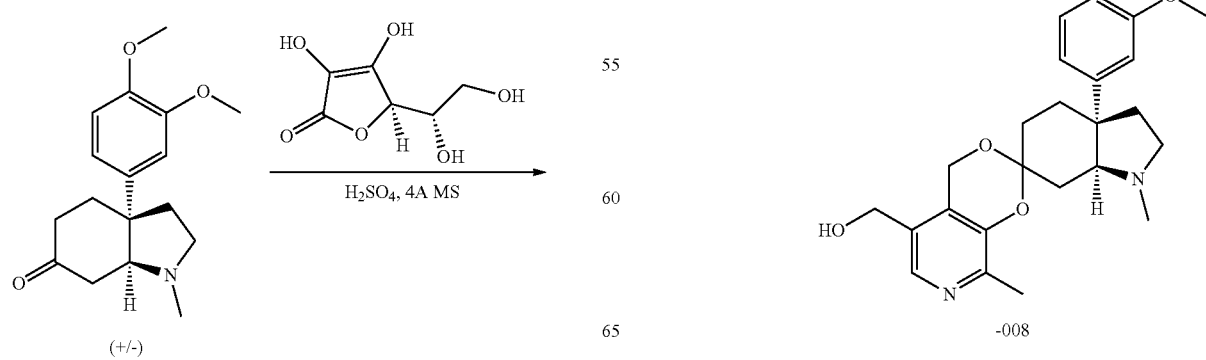

Example 15

Synthesis of Compound 36

Step 1—N-[[(3a5,7a5)-3a-(3,4-dimethoxyphenyl)-1-methyl-2,3,4,5,7,7a-hexahydroindol ylidene]amino] pyridine-3-carboxamide (036)

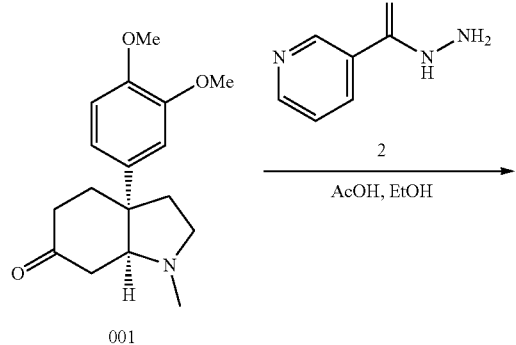

To a solution of 3a-(3,4-dimethoxyphenyl)-1-methyl-2,3,4,5,7,7a-hexahydroindol-6-one (200 mg, 691 umol) and pyridine-3-carbohydrazide (142 mg, 1.04 mmol) in EtOH (2 mL) was added AcOH (4.15 mg, 69.2 umol, 3.95 uL). The mixture was stirred at 60° C. for 2 hr. On completion, the reaction mixture was concentrated in vacuo to give the residue. The residue was purified by prep-HPLC (column: Welch Xtimate $C_{18\ 150*25}$ mm*5 um; mobile phase: [water (NH$_3$H$_2$O)-ACN]; B %: 10%-40%, 8 min) to give the N-[[(3aS,7aS)-3a-(3,4-dimethoxyphenyl)-1-methyl-2,3,4,5,7,7a-hexahydroindol-6-ylidene]amino]pyridine-3-carboxamide (237 mg) as a yellow solid. LC-MS (ESI$^+$) m/z 409.3 (M+H). $^1$H NMR (400 MHz, CHLOROFORM-d) δ 9.22-8.88 (m, 1H), 9.26-8.47 (m, 1H), 8.88-8.44 (m, 1H), 8.27-8.07 (m, 1H), 7.49-7.35 (m, 1H), 6.98-6.76 (m, 3H), 3.96-3.82 (m, 6H), 3.04 (t, J=7.8 Hz, 1H), 2.98-2.75 (m, 2H), 2.72-2.51 (m, 1H), 2.48-2.25 (m, 5H), 2.24-2.18 (m, 1H), 2.17 (br s, 2H), 2.09-1.97 (m, 2H).

Example 16

Synthesis of Compounds 35 and 38

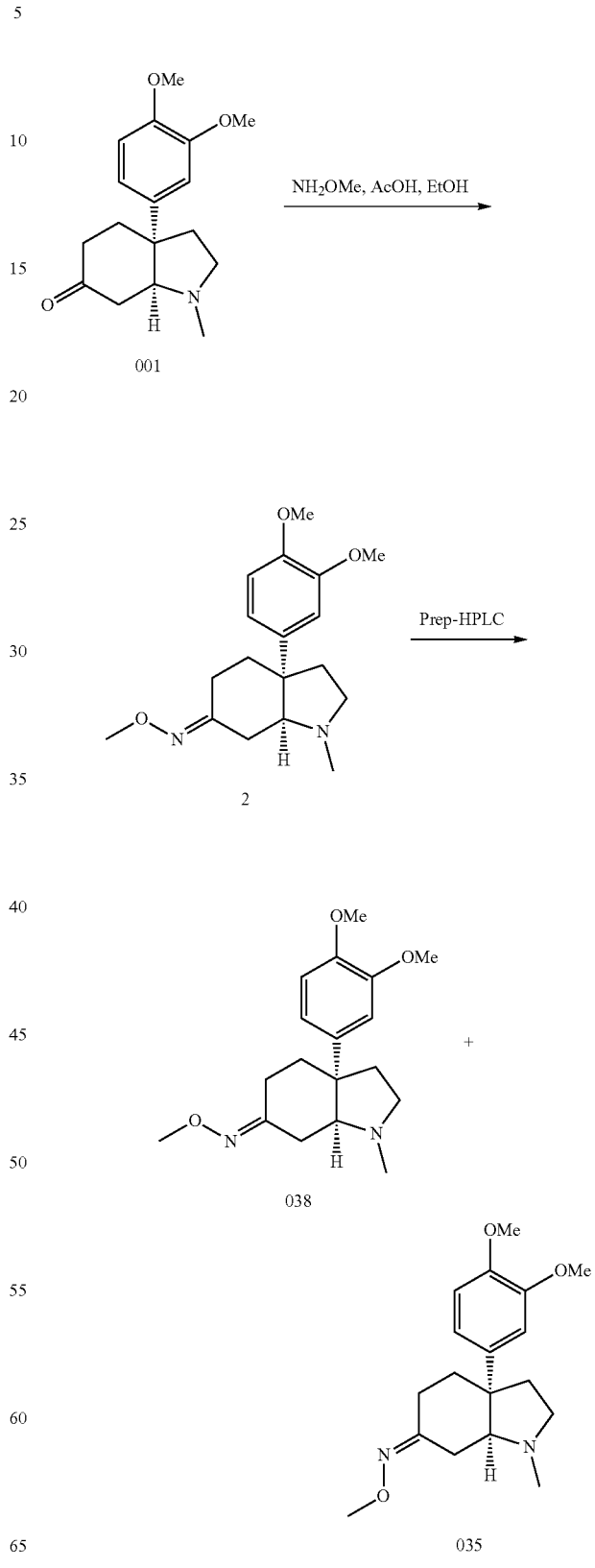

Step 1—3-[3-(3-Hydroxypropoxy)propoxy]propyl 4-methylbenzenesulfonate (2)

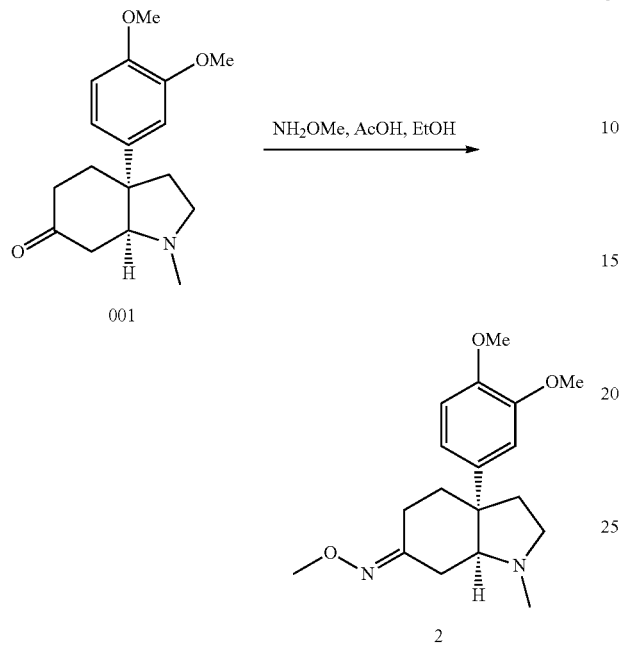

To a solution of (3aS,7aS)-3a-(3,4-dimethoxyphenyl)-1-methyl-2,3,4,5,7,7a-hexahydroindol-6-one (200 mg, 691 umol) in EtOH (10 mL) was added AcOH (420 mg, 6.99 mmol, 0.4 mL) and O-methylhydroxylamine; hydrochloride (115 mg, 1.38 mmol). The mixture was stirred at 60° C. for 16 hours. The reaction mixture was quenched by addition saturated sodium bicarbonate solution 5 mL at 25° C., and then diluted with H$_2$O 10 mL at 25° C., and extracted with EtOAc 30 mL (10 mL×3). The combined organic layers were filtered and concentrated under reduced pressure to give (3aS,7aS)-3a-(3,4-dimethoxyphenyl)-N-methoxy-1-methyl-2,3,4,5,7,7a-hexahydro indol-6-imine (150 mg) was obtained as brown oil.

Step 2—(E,3aS,7aS)-3a-(3,4-dimethoxyphenyl)-N-methoxy-1-methyl-2,3,4,5,7,7a-hexahydroindol-6-imine (038) and (Z,3a5,7a5)-3a-(3,4-dimethoxyphenyl)-N-methoxy-1-methyl-2,3,4,5,7,7a-hexahydroindol-6-imine (035)

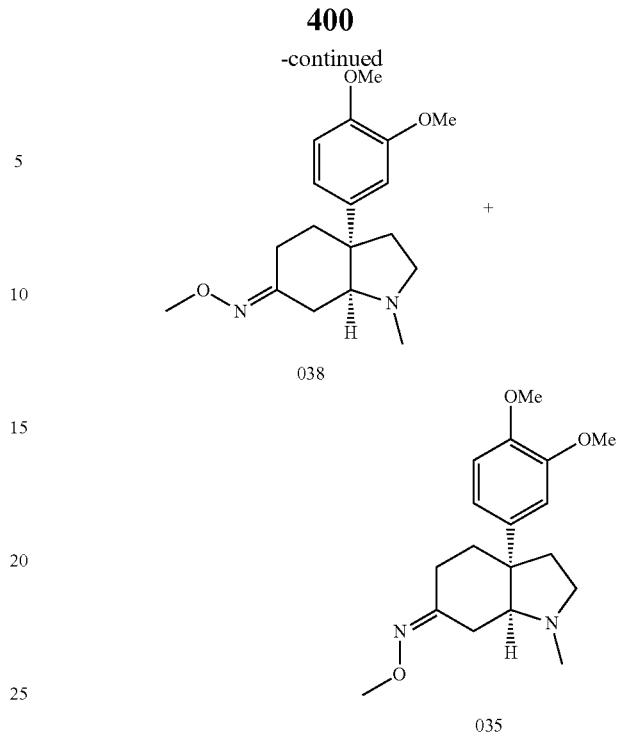

The residue was purified by prep-HPLC (neutral condition: column: Waters xbridge 150*25 mm 10 um; mobile phase: [water (NH$_4$HCO$_3$)-ACN]; B %: 22%-52%, 11 min). The reaction mixture was filtered, concentrated in vacuo to give (E,3aS,7aS)-3a-(3,4-dimethoxyphenyl)-N-methoxy-1-methyl-2,3,4,5,7,7a-hexahydroindol-6-imine (038, 66.3 mg) as a yellow gum and (Z,3aS,7aS)-3a-(3,4-dimethoxyphenyl)-N-methoxy-1-methyl-2,3,4,5,7,7a-hexahydroindol-6-imine (035, 18.6 mg) as a yellow gum.

038: LC-MS (ESI$^+$) m/z 319.0 (M+H)$^+$. $^1$H NMR (400 MHz, CDCl$_3$) δ 6.92-6.85 (m, 2H), 6.85-6.82 (m, 1H), 3.89 (d, J=5.6 Hz, 6H), 3.83 (s, 3H), 3.12-3.03 (m, 1H), 2.86 (t, J=4.8 Hz, 1H), 2.62-2.47 (m, 3H), 2.38 (s, 3H), 2.30 (dt, J=7.2, 9.6 Hz, 1H), 2.25-2.11 (m, 2H), 2.10-1.86 (m, 3H).

035: LC-MS (ESI$^+$) m/z 319.6 (M+H)$^+$. $^1$H NMR (400 MHz, CDCl$_3$) δ 6.96-6.88 (m, 2H), 6.87-6.83 (m, 1H), 3.91 (d, J=6.0 Hz, 6H), 3.85 (s, 3H), 3.38 (dd, J=2.4, 16.0 Hz, 1H), 3.28-3.19 (m, 1H), 2.81 (s, 1H), 2.39 (s, 3H), 2.37-2.27 (m, 2H), 2.21-2.04 (m, 4H), 2.04-1.91 (m, 2H).

Example 17

Synthesis of Compounds 37 and 68

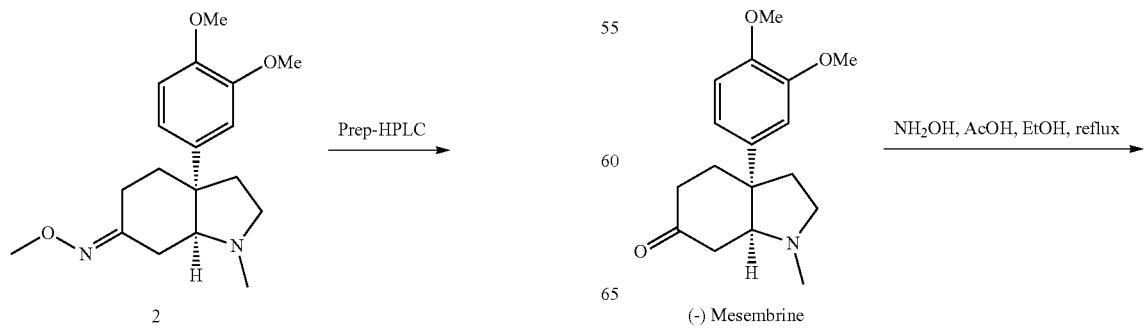

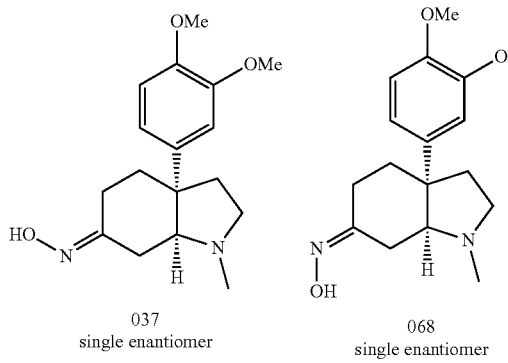

037
single enantiomer 068
single enantiomer

To a solution of (3aS,7aS)-3a-(3,4-dimethoxyphenyl)-1-methyl-2,3,4,5,7,7a-hexahydroindol-6-one (100 mg, 345 umol) in EtOH (5.0 mL) was added AcOH (2.08 mg, 34.56 umol) and $NH_2OH \cdot HCl$ (48.0 mg, 691 umol). The reaction mixture was allowed to stir at 60° C. for 2 hr and then filtered and concentrated in vacuo. The residue was purified by prep-HPLC (basic condition:column:Welch Xtimate $C_{18}$ $_{150*25}$ mm*5 um; mobile phase: [water(NH3H2O)-ACN]; B %: 15%-45%, 8 min) to give a mixure of E/Z isomers, 037 and 068, (20.0 mg, 28%) as a white solid. LC-MS (ESI+) m/z 305.4 (M+H) + 1H NMR (400 MHz, CDCl3) δ 7.31 (s, 1H), 6.84-6.73 (m, 3H), 3.81 (d, J=6.4 Hz, 6H), 3.03 (s, 1H), 2.82 (s, 1H), 2.63-2.43 (m, 3H), 2.33 (s, 3H), 2.29-2.21 (m, 1H), 2.15 (ddd, J=5.2, 8.4, 18.0 Hz, 1H), 2.09-1.91 (m, 3H), 1.90-1.78 (m, 1H).

Example 18

Synthesis of a Compound

To a solution of 3a-(3,4-dimethoxyphenyl)-1-methyl-2,3,4,5,7,7a-hexahydroindol-6-one (20 mg, 69.12 umol,) in THF (2 mL) was added $Ac_2O$ (8.47 mg, 82.94 umol) at −78° C. with stirring. The mixture was stirred at −78° C. for 30 min, and then to the mixture was added t-BuOK (6.98, 6.20 umol) under $N_2$. The mixture was stirred at 25° C. for 16 hour. On completion, the reaction mixture was filtered and concentrated in vacuo. The residue was purified by prep-HPLC (column:Welch Xtimate $C_{18}$ 150*25 mm*5 um; mobile phase: [water ($NH_3H_2O$)-ACN]; B %: 10%-40%, 8 min basic condition) to give the title compound (20 mg) as a yellow oil. LC-MS (ESI+) m/z 332.0 (M+H)+. 1H NMR (400 MHz, CHLOROFORM-d) δ=7.17 (d, J=10.4 Hz, 1H), 7.06 (dd, J=1.2, 10.4 Hz, 1H), 6.90-6.78 (m, 3H), 6.20 (d, J=10.0 Hz, 1H), 3.94-3.86 (m, 6H), 3.36-3.20 (m, 2H), 3.15-3.05 (m, 1H), 2.91 (s, 2H), 2.87 (s, 1H), 2.51-2.12 (m, 5H), 2.02 (s, 3H), 1.95 (s, 1H).

Example 19

Synthesis of Compound 026

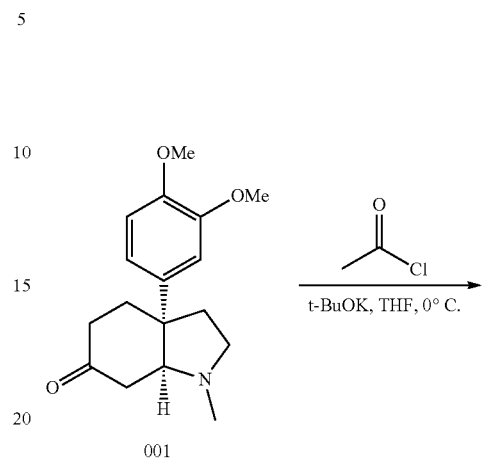

001

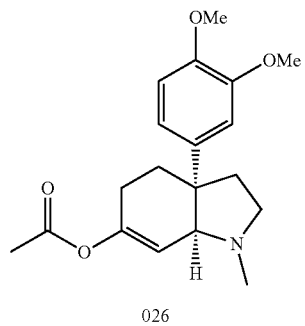

026

To a solution of (3aS,7aS)-3a-(3,4-dimethoxyphenyl)-1-methyl-2,3,4,5,7,7a-hexahydroindol-6-one (100 mg, 345 umol) in THF (4 mL) was added t-BuOK (1 M in THF, 691 uL) at 0° C., then the mixture was stirred at 0° C. for 30 mins. Then acetyl chloride (29.8 mg, 380 umol, 27.1 uL) was added and the mixture was stirred at 0° C. for 2 hours. On completion, the reaction mixture was filtered, concentrated in vacuo to give the residue. The residue was purified by prep-HPLC (column: Phenomenex luna $C_{18}$ $_{150*25}$ mm*10 um; mobile phase: [water(FA)-ACN]; B %: 12%-42%, 8 min) to give [(3aS,7aS)-3a-(3,4-dimethoxyphenyl)-1-methyl-3,4,5,7a-tetrahydro-2H-indol-6-yl] acetate (15.3 mg, 43.92 umol, 29.11% yield, 91% purity) as a yellow gum.

LC-MS (ESI+) m/z 332.1 (M+H)+.

1H NMR (400 MHz, $CDCl_3$) δ=6.94-6.75 (m, 3H), 5.75 (d, J=2.8 Hz, 1H), 3.90-3.88 (m, 6H), 3.50-3.47 (m, 1H), 3.40-3.20 (m, 1H), 2.60-2.56 (m, 3H), 2.40-2.27 (m, 4H), 2.26 (s, 3H), 2.01-1.75 (m, 3H).

Example 22

Synthesis of 081

Step 1—(3'aS,4R,7'aS)-3'a-(3,4-dimethoxyphenyl)-1'-methyl-4-phenyl-spiro[1,3-dioxolane-2,6'-2,3,4,5,7,7a-hexahydroindole] (081)

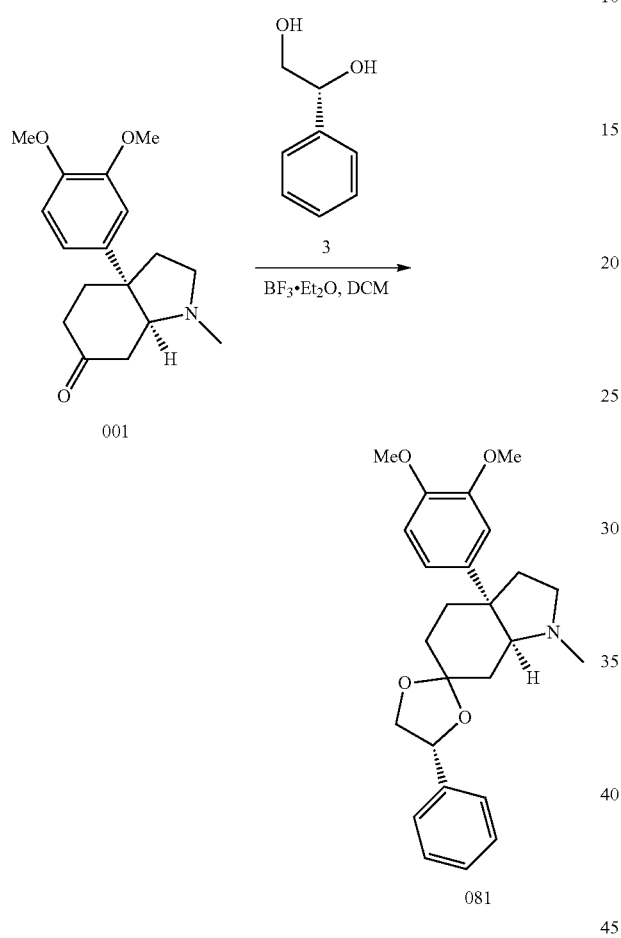

To a solution of (3aS,7aS)-3a-(3,4-dimethoxyphenyl)-1-methyl-2,3,4,5,7,7a-hexahydroindol-6-one (200 mg, 691 umol) and (1R)-1-phenylethane-1,2-diol (1.91 g, 13.8 mmol), 4A MS (30.0 mg, 691 umol) in DCM (5.0 mL) was added dropwise BF$_3$.Et$_2$O (196 mg, 1.38 mmol, 170 uL) at 0° C., and then the mixture was stirred at 25° C. for 16 hours. On completion, the reaction mixture was quenched by adding it to a cold saturated aqueous sodium hydroxide solution till pH=7. The aqueous layer was extracted with ethyl acetate (35 mL). The organic layer was separated, dried over anhydrous Na$_2$SO$_4$, filtered and concentrated under reduced pressure to give the residue. The residue was purified by prep-HPLC (neutral condition: column: Phenomenex C$_{18}$ $_{150*25}$ mm*10 um; mobile phase: [water (NH$_4$HCO$_3$)-ACN]; B %: 30%-60%, 5 min) to give (3'aS, 4R,7'aS)-3'a-(3,4-dimethoxyphenyl)-1'-methyl-4-phenyl-spiro[1,3-dioxolane-2,6'-2,3,4,5,7,7a-hexahydroindole] (143 mg) was obtained as a brown gum.

LC-MS (ESI$^+$) m/z 410.1 (M+H)$^+$ $^1$H NMR (400 MHz, CDCl$_3$) δ 7.43-7.29 (m, 5H), 6.99-6.91 (m, 2H), 6.87-6.82 (m, 1H), 5.18-5.01 (m, 1H), 4.42 (dd, J=6.0, 8.4 Hz, 1H), 3.99-3.84 (m, 6H), 3.77-3.67 (m, 1H), 3.41-3.19 (m, 1H), 2.89-2.71 (m, 1H), 2.43 (s, 1H), 2.39-2.18 (m, 3H), 2.17-1.98 (m, 3H), 1.97-1.86 (m, 1H), 1.83-1.73 (m, 1H), 1.72-1.43 (m, 3H).

Example 23

(3'aS,7'aS)-3'a-(3,4-dimethoxyphenyl)-1'-methyl-4-(3-pyridyl)spiro[1,3-dioxolane-2,6'-2,3,4,5,7,7a-hexahydroindole] (109)

Step 1—1-(3-pyridyl)ethane-1,2-diol (2)

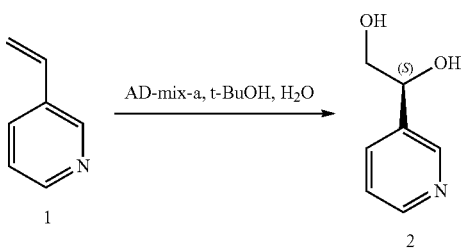

To a solution of 1,4-bis[(S)-[(2R,4S,5R)-5-ethylquinuclidin-2-yl]-(6-methoxy-4-quinolyl)methoxy] phthalazine (9.39 g, 12.0 mmol) in t-BuOH (30 mL) an H₂O (30 mL) was added 3-vinylpyridine (700 mg, 6.66 mmol). The mixture was stirred at 25° C. for 96 hours with excluded light. The reaction mixture was then cooled to 0° C., and Na₂SO₃ (839 mg, 6.66 mmol) was added. The mixture was then stirred at 25° C. for 1 hour. On completion, the mixture was poured to the water (20 mL) and extracted with ethyl acetate (200 mL). The organic layers was dried by sodium sulfate, filtered and concentrated in vacuo to give the residue. The crude product was purified by reversed-phase HPLC (0.1% NH₃·H₂O) to give 1-(3-pyridyl)ethane-1,2-diol (170 mg, 17% yield) as a yellow oil.

LC-MS (ESI⁺) m/z 140.1 (M+H)⁺

¹H NMR (400 MHz, DMSO-d₆) δ 8.53 (d, J=2.0 Hz, 1H), 8.44 (dd, J=1.6, 4.8 Hz, 1H), 7.76-7.70 (m, 1H), 7.34 (ddd, J=0.8, 4.8, 8.0 Hz, 1H), 5.41 (d, J=4.4 Hz, 1H), 4.80 (t, J=5.6 Hz, 1H), 4.63-4.53 (m, 1H), 3.57-3.48 (m, 1H), 3.48-3.40 (m, 1H).

Step 2—(3'aS,7'aS)-3'a-(3,4-dimethoxyphenyl)-1'-methyl-4-(3-pyridyl)spiro[1,3-dioxolane-2,6'-2,3,4,5,7,7a-hexahydroindole] (109)

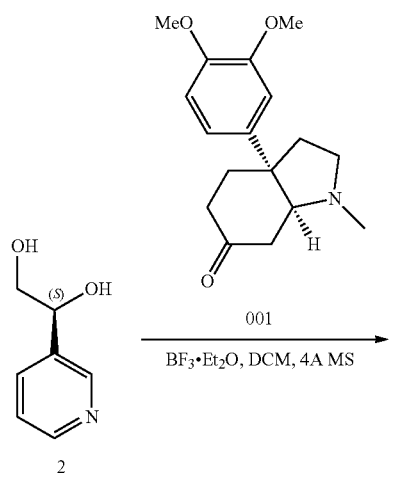

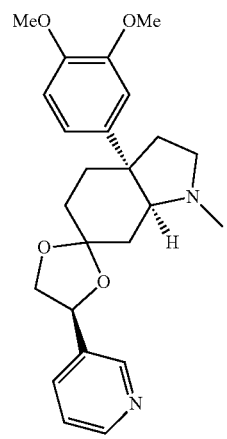

To a solution of (3aS,7aS)-3a-(3,4-dimethoxyphenyl)-1-methyl-2,3,4,5,7,7a-hexahydroindol-6-one (100 mg, 345 umol) and 1-(3-pyridyl)ethane-1,2-diol (96.1 mg, 691 umol) in THF (1.0 mL) was added BF₃·Et₂O (98.1 mg, 691 umol, 85.3 uL). The mixture was stirred at 60° C. for 16 hours. On completion, the reaction mixture concentrated in vacuo to give the residue. And then the residue was quenched by adding it to a cold saturated aqueous sodium hydrogen carbonate solution till pH=8. The aqueous layer was extracted with ethyl acetate (60 mL). The organic layer was separated, dried over anhydrous Na₂SO₄, filtered and concentrated under reduced pressure to give the residue. The residue was purified by prep-HPLC (basic condition:column: Welch Xtimate C₁₈ 150*25 mm*5 um; mobile phase: [water(NH₃H₂O)-ACN]; B %: 30%-60%, 8 min) to give (3'aS,7'aS)-3'a-(3,4-dimethoxyphenyl)-1'-methyl-4-(3-pyridyl)spiro[1,3-dioxolane-2,6'-2,3,4,5,7,7a-hexahydroindole] (56.22 mg, 38% yield) as a yellow gum.

LC-MS (ESI⁺) m/z 411.3 (M+H)⁺

¹H NMR (400 MHz, CDCl₃) δ 8.75-8.48 (m, 2H), 7.72 (d, J=9.2 Hz, 1H), 7.32 (s, 1H), 7.07-6.72 (m, 3H), 5.30-4.93 (m, 1H), 4.58-4.19 (m, 1H), 4.00-3.83 (m, 6H), 3.81-3.58 (m, 1H), 3.50-3.09 (m, 1H), 2.76 (s, 1H), 2.58-2.35 (m, 3H), 2.34-2.16 (m, 3H), 2.10-1.97 (m, 2H), 1.97-1.77 (m, 2H), 1.75-1.63 (m, 1H), 1.28 (s, 1H).

Example 24

(3'aS,7'aS)-3'a-(3,4-dimethoxyphenyl)-1'-methyl-4-(4-pyridyl)spiro[1,3-dioxolane-2,6'-2,3,4,5,7,7a-hexahydroindole] (110)

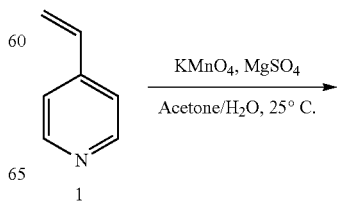

-continued

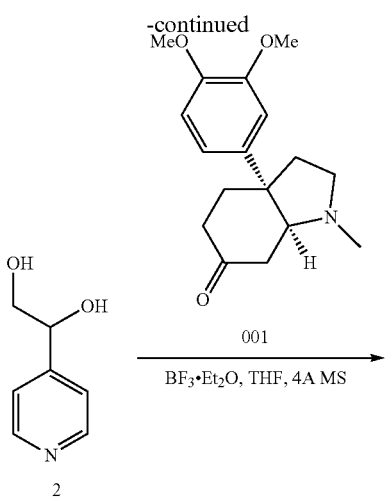

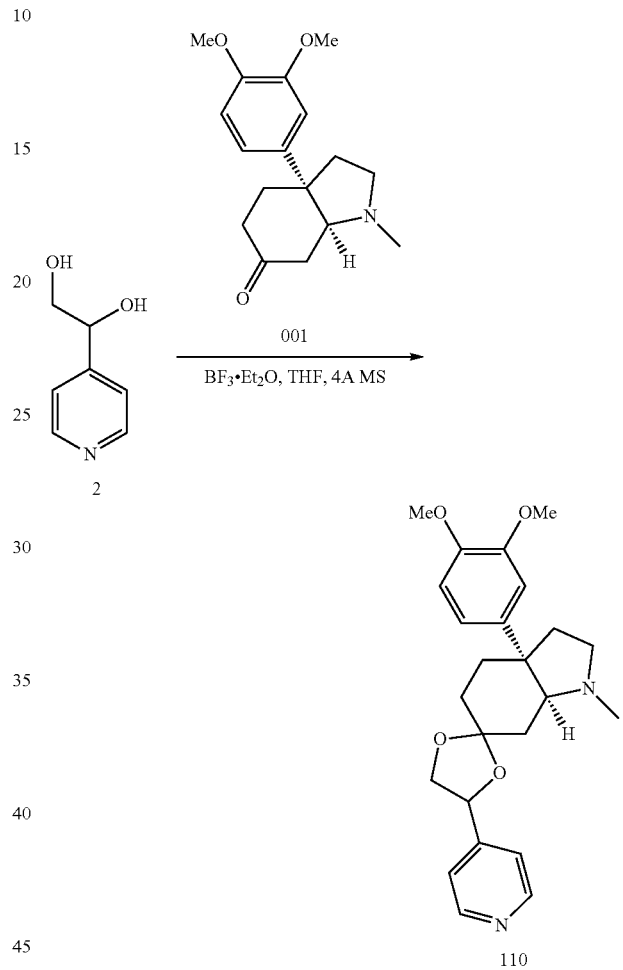

Step 1—1-(4-pyridyl)ethane-1,2-diol (2)

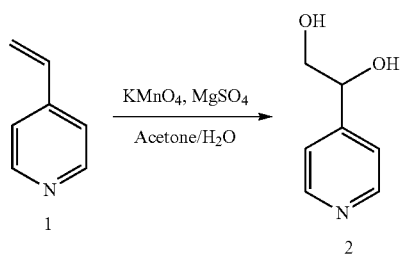

To a solution of 4-vinylpyridine (10 g, 95.1 mmol, 10.2 mL) in acetone (120 mL) was added dropwise KMnO$_4$ (10.5 g, 66.5 mmol) and MgSO$_4$ (3.43 g, 28.5 mmol) in H$_2$O (200 mL) at 0° C., Then the mixture was stirred at 25° C. for 16 hours. After addition, the mixture was stirred at this temperature for 10 min, and then benzene-1,4-diol (1.05 g, 9.51 mmol, 1.42 mL) was added dropwise at 25° C. The mixture was diluted by ethyl acetate (300 mL) and washed by brine (200 mL). The organic layers was dried by sodium sulfate, filtered and concentrated in vacuo to give the residue. The crude product was purified by reversed-phase HPLC (0.1% NH$_3$H$_2$O) to give 1-(4-pyridyl)ethane-1,2-diol (1.8 g, 12.2% yield) was obtained as a brown oil.

LC-MS (ESI$^+$) m/z 140.1 (M+H)$^+$ $^1$H NMR (400 MHz, DMSO-d$_6$) δ 8.51-8.47 (m, 2H), 7.37-7.32 (m, 2H), 5.48 (d, J=4.4 Hz, 1H), 4.82 (s, 1H), 4.59-4.51 (m, 1H), 3.46 (s, 2H).

Step 2—(3'aS,7'aS)-3'a-(3,4-dimethoxyphenyl)-1'-methyl-4-(4-pyridyl)spiro[1,3-dioxolane-2,6'-2,3,4,5,7,7a-hexahydroindole] (110)

To a solution of (3aS,7aS)-3a-(3,4-dimethoxyphenyl)-1-methyl-2,3,4,5,7,7a-hexahydroindol-6-one (200 mg, 691 umol), 1-(4-pyridyl)ethane-1,2-diol (192.3 mg, 1.38 mmol) and 4A MS (50 mg) in THF (1.0 mL) was added BF$_3$.Et$_2$O (196 mg, 1.38 mmol, 170 uL). The mixture was stirred at 75° C. for 48 hours. On completion, the reaction mixture concentrated in vacuo to give the residue. And then the residue was quenched by adding it to a cold saturated aqueous sodium hydrogen carbonate solution till pH=8. The aqueous layer was extracted with ethyl acetate (60 mL). The organic layer was separated, dried over anhydrous Na$_2$SO$_4$, filtered and concentrated under reduced pressure to give the residue. The residue was purified by prep-HPLC (basic condition: column: Welch Xtimate C$_{18\ 150*25}$ mm*5 um; mobile phase: [water(NH$_3$H$_2$O)-ACN]; B %: 30%-60%, 8 min) to give (3'aS,7'aS)-3'a-(3,4-dimethoxyphenyl)-1'-methyl-4-(4-pyridyl)spiro[1,3-dioxolane-2,6'-2,3,4,5,7,7a-hexahydroindole] (85.52 mg, 29% yield) was obtained as a yellow gum.

LC-MS (ESI$^+$) m/z 411.2 (M+H)$^+$

¹H NMR (400 MHz, CDCl₃) δ 8.70-8.49 (m, 2H), 7.31-7.31 (m, 1H), 7.34-7.29 (m, 1H), 6.98-6.90 (m, 2H), 6.87-6.81 (m, 1H), 5.20-4.97 (m, 1H), 4.54-4.23 (m, 1H), 3.97-3.86 (m, 6H), 3.82-3.60 (m, 1H), 3.40-3.17 (m, 1H), 2.79 (d, J=16.0 Hz, 1H), 2.56-2.42 (m, 3H), 2.28-2.27 (m, 2H), 2.41-2.20 (m, 2H), 2.04 (d, J=13.2 Hz, 2H), 1.95-1.75 (m, 2H), 1.75-1.40 (m, 1H).

Example 25

(3'aS,7'aS)-3'a-(3,4-dimethoxyphenyl)-4-(3-methoxyphenyl)-1'-methyl-spiro[1,3-dioxolane-2,6'-2,3,4,5,7,7a-hexahydroindole] (111)

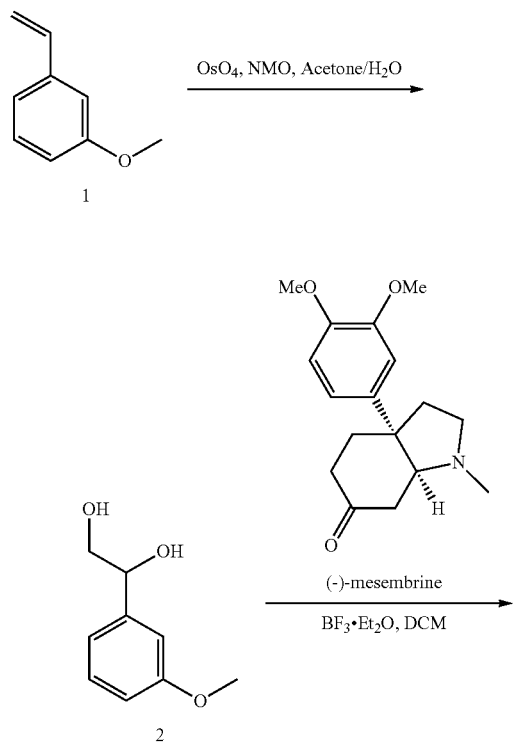

Step 1—1-(3-methoxyphenyl)ethane-1,2-diol (Int2)

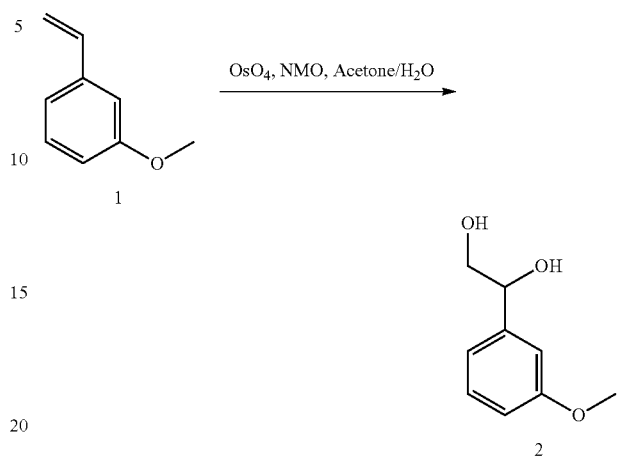

To a solution of 1-methoxy-3-vinyl-benzene (2 g, 14.9 mmol, 2.07 mL) in Acetone (4.5 mL) and H₂O (0.5 mL) was added NMO (2.62 g, 22.3 mmol, 2.36 mL) and OsO₄ (379 mg, 1.49 mmol, 77.3 uL) at 0° C. The mixture was stirred at 25° C. for 12 hours. The mixture was poured to the aq.Na₂S₂O₄ (50 mL), after quenching, a wet starch potassium iodide test paper was negative (pH<8), then add extracted with ethyl acetate (50 mL). After extraction, the water phase was tested negative with wet starch potassium iodide paper (PH<8), and the waste liquid was poured into the waste liquid barrel. The organic layers was dried by sodium sulfate, filtered and concentrated in vacuo to give the residue. The crude product was purified by reversed-phase HPLC (0.1% NH₃·H₂O). The 1-(3-methoxyphenyl)ethane-1,2-diol (1.80 g, 71% yield) was obtained as a yellow solid.

¹H NMR (400 MHz, CDCl₃) δ 7.25-7.20 (m, 1H), 6.89-6.84 (m, 2H), 6.80-6.75 (m, 1H), 4.81-4.69 (m, 1H), 3.74 (s, 3H), 3.72-3.67 (m, 1H), 3.63-3.56 (m, 1H), 2.36-1.96 (m, 2H)

Step 2—(3'aS,7'aS)-3'a-(3,4-dimethoxyphenyl)-4-(3-methoxyphenyl)-1'-methyl-spiro[1,3-dioxolane-2,6'-2,3,4,5,7,7a-hexahydroindole]

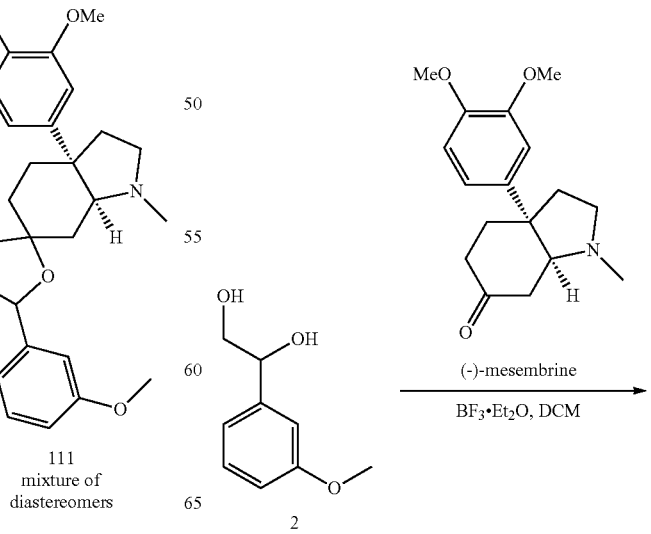

-continued

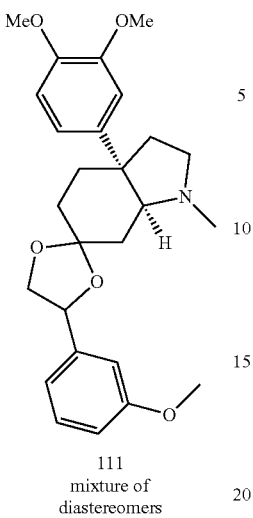

111
mixture of diastereomers

To a solution of (3aS,7aS)-3a-(3,4-dimethoxyphenyl)-1-methyl-2,3,4,5,7,7a-hexahydroindol-6-one (200 mg, 691 umol) and 1-(3-methoxyphenyl)ethane-1,2-diol (1.16 g, 6.91 mmol) in DCM (5 mL) was added BF3.Et2O (490 mg, 3.46 mmol, 426 uL). The mixture was stirred at 25° C. for 2 hr. The mixture was poured to the water (50 mL) and extracted with DCM (30 mL). The organic layers was dried by sodium sulfate, filtered and concentrated in vacuo to give the residue. The residue was purified by prep-HPLC (column: Phenomenex luna $C_{18}$ 150*25 mm*10 um; mobile phase: [water(FA)-ACN]; B %: 23%-53%, 15 min) to give the (3'aS,7'aS)-3'a-(3,4-dimethoxyphenyl)-4-(3-methoxyphenyl)-1'-methyl-spiro[1,3-dioxolane-2,6'-2,3,4,5,7,7a-hexahydroindole] (123 mg, 36.4% yield) as a gray solid.

LC-MS (ESI$^+$) m/z 440.5 (M+H)$^+$.

$^1$H NMR (400 MHz, CDCl$_3$) δ 8.25-7.62 (m, 1H), 7.18-7.13 (m, 1H), 6.96-6.58 (m, 6H), 5.33-4.96 (m, 1H), 4.63-4.26 (m, 1H), 4.23-4.02 (m, 1H), 3.90 (br d, J=8.0 Hz, 1H), 3.83 (d, J=19.0 Hz, 6H), 3.78-3.66 (m, 2H), 3.64-3.64 (m, 1H), 3.67 (s, 1H), 3.40-3.23 (m, 1H), 3.17-3.04 (m, 3H), 2.42-2.20 (m, 3H), 2.16-2.04 (m, 2H), 1.89-1.53 (m, 3H).

Example i26

(3'aS,7'aS)-3'a-(3,4-dimethoxyphenyl)-1'-methyl-4-(3-nitrophenyl)spiro[1,3-dioxolane-2,6'-2,3,4,5,7,7a-hexahydroindole] (113)

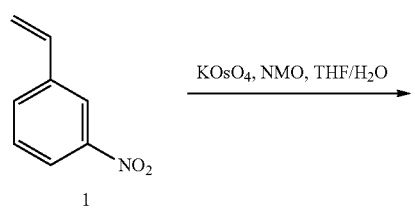

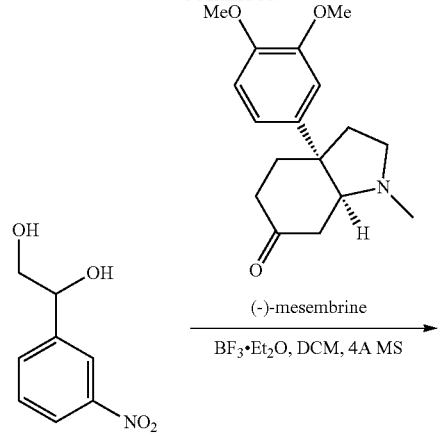

2

(-)-mesembrine
────────────→
BF$_3$·Et$_2$O, DCM, 4A MS

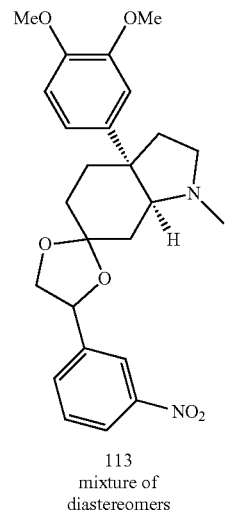

113
mixture of diastereomers

Step 1—1-1-nitro-3-vinyl-benzene

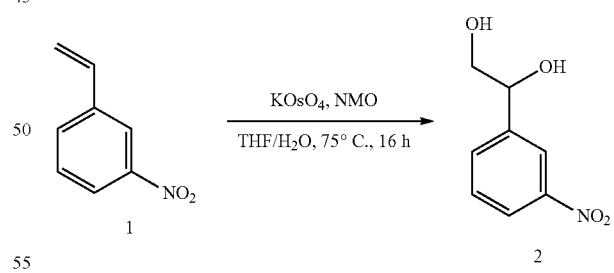

To a solution of 1-nitro-3-vinyl-benzene (500 mg, 3.35 mmol, CAS #586-39-0) in THF (5 mL) and H$_2$O (1 mL) was added was added dipotassium; dioxido(dioxo)osmium; dihydrate (1.85 g, 5.03 mmol) and 4-methyl-4-oxido-morpholin-4-ium (1.18 g, 10.0 mmol, 1.06 mL), and then mixture stirred at 75° C. for 16 hours. On completion, the mixture was quenched with water (20 mL) and extracted with ethyl acetate (30 mL×3), the combined organic phase was dried over anhydrous sodium sulfate, filtered and concentrated to give a residue. The residue was purified by column chromatography (SiO₂, Dichloromethane/Methanol=20/1) to give the title compound (126 mg, 687 umol, 20% yield) as yellow solid.

¹H NMR (400 MHz, CDCl₃) δ=8.29 (s, 1H), 8.17 (dd, J=1.2, 8.4 Hz, 1H), 7.73 (d, J=7.6 Hz, 1H), 7.60-7.54 (m, 1H), 4.96 (dd, J=3.6, 8.0 Hz, 1H), 4.13 (d, J=7.4 Hz, 1H), 3.92-3.62 (m, 3H).

Step 2—(3'aS,7'aS)-3'a-(3,4-dimethoxyphenyl)-1'-methyl-4-(3-nitrophenyl)spiro[1,3-dioxolane-2,6'-2,3,4,5,7,7a-hexahydroindole]

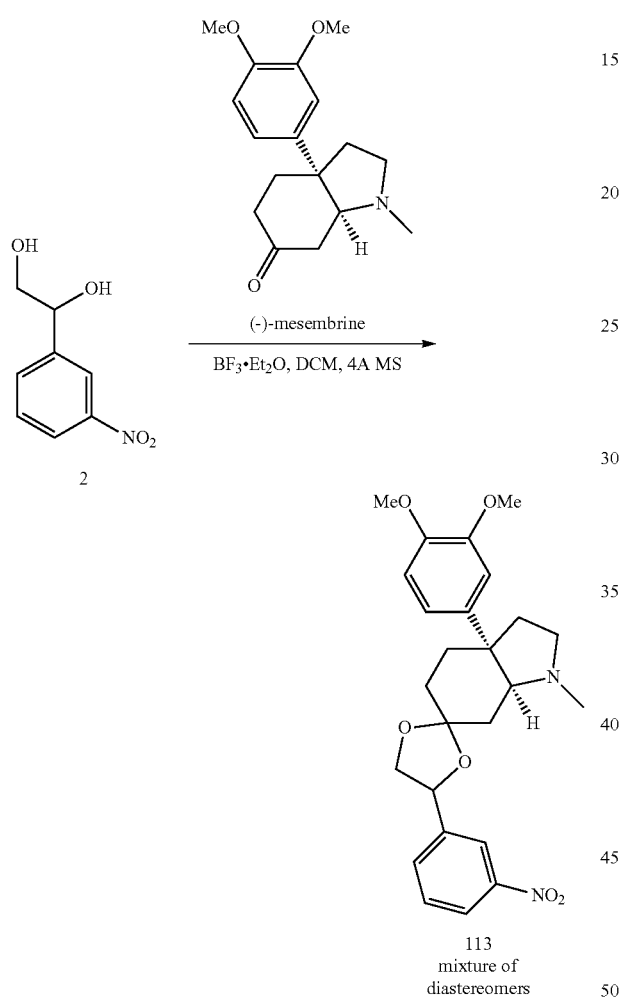

To a solution of 1-(3-nitrophenyl)ethane-1,2-diol (100 mg, 545 umol) and (3aS,7aS)-3a-(3,4-dimethoxyphenyl)-1-methyl-2,3,4,5,7,7a-hexahydroindol-6-one (110.59 mg, 382 umol) in DCM (3 mL) was added BF₃.Et₂O (232 mg, 1.64 mmol, 202 uL) at 0° C. The mixture was stirred at 25° C. for 16 hours. On completion, the reaction mixture was filtered and concentrated in vacuo. The residue was purified by prep-HPLC (column: Phenomenex luna C₁₈ 150*25 mm*10 um; mobile phase: [water(FA)-ACN]; B %: 15%-45%, 10 min), to give the title compound (34.2 mg, 40% yield) as a yellow oil.

LC-MS (ESI+) m/z 455 (M+H)+

1H NMR (400 MHz, CDCl3) δ=8.29-8.13 (m, 2H), 7.80 (s, 2H), 6.89 (br s, 3H), 5.65-5.00 (m, 1H), 4.78-4.44 (m, 1H), 4.36-4.13 (m, 1H), 4.07-3.51 (m, 8H), 3.21-3.09 (m, 1H), 3.02 (s, 3H), 2.30 (br d, J=14.4 Hz, 6H), 2.06-1.72 (m, 2H).

Example 27

–(3a'S,7a'S)-3a'-(3,4-dimethoxyphenyl)-1'-methyl-4-(4-nitrophenyl)octahydrospiro[[1,3]dioxolane-2,6'-indole](114)

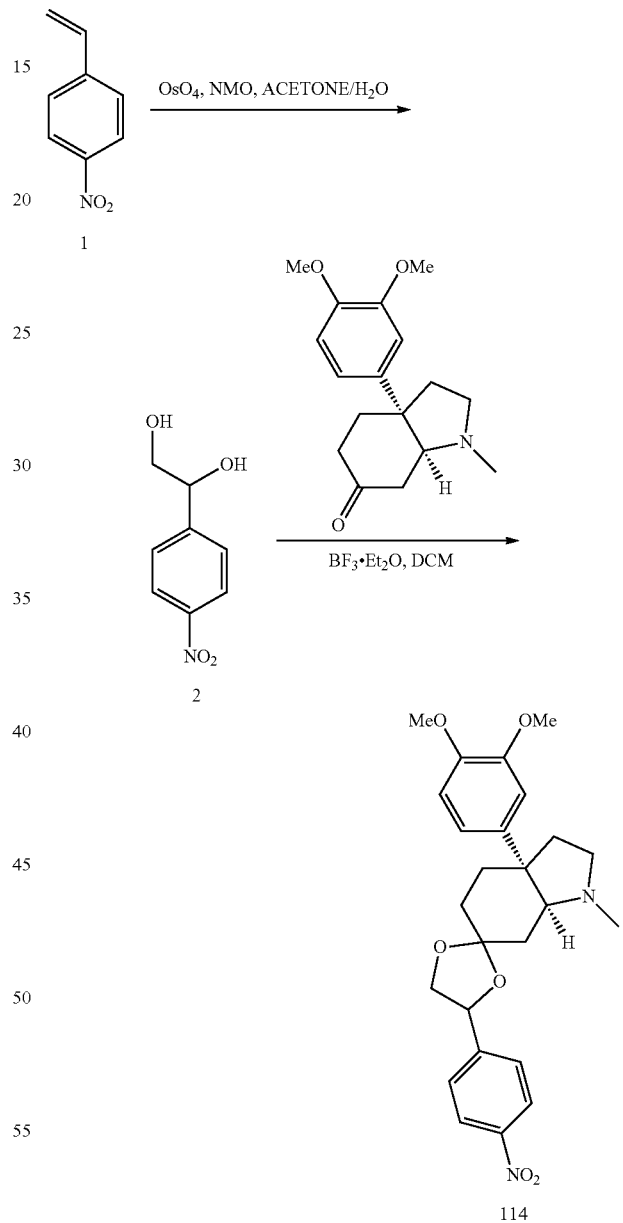

To a solution of 1-(4-nitrophenyl)ethane-1,2-diol (200 mg, 1.09 mmol,) and (3aS,7aS)-3a-(3,4-dimethoxyphenyl)-1-methyl-2,3,4,5,7,7a-hexahydroindol-6-one (220 mg, 763 umol) in DCM (3 mL) was added BF₃.Et₂O (464 mg, 3.27 mmol, 403 uL). The mixture was stirred at 120° C. for 16 hours. On completion, the reaction mixture was quenched by addition Saturated sodium thiosum thiosulfate solution 20 mL at 0° C., and then diluted with water 20 mL and extracted with EtOAc (20 mL*3). The combined organic layers were washed with saturated salt solution (30 mL*2), dried over [Na₂SO₄], filtered and concentrated under reduced pressure to give a residue. The residue was purified by prep-HPLC (column: Phenomenex luna C$_{18}$ $_{150*25}$ mm*10 um; mobile phase: [water(FA)-ACN]; B %: 18%-48%, 10 min) to give (3'aS,7'aS)-3'a-(3,4-dimethoxyphenyl)-1'-methyl-4-(4-nitrophenyl)spiro[1,3-dioxolane-2,6'-2,3,4,5,7,7a-hexahydroindole] (114 mg, 23% yield) as a white solid.

114: LC-MS (ESI⁺) m/z 455.21 (M+H)⁺;

¹H NMR (400 MHz, CDCl₃) δ=8.29-8.17 (m, 2H), 7.68-7.58 (m, 1H), 7.55-7.46 (m, 1H), 6.92-6.81 (m, 3H), 5.66-5.15 (m, 1H), 4.79-4.20 (m, 2H), 3.92 (d, J=10.0 Hz, 8H), 3.33-2.86 (m, 4H), 2.50-1.73 (m, 8H).

Example 28

N-[[(3aS,7aS)-3a-(3,4-dimethoxyphenyl)-1-methyl-2,3,4,5,7,7a-hexahydroindol-6-ylidene]amino]-5-[(3aS,4S,6aR)-2-oxo-1,3,3a,4,6,6a-hexahydrothieno[3,4-d]imidazol-4-yl]pentanamide (158)

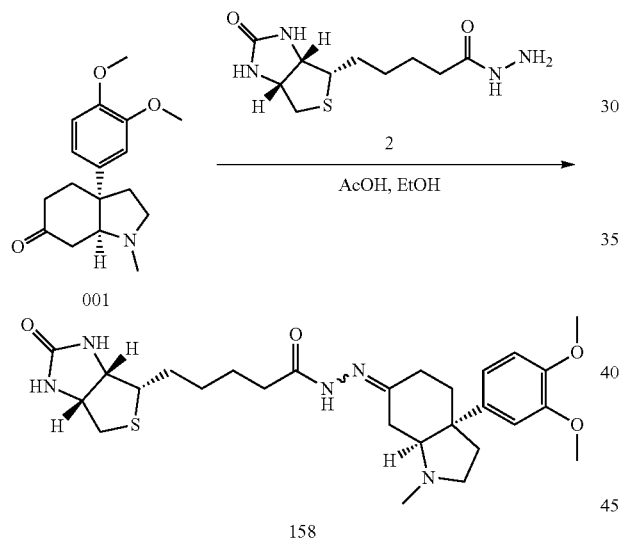

To a solution of (3aS,7aS)-3a-(3,4-dimethoxyphenyl)-1-methyl-2,3,4,5,7,7a-hexahydroindol-6-one (200 mg, 691 umol) and 5-[(3aS,4S,6aR)-2-oxo-1,3,3a,4,6,6a-hexahydrothieno[3,4-d]imidazol-4-yl] pentanehydrazide (357 mg, 1.38 mmol) in EtOH (4.0 mL) was added AcOH (4.15 mg, 69.1 umol). The mixture was stirred at 60° C. for 2 hours. On completion, the residue was purified by prep-HPLC (neutral condition: column: Phenomenex C$_{18}$ $_{150*25}$ mm*10 um; mobile phase: [water(NH₄HCO₃)-ACN]; B %: 12%-42%, 8 min) to give N-[[(3aS,7aS)-3a-(3,4-dimethoxyphenyl)-1-methyl-2,3,4,5,7,a-hexahydroindol-6-ylidene]amino]-5-[(3aS,4S,6aR)-2-oxo-1,3,3a,4,6,6a-hexahydrothieno[3,4-d]imidazol-4-yl]pentanamide (50 mg, 13% yield) as a white solid.

LC-MS (ESI⁺) m/z 530.2 (M+H)⁺

¹H NMR (400 MHz, DMSO-d₆) δ 10.10-9.74 (m, 1H), 7.07-6.75 (m, 3H), 6.50-6.27 (m, 2H), 4.32 (d, J=7.2 Hz, 1H), 4.14 (d, J=3.2 Hz, 1H), 3.85-3.64 (m, 6H), 3.19-3.02 (m, 2H), 2.89-2.75 (m, 2H), 2.58 (d, J=12.4 Hz, 2H), 2.39-2.25 (m, 5H), 2.23-2.12 (m, 2H), 2.10-1.89 (m, 4H), 1.68-1.44 (m, 5H), 1.40-1.30 (m, 2H), 1.28-1.22 (m, 1H).

Example 29

N-[[(3aS,7aS)-3a-(3,4-dimethoxyphenyl)-1-methyl-2,3,4,5,7,7a-hexahydroindol-6-ylidene]amino]pyridine-4-carboxamide (157)

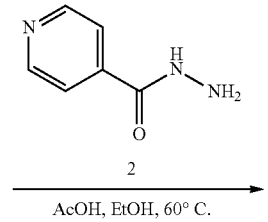

To a solution of (3aS, 7aS)-3a-(3, 4-dimethoxyphenyl)-1-methyl-2,3,4,5,7,7a-hexahydroindol-6-one (200 mg, 691 umol) and pyridine-4-carbohydrazide (142 mg, 1.04 mmol) in EtOH (2 mL) was added AcOH (2.08 mg, 34.5 umol, 1.98 uL), then the mixture was stirred at 60° C. for 2 hours. On completion, the reaction mixture was filtered, concentrated in vacuo to give the residue. The residue was purified by prep-HPLC (basic condition)(column: Welch Xtimate C$_{18}$ $_{150*25}$ mm*5 um; mobile phase:[water(NH₃H₂O)-ACN]; B %: 12%-42%, 8 min) to give the crude, then the crude was purified by SFC (column: DAICEL CHIRALCEL OD (250 mm*30 mm, 10 um); mobile phase: [Neu-ETOH]; B %: 30%-30%, C; 8.5; 40 min) to give N-[[(3aS,7aS)-3a-(3,4-dimethoxyphenyl)-1-methyl-2,3,4,5,7,7a-hexahydroindol-6-ylidene]amino]pyridine-4-carboxamide (38.5 mg, 38% yield) as an off-white solid.

LC-MS (ESI⁺) m/z 409.2 (M+H)

¹H NMR (400 MHz, CDCl₃) δ=8.90-8.60 (m, 3H), 7.70-7.55 (m, 2H), 6.80-6.60 (m, 3H), 3.10-2.88 (m, 3H), 2.50-2.40 (m, 3H), 2.35-2.10 (m, 3H), 2.10-1.89 (m, 5H).

Example 30

N-[[(3aS,7aS)-3a-(3,4-dimethoxyphenyl)-1-methyl-2,3,4,5,7,7a-hexahydroindol-6-ylidene]amino]-2-phenyl-ethanamine (159)

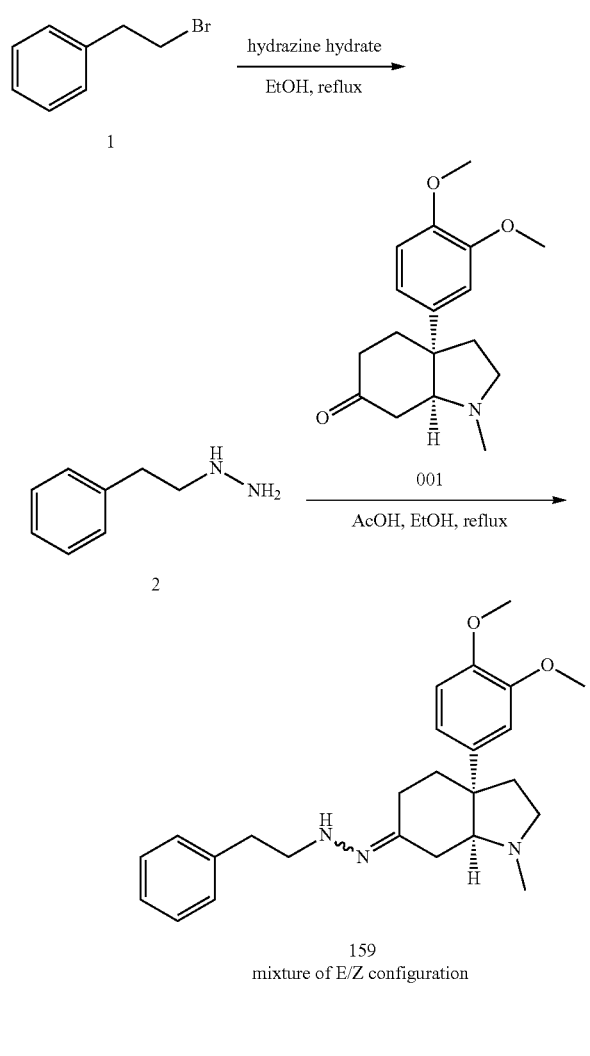

159
mixture of E/Z configuration

Step 1 2-phenylethylhydrazine (2)

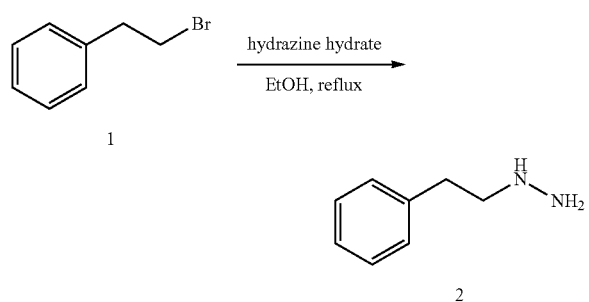

To a solution of 2-bromoethylbenzene (2.00 g, 10.8 mmol, 1.46 mL) in EtOH (10 mL) was added N₂H₄·H₂O (10.3 g, 174 mmol, 10 mL, 85% purity). The mixture was stirred at 60° C. for 2 hours. On completion, the reaction mixture was quenched by adding it to a cold saturated aqueous 2N HCl solution (5 mL) adjusted to pH=1-2. The aqueous layer was extracted with ethylacetate (5 mL×2). The organic layer was separated, dried over anhydrous Na₂SO₄, filtered and concentrated under reduced pressure to give the residue. The residue was purified by reverse phase flash [ACN/(0.1% NH₃·H₂O in water), 0% to 90%] to give the title compound (900 mg, 61% yield) as yellow oil.

LC-MS (ESI+) m/z 137.0 (M+H)⁺.

¹H NMR (400 MHz, DMSO-d₆) δ 10.52-9.87 (m, 1H), 9.57-8.94 (m, 1H), 7.37-7.18 (m, 5H), 3.11 (s, 2H), 2.87 (d, J=2.0 Hz, 2H).

Step 2 N-[[(3a5,7a5)-3a-(3,4-dimethoxyphenyl)-1-methyl-2,3,4,5,7,7a-hexahydroindol-6-ylidene]amino]-2-phenyl-ethanamine (159)

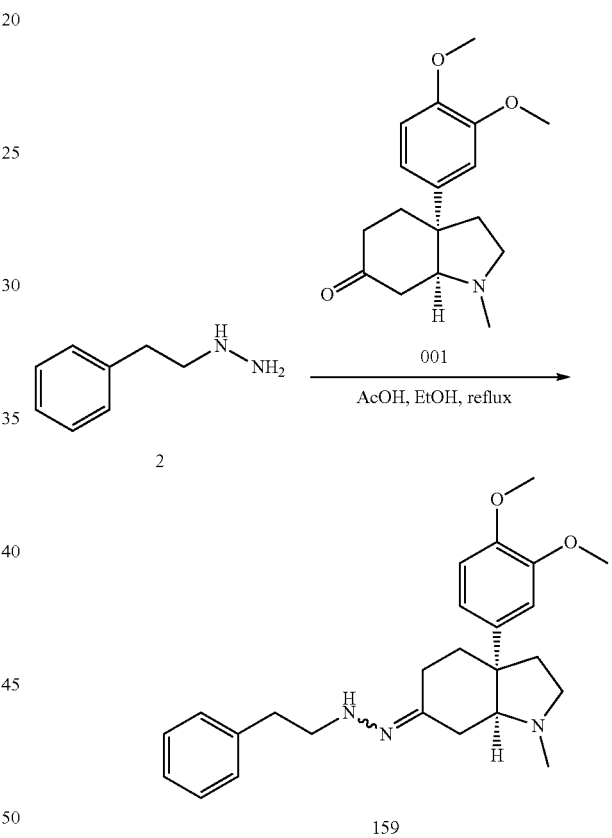

159

To a solution of 2-phenylethylhydrazine (358 mg, 2.07 mmol, HCl), (3aS,7aS)-3a-(3,4-dimethoxyphenyl)-1-methyl-2,3,4,5,7,7a-hexahydroindol-6-one (400 mg, 1.38 mmol) in EtOH (5 mL) was added AcOH (498 mg, 8.29 mmol, 474 uL). The mixture was stirred at 25° C. for 1 hour. On completion, the reaction mixture was concentrated in vacuo to give a residue. The residue was purified by prep-HPLC (column: Welch Ultimate XB—SiOH 250*50*10 um; mobile phase: [Hexane-EtOH (0.1% NH3·H2O)]; B %: 5%-35%, 20 min) to give the title compound (47.4 mg, 47% yield) as yellow gum.

LC-MS (ESI+) m/z 408.4 (M+H)⁺.

¹H NMR (400 MHz, CDCl₃) δ 7.30 (s, 1H), 7.25 (s, 1H), 7.23-7.08 (m, 3H), 6.94-6.73 (m, 3H), 3.88 (d, J=7.2 Hz, 6H), 3.52-3.41 (m, 1H), 3.39-3.27 (m, 1H), 3.22-3.03 (m,

1H), 2.92-2.74 (m, 3H), 2.56-2.28 (m, 4H), 2.16-1.89 (m, 4H), 1.69-1.49 (m, 3H), 1.36-1.20 (m, 2H).
Example 31
(2S)-5-[2-[(3aS,7aS)-3a-(3,4-dimethoxyphenyl)-1-methyl-2,3,4,5,7,7a-hexahydroindol-6-ylidene]hydrazino]-2-[[4-[(2-amino-4-hydroxy-pteridin-6-yl)methylamino]benzoyl]amino]-5-oxo-pentanoic acid (172)
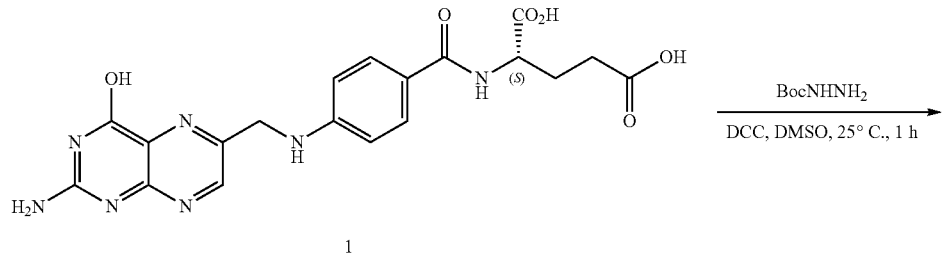
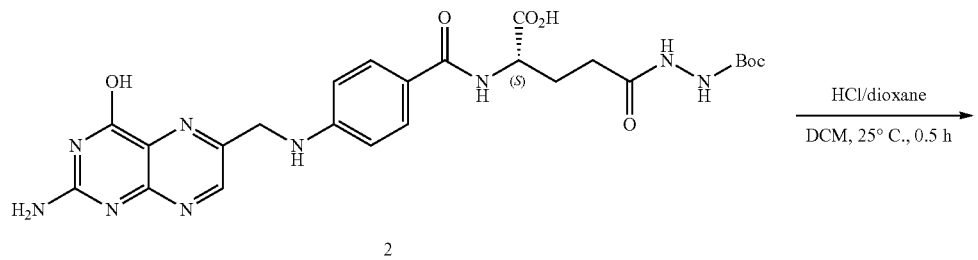
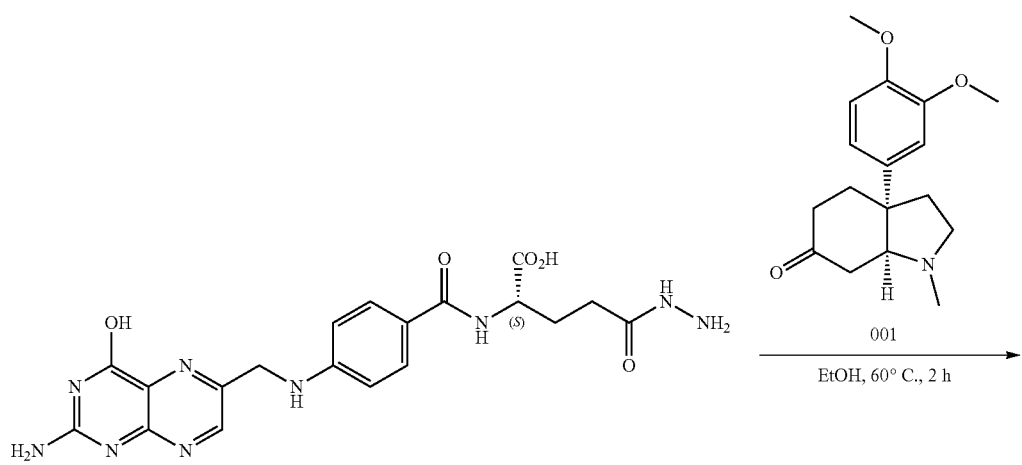

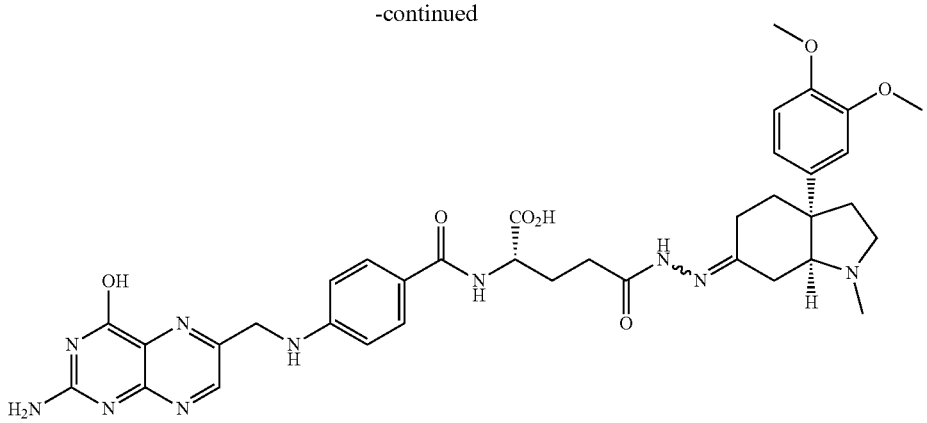

172

Step-1-(2S)-2-[[4-[(2-amino-4-hydroxy-pteridin-6-yl)methylamino]benzoyl]amino]-5-(2-tert-butoxy-carbonylhydrazino)-5-oxo-pentanoic acid (2)

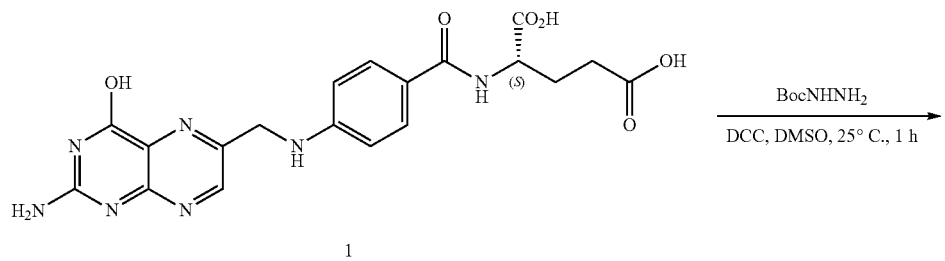

To a solution of (2S)-2-[[4-[(2-amino-4-hydroxy-pteridin-6-yl)methylamino]benzoyl]amino]pentanedioic acid (3.00 g, 6.80 mmol, CAS: 59-30-3) in DMSO (30 mL) was added DCC (1.40 g, 6.80 mmol) and tert-butyl N-aminocarbamate (898 mg, 6.80 mmol). The mixture was stirred at 25° C. for 1 hours. On completion, the mixture was filtered was residue was purified by reversed-phase HPLC (0.1% $NH_3H_2O$) to give (2S)-2-[[4-[(2-amino-4-hydroxy-pteridin-6-yl) methyl-amino]benzoyl]amino]-5-(2-tert-butoxycarbonylhydrazino)-5-oxo-pentanoic acid (610 mg, 977 umol, 15.51% yield, 96% purity) was obtained as a yellow solid.

LC-MS (ESI+) m/z 556.2 (M+H)$^+$, $^1$H NMR (400 MHz, DMSO-$d_6$) δ 9.51 (br s, 1H), 8.64 (s, 2H), 8.11-7.95 (m, 1H), 7.70-7.58(m, 2H), 7.09-6.87(m, 3H), 6.64 (br d, J=8.2 Hz, 2H), 4.48 (br d, J=5.4 Hz, 3H), 4.32-4.19 (m, 1H), 2.10-1.85 (m, 3H), 1.38 (br s, 9H).

Step—2-(2S)-2-[[4-[(2-amino-4-hydroxyl-pteridin-6-yl) methylamino]benzoyl] amino]-5-hydrazino-5-oxo-pentanoic acid (3)

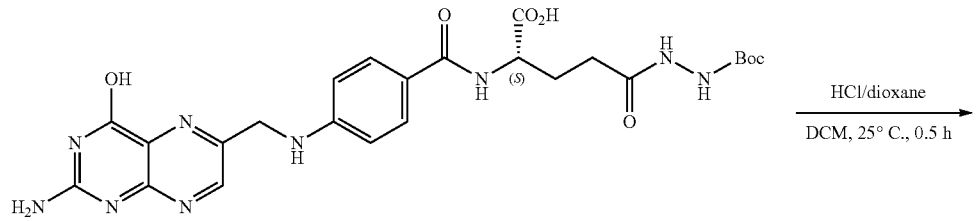

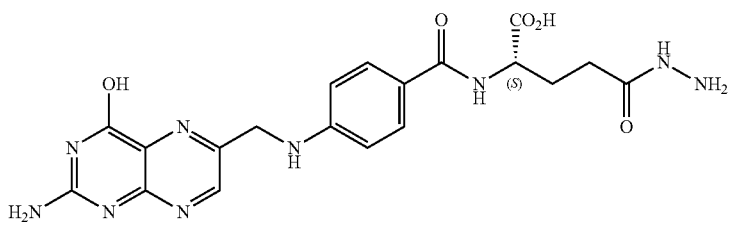

To a solution of (2S)-2-[[4-[(2-amino-4-hydroxyl-pteridin-6-yl) methylamino]benzoyl]amino]-5-(2-tert-butoxycarbonylhydrazino)-5-oxo-pentanoic acid (500 mg, 990.02 umol) in DCM (2 mL) was added HCl/dioxane (3 mL, 1 M). The mixture was stirred at 25° C. for 0.5 hours. On completion, the reaction mixture was concentrated in vacuo to give a residue. The crude product (2S)-2-[[4-[(2-amino-4-hydroxyl-pteridin-6-yl) methylamino]benzoyl]amino]-5-hydrazino-5-oxo-pentanoic acid (580 mg, 891.47 umol, 90.05% yield, 70% purity) was used into the next step without further purification.

3: LC-MS (ESI+) m/z 455.9 (M+H)$^+$,
$^1$H NMR (400 MHz, DMSO-$d_6$) δ 11.18-10.82 (m, 1H), 8.74 (s, 1H), 8.27-8.15 (m, 2H), 7.73-7.62 (m, 2H), 7.33 (s, 1H), 7.21 (s, 1H), 7.08 (s, 1H), 6.66 (d, J=8.2 Hz, 2H), 4.57 (s, 2H), 4.46-4.28 (m, 2H), 2.36-2.30 (m, 2H), 2.20-1.90 (m, 3H).

Step-3—(2S)-5-[2-[(3aS,7aS)-3a-(3,4-dimethoxyphenyl)-1-methyl-2,3,4,5,7,7a-hexahydroindol-6-ylidene]hydrazino]-2-[[4-[(2-amino-4-hydroxy-pteridin-6-yl)methylamino]benzoyl]amino]-5-oxo-pentanoic acid (172)

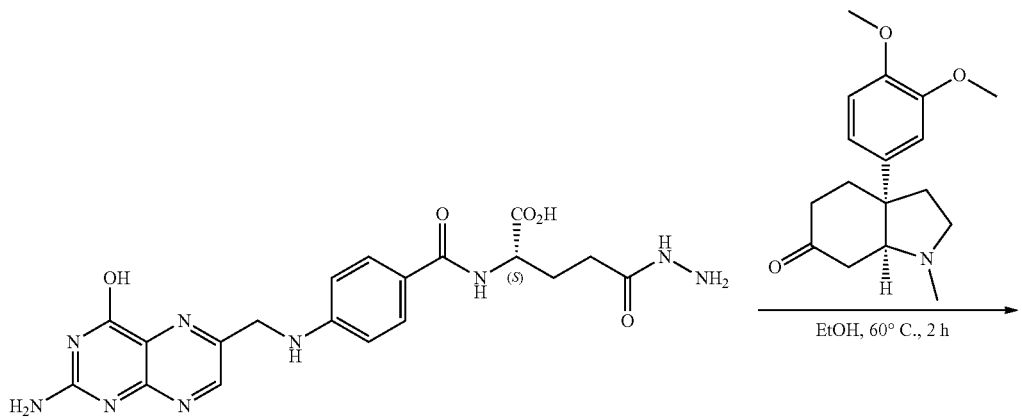

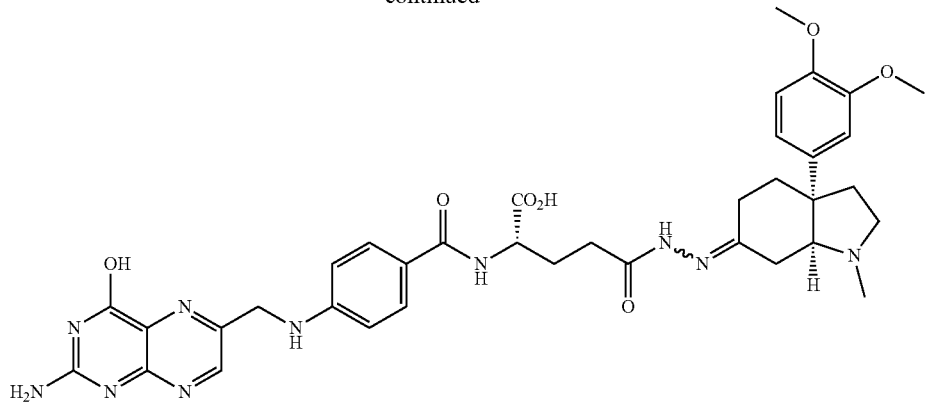

172

To a solution of (2S)-2-[[4-[(2-amino-4-hydroxyl-pteridin-6-yl)methylamino]benzoyl]amino]-5-hydrazino-5-oxo-pentanoic acid (307 mg, 674.09 umol) and (3aS, 7aS)-3a-(3,4-dimethoxyphenyl)-1-methyl-2,3,4,5,7,7a-hexahydroindol-6-one (234 mg, 808.91 umol) in EtOH (2 mL). The mixture was stirred at 60° C. for 2 hours. On completion, the mixture was filtered was residue. The crude product was triturated with THE (1 mL) at 25° C. for 12 h, to give (2S)-5-[2-[(3aS,7aS)-3a-(3,4-dimedioxyphenyl)-1-methyl-2,3,4,5,7,7a-hexahydroindol-6-ylidene]hydrazino]-2-[[4-[(2-amino-4-hydroxy-pteridin-6-yl) methylamino] benzoyl] amino]-5-oxo-pentanoic acid (260 mg, 48.19% yield, 90.81% purity). The crude product was triturated with ACN (1 mL) at 25° C. for 30 min and the crude product was triturated with EtOH 1 mL) at 65° C. for 1 h was obtained as a yellow solid (12.55 mg. 97.61% purity).

LC-MS (ESI+) m/z 727.3 (M+H)+, $^1$H NMR (400 MHz, DMSOd$_6$) δ 8.65 (s, 1H), 7.68-7.61 (m, 3H), 7.00-6.85 (m, 5H), 6.66-6.60 (m, 3H), 4.50-4.46 (m, 3H), 3.80-3.70 (m, 6H), 2.98-2.82 (m, 5H), 2.73(s, 1H), 2.31-2.27(m, 1H), 2.23-1.86 (m, 8H).

Example 32

10-[(2S,3S)-3-[(3'aS,4R)-3'a-(3,4-dimethoxyphenyl)-1'-methyl-spiro[1,3-dioxolane-2,6'-2,3,4,5,7,7a-hexahydroindole]-4-yl]-2,3-dihydroxy-propyl]-7,8-dimethyl-benzol[g]pteridine-2,4-dione (174) and 10-[(2S)-2-[(3'aS,4S,5R)-3'a-(3,4-dimethoxyphenyl)-5-(hydroxymethyl)-1'-methyl-spiro[1,3-dioxolane-2,6'-2,3,4,5,7,7a-hexahydroindole]-4-yl]-2-hydroxy-ethyl]-7,8-dimethyl-benzo[g]pteridine-2,4-dione (196)

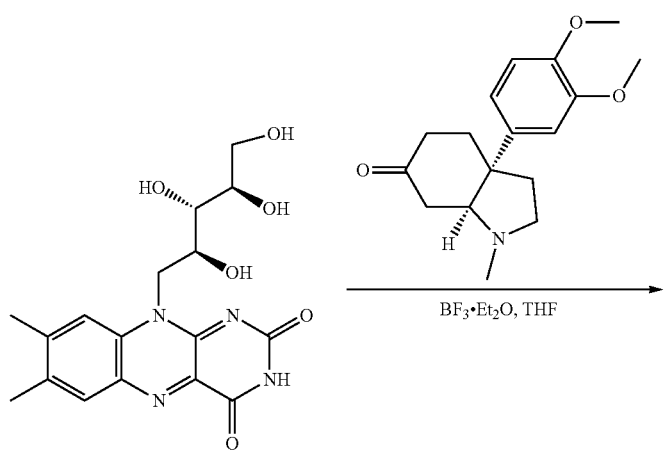

1

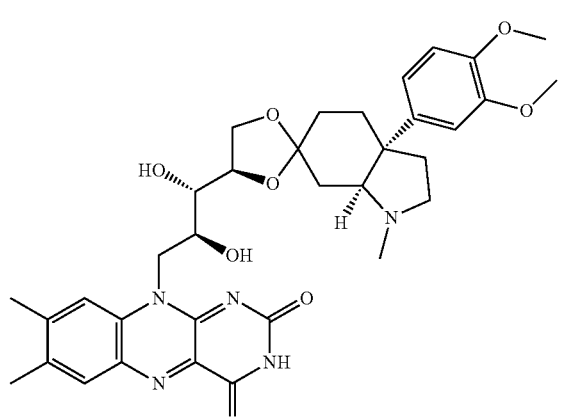

174

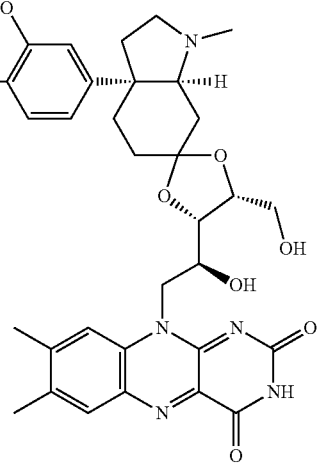

196

To a solution of 7,8-dimethyl-10-[(2S,3S,4R)-2,3,4,5-tetrahydroxypentyl]benzo[g]pteridine-2,4-dione (2.60 g, 6.91 mmol,) in THF (10 mL) was added BF3.Et2O (981 mg, 6.91 mmol,) and 4 A MS (6.91 mmol) at 25° C. Then the mixture was added (3aS,7aS)-3a-(3,4-dimethoxyphenyl)-1-methyl-2,3,4,5,7,7a-hexahydroindol-6-one (1.00 g, 3.46 mmol). The mixture was stirred at 75° C. for 48 hours. The mixture was poured to the NaHCO$_3$ solution (50 ml) and extracted with ethyl acetate (300 mL). The organic layers was dried by sodium sulfate, filtered and concentrated in vacuo to give the residue. The residue was purified by column: Phenomenex Luna C$_{18}$ $_{200*40}$ mm*10 um; mobile phase: [water(TFA)-ACN]; B %: 10%-40%, 10 min to give the 10-[(2S,3S)-3-[(3'aS,4R,7'aS)-3'a-(3,4-dimethoxyphenyl)-1'-methyl-spiro[1,3-dioxolane-2,6'-2,3,4,5,7,7a-hexahydroindole]-4-yl]-2,3-dihydroxy-propyl]-7,8-dimethyl-benzo[g]pteridine-2,4-dione (210 mg, 35% yield) was obtained as a red solid.

10-[(2S,3S)-3-[(3'aS,4R,7'aS)-3'a-(3,4-dimethoxyphenyl)-1'-methyl-spiro[1,3-dioxolane-2,6'-2,3,4,5,7,7a-hexahydroindole]-4-yl]-2,3-dihydroxy-propyl]-7,8-dimethyl-benzo[g]pteridine-2,4-dione was separated by SFC (column: DAICEL CHIRALPAK IE(250 mm*30 mm,10 um); mobile phase: [Neu-ETOH]; B %: 20%-20%, C$_{20;\ 80}$ min) to give the peak 1 and peak 2. The peak1 was purified by prep-HPLC (column: Welch Xtimate C$_{18}$ $_{150*25}$ mm*5 um; mobile phase: [water(TFA)-ACN]; B %: 10%-40%, 10 min) to give the 10-[(2S,3S)-3-[(3'aS,4R)-3'a-(3,4-dimethoxyphenyl)-1'-methyl-spiro[1,3-dioxolane-2,6'-2,3,4,5,7,7a-hexahydroindole]-4-yl]-2,3-dihydroxy-propyl]-7,8-dimethyl-benzo[g]pteridine-2,4-dione (10.9 mg, 5% yield) was obtained as a orange solid The peak2 was (1aR,3aR,6aS,6bR)-6a-(3,4-dimethoxyphenyl)-4-methyl-1a,3,3a,5,6,6b-hexahydrooxireno[2,3-e]indol-2-one (66.2 mg, 29% yield) obtained as an orange solid.

174: LC-MS (ESI$^+$) m/z 648.2 (M+H)$^+$; $^1$H NMR (400 MHz, METHANOL-d$_4$) δ=8.01 (s, 1H), 7.98 (s, 1H), 7.02 (s, 1H), 7.00 (s, 2H), 5.00-5.00 (m, 1H), 5.13-4.98 (m, 1H), 4.98-4.94 (m, 1H), 4.55 (d, J=6.0Hz, 1H), 4.45 (d, J=4.4 Hz, 1H), 4.29-4.21 (m, 2H), 4.21-4.15 (m, 2H), 3.96-3.89 (m, 1H), 3.87 (d, J=8.4 Hz, 6H), 3.43-3.35 (m, 2H), 3.19 (s, 3H), 2.61 (s, 3H), 2.51 (s, 3H), 2.48 (s, 2H), 2.36-2.22 (m, 2H), 2.17-2.10 (m, 1H), 2.06-1.95 (m, 1H), 1.80-1.71 (m, 1H), 1.65-1.57 (m, 1H), 1.81-1.56 (m, 1H)

196: LC-MS (ESI$^+$) m/z 648.1 (M+H)$^±$; $^1$H NMR (400 MHz, METHANOL-d$_4$) δ=7.91 (s, 1H), 7.84 (s, 1H), 7.00-6.95 (m, 1H), 7.00-6.95 (m, 1H), 6.95-6.84 (m, 1H), 6.94-6.81 (m, 1H), 5.31-5.03 (m, 1H), 4.78 (d, J=12.0 Hz, 1H), 4.39-4.29 (m, 2H), 4.28-4.14 (m, 1H), 4.13-4.04 (m, 1H), 3.81-3.81 (m, 1H), 3.86-3.81 (m, 2H), 3.79 (d, J=7.6 Hz, 6H), 3.19 (s, 1H), 2.99 (d, J=6.4 Hz, 1H), 2.44-2.38 (m, 6H), 2.31 (s, 3H), 2.25-2.18 (m, 1H), 2.18-2.05 (m, 3H), 2.05-1.95 (m, 2H), 1.88 (s, 1H), 1.79 (d, J=14.0 Hz, 1H), 1.69-1.59 (m, 1H), 1.58-1.58 (m, 1H), 1.56-1.44 (m, 1H), 1.57-1.44 (m, 1H), 1.42 (d, J=2.8 Hz, 1H), 1.29 (s, 2H).

Example 33

3a-(3,4-dimethoxyphenyl)-6,6-dimethoxy-1-methyl-2,3,4,5,7,7a-hexahydroindole (190)

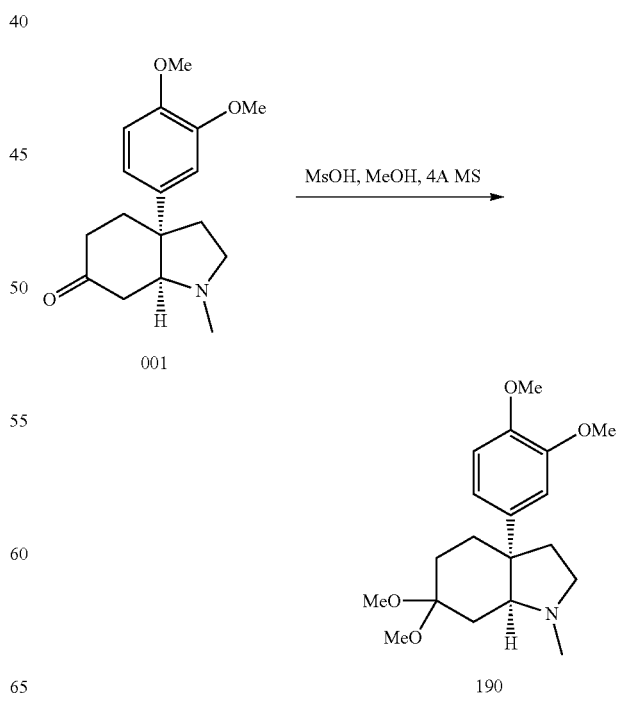

A mixture of (3aS,7aS)-3a-(3,4-dimethoxyphenyl)-1-methyl-2,3,4,5,7,7a-hexahydroindol-6-one (200 mg, 691 umol), 4 A MS (30 mg), BF₃.Et₂O (196 mg, 1.38 mmol, 170 uL) in MeOH (2.0 mL) was degassed and purged with N₂ for 3 times, and then the mixture was stirred at 25° C. for 2 hours under N₂ atmosphere. On completion, the reaction mixture was quenched by adding it to a cold saturated sodium bicarbonate solution till pH=8. The aqueous layer was extracted with ethyl acetate (50 mL). The organic layer was separated, dried over anhydrous Na₂SO₄, filtered and concentrated under reduced pressure to give the residue. The residue was purified by prep-HPLC (neutral condition: column: Phenomenex C₁₈ ₁₅₀*₂₅ mm*10 um; mobile phase: [water(NH₄HCO₃)-ACN]; B %: 10%-40%, 8 min) to give (3aS,7aS)-3a-(3,4-dimethoxyphenyl)-6,6-dimethoxy-1-methyl-2,3,4,5,7,7a-hexahydroindole (43.1 mg, 18% yield) as a colorless oil.

LC-MS (ESI⁺) m/z 336.0 (M+H)⁺

¹H NMR (400 MHz, CDCl₃) δ 6.92 (s, 2H), 6.83 (d, J=8.0 Hz, 1H), 3.90 (d, J=9.6 Hz, 6H), 3.25 (s, 3H), 3.20 (s, 3H), 3.14-3.01 (m, 1H), 2.92 (d, J=5.6 Hz, 1H), 2.39 (s, 4H), 2.14-1.97 (m, 4H), 1.96-1.83 (m, 2H), 1.80-1.72 (m, 1H), 1.54-1.41 (m, 1H).

Example 34

[[(3aS,7aS)-3a-(3,4-dimethoxyphenyl)-1-methyl-2,3,4,5,7,7a-hexahydroindol-6-ylidene]amino]urea (197)

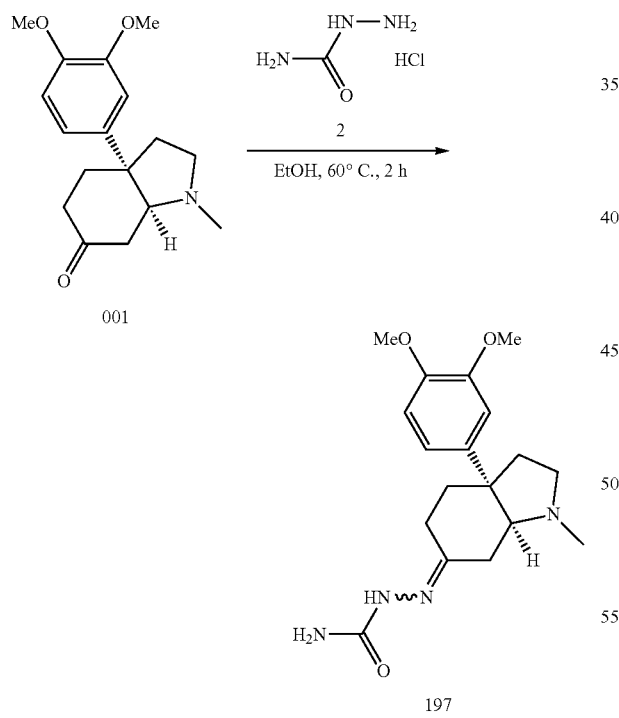

To a solution of (3aS,7aS)-3a-(3,4-dimethoxyphenyl)-1-methyl-2,3,4,5,7,7a-hexahydroindol-6-one (200 mg, 691 umol, 001) in EtOH (1 mL) was added aminourea;hydrochloride (77.0 mg, 69 umol). The mixture was stirred at 60° C. for 2 hours. On completion, the reaction mixture was concentrated to give the crude. The crude product was triturated with (DCM:PE=5:1) at 25° C. for 30 mins to give [[(3aS, 7aS)-3a-(3,4-dimethoxyphenyl)-1-methyl-2,3,4,5,7,7a-hexahydroindol-6-ylidene] amino] urea (92.3 mg, 40% yield) as a yellow solid.

LC-MS (ESI+) m/z 347.2 (M+H)⁺,

¹H NMR (400 MHz, DMSO-d₆) δ=8.95 (s, 1H), 6.96-6.88 (m, 2H), 6.84-6.81 (m, 1H), 6.27-6.19 (m, 2H), 4.08(br s, 1H), 3.74(d, J=4.4 Hz, 6H), 3.58-3.48 (m, 1H), 3.01-2.85 (m, 5H), 2.25(br d, J=15.4 Hz, 4H), 2.00 (br d, J=10.0 Hz, 1H), 1.93-1.78 (m, 1H), 1.73-1.57 (m, 1H).

Example 35

N-1-[[(3aR)-3a-(3,4-dimethoxyphenyl)-1-methyl-2,3,4,5,7,7a-hexahydroindol-6-ylidene]amino]-3-phenyl-urea (198)

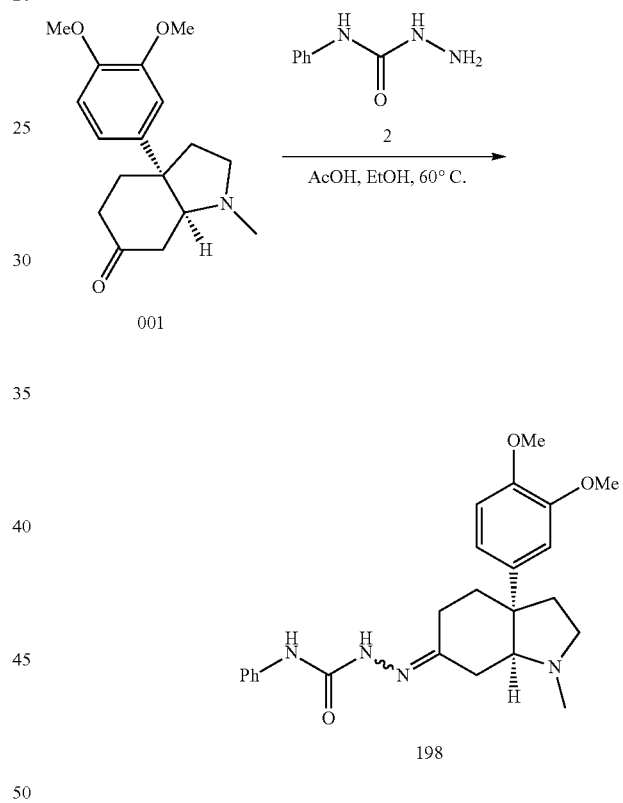

To a solution of (3aS)-3a-(3,4-dimethoxyphenyl)-1-methyl-2,3,4,5,7,7a-hexahydroindol-6-one (50.0 mg, 172 umol) and 1-amino-3-phenyl-urea (26.1 mg, 173 umol) in EtOH (2 mL) was added CH₃COOH (10.4 mg, 173 umol). The mixture was stirred at 60° C. for 12 hours. On completion, the reaction mixture was concentrated in vacuo to give 1-[[(3aR)-3a-(3,4-dimethoxyphenyl) methyl-2,3,4,5,7,7a-hexahydroindol-6-ylidene]amino]-3-phenyl-urea (38.1 mg, 95% yield) as a yellow solid.

LC-MS (ESI⁺) m/z 423.2 (M+H)⁺

¹H NMR (400 MHz, CDCl₃) δ=8.28-8.18 (m, 1H), 7.76-7.72 (m, 1H), 7.54 (s, 2H), 7.52-7.47 (m, 2H), 7.36-7.30 (m, 1H), 6.83 (d, J=2.4 Hz, 2H), 3.94-3.85 (m, 6H), 3.16-3.01 (m, 1H), 3.00-2.84 (m, 1H), 2.80-2.60 (m, 2H), 2.56-2.47 (m, 1H), 2.40 (d, J=12.8 Hz, 3H), 2.36-2.28 (m, 2H), 2.27-2.21 (m, 1H), 2.08 (s, 2H), 2.04-1.95 (m, 2H).

Example 36

(3aS)-N-tert-butoxy-3a-(3,4-dimethoxyphenyl)-1-methyl-2,3,4,5,7,7a-hexahydroindol-6-imine) (199)

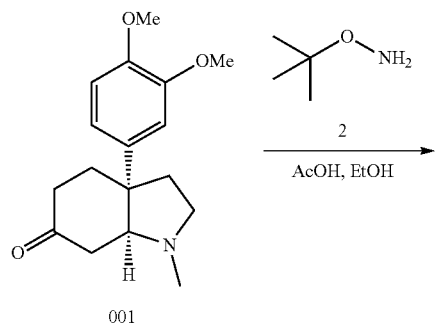

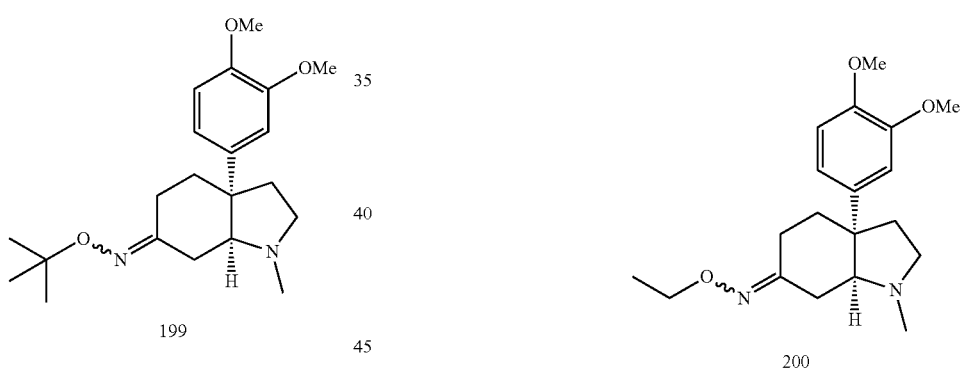

To a solution of (3aS,7aS)-3a-(3,4-dimethoxyphenyl)-1-methyl-2,3,4,5,7,7a-hexahydroindol-6-one (200 mg, 691 umol) in EtOH (2 mL) was added $CH_3COOH$ (4.15 mg, 69.1 umol,) and O-tert-butylhydroxylamine;hydrochloride (173 mg, 1.38 mmol). The mixture was stirred at 60° C. for 3 hours. On completion, the reaction mixture was concentrated in vacuo to give the residue. The residue was purified by prep-HPLC column: Phenomenex $C_{18\ 150*25}$ mm*10 um; mobile phase: [water($NH_4HCO_3$)-ACN]; B %: 44%-74%, 8 min) to give (3aS,7aS)-N-tert-butoxy-3a-(3,4-dimethoxyphenyl)-1-methyl-2,3,4,5,7,7a-hexahydroindol-6-imine (54 mg, 27% yield) as a yellow gum.

LC-MS (ESI$^+$) m/z 361.3 (M+H)$^+$ $^1$H NMR (400 MHz, $CDCl_3$) δ 6.87-6.70 (m, 3H), 5.20-5.05 (m, 1H), 3.86-3.76 (m, 6H), 3.75-3.38 (m, 2H), 3.07-2.73 (m, 2H), 2.68-2.41 (m, 3H), 2.31 (s, 3H), 2.23 (d, J=4.8 Hz, 2H), 2.16-1.97 (m, 3H), 1.94 (s, 1H), 1.89-1.80 (m, 1H), 1.78-1.60 (m, 2H), 1.51-1.45 (m, 2H), 1.30-1.15 (m, 1H).

Example 37

(3aS,7aS)-3a-(3,4-dimethoxyphenyl)-N-ethoxy-1-methyl-2,3,4,5,7,7a-hexahydroindol-6-imine (200)

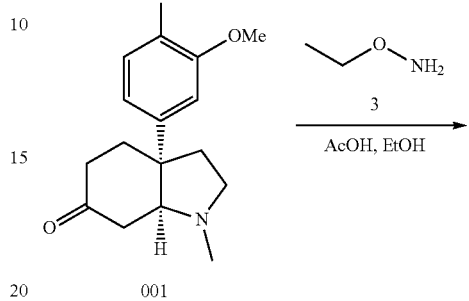

To a solution of (3aS,7aS)-3a-(3,4-dimethoxyphenyl)-1-methyl-2,3,4,5,7,7a-hexahydroindol-6-one (150 mg, 518. umol,) in EtOH (2 mL) was added $CH_3COOH$ (3.11 mg, 51.8 umol, 2.96 uL) and O-ethylhydroxylamine;hydrochloride (101 mg, 1.04 mmol). The mixture was stirred at 60° C. for 2 hours. On completion, the reaction mixture was concentrated in vacuo to give the residue. The residue was purified by prep-HPLC (column: Phenomenex $C_{18\ 150*25}$ mm*10 um; mobile phase: [water($NH_4HCO_3$)-ACN]; B %: 25%-55%, 8 min) to give (3aS,7aS)-3a-(3,4-dimethoxyphenyl)-N-ethoxy-1-methyl-2,3,4,5,7,7a-hexahydroindol-6-imine (119 mg, 77% yield) as a yellow oil.

LC-MS (ESI+) m/z 330. (M+H)+

$^1$H NMR (400 MHz, $CD_3OD$) δ=7.02-6.82 (m, 3H), 4.09-3.96 (m, 2H), 3.86-3.76 (m, 6H), 3.23-3.09 (m, 1H), 3.05-2.96 (m, 1H), 2.96-2.86 (m, 1H), 2.69-2.60 (m, 1H), 2.49-2.43 (m, 1H), 2.40-2.33 (m, 3H), 2.32-2.24 (m, 1H), 2.23-1.90 (m, 6H), 1.36-1.12 (m, 3H).

Example 38

2-[[(3aS,7aS)-3a-(3,4-dimethoxyphenyl)-1-methyl-2,3,4,5,7,7a-hexahydroindol-6-ylidene]amino]oxy-acetic acid (201)

Example 39 tert-butyl 2-[[(3aS,7aS)-3a-(3,4-dimethoyphenyl)-1-methyl-2,3,4,5,7,7a-hexahydroindol-6-ylidene]amino]oxyacetate (202)

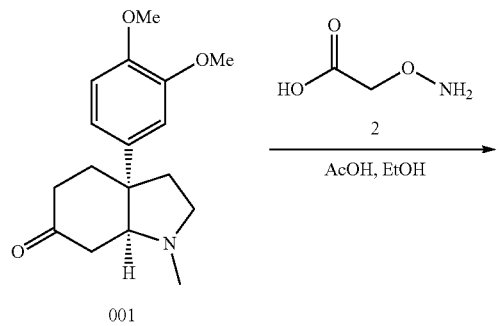

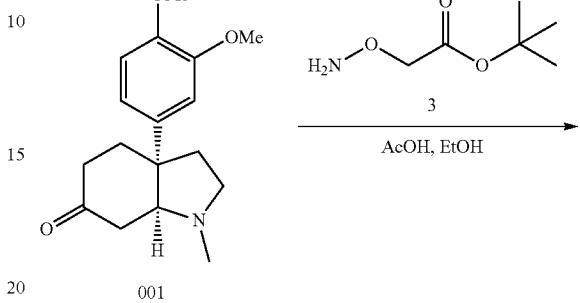

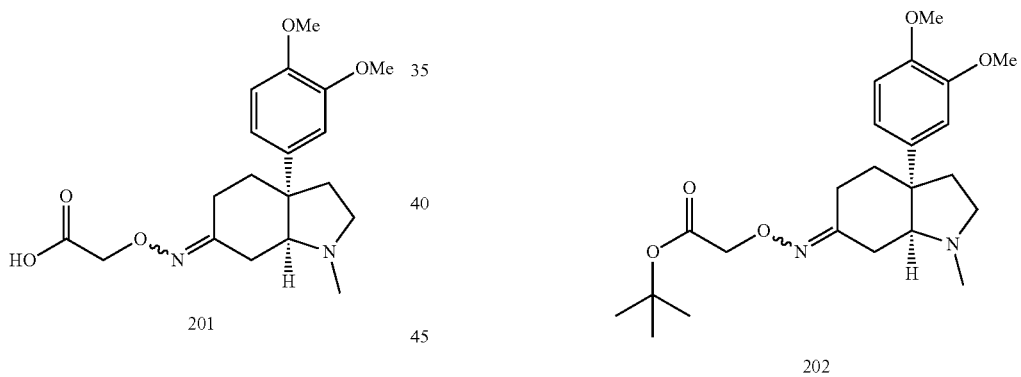

A mixture of (3aS,7aS)-3a-(3,4-dimethoxyphenyl)-1-methyl-2,3,4,5,7,7a-hexahydroindol-6-one (200 mg, 691 umol), 2-aminooxyacetic acid (176 mg, 1.38 mmol), AcOH (4.15 mg, 69.1 umol, 3.95 uL) in EtOH (2.0 mL) was degassed and purged with $N_2$ for 3 times, and then the mixture was stirred at 60° C. for 2 hours under $N_2$ atmosphere. On completion, the reaction mixture was concentrated in vacuo to give the residue. The residue was purified by prep-HPLC (neutral condition:column: Phenomenex Luna $C_{18}$ 150*25 mm*10 um; mobile phase: [water(NH$_4$HCO$_3$)-ACN]; B %: 7%-37%, 8 min) to give 2-[[(3aS,7aS)-3a-(3,4-dimethoxyphenyl)-1-methyl-2,3,4,5,7,7a-hexahydroindol-6-ylidene]amino]oxyacetic acid (44.57 mg, 21% yield) as a white solid.

LC-MS (ESI$^+$) m/z 363.0 (M+H)$^+$ $^1$H NMR (400 MHz, CDCl$_3$) δ 6.83-6.65 (m, 3H), 4.50-4.31 (m, 2H), 3.87-3.75 (m, 6H), 3.51-3.40 (m, 1H), 3.67-3.28 (m, 1H), 2.90-2.66 (m, 3H), 2.58 (s, 2H), 2.57-2.47 (m, 1H), 2.41-2.17 (m, 2H), 2.16-1.97 (m, 3H), 1.96-1.75 (m, 1H).

A mixture of (3aS,7aS)-3a-(3,4-dimethoxyphenyl)-1-methyl-2,3,4,5,7,7a-hexahydroindol-6-one (200 mg, 691 umol), tert-butyl 2-aminooxyacetate (203 mg, 1.38 mmol), AcOH (4.15 mg, 69.1 umol, 3.95 uL) in EtOH (2.0 mL) was degassed and purged with $N_2$ for 3 times, and then the mixture was stirred at 60° C. for 2 hours under $N_2$ atmosphere. On completion, the reaction mixture was concentrated in vacuo to give the residue. The residue was purified by prep-HPLC (neutral condition: column: Phenomenex $C_{18}$ 150*25 mm*10 um; mobile phase: [water(NH$_4$HCO$_3$)-ACN]; B %: 41%-71%, 8 min) to give tert-butyl 2-[[(3aS,7aS)-3a-(3,4-dimethoxyphenyl)-1-methyl-2,3,4,5,7,7a-hexahydroindol-6-ylidene]amino]oxyacetate (224 mg, 74% yield) as a yellow gum.

LC-MS (ESI$^+$) m/z 419.3 (M+H)$^+$ $^1$H NMR (400 MHz, CD$_3$OD) δ 7.07-6.88 (m, 3H), 4.45 (d, J=12.0 Hz, 2H), 3.92-3.75 (m, 6H), 3.20-2.88 (m, 2H), 2.68-2.45 (m, 2H), 2.41-2.36 (m, 3H), 2.36-2.16 (m, 3H), 2.15-1.95 (m, 4H), 1.49 (s, 9H).

Example 40

2-[[(3aS,7aS)-3a-(3,4-dimethoxyphenyl)-1-methyl-2,3,4,5,7,7a-hexahydroindol-6-ylidene]amino]oxyethanol (203)

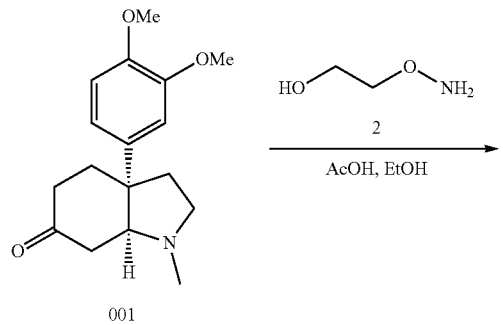

To a solution of (3aS,7aS)-3a-(3,4-dimethoxyphenyl)-1-methyl-2,3,4,5,7,7a-hexahydroindol-6-one (100 mg, 345 umol) in EtOH (1.0 mL) was added AcOH (2.08 mg, 34.5 umol, 1.98 uL) and 2-aminooxyethanol (53.3 mg, 691 umol). The mixture was stirred at 60° C. for 2 hours. The reaction mixture was concentrated in vacuo to give the residue. The residue was purified by prep-HPLC (column: Phenomenex $C_{18\ 150*25}$ mm*10 um; mobile phase: [water (NH$_4$HCO$_3$)-ACN]; B %: 12%-42%, 8 min) to give the 2-[[(3aS,7aS)-3a-(3,4-dimethoxyphenyl)-1-methyl-2,3, 4,5, 7,7a-hexahydroindol-6-ylidene]amino]oxyethanol (140 mg, 93% yield) as a yellow solid.

LC-MS (ESI$^+$) m/z 304.1 (M+H)$^+$.

$^1$H NMR (400 MHz, CDCl$_3$) δ 6.96-6.82 (m, 3H), 4.22-4.12 (m, 2H), 3.93-3.89 (m, 6H), 3.87-3.47 (m, 2H), 3.50-3.19 (m, 1H), 3.08 (br t, J=8.0 Hz, 1H), 2.88 (br d, J=12.6 Hz, 1H), 2.64-2.46 (m, 2H), 2.44-2.35 (m, 3H), 2.35-2.19 (m, 2H), 2.19-2.11 (m, 2H), 2.10-2.03 (m, 1H), 2.02-1.89 (m, 2H).

Example 41

–(E,3aS,7aS)-3a-(3,4-dimethoxyphenyl)-N-(1-methoxy-1-methyl-ethoxy)-1-methyl-2,3,4,5,7,7a-hexahydroindol-6-imine (204) and (Z,3aS,7aS)-3a-(3,4-dimethoxyphenyl)-N-(1-methoxy-1-methyl-ethoxy)-1-methyl-2,3,4,5,7,7a-hexahydroindol-6-imine (219)

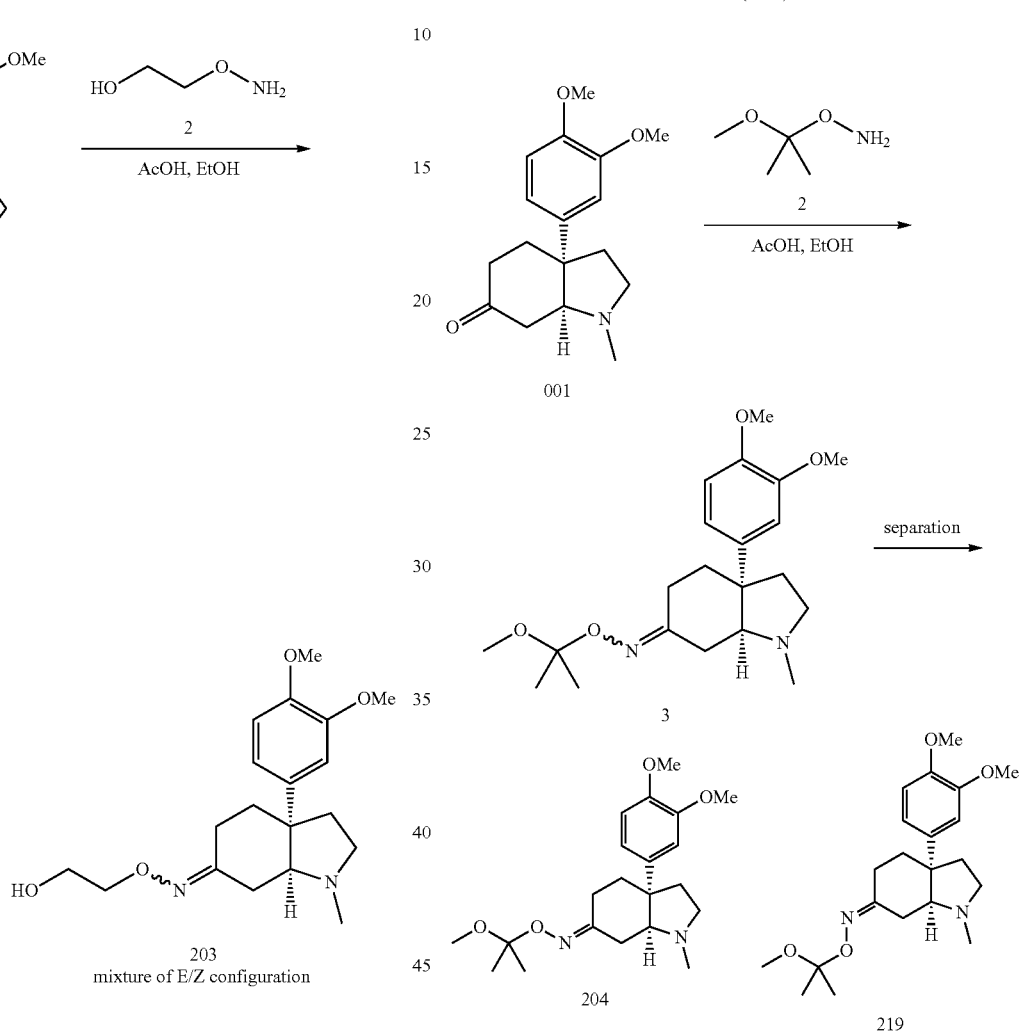

To a solution of (3aS,7aS)-3a-(3,4-dimethoxyphenyl)-1-methyl-2,3,4,5,7,7a-hexahydroindol-6-one (200 mg, 691 umol) in EtOH (1.0 mL) was added AcOH (4.15 mg, 69.1 umol, 3.95 uL) and O-(1-methoxy-1-methyl-ethyl)hydroxylamine (145 mg, 1.38 mmol). The mixture was stirred at 60° C. for 2 hours. The reaction mixture was concentrated in vacuo to give the (3aS,7aS)-3a-(3,4-dimethoxyphenyl)-N-(1-methoxy-1-methyl-ethoxy)-1-methyl-2,3,4,5,7,7a-hexahydroindol-6-imine (200 mg, 50% yield) as a yellow oil.

LC-MS (ESI$^+$) m/z 377.2 (M+H)$^+$.

The (3aR,7aS)-3a-(3-cyclopropyl-4,5-dimethoxy-phenyl)-1-methyl-2,3,7,7a-tetrahydroindol one was purified by prep-HPLC (column: Welch Xtimate $C_{18\ 150*25}$ mm*5 um; mobile phase: [water(NH3H2O)-ACN]; B %: 35%-65%, 8 min) to give the (E,3aS,7aS)-3a-(3,4-dimethoxyphenyl)-N-(1-methoxy-1-methyl-ethoxy)-1-methyl-2,3,4,5,7,7a-hexahydroindol-6-imine (134 mg, 66% yield) as a colorless oil and(Z,3aS,7aS)-3a-(3,4-dimethoxyphenyl)-N-(1-methoxy- 1-methyl-ethoxy)-1-methyl-2,3,4,5,7,7a-hexahydroindol-6-imine (34.0 mg, 16% yield) as a yellow oil.

204

LC-MS (ESI+) m/z 337.2 (M+H)+.

1H NMR (400 MHz, CDCl₃) δ 6.90-6.83 (m, 2H), 6.82-6.78 (m, 1H), 3.89 (d, J=12 Hz, 6H), 3.17 (s, 3H), 3.07 (br d, J=1.6 Hz, 1H), 2.97-2.83 (m, 1H), 2.80-2.66 (m, 1H), 2.65-2.53 (m, 1H), 2.52-2.47 (m, 1H), 2.46-2.37 (m, 3H), 2.34-2.26 (m, 1H), 2.24-2.01 (m, 4H), 1.98-1.87 (m, 1H), 1.47 (s, 3H), 1.40 (s, 3H).

219

LC-MS (ESI+) m/z 337.2 (M+H)+.

1H NMR (400 MHz, CDCl₃) δ 6.97-6.88 (m, 2H), 6.87-6.82 (m, 1H), 3.90 (br d, J=7.4 Hz, 6H), 3.43 (br d, J=16 Hz, 1H), 3.24 (s, 3H), 3.21-3.14 (m, 1H), 2.88-2.74 (m, 1H), 2.47-2.40 (m, 1H), 2.36 (s, 3H), 2.33-2.24 (m, 1H), 2.19-1.94 (m, 6H), 1.47 (br d, J=4.4 Hz, 6H)

Example 42

(3aS,7aS)-N-(cyclopropylmethoxy)-3a-(3,4-dimethoxyphenyl)-1-methyl-2,3,4,5,7,7a-hexahydroindol-6-imine (205)

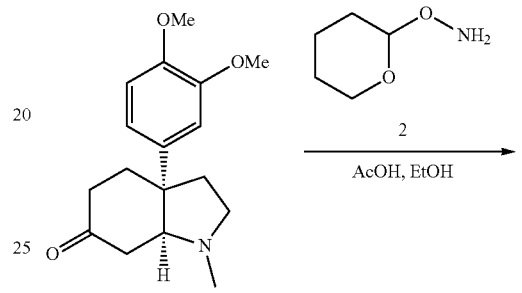

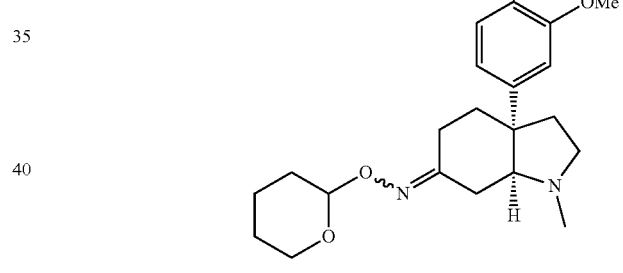

A mixture of (3aS,7aS)-3a-(3,4-dimethoxyphenyl)-1-methyl-2,3,4,5,7,7a-hexahydroindol-6-one (100 mg, 345 umol), O-(cyclopropylmethyl)hydroxylamine (85.4 mg, 691 umol), AcOH (2.08 mg, 34.5 umol) in EtOH (1 mL) was degassed and purged with N₂ for 3 times, and then the mixture was stirred at 60° C. for 1 hours under N2 atmosphere. On completion, the reaction mixture was concentrated in vacuo to give the residue. The residue was purified by prep-HPLC (column: Phenomenex C₁₈ ₁₅₀*₂₅ mm*10 um; mobile phase: [water(NH₄HCO₃)-ACN]; B %: 34%-64%, 8 min)) to give (3aS,7aS)-N-(cyclopropylmethoxy)-3a-(3,4-dimethoxyphenyl)-1-methyl-2,3,4,5,7,7a-hexahydroindol-6-imine (20 mg, 20% yield) as a yellow oil.

LC-MS (ESI⁺) m/z 358.2 (M+H)⁺

¹H NMR (400 MHz, CDCl₃) δ=7.04-6.78 (m, 3H), 3.95-3.83 (m, 8H), 3.52-3.00 (m, 1H), 2.91-2.75 (m, 1H), 2.43-2.24 (m, 6H), 2.20-2.17 (m, 2H), 2.17-2.03 (m, 2H), 2.00-1.88 (m, 2H), 1.24-1.00 (m, 1H), 0.67-0.45 (m, 2H), 0.38-0.14 (m, 2H).

Example 43

(3aS,7aS)-3a-(3,4-dimethoxyphenyl)-1-methyl-N-tetrahydropyran-2-yloxy-2,3,4,5,7,7a-hexahydroindol-6-imine (206)

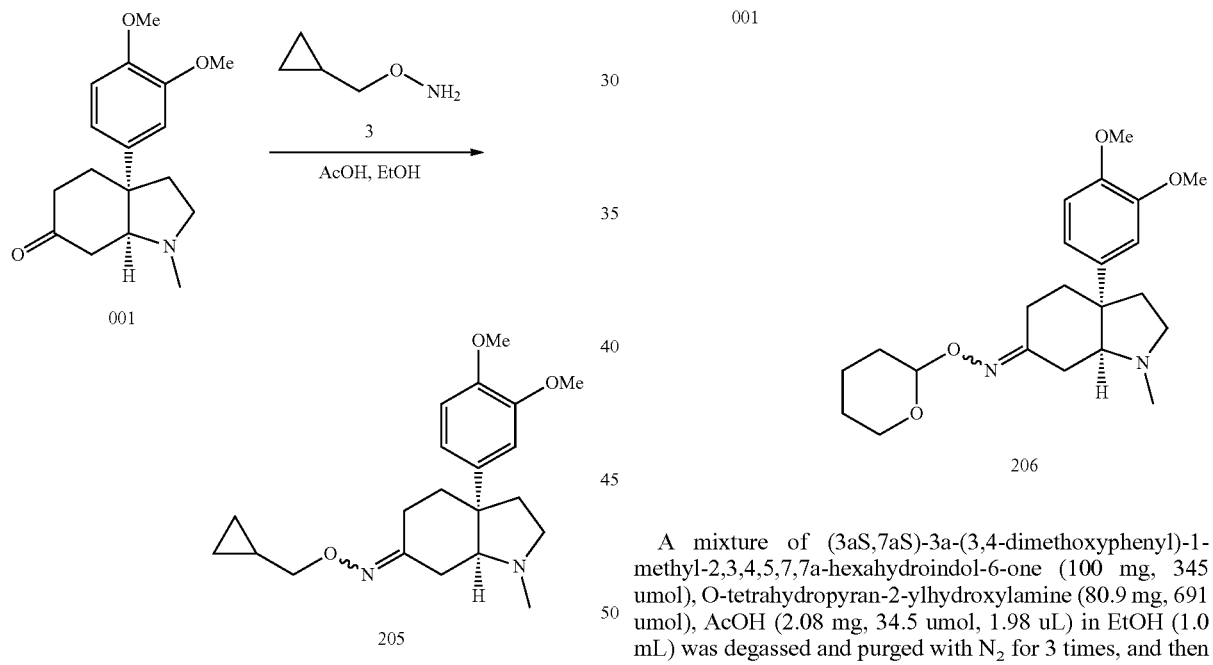

A mixture of (3aS,7aS)-3a-(3,4-dimethoxyphenyl)-1-methyl-2,3,4,5,7,7a-hexahydroindol-6-one (100 mg, 345 umol), O-tetrahydropyran-2-ylhydroxylamine (80.9 mg, 691 umol), AcOH (2.08 mg, 34.5 umol, 1.98 uL) in EtOH (1.0 mL) was degassed and purged with N₂ for 3 times, and then the mixture was stirred at 60° C. for 2 hours under N₂ atmosphere. On completion, the reaction mixture was concentrated in vacuo to give the residue. The residue was purified by prep-HPLC (column: Welch Xtimate C₁₈ ₁₅₀*₂₅ mm*5 um; mobile phase: [water (ammonia hydroxide v/v)-ACN]; B %: 34%-64%, 2 min) to give (3aS,7aS)-3a-(3,4-dimethoxyphenyl)-1-methyl-N-tetrahydropyran-2-yloxy-2,3,4,5,7,7a-hexahydroindol-6-imine (66.4 mg, 54% yield) as a colorless gum.

LC-MS (ESI⁺) m/z 389.2 (M+H)⁺

¹H NMR (400 MHz, CDCl₃) δ 6.87-6.70 (m, 3H), 5.20-5.05 (m, 1H), 3.86-3.76 (m, 6H), 3.75-3.38 (m, 2H), 3.07-2.73 (m, 2H), 2.68-2.41 (m, 3H), 2.31 (s, 3H), 2.23 (d, J=5.0 Hz, 2H), 2.16-1.97 (m, 3H), 1.94 (s, 1H), 1.89-1.80 (m, 1H), 1.78-1.60 (m, 2H), 1.51-1.45 (m, 2H), 1.30-1.15 (m, 1H).

Example 44

(3aS,7aS)-3a-(3,4-dimethoxyphenyl)-1-methyl-N-phenoxy-2,3,4,5,7,7a-hexahydroindol-6-imine (207)

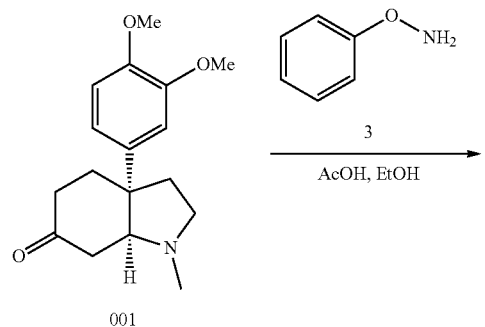

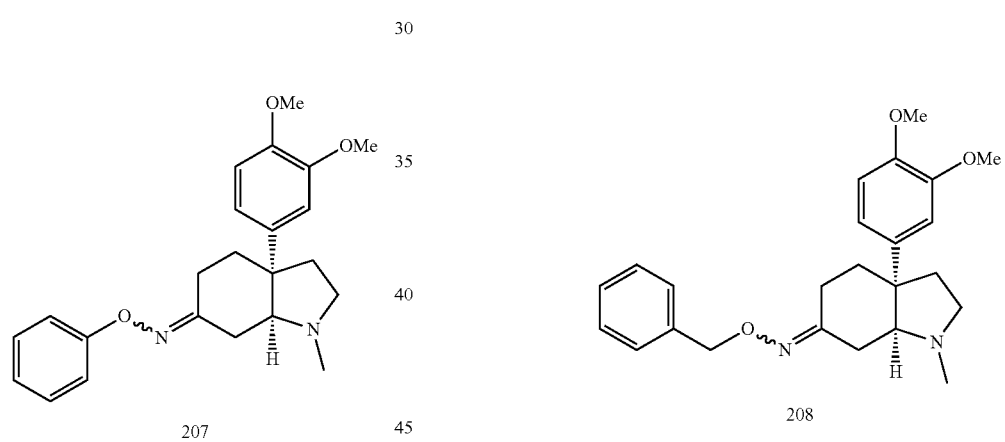

A mixture of (3aS,7aS)-3a-(3,4-dimethoxyphenyl)-1-methyl-2,3,4,5,7,7a-hexahydroindol-6-one (200 mg, 691 umol), O-phenylhydroxylamine; hydrochloride (201 mg, 1.38 mmol) in EtOH (2 mL) was added AcOH (4.15 mg, 69.1 umol), and then the mixture was stirred at 60° C. for 2 hours under $N_2$ atmosphere. On completion, the reaction mixture was concentrated in vacuo to give the residue. The residue was purified by prep-HPLC (column: Phenomenex $C_{18}$ 150*25 mm*10 um; mobile phase: [water(NH4HCO3)-ACN]; B %: 45%-75%, 8 min) to give (3aS,7aS)-3a-(3,4-dimethoxyphenyl)-1-methyl-N-phenoxy-2,3,4,5,7,7a-hexahydroindol-6-imine (30 mg, 14% yield) as a white oil.

LC-MS (ESI$^+$) m/z 381.2 (M+H)$^+$ $^1$H NMR (400 MHz, CDCl$_3$) δ=7.35-7.28 (m, 2H), 7.22-7.12 (m, 2H), 7.04-6.95 (m, 1H), 6.94-6.89 (m, 1H), 6.88 (d, J=1.6 Hz, 1H), 6.86-6.82 (m, 1H), 4.05-3.79 (m, 6H), 3.29-3.05 (m, 1H), 2.90 (br d, J=12.8 Hz, 1H), 2.83-2.62 (m, 2H), 2.59-2.37 (m, 4H), 2.36-2.16 (m, 3H), 2.09-1.93 (m, 3H).

Example 45

(3aS,7aS)-N-benzyloxy-3a-(3,4-dimethoxyphenyl)-1-methyl-2,3,4,5,7,7a-hexahydroindol-6-imine (208)

A mixture of (3aS,7aS)-3a-(3,4-dimethoxyphenyl)-1-methyl-2,3,4,5,7,7a-hexahydroindol-6-one (200 mg, 691 umol), O-benzylhydroxylamine (85.1 mg, 533 umol), AcOH (4.15 mg, 69.1 umol, 3.95 uL), in EtOH (1 mL) was degassed and purged with N2 for 3 times, and then the mixture was stirred at 60° C. for 2 hr under $N_2$ atmosphere. On completion, the reaction mixture was concentrated in vacuo to give the residue. The residue was purified by prep-HPLC (column: Welch Xtimate $C_{18}$ 150*25 mm*5 um; mobile phase: [water(NH3H2O)-ACN]; B %: 45%-75%, 8 min) to (3aS,7aS)-N-benzyloxy-3a-(3,4-dimethoxyphenyl)-1-methyl-2,3,4,5,7,7a-hexahydroindol-6-imine (40 mg, 19% yield) as a white oil.

LC-MS (ESI$^+$) m/z 395.2 (M+H)$^+$ $^1$H NMR (400 MHz, CDCl$_3$) δ=7.31-7.25 (m, 2H), 7.22-7.17 (m, 3H), 6.96-6.63 (m, 3H), 5.18-4.71 (m, 2H), 3.98-3.68 (m, 6H), 3.22-2.88 (m, 1H), 2.85-2.64 (m, 1H), 2.61-2.40 (m, 3H), 2.29 (s, 3H), 2.24-2.15 (m, 2H), 2.11-2.04 (m, 2H), 1.94-1.76 (m, 2H).

Example 46

(3aS,7aS)-3a-(3,4-dimethoxyphenyl)-N-ethoxy-1-methyl-2,3,4,5,7,7a-hexahydroindol-6-imine (209)

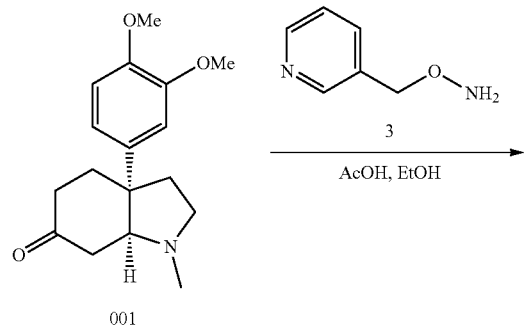

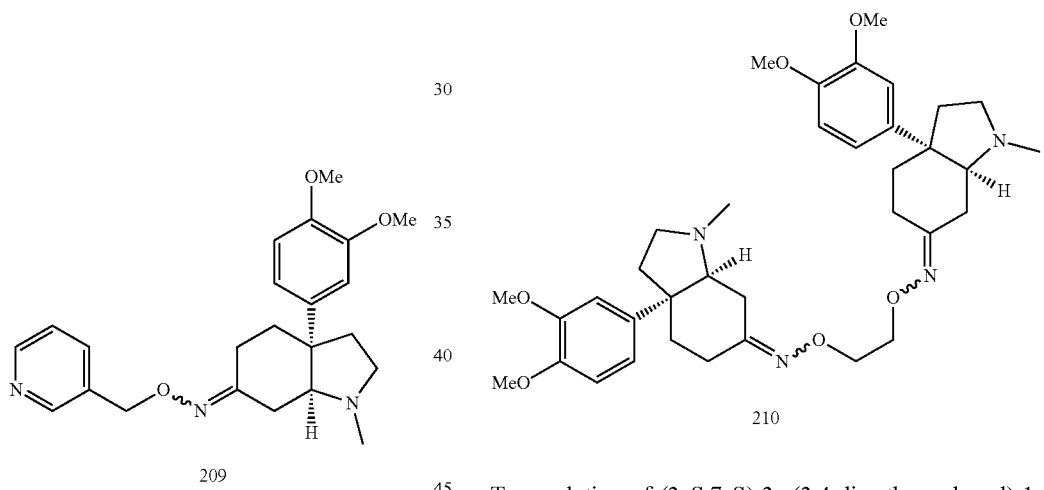

To a solution of (3aS,7aS)-3a-(3,4-dimethoxyphenyl)-1-methyl-2,3,4,5,7,7a-hexahydroindol-6-one (150 mg, 518 umol) in EtOH (1 mL) was added $CH_3COOH$ (3.11 mg, 51.8 umol) and O-(3-pyridylmethyl)hydroxylamine (96.5 mg, 777 umol). The mixture was stirred at 60° C. for 2 hours. On completion, the reaction mixture was concentrated in vacuo to give the residue. The residue was purified by prep-HPLC (column: Phenomenex $C_{18\ 150*25}$ mm*10 um; mobile phase: [water (NH$_4$HCO$_3$)-ACN]; B %: 22%-52%, 8 min) to give (3aS)-3a-(3,4-dimethoxyphenyl)-1-methyl-N-(3-pyridylmethoxy)-2,3,4,5,7,7a-hexahydroindol-6-imine (99 mg 66% yield) as a yellow oil.

LC-MS (ESI+) m/z 396.1 (M+H)+

1H NMR (400 MHz, METHANOL-d4) δ=8.53-8.44 (m, 1H), 7.94-7.72 (m, 1H), 7.51-7.31 (m, 1H), 7.02-6.83 (m, 3H), 5.23-4.98 (m, 2H), 3.89-3.75 (m, 6H), 3.00 (d, J=2.0 Hz, 1H), 2.91 (d, J=5.2 Hz, 1H), 2.70-2.59 (m, 1H), 2.58-2.41 (m, 2H), 2.40-2.32 (m, 3H), 2.32-2.23 (m, 1H), 1.97 (d, J=6.8 Hz, 5H)

Example 47

(3aS,7aS)-N-[2-[[(3aS,7aS)-3a-(3,4-dimethoxyphenyl)-1-methyl-2,3,4,5,7,7a-hexahydroindol-6-ylidene]amino]oxyethoxy]-3a-(3,4-dimethoxyphenyl)-1-methyl-2,3,4,5,7,7a-hexahydroindol-6-imine (210)

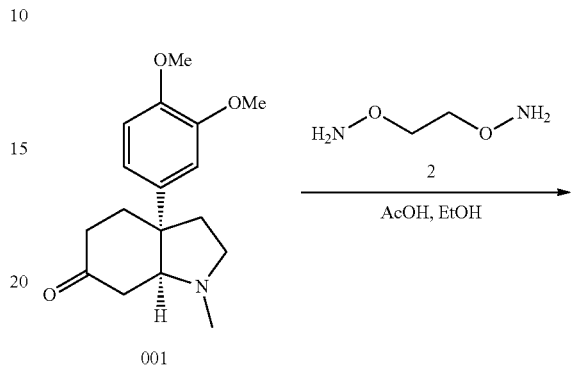

To a solution of (3aS,7aS)-3a-(3,4-dimethoxyphenyl)-1-methyl-2,3,4,5,7,7a-hexahydroindol-6-one (105 mg, 363 umol) in EtOH (1.0 mL) was added 2-azaniumyloxyethoxyammonium; dichloride (30.0 mg, 181 umol). The mixture was stirred at 60° C. for 2 hours. The reaction mixture was concentrated in vacuo to give the residue. The residue was purified by prep-HPLC (column: Waters xbridge 150*25 mm 10 um; mobile phase: [water (NH4HCO3)-ACN]; B %: 38%-68%,8 min) to give the (3aS,7aS)-N-[2-[[(3aS,7aS)-3a-(3,4-dimethoxyphenyl)-1-methyl-2,3,4,5,7,7a-hexahydroindol-6-ylidene]amino]oxyethoxy]-3a-(3,4-dimethoxyphenyl)-1-methyl-2,3,4,5,7,7a-hexahydroindol-6-imine (89.3 mg., 88% yield) as a white solid.

LC-MS (ESI$^+$) m/z 635.4 (M+H)$^+$.

$^1$H NMR (400 MHz, CDCl$_3$) δ 6.86-6.72 (m, 6H), 4.20-4.11 (m, 4H), 3.85-3.77 (m, 12H), 3.39-3.26 (m, 1H), 3.15-3.04 (m, 1H), 2.97 (br t, J=8.0 Hz, 1H), 2.79-2.65 (m, 2H), 2.53-2.39 (m, 4H), 2.30-2.26 (m, 4H), 2.25-2.16 (m, 4H), 2.15-2.10 (m, 1H), 2.09-2.01 (m, 3H), 2.00-1.93 (m, 3H), 1.92-1.85 (m, 3H), 1.84-1.74 (m, 2H), 1.55-1.55 (m, 1H).

Example 48

3'aS,7'aS)-3'a-(3,4-dimethoxyphenyl)-1',4-dimethyl-spiro[1,3-dioxolane-2,6'-2,3,4,5,7,7a -hexahydroindole] (211)

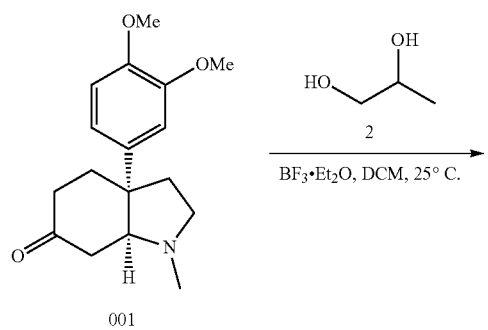

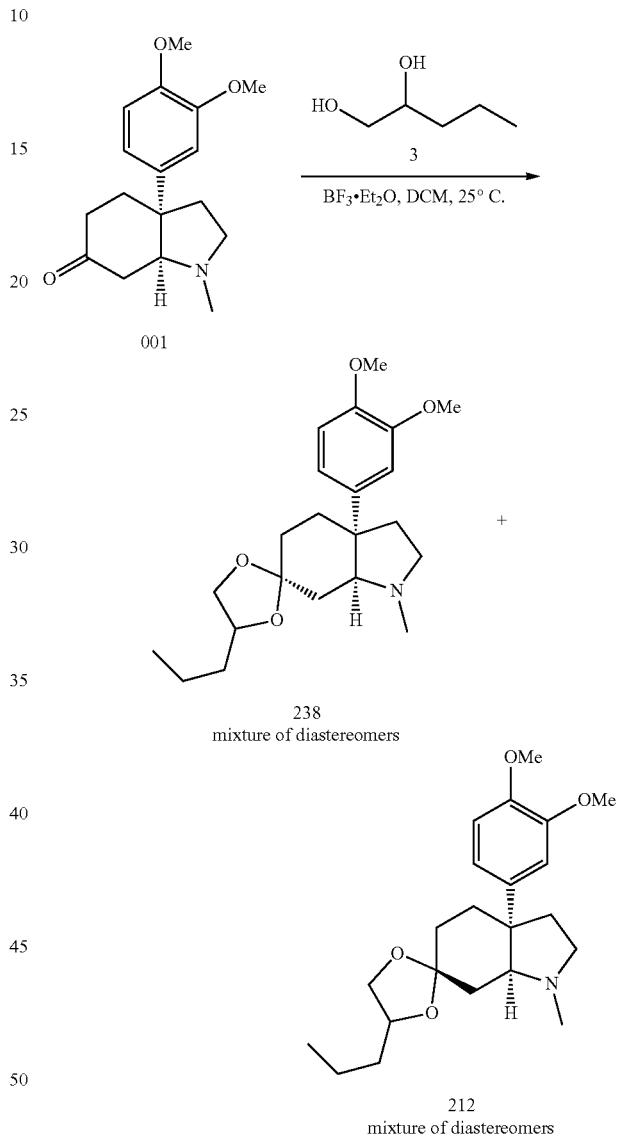

A mixture of (3aS,7aS)-3a-(3,4-dimethoxyphenyl)-1-methyl-2,3,4,5,7,7a-hexahydroindol-6-one (100 mg, 345 umol), propane-1,2-diol (316 mg, 4.20 mmol), BF3.Et$_2$O (4.90 mg, 34.6 umolL) in DCM (3 mL) was degassed and purged with N$_2$ for 3 times, and then the mixture was stirred at 25° C. for 4 hours under N$_2$ atmosphere. On completion, the reaction liquid was dried with a rotary evaporator. The residue was purified by prep-HPLC (neutral condition:column:Waters xbridge 150*25 mm 10 um; mobile phase: [water(NH4HCO3)-ACN]; B %: 15%-45%, 9 min) to give the title compound (37.21 mg, 30.4% yield) as yellow gum.

LC-MS (ESI+) m/z 348.2 (M+H)+.

$^1$H NMR (400 MHz, CDCl$_3$) δ 6.99-6.85 (m, 2H), 6.84-6.77 (m, 1H), 4.23-4.07 (m, 1H), 3.88 (d, J=8.0 Hz, 6H), 3.57-3.39 (m, 1H), 3.36-3.14 (m, 1H), 2.79-2.59 (m, 1H), 2.38 (s, 3H), 2.29-2.16 (m, 2H), 2.11-1.81 (m, 5H), 1.72-1.61 (m, 2H), 1.38-1.27 (m, 4H).

Example 49

(2S,3'aS)-3'a-(3,4-dimethoxyphenyl)-1'-methyl-4-propyl-spiro[1,3-dioxolane-2,6'-2,3,4,5,7,7a-hexahydroindole] (238) and (2R,3'aS)-3'a-(3,4-dimethoxyphenyl)-1'-methyl-4-propyl-spiro[1,3-dioxolane-2,6'-2,3,4,5,7,7a-hexahydroindole] (212)

To a solution of (3aS,7aS)-3a-(3,4-dimethoxyphenyl)-1-methyl-2,3,4,5,7,7a-hexahydroindol one (100 mg, 346 umol), pentane-1,2-diol (540 mg, 5.18 mmol) and pentane-1,2-diol (540 mg, 5.18 mmol) in DCM (3 mL) was added BF$_3$.Et$_2$O (49.1 mg, 345 umol). The mixture was stirred at 25° C. for 2 hours. On completion, the reaction mixture was concentrated in vacuo to give a residue. The residue was purified by prep-HPLC (column: Waters xbridge 150*25 mm 10 um; mobile phase: [water(NH$_3$H$_2$O)-ACN]; B %: 52%-82%, 9 min) to give (2S,3'aS)-3'a-(3,4-dimethoxyphenyl)-1'-methyl-4-propyl-spiro[1,3-dioxolane-2,6'-2,3,4,5,7, 7a-hexahydroindole] (30 mg, 23% yield) as white oil and (2R,3'aS)-3'a-(3,4-dimethoxyphenyl)-1'-methyl-4-propylspiro[1,3-dioxolane-2,6'-2,3,4,5,7,7a-hexahydroindole] (30 mg, 22% yield) as a white oil. 238

LC-MS (ESI+) m/z 454.3 (M+H)+

¹H NMR (400 MHz, CDCl₃) δ 6.94-6.88 (m, 2H), 6.81 (d, J=8.4 Hz, 1H), 4.18-4.12 (m, 1H), 4.03-3.92 (m, 1H), 3.88 (d, J=8.0 Hz, 6H), 3.59-3.43 (m, 1H), 3.24-3.02 (m, 1H), 2.75 (d, J=12.8 Hz, 1H), 2.34 (d, J=12.8 Hz, 3H), 2.25-2.12 (m, 1H), 2.08-1.92 (m, 4H), 1.85-1.63 (m, 3H), 1.55-1.45 (m, 2H), 1.44-1.27 (m, 3H), 0.95 (dt, J=2.0, 7.2 Hz, 3H). 212

LC-MS (ESI+) m/z 376.2 (M+H)+

¹H NMR (400 MHz, CDCl₃) δ=6.94-6.88 (m, 2H), 6.81 (d, J=8.4 Hz, 1H), 4.03-3.92 (m, 3H), 3.88 (d, J=8.0 Hz, 6H), 3.59-3.43 (m, 1H), 3.24-3.02 (m, 1H), 2.75 (d, J=12.8 Hz, 1H), 2.34 (d, J=12.8 Hz, 3H), 2.25-2.12 (m, 1H), 2.08-1.92 (m, 4H), 1.85-1.63 (m, 2H), 1.44-1.27 (m, 4H), 0.95 (dt, J=2.2, 7.2 Hz, 3H).

Example 50

(3'aS,7'aS)-3'a-(3,4-dimethoxyphenyl)-1'-methyl-4,5-divinyl-spiro[1,3-dioxolane-2,6'-2,3,4,5,7,7a-hexahydroindole] (213)

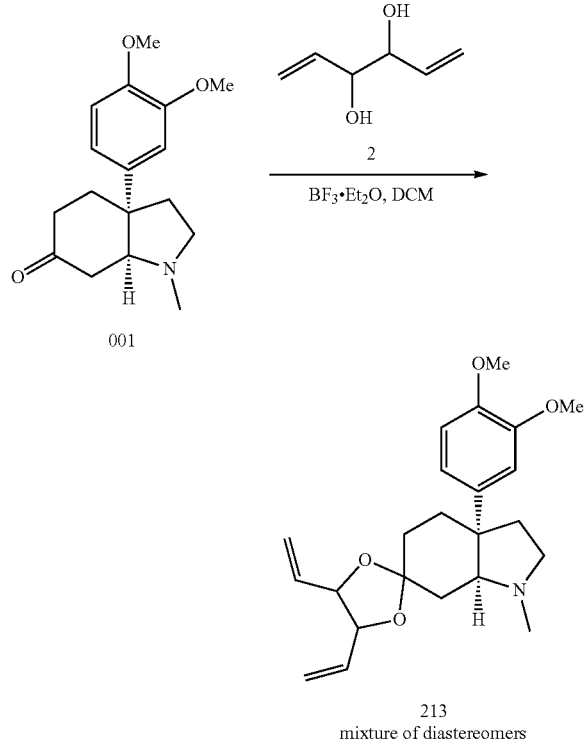

213
mixture of diastereomers

To a solution of (3aS,7aS)-3a-(3,4-dimethoxyphenyl)-1-methyl-2,3,4,5,7,7a-hexahydroindol-6-one (200 mg, 691 nmol, 001) in DCM (2 mL) was added hexa-1,5-diene-3,4-diol (158 mg, 1.38 mmol) and BF₃.Et₂O (294 mg, 2.07 mmol). The mixture was stirred at 25° C. for 12 hours. On completion, the mixture was filtered and concentrated to give a residue. The residue was purified by prep-TLC(SiO₂, DCM: MeOH=10:1) to give (3'aS,7'aS)-3'a-(3,4--dimethoxyphenyl)-1'-methyl-4,5-divinyl-spiro[1,3-dioxolane-2,6'-2,3,4,5,7,7a-hexahydroindole] (68.8 mg, 24% yield) as a yellow gum.

LC-MS (ESI+) nih 385.23 (M+H)+,

¹H NMR (400 MHz, DMSO-d₆) δ 7.05-6.81 (m, 3H), 5.94-5.59 (m, 2H), 5.41-5.14 (m, 4H), 4.80-4.47 (m, 1H), 4.26-3.99(m, 1H), 3.74 (br d, J=6.4 Hz, 6H), 3.13-2.69 (m, 2H), 2.27-2.14 (m, 3H), 2.13-1.80 (m, 5H), 1.79-1.58 (m, 2H), 1.37-1.09 (m, 2H).

Example 51

(3'aS,7'aS)-4-(benzyloxymethyl)-3'a-(3,4-dimethoxyphenyl)-1'-methyl-spiro[1,3-dioxolane-2,6'-2,3,4,5,7,7a-hexahydroindole] (215)

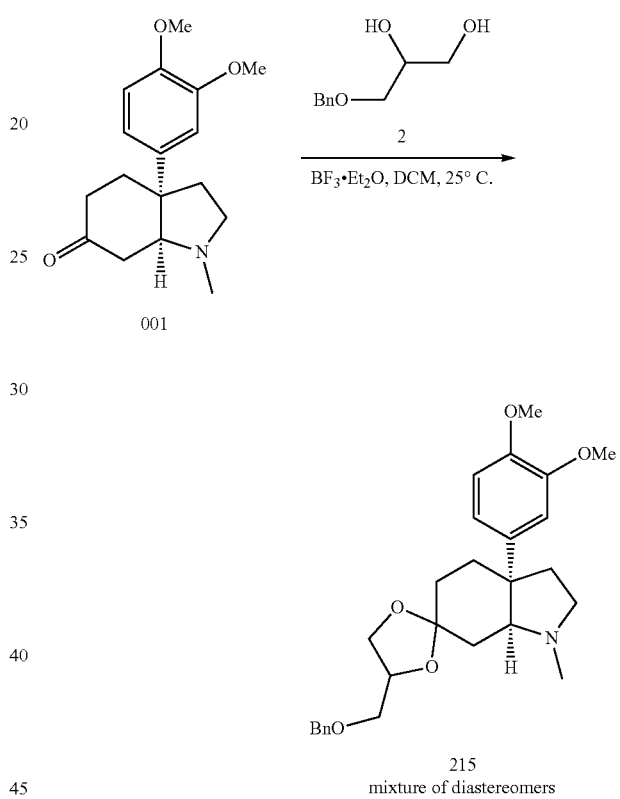

215
mixture of diastereomers

A mixture of (3aS,7aS)-3a-(3,4-dimethoxyphenyl)-1-methyl-2,3,4,5,7,7a-hexahydroindol-6-one (100 mg, 346 umol), 3-benzyloxypropane-1,2-diol (756 mg, 4.20 mmol), BF₃.Et₂O (4.90 mg, 34.6 umol, 4.27 uL) in DCM (2 mL) was degassed and purged with N₂ for 3 times, and then the mixture was stirred at 25° C. for 4 hours under N₂ atmosphere. On completion, the reaction mixture was concentrated in vacuo to give a residue. The residue was purified by prep-HPLC (neutral condition:column: Phenomenex C₁₈ 150*25 mm*10 um; mobile phase: [water(NH4HCO3)-ACN]; B %: 30%-60%, 8 min) to give the title compound (75.0 mg, 46% yield) as yellow gum.

LC-MS (ESI+) m/z 454.2 (M+H)+.

¹H NMR (400 MHz, CDCl₃) δ 7.39-7.28 (m, 5H), 6.93-6.85 (m, 2H), 6.80 (dd, J=1.2, 8.2 Hz, 1H), 4.64-4.47 (m, 2H), 4.39-4.19 (m, 1H), 4.18-4.01 (m, 1H), 3.88 (d, J=6.0 Hz, 6H), 3.60-3.36 (m, 2H), 3.32-3.11 (m, 1H), 2.69 (d, J=11.2 Hz, 1H), 2.41-2.32 (m, 3H), 2.30-2.16 (m, 2H), 2.11-1.92 (m, 4H), 1.71-1.61 (m, 2H), 1.45-1.23 (m, 1H).

Example 52

(3'aS,7'aS)-3'a-(3,4-dimethoxyphenyl)-4-[(2-methoxyphenoxy)methyl]-1'-methyl-spiro[1,3-dioxolane-2,6'-2,3,4,5,7,7a-hexahydroindole] (216)

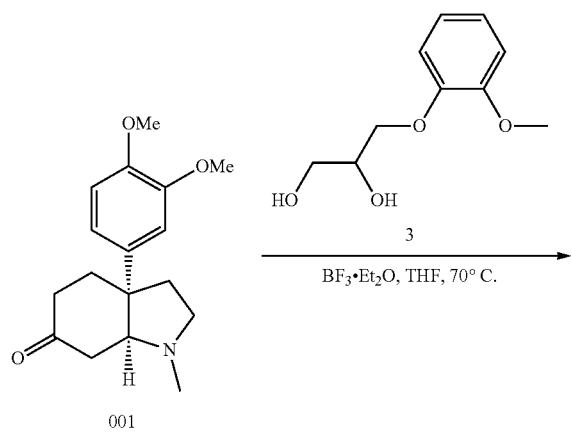

216
mixture of diastereomers

To a solution of (3aS,7aS)-3a-(3,4-dimethoxyphenyl)-1-methyl-2,3,4,5,7,7a-hexahydroindol-6-one (100 mg, 345 umol), 3-(2-methoxyphenoxy)propane-1,2-diol (102 mg, 518 umol) in DCM (3 mL) was added $BF_3.Et_2O$ (49.0 mg, 345 umol, 42.6 uL). The mixture was stirred at 25° C. for 1 hours. On completion, the reaction mixture was concentrated in vacuo to give a residue. The residue was purified by prep-HPLC (column: Phenomenex $C_{18}$ 150*25 mm*10 um; mobile phase: [water ($NH_4HCO_3$)-ACN]; B %: 28%-58%, 8 min) to give the title compound (118 mg, 73% yield) as white oil. LC-MS (ESI+) m/z 470.2 (M+H)+. $^1$H NMR (400 MHz, $CDCl_3$) δ=7.00-6.86 (m, 6H), 6.81 (dd, J=3.2, 8.2 Hz, 1H), 4.64-4.54 (m, 1H), 4.30-4.14 (m, 1H), 4.12-4.03 (m, 1H), 4.01-3.92 (m, 2H), 3.88 (d, J=6.8 Hz, 6H), 3.86-3.82 (m, 3H), 3.35-3.18 (m, 1H), 2.71 (d, J=0.8 Hz, 1H), 2.42-2.33 (m, 3H), 2.30-2.20 (m, 2H), 2.12 (d, J=16.0 Hz, 1H), 2.08-1.94 (m, 3H), 1.92-1.80 (m, 1H), 1.69 (d, J=8.0 Hz, 1H), 1.49-1.22 (m, 1H).

Example 53

N-[[(3aS)-3a-(3,4-dimethoxyphenyl)-1-methyl-2,3,4,5,7,7a-hexahydroindol-6-ylidene]amino]-4-fluoro-benzamide (220)

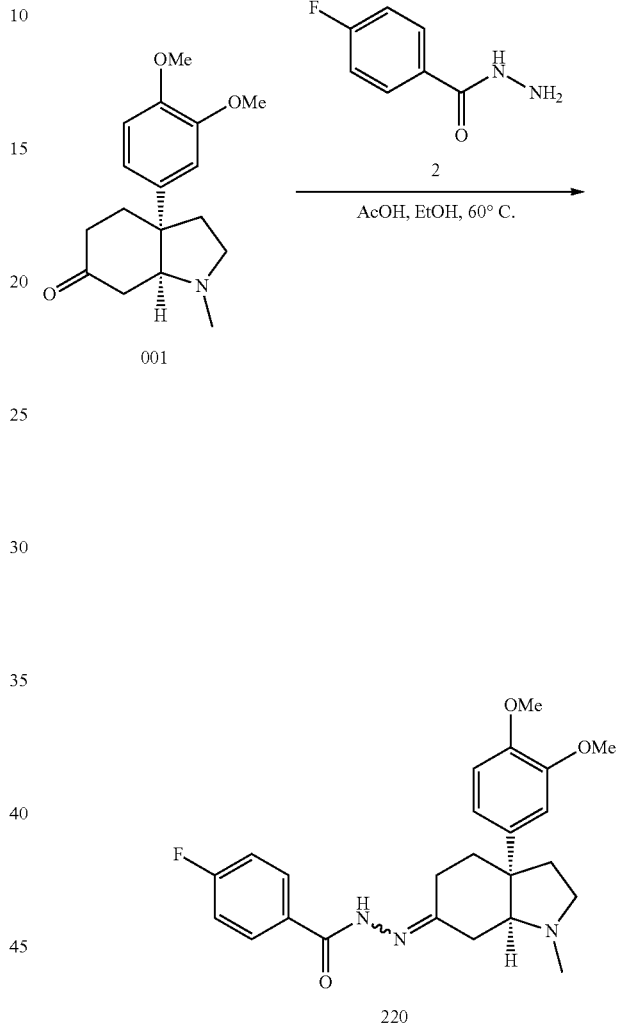

To a solution of (3aS)-3a-(3,4-dimethoxyphenyl)-1-methyl-2,3,4,5,7,7a-hexahydroindol-6-one (100 mg, 346 umol) and 4-fluorobenzohydrazide (53.3 mg, 346 umol) in EtOH (2 mL) was added $CH_3COOH$ (20.8 mg, 346 umol, 19.8 uL). The mixture was stirred at 60° C. for 1 hours. On completion, the reaction mixture was concentrated in vacuo to give a residue to give N-[[(3aS)-3a-(3,4-dimethoxyphenyl)-1-methyl-2,3,4,5,7,7a-hexahydroindol-6-ylidene]amino]-4-fluoro-benzamide (11.87 mg, 7.7% yield) as Off-White Solid.

LC-MS (ESI$^+$) m/z 462.2 (M+H)$^+$ $^1$H NMR (400 MHz, $CDCl_3$) δ 8.63-8.45 (m, 1H), 7.79 (s, 2H), 7.12 (t, J=8.8 Hz, 2H), 6.99-6.77 (m, 3H), 3.92-3.83 (m, 6H), 3.07 (t, J=8.0 Hz, 1H), 2.99-2.84 (m, 2H), 2.82-2.63 (m, 1H), 2.45-2.36 (m, 4H), 2.35-2.20 (m, 2H), 2.12 (s, 2H), 2.10-1.97 (m, 2H).

Example 54

N-[[(3aS, 7aS)-3a-(3,4-dimethoxyphenyl)-1-methyl-2,3,4,5,7,7a-hexahydroindol-6-ylidene]amino]-4-chloro-aniline (221)

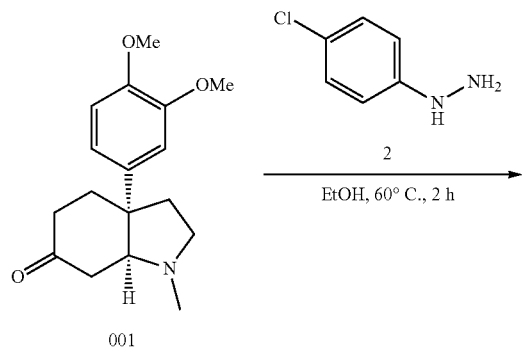

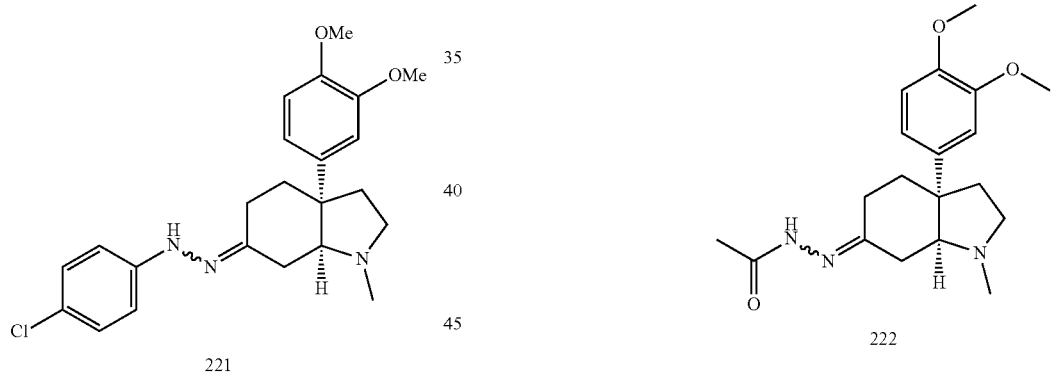

To a solution of (3aS,7aS)-3a-(3,4-dimethoxyphenyl)-1-methyl-2,3,4,5,7,7a-hexahydroindol-6-one (100 mg, 345.58 umol, 001) in EtOH (1 mL) and (4-chlorophenyl)bydrazine (98 mg, 691 umol) was added AcOH (2 mg, 34.5 umol). The mixture was stirred at 60° C. for 2 hours. On completion, the mixture was filtered and concentrated to give the crude. The crude product was purified by reversed-phase HPLC(column: Phenomenex $C_{18}$ $_{150*25}$ mm*10 um; mobile phase: [water (NH4HCO3)-ACN]; B %: 41%-71%, 8 min), to give N-[[(3aS, 7aS)-3a-(3,4-dimethoxyphenyl)-1methyl-2,3,4,5,7,7a-hexahydroindol-6-ylidene]amino]-4-chloro-aniline (25.4 mg, 13% yield) as a yellow solid.

LC-MS (ESI+) m/z 414.1 (M+H)$^+$, $^1$H NMR (400 MHz, DMSO-d$_6$) δ=8.68 (s, 1H), 7.15 (br d, J=8.8 Hz, 2H), 7.02 (br d, J=9.4 Hz, 2H), 6.88 (br d, J=2.0 Hz, 3H), 3.72 (d, J=3.4 Hz, 6H), 2.90 (br d, J=7.2 Hz, 1H), 2.79-2.73 (m, 1H), 2.64-2.60 (m, 1H), 2.24 (s, 3H), 2.21-2.06 (m, 4H), 2.05-1.81 (m, 4H).

Example 55

N-[[(3aS,7aS)-3a-(3,4-dimethoxyphenyl)-1-methyl-2,3,4,5,7,7a-hexahydroindol-6-ylidene]amino]acetamide (222)

To a solution of (3aS,7aS)-3a-(3,4-dimethoxyphenyl)-1-methyl-2,3,4,5,7,7a-hexahydroindol-6-one (001; 100 mg, 345 umol) and acetohydrazide (25.6 mg, 345 umol) in EtOH (5 mL) was added AcOH (10.4 mg, 172 umol,). The mixture was stirred at 60° C. for 12 hours. On completion, the mixture was filtered and concentrated in vacuo to give the residue. The residue was purified by pre-HPLC (column: Waters xbridge 150*25 mm 10 um; mobile phase: [water (NH$_4$HCO$_3$)-ACN]; B %: 10%-40%, 8 min). to give N-[[(3aS,7aS)-3a-(3,4-dimethoxyphenyl)-1-methyl-2,3,4,5,7,7a-hexahydroindol-6-ylidene]amino]acetamide (38.0 mg, 32% yield) as a white solid.

LC-MS (ESI$^+$) m/z 346.20 (M+H).

$^1$H NMR (400 MHz, CDCl$_3$) δ=8.39-7.95 (m, 1H), 6.95-6.77 (m, 3H), 3.96-3.83 (m, 6H), 3.27-3.03 (m, 1H), 3.02-2.86 (m, 1H), 2.81-2.69 (m, 1H), 2.66-2.48 (m, 1H), 2.47-2.32 (m, 4H), 2.28 (s, 3H), 2.26-2.10 (m, 3H), 2.09-1.85 (m, 3H).

Example 56

N-[[(3aS,7aS)-3a-(3,4-dimethoxyphenyl)-1-methyl-2,3,4,5,7,7a-hexahydroindol-6-ylidene]amino]-2-phenoxy-acetamide (223)

Example 57

(3aS,7aS)-3a-(3,4-dimethoxyphenyl)-1-methyl-N-(2-phenoxyethoxy)-2,3,4,5,7,7a-hexahydrondol-6-imine (234)

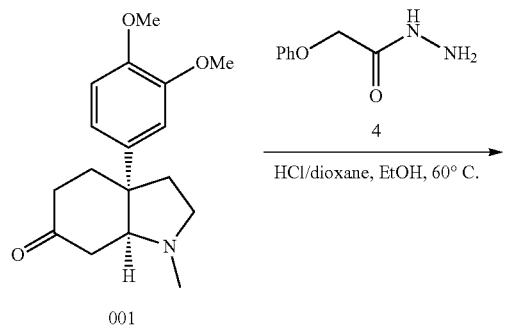

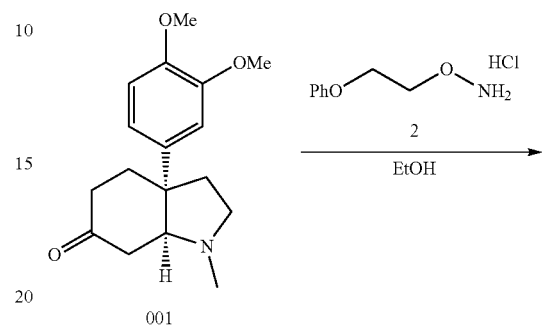

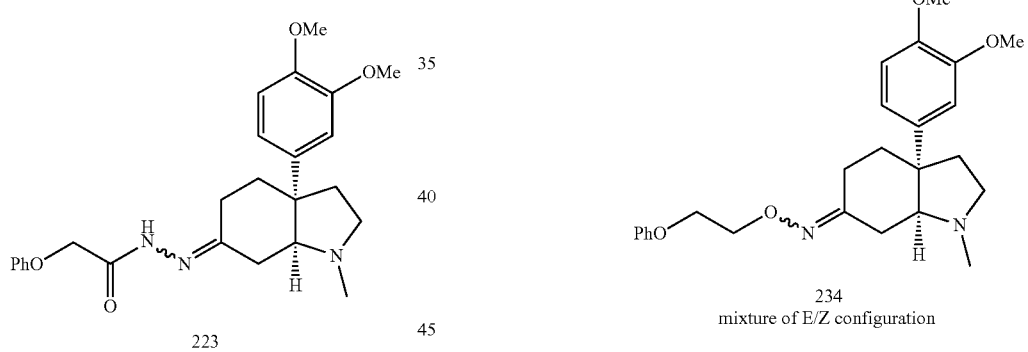

A mixture of (3aS,7aS)-3a-(3,4-dimethoxyphenyl)-1-methyl-2,3,4,5,7,7a-hexahydroindol-6-one (150 mg, 518 umol), 2-phenoxyacetohydrazide (86.1 mg, 518 umol), HCl/dioxane (4 M, 1.3 uL) in EtOH (3 mL) was degassed and purged with $N_2$ for 3 times, and then the mixture was stirred at 60° C. for 4 hours under $N_2$ atmosphere. The residue was purified by prep-HPLC (basic condition: column: Welch Xtimate $C_{18\ 150*25}$ mm*5 um; mobile phase: [water ($NH_3H_2O$)-ACN]; B %: 30%-60%, 8 min) and prep-HPLC (neutral condition: column: Phenomenex $C_{18\ 150*25}$ mm*10 um; mobile phase: [water (NH4HCO3)-ACN]; B %: 26%-56%, 8 min) to give the title compound (78.2 mg, 32% yield) as white solid.

LC-MS (ESI+) m/z 438.1 (M+H)+.

$^1$H NMR (400 MHz, CDCl$_3$) δ 9.08 (s, 1H), 7.32 (t, J=8.0 Hz, 2H), 7.14-6.94 (m, 2H), 6.90 (d, J=8.0 Hz, 2H), 6.85-6.79 (m, 2H), 5.10-4.44 (m, 2H), 3.94-3.85 (m, 6H), 3.46-2.92 (m, 2H), 2.90-2.47 (m, 3H), 2.45-2.14 (m, 6H), 2.12-1.78 (m, 3H).

To a solution of (3aS,7aS)-3a-(3,4-dimethoxyphenyl)-1-methyl-2,3,4,5,7,7a-hexahydroindol-6-one (100 mg, 345 umol) in EtOH (1.0 mL) was added O-(2-phenoxyethyl) hydroxylamine; hydrochloride (131 mg, 691 umol). The mixture was stirred at 60° C. for 2 hours. The reaction mixture was concentrated in vacuo to give the residue. The residue was purified by prep-HPLC (column: Waters xbridge 150*25 mm 10 um; mobile phase: [water ($NH_4HCO_3$)-ACN]; B %: 42%-72%, 8 min) to give the (3aS,7aS)-3a-(3,4-dimethoxyphenyl)-1-methyl-N-(2-phenoxyethoxy)-2,3,4,5,7,7a-hexahydroindol-6-imine (78.0 mg, 52% yield) as a colorless gum.

LC-MS (ESI$^+$) m/z 425.4 (M+H)$^+$.

$^1$H NMR (400 MHz, CDCl$_3$) δ 7.30 (s, 1H), 7.26 (d, J=2.0 Hz, 1H), 6.98-6.89 (m, 3H), 6.89-6.75 (m, 3H), 4.41-4.34 (m, 2H), 4.24-4.16 (m, 2H), 3.92-3.83 (m, 6H), 3.28-2.99 (m, 1H), 2.90-2.74 (m, 1H), 2.61-2.51 (m, 2H), 2.35 (br d, J=13.8 Hz, 3H), 2.32-2.21 (m, 2H), 2.18-2.01 (m, 3H), 2.00-1.93 (m, 1H), 1.92-1.84 (m, 1H).

Example 58

N-[[(3aS,7aS)-3a-(3,4-dimethoxyphenyl)-1-methyl-2,3,4,5,7,7a-hexahydroindol-6-ylidene]amino]-4-chloro-benzamide (240)

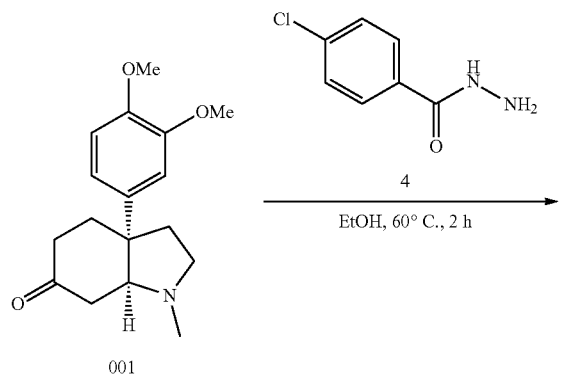

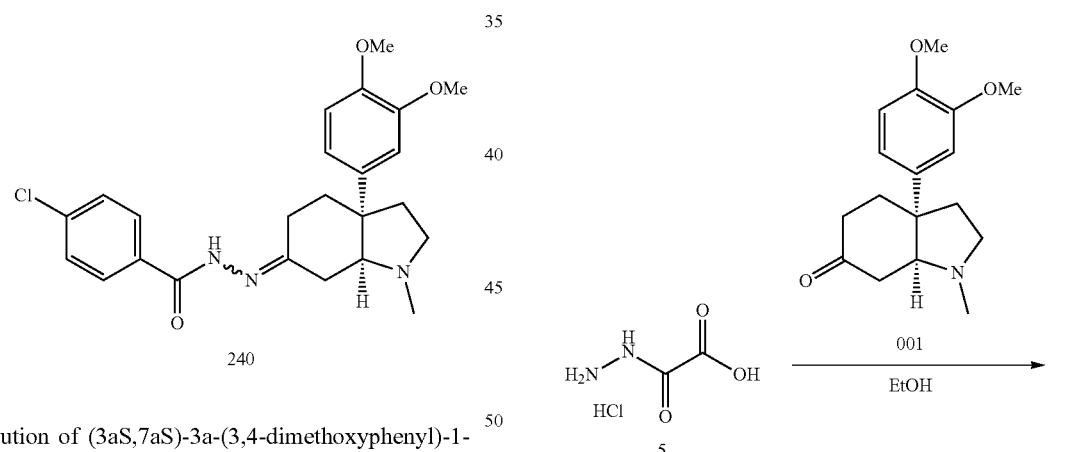

To a solution of (3aS,7aS)-3a-(3,4-dimethoxyphenyl)-1-methyl-2,3,4,5,7,7a-hexahydroindol-6-one (100 mg, 345 umol) 4-chlorobenzohydrazide (118 mg, 691 umol) in EtOH (1 mL) was added AcOH (2 mg, 34.5 umol) and. The mixture was stirred at 60° C. for 2 hours. On completion, the mixture was filtered and concentrated to give the residue, the residue was purified by prep-TLC (SiO$_2$, DCM: MeOH=10:1) to N-[[(3aS,7aS)-3a-(3,4-dimethoxyphenyl)-1-methyl-2,3,4,5,7,7a-hexahydroindol-6-ylidene]amino]-4-chloro-benzamide (41.7 mg, 17% yield) as a yellow solid.

LC-MS (ESI+) m/z 442.1 (M+H)$^+$m $^1$H NMR (400 MHz, DMSO-d$_6$) δ=10.82-10.23 (m, 1H), 7.83 (br d, J=8.8 Hz, 2H), 7.63-7.45 (m, 2H), 7.01-6.82 (m, 3H), 3.79-3.71 (m, 6H), 3.10-3.00 (m, 1H), 2.94 (br t, J=7.6 Hz, 1H), 2.80 (br d, J=3.2 Hz, 1H), 2.65-2.56 (m, 2H), 2.48-2.17 (m, 5H), 2.08-2.02 (m, 1H), 2.00-1.88 (m, 3H).

Example 59

2-[2-[(3aS,7aS)-3a-(3,4-dimethoxyphenyl)-1-methyl-2,3,4,5,7,7a-hexahydroindol-6-ylidene]hydrazino]-2-oxo-acetic acid (241)

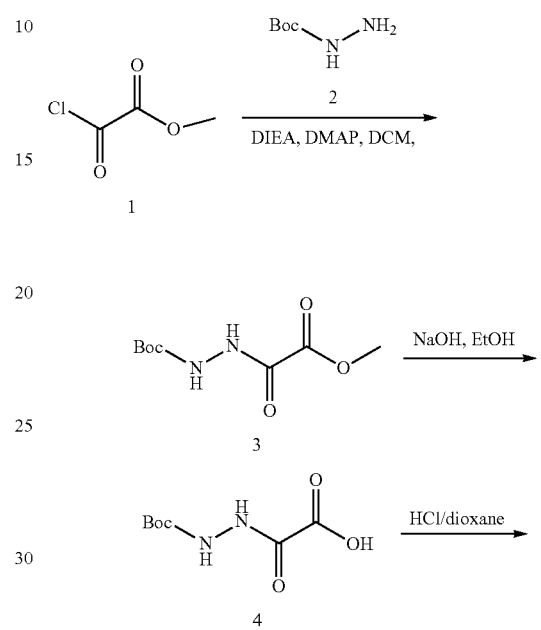

methyl 2-(2-tert-butoxycarbonylhydrazino)-2-oxo-acetate (Int3)

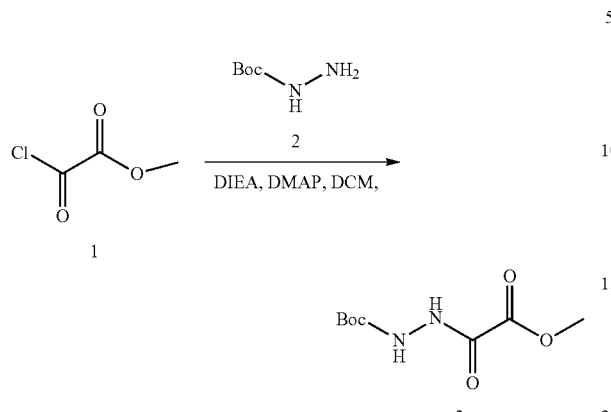

To a solution of tert-butyl N-aminocarbamate (2.00 g, 15.1 mmol) in DCM (5.0 mL) was added DIEA (3.91 g, 30.2 mmol, 5.27 mL) and DMAP (369 mg, 3.03 mmol) then add methyl 2-chloro-2-oxo-acetate (2.04 g, 16.6 mmol, 1.53 mL) to the mixture. The mixture was stirred at 0° C. for 2 hours. The mixture was poured to the water (100 mL) and extracted with DCM (30 mL). The organic layers was dried by sodium sulfate, filtered and concentrated in vacuo to give the residue. The residue was purified by column chromatography (SiO$_2$, DCM:MeOH=10:1) to give the methyl 2-(2-tert-butoxycarbonylhydrazino)-2-oxo-acetate (500 mg, 14% yield) as a yellow solid.

$^1$H NMR (400 MHz, CDCl$_3$) δ 8.63 (br s, 1H), 6.77-6.43 (m, 1H), 3.86 (s, 3H), 1.42 (s, 9H)

Step 2—2-(2-tert-butoxycarbonylhydrazino)-2-oxo-acetic acid (Int4

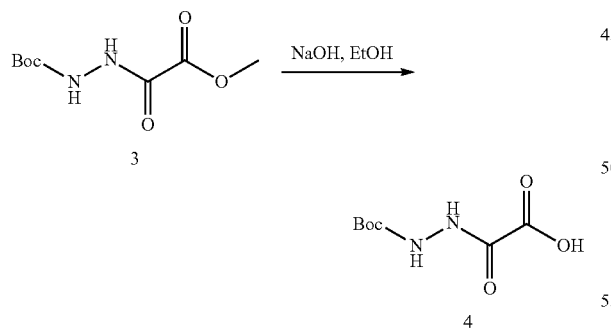

To a solution of methyl 2-(2-tert-butoxycarbonylhydrazino)-2-oxo-acetate (400 mg, 1.83 mmol) in EtOH (3.0 mL) was added NaOH (1 M, 1.83 mL). The mixture was stirred at 25° C. for 6 hours. The reaction mixture was concentrated in vacuo to give the residue. The reaction mixture was concentrated in vacuo to give the 2-(2-tert-butoxycarbonylhydrazino)-2-oxo-acetic acid (360 mg, 93% yield) as a yellow solid.

$^1$H NMR (400 MHz, CDCl$_3$) δ 1.40 (s, 9H)

Step 3—2-hydrazino-2-oxo-acetic acid (Int 5)

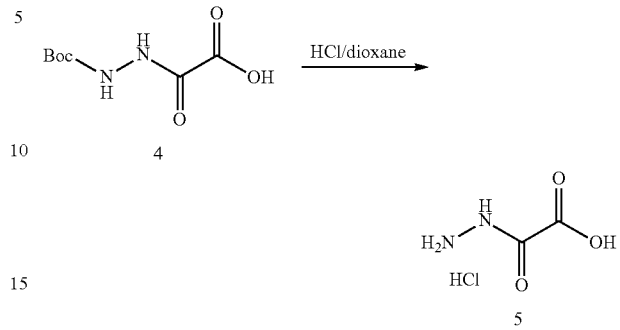

To a solution of 2-(2-tert-butoxycarbonylhydrazino)-2-oxo-acetic acid (350 mg, 1.71 mmol) in DCM (5.0 mL) was added HCl/dioxane (4 M, 1.0 mL). The mixture was stirred at 25° C. for 1 hour. The reaction mixture was filtered, concentrated in vacuo to give the 2-hydrazino-2-oxo-acetic acid (235 mg, 88% yield, HCl) was obtained as a yellow solid.

Step 4—2-[2-[(3a5,7a5)-3a-(3,4-dimethoxyphenyl)-1-methyl-2,3,4,5,7,7a-hexahydroindol-6-ylidene]hydrazino]-2-oxo-acetic acid (241)

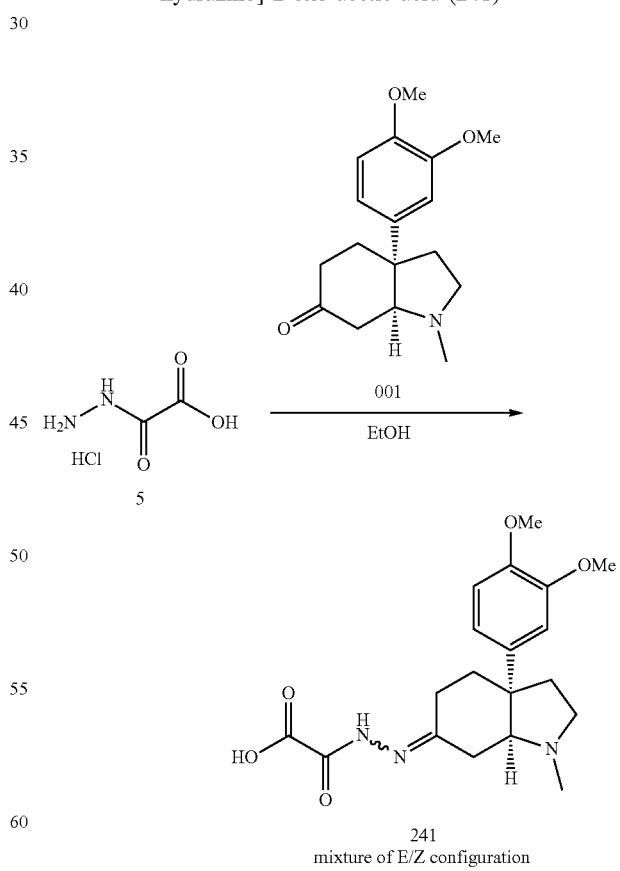

241
mixture of E/Z configuration

To a solution of (3aS,7aS)-3a-(3,4-dimethoxyphenyl)-1-methyl-2,3,4,5,7,7a-hexahydroindol-6-one (200 mg, 691 umol) in EtOH (1.0 mL) was added AcOH (41.5 mg, 691 umol, 39.5 uL) and 2-hydrazino-2-oxo-acetic acid (215 mg, 2.07 mmol). The mixture was stirred at 60° C. for 2 hours. The reaction mixture was concentrated in vacuo to give the residue. The residue was purified by prep-HPLC (column: Waters xbridge 150*25 mm 10 um; mobile phase: [water (NH₄HCO₃)-ACN]; B %: 0%-30%, 9 min) to give the 2-[2-[(3aS,7aS)-3a-(3,4-dimethoxyphenyl)-1-methyl-2,3,4,5,7,7a-hexahydroindol-6-ylidene]hydrazino]-2-oxo-acetic acid (42.6 mg, 16% yield) as a yellow solid.

LC-MS (ESI⁺) m/z 376.2 (M+H)⁺.

¹H NMR (400 MHz, CDCl₃) δ 10.14 (br s, 1H), 8.11-7.36 (m, 1H), 7.01-6.64 (m, 3H), 3.95-3.78 (m, 6H), 3.74-3.59 (m, 1H), 3.32-3.17 (m, 1H), 3.05-2.96 (m, 1H), 2.81 (br s, 2H), 2.72-2.62 (m, 1H), 2.53 (br d, J=11.8 Hz, 1H), 2.46-2.33 (m, 3H), 2.30-2.23 (m, 1H), 2.22-2.13 (m, 1H), 2.02 (br d, J=9.2 Hz, 1H).

Example 60

3-[2-[2-[(3aS,7aS)-3a-(3,4-dimethoxyphenyl)-1-methyl-2,3,4,5,7,7a-hexahydroindol-6-ylidene]hydrazino]-2-oxo-ethyl]-5-methyl-hexanoic acid (242)

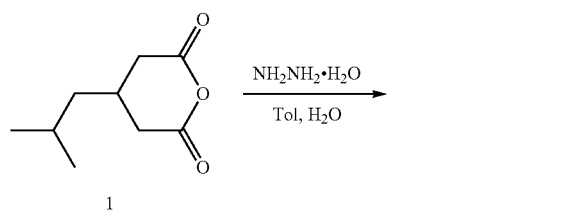

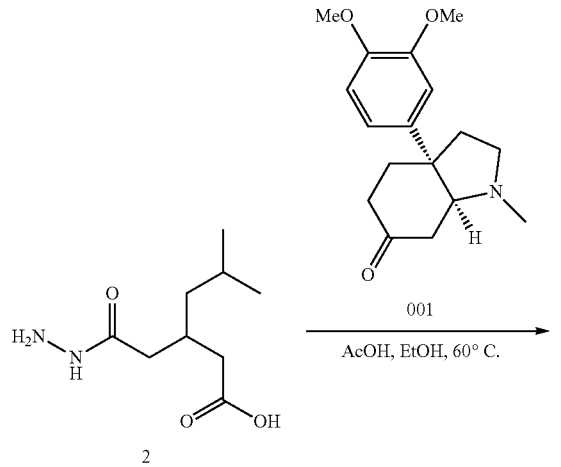

Step 1—3-(2-hydrazino-2-oxo-ethyl)-5-methyl-hexanoic acid (Int2)

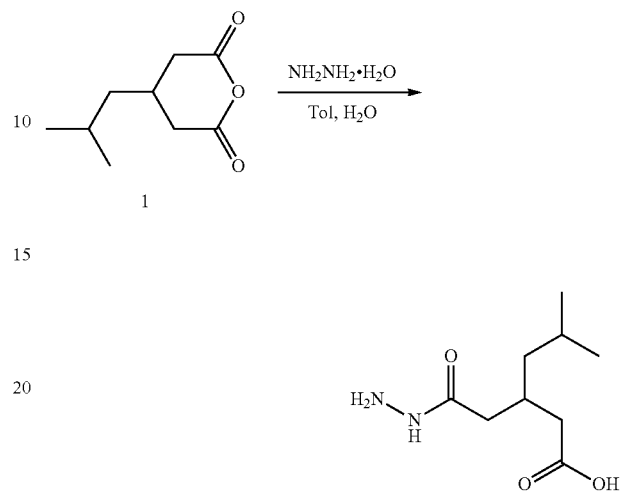

TA mixture of N₂H₄H₂O (780 mg, 15.3 mmol, 757 uL, 98% purity, 1.3 eq) and NaOH (470 mg, 11.7 mmol) in H₂O (6 mL) was degas sed and purged with N₂ for 3 times, and then the mixture of 4-isobutyltetrahydropyran-2,6-dione (2 g, 11.7 mmol) in Tol (8 mL) was added above mixture. The mixture was stirred 0° C. for 2 hours. On complete, the reaction mixture was filtered, concentrated in vacuo to give the residue 3-(2-hydrazino-2-oxo-ethyl)-5-methyl-hexanoic acid (2 g, 8.90 mmol, 75% yield) as a white solid.

¹H NMR (400 MHz, CD₃OD) δ=2.26-1.95 (m, 5H), 1.60-1.44 (m, 1H), 1.19-0.97 (m, 2H), 0.77 (dd, J=1.9, 6.6 Hz, 6H)

Step 2—3-[2-[2-[(3aS,7aS)-3a-(3,4-dimethoxyphenyl)-1-methyl-2,3,4,5,7,7a-hexahydroindol-6-ylidene]hydrazino]-2-oxo-ethyl]-5-methyl-hexanoic acid

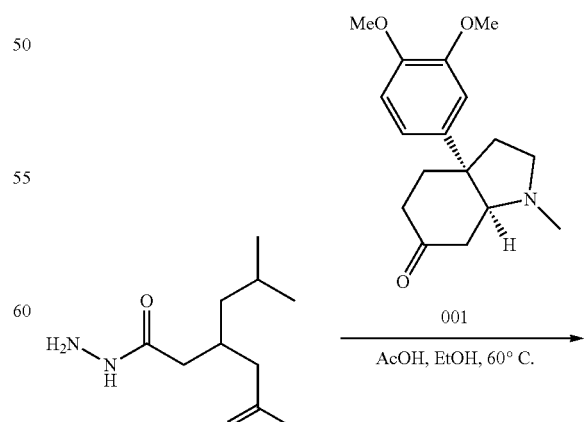

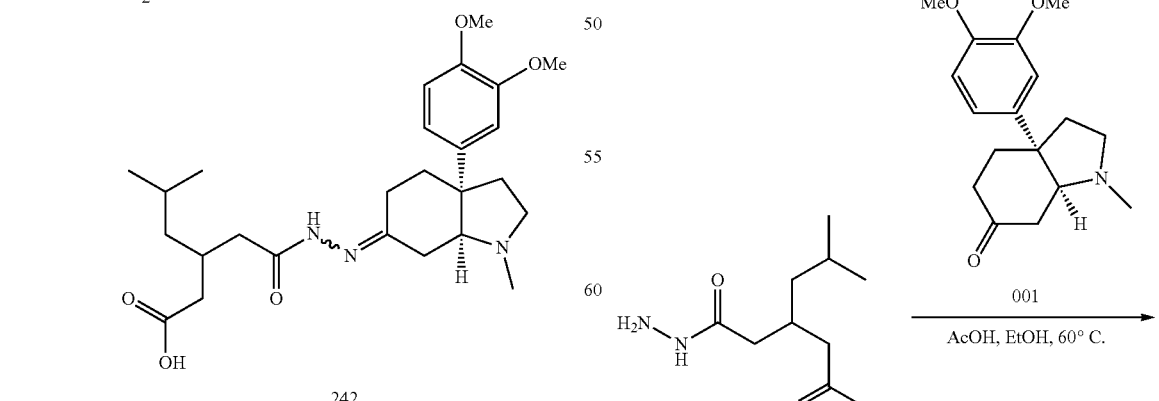

-continued

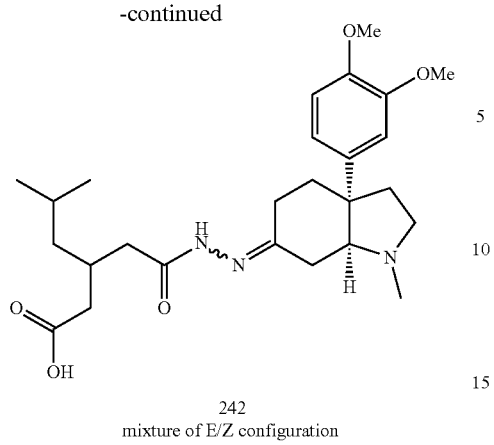

242
mixture of E/Z configuration

To a solution of (3 aS,7aS)-3 a-(3,4-dimethoxyphenyl)-1-methyl-2,3,4,5,7,7a-hexahydroindol-6-one (200.00 mg, 691.16 umol, 1 eq) in EtOH (1 mL) was added AcOH (4.15 mg, 69.1 umol) and 3-(2-hydrazino-2-oxo-ethyl)-5-methyl-hexanoic acid (209 mg, 1.04 mmol,). The mixture was stirred at 60° C. for 1 hr. On complete, the reaction mixture was filtered, concentrated in vacuo to give the residue. The residue was purified by prep-HPLC (column: Welch Xtimate $C_{18}$ $_{150*25}$ mm*5 um; mobile phase: [water (ammonia hydroxide v/v)-ACN]; B %: 0%-30%, 2 min) to give 3-[2-[2-[(3aS,7aS)-3a-(3,4-dimethoxyphenyl)-1-methyl-2,3,4,5,7,7a-hexahydroindol-6-ylidene]hydrazino]-2-oxo-ethyl]-5-methyl-hexanoic acid (41.1 mg, 12% yield) as a white solid.)

LC-MS (ESI+) m/z 475.1 (M+H)+.

1H NMR (400 MHz, CDCl₃) 6.94-6.60 (m, 3H), 5.12-4.19 (m, 2H), 4.07-3.64 (m, 6H), 3.49-3.00 (m, 4H), 2.80-2.74 (m, 1H), 2.70-2.60 (m, 1H), 2.55-2.48 (m, 3H), 2.45-2.40 (m, 1H), 2.40-2.30 (m, 3H), 2.28-2.20 (m, 2H), 2.20-2.10 (m, 2H), 2.10-2.00 (m, 3H), 1.64 (m, 1H), 1.27-1.09 (m, 1H), 0.92-0.68 (m, 6H).

Example 61

1-1-[[[(3aS,7aS)-3a-(3,4-dimethoxyphenvl)-1-methyl-2,3,4,5,7,7a-hexahydroindol-6-ylidene]amino]carbamoyl]cyclopropanecarboxylic acid (243)

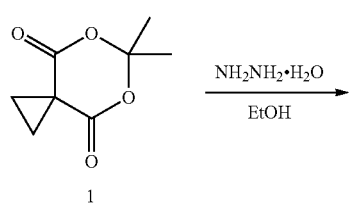

-continued

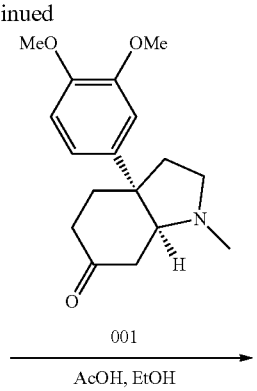

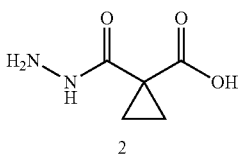

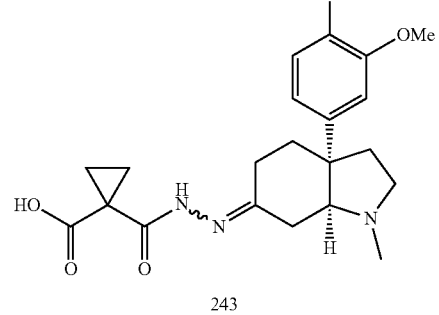

243

Step 1—1-(hydrazinecarbonyl)cyclopropanecarboxylic acid (Int 2)

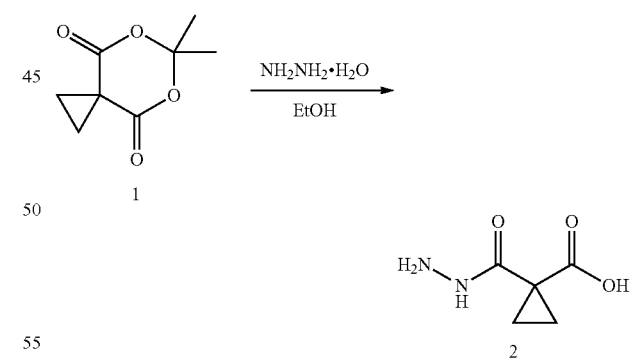

To a solution of 6,6-dimethyl-5,7-dioxaspiro[2.5]octane-4,8-dione (500 mg, 2.94 mmol) in ACN (5.0 mL) was added hydrazine; hydrate (173 mg, 2.94 mmol, 168 uL, 85% purity) in ACN (1 mL) for 5 minutes. The mixture was stirred at 20° C. for 16 hours. On completion, the reaction mixture was filtered, concentrated in vacuo to give 1-(hydrazinecarbonyl)cyclopropanecarboxylic acid (300 mg, 49% yield) as a brown solid.

¹H NMR (400 MHz, DMSO-d₆) δ 1.25-1.06 (m, 4H).

Step 2—1-[[[(3aS,7aS)-3a-(3,4-dimethoxyphenyl)-1-methyl-2,3,4,5,7,7a-hexahydroindol-6-ylidene]amino]carbamoyl]cyclopropanecarboxylic acid (243)

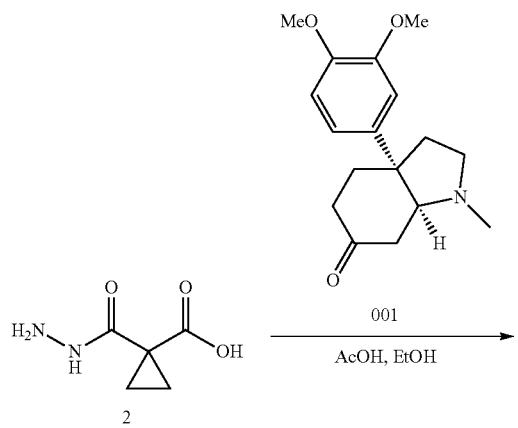

A mixture of (3aS,7aS)-3a-(3,4-dimethoxyphenyl)-1-methyl-2,3,4,5,7,7a-hexahydroindol-6-one (150 mg, 518 umol), 1-(hydrazinecarbonyl)cyclopropanecarboxylic acid (149 mg, 1.04 mmol), AcOH (3.11 mg, 51.8 umol, 2.96 uL) in EtOH (1.0 mL) was degassed and purged with N₂ for 3 times, and then the mixture was stirred at 60° C. for 2 hours under N₂ atmosphere. On completion, the reaction mixture was filtered, concentrated in vacuo to give the residue. The crude product was purified by re-crystallization from ethyl acetate (6.0 mL) at 25° C. and column chromatography (SiO₂, by prep-TLC (SiO₂, DCM:MeOH=10:1) to give 1-[[[(3aS,7aS)-3a-(3,4-dimethoxyphenyl)-1-methyl-2,3,4,5,7,7a-hexahydroindol-6-ylidene]amino]carbamoyl]cyclopropanecarboxylic acid (31.6 mg, 26% yield) as a yellow solid.

LC-MS (ESI⁺) m/z 416.1 (M+H)⁺

¹H NMR (400 MHz, CDCl₃) δ 13.27 (s, 1H), 6.91-6.63 (m, 3H), 3.83 (d, J=9.0 Hz, 6H), 3.64-3.47 (m, 2H), 3.07 (s, 2H), 2.79 (d, J=17.3 Hz, 2H), 2.70 (s, 4H), 2.59-2.43 (m, 2H), 2.40-2.30 (m, 1H), 2.27-2.15 (m, 1H), 2.08-2.00 (m, 1H), 1.62-1.53 (m, 1H), 1.41-1.31 (m, 2H), 1.43-1.28 (m, 1H).

Example 62

2-[[[(3aS,7aS)-3a-(3,4-dimethoxyphenyl)-1-methyl-2,3,4,5,7,7a-hexahydroindol-6-ylidene]amino]carbamoyl]benzoic acid (244)

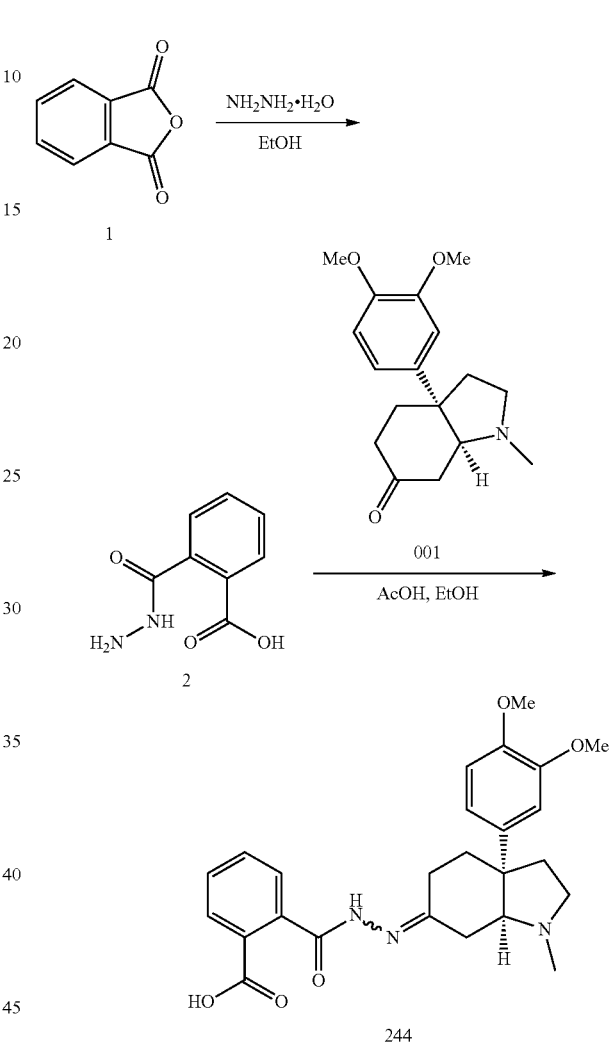

Step 1—2-(hydrazinecarbonyl)benzoic acid (2)

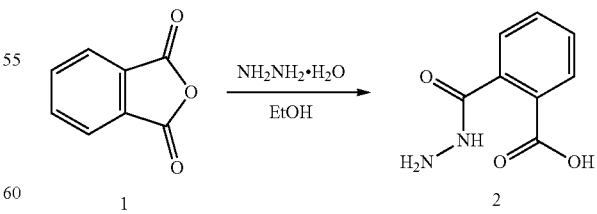

To a solution of isobenzofuran-1,3-dione (2.0 g, 13.5 mmol) in ACN (20 mL) was added hydrazine; hydrate (795 mg, 13.5 mmol, 772 uL, 85% purity) in ACN (5.0 mL) for 10 minutes. The mixture was stirred at 20° C. for 16 hours. On completion, the reaction mixture was filtered, concentrated in vacuo to give the residue. The crude product was purified by re-crystallization from H$_2$O (10 mL) at 20° C. to give 2-(hydrazinecarbonyl)benzoic acid (2.1 g, 69% yield) as a white solid.

$^1$H NMR (400 MHz, DMSO-d$_6$) δ 8.08 (dd, J=3.6, 6.0 Hz, 1H), 7.89 (dd, J=3.2, 6.0 Hz, 1H), 7.74-7.66 (m, 2H), 7.52-7.49 (m, 1H).

Step 2—2-[[[(3a5,7a5)-3a-(3,4-dimethoxyphenyl)-1-methyl-2,3,4,5,7,7a-hexahydroindol-6-ylidene]amino]carbamoyl]benzoic acid (244)

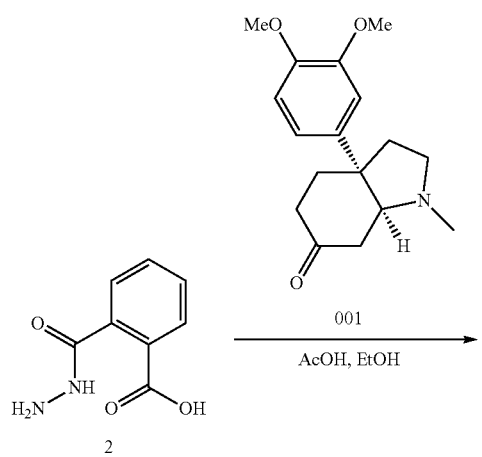

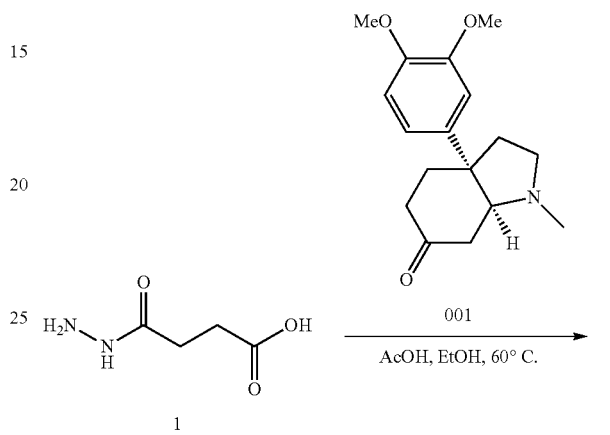

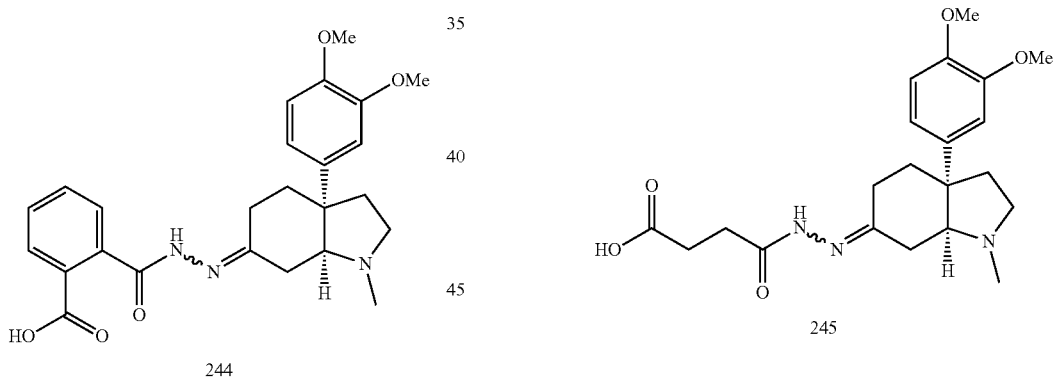

A mixture of (3aS,7aS)-3a-(3,4-dimethoxyphenyl)-1-methyl-2,3,4,5,7,7a-hexahydroindol-6-one (200 mg, 691 umol), 2-(hydrazinecarbonyl)benzoic acid (249 mg, 1.38 mmol), AcOH (4.15 mg, 69.1 umol, 3.95 uL) in EtOH (3.0 mL) was degassed and purged with N$_2$ for 3 times, and then the mixture was stirred at 40° C. for 2 hours under N$_2$ atmosphere. On completion, the reaction mixture was filtered, concentrated in vacuo to give the residue. The crude product was purified by re-crystallization from ethyl acetate (10 mL) at 20° C. and column chromatography (SiO$_2$, by prep-TLC (SiO$_2$, DCM:MeOH=10:1) to give 2-[[[(3aS,7aS)-3a-(3,4-dimethoxyphenyl)-1-methyl-2,3,4,5,7,7a-hexahydroindol-6-ylidene]amino]carbamoyl]benzoic acid (11. 59 mg, 10% yield) as a brown gum.

LC-MS (ESI$^+$) m/z 452.1 (M+H)$^+$ $^1$H NMR (400 MHz, CDCl$_3$) δ 7.92-7.48 (m, 2H), 7.41-7.23 (m, 2H), 6.91-6.49 (m, 3H), 3.88-3.72 (m, 6H), 3.69-3.44 (m, 2H), 3.25-2.97 (m, 2H), 2.72 (s, 3H), 2.54 (d, J=3.6 Hz, 1H), 2.47-2.27 (m, 3H), 2.20-2.01 (m, 2H), 1.99-1.80 (m, 2H).

Example 63

4-[2-[(3aS,7aS)-3a-(3,4-dimethoxyphenyl)-1-methyl-2,3,4,5,7,7a-hexahydroindol-6-ylidene]hydrazino]-4-oxo-butanoic acid (245)

To a solution of (3aS,7aS)-3a-(3,4-dimethoxyphenyl)-1-methyl-2,3,4,5,7,7a-hexahydroindol-6-one (150 mg, 518 umol) in EtOH (2 mL) was added 4-hydrazino-4-oxo-butanoic acid; hydrochloride (131 mg, 777 umol). The mixture was stirred at 60° C. for 2 hours. On completion, the reaction mixture was filtered, concentrated in vacuo to give the residue. The residue was purified by prep-HPLC (column: Welch Xtimate C$_{18}$ $_{150*25}$ mm*5 um; mobile phase: [water(NH$_3$H$_2$O)-ACN]; B %: 1%-30%, 8 min) to give the 4-[2-[(3aS,7aS)-3a-(3,4-dimethoxyphenyl)-1-methyl-2,3,4,5,7,7a-hexahydroindol-6-ylidene]hydrazino]-4-oxo-butanoic acid (21mg, 5.1% yield) as white solid.

LC-MS (ESI+) m/z 404.1 (M+H)+.

$^1$H NMR (400 MHz, CD$_3$OD) δ=7.05-6.84 (m, 3H), 3.89-3.78 (m, 6H), 3.57-3.45 (m, 1H), 2.99-2.84 (m, 1H), 2.80-2.62 (m, 5H), 2.60-2.52 (m, 3H), 2.52-2.47 (m, 1H), 2.41-2.40 (m, 1H), 2.40-2.31 (m, 1H), 2.31-2.15 (m, 2H), 2.15-1.85 (m, 3H).

Example 64

(3aS,7aS)-3a-(3,4-dimethoxyphenyl)-1-methyl-2,3,4,5,7,7a-hexahydroindol-6-one (249 and 270)

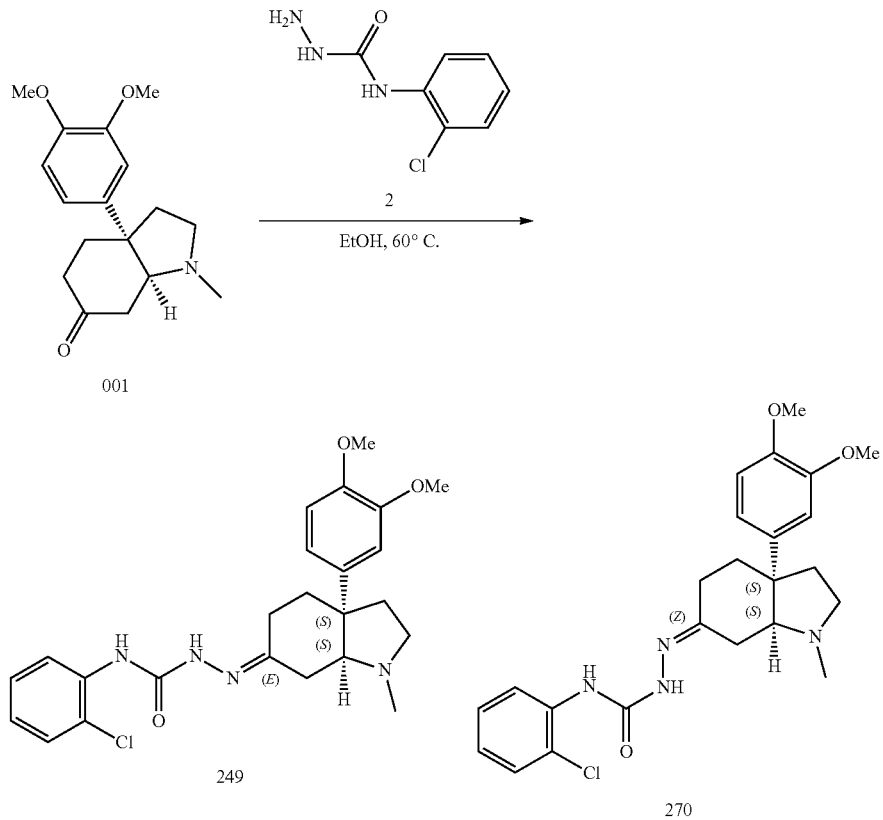

To a solution of (3aS,7aS)-3a-(3,4-dimethoxyphenyl)-1-methyl-2,3,4,5,7,7a-hexahydroindol-6-one (99.78 mg, 344.81 umol, 1 eq) and 1-amino-3-(2-chlorophenyl)urea (64 mg, 344.81 umol, 1 eq) in EtOH (2 mL) was added AcOH (207.07 ug, 3.45 umol, 1.97e-1 uL, 0.01 eq). The mixture was stirred at 60° C. for 16 hr. On completion, filtered to remove the insoluble. The filter liquor was concentrated in vacuo. The residue was purified by prep-HPLC (basic condition column: Welch Xtimate $C_{18\ 150*25}$ mm*5 um; mobile phase: [water (ammonia hydroxide v/v)-ACN]; B %: 38%-68%, 2 min). to give 1-[(E)-[(3aS,7aS)-3a-(3,4-dimethoxyphenyl)-1-methyl-2,3,4,5,7,7a-hexahydroindol-6-ylidene]amino]-3-(2-chlorophenyl)urea (42.62 mg, 27.05% yield) was obtained as a white solid and 1-[(Z)-[(3aS,7aS)-3a-(3,4-dimethoxyphenyl)-1-methyl-2,3,4,5,7,7a-hexahydroindol-6-ylidene]amino]-3-(2-chlorophenyl)urea (6.52 mg, 4.14% yield) was obtained as a white solid.

249: LC-MS (ESI$^+$) m/z 457.10 (M+H)

$^1$H NMR (400 MHz, CDCL$_3$) δ=8.92 (s, 1H), 8.33 (dd, J=1.4, 8.3 Hz, 1H), 7.49 (s, 1H), 7.37 (dd, J=1.4, 8.0 Hz, 1H), 7.25 (br d, J=1.4 Hz, 1H), 6.99 (dt, J=1.5, 7.7 Hz, 1H), 6.90-6.79 (m, 3H), 3.88 (d, J=2.3 Hz, 6H), 3.05 (br s, 1H), 2.89 (br s, 1H), 2.73 (br d, J=4.1 Hz, 1H), 2.64 (br s, 1H), 2.39 (s, 3H), 2.36-2.26 (m, 2H), 2.21 (br s, 1H), 2.15-1.96 (m, 4H)

270: LC-MS (ESI$^+$) m/z 457.10 (M+H)

$^1$H NMR (400 MHz, CDCL$_3$) δ=8.94 (s, 1H), 8.35 (dd, J=1.3, 8.3 Hz, 1H), 7.88 (br s, 1H), 7.36 (dd, J=1.4, 8.0 Hz, 1H), 7.27-7.23 (m, 1H), 7.03-6.81 (m, 4H), 3.90 (d, J=7.4 Hz, 6H), 3.31-3.17 (m, 1H), 2.93 (br s, 1H), 2.89-2.78 (m, 1H), 2.64-2.51 (m, 1H), 2.38 (s, 3H), 2.38-2.32 (m, 1H), 2.27 (ddd, J=3.9, 10.3, 14.4 Hz, 2H), 2.22-2.13 (m, 1H), 2.12-2.03 (m, 3H).

Example 65

1-[[(3aS,7aS)-3a-(3,4-dimethoxyphenyl)-1-methyl-2,3,4,5,7,7a-hexahydroindol-6-ylidene]amino]-3-(4-methoxyphenyl)urea (254)

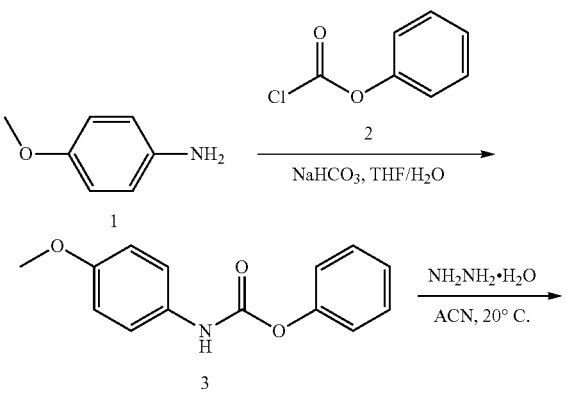

-continued

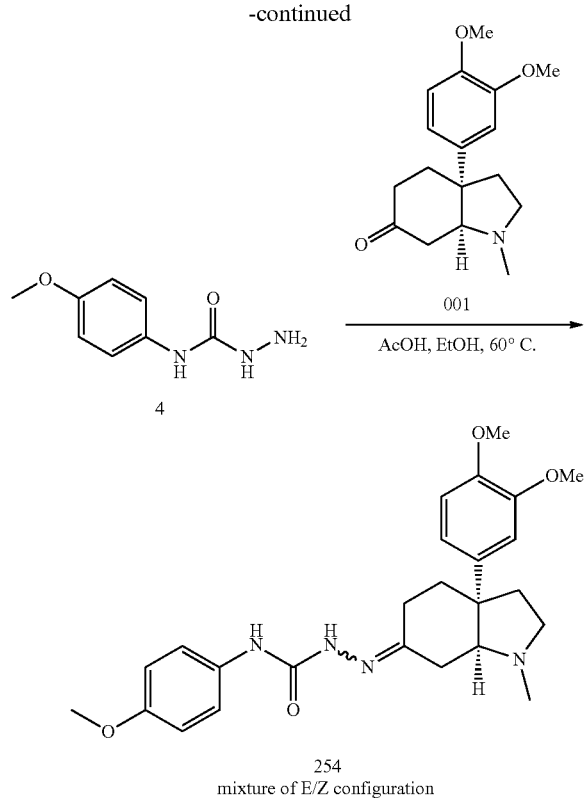

254
mixture of E/Z configuration

Step 1—phenyl N-(4-methoxyphenyl)carbamate (Int3)

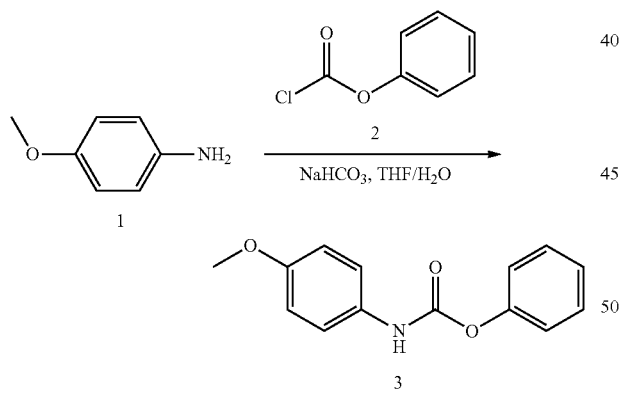

A mixture of 4-methoxyaniline (2.0 g, 16.2 mmol), phenyl carbonochloridate (2.80 g, 17.8 mmol, 2.24 mL,), NaHCO₃ (2.73 g, 32.5 mmol) in THF (10 mL) and H₂O (10 mL) was degassed and purged with N₂ for 3 times, and then phenyl carbonochloridate (2.80 g, 17.7 mmol) was added above mixture, the mixture was stirred at 0° C. for 1 hour under N₂ atmosphere. On completion, the mixture was poured to the water (100 mL) and extracted with ethyl acetate (30 mL*3). The organic layers was dried by sodium sulfate, filtered and concentrated in vacuo to give phenyl N-(4-methoxyphenyl) carbamate (2.4 g, 8.39 mmol, 51% yield,) as a gray solid.

LC-MS (ESI+) m/z 244.2 (M+H)⁺

1H NMR (400 MHz, CDCl₃) δ=7.42 (q, J=8.0 Hz, 3H), 7.31-7.28 (m, 1H), 7.26-7.20 (m, 1H), 6.97-6.89 (m, 2H), 6.88-6.81 (m, 2H), 3.84 (s, 3H).

Step 2—1-amino-3-(4-methoxyphenyl)urea (Int 4)

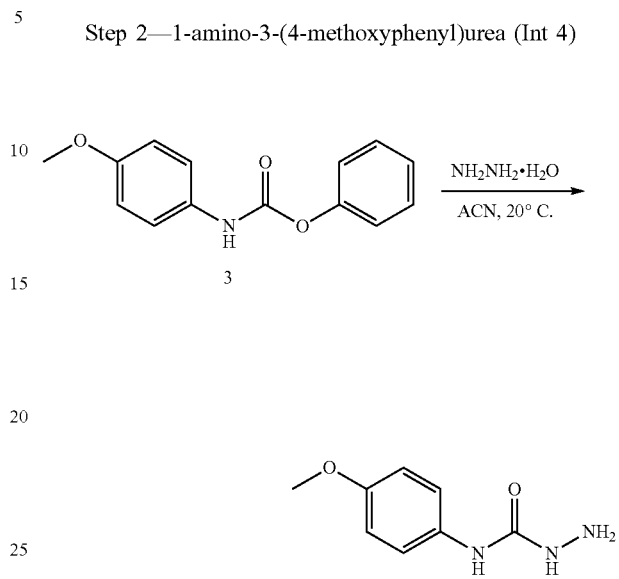

A mixture of phenyl N-(4-methoxyphenyl)carbamate (1.0 g, 4.11 mmol), N₂H₄·H₂O (605 mg, 10.2 mmol, 587 uL, 85% purity) in ACN (10 mL) was degassed and purged with N₂ for 3 times, and then the mixture was stirred at 25° C. for 16 hours under N₂ atmosphere. On completion, the reaction mixture was filtered, concentrated in vacuo to give the residue. The residue was triturated with EA for 10 mins to give 1-amino-3-(4-methoxyphenyl)urea (560 mg, 75% yield) as a white solid.

LC-MS (ESI+) m/z 183.1 (M+H)⁺

¹H NMR (400 MHz, CDCl₃) δ=7.96 (br s, 1H), 7.39-7.37 (m, 1H), 7.37-7.34 (m, 1H), 6.89-6.87 (m, 1H), 6.86-6.84 (m, 1H), 6.16 (br s, 1H), 3.95-3.57 (m, 3H)

Step-3-1-[[(3aS,7aS)-3a-(3,4-dimethoxyphenyl)-1-methyl-2,3,4,5,7,7a-hexahydroindol-6-ylidene]amino]-3-(4-methoxyphenyl)urea (254)

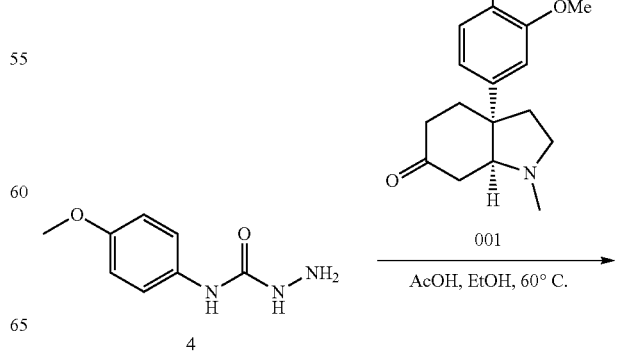

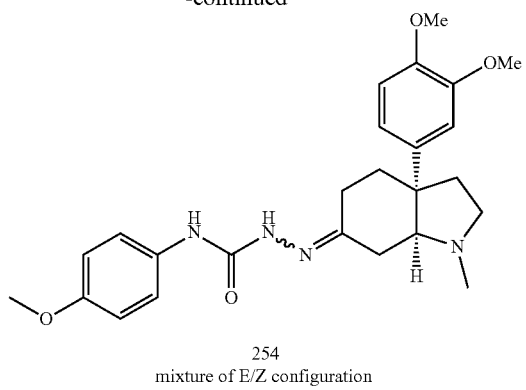

254
mixture of E/Z configuration

A mixture of 1-amino-3-(4-methoxyphenyl)urea (93.9 mg, 518. umol,), (3aS,7aS)-3a-(3,4-dimethoxyphenyl)-1-methyl-2.3,4,5.7,7a-hexahydroindol-6-one (150 mg, 518 umol,), AcOH (3.11 mg, 51.8 umol) in EtOH (1 mL) was degassed and purged with N for 3 dines, and then the mixture was stirred at 60° C. for 1 hr under N₂ atmosphere. On completion, the mixture was filtered to give residue, the residue purified by prep-TLC (DCM:MeOH=5:1) to give 1-[(E)-[(3aS,7aS)-3a-(3,4-dimetho xyphenyl)-1-methyl-2,3,4,5,7,7a-hexahydroindol-6-ylidene]amino]-3-(4-methoxyphenyl)urea (61.0 mg, 59% yield) as a yellow solid LC-MS (ESI+) m/z 453.2 (M+H)⁺, 1H NMR (400 MHz, CDCl₃) δ=8.04 (s, 1H), 7.49-7.38 (m, 2H), 7.29 (br s, 1H), 7.27 (s, 1H), 6.90-6.88 (m, 1H), 6.87-6.86 (m, 2H), 3.94-3.87 (m, 6H), 3.85-3.78 (m, 3H), 3.16-2.84 (m, 2H), 2.97-2.52 (m, 2H), 2.46-2.36 (m, 3H), 2.31-2.19 (m, 3H), 2.15-1.94 (m, 4H).

Example 66

1-[[(3aS,7aS)-3a-(3,4-dimethoxyphenyl)-1-methyl-2,3,4,5,7,7a-hexahydroindol-6-ylidene]amino]-3-(4-methylsulfonylphenyl)urea (255)

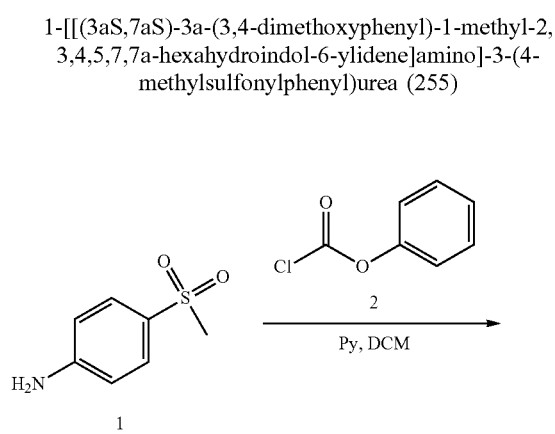

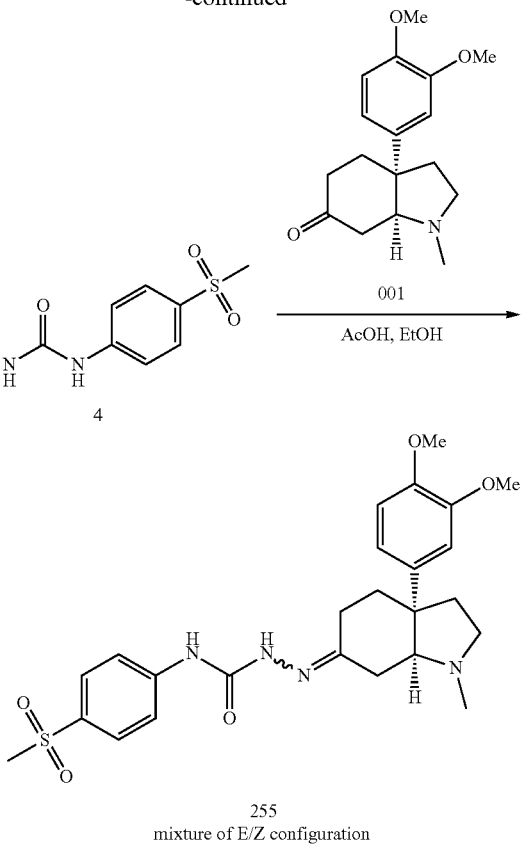

255
mixture of E/Z configuration

Step 1 phenyl N-(4-methylsulfonylphenyl)carbamate (3)

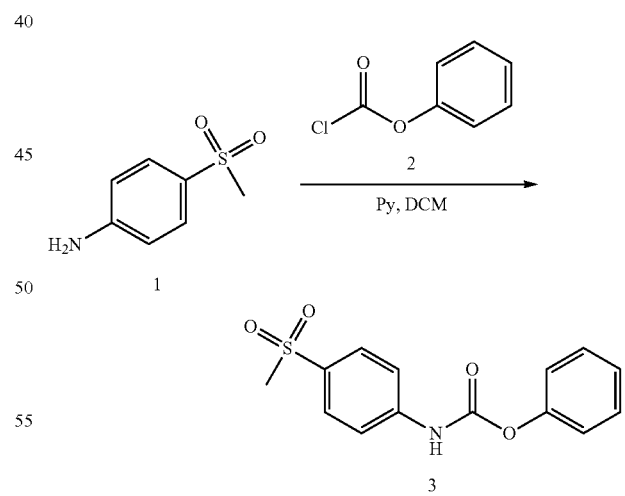

A mixture of 4-methylsulfonylaniline (1.00 g, 5.84 mmol) CAS #5470-49-5, phenyl carbonochloridate (210 mg, 1.34 mmol, 168 uL) CAS #1885-14-9, Py (196 mg, 2.48 mmol, 0.200 mL) in DCM (10 mL) was degassed and purged with N₂ for 3 times, and then the mixture was stirred at 25° C. for 12 hours under N₂ atmosphere. On completion, the mixture was quenched with water (10 mL) and extracted with ethyl acetate (15 mL×3), the combined organic phase was dried over anhydrous sodium sulfate, filtered and concentrated to give a residue. The residue was purified by column chromatography (SiO$_2$, Petroleum ether/Ethyl acetate=1/1 to 0/1) to give the title compound (760 mg, 44% yield) as white solid.

LC-MS (ESI+) m/z 291.8 (M+H)+.

$^1$H NMR (400 MHz, CDCl$_3$) δ 7.84 (d, J=8.8 Hz, 2H), 7.58 (d, J=8.8 Hz, 2H), 7.40-7.30 (m, 2H), 7.22-7.18 (m, 1H), 7.12 (d, J=8.0 Hz, 2H), 2.98 (s, 3H).

Step 2 1-amino-3-(4-methylsulfonylphenyl)burea (4)

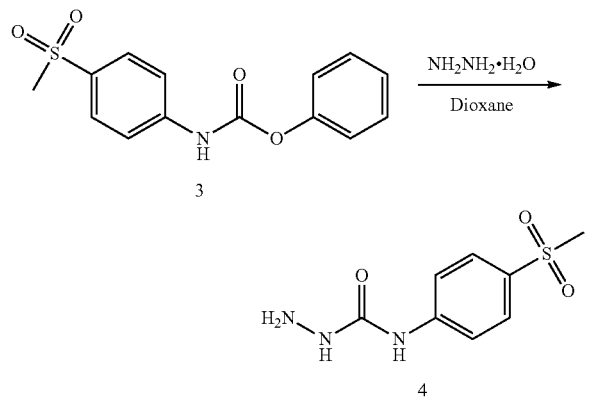

A mixture of phenyl N-(4-methylsulfonylphenyl)carbamate (660 mg, 2.27 mmol), NH$_2$NH$_2$·H$_2$O (667 mg, 11.3 mmol, 647 uL, 85% purity) in dioxane (10 mL) was degassed and purged with N$_2$ for 3 times, and then the mixture was stirred at 100° C. for 5 hours under N$_2$ atmosphere. On completion, the reaction mixture was filtered. The crude compound was used into the next step without further purification to give the title compound (400 mg, 69% yield) as white solid.

LC-MS (ESI+) m/z 230.0 (M+H)+.

$^1$H NMR (400 MHz, DMSO-d$_6$) δ 9.14 (s, 1H), 7.85-7.72 (m, 4H), 4.42 (s, 2H), 3.13 (s, 3H).

Step 3 1-[[(3a5,7a5)-3a-(3,4-dimethoxyphenyl)-1-methyl-2,3,4,5,7,7a-hexahydroindol-6-ylidene]amino]-3-(4-methylsulfonylphenyl)urea (255)

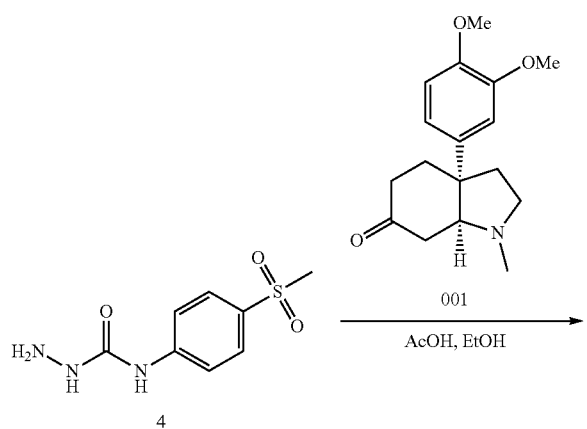

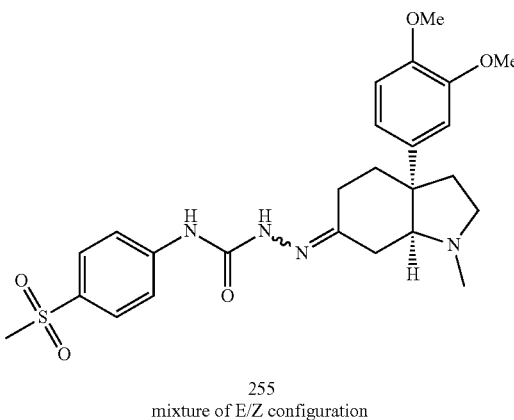

255
mixture of E/Z configuration

A mixture of (3aS,7aS)-3a-(3,4-dimethoxyphenyl)-1-methyl-2,3,4,5,7,7a-hexahydroindol-6-one (467 mg, 1.61 mmol), 1-amino-3-(4-methylsulfonylphenyl)urea (370 mg, 1.61 mmol), AcOH (96.9 mg, 1.61 mmol, 92.3 uL) in EtOH (7 mL) was degassed and purged with N$_2$ for 3 times, and then the mixture was stirred at 60° C. for 1 hour under N$_2$ atmosphere. On completion, the reaction mixture was concentrated in vacuo to give a residue. The crude compound was used into the next step without further purification to give the title compound (700 mg, 79% yield) as off-white solid.

LC-MS (ESI+) m/z 501.2 (M+H)+.

$^1$H NMR (400 MHz, CDCl$_3$) δ 8.59-8.54 (m, 2H), 7.88 (d, J=8.4 Hz, 2H), 7.76-7.71 (m, 2H), 6.83 (s, 3H), 3.88 (d, J=4.8 Hz, 6H), 3.15 (t, J=7.6 Hz, 1H), 3.05 (s, 3H), 2.80-2.66 (m, 2H), 2.46-2.43 (m, 3H), 2.28-2.22 (m, 1H), 2.15-2.10 (m, 2H), 2.07-2.02 (m, 5H).

Example 67

[[(3aS,7aS)-3a-(3,4-dimethoxyphenyl)-1-methyl-2,3,4,5,7,7a-hexahydroindol-6-ylidene]amino]-3-[2-(2-thienyl)ethyl]urea (256)

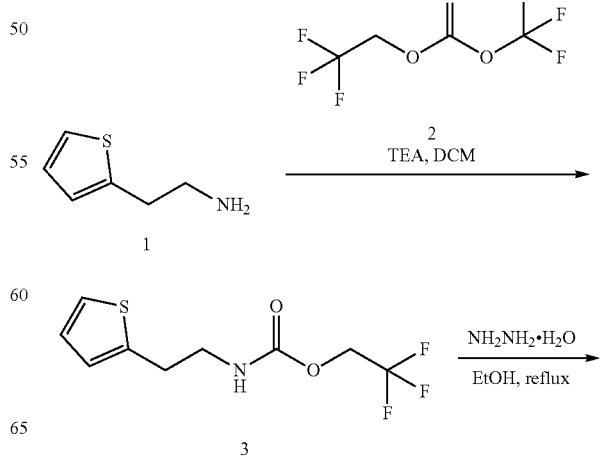

-continued

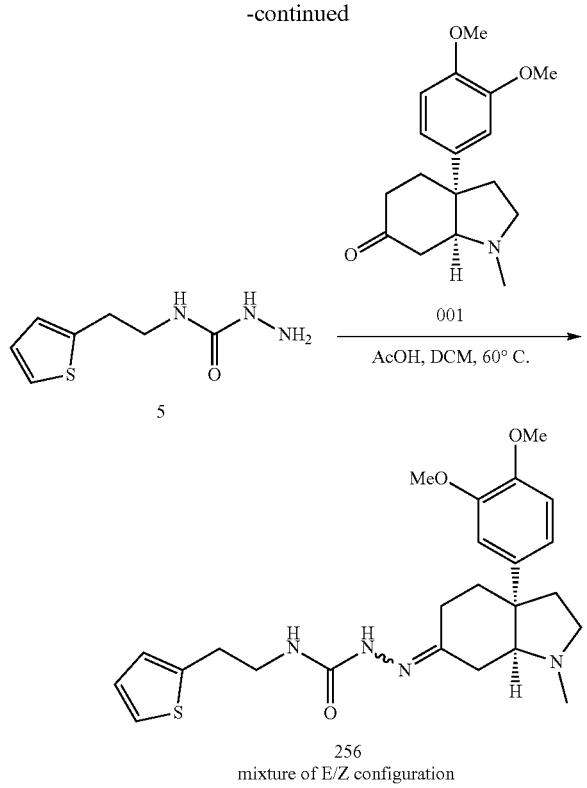

256
mixture of E/Z configuration

Step 1—2,2,2-trifluoroethyl N-[2-(2-thienyl)ethyl]carbamate

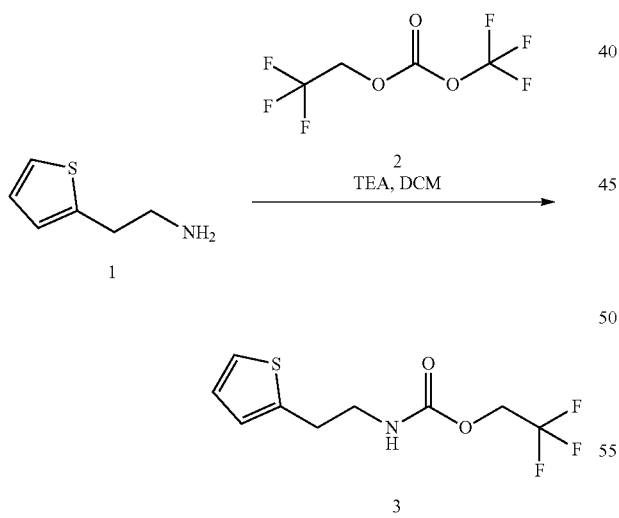

To a solution of 2-(2-thienyl) ethanamine (1.0 g, 7.86 mmol, 917 uL) bis (2,2,2-trifluoroethyl, CAS#30433-91-1) carbonate (1.95 g, 8.65 mmol) in DCM (10 mL) was added TEA (875 mg, 8.65 mmol, 1.20 mL). The mixture was stirred at 25° C. for 3 hours. On completion, the reaction mixture was concentrated in vacuo to give a residue. It wasn't purification to give 2,2,2-trifluoroethyl N-[2-(2-thienyl)ethyl] Carbamate (2.00 g, 70% yield) as white oil.

$^1$H NMR (400 MHz, CDCl$_3$) δ 7.19 (d, J=5.2 Hz, 1H), 6.97 (dd, J=3.6, 5.2 Hz, 1H), 6.85 (d, J=3.2 Hz, 1H), 5.06 (s, 1H), 4.47 (q, J=8.4 Hz, 2H), 3.51 (q, J=6.4 Hz, 2H), 3.07 (t, J=6.4 Hz, 2H).

Step 2—1-amino-3-[2-(2-thienyl)ethyl]urea

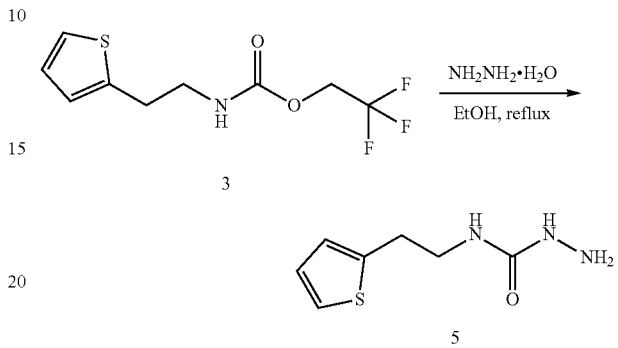

To a solution of 2,2,2-trifluoro-N-[2-(2-thienyl)ethyl] acetamide (1.8 g, 8.06 mmol) in EtOH (6 mL) was added hydrazine; hydrate (2.37 g, 40.3 mmol, 2.31 mL, 85% purity). The mixture was stirred at 60° C. for 1.5 hours. On completion, the reaction mixture was quenched by adding it to a cold saturated aqueous NH$_4$Cl solution (5 mL). The aqueous layer was extracted with ethyl acetate (5 mL×2). The organic layer was separated, dried over anhydrous Na$_2$SO$_4$, filtered and concentrated under reduced pressure to give the residue. The residue was used to the next step directly without further purification. Gave 1-amino-3-[2-(2-thienyl)ethyl]urea (2.00 g, 70% yield) as white oil.

LC-MS (ESI$^+$) m/z 186.0 (M+H)$^+$ $^1$H NMR (400 MHz, CDCl$_3$) δ 7.16 (dd, J=1.2, 5.2 Hz, 1H), 6.96 (dd, J=3.6, 5.2 Hz, 1H), 6.86 (d, J=3.2 Hz, 1H), 6.21 (s, 1H), 5.89-5.74 (m, 1H), 3.54 (q, J=6.4 Hz, 2H), 3.06 (t, J=6.8 Hz, 2H).

Step 3—1-[[(3aS,7aS)-3a-(3,4-dimethoxyphenyl)-1-methyl-2,3,4,5,7,7a-hexahydroindol-6-ylidene]amino]-3-[2-(2-thienyl)ethyl]urea (256)

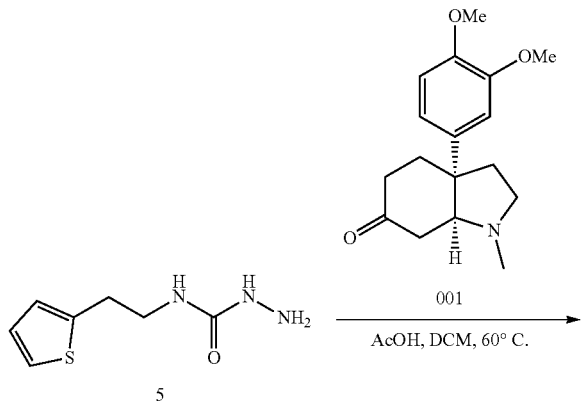

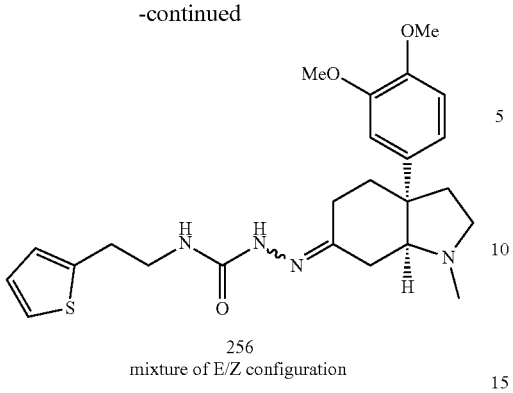

256
mixture of E/Z configuration

To a solution of (3aS,7aS)-3a-(3,4-dimethoxyphenyl)-1-methyl-2,3,4,5,7,7a-hexahydroindol-6-one (100 mg, 346 umol) and 1-amino-3-[2-(2-thienyl)ethyl]urea (64.0 mg, 346 umol) in EtOH (3 mL) was added AcOH (20.8 mg, 346 umol, 19.8 uL). The mixture was stirred at 60° C. for 1 hours. On completion, the reaction mixture was concentrated in vacuo to give a residue. It wasn't purification to give 1-[[(3aS,7aS)-3a-(3,4-dimethoxyphenyl)-1-methyl-2,3,4,5,7,7a-hexahydroindol-6-ylidene]amino]-3-[2-(2-thienyl)ethyl]urea (148 mg, 88% yield) as yellow Gum.

LC-MS (ESI+) m/z 457.2 (M+H)+

$^1$H NMR (400 MHz, CDCl$_3$) δ 8.20 (s, 1H), 7.19-7.13 (m, 1H), 7.00-6.93 (m, 1H), 6.89-6.85 (m, 1H), 6.82-6.78 (m, 2H), 6.48-6.40 (m, 1H), 3.91-3.86 (m, 6H), 3.57 (tt, J=6.8, 14.0 Hz, 4H), 3.15-3.01 (m, 3H), 2.99-2.87 (m, 1H), 2.74-2.49 (m, 2H), 2.42-2.38 (m, 3H), 2.29-2.20 (m, 3H), 2.37-2.20 (m, 3), 2.17-2.07 (m, 2H), 2.02-1.92 (m, 2H).

Example 68

1-[[(3aS,7aS)-3a-(3,4-dimethoxyphenyl)-1-methyl-2,3,4,5,7,7a-hexahydroindol-6-ylidene]amino]-3-[4-(4-methylpiperazin-1-yl)phenyl]urea (257)

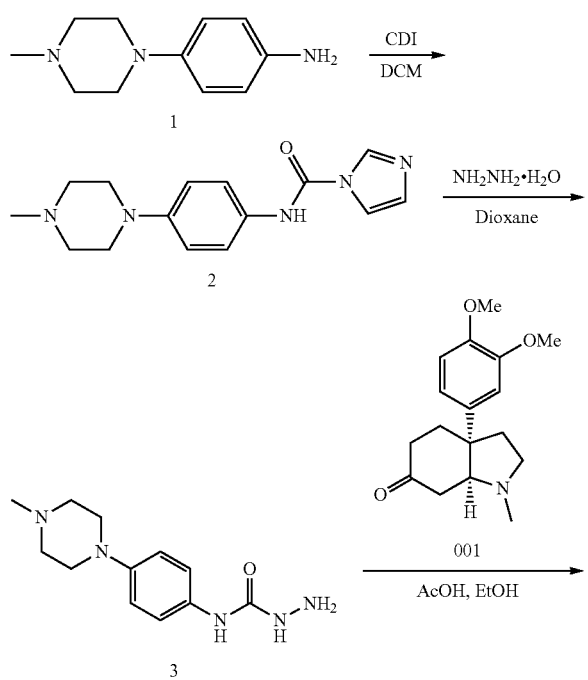

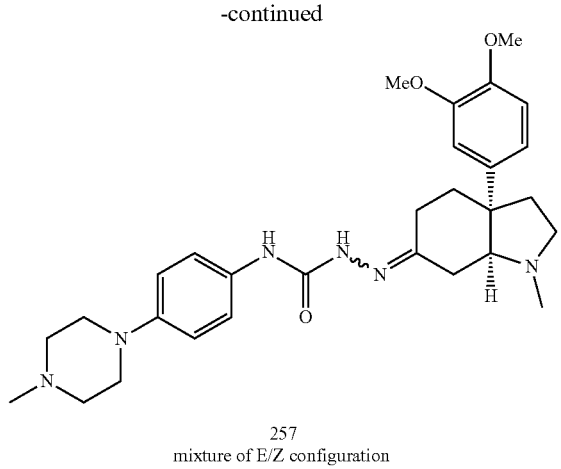

257
mixture of E/Z configuration

Step 1 N-[4-(4-methylpiperazin-1-yl)phenyl]imidazole-1-carboxamide (2)

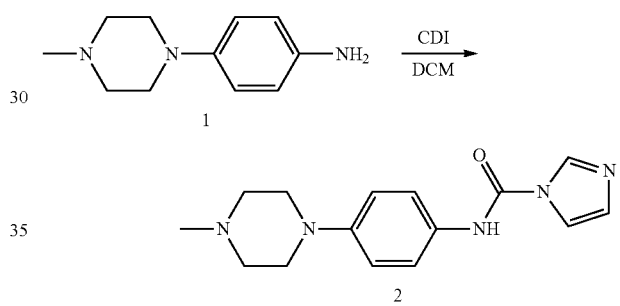

A mixture of 4-(4-methylpiperazin-1-yl)aniline (1.00 g, 5.23 mmol) CAS#16153-81-4, CDI (1.06 g, 6.54 mmol) CAS#530-62-1 in DCM (20 mL) was degassed and purged with N$_2$ for 3 times, and then the mixture was stirred at 25° C. for 1 hour under N$_2$ atmosphere. On completion, the reaction mixture was concentrated in vacuo to give a residue. The crude compound was used into the next step without further purification to give the title compound (3.4 g, crude) as black solid.

$^1$H NMR (400 MHz, CDCl$_3$) δ 7.69 (s, 3H), 7.45 (d, J=8.8 Hz, 1H), 7.23 (d, J=8.8 Hz, 1H), 7.11 (s, 5H), 6.98-6.78 (m, 2H), 3.18 (td, J=4.8, 16.8 Hz, 4H), 2.67-2.52 (m, 4H), 2.45-2.39 (m, 1H), 2.37 (d, J=2.0 Hz, 2H)

Step 2 1-amino-3-[4-(4-methylpiperazin-1-yl)phenyl]urea (3)

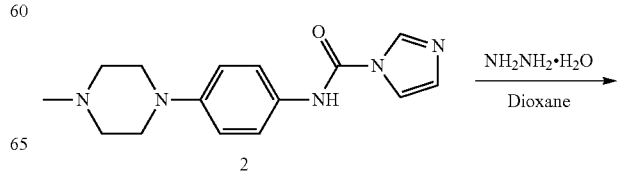

477

-continued

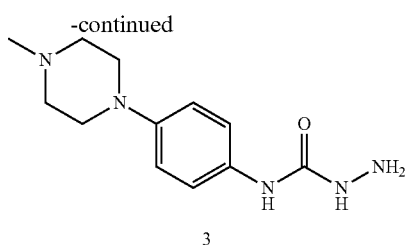

3

A mixture of N-[4-(4-methylpiperazin-1-yl)phenyl]imidazole-1-carboxamide (3.00 g, 10.5 mmol), NH2NH2·H2O (6.19 g, 105 mmol, 6.01 mL, 85% purity) in dioxane (20 mL) was degassed and purged with $N_2$ for 3 times, and then the mixture was stirred at 45° C. for 1 hour under $N_2$ atmosphere. On completion, the reaction mixture was filtered. The residue was purified by reverse-phase (basic condition) to give the title compound (250 mg, 8% yield) as brown solid.

LC-MS (ESI+) m/z 250.2 (M+H)+.

$^1$H NMR (400 MHz, CDCl$_3$) δ 7.88 (d, J=1.6 Hz, 1H), 7.38-7.32 (m, 2H), 6.93-6.88 (m, 2H), 5.84 (s, 1H), 3.82 (s, 2H), 3.21-3.15 (m, 4H), 2.62-2.58 (m, 4H), 2.37 (s, 3H).

Step 3 1-[[(3a5,7a5)-3a-(3,4-dimethoxyphenyl)-1-methyl-2,3,4,5,7,7a-hexahydroindol-6-ylidene]amino]-3-[4-(4-methylpiperazin-1-yl)phenyl]urea (257)

478

A mixture of (3 aS,7aS)-3a-(3,4-dimethoxyphenyl)-1-methyl-2,3,4,5,7,7a-hexahydroindol-6-one (255 mg, 882 umol), 1-amino-3-[4-(4-methylpiperazin-1-yl)phenyl]urea (220 mg, 882 umol, AcOH (53.0 mg, 882 umol, 50.5 uL) in EtOH (5 mL) was degassed and purged with $N_2$ for 3 times, and then the mixture was stirred at 60° C. for 1 hour under $N_2$ atmosphere. On completion, the reaction mixture was concentrated in vacuo to give a residue. The crude compound was used into the next step without further purification to give the title compound (420 mg, 84% yield) as brown solid.

LC-MS (ESI+) m/z 521.3 (M+H)+.

$^1$H NMR (400 MHz, CDCl$_3$) δ 8.36 (s, 1H), 8.23-7.97 (m, 1H), 7.39 (d, J=8.8 Hz, 2H), 6.97-6.85 (m, 3H), 6.82 (s, 2H), 3.93-3.85 (m, 6H), 3.24-3.20 (m, 3H), 3.14 (t, J=7.2 Hz, 1H), 3.02 (t, J=5.2 Hz, 1H), 2.80-2.77 (m, 3H), 2.75-2.57 (m, 2H), 2.44 (d, J=1.6 Hz, 3H), 2.42-2.29 (m, 3H), 2.24-2.09 (m, 3H), 2.03 (s, 6H).

Example 69

4-[[[[(3aS,7aS)-3a-(3,4-dimethoxyphenyl)-1-methyl-2,3,4,5,7,7a-hexahydroindol-6-ylidene]amino]carbamoylamino]methyl]cyclohexanecarboxylic acid (258)

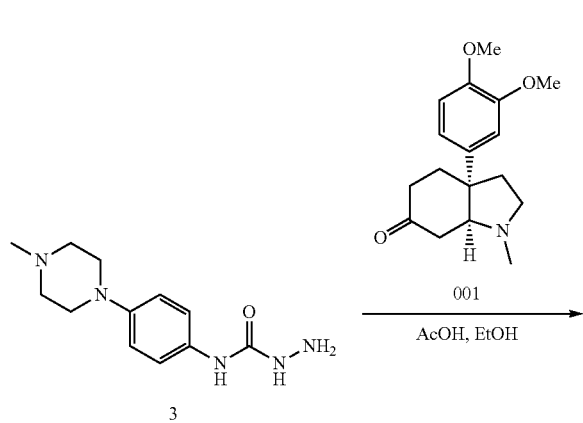

257
mixture of E/Z configuration

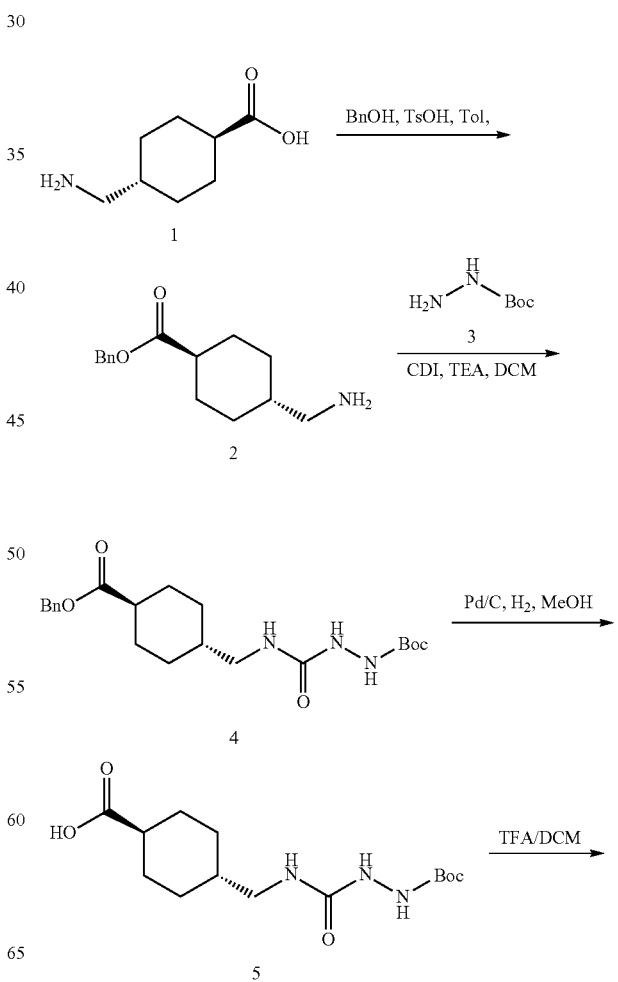

479

-continued

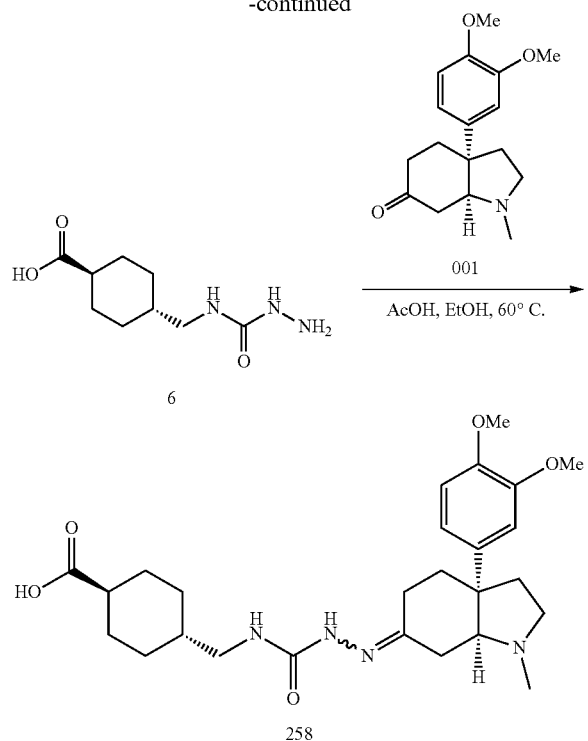

Step 1—4-(aminomethyl)cyclohexanecarboxylic acid (2)

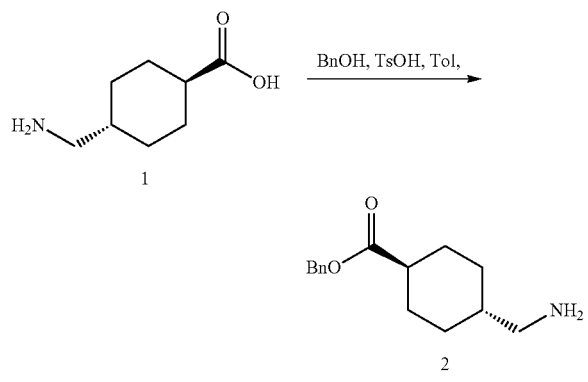

To a solution of 4-(aminomethyl)cyclohexanecarboxylic acid (0.5 g, 3.18 mmol) and phenylmethanol (2.60 g, 24.04 mmol, 2.50 mL) in toluene (10 mL) was added TsOH (629 mg, 3.66 mmol). The mixture was stirred at 130° C. for 24 hour. On completion, The solution was allowed to cool to room temp, and the product crystallized. The mixture was vacuum filtered, washed with ether and dried in a vacuum oven to give benzyl 4-(aminomethyl)cyclohexanecarboxylate (0.5 g, 63% yield) was obtained as a white solid.

2: LC-MS (ESI$^+$) m/z 248.16 (M+H)$^+$;

$^1$H NMR (400 MHz, CD$_3$OD) δ=7.76-7.68 (m, 2H), 7.40-7.29 (m, 2H), 7.24 (d, J=8.0 Hz, 2H), 5.15-5.10 (m, 2H), 2.83-2.75 (m, 3H), 2.43-2.26 (m, 4H), 2.12-2.00 (m, 3H), 1.95-1.80 (m, 3H), 1.69-1.54 (m, 2H), 1.53-1.34 (m, 3H), 1.16-0.98 (m, 3H)

480

Step 2—benzyl 4-(aminomethyl)cyclohexanecarboxylate (4)

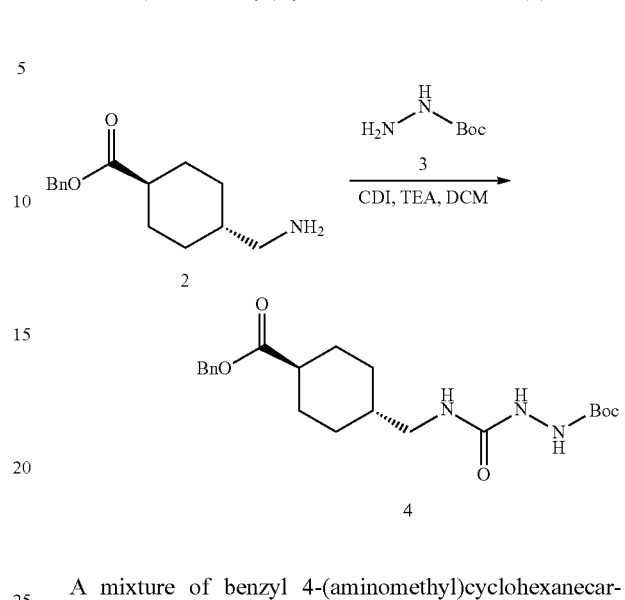

A mixture of benzyl 4-(aminomethyl)cyclohexanecarboxylate (0.5 g, 2.02 mmol, 1 eq), CDI (327 mg, 2.02 mmol), Boc-NHNH2 (267 mg, 2.02 mmol) and TEA (145 mg, 1.44 mmol, 0.2 mL) in DMF (5 mL) was degassed and purged with N$_2$ for 3 times, and then the mixture was stirred at 25° C. for 3 hr under N$_2$ atmosphere. On completion, filtered to remove the insoluble. The filter liquor was concentrated in vacuo. The crude product was purified by reversed-phase HPLC(0.1% NH$_3$·H$_2$O) to give benzyl 4-[[(tert-butoxycarbonylamino)carbamoylamino]methyl] cyclohexanecarboxylate (0.2 g, 24% yield) as a white solid.

LC-MS (ESI$^+$) m/z 306.10 (M+H-100)$^+$;

$^1$H NMR (400 MHz, CD$_3$OD) δ=7.34 (s, 2H), 5.10 (s, 2H), 3.06-2.93 (m, 2H), 2.38-2.20 (m, 1H), 2.05-1.93 (m, 2H), 1.84 (br dd, J=2.4, 13.2 Hz, 2H), 1.47 (s, 9H), 1.44 (br d, J=3.4 Hz, 1H), 1.43-1.32 (m, 2H), 1.05-0.90 (m, 2H)

Step 3—benzyl 4-[[(tert-butoxycarbonylamino)carbamoylamino]methyl]cyclohexanecarboxylate (int 5)

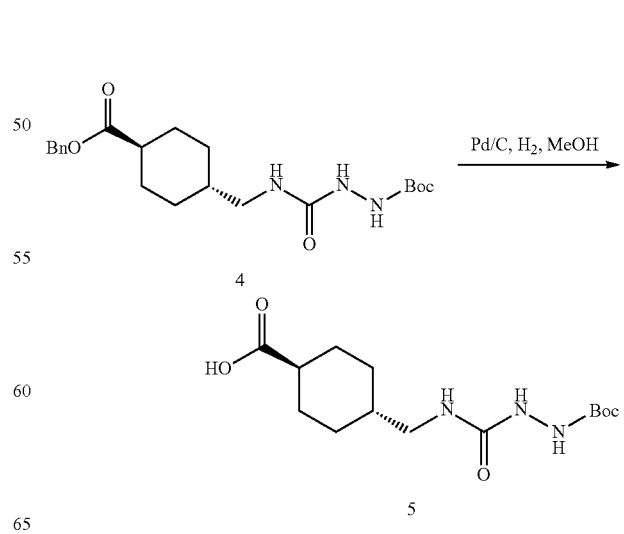

A mixture of benzyl 4-[[[(tert-butoxycarbonylamino)carbamoylamino]methyl]cyclohexanecarboxylate (0.2 g, 493.23 umol, 1 eq), Pd/C (20 mg, 493.23 umol, 0.5 mL, 10% purity, 1 eq) in MeOH (4 mL) was degassed and purged with N₂ for 3 times, and then the mixture was stirred at 25° C. for 3 hr under H₂ atmosphere. On completion, filtered to remove the insoluble. The filter liquor was concentrated in vacuo to give 4-[[(tert-butoxycarbonylamino)carbamoylamino]methyl]cyclohexanecarboxylic acid (120 mg, 77.15% yield) was obtained as a white solid.

LC-MS (ESI⁺) m/z 316.18 (M+H)⁺;

¹H NMR (400 MHz, MeOD) δ=2.97 (d, J=6.8 Hz, 2H), 2.21-2.09 (m, 1H), 1.94 (br dd, J=2.6, 13.3 Hz, 2H), 1.84-1.72 (m, 2H), 1.43 (s, 9H), 1.39-1.28 (m, 2H), 1.00-0.87 (m, 2H)

Step 4—4-[[(tert-butoxycarbonylamino)carbamoylamino]methyl]cyclohexanecarboxylic acid (6)

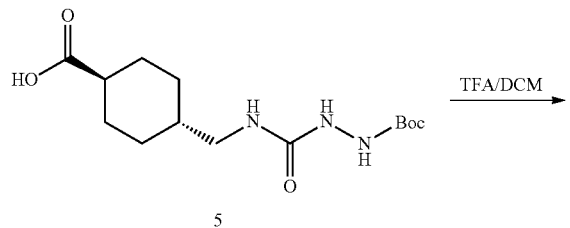

To a solution of 4-[[(tert-butoxycarbonylamino)carbamoylamino]methyl]cyclohexanecarboxylic acid (120 mg, 380 umol, 1 eq) in DCM (1 mL) was added TFA (770 mg, 6.75 mmol, 0.5 mL). The mixture was stirred at 0° C. for 1 hr. On completion, filtered to remove the insoluble. The filter liquor was concentrated in vacuo to give 4-[(hydrazinecarbonylamino)methyl]cyclohexanecarboxylic acid (80 mg, 97% yield) as a white solid.

¹H NMR (400 MHz, CD₃OD) δ=3.13-2.95 (m, 2H), 2.22 (ddd, J=3.6, 8.6, 12.1 Hz, 1H), 2.05-1.94 (m, 2H), 1.89-1.77 (m, 2H), 1.47 (s, 1H), 1.40 (dt, J=3.3, 12.7 Hz, 2H), 1.08-0.92 (m, 2H)

Step 5-4-[[[[(3aS,7aS)-3a-(3,4-dimethoxyphenyl)-1-methyl-2,3,4,5,7,7a-hexahydroindol-6-ylidene]amino]carbamoylamino]methyl]cyclohexanecarboxylic acid (258)

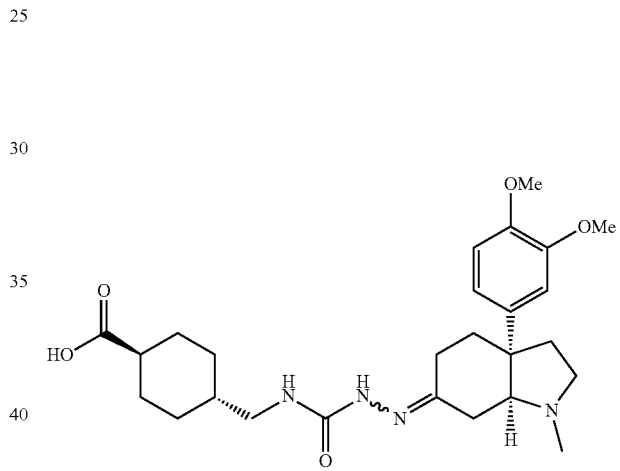

To a solution of (3aS,7aS)-3a-(3,4-dimethoxyphenyl)-1-methyl-2,3,4,5,7,7a-hexahydroindol-6-one (70 mg, 241 umol, EC3674-161-P1) and 4-[(hydrazinecarbonylamino)methyl]cyclohexanecarboxylic acid (52.0 mg, 241 umol) in EtOH (2 mL) was added AcOH (145 ug, 2.42 umol). The mixture was stirred at 60° C. for 16 hr. On completion, filtered to remove the insoluble. The filter liquor was concentrated in vacuo. The crude product was purified by prep-HPLC (column: Waters xbridge 150*25 mm 10 um; mobile phase: [water(NH4HCO3)-ACN]; B %: 3%-33%, 9 min). to give 4-[[[[(3aS,7aS)-3a-(3,4-dimethoxyphenyl)-1-methyl-2,3,4,5,7,7a-hexahydroindol-6-ylidene]amino]carbamoylamino]methyl]cyclohexanecarboxylic acid (30 mg, 25% yield) as a white solid.

LC-MS (ESI⁺) m/z 487.20 (M+H)⁺;

¹H NMR (400 MHz, CDCl₃) δ=7.89 (s, 1H), 6.85-6.73 (m, 3H), 6.29 (br t, J=6.4 Hz, 1H), 3.88 (s, 6H), 3.27-3.22 (m, 1H), 3.07 (br dd, J=6.8, 13.4 Hz, 2H), 2.97 (br t, J=4.6 Hz, 1H), 2.73-2.67 (m, 1H), 2.63-2.57 (m, 1H), 2.42-2.38 (m, 3H), 2.31-2.18 (m, 4H), 2.10-1.93 (m, 6H), 1.87 (br d, J=11.0 Hz, 2H), 1.53-1.46 (m, 1H), 1.45-1.36 (m, 2H), 1.06-0.96 (m, 2H).

Example 70

4-[[[(3aS,7aS)-3a-(3,4-dimethoxyphenyl)-1-methyl-2,3,4,5,7,7a-hexahydroindol-6-ylidene]amino]carbamoylamino]benzoic acid (259)

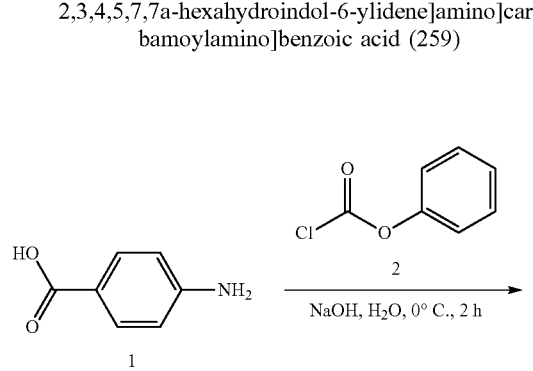

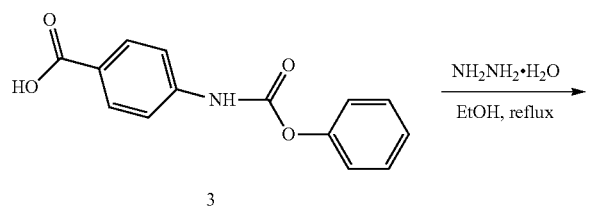

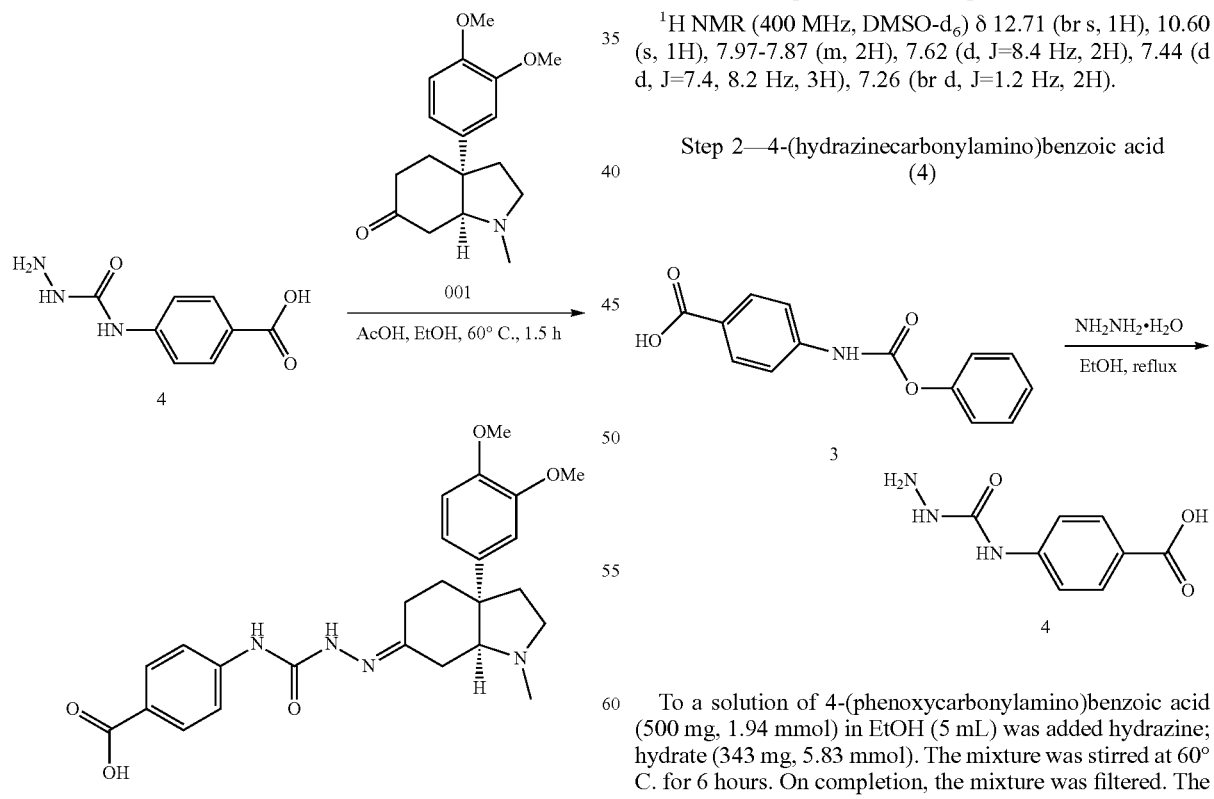

259
mixture of E/Z configuration

Step 1—4-(phenoxycarbonylamino)benzoic acid (3)

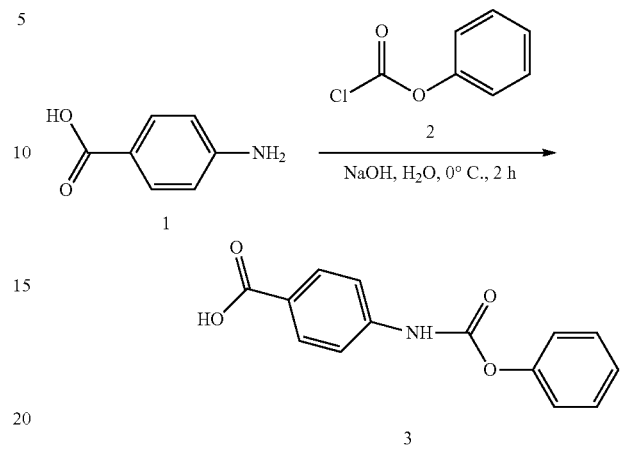

To a solution of 4-aminobenzoic acid (1.00 g, 7.29 mmol, CAS-15043-0) in $H_2O$ (2 was added NaOH (1 M, 7.29 mL) and phenyl carbonochloridate (1.14 g, 7.29 mmol). The mixture was stirred at 0° C. for 2 hours. On completion, the mixture was quenched with water (20 mL) and extracted with ethyl acetate (25 mL×3), the combined organic phase was dried over anhydrous sodium sulfate, filtered and concentrated to give a residue. The crude product 4-(phenoxycarbonylamino)benzoic acid (1.0 g, 53% yield) was used into the next step without further purification.

$^1$H NMR (400 MHz, DMSO-$d_6$) δ 12.71 (br s, 1H), 10.60 (s, 1H), 7.97-7.87 (m, 2H), 7.62 (d, J=8.4 Hz, 2H), 7.44 (dd, J=7.4, 8.2 Hz, 3H), 7.26 (br d, J=1.2 Hz, 2H).

Step 2—4-(hydrazinecarbonylamino)benzoic acid (4)

To a solution of 4-(phenoxycarbonylamino)benzoic acid (500 mg, 1.94 mmol) in EtOH (5 mL) was added hydrazine; hydrate (343 mg, 5.83 mmol). The mixture was stirred at 60° C. for 6 hours. On completion, the mixture was filtered. The crude product 4-(hydrazinecarbonylamino)benzoic acid (300 mg, 79% yield) was used into the next step without further purification. $^1$H NMR (400 MHz, DMSO-$d_6$) δ 9.04 (br s, 1H), 7.86-7.72 (m, 2H), 7.71-7.53 (m, 2H).

485

Step-3—4-[[[(3aS,7aS)-3a-(3,4-dimethoxyphenyl)-1-methyl-2,3,4,5,7,7a-hexahydroindol-6-ylidene]amino]carbamoylamino]benzoic acid (259)

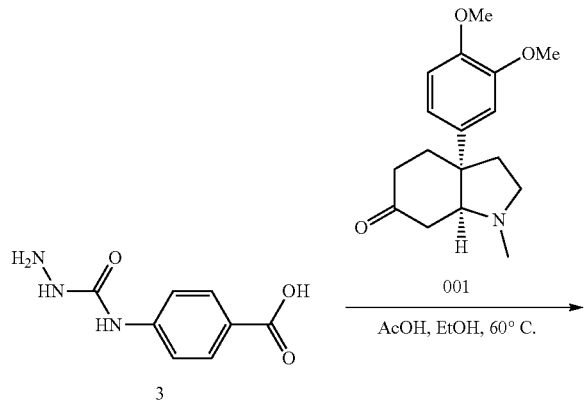

To a solution of 4-(hydrazinecarbonylamino)benzoic acid (70 mg, 358 umol) and (3aS,7aS)-3a-(3,4-dimethoxyphenyl)-1-methyl-2,3,4,5,7,7a-hexahydroindol-6-one (103 mg, 358 umol) in EtOH (1 mL) was added AcOH (2 mg, 35.9 umol). The mixture was stirred at 60° C. for 1.5 hours. On completion, the mixture was filtered. The crude product was triturated with EtOH (1 mL) at 25° C. for 1.0 min to give 4-[[[(3aS,7aS)-3a-(3,4-dimethoxyphenyl)-1-methyl-2,3,4,5,7,7a-hexahydroindol-6-ylidene]amino]carbamoylamino]benzoic acid (130 mg, 95% purity) as a of-white solid.

LC-MS (ESI+) m/z 467.2 (M+H)+, $^1$H NMR (400 MHz, DMSO-$d_6$) δ 9.49 (s, 1H), 9.11-8.90 (m, 1H), 7.89-7.79 (m, 2H), 7.73(d, J=8.4 Hz, 2H), 6.94-6.81 (m, 3H), 3.74 (d, J=11.2 Hz, 6H), 2.91(br t, J=7.2 Hz, 1H), 2.77 (t, J=4.4 Hz, 1H), 2.65 (br dd, J=3.2, 14.4 Hz, 1H), 2.38-2.31 (m, 1H), 2.27(s, 3H), 2.22-2.13(m, 1H), 2.12-1.84 (m, 6H).

Example 71

N-[[(3aS,7aS)-3a-(3,4-dimethoxyphenyl)-1-methyl-3,4,5,7a-tetrahydro-2H-indol-6-yl]pentanoate (268)

To a solution of (3aS,7aS)-3a-(3,4-dimethoxyphenyl)-1-methyl-2,3,4,5,7,7a-hexahydroindol one (150 mg, 518 umol) and pentanoyl pentanoate (193 mg, 1.04 mmol CAS#2082-59-9) in THF (3 mL) was added LDA (2 M, 259 uL). The mixture was stirred at −78-25° C. for 1 hour. On completion, the reaction mixture was quenched by adding it to a cold saturated aqueous NH$_4$Cl solution (3 mL). The aqueous layer was extracted with ethyl acetate (5 mL×2). The organic layer was separated, dried over anhydrous Na$_2$SO$_4$, filtered and concentrated under reduced pressure to give the residue. The residue was purified by prep-TLC (SiO$_2$, DCM: MeOH=10:1) to give N-[[(3aS,7aS)-3a-(3,4-dimethoxyphenyl)-1-methyl-3,4,5,7a-tetrahydro-2H-indol-6-yl] pentanoate (24 mg, 59% yield) as an off-white gum.

LC-MS (ESI+) m/z 374.4 (M+H)+

$^1$H NMR (400 MHz, CDCl$_3$) δ 6.99-6.79 (m, 3H), 5.71-5.68 (m, 1H), 3.94-3.83 (m, 6H), 3.20 (dt, J=2.0, 8.4 Hz, 1H), 2.85 (d, J=4.4 Hz, 1H), 2.65-2.44 (m, 1H), 2.40-2.37 (m, 3H), 2.31-2.10 (m, 4H), 2.05-1.86 (m, 2H), 1.83 (d, J=4.4 Hz, 1H), 1.78-1.70 (m, 1H), 1.70-1.56 (m, 2H), 1.40-1.29 (m, 2H), 0.92 (t, J=7.2 Hz, 3H).

487

Example 72

1 N-[[(3aS,7aS)-3a-(3,4-dimethoxyphenyl)-1-methyl-2,3,4,5,7,7a-hexahydroindol-6-ylidene]amino]adamantane-1-carboxamide (271)

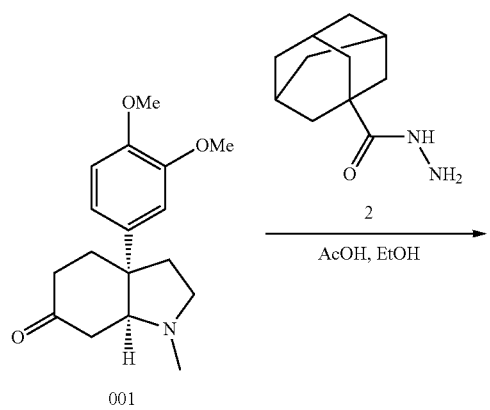

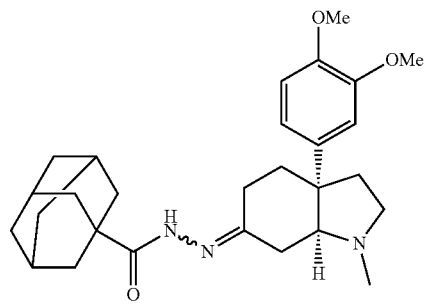

A mixture of (3aS,7aS)-3a-(3,4-dimethoxyphenyl)-1-methyl-2,3,4,5,7,7a-hexahydroindol-6-one (100 mg, 345 umol), adamantane-1-carbohydrazide (67.1 mg, 345 umol, CAS#17846-15-0) in EtOH (2.00 mL) was degassed and purged with N₂ for 3 times, and then the mixture was stirred at 60° C. for 2 hours under N₂ atmosphere. On completion, the reaction mixture was concentrated in vacuo to give a residue. The crude compound was used into the next step without further purification to give the title compound (110 mg, 77% yield) as white solid.

LC-MS (ESI+) m/z 466.3 (M+H)+.

$^1$H NMR (400 MHz, CDCl$_3$) δ 8.20 (s, 1H), 6.87-6.78 (m, 3H), 4.00-3.81 (m, 6H), 3.27-2.78 (m, 2H), 2.74 (s, 1H), 2.42 (d, J=1.2 Hz, 3H), 2.31 (dd, J=4.8, 9.6 Hz, 3H), 2.04 (s, 4H), 2.00-1.83 (m, 7H), 1.81-1.51 (m, 9H)

488

Example 73

1-[(E,3aS,7aS)-N-(1-adamantylmethoxy)-3a-(3,4-dimethoxyphenyl)-1-methyl-2.3.4.5.7.7a-hexahydroindol-6-imine- (275)

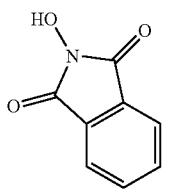
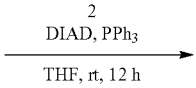
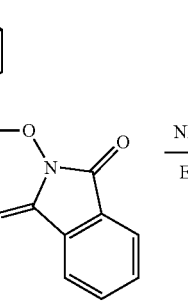
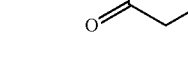
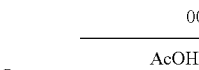
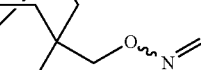

489

Step 1—N-[2-(1-adamantylmethoxy)isoindoline-1,3-dione (Int 3)

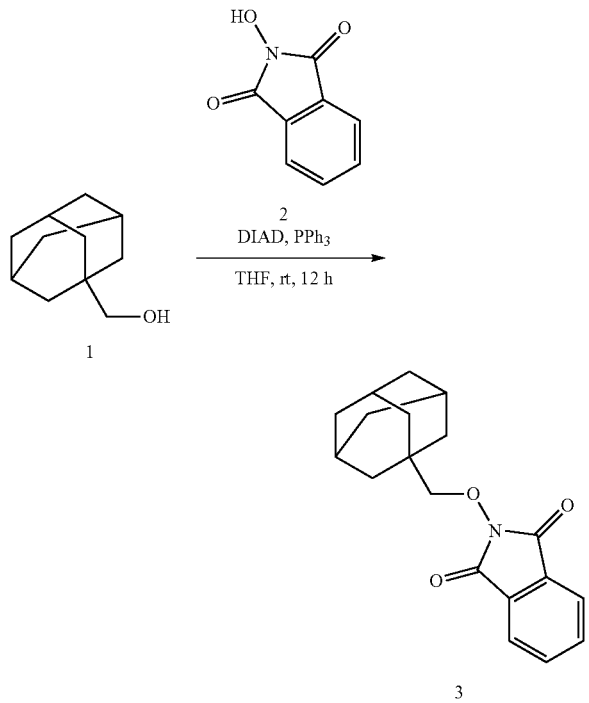

To a solution of 1-adamantylmethanol (2 g, 12.0 mmol CAS#17471-43-1) and 2-hydroxyisoindoline-1, 3-dione (1.96 g, 12.0 mmol CAS# 524-38-9) in THF (10 mL) was added PPh3 (4.73 g, 18.0 mmol) and DIAD (3.65 g, 18.0 mmol, 3.51 mL). The mixture was stirred at 25° C. for 12 hours. On completion, the reaction mixture was concentrated in vacuo to give a residue. The residue was purified by column chromatography (SiO$_2$, Petroleum ether/Ethyl acetate=10:1) to give N-[2-(1-adamantylmethoxy) isoindoline-1, 3-dione (1g, 30% yield) as off-white oil.

LC-MS (ESI$^+$) m/z 311.9 (M+H)$^+$ $^1$H NMR (400 MHz, CDCl$_3$) δ 7.83 (dd, J=3.2, 5.2 Hz, 2H), 7.74 (dd, J=3.2, 5.6 Hz, 2H), 3.80 (s, 2H), 2.04 (s, 3H), 1.80-1.70 (m, 12H).

Step2—O-(1-adamantylmethyl)hydroxylamine- (Int 4)

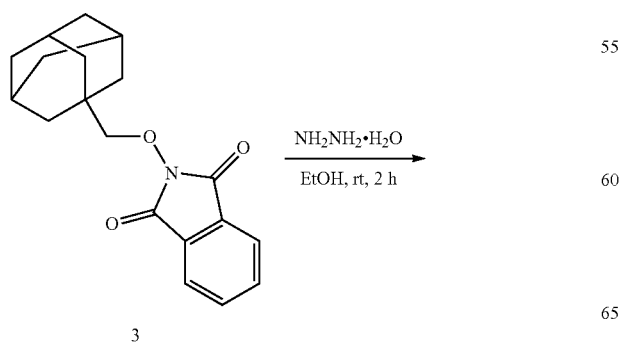

490

-continued

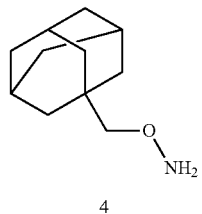

To a solution of 2-(1-adamantylmethoxy) isoindoline-1, 3-dione (500 mg, 1.61 mmol) in EtOH (5 mL) was added NH$_2$NH$_2$·H$_2$O (473 mg, 8.03 mmol, 459 uL, 85% purity). The mixture was stirred at 60° C. for 3 hours. On completion, the reaction mixture was quenched by adding it to a cold saturated aqueous NH$_4$Cl solution (5 mL). The aqueous layer was extracted with ethyl acetate (5 mL×2). The organic layer was separated, dried over anhydrous Na$_2$SO$_4$, filtered and concentrated under reduced pressure to give the residue. The residue was purified by column chromatography (SiO$_2$, Petroleum ether/Ethyl acetate=10/1 to 0/1) to give O-(1-adamantylmethyl) hydroxylamine (270 mg, 38% yield) as a yellow solid.

LC-MS (ESI$^+$) m/z 311.9 (M+H)$^+$ $^1$H NMR (400 MHz, CDCl$_3$) δ=5.58-5.13 (m, 2H), 3.30-3.30 (m, 2H), 1.97 (s, 3H), 1.77-1.60 (m, 7H), 1.55 (d, J=2.4 Hz, 6H).

Step3—1-[(E,3aS,7aS)-N-(1-adamantylmethoxy)-3a-(3,4-dimethoxyphenyl)-1-methyl-2,3,4,5,7,7a-hexahydroindol-6-imine- (275)

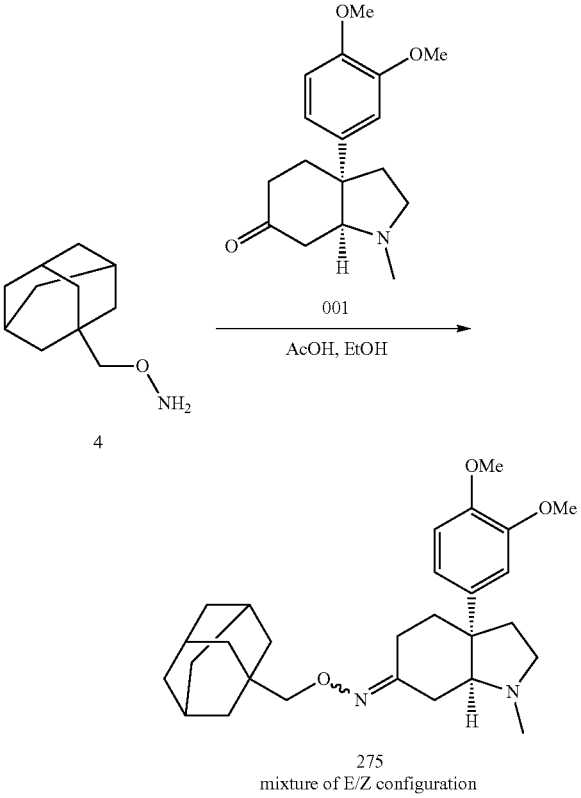

275
mixture of E/Z configuration

To a solution of (3aS,7aS)-3a-(3,4-dimethoxyphenyl)-1-methyl-2,3,4,5,7,7a-hexahydroindol-6-one (100 mg, 346 umol) and O-(1-adamantylmethyl)hydroxylamine (62.7 mg, 346 umol) in EtOH (3 mL) was added AcOH (20.8 mg, 346 umol, 19.8 uL). The mixture was stirred at 60° C. for 1 hour. On completion, the reaction mixture was concentrated in vacuo to give a residue. The residue was purified by prep-HPLC (column: Phenomenex luna $C_{18\ 150*25}$ mm*10 um; mobile phase: [water(FA)-ACN]; B %: 24%-54%, 9 min). to give 1-[(E,3aS,7aS)-N-(1-adamantylmethoxy)-3a-(3,4-dimethoxyphenyl)-1-methyl-2,3,4,5,7,7a-hexahydroindol-6-imine (108 mg, 68% yield) as a white gum.

LC-MS (ESI$^+$) m/z 457.2 (M+H)$^+$ $^1$H NMR (400 MHz, CDCl$_3$) δ=6.82-6.75 (m, 3H), 3.92-3.85 (m, 6H), 3.68-3.58 (m, 2H), 3.52-3.37 (m, 1H), 3.36-3.24 (m, 1H), 2.83-2.70 (m, 3H), 2.62 (s, 4H), 2.55-2.47 (m, 3H), 2.45-2.37 (m, 3H), 2.29 (dd, J=6.6, 10.4 Hz, 2H), 2.18-2.06 (m, 2H), 2.01-1.86 (m, 4H), 1.74-1.66 (m, 3H), 1.61 (d, J=13.6 Hz, 3H).

Example 74

(3aS,7aS)-N-[2-(1-adamantyl)ethoxy]-3a-(3,4-dimethoxyphenyl)-1-methyl-2,3,4,5,7,7a-hexahydroindol-6-imine- (276)

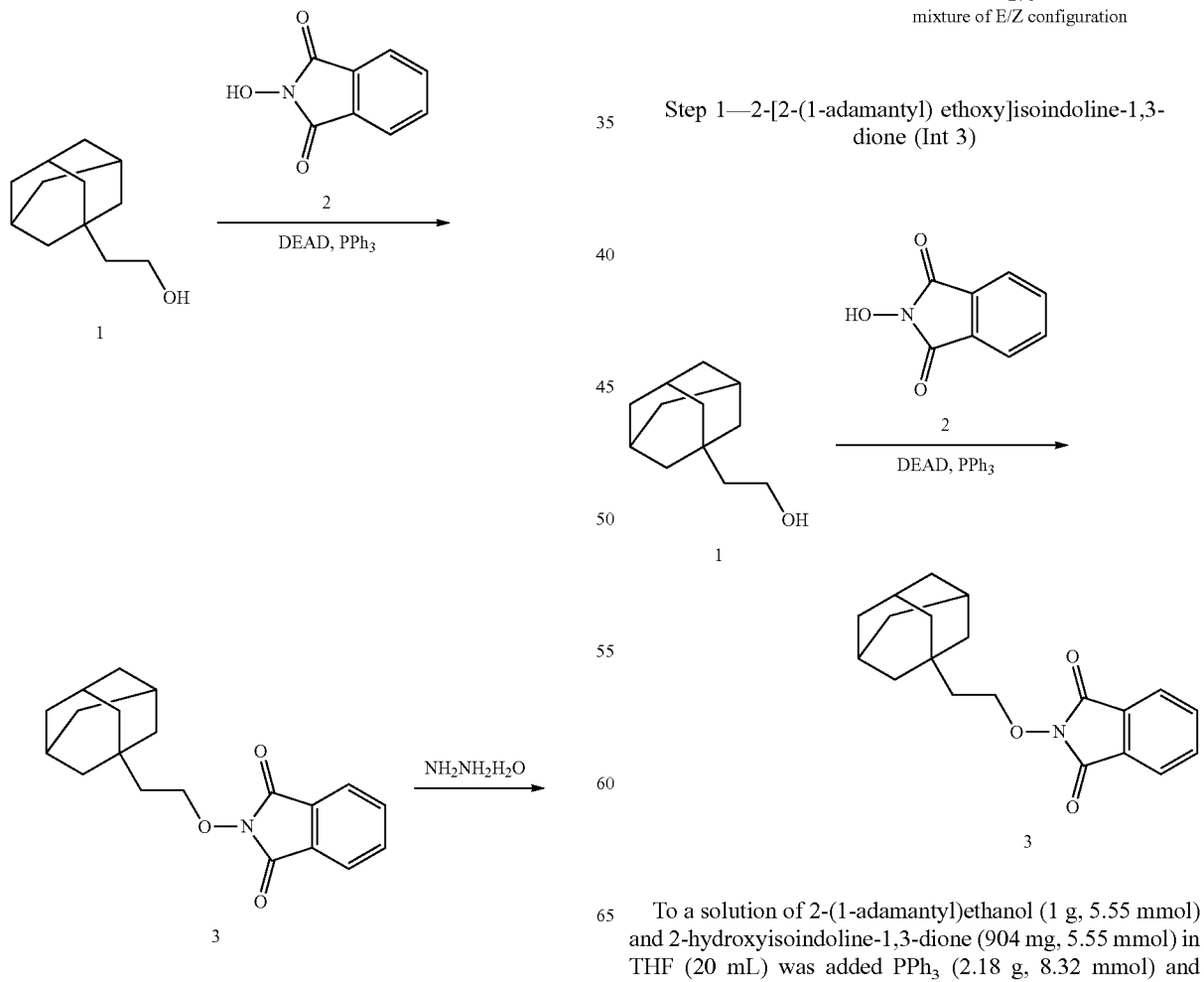

Step 1—2-[2-(1-adamantyl) ethoxy]isoindoline-1,3-dione (Int 3)

To a solution of 2-(1-adamantyl)ethanol (1 g, 5.55 mmol) and 2-hydroxyisoindoline-1,3-dione (904 mg, 5.55 mmol) in THF (20 mL) was added PPh$_3$ (2.18 g, 8.32 mmol) and DIAD (1.68 g, 8.32 mmol, 1.62 mL,). The mixture was stirred at 0° C. for 5 hours. On completion, the reaction mixture was quenched by addition water 20 mL at 25° C., and then diluted with water 20 mL and extracted with EtOAc (50 mL*3). The combined organic layers were washed with saturated salt solution 20 mL (20 mL*2), dried over [Na₂SO₄], filtered and concentrated under reduced pressure to give a residue. The residue was purified by column chromatography (SiO₂, Petroleum ether/Ethyl acetate=10/1 to 10/1) to give 2-[2-(1-adamantyl) ethoxy]isoindoline-1,3-dione (0.7 g, 38% yield) as a white solid.

2: LC-MS (ESI⁺) m/z 326.00 (M+H)⁺;

¹H NMR (400 MHz, CDCl₃) δ 7.89-7.69 (m, 4H), 4.28 (t, J=7.4 Hz, 2H), 1.97 (br s, 3H), 1.73-1.62 (m, 8H), 1.58 (d, J=2.4 Hz, 6H)

Step 2—O-[2-(1-adamantyl)ethyl]hydroxylamine (int 4)

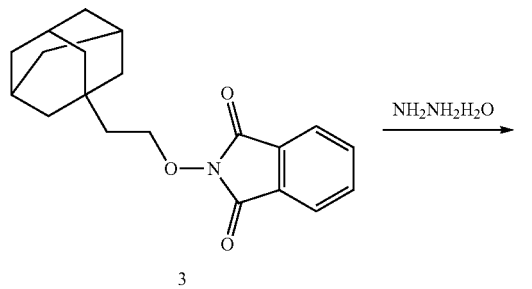

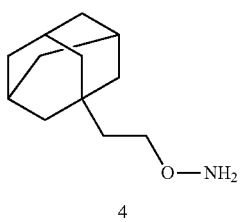

To a solution of 2-[2-(1-adamantyl)ethoxy]isoindoline-1, 3-dione (0.7 g, 2.15 mmol) in DCM (2.5 mL) and EtOH (0.5 mL) was added NH₂NH₂·H₂O (430 mg, 8.60 mmol, 418 uL). The mixture was stirred at 25° C. for 16 hours. On completion, the mixture was filtered to remove the insoluble. The filter liquor was concentrated in vacuo to give O-[2-(1-adamantyl)ethyl]hydroxylamine (130 mg, 30% yield) as a colourless oil.

4: LC-MS (ESI⁺) m/z 196.17 (M+H–100)⁺;

¹H NMR (400 MHz, CDCl₃) δ 5.74-4.98 (m, 2H), 3.73 (t, J=7.4 Hz, 2H), 1.94 (br s, 3H), 1.72-1.60 (m, 6H), 1.52 (d, J=2.4 Hz, 6H), 1.36 (t, J=7.4 Hz, 2H)

Step 3—(3a5,7a5)-N-[2-(1-adamantyl)ethoxy]-3a-(3,4-dimethoxyphenyl)-1-methyl-2,3,4,5,7,7a-hexahydroindol-6-imine (276)

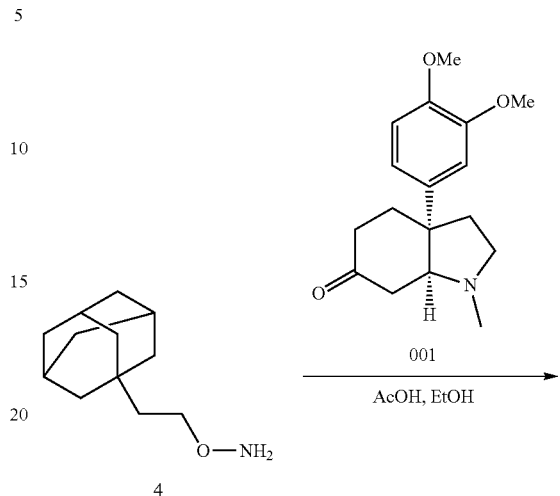

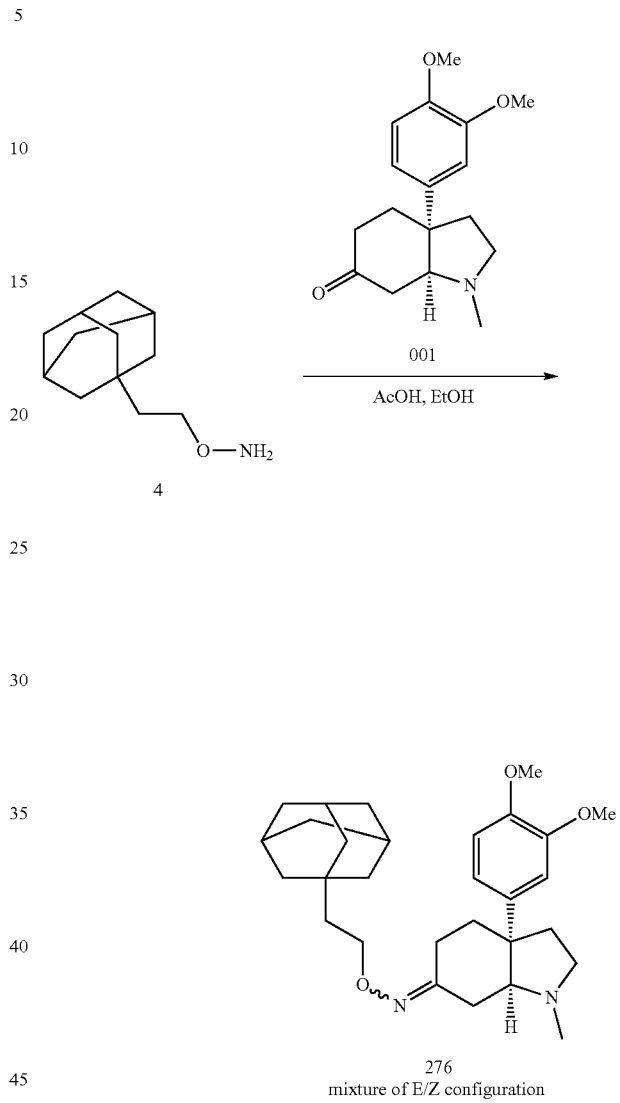

276
mixture of E/Z configuration

To a solution of (3aS,7aS)-3a-(3,4-dimethoxyphenyl)-1-methyl-2,3,4,5,7,7a-hexahydroindol-6-one (150 mg, 518 umol) in EtOH (2 mL) was added AcOH (3.11 mg, 51.8 umol, 2.96 uL) and O-[2-(1-adamantyl)ethyl]hydroxylamine (121 mg, 622 umol). The mixture was stirred at 60° C. for 3 hours. On completion, filtered to remove the insoluble. The filter liquor was concentrated in vacuo. The crude product was purified by prep-HPLC (column: Waters xbridge 150*25 mm 10 um; mobile phase: [water (NH₄HCO₃)-ACN]; B %: 80%-100%, 8 min) to give (3aS, 7aS)-N-[2-(1-adamantyl)ethoxy]-3a-(3,4-dimethoxyphenyl)-1-methyl-2,3,4,5,7,7a-hexahydroindol-6-imine (130 mg, 53% yield) as a white gum.

LC-MS (ESI⁺) m/z 46720 (M+H)⁺;

¹H NMR (400 MHz, CDCl₃) δ=6.94-6.79 (m, 3H), 4.13-4.01 (m, 2H), 3.92-3.84 (m, 6H), 3.25-3.00 (m, 1H), 2.89-2.72 (m, 1H), 2.62-2.46 (m, 2H), 2.37 (s, 3H), 2.32-2.24 (m, 1H), 2.22-2.11 (m, 2H), 2.10-1.99 (m, 2H), 1.97-1.89 (m, 4H), 1.72-1.67 (m, 3H), 1.62 (br d, J=10.6 Hz, 4H), 1.56-1.49 (m, 6H), 1.47-1.37 (m, 2H).

Example 75

(3'aS,7'aS)-4-(1-adamantyl)-3'a-(3,4-dimethoxyphenyl)-1'-methyl-spiro[1,3-dioxolane-2,6'-2,3,4,5,7,7a-hexahydroindole]- (281)

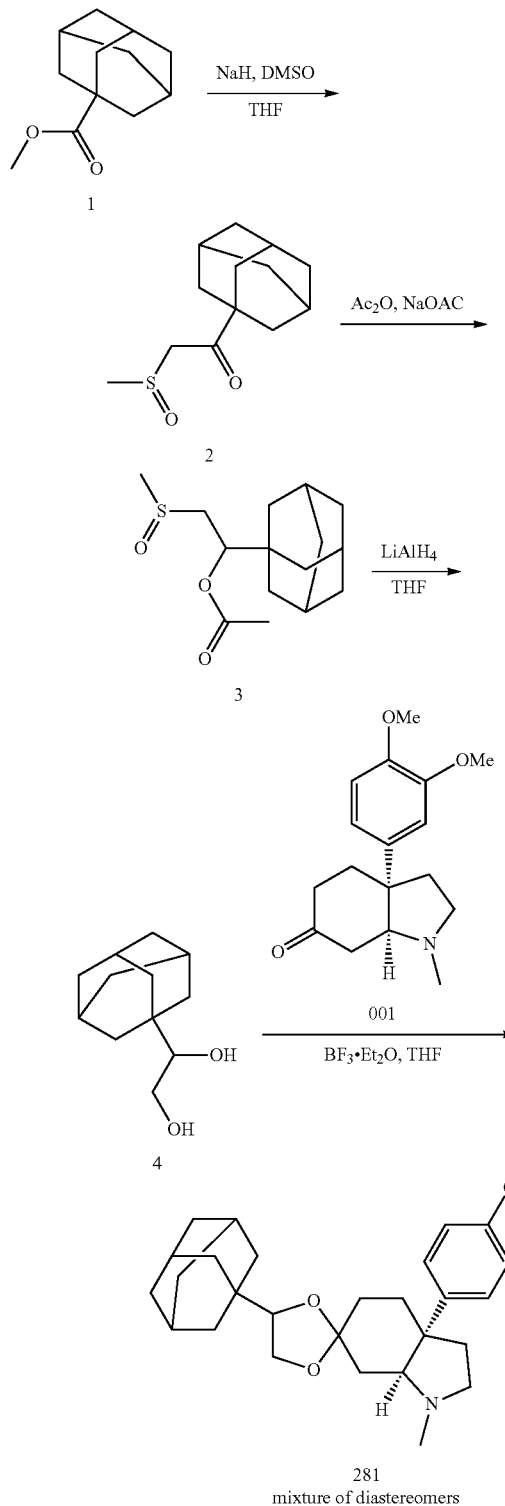

281
mixture of diastereomers

Step 1 1-(1-adamantyl)-2-methylsulfinyl-ethanone- (int.2)

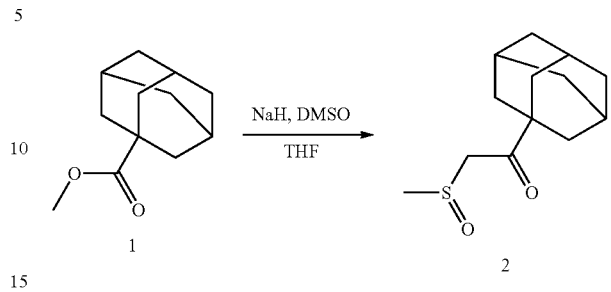

To a solution of DMSO (6.00 g, 76.81 mmol, 6.00 mL) was added NaH (576 mg, 14.4 mmol, 60% purity) at 0° C. Then ethyl adamantane-1-carboxylate (1 g, 4.80 mmol) in THF (5 mL) was added dropwise to the mixture. The mixture was stirred at 65° C. for 1 hour under $N_2$ atmosphere. On completion, the mixture was poured to $NH_4Cl$ aq (20 mL) and extracted with ethyl acetate (50 mL). The organic layers was dried by sodium sulfate, filtered and concentrated in vacuo to give the 1-(1-adamantyl)-2-methylsulfinyl-ethanone (1.2 g, 83% yield) as yellow solid.

LC-MS (ESI+) m/z 241.1 (M+H)+.

$^1$H NMR (400 MHz, CDCl$_3$) δ=4.18 (d, J=15.2 Hz, 1H), 3.80 (d, J=15.2 Hz, 1H), 2.73 (s, 3H), 2.09 (s, 3H), 1.83 (d, J=2.4 Hz, 5H), 1.68 (s, 7H).

Step 2 [1-(1-adamantyl)-2-methylsulfanyl-2-oxo-ethyl] acetate- (int.3)

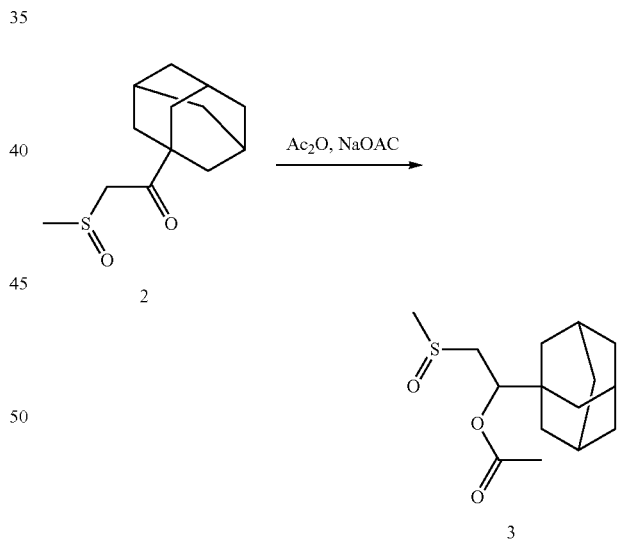

To a solution of 1-(1-adamantyl)-2-methylsulfinyl-ethanone (1.2 g, 4.99 mmol) was added sodium; acetate (901 mg, 11.0 mmol) and Ac$_2$O (10.7 g, 104 mmol, 9.82 mL). The mixture was stirred at 110° C. for 4 hours. On completion, the mixture was poured to the water (10 mL) and extracted with ethyl acetate (30 mL). The organic layers was dried by sodium sulfate, filtered and concentrated in vacuo to give the [1-(1-adamantyl)-2-methylsulfanyl-2-oxo-ethyl] acetate (900 mg, 64% yield) as a yellow solid.

$^1$H NMR (400 MHz, CDCl$_3$) δ=6.21 (s, 1H), 2.14 (s, 3H), 2.02 (s, 3H), 1.97-1.90 (m, 6H), 1.85-1.63 (m, 12H)

Step 3 1-(1-adamantyl)ethane-1,2-diol- (int.4)

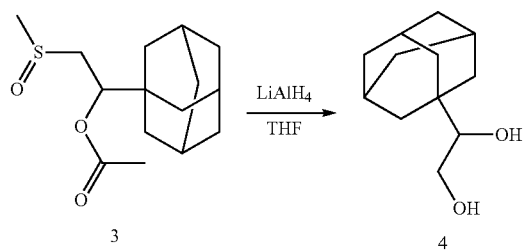 [SMILES: CC(=O)OC(CS(C)=O)C12CC3CC(CC(C3)C1)C2 ; "LiAlH4" ; OCC(O)C12CC3CC(CC(C3)C1)C2 ; "THF"]

To a solution of [1-(1-adamantyl)-2-methylsulfanyl-2-oxo-ethyl] acetate (450 mg, 1.59 mmol) in THF (5 mL) was added LiAlH4 (90.7 mg, 2.39 mmol) in THF (5 mL) at 0° C. The mixture was stirred at 70° C. for 3 hours. On completion, the mixture was poured to the water (10 mL) and extracted with ethyl acetate (30 mL). The organic layers was dried by sodium sulfate, filtered and concentrated in vacuo to give the residue. The residue purified by prep-TLC (petroleum ether:ethyl acetate=5:1).to give 1-(1-adamantyl) ethane-1,2-diol (100 mg, 30% yield) as a white solid.

$^1$H NMR (400 MHz, CDCl$_3$-d) δ=3.82-3.65 (m, 1H), 3.62-3.50 (m, 1H), 3.27-3.14 (m, 1H), 1.97 (s, 3H), 1.77-1.45 (m, 14H)

Step 3 (3'aS,7'aS)-4-(1-adamantyl)-3'a-(3,4-dimethoxyphenyl)-1'-methyl-spiro[1,3-dioxolane-2,6'-2,3,4,5,7,7a-hexahydroindole]- (281)

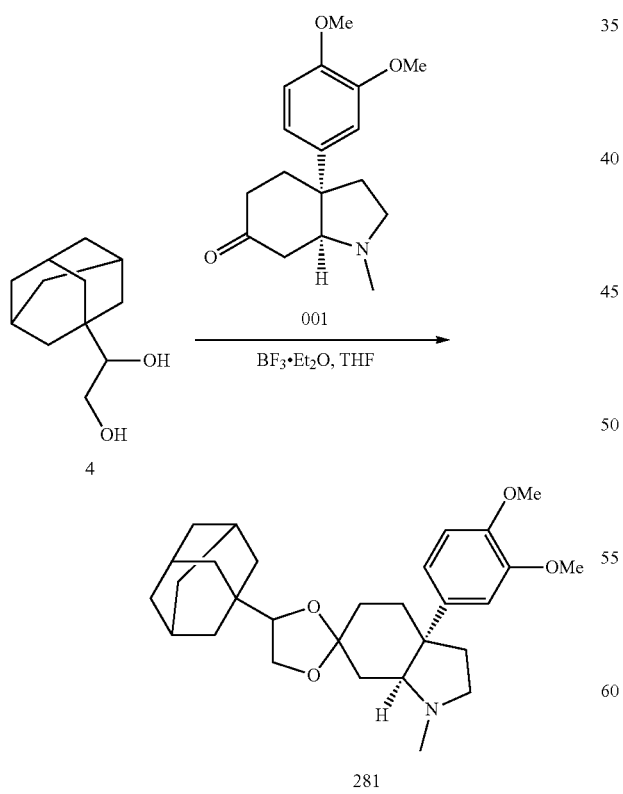

To a solution of (3aS,7aS)-3a-(3,4-dimethoxyphenyl)-1-methyl-2,3,4,5,7,7a-hexahydroindol-6-one (29.4 mg, 101 umol) and 1-(1-adamantyl)ethane-1,2-diol (60 mg, 305 umol) in THF (1 mL) was added BF3.Et2O (28.9 mg, 204 umol, 25.2 uL,) and 4A MS (102 umol). The mixture was stirred at 70° C. for 72 hours. On completion, the reaction mixture was filtered, concentrated in vacuo to give the residue. The residue was purified by prep-HPLC (column: Phenomenex luna C$_{18}$ $_{150*25}$ mm*10 um; mobile phase: [water(FA)-ACN]; B %: 32%-62%, 58 min) to give (3'aS, 7'aS)-4-(1-adamantyl)-3'a-(3,4-dimethoxyphenyl)-1'-methyl-spiro[1,3-dioxolane-2,6'-2,3,4,5,7,7a-hexahydroindole] (7.00 mg, 7.0% yield) as a white solid.

LC-MS (ESI+) m/z 468.2 (M+H)+.

$^1$H NMR (400 MHz, CDCl3) δ=6.89-6.79 (m, 3H), 4.37 (d, J=7.2 Hz, 1H), 4.20-4.07 (m, 1H), 3.93 (s, 3H), 3.89 (s, 3H), 3.85-3.80 (m, 1H), 3.77-3.67 (m, 1H), 3.44 (s, 1H), 3.23-3.08 (m, 3H), 2.40-2.32 (m, 1H), 2.31-2.25 (m, 2H), 2.20-2.09 (m, 3H), 1.97 (s, 3H), 1.73-1.63 (m, 12H), 1.46 (s, 2H), 1.30-1.25 (m, 1H).

Example 76

[(3a5,7a5)-3a-(3,4-dimethoxyphenyl)-1-methyl-3,4,5,7a-tetrahydro-2H-indol-6-yl] 2-methylbenzoate (298)

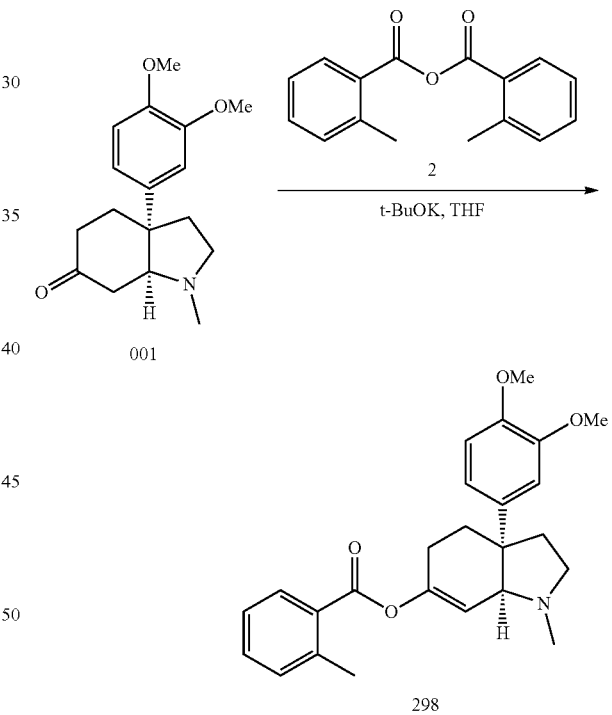

To a solution of (3 aS,7aS)-3a-(3,4-dimethoxyphenyl)-1-methyl-2,3,4,5,7,7a-hexahydroindol-6-one (100 mg, 345 umol) in THF (1.0 mL) was added t-BuOK (1 M, 691 uL) and (2-methylbenzoyl) 2-methylbenzoate (175 mg, 691 umol) at 0° C. The mixture was stirred at 25° C. for 2 hours. The reaction mixture was concentrated in vacuo to give the residue. The residue purified by prep-TLC (DCM: MeOH=10:1) to give the [(3aS,7aS)-3a-(3,4-dimethoxyphenyl)-1-methyl-3,4,5,7a-tetrahydro-2H-indol-6-yl] 2-methylbenzoate (52.1 mg, 35% yield) was obtained as a white solid.

LC-MS (ESI$^+$) m/z 408.1 (M+H)$^+$.

¹H NMR (400 MHz, CDCl₃) δ 7.94-7.85 (m, 1H), 7.40-7.31 (m, 1H), 7.22-7.19 (m, 1H), 7.17 (s, 1H), 6.88 (d, J=1.8 Hz, 1H), 6.85-6.75 (m, 2H), 5.78 (d, J=4.4 Hz, 1H), 3.87 (s, 3H), 3.81 (s, 3H), 3.19 (br t, J=7.6 Hz, 1H), 2.90 (br s, 1H), 2.52 (s, 3H), 2.37 (s, 3H), 2.32-2.22 (m, 2H), 2.18-2.06 (m, 2H), 1.91 (br d, J=6.4 Hz, 2H), 1.77-1.68 (m, 1H).

Example 77

1-[[(3aS,7aS)-3a-(3,4-dimethoxyphenyl)-1-methyl-2,3,4,5,7,7a-hexahydroindol-6-ylidene]amino]-3-(3-pyridyl)urea (299)

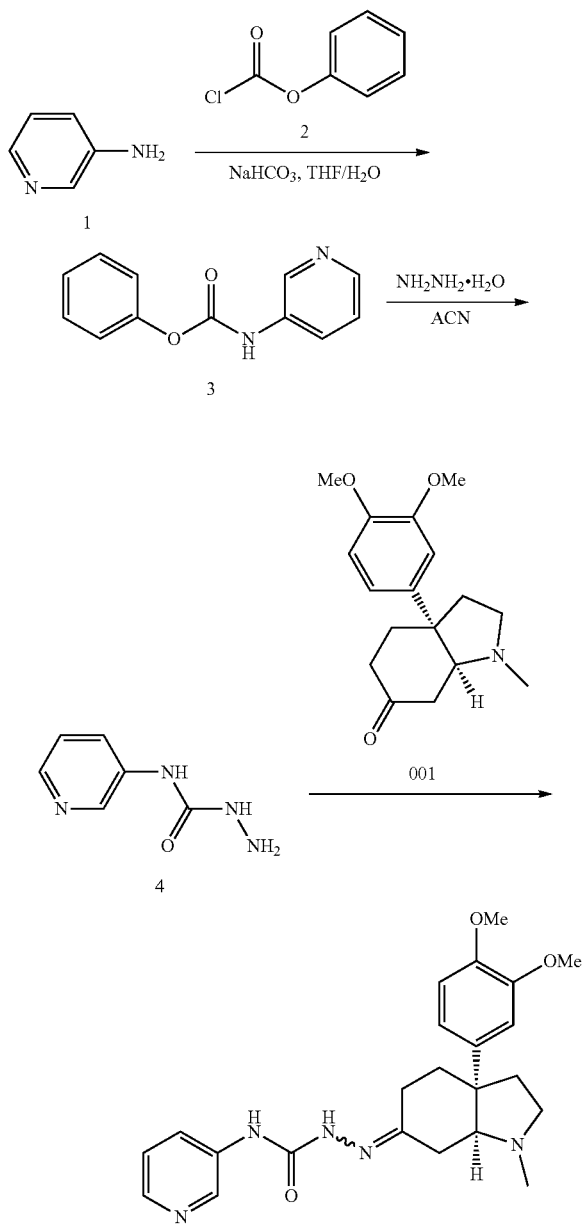

Step 1—phenyl N-(3-pyridyl)carbamate (Int3)

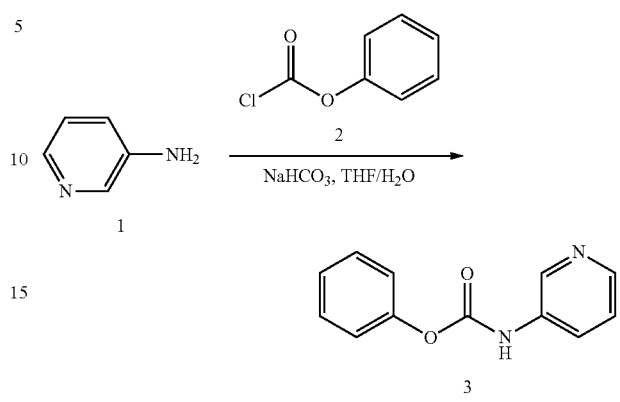

To a solution of pyridin-3-amine (2.00 g, 21.2 mmol) in THF (5.0 mL) and H₂O (5.0 mL) was added NaHCO₃ (1.79 g, 21.2 mmol, 826 uL) and phenyl carbonochloridate (3.33 g, 21.2 mmol, 2.66 mL) at 0° C. The mixture was stirred at 25° C. for 0.5 hour. The mixture was poured to the water (50 mL) and extracted with ethyl acetate (50 mL). The organic layers was dried by sodium sulfate, filtered and concentrated in vacuo to give the residue. The residue was purified by column chromatography (SiO₂, petroleum ether:ethyl acetate=5:1) to give the phenyl N-(3-pyridyl)carbamate (4.00 g, 59% yield) as a yellow solid.

LC-MS (ESI⁺) m/z 215.0 (M+H)⁺.

¹H NMR (400 MHz, DMSO-d₆) δ 10.46 (br s, 1H), 8.70 (d, J=2.4 Hz, 1H), 8.33-8.20 (m, 1H), 7.94 (br d, J=8.4 Hz, 1H), 7.47-7.43 (m, 1H), 7.39-7.34 (m, 1H), 7.30-7.22 (m, 3H).

Step 2—1-amino-3-(3-pyridyl)urea (Int4)

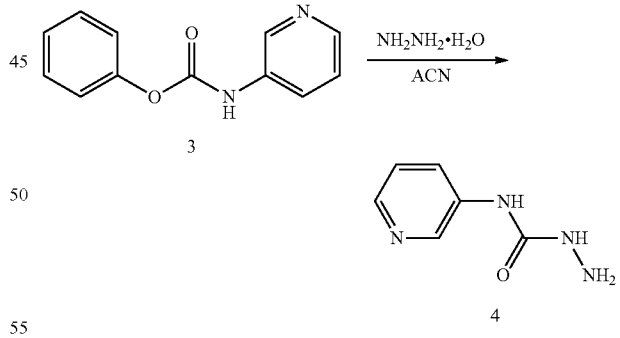

To a solution of phenyl N-(3-pyridyl)carbamate (2.00 g, 9.34 mmol) in ACN (10 mL) was added NH2NH2·H2O (1.37 g, 23.3 mmol, 1.33 mL, 85% purity). The mixture was stirred at 25° C. for 2 hours. The reaction mixture was concentrated in vacuo to give the 1-amino-3-(3-pyridyl)urea (970 mg, 67% yield) as a white solid.

LC-MS (ESI⁺) m/z 153.1 (M+H)⁺.

¹H NMR (400 MHz, CDCl₃) δ 8.54 (d, J=2.4 Hz, 1H), 8.33-8.25 (m, 2H), 8.16-8.11 (m, 1H), 7.26-7.23 (m, 1H), 6.09 (br s, 1H)

Step 3 1-[[(3a5,7a5)-3a-(3,4-dimethoxyphenyl)-1-methyl-2,3,4,5,7,7a-hexahydroindol-6-ylidene]amino]-3-(3-pyidyl)urea (299)

Example 78

(3'aS,7'aS)-3'a-(3,4-dimethoxyphenyl)-1'-methyl-spiro[1,3-benzodioxole-2,6'-2,3,4,5,7,7a-hexahydroindole] (300)

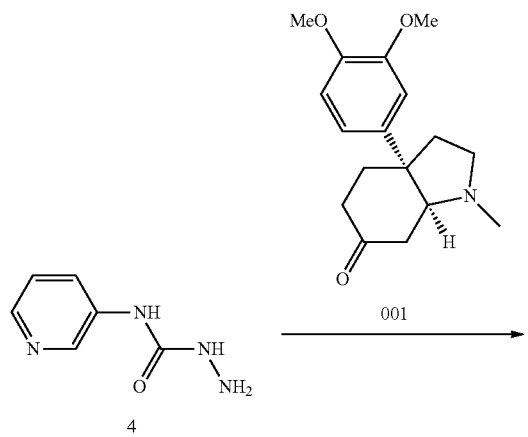

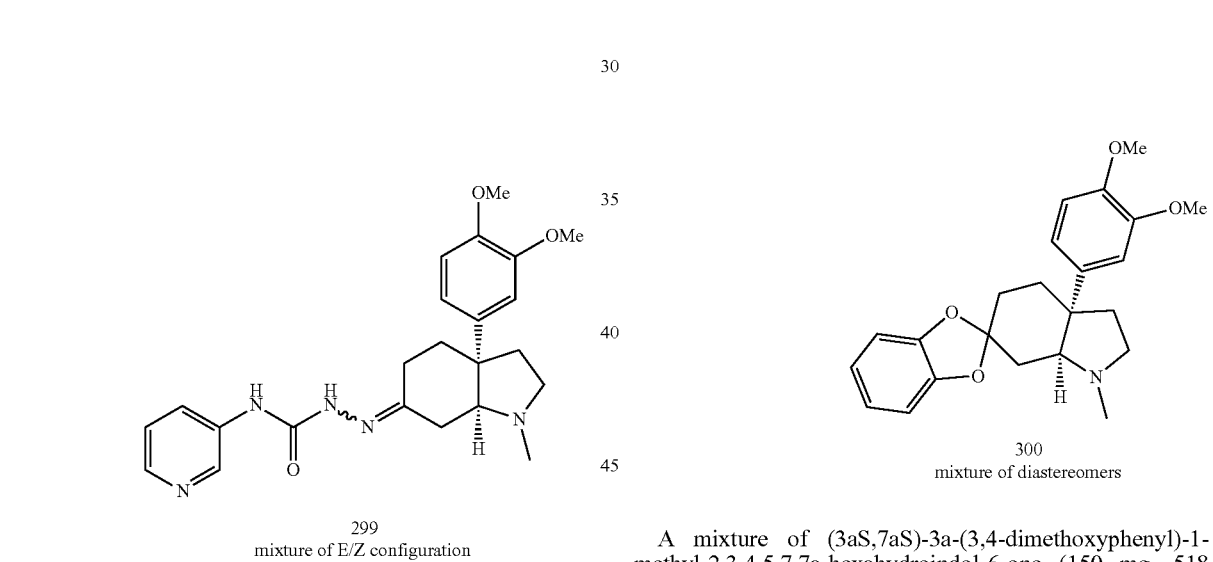

To a solution of (3aS,7aS)-3a-(3,4-dimethoxyphenyl)-1-methyl-2,3,4,5,7,7a-hexahydroindol-6-one (100 mg, 345 umol) in EtOH (1.0 mL) was added AcOH (2.08 mg, 34.5 umol, 1.98 uL) and 1-amino-3-(3-pyridyl)urea (78.8 mg, 518 umol). The mixture was stirred at 60° C. for 2 hours. The reaction mixture was concentrated in vacuo to give the residue. The residue purified by prep-TLC (DCM: MeOH=10:1) to give the 1-[[(3aS,7aS)-3a-(3,4-dimethoxyphenyl)-1-methyl-2,3,4,5,7,7a-hexahydroindol-6-ylidene]amino]-3-(3-pyridyl)urea (29.0 mg, 19% yield) as a white solid.

LC-MS (ESI$^+$) m/z 424.2 (M+H)$^+$.

$^1$H NMR (400 MHz, CDCl$_3$) δ 8.59 (br d, J=2.8 Hz, 1H), 8.30 (br d, J=16.8 Hz, 2H), 8.21-8.07 (m, 1H), 7.66 (br d, J=1.8 Hz, 1H), 7.28 (br d, J=2.8 Hz, 1H), 6.85 (br d, J=2.4 Hz, 3H), 3.95-3.84 (m, 6H), 3.28-3.02 (m, 1H), 2.98-2.84 (m, 1H), 2.82-2.70 (m, 1H), 2.69-2.51 (m, 1H), 2.41 (br s, 3H), 2.37 (br s, 2H), 2.27-2.18 (m, 1H), 2.17-1.93 (m, 4H).

A mixture of (3aS,7aS)-3a-(3,4-dimethoxyphenyl)-1-methyl-2,3,4,5,7,7a-hexahydroindol-6-one (150 mg, 518 umol), benzene-1,2-diol (285 mg, 2.59 mmol, 432 uL), BF$_3$.Et$_2$O (147 mg, 1.04 mmol, 127 uL), 4A MS (10 mg, 518.37 umol) in DCM (2.0 mL) was degassed and purged with N$_2$ for 3 times, and then the mixture was stirred at 25° C. for 2 hours under N$_2$ atmosphere. On completion, the reaction mixture was filtered, concentrated in vacuo to give the residue. The residue was purified by prep-HPLC (neutral condition: column: Waters xbridge 150*25 mm 10 um; mobile phase: [water(NH$_4$HCO$_3$)-ACN]; B %: 43%-73%, 11 min) to give (3'aS,7'aS)-3'a-(3,4-dimethoxyphenyl)-1'-methyl-spiro[1,3-benzodioxole-2,6'-2,3,4,5,7,7a-hexahydroindole] (25.51 mg, 16% yield) as an off-white solid.

LC-MS (ESI$^+$) m/z 382.1 (M+H)$^+$ $^1$H NMR (400 MHz, CDCl$_3$) δ 6.89-6.84 (m, 1H), 6.84-6.79 (m, 2H), 6.79-6.74 (m, 1H), 6.73-6.66 (m, 2H), 6.65-6.59 (m, 1H), 3.82 (d, J=8.0 Hz, 6H), 3.31-3.19 (m, 1H), 2.72 (s, 1H), 2.42-2.36 (m, 1H), 2.35-2.32 (m, 1H), 2.31 (s, 3H), 2.21 (q, J=9.2 Hz, 1H), 2.10-1.89 (m, 4H), 1.88-1.78 (m, 1H), 1.61 (dt, J=3.2, 13.2 Hz, 1H).

Example 79

(Z,3aS,7aS)-N-(1-adamantyloxy)-3a-(3,4-dimethoxyphenyl)-1-methyl-2,3,4,5,7,7a-hexahydroindol-6-imine (274) and (Z,3aS,7aS)-N-(1-adamantyloxy)-3a-(3,4-dimethoxyphenyl)-1-methyl-2,3,4,5,7,7a-hexahydroindol-6-imine (301)

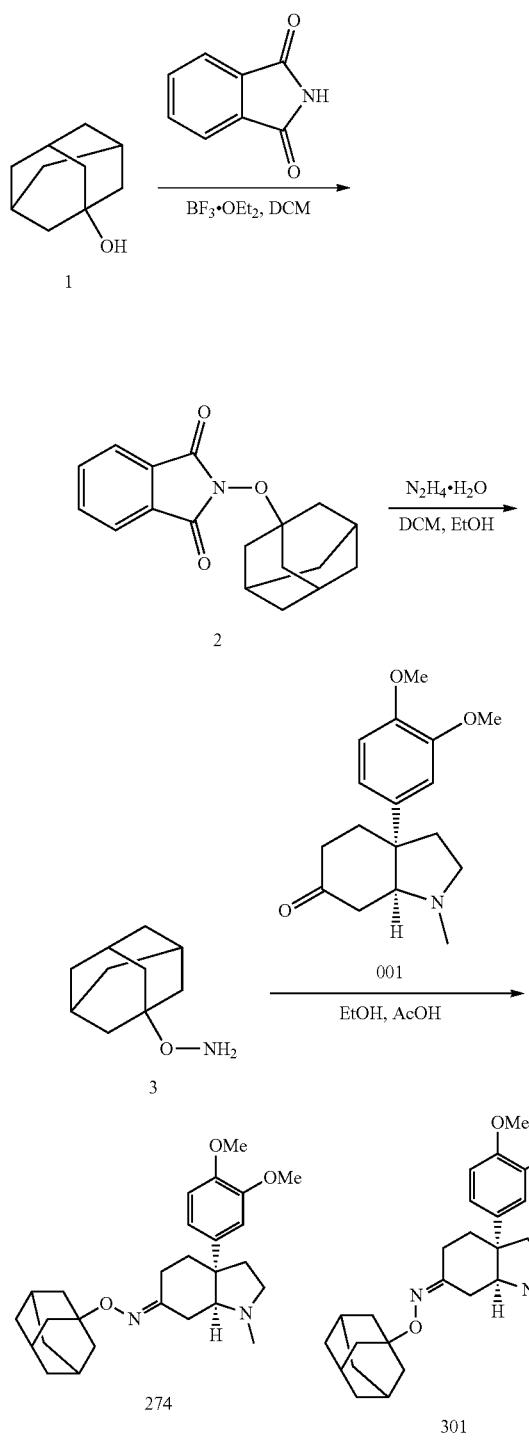

Step 1—2-(1-adamantyloxy)isoindoline-1,3-dione

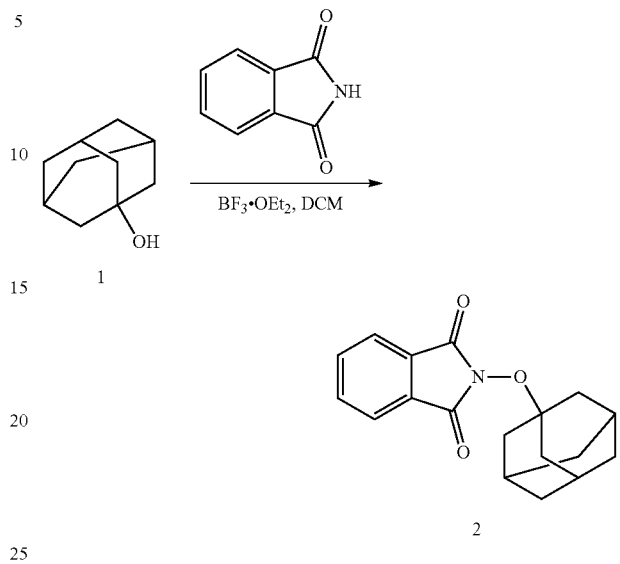

To a solution of 2-hydroxyisoindoline-1,3-dione (2.00 g, 12.3 mmol) and adamantan-1-ol (1.87 g, 12.2 mmol) in DCM (10 mL) was added BF$_3$.Et$_2$O (3.48 g, 24.5 mmol, 3.03 mL) at 0° C. The mixture was stirred at 25° C. for 16 hours. On completion, the reaction mixture was filtered, concentrated in vacuo to give the residue. The residue was purified by column chromatography (SiO$_2$, petroleum ether:ethyl acetate=10:1) to give 2-(1-adamantyloxy)isoindoline-1,3-dione (1.40 g, 35% yield) as a white solid.

$^1$H NMR (400 MHz, DMSO-d$_6$) δ=7.86 (s, 4H), 3.32 (s, 6H), 2.15 (s, 3H), 1.85 (d, J=2.6 Hz, 7H), 1.58 (s, 7H)

Step 2—1-amino-3-(4-pyridyl)urea

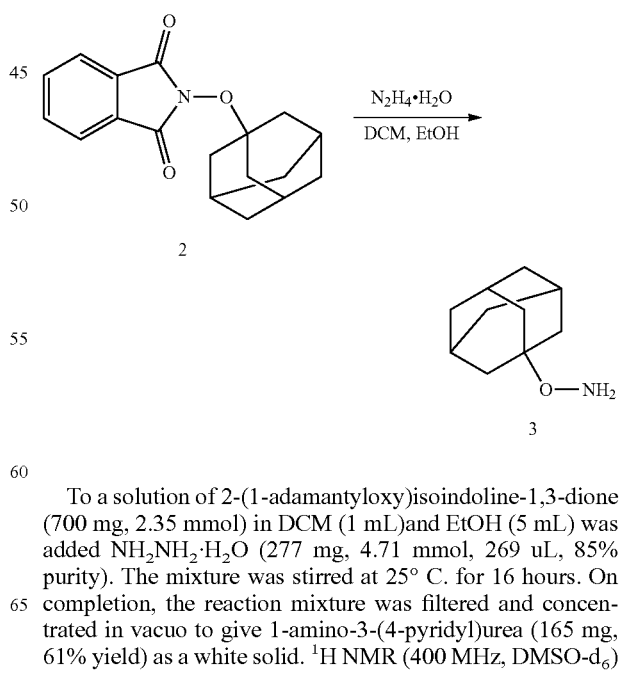

To a solution of 2-(1-adamantyloxy)isoindoline-1,3-dione (700 mg, 2.35 mmol) in DCM (1 mL) and EtOH (5 mL) was added NH$_2$NH$_2$·H$_2$O (277 mg, 4.71 mmol, 269 uL, 85% purity). The mixture was stirred at 25° C. for 16 hours. On completion, the reaction mixture was filtered and concentrated in vacuo to give 1-amino-3-(4-pyridyl)urea (165 mg, 61% yield) as a white solid. $^1$H NMR (400 MHz, DMSO-d$_6$)

δ=5.30 (s, 2H), 2.07 (s, 3H), 1.65 (d, J=2.8 Hz, 6H), 1.62-1.59 (m, 1H), 1.62-1.49 (m, 5H)

Step 3—1-amino-3-(4-pyridyl)urea

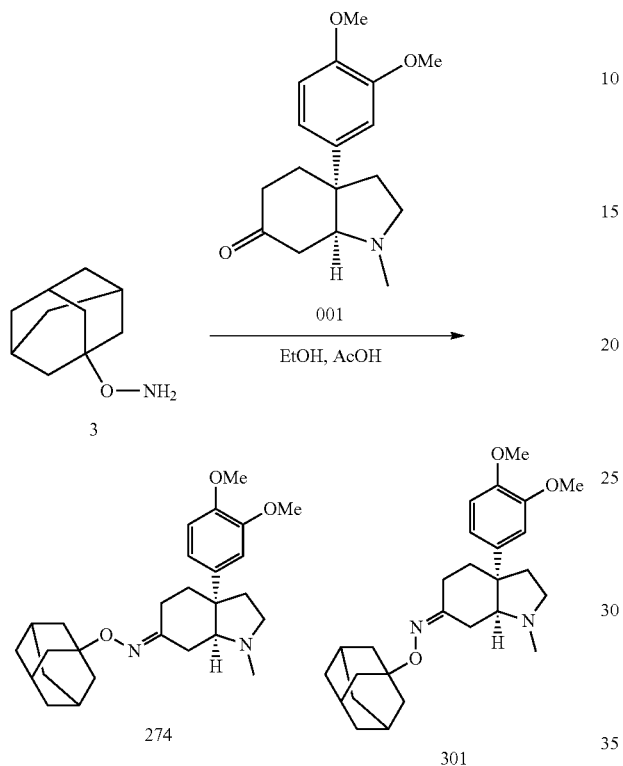

To a solution of O-(1-adamantyl)hydroxylamine (52.5 mg, 314 umol) and (3aS,7aS)-3a-(3,4-dimethoxyphenyl)-1-methyl-2,3,4,5,7,7a-hexahydroindol-6-one (100 mg, 346 umol) in EtOH (2 mL) was added CH₃COOH (1.89 mg, 31.4 umol). The mixture was stirred at 60° C. for 2 hours. On completion, the reaction mixture was filtered, concentrated in vacuo to give the residue. The residue was purified by prep-HPLC (column: Waters xbridge 150*25 mm 10 um; mobile phase: [water(NH₄HCO₃)-ACN]; B %: 65%-95%, 8 min) to give (Z,3aS,7aS)-N-(1-adamantyloxy)-3a-(3,4-dimethoxyphenyl)-1-methyl-2,3,4,5,7,7a-hexahydroindol-6-imine (46.5 mg, 31% yield) as white gum and (Z,3aS,7aS)-N-(1-adamantyloxy)-3a-(3,4-dimethoxyphenyl)-1-methyl-2,3,4,5,7,7a-hexahydroindol-6-imine (20 mg, 13% yield) as a white solid.

274
LC-MS (ESI⁺) m/z 439.2 (M+H)⁺
¹H NMR (400 MHz, CDCl₃) δ=6.88-6.76 (m, 3H), 3.88 (d, J=6.5 Hz, 6H), 3.11-2.95 (m, 1H), 2.83 (d, J=2.0 Hz, 1H), 2.74-2.60 (m, 1H), 2.43 (d, J=5.0 Hz, 2H), 2.37 (s, 3H), 2.31-2.23 (m, 1H), 2.15 (s, 4H), 2.08 (br d, J=4.9 Hz, 1H), 1.98 (d, J=4.0 Hz, 1H), 1.92-1.85 (m, 1H), 1.81 (d, J=2.4 Hz, 6H), 1.71-1.54 (m, 9H)
LC-MS (ESI⁺) m/z 439.2 (M+H)⁺
¹H NMR (400 MHz, CDCl₃-d) δ=6.99-6.79 (m, 3H), 3.89 (d, J=6.0 Hz, 6H), 3.52-3.36 (m, 1H), 3.42 (d, J=16.4 Hz, 1H), 3.16 (s, 1H), 2.73 (s, 1H), 2.35 (s, 4H), 2.30-2.22 (m, 1H), 2.21-2.10 (m, 5H), 2.08 (d, J=5.3 Hz, 1H), 2.03-1.97 (m, 2H), 1.86 (s, 6H), 1.66 (s, 6H), 1.57 (s, 3H).

Example 80

N-[[(3aS,7aS)-3a-(3,4-dimethoxyphenyl)-1-methyl-3,4,7,7a-tetrahydro-2H-indol-6-yl] 3,4-dimethoxybenzoate (302)

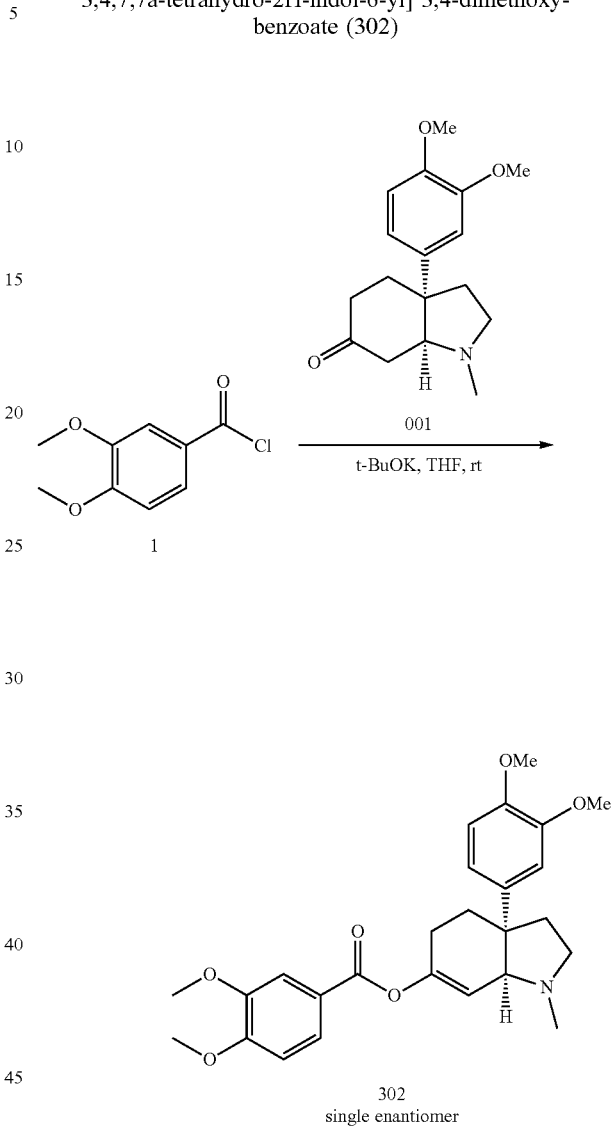

To a solution of (3aS,7aS)-3a-(3,4-dimethoxyphenyl)-1-methyl-2,3,4,5,7,7a-hexahydroindol-6-one (100 mg, 346 umol) and 3,4-dimethoxybenzoyl chloride (139 mg, 692 umol) in THF (2 mL) was added t-BuOK (1 M, 691 uL). The mixture was stirred at 25° C. for 1 hour. On completion, the reaction mixture was concentrated in vacuo to give a residue. The residue was purified by prep-HPLC (column: Welch Ultimate C₁₈ ₁₅₀*₂₅ mm*5 um; mobile phase: [water (FA)-ACM]; B %: 12%-42%, 10 min) to give N-[[(3aS, 7aS)-3a-(3,4-dimethoxyphenyl)-1-methyl-3,4,7,7a-tetrahydro-2H-indol-6-yl]3,4-dimethoxybenzoate (60.3 mg, 49% yield) as White Solid.

LC-MS (ESI⁺) m/z 454.1 (M+H)⁺
¹H NMR (400 MHz, CDCl₃) δ 7.75-7.51 (m, 2H), 7.01-6.79 (m, 3H), 5.85 (d, J=4.4 Hz, 1H), 3.98-3.87 (m, 12H), 3.33-3.16 (m, 1H), 2.92 (d, J=1.2 Hz, 1H), 2.42 (s, 2H), 2.37-2.11 (m, 3H), 1.98 (d, J=6.4 Hz, 1H), 1.80 (d, J=13.2 Hz, 1H), 1.63-1.54 (m, 3H).

Example 81

N-[[(3aS,7aS)-3a-(3,4-dimethoxyphenyl)-1-methyl-3,4,7,7a-tetrahydro-2H-indol-6-yl] 4-methylbenzoate (303)

Example 82

(3aS,7aS)-3a-(3,4-dimethoxyphenyl)-1-methyl-2,3,4,5,7,7a-hexahydroindol-6-one (304)

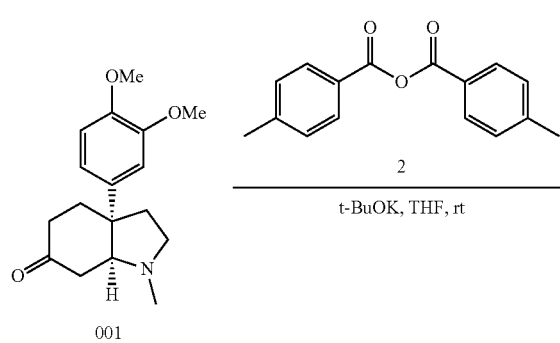

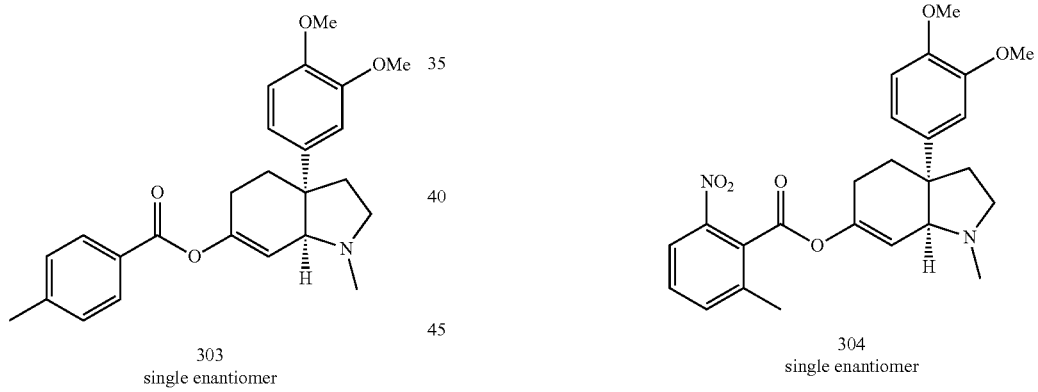

303
single enantiomer 304
single enantiomer

To a solution of (3aS,7aS)-3a-(3,4-dimethoxyphenyl)-1-methyl-2,3,4,5,7,7a-hexahydroindol-6-one (100 mg, 346 umol) and (4-methylbenzoyl) 4-methylbenzoate (176 mg, 691 umol) in THF (2 mL) was added t-BuOK (1 M, 691 uL) and. The mixture was stirred at 25° C. for 1 hours. On completion, the reaction mixture was concentrated in vacuo to give a residue. The residue was purified by prep-HPLC (column: Phenomenex luna $C_{18\ 150*25}$ mm*10 um; mobile phase: [water(FA)-ACN]; B %: 19%-49%, 58 min) to give N-[[(3aS,7aS)-3a-(3,4-dimethoxyphenyl)-1-methyl-3,4,7,7a-tetrahydro-2H-indol-6-yl] 4-methylbenzoate (66.2 mg, 45.6% yield) as white gum.

LC-MS (ESI$^+$) m/z 408.3 (M+H)$^+$ $^1$H NMR (400 MHz, CDCl$_3$) δ 8.48 (s, 1H), 7.95 (d, J=8.0 Hz, 2H), 7.25 (s, 1H), 6.87 (s, 3H), 5.89 (dd, J=1.6, 4.8 Hz, 1H), 3.91 (d, J=18.4 Hz, 6H), 3.76-3.49 (m, 2H), 2.82 (dd, J=2.4, 6.8 Hz, 1H), 2.70 (s, 3H), 2.43 (s, 3H), 2.40-2.36 (m, 3H), 2.16-1.94 (m, 2H), 1.86 (dd, J=2.8, 13.2 Hz, 1H).

To a solution of (3aS,7aS)-3a-(3,4-dimethoxyphenyl)-1-methyl-2,3,4,5,7,7a-hexahydroindol-6-one (100 mg, 345.58 umol, 1 eq) and (2-methyl-6-nitro-benzoyl) 2-methyl-6-nitro-benzoate (237.95 mg, 691.16 umol, 2 eq) in THF (2 mL) was added t-BuOK (38.78 mg, 345.58 umol, 1 eq). The mixture was stirred at 25° C. for 16 hr. On completion, filtered to remove the insoluble. The filter liquor was concentrated in vacuo. The residue was purified by prep-HPLC (column: Waters xbridge 150*25 mm 10 um; mobile phase: [water(NH4HCO3)-ACN]; B %: 43%-73%, 9 min). to give [(3aS,7aS)-3a-(3,4-dimethoxyphenyl)-1-methyl-3,4,5,7a-tetrahydro-2H-indol-6-yl]2-methyl-6-nitro-benzoate (10 mg, 6.39% yield) as a yellow solid.

LC-MS (ESI$^+$) m/z 453.10 (M+H)

$^1$H NMR (400 MHz, CDCl$_3$) δ=8.04 (d, J=8.4 Hz, 1H), 7.63-7.41 (m, 2H), 6.97-6.82 (m, 3H), 5.99 (br d, J=3.2 Hz, 1H), 3.90 (d, J=17.2 Hz, 6H), 3.33-3.17 (m, 1H), 3.03-2.87 (m, 1H), 2.57-2.40 (m, 6H), 2.37-2.16 (m, 4H), 2.12-1.98 (m, 2H), 1.88-1.79 (m, 1H).

Example 83

[(3aS,7aS)-3a-(3,4-dimethoxyphenyl)-1-methyl-3,4,7,7a-tetrahydro-2H-indol-6-yl] 4-tert-butylbenzoate (305)

Example 84

[(3aS,7aS)-3a-(3,4-dimethoxyphenyl)-1-methyl-3,4,7,7a-tetrahydro-2H-indol-6-yl] 4-tert-butylbenzoate (306)

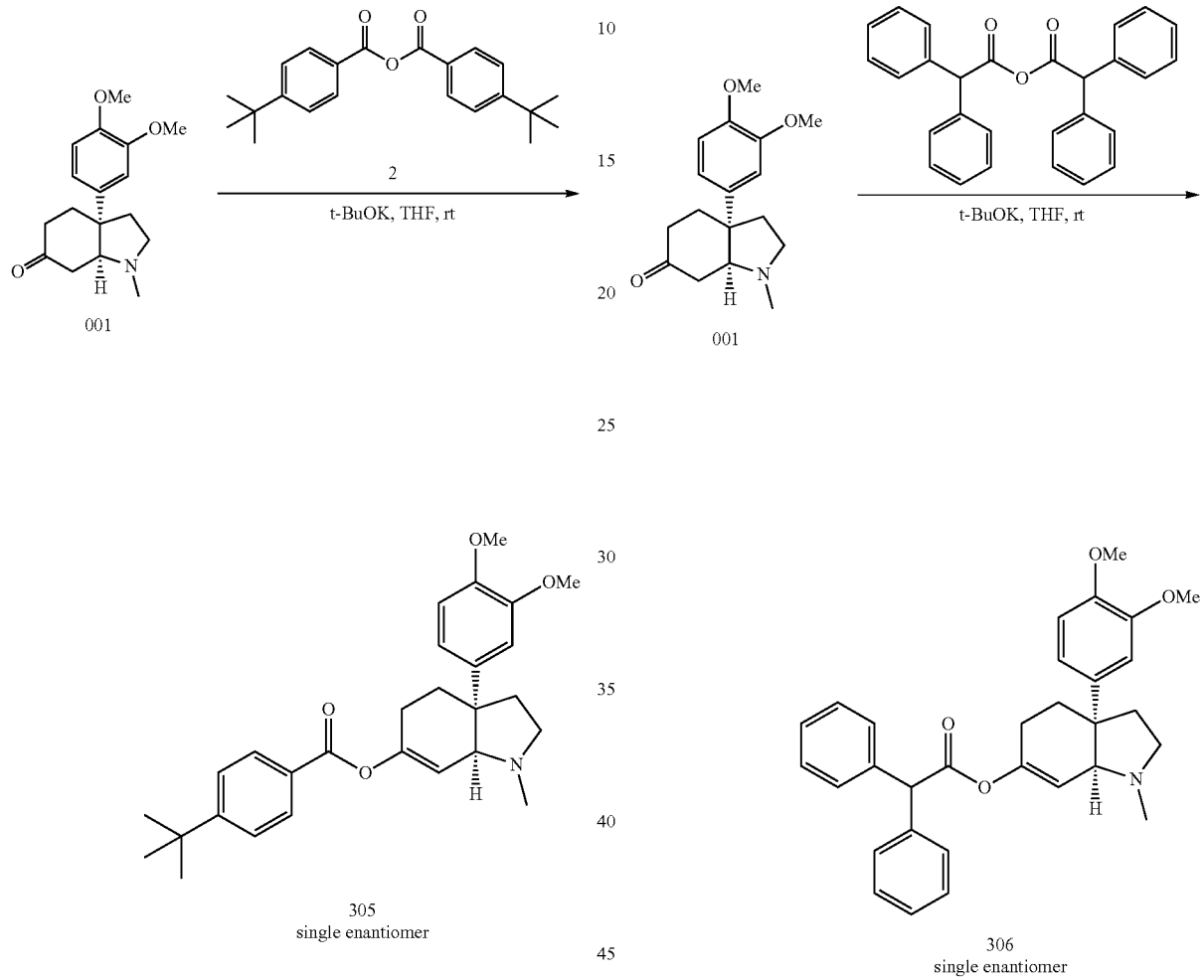

To a solution of (3aS,7aS)-3a-(3,4-dimethoxyphenyl)-1-methyl-2,3,4,5,7,7a-hexahydroindol-6-one (100 mg, 345 umol) in THF (1 mL) was added t-BuOK (1 M, 691 uL) at 0° C. for 30 min. Then the mixture was added (4-tert-butylbenzoyl) 4-tert-butylbenzoate (233 mg, 691 umol). The mixture was stirred at 25° C. for 2 hours. On completion, the reaction mixture was filtered, concentrated in vacuo to give the residue. The residue was purified by prep-HPLC (column: Waters xbridge 150*25 mm 10 um; mobile phase: [water(NH$_4$HCO$_3$)-ACN]; B %: 60%-90%, 8 min) to give [(3aS,7aS)-3a-(3,4-dimethoxyphenyl)-1-methyl-3,4,7,7a-tetrahydro-2H-indol-6-yl] 4-tert-butylbenzoate (10 mg, 6% yield,) as an off-white solid.

LC-MS (ESI$^+$) m/z 450.1 (M+H)$^+$ $^1$H NMR (400 MHz, CDCl$_3$) δ=8.02-7.95 (m, 2H), 7.47 (d, J=8.8 Hz, 2H), 6.96-6.84 (m, 3H), 5.85 (d, J=4.8 Hz, 1H), 3.94 (s, 3H), 3.91-3.86 (m, 3H), 3.30-3.17 (m, 1H), 3.01-2.88 (m, 1H), 2.42 (s, 3H), 2.21 (s, 1H), 2.35-2.13 (m, 3H), 1.97 (d, J=6.0 Hz, 2H), 1.84-1.73 (m, 1H), 1.59 (s, 11H), 1.35 (s, 9H).

To a solution of (3aS,7aS)-3a-(3,4-dimethoxyphenyl)-1-methyl-2,3,4,5,7,7a-hexahydroindol-6-one (95.4 mg, 329 umol) in THF (1 mL) was added t-BuOK (1 M, 659.21 uL) at 0° C. for 30 mins. Then the mixture was added (2,2-diphenylacetyl) 2,2-diphenylacetate (267.8 mg, 659 umol). The mixture was stirred at 25° C. for 2 hours. On completion, the reaction mixture was filtered, concentrated in vacuo to give the residue. The residue was purified by prep-HPLC (column: Waters xbridge 150*25 mm 10 um; mobile phase: [water(NH$_4$HCO$_3$)-ACN]; B %: 50%-80%, 8 min) to give [(3aS,7aS)-3a-(3,4-dimethoxyphenyl)-1-methyl-3,4,5,7a-tetrahydro-2H-indol-6-yl] 2,2-diphenylacetate (20 mg, 13% yield) as a white gum.

LC-MS (ESI$^+$) m/z 484.2 (M+H)$^+$ $^1$H NMR (400 MHz, CDCl$_3$) δ=7.36-7.28 (m, 9H), 7.26 (s, 1H), 6.88-6.78 (m, 3H), 5.72 (d, J=4.8 Hz, 1H), 5.19-5.18 (m, 1H), 5.07 (s, 1H), 3.87 (d, J=6.8 Hz, 6H), 3.23-3.09 (m, 1H), 2.91-2.80 (m, 1H), 2.37 (s, 3H), 2.31-2.10 (m, 4H), 1.81 (d, J=8.8 Hz, 2H), 1.75-1.69 (m, 1H).

Example 85

[(3aS,7aS)-3a-(3,4-dimethoxyphenyl)-1-methyl-3,4,5,7a-tetrahydro-2H-indol-6-yl] 3-(dimethylamino)benzoate (307)

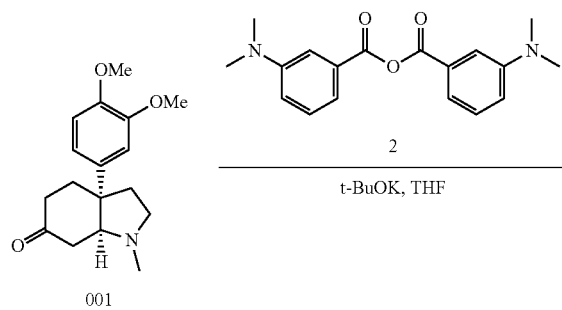
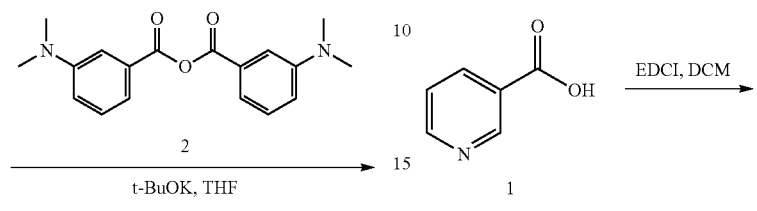

A mixture of (3aS,7aS)-3a-(3,4-dimethoxyphenyl)-1-methyl-2,3,4,5,7,7a-hexahydroindol-6-one (100 mg, 345 umol), [3-(dimethylamino)benzoyl] 3-(dimethylamino)benzoate (215 mg, 691 umol) CAS#4629-50-9, t-BuOK (1 M, 691 uL) in THF (3 mL) was degassed and purged with N₂ for 3 times, and then the mixture was stirred at 25° C. for 1 hour under N₂ atmosphere. On completion, the reaction mixture was concentrated in vacuo to give a residue. The residue was purified by prep-HPLC (neutral condition: column: Waters xbridge 150*25 mm 10 um; mobile phase: [water (NH₄HCO₃)-ACN]; B %: 44%-74%, 8 min) to give the title compound (55.0 mg, 36% yield) as white solid.

LC-MS (ESI+) m/z 437.1 (M+H)+.

¹H NMR (400 MHz, CDCl₃) δ 7.45-7.34 (m, 2H), 7.33-7.28 (m, 1H), 6.98-6.89 (m, 3H), 6.89-6.83 (m, 1H), 5.85 (d, J=4.4 Hz, 1H), 3.98-3.84 (m, 6H), 3.24 (t, J=7.2 Hz, 1H), 3.00 (s, 6H), 2.93 (s, 1H), 2.42 (s, 3H), 2.37-2.14 (m, 4H), 2.03-1.94 (m, 2H), 1.83-1.76 (m, 1H).

Example 86

[(3aS,7aS)-3a-(3,4-dimethoxyphenyl)-1-methyl-3,4,7,7a-tetrahydro-2H-indol-6-yl] pyridine-3-carboxylate (308)

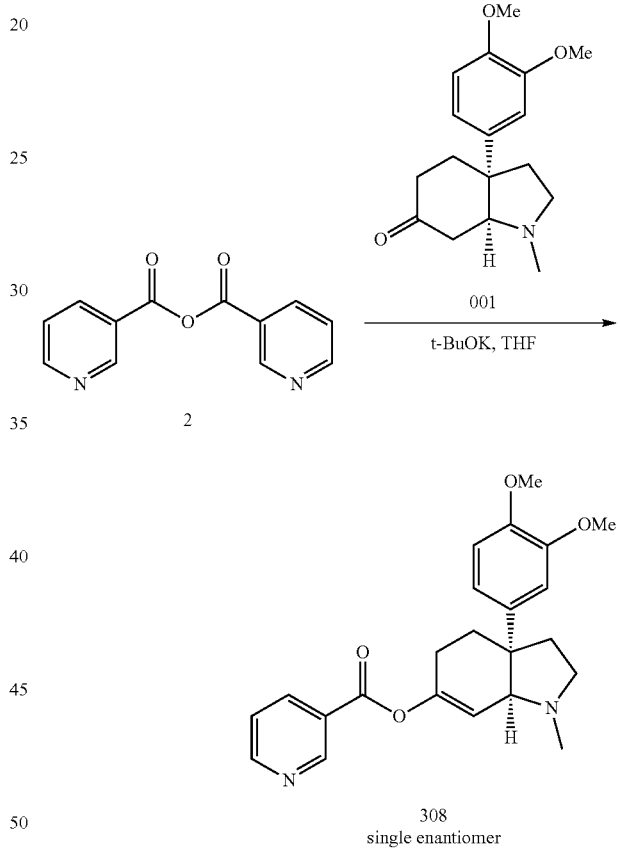

Step 1—pyridine-3-carbonyl pyridine-3-carboxylate (2)

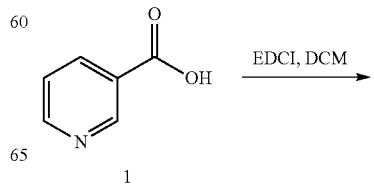

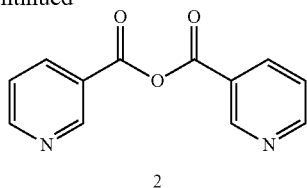

2

To a solution of nicotinic acid (1 g, 8.12 mmol) in DCM (10 mL) was added 3-(ethyliminomethyleneamino)-N,N-dimethyl-propan-1-amine; hydrochloride (1.56 g, 8.12 mmol). The mixture was stirred at 25° C. for 4 hours. On completion, the mixture was diluted by dichloromethane (50 mL) and washed by water (50 mL) and saturated sodium bicarbonate solution (50 mL). The organic layers was dried by sodium sulfate, filtered and concentrated in vacuo to give pyridine-3-carbonyl pyridine-3-carboxylate (500 mg, 18% yield) as a white solid.

LC-MS (ESI$^+$) m/z 228.8 (M+H)$^+$ $^1$H NMR (400 MHz, CDCl$_3$) δ 10.01 (s, 2H), 9.57 (d, J=1.6 Hz, 2H), 9.09 (s, 2H), 8.19 (s, 2H).

Step 2—[(3a5,7a5)-3a-(3,4-dimethoxyphenyl)-1-methyl-3,4,7,7a-tetrahydro-2H-indol-6-yl]pyridine-3-carboxylate (308)

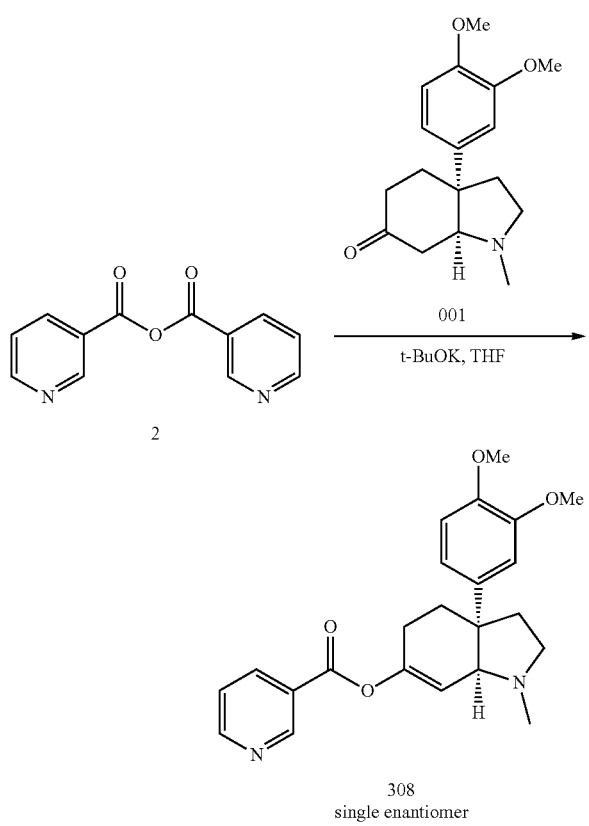

To a solution of (3aS,7aS)-3a-(3,4-dimethoxyphenyl)-1-methyl-2,3,4,5,7,7a-hexahydroindol-6-one (100 mg, 345 umol) in THF (2.0 mL) was added t-BuOK (1 M, 691 uL) was stirred at 0° C. for 10 minutes. Then pyridine-3-carbonyl pyridine-3-carboxylate (157 mg, 691 umol) was added in the mixture. The mixture was stirred at 40° C. for 2 hours. On completion, the reaction mixture was filtered, concentrated in vacuo to give the residue. The residue was purified by prep-HPLC (neutral condition: column: Waters xbridge 150*25 mm 10 um; mobile phase: [water (NH$_4$HCO$_3$)-ACN]; B %: 25%-55%, 8 min) to give [(3aS,7aS)-3a-(3,4-dimethoxyphenyl)-1-methyl-3,4,5,7a-tetrahydro-2H-indol-6-yl]pyridine-3-carboxylate (30.97 mg, 19% yield) as a yellow solid.

LC-MS (ESI$^+$) m/z 395.0 (M+H)$^+$ $^1$H NMR (400 MHz, CDCl$_3$) δ 9.27 (d, J=1.6 Hz, 1H), 8.82 (dd, J=1.2, 4.8 Hz, 1H), 8.33 (d, J=8.0 Hz, 1H), 7.43 (dd, J=4.8, 8.0 Hz, 1H), 7.04-6.71 (m, 3H), 5.92 (d, J=4.4 Hz, 1H), 3.93 (d, J=18.4 Hz, 5H), 3.31 (d, J=7.6 Hz, 1H), 3.10-2.93 (m, 1H), 2.48 (s, 3H), 2.35-2.31 (m, 1H), 2.30-2.19 (m, 2H), 2.02 (d, J=3.2 Hz, 2H), 1.95-1.88 (m, 1H), 1.84 (d, J=13.2 Hz, 1H).

Example 87

[(3aS,7aS)-3a-(3,4-dimethoxyphenyl)-1-methyl-3,4,5,7a-tetrahydro-2H-indol-6-yl] 2,2-dimethylpropanoate (309)

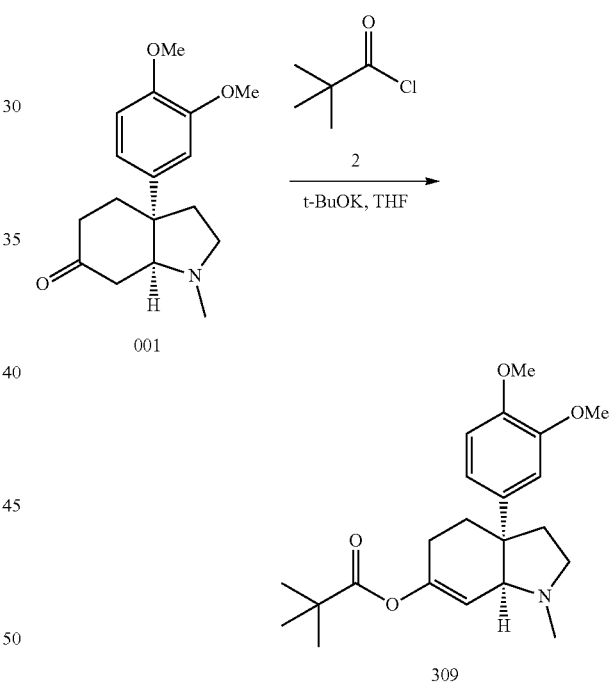

To a solution of (3aS,7aS)-3a-(3,4-dimethoxyphenyl)-1-methyl-2,3,4,5,7,7a-hexahydroindol-6-one (100 mg, 345 umol) in THF (1.0 mL) was added t-BuOK (1 M, 691 uL) was stirred at 0° C. for 10 minutes. Then 2,2-dimethylpropanoyl chloride (83.3 mg, 691 umol) was added in the mixture. The mixture was stirred at 25° C. for 2 hours. On completion, the reaction mixture was filtered, concentrated in vacuo to give the residue. The residue was purified by prep-HPLC (column: Waters xbridge 150*25 mm 10 μm; mobile phase: [water(NH$_4$HCO$_3$)-ACN]; B %: 40%-70%, 9 min) to give [(3aS,7aS)-3a-(3,4-dimethoxyphenyl)-1-methyl-3,4,5,7a-tetrahydro-2H-indol-6-yl]2,2-dimethylpropanoate (42.8 mg, 85% yield) as a white solid.

LC-MS (ESI$^+$) m/z 374.1 (M+H)$^+$

¹H NMR (400 MHz, CDCl₃) δ 6.99-6.76 (m, 3H), 5.67 (d, J=4.8 Hz, 1H), 3.89 (d, J=13.2 Hz, 6H), 3.25-3.17 (m, 1H), 2.87 (d, J=3.6 Hz, 1H), 2.39 (s, 3H), 2.34-2.07 (m, 4H), 1.81 (d, J=7.2 Hz, 2H), 1.79-1.71 (m, 1H), 1.23 (s, 9H).

Example 88

N-[[(3aS,7aS)-3a-(3,4-thMethoxyphenyl)-1-methyl-3,4,5,7a-tetrahydro-2H-indol-6-yl] 4-(trifluoromethyl)benzoate (310)

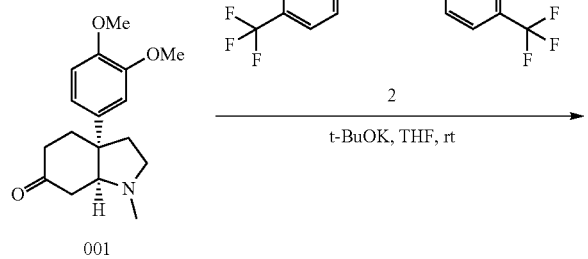

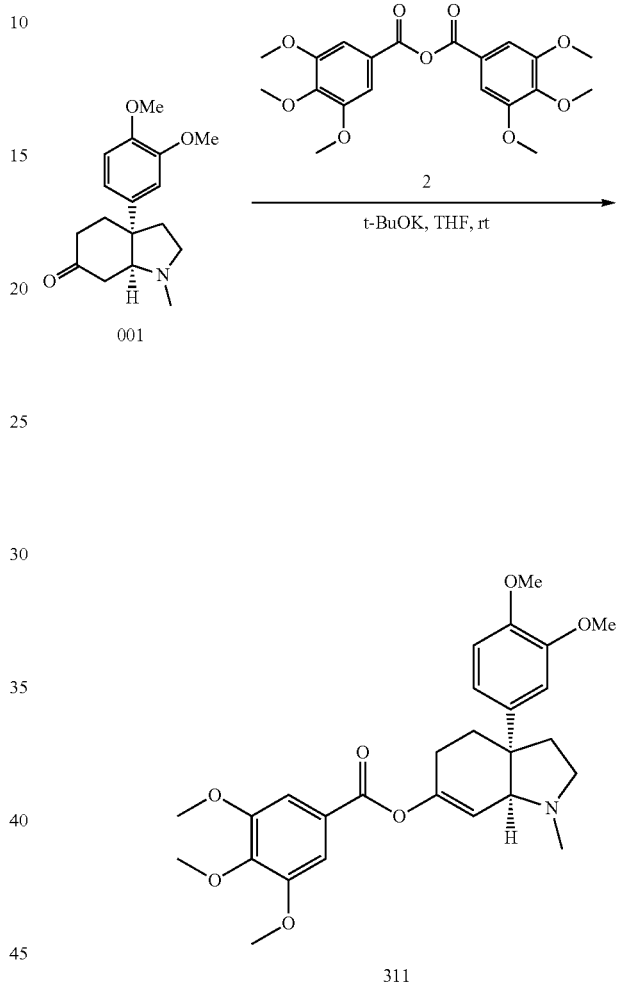

To a solution of (3aS,7aS)-3a-(3,4-dimethoxyphenyl)-1-methyl-2,3,4,5,7,7a-hexahydroindol-6-one (100 mg, 346 umol) and [4-(trifluoromethyl)benzoyl] 4-(trifluoromethyl)benzoate (313 mg, 864 umol) in THF (2 mL) was added t-BuOK (1 M, 692 uL). The mixture was stirred at 25° C. for 1 hour. On completion, the reaction mixture was concentrated in vacuo to give a residue. The residue was purified by prep-HPLC (column: Phenomenex luna C₁₈ 150*25 mm*10 um; mobile phase: [water(FA)-ACN]; B %: 20%-50%, 58 min) to give N-[[(3aS,7aS)-3a-(3,4-dimethoxyphenyl)-1-methyl-3,4,7,7a-tetrahydro-2H-indol-6-yl] 4-(trifluoromethyl)benzoate (52.6 mg, 31% yield) as yellow gum.

LC-MS (ESI⁺) m/z 462.3 (M+H)⁺

¹H NMR (400 MHz, CDCl₃) δ 8.19 (d, J=8.4 Hz, 2H), 7.74 (d, J=8.4 Hz, 2H), 6.91-6.80 (m, 3H), 5.95 (d, J=3.6 Hz, 1H), 3.92 (d, J=16.4 Hz, 6H), 3.84-3.67 (m, 2H), 2.96-2.83 (m, 1H), 2.76 (s, 3H), 2.51-2.31 (m, 3H), 2.19-1.98 (m, 2H), 1.90 (d, J=12.8 Hz, 1H).

Example 89

N-[[(3aS,7aS)-3a-(3,4-dimethoxyphenyl)-1-methyl-3,4,7,7a-tetrahvdro-2H-indol-6-yl] 3,4,5-trimethoxybenzoate (311)

To a solution of (3aS,7aS)-3a-(3,4-dimethoxyphenyl)-1-methyl-2,3,4,5,7,7a-hexahydroindol-6-one (100 mg, 346 umol) and [4-(trifluoromethyl)benzoyl] 4-(trifluoromethyl)benzoate (313 mg, 864 umol) in THF (2 mL) was added t-BuOK (1 M, 692 uL). The mixture was stirred at 25° C. for 1 hours. On completion, the reaction mixture was concentrated in vacuo. The residue was purified by prep-HPLC (column: Phenomenex luna C₁₈ 150*25 mm*10 um; mobile phase: [water(FA)-ACN]; B %: 12%-42%, 58 min) to give a residue. N-[[(3aS, 7aS)-3a-(3,4-dimethoxyphenyl)-1-methyl-3,4,7,7a-tetrahydro-2H-indol-6-yl] 3,4,5-trimethoxybenzoate (46.0 mg, 38% yield) as yellow gum.

LC-MS (ESI⁺) m/z 484.0 (M+H)⁺

¹H NMR (400 MHz, CDCl₃) δ 7.26-7.21 (m, 2H), 6.84-6.81 (m, 2H), 5.83 (dd, J=1.6, 4.4 Hz, 1H), 3.91-3.79 (m, 15H), 3.75-3.63 (m, 1H), 3.59 (d, J=2.0 Hz, 1H), 2.87-2.74 (m, 1H), 2.72-2.62 (m, 3H), 2.41-2.28 (m, 2H), 2.09-1.94 (m, 2H), 1.87-1.79 (m, 1H).

Example 90

[(3aS,7aS)-3a-(3,4-dimethoxyphenyl)-1-methyl-3,4,5,7a-tetrahydro-2H-indol-6-yl] cyclopropanecarboxylate (312)

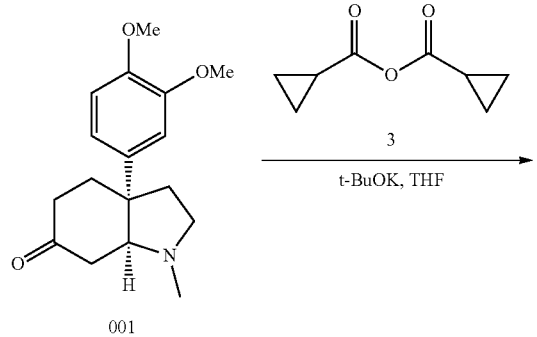

Synthesis 91: [(3aS,7aS)-3a-(3,4-dimethoxyphenyl)-1-methyl-3,4,5,7a-tetrahydro-2H-indol-6-yl](E)-2-methylbut-2-enoate (313)

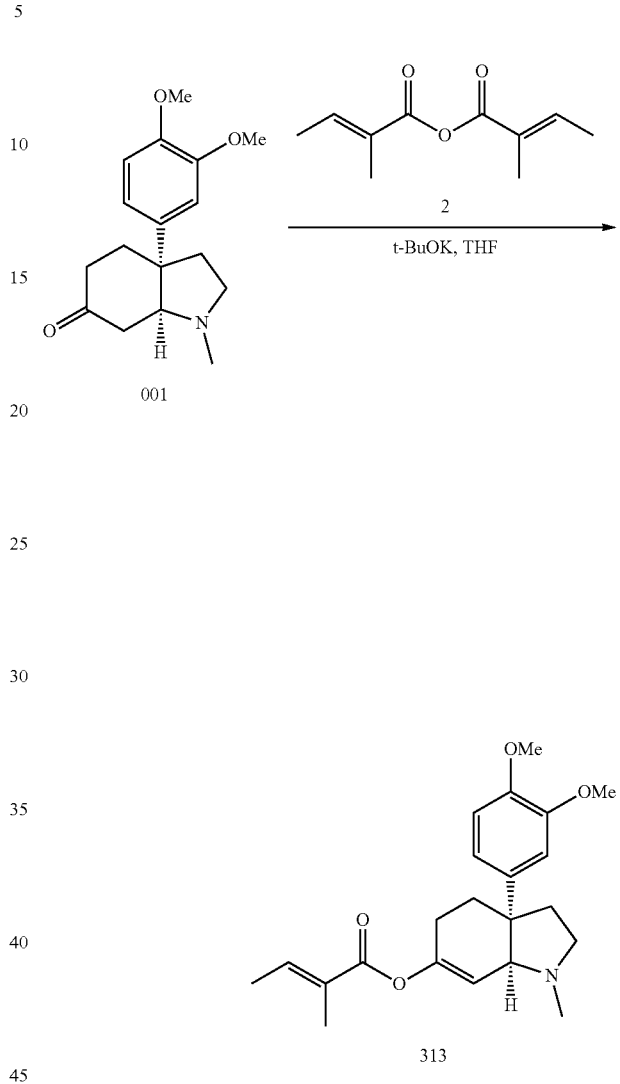

To a solution of (3aS,7aS)-3a-(3,4-dimethoxyphenyl)-1-methyl-2,3,4,5,7,7a-hexahydroindol-6-one (100 mg, 345 umol) in THF (1.0 mL) was added t-BuOK (1 M, 691 uL) was stirred at 0° C. for 10 minutes. Then cyclopropanecarbonyl cyclopropanecarboxylate (106 mg, 691 umol) was added in the mixture. The mixture was stirred at 25° C. for 1 hour. On completion, the reaction mixture was filtered, concentrated in vacuo to give the residue. The residue was purified by prep-HPLC (neutral condition:column: Waters xbridge 150*25 mm 10 um; mobile phase: [water(NH$_4$HCO$_3$)-ACN]; B %: 30%-60%, 8 min) to give [(3aS,7aS)-3a-(3,4-dimethoxyphenyl)-1-methyl-3,4,5,7a-tetrahydro-2H-indol-6-yl] cyclopropanecarboxylate (44.6 mg, 43% yield) as a yellow gum.

LC-MS (ESI$^+$) m/z 358.2 (M+H)$^+$ $^1$H NMR (400 MHz, CDCl$_3$) δ 7.02-6.75 (m, 3H), 5.73 (dd, J=1.6, 4.8 Hz, 1H), 3.89 (d, J=9.2 Hz, 6H), 3.28-3.16 (m, 1H), 2.87 (d, J=4.0 Hz, 1H), 2.40 (s, 3H), 2.35-2.09 (m, 4H), 1.92-1.80 (m, 2H), 1.75 (d, J=14.0 Hz, 1H), 1.67 (dt, J=4.0, 8.4 Hz, 1H), 1.06 (s, 2H), 0.98-0.87 (m, 2H).

To a solution of (3aS,7aS)-3a-(3,4-dimethoxyphenyl)-1-methyl-2,3,4,5,7,7a-hexahydroindol-6-one (100 mg, 345 umol) in THF (1.0 mL) was added t-BuOK (1 M, 691 uL) and [(E)-2-methylbut-2-enoyl] (E)-2-methylbut-2-enoate (126 mg, 691 umol) at 0° C. The mixture was stirred at 25° C. for 1 hour. The reaction mixture was concentrated in vacuo to give the residue. The residue was purified by prep-HPLC (column: Waters xbridge 150*25 mm 10 um; mobile phase: [water(NH4HCO3)-ACN]; B %: 38%-68%, 8 min) to give the[(3aS,7aS)-3a-(3,4-dimethoxyphenyl)-1-methyl-3,4,5,7a-tetrahydro-2H-indol-6-yl](E)-2-methylbut-2-enoate (66.1 mg, 64% yield) as a yellow gum.

LC-MS (ESI$^+$) m/z 372.2 (M+H)$^+$.

$^1$H NMR (400 MHz, CDCl$_3$) δ 6.99-6.80 (m, 4H), 5.74 (d, J=4.6 Hz, 1H), 3.90 (d, J=15.6 Hz, 6H), 3.25 (br t, J=7.8 Hz, 1H), 2.93 (br s, 1H), 2.43 (s, 3H), 2.37-2.13 (m, 4H), 1.91-1.87 (m, 2H), 1.85 (d, J=1.0 Hz, 3H), 1.84 (s, 2H), 1.79 (br d, J=3.2 Hz, 1H), 1.76 (br d, J=3.2 Hz, 1H).

Example 92

[(3aS,7aS)-3a-(3,4-dimethoxyphenyl)-1-methyl-3,4,7,7a-tetrahydro-2H-indol-6-yl] cyclohexanecarboxylate (314)

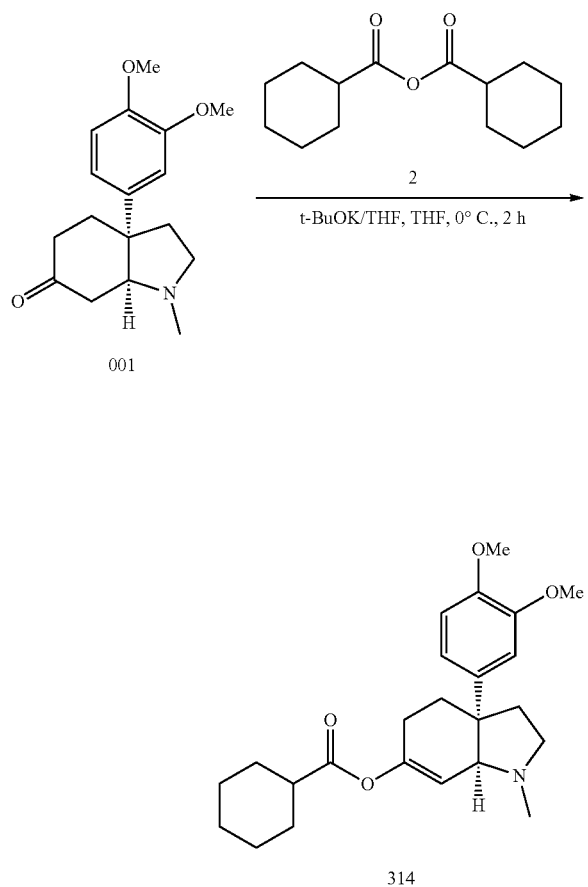

To a solution of (3aS,7aS)-3a-(3,4-dimethoxyphenyl)-1-methyl-2,3,4,5,7,7a-hexahydroindol-6-one (150 mg, 518.37 μmol) cyclohexanecarbonyl cyclohexanecarboxylate (247 mg, 1.04 mmol) in THF (1 mL) was added potassium; 2-methylpropan-2-olate (174 mg, 1.56 mmol), the mixture was stirred at 0° C. for 2 hours. On completion, the mixture was filtered and concentrated to give a residue. The crude product was purified by reversed-phase HPLC(column: Welch Xtimate $C_{18\ 150*25}$ mm*5 um; mobile phase: [water(NH₄HCO₃)-ACN]; B %: 45%-75%, 2 min) to give [(3aS,7aS)-3a-(3,4-dimethoxyphenyl)-1-methyl-3,4,5,7a-tetrahydro-2H-indol-6-yl]cyclohexanecarboxylate (70 mg, 86% purity). The residue was purified by prep-TLC (SiO₂, DCM: MeOH=10:1) to give [(3aS,7aS)-3a-(3,4-dimethoxyphenyl)-1-methyl-3,4,5,7a-tetrahydro-2H-indol-6-yl]cyclohexanecarboxylate (24.0 mg, 95% purity) as a yellow gum.

LC-MS (ESI+) m/z 400.2 (M+H)⁺,

1H NMR (400 MHz, CDCl₃) δ 6.90-6.78 (m, 3H), 5.69 (br d, J=4.4 Hz, 1H), 3.88 (d, J=12.4 Hz, 6H), 3.35-3.13 (m, 1H), 3.03-2.82 (m, 1H), 2.48-2.36 (m, 3H), 2.29-2.15 (m, 3H), 1.96-1.88 (m, 2H), 1.84 (br s, 2H), 1.78-1.71 (m, 3H), 1.66 (br s, 4H), 1.36-1.20 (m, 4H).

Example 93

[(3aS,7aS)-3a-(3,4-dimethoxyphenyl)-1-methyl-3,4,5,7a-tetrahydro-2H-indol-6-yl]-2-methylprop-2-enoate (315)

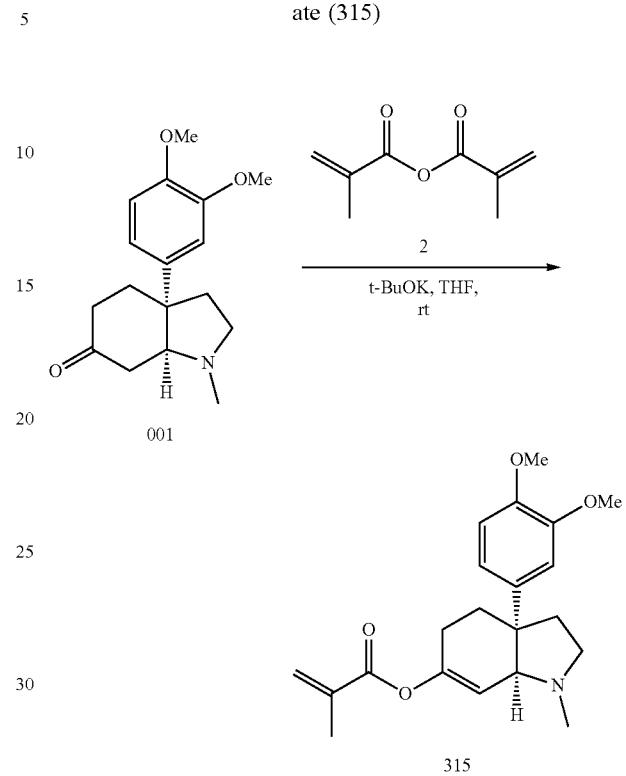

To a solution of (3aS,7aS)-3a-(3,4-dimethoxyphenyl)-1-methyl-2,3,4,5,7,7a-hexahydroindol-6-one (100 mg, 345 umol) and 2-methylprop-2-enoyl 2-methylprop-2-enoate (112 mg, 95% purity) in THF (2 mL) was added t-BuOK (38.9 mg, 346 umol). The mixture was stirred at 25° C. for 16 hours. On completion, filtered to remove the insoluble. The filter liquor was concentrated in vacuo. The residue was purified by prep-HPLC (column: Waters xbridge 150*25 mm 10 um; mobile phase: [water(NH4HCO3)-ACN]; B %: 30%-60%, 9 min) to give [(3aS,7aS)-3a-(3,4-dimethoxyphenyl)-1-methyl-3,4,5,7a-tetrahydro-2H-indol-6-yl] 2-methylprop-2-enoate (34.62 mg, 28.03% yield) as a yellow gum.

LC-MS (ESI⁺) m/z 358.10 (M+H)

¹H NMR (400 MHz, CDCl₃) δ=6.90-6.81 (m, 3H), 6.16 (s, 1H), 5.76 (d, J=4.8 Hz, 1H), 5.64 (t, J=1.6 Hz, 1H), 3.89 (d, J=14.4 Hz, 6H), 3.29-3.19 (m, 1H), 2.92 (br d, J=2.4 Hz, 1H), 2.42 (s, 3H), 2.26-2.20 (m, 2H), 1.95 (s, 3H), 1.88 (br d, J=6.4 Hz, 2H), 1.79-1.74 (m, 1H), 1.52-1.30 (m, 2H).

Example 94

[(3aS,7aS)-3a-(3,4-dimethoxy phenyl)-1-methyl-3,4,5,7a-tetrahydro-2H-indol-6-yl] 3-methyl pentanoate (316)

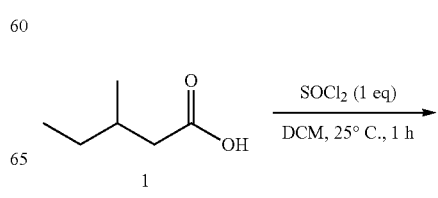

521
-continued

522
Step 2—[(3As,7aS)-3a-(3,4-dimethoxy phenyl)-1-methyl-3,4,5,7a-tetrahydro-2H-indol-6-yl] 3-methyl pentanoate (316)

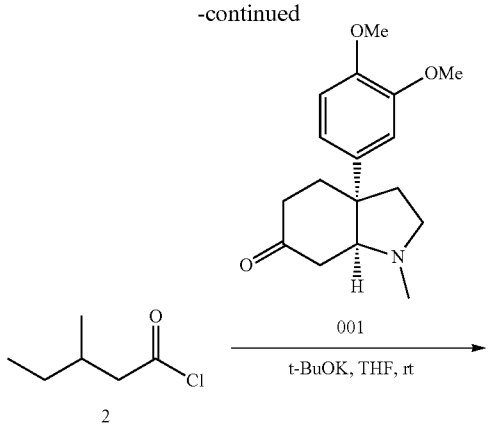

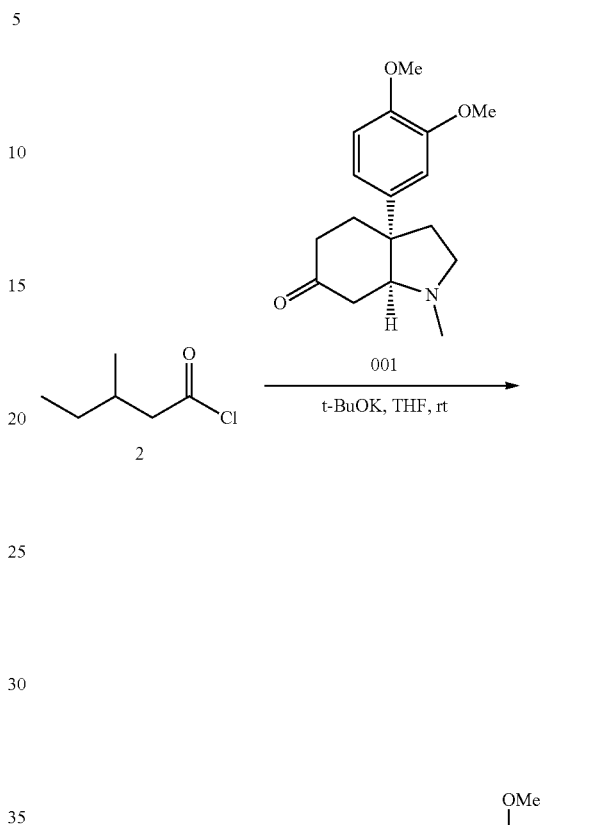

Step 1—3-methylpentanoyl chloride

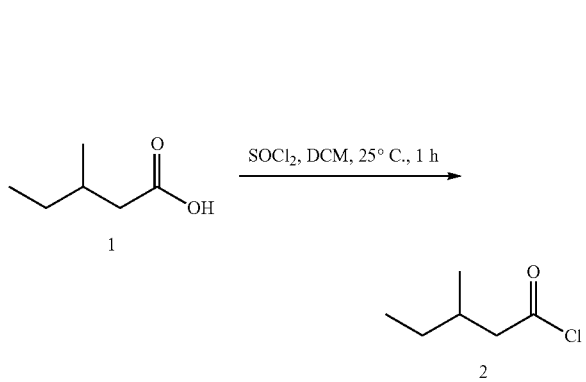

To a solution of 3-methylpentanoic acid (500 mg, 4.30 mmol) in DCM (5 mL) was add dropwise $SOCl_2$ (512 mg, 4.30 mmol). The mixture was stirred at 25° C. for 1 hours under $N_2$ atmosphere. On completion, the mixture was concentrated to give 3-methylpentanoyl chloride (500 mg) as a yellow oil.

2:

1H NMR (400 MHz, $CDCl_3$) δ 2.89 (dd, J=6.0, 16.4 Hz, 1H), 2.69 (dd, J=8.0, 16.4 Hz, 1H), 2.10-1.88 (m, 1H), 1.47-1.25 (m, 2H), 1.14-0.80 (m, 6H).

To a solution of (3aS,7aS)-3a-(3,4-dimethoxyphenyl)-1-methyl-2,3,4,5,7,7a-hexahydroindol-6-one (150 mg, 518 umol) and 3-methylpentanoyl chloride (139 mg, 1.04 mmol) in THF (2 mL) was added t-BuOK (174 mg, 1.56 mmol). The mixture was stirred at 25° C. for 1 hours under $N_2$ atmosphere. On completion, the mixture was filtered and concentrated to give a residue. The residue was purified by prep—HPLC (column: Phenomenex luna $C_{18\ 150*25}$ mm*10 um; mobile phase: [water(FA)-ACN]; B %: 37%-67%, 58 min) to give [(3aS,7aS)-3a-(3,4-dimethoxy phenyl)-1-methyl-3, 4, 5, 7a-tetrahydro-2H-indol-6-yl] 3-methyl pentanoate (45.55 mg, 96.54% purity) as a brown gum.

LC-MS (ESI+) m/z 388.4 (M+H)+,

1H NMR (400 MHz, $CDCl_3$) δ 6.87-6.76 (m, 3H), 5.75 (br d, J=4.4 Hz, 1H), 3.93-3.69 (m, 8H), 3.10-2.92 (m, 1H), 2.79 (s, 3H), 2.53-2.34 (m, 4H), 2.19 (ddd, J=3.2, 8.4, 14.8 Hz, 1H), 2.09-2.00 (m, 1H), 1.97-1.81 (m, 3H), 1.42-1.18 (m, 2H), 1.04-0.79 (m, 6H).

Example 95

[(3aS,7aS)-3a-(3,4-dimethoxyphenyl)-1-methyl-3,4,5,7a-tetrahydro-2H-indol-6-yl] propanoate (317)

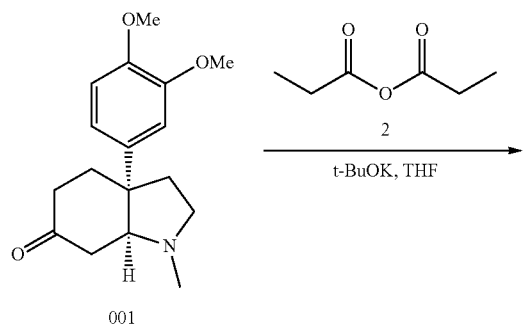

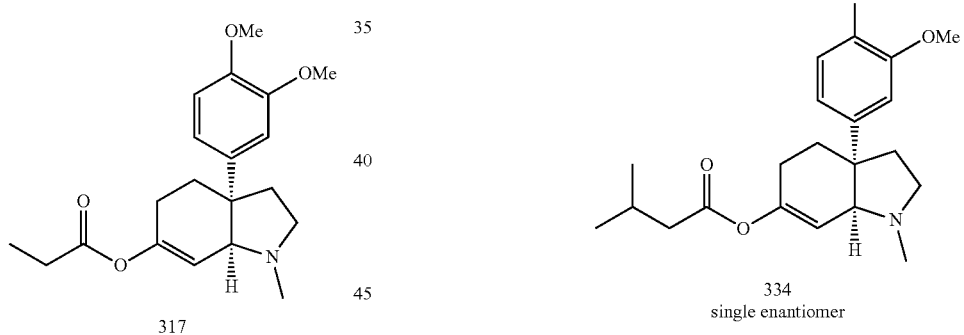

Example 96

[(3aS,7aS)-3a-(3,4-dimethoxyphenyl)-1-methyl-3,4,5,7a-tetrahydro-2H-indol-6-yl] 3-methylbutanoate (334)

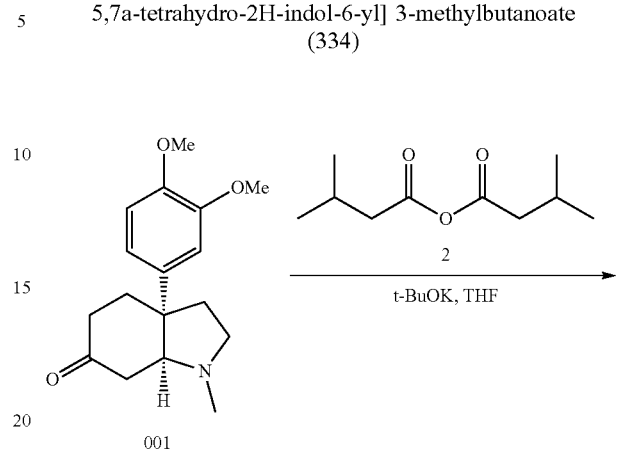

A mixture of (3aS,7aS)-3a-(3,4-dimethoxyphenyl)-1-methyl-2,3,4,5,7,7a-hexahydroindol-6-one (100 mg, 345 umol), propanoyl propanoate (89.9 mg, 691. umol, 89.1 uL), t-BuOK (1 M, 691 uL) in THF (3.00 mL) was degassed and purged with N₂ for 3 times, and then the mixture was stirred at 0-25° C. for 1 hour under N₂ atmosphere. On completion, the reaction mixture was concentrated in vacuo to give a residue. The residue was purified by prep-HPLC (neutral condition:column: Waters xbridge 150*25 mm 10 um; mobile phase: [water(NH₄HCO₃)-ACN]; B %: 28%-58%, 9 min) to give the title compound (45.0 mg, 36% yield) as white gum.

LC-MS (ESI+) m/z 346.1 (M+H)+.

¹H NMR (400 MHz, CDCl₃) δ 7.01-6.74 (m, 3H), 5.86-5.61 (m, 1H), 3.88 (d, J=12.8 Hz, 6H), 3.32-3.12 (m, 1H), 2.86 (d, J=4.0 Hz, 1H), 2.44-2.40 (m, 2H), 2.39-2.35 (m, 3H), 2.32-2.12 (m, 4H), 1.84 (d, J=3.6 Hz, 1H), 1.78-1.72 (m, 2H), 1.16 (t, J=7.6 Hz, 3H).

A mixture of (3aS,7aS)-3a-(3,4-dimethoxyphenyl)-1-methyl-2,3,4,5,7,7a-hexahydroindol-6-one (100 mg, 345 umol), 3-methylbutanoyl 3-methylbutanoate (128 mg, 691 umol), t-BuOK (1 M, 691 uL) in THF (3 mL) was degassed and purged with N₂ for 3 times, and then the mixture was stirred at 0-25° C. for 2 hours under N₂ atmosphere. On completion, the reaction mixture was filtered and the filtrate was concentrated under reduced pressure to give a residue. The residue was purified by prep-HPLC (FA condition: column: Phenomenex luna C₁₈ 150*25 mm*10 um; mobile phase: [water(FA)-ACN]; B %: 32%-62%, 10 min) to give the title compound (20.0 mg, 14% yield) as yellow gum.

LC-MS (ESI+) m/z 374.2 (M+H)+.

¹H NMR (400 MHz, CDCl₃) δ 6.83 (s, 2H), 5.77-5.68 (m, 1H), 3.89 (d, J=9.2 Hz, 6H), 3.73-3.44 (m, 2H), 2.78 (s, 1H), 2.65 (s, 3H), 2.54-2.21 (m, 5H), 2.19-2.05 (m, 1H), 2.03-1.72 (m, 3H), 0.98 (dd, J=1.2, 6.6 Hz, 6H).

Example 97

[(3aS,7aS)-3a-(3,4-dimethoxyphenyl)-1-methyl-3,4,5,7a-tetrahydro-2H-indol-6-yl]4-(dimethylamino)benzoate (355)

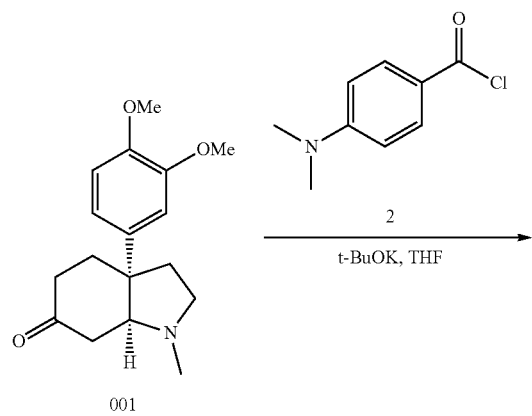

To a solution of (3aS,7aS)-3a-(3,4-dimethoxyphenyl)-1-methyl-2,3,4,5,7,7a-hexahydroindol-6-one (100 mg, 345 umol) in THF (1.0 mL) was added t-BuOK (1 M, 691 uL) and 4-(dimethylamino) benzoyl chloride (127 mg, 691 umol) at 0° C. The mixture was stirred at 25° C. for 2 hours. The reaction mixture was filtered, concentrated in vacuo to give the residue. The residue was purified by prep-HPLC (column: Welch Ultimate $C_{18}$ 150*25 mm*5 um; mobile phase: [water(FA)-ACN]; B %: 18%-48%, 10 min) to give the [(3aS,7aS)-3a-(3,4-dimethoxyphenyl)-1-methyl-3,4,5,7a-tetrahydro-2H-indol-6-yl] 4-(dimethylamino)benzoate (15.2 mg, 15% yield) as a white solid.

LC-MS (ESI$^+$) m/z 437.3 (M+H)$^+$.

$^1$H NMR (400 MHz, CDCl$_3$) δ 7.91 (d, J=8.4 Hz, 2H), 6.95-6.81 (m, 3H), 6.65 (d, J=8.6 Hz, 2H), 5.83 (br d, J=4.0 Hz, 1H), 3.96-3.85 (m, 6H), 3.76-3.50 (m, 2H), 3.44-3.35 (m, 1H), 3.06 (s, 6H), 2.61 (s, 3H), 2.43-2.26 (m, 3H), 2.11-1.92 (m, 2H), 1.82 (br d, J=12.0 Hz, 1H).

Example 98

1-4-[2-[(3aS,7aS)-3a-(3,4-dimethoxyphenyl)-1-methyl-2,3,4,5,7,7a-hexahydroindol-6-ylidene]hydrazino]benzoic acid (363)

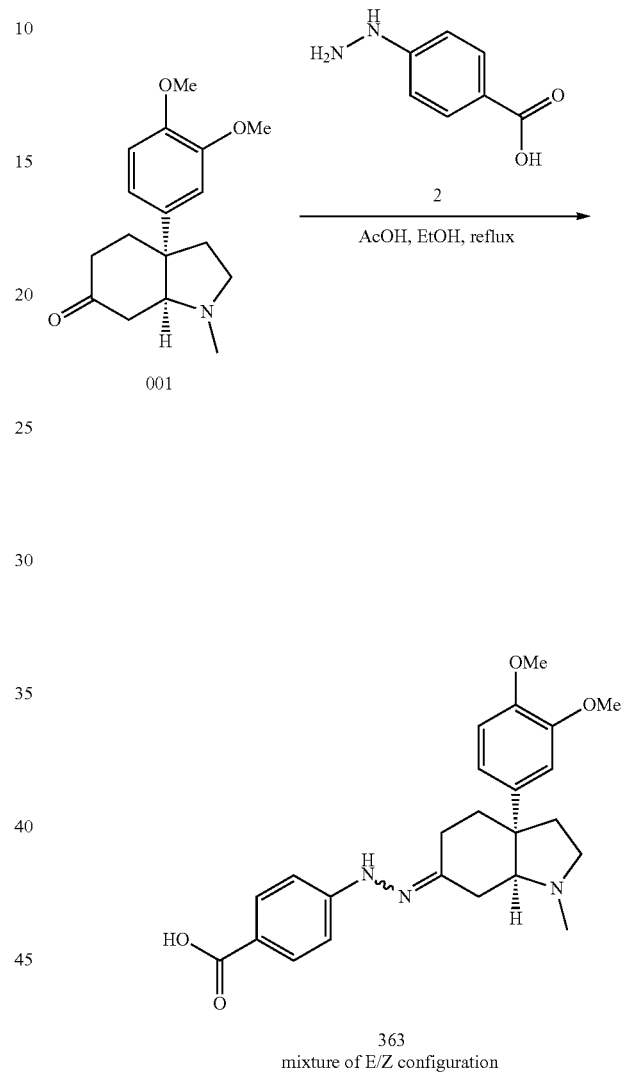

To a solution of (3aS,7aS)-3a-(3,4-dimethoxyphenyl)-1-methyl-2,3,4,5,7,7a-hexahydroindol-6-one (100 mg, 345 umol) and 4-hydrazinobenzoic acid (55.2 mg, 362 umol) in EtOH (1 mL) was added AcOH (2.08 mg, 34.5 umol), The mixture was stirred at 60° C. for 2 hours. On completion, The mixture was lyophilization to give 4-[2-[(3aS, 7aS)-3a-(3,4-dimethoxy phenyl)-1-methyl-2,3,4,5,7,7a-hexahydroindol-6-ylidene] hydrazine] benzoic acid (146 mg, 98% yield) as an orange solid.

LC-MS (ESI+) m/z 424.3 (M+H)$^+$, $^1$H NMR (400 MHz, DMSO-d$_6$) δ 9.11 (s, 1H), 7.73 (d, J=8.8 Hz, 2H), 7.05 (d, J=8.8 Hz, 2H), 6.92-6.86 (m, 3H), 3.74-3.70 (m, 6H), 2.90 (br t, J=7.2 Hz, 1H), 2.77 (br t, J=4.4 Hz, 1H), 2.70-2.64 (m, 1H), 2.43-2.31 (m, 2H), 2.29-2.23 (m, 3H), 2.20-2.07 (m, 3H), 2.00-1.92 (m, 3H).

Example 99

1-N-[[(3aS,7aS)-3a-(3,4-dimethoxyphenyl)-1-methyl-2,3,4,5,7,7a-hexahydroindol-6-vlidene]amino]pvrazin-2-amine (365)

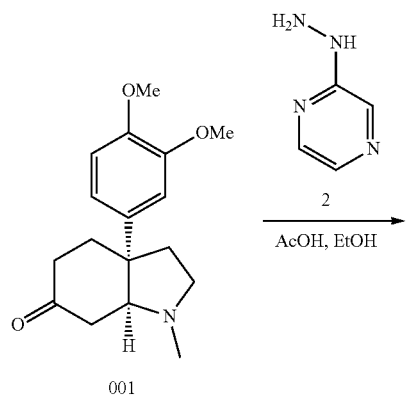

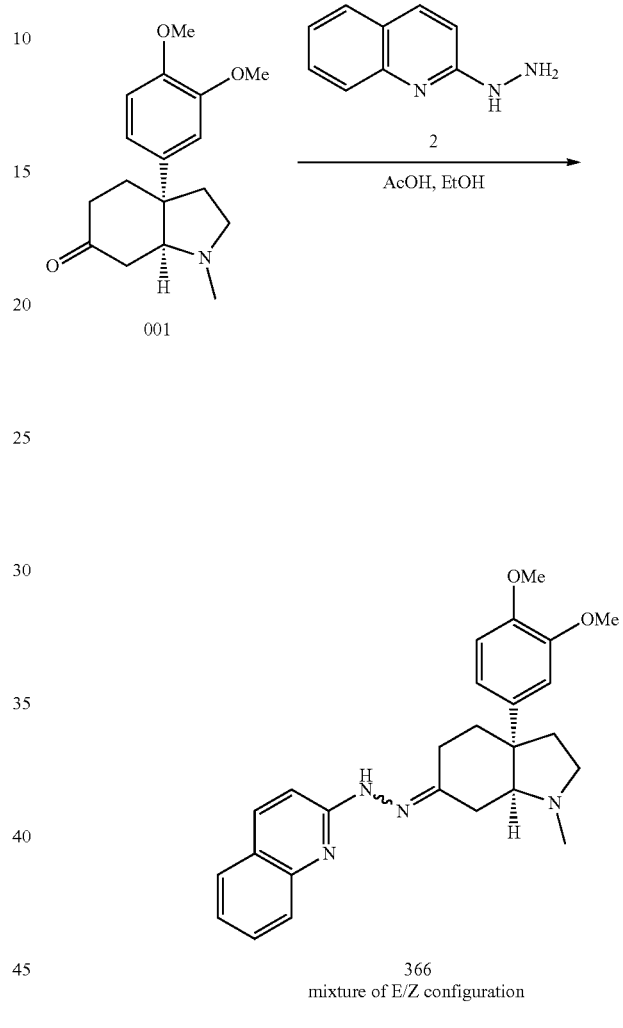

Example 100

N-[[(3aS,7aS)-3a-(3,4-dimethoxyphenyl)-1-methyl-2,3,4,5,7,7a-hexahydroindol-6-ylidene] amino]quinolin-2-amine 366)

To a solution of (3aS,7aS)-3a-(3,4-dimethoxyphenyl)-1-methyl-2,3,4,5,7,7a-hexahydroindol-6-one (100 mg, 345.58 umol) and pyrazin-2-ylhydrazine (38.0 mg, 345 umol) in EtOH (1 mL) was added AcOH (2.08 mg, 34.56 umol), The mixture was stirred at 60° C. for 2 hours. On completion, the mixture was concentrated to give a residue. The crude product was purified by reversed-phase HPLC (column: Waters xbridge 150*25 mm 10 um; mobile phase: [water (NH$_4$HCO$_3$)-ACN]; B %: 18%-48%, 8 min) to give N-[[(3aS,7aS)-3a -(3,4-dimethoxy phenyl) -1-methyl-2,3,4,5,7,7a-hexahydroindol-6-ylidene]amino]pyrazine-2-amine (49.7 mg, 37% yield) as a brown gum.

LC-MS (ESI+) m/z 382.1 (M+H)$^+$, $^1$H NMR (400 MHz, DMSO-d$_6$) δ 9.52 (s, 1H), 8.49-8.36 (m, 1H), 8.05 (dd, J=1.6, 2.4 Hz, 1H), 7.95-7.86 (m, 1H), 6.94-6.86 (m, 3H), 3.73 (d, J=7.2 Hz, 6H), 2.94-2.87 (m, 1H), 2.77 (br t, J=4.4 Hz, 1H), 2.70-2.63 (m, 2H), 2.34-2.27 (m, 1H), 2.25 (s, 3H), 2.21-2.14 (m, 2H), 2.10-2.04 (m, 1H), 2.00-1.91 (m, 3H).

To a solution of (3aS,7aS)-3a-(3,4-dimethoxyphenyl)-1-methyl-2,3,4,5,7,7a-hexahydroindol-6-one (100 mg, 345 umol) in EtOH (1.0 mL) was added AcOH (2.08 mg, 34.5 umol, 1.98 uL) and 2-quinolylhydrazine (110 mg, 691 umol). The mixture was stirred at 60° C. for 2 hours. The reaction mixture was concentrated in vacuo to give the residue. The residue was purified by prep-HPLC (column: Welch Xtimate C$_{18}$ $_{150*25}$ mm*5 um; mobile phase: [water (NH3H2O)-ACN]; B %: 36%-66%, 8 min) to give the N-[[(3aS,7aS)-3a-(3,4-dimethoxyphenyl)-1-methyl-2,3,4,5, 7,7a-hexahydroindol-6-ylidene]amino]quinolin-2-amine (54.9 mg, 55% yield) as a yellow solid.

LC-MS (ESI$^+$) m/z 431.3 (M+H)$^+$.

$^1$H NMR (400 MHz, CDCl$_3$) δ 8.08-7.96 (m, 1H), 7.76-7.62 (m, 2H), 7.62-7.50 (m, 2H), 7.34-7.28 (m, 1H), 7.01-6.83 (m, 2H), 6.83-6.75 (m, 1H), 3.94-3.82 (m, 6H), 3.13-2.99 (m, 1H), 2.97-2.89 (m, 1H), 2.89-2.78 (m, 1H), 2.72-2.56 (m, 1H), 2.41 (s, 3H), 2.40-2.21 (m, 3H), 2.19-1.97 (m, 4H).

Example 101

N-[(3aS,7aS)-3a-3,4-imethoxyphenyl)-methyl-,3,4,5,7,7a-hexahydroindol-ylidene] amino-m-tolyl)methanamine (367)

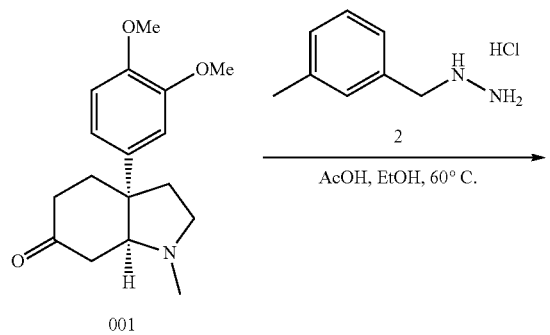

Example 102

N-[[(3aS,7aS)-3a-(3,4-dimethoxyphenyl)-1-methyl-2,3,4,5,7,7a-hexahydroindol-6-ylidene]amino]-1-(3-pyridyl)methanamine (370)

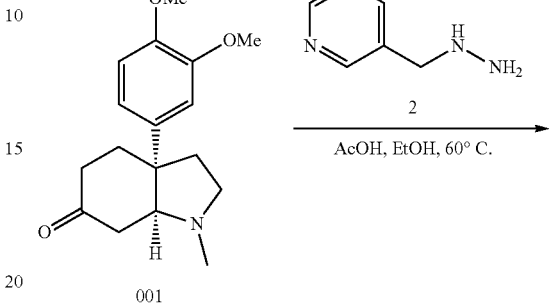

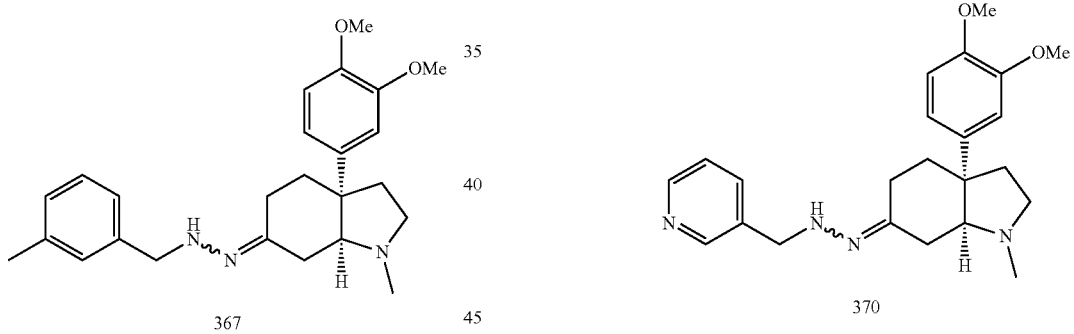

To a solution of (3aS,7aS)-3a-(3,4-dimethoxyphenyl)-1-methyl-2,3,4,5,7,7a-hexahydroindol one (100 mg, 345 umol) in EtOH (5 mL) was added m-tolylmethylhydrazine (71.6 mg, 414 umol, HCl). The mixture was stirred at 60° C. for 4 hours. On completion, filtered to remove the insoluble. The filter liquor was concentrated in vacuo. The residue was purified by prep-HPLC (column: Welch Xtimate $C_{18}$ 150*25 mm*5 um; mobile phase: [water(NH3H2O)-ACN]; B %: 28%-58%, 8 min) to give N-[[(3aS,7aS)-3a-(3,4-dimethoxyphenyl)-1-methyl-2,3,4,5,7,7a-hexahydroindol-6-ylidene]amino]-1-(m-tolyl)methanamine (10 mg, 24.2 umol, 7.1% yield) as a yellow gum.

LC-MS (ESI$^+$) m/z 408.4)

$^1$H NMR (400 MHz, CDCl$_3$) δ=7.23-7.05 (m, 4H), 6.86-6.75 (m, 3H), 4.34-4.25 (m, 2H), 3.87 (d, J=5.1 Hz, 6H), 3.06-2.97 (m, 1H), 2.86 (t, J=5.4 Hz, 1H), 2.72 (dd, J=4.8, 14.8 Hz, 1H), 2.56-2.50 (m, 1H), 2.37 (s, 3H), 2.34 (s, 3H), 2.28-2.21 (m, 2H), 2.20-2.10 (m, 2H), 2.07-1.99 (m, 2H), 1.95-1.87 (m, 2H).

To a solution of (3aS,7aS)-3a-(3,4-dimethoxyphenyl)-1-methyl-2,3,4,5,7,7a-hexahydroindol-6-one (150 mg, 518 umol) and 3-pyridylmethylhydrazine (63.8 mg, 518 umol) in EtOH (2 mL) was added AcOH (3.11 mg, 51.8 umol, 2.96 uL). The mixture was stirred at 60° C. for 2 hours. On completion, the reaction mixture was filtered, concentrated in vacuo to give the residue. The residue was purified by prep-HPLC (column: Welch Xtimate $C_{18}$ 150*25 mm*5 um;mobile phase: [water(NH$_3$H$_2$O)-ACN]; B %: 15%-45%, 8 min) to give N-[[(3aS,7aS)-3a-(3,4-dimethoxyphenyl)-1-methyl-2,3,4,5,7,7a-hexahydroindol-6-ylidene]amino]-1-(3-pyridyl)methanamine (78.3 mg, 52% yield) as a yellow gum.

LC-MS (ESI$^+$) m/z 395.4 (M+H)

$^1$H NMR (400 MHz, CDCl$_3$) δ=8.58 (d, J=2.0 Hz, 1H), 8.54-8.49 (m, 1H), 7.68 (d, J=7.9 Hz, 1H), 7.26-7.22 (m, 1H), 6.93-6.70 (m, 3H), 4.89-4.42 (m, 1H), 4.40-4.28 (m, 2H), 3.95-3.80 (m, 6H), 3.02 (s, 1H), 2.93-2.78 (m, 1H), 2.77-2.61 (m, 1H), 2.58-2.48 (m, 1H), 2.42-2.32 (m, 3H), 2.31-2.18 (m, 2H), 2.17-1.99 (m, 3H), 1.96-1.80(m, 2H).

Example 103

Synthesis of (3aS,7aS)-3a-(3,4-dimethoxyphenyl)-1-methyloctahydrospiro[indole-6,2'-[1,3]dioxolane]-4'-carboxylic acid (214)

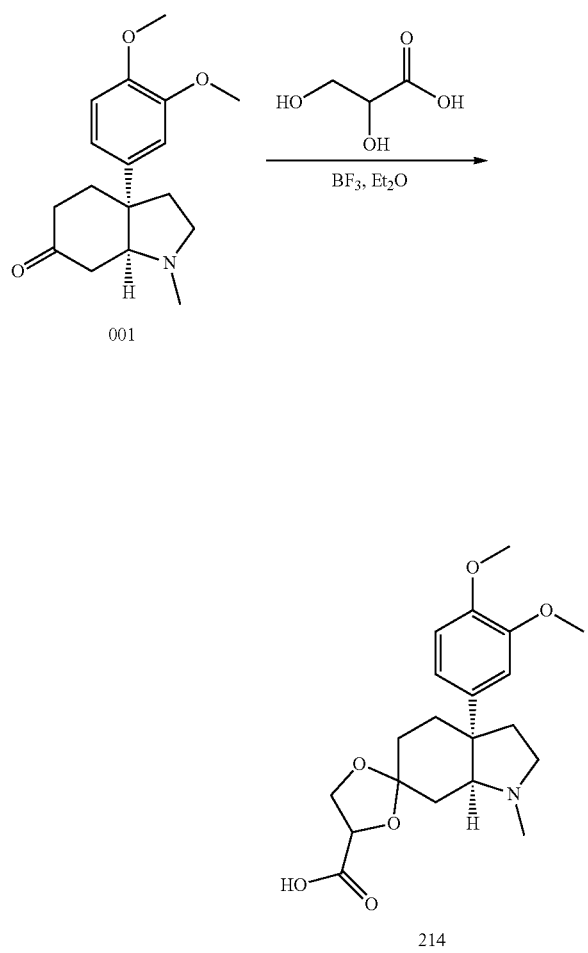

A mixture of (3aS,7aS)-3a-(3,4-dimethoxyphenyl)-1-methyloctahydro-6H-indol-6-one (200 mg, 691 umol), 2,3-dihydroxypropanoic acid (733 mg, 6.91 mmol), and BF$_3$Et$_2$O (98.1 mg, 691 umol, 85.3 uL) in toluene (3 mL) was degassed and purged with N$_2$ 3 times. The reaction mixture was allowed to stir at 60° C. for 12 hr under an atmosphere of N$_2$. The reaction mixture was concentrated in vacuo and the residue was purified by prep-HPLC (neutral condition: column: Waters xbridge 150*25 mm 10 um; mobile phase: [water (NH$_4$HCO$_3$)-ACN]; B %: 1%-30%, 8 min) and prep-HPLC (neutral condition: column: Waters xbridge 150*25 mm 10 um; mobile phase: [water (NH$_4$HCO$_3$)-ACN]; B %: 0%-30%, 9 min) to give 214 (15.0 mg, 28%) as white solid. LC-MS (ESI+) m/z 377.9 (M+H)+. $^1$H NMR (400 MHz, CDCl$_3$) δ 6.88-6.82 (m, 1H), 6.79-6.74 (m, 2H), 4.71-4.62 (m, 1H), 4.54 (t, J=8.4 Hz, 1H), 4.25 (dd, J=7.2, 8.4 Hz, 1H), 4.00 (dt, J=6.4, 12.4 Hz, 1H), 3.90 (d, J=5.6 Hz, 6H), 3.65 (d, J=5.2 Hz, 1H), 3.10 (dd, J=5.6, 12.0 Hz, 1H), 2.88 (s, 3H), 2.70 (d, J=14.8 Hz, 2H), 2.45-2.35 (m, 3H), 2.08 (d, J=14.4 Hz, 1H), 1.93 (dd, J=5.2, 15.2 Hz, 1H), 1.79-1.63 (m, 2H).

Example 104

Synthesis of 5-(2-((3aS,7aS)-3a-(3,4-dimethoxyphenyl)-1-methyloctahydro-6H-indol-6-ylidene)hydrazineyl)-5-oxopentanoic acid (246)

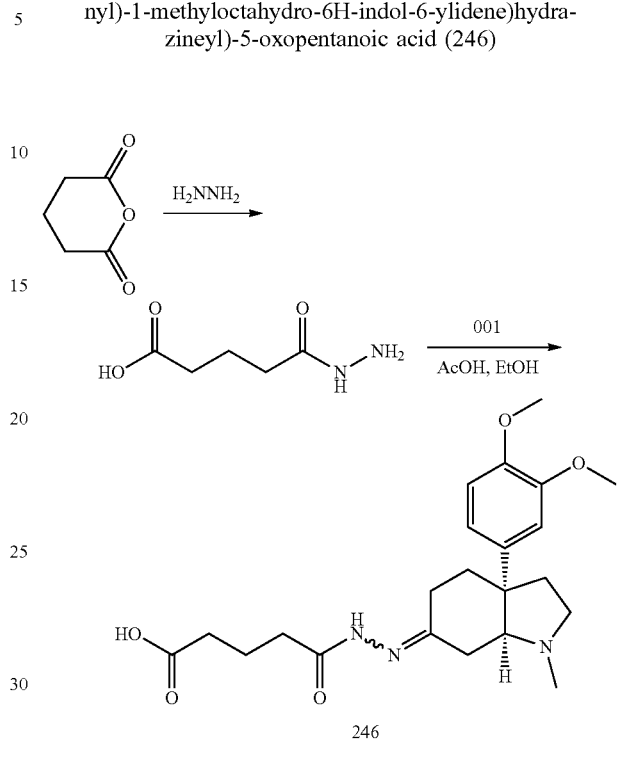

Step 1: Synthesis of 5-hydrazineyl-5-oxopentanoic acid

To a solution of hydrazine hydrate (5.16 g, 87.6 mmol, 5.01 mL, 85% purity) in ACN (100 mL) was added tetrahydropyran-2,6-dione (10 g, 87.6 mmol) in ACN (100 mL). The reaction mixture was allowed to stir at 25° C. for 0.5 hr and then filtered and concentrated in vacuo to give 5-hydrazineyl-5-oxopentanoic acid (10 g, 70%) as a white solid. $^1$H NMR (400 MHz, DMSO-d$_6$) δ=7.69-5.56 (m, 4H), 2.25-1.96 (m, 4H), 1.80-1.56 (m, 2H).

Step 2: Synthesis of 5-(2-((3aS,7aS)-3a-(3,4-dimethoxyphenyl)-1-methyloctahydro-6H-indol-6-ylidene)hydrazineyl)-5-oxopentanoic acid (246)

To a solution of 001 (100 mg, 345 umol) in EtOH (1 mL) was added CH$_3$COOH (2.08 mg, 34.6 umol) and 5-hydrazineyl-5-oxopentanoic acid (60.6 mg, 415 umol). The reaction mixture was allowed to stir at 60° C. for 2 hr and then filtered. The solution was concentrated in vacuo and the residue was purified by prep-HPLC (column: Welch Xtimate C$_{18}$ 150*25 mm*5 um; mobile phase: [water (NH$_3$H$_2$O)-ACN]; B %: 1%-25%, 8 min) to give 246 (8.00 mg, 5.6%) as an off-white solid. LC-MS (ESI+) m/z 418.3 (M+H)$^+$ $^1$H NMR (400 MHz, CDCl$_3$) δ=8.60 (s, 1H), 6.98-6.78 (m, 3H), 3.99-3.82 (m, 6H), 3.42-3.31 (m, 1H), 3.22-3.15 (m, 2H), 2.97 (s, 1H), 2.85 (d, J=3.6 Hz, 1H), 2.61 (d, J=3.6 Hz, 1H), 2.71-2.60 (m, 1H), 2.55 (s, 2H), 2.51-2.40 (m, 2H), 2.37-2.28 (m, 3H), 2.27-2.15 (m, 2H), 2.13-2.06 (m, 2H), 2.02 (d, J=6.8 Hz, 2H).

Example 105

Synthesis of 2-((3aS,7aS)-3a-(3,4-dimethoxyphenyl)-1-methyloctahydro-6H-indol-6-ylidene)-N-(pyridin-4-yl)hydrazine-1-carboxamide (252)

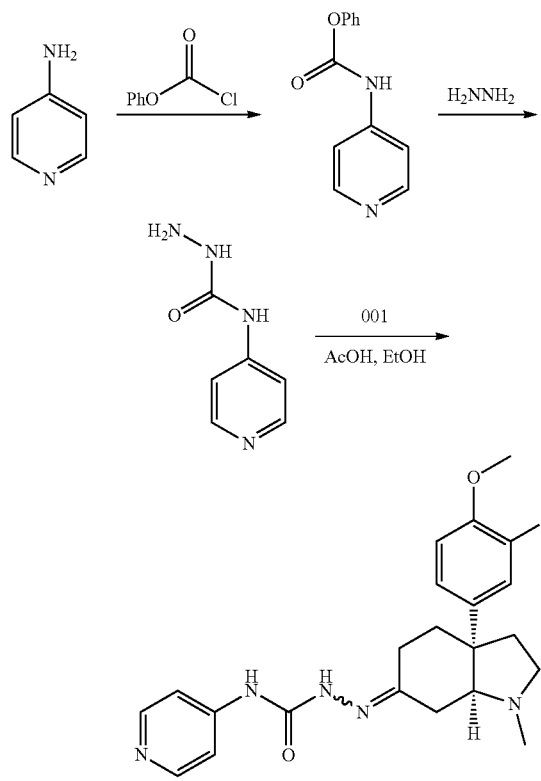

Step 1: Synthesis of phenyl pyridin-4-ylcarbamate

To a solution of pyridin-4-amine (1 g, 10.6 mmol, 1.79 mL) in THF (20 mL) and H$_2$O (2 mL) was added NaHCO$_3$ (1.07 g, 12.7 mmol) at 0° C. Phenyl carbonochloridate (1.75 g, 11.2 mmol, 1.40 mL) in THF (20 mL) was added and the reaction mixture was allowed to stir at 25° C. for 0.5 hour. The reaction mixture was concentrated in vacuo to give phenyl pyridin-4-ylcarbamate (550 mg, 22%) as a white solid. $^1$H NMR (400 MHz, DMSO-d$_6$) δ=10.70 (s, 1H), 8.48-8.41 (m, 2H), 7.50-7.42 (m, 4H), 7.34-7.22 (m, 3H).

Step 2: Synthesis of N-(pyridin-4-yl)hydrazinecarboxamide

To a solution of phenyl pyridin-4-ylcarbamate (360 mg, 1.68 mmol) in ACN (5 mL) was added hydrazine hydrate (198 mg, 3.36 mmol). The reaction mixture was allowed to stir at 25° C. for 3 hr and then filtered. The solution was concentrated in vacuo to give N-(pyridin-4-yl)hydrazinecarboxamide (165 mg, 61%) as a white solid. $^1$H NMR (400 MHz, DMSO-d$_6$) δ=9.04 (s, 1H), 8.32-8.27 (m, 2H), 7.70 (d, J=1.2 Hz, 1H), 7.55 (s, 2H), 4.42 (s, 2H).

Step 3: Synthesis of 2-((3aS,7aS)-3a-(3,4-dimethoxyphenyl)-1-methyloctahydro-6H-indol-6-ylidene)-N-(pyridin-4-yl)hydrazine-1-carboxamide (252)

To a solution of 001 (313 mg, 1.08 mmol) and N-(pyridin-4-yl)hydrazinecarboxamide (165 mg, 1.08 mmol) in EtOH (5 mL) was added CH$_3$COOH (6.51 mg, 108 umol). The reaction mixture was allowed to stir at 60° C. for 2 hr. The reaction mixture was filtered and concentrated in vacuo to give 252 (334 mg, 70% yield) as white solid. LC-MS (ESI$^+$) m/z 424.2 (M+H)$^+$ $^1$H NMR (400 MHz, CDCl$_3$) δ=8.51-8.42 (m, 3H), 8.18 (s, 1H), 7.63-7.39 (m, 2H), 7.01-6.74 (m, 3H), 3.95-3.84 (m, 6H), 3.10 (t, J=7.6 Hz, 1H), 2.97 (t, J=4.8 Hz, 1H), 2.82-2.57 (m, 2H), 2.57-2.48 (m, 1H), 2.47-2.29 (m, 5H), 2.29-2.20 (m, 1H), 2.16-2.09 (m, 2H), 2.05-1.98 (m, 1H).

Example 106

Synthesis of 2-((3aS,7aS)-3a-(3,4-dimethoxyphenyl)-1-methyloctahydro-6H-indol-6-ylidene)-N-(pyridin-2-yl)hydrazine-1-carboxamide (253)

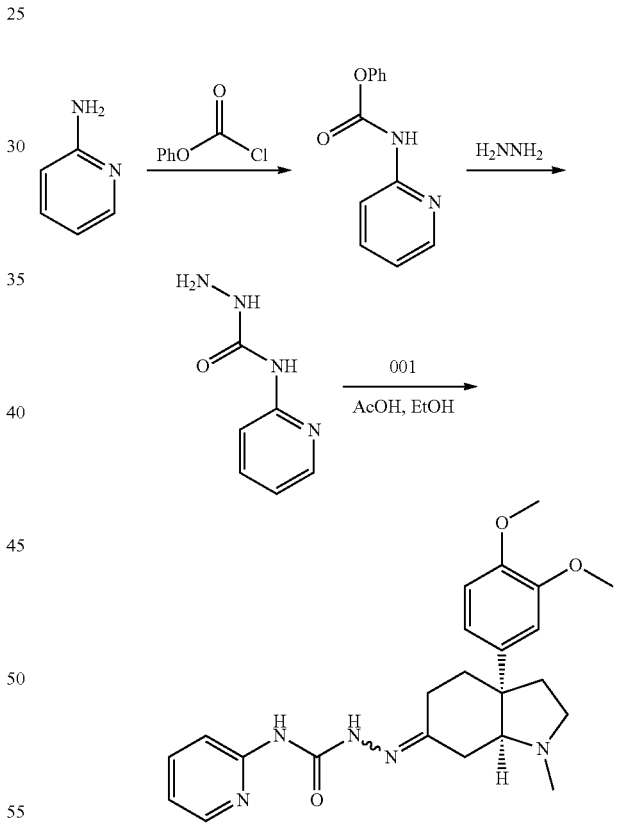

Step 1: Synthesis of phenyl pyridin-2-ylcarbamate

To a solution of pyridin-2-amine (2.00 g, 21.2 mmol) in THF (5.0 mL) and H$_2$O (5.0 mL) was added NaHCO$_3$ (1.79 g, 21.2 mmol, 826 uL) and phenyl carbonochloridate (3.33 g, 21.2 mmol, 2.66 mL) at 0° C. The mixture was allowed to stir at 25° C. for 10 min. The reaction mixture was poured into water (100 mL) and extracted with ethyl acetate (100 mL). The organic solutions were combined and dried over sodium sulfate, filtered and concentrated in vacuo. The residue was purified by column chromatography (SiO$_2$, petroleum ether:ethyl acetate=5:1) to give phenyl pyridin-2-ylcarbamate (210 mg, 3.7%) as a yellow solid. LC-MS (ESI+) m/z 215.2 (M+H)+. $^1$H NMR (400 MHz, CDCl$_3$) δ 9.26 (s, 1H), 8.36-8.28 (m, 1H), 7.98 (d, J=8.4 Hz, 1H), 7.70-7.62 (m, 1H), 7.40-7.31 (m, 2H), 7.23-7.20 (m, 1H), 7.18-7.13 (m, 2H), 7.01-6.92 (m, 1H).

Step 2: Synthesis of N-(pyridin-2-yl)hydrazinecarboxamide

To a solution of phenyl pyridin-2-ylcarbamate (210 mg, 980 umol) in ACN (5.0 mL) was added NH$_2$NH$_2$·H$_2$O (144 mg, 2.45 mmol, 140 uL, 85% purity). The mixture was allowed to stir at 25° C. for 2 hr. The reaction mixture was filtered and concentrated in vacuo to give N-(pyridin-2-yl)hydrazinecarboxamide (50.0 mg, 33%) as a yellow solid. LC-MS (ESI+) m/z 153.1 (M+H)+.
$^1$H NMR (400 MHz, CDCl3) δ 10.82-9.56 (m, 1H), 8.63 (br s, 1H), 8.13 (br d, J=4.4 Hz, 1H), 7.60-7.49 (m, 1H), 7.08-6.66 (m, 2H), 4.29-3.58 (m, 2H).

Step 3: Synthesis of 2-((3aS,7aS)-3a-(3,4-dimethoxyphenyl)-1-methyloctahydro-6H-indol-6-ylidene)-N-(pyridin-2-yl)hydrazine-1-carboxamide (253)

To a solution of 001 (50 mg, 173 umol) in EtOH (1.0 mL) was added N-(pyridin-2-yl)hydrazinecarboxamide (39.4 mg, 259 umol) and AcOH (1.04 mg, 17.2 umol). The mixture was allowed to stir at 60° C. for 2 hr. The reaction mixture was filtered and concentrated in vacuo. The residue was purified by re-crystallization from EtOAc (10 mL) at 25° C. to give 253 (23.0 mg, 31%) as a white solid. LC-MS (ESI$^+$) m/z 424.3 (M+H)$^+$. $^1$H NMR (400 MHz, CDCl$_3$) δ 8.96-8.54 (m, 1H), 7.60 (t, J=8.0 Hz, 1H), 6.96-6.70 (m, 4H), 3.85-3.78 (m, 6H), 3.23-2.91 (m, 1H), 2.87-2.74 (m, 1H), 2.73-2.43 (m, 2H), 2.38-2.09 (m, 6H), 2.08-1.87 (m, 4H).

Example 107

Synthesis of 4-(2-((3aS,7aS)-3a-(3,4-dimethoxyphenyl)-1-methyloctahydro-6H-indol-6-ylidene)hydrazine-1-carboxamido)butanoic acid (260)

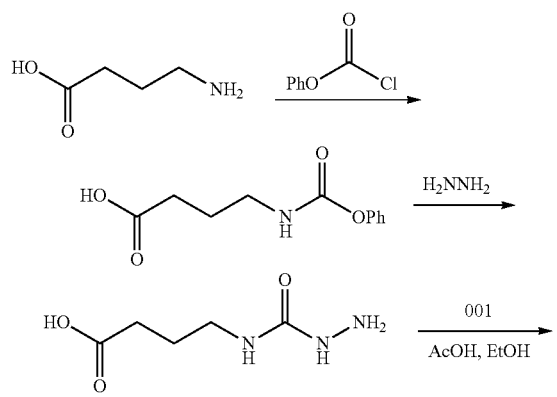

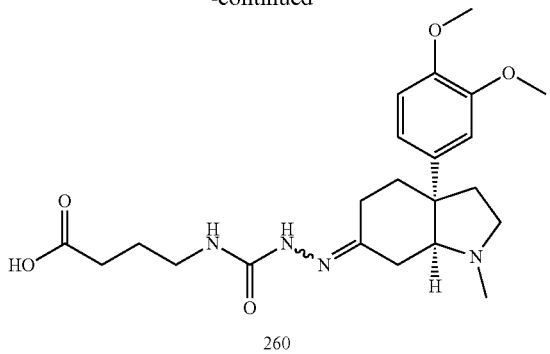

260

Step 1: Synthesis of 4-(phenoxycarbonylamino)butanoic acid

To a solution of 4-aminobutanoic acid (5 g, 48.49 mmol) in H$_2$O (5 mL) was added dropwise NaOH (1 M, 5 mL) and then phenyl carbonochloridate (7.59 g, 48.5 mmol). The mixture was allowed to stir at 0° C. for 2 hr under an atmosphere of N$_2$. The reaction was quenched by the addition of water (20 mL) and the solution was extracted with ethyl acetate (25 mL×3). The organic solutions were combined, dried over anhydrous sodium sulfate, filtered and concentrated. The residue was purified by column chromatography (SiO$_2$, Petroleum ether/Ethyl acetate=1:1 to 0:1) to give 4-(phenoxycarbonylamino) butanoic acid (1 g) as a yellow solid which was used without purification. $^1$H NMR (400 MHz, CDCl3) δ 7.41-7.33 (m, 2H), 7.24-7.18 (m, 1H), 7.13 (br d, J=7.6 Hz, 2H), 5.18 (br s, 1H), 3.36 (q, J=6.4 Hz, 2H), 2.48 (t, J=7.2 Hz, 2H), 2.01-1.86 (m, 2H).

Step 3: Synthesis of 4-(hydrazinecarbonylamino)butanoic acid

To a solution of 4-(phenoxycarbonylamino)butanoic acid (300 mg, 1.34 mmol) in EtOH (2 mL) was added hydrazine hydrate (395 mg, 6.72 mmol, 85% purity). The mixture was allowed to stir at 60° C. for 6 hr under an atmosphere of N$_2$. The reaction mixture was concentrated and the residue was triturated with EtOH:PE (2:1) at 25° C. for 10 mins to give 4-(hydrazinecarbonylamino)butanoic acid (150 mg, 58%) as a yellow solid. $^1$H NMR (400 MHz, DMSO-d6) δ 6.87 (br s, 1H), 6.36 (br s, 1H), 3.15-2.85 (m, 2H), 2.09 (t, J=7.4 Hz, 2H), 1.58 (m, 2H).

Step 3: Synthesis of 4-(2-((3aS,7aS)-3a-(3,4-dimethoxyphenyl)-1-methyloctahydro-6H-indol-6-ylidene)hydrazine-1-carboxamido)butanoic acid (260)

To a solution of 4-(hydrazinecarbonylamino) butanoic acid (60.0 mg, 372 umol) and (3aS,7aS)-3a-(3,4-dimethoxyphenyl)-1-methyl-2,3,4,5,7,7a-hexahydroindol-6-one (107 mg, 372 umol) in EtOH (1 mL) was added AcOH (11.0 mg, 186 umol). The mixture was allowed to stir at 60° C. for 2 hr under N$_2$ atmosphere. On completion, the mixture was filtered and concentrated to give a residue. The residue was purified by prep-HPLC (column: Welch Xtimate C$_{18}$ 150*25 mm*5 um; mobile phase: [water(NH$_3$H$_2$O)-ACN]; B %: 1%-27%,8 min) to give 4-[[[(3aS,7aS)-3a-(3,4-dimethoxyphenyl)-1-methyl-2,3,4,5,7,7a-hexahydroindol-6-ylidene]amino]carbamoyl amino] butanoic acid (50.0 mg, 76% purity) as a white solid. Then the residue was purified by prep-HPLC (column: Waters xbridge 150*25 mm 10 um; mobile phase: [water(NH₄HCO₃)-ACN]; B %: 1%-31%, 8 min) to give 260 (10.0 mg, 6.7%) as a white solid. LC-MS (ESI+) m/z 433.1 (M+H)⁺. ¹H NMR (400 MHz, CDCl₃) δ 8.23 (s, 1H), 6.91-6.82 (m, 3H), 6.34 (br dd, J=2.4, 9.2 Hz, 1H), 3.92-3.87 (m, 6H), 3.74 (dt, J=7.8, 15.2 Hz, 1H), 3.25 (td, J=4.8, 9.2 Hz, 1H), 3.21-3.11 (m, 2H), 2.71-2.68 (m, 1H), 2.46 (s, 3H), 2.38 (br d, J=8.4 Hz, 2H), 2.35-2.30 (m, 2H), 2.28-2.24 (m, 1H), 2.23-2.17 (m, 2H), 2.16-2.11 (m, 1H), 2.10-1.98 (m, 3H), 1.95-1.87 (m, 2H).

Example 108

Synthesis of (3aS,7aS)-3a-(3,4-dimethoxyphenyl)-6-(2-(4-fluorophenyl)-hydrazineylidene)-1-methyloctahydro-1H-indole (361)

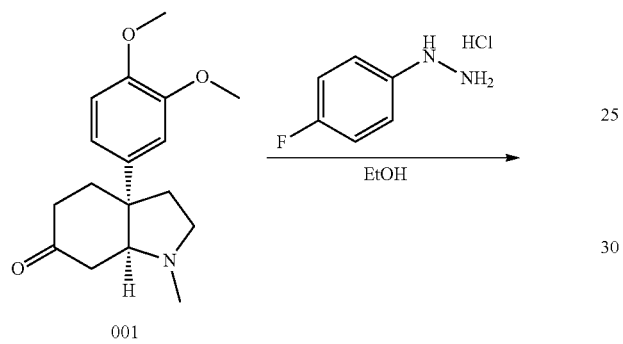

Example 109

Synthesis of (3aS,7aS)-3a-(3,4-dimethoxyphenyl)-1-methyl-6-(2-(3-methylpyridin-2-yl)hydrazineylidene)octahydro-1H-indole (364)

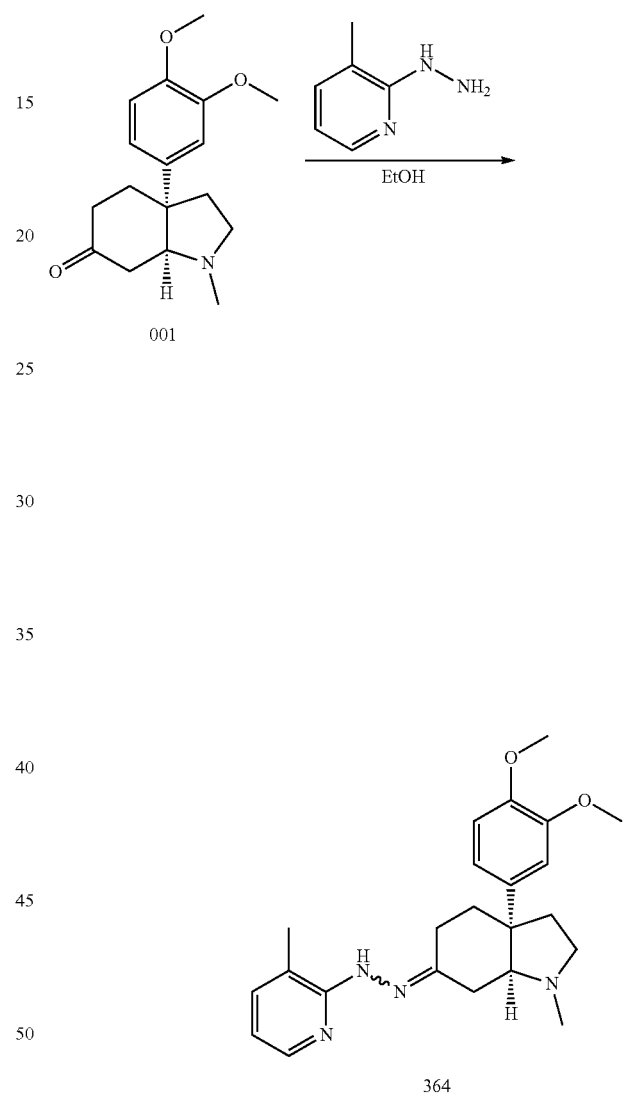

A solution of 001 (100 mg, 346 umol) and (4-fluorophenyl) hydrazine hydrochloride (56.2 mg, 346 umol) in EtOH (2 mL) was allowed to stir at 60° C. for 1 hr. The reaction mixture was concentrated in vacuo and the residue was purified by prep-HPLC (column: Waters Xbridge 150*25 mm*5 um; mobile phase: [water (NH₄HCO₃)-ACN]; B %: 33%-63%, 10 min) to give 361 (10.6 mg, 10%) as a yellow solid. LC-MS (ESI⁺) m/z 398.3 (M+H)⁺. ¹H NMR (400 MHz, CDCl₃) δ 6.96-6.91 (m, 3H), 6.88-6.84 (m, 1H), 6.83-6.78 (m, 2H), 6.68 (s, 1H), 3.85 (d, J=13.6 Hz, 6H), 3.08 (s, 1H), 3.02-2.92 (m, 1H), 2.86 (dd, J=4.4, 14.8 Hz, 1H), 2.72-2.57 (m, 1H), 2.44 (s, 2H), 2.36-2.27 (m, 1H), 2.36-2.24 (m, 3H), 2.20-2.14 (m, 1H), 2.03-1.93 (m, 2H), 1.36-1.22 (m, 3H).

To a solution of 001 (46.8 mg, 380 umol) in EtOH (1.0 mL) was added AcOH (2.08 mg, 34.5 umol). The reaction mixture was allowed to stir at 60° C. for 2 hr and then filtered and concentrated in vacuo. The resulting residue was purified by reversed-phase HPLC (0.1% NH₃·H₂O) to give 364 (87.5 mg, 62%) as a brown gum. LC-MS (ESI+) m/z 395.3 (M+H)⁺ ¹H NMR (400 MHz, CDCl₃) δ 8.19 (d, J=4.4 Hz, 1H), 7.31 (d, J=6.8 Hz, 1H), 7.10 (s, 1H), 6.91-6.85 (m, 2H), 6.84-6.79 (m, 1H), 6.70 (dd, J=5.2, 7.2 Hz, 1H), 3.86 (d, J=5.2 Hz, 5H), 3.04-3.03 (m, 1H), 3.06-2.97 (m, 2H), 2.96-2.91 (m, 1H), 2.71 (dd, J=6.4, 14.4 Hz, 1H), 2.40 (s, 3H), 2.38-2.30 (m, 2H), 2.29 (s, 1H), 2.16 (s, 1H), 2.13 (s, 3H), 2.07 (s, 1H), 2.05-1.96 (m, 2H).

Example 110

Synthesis of (3aS,7aS)-3a-(3,4-dimethoxyphenyl)-1-methyl-6-(2-(pyridin-2-ylmethyl)hydrazineylidene)octahydro-1H-indole (369)

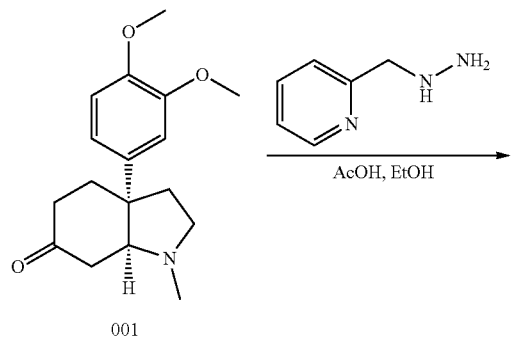

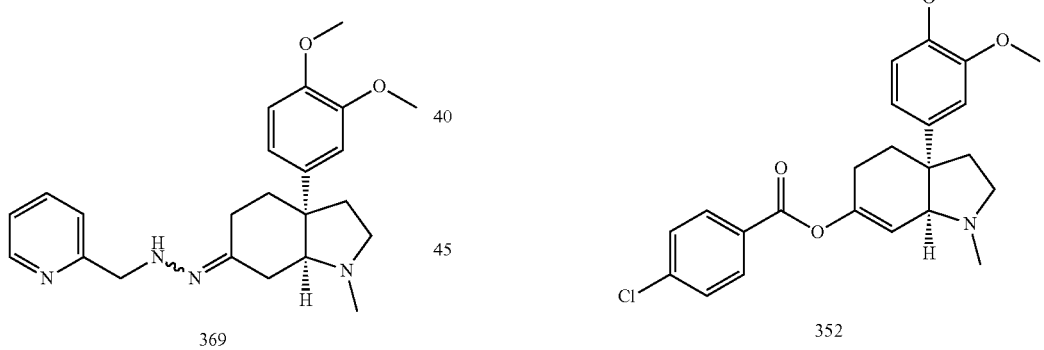

To a solution of 001 (200 mg, 691 umol) in EtOH (1.0 mL) was added AcOH (4.15 mg, 69.1 umol, 3.95 uL) and 2-pyridylmethylhydrazine;hydrochloride (110 mg, 691 umol). The reaction mixture was allowed to stir at 60° C. for 2 hr and then concentrated in vacuo. The resulting residue was purified by prep-HPLC (column: Waters xbridge 150*25 mm 10 um; mobile phase: [water(NH$_4$HCO$_3$)-ACN]; B %: 18%-48%, 8 min) to give 369 (19.8 mg, 9.6%) as a yellow solid. LC-MS (ESI$^+$) m/z 395.3 (M+H)$^+$. $^1$H NMR (400 MHz, CDCl$_3$) δ 8.61-8.42 (m, 1H), 7.64 (t, J=8.0 Hz, 1H), 7.37-7.29 (m, 1H), 7.21-7.09 (m, 1H), 6.96-6.77 (m, 3H), 4.54-4.32 (m, 2H), 3.92-3.85 (m, 6H), 3.10-2.94 (m, 1H), 2.93-2.77 (m, 1H), 2.61 (br s, 1H), 2.58-2.43 (m, 1H), 2.39-2.31 (m, 3H), 2.30-2.19 (m, 3H), 2.17-2.00 (m, 3H), 1.99-1.92 (m, 1H).

Example 111

Synthesis of (3aS,7aS)-6-((4-chlorobenzyl)oxy)-3a-(3,4-dimethoxyphenyl)-1-methyl-2,3,3a,4,5,7a-hexahydro-1H-indole (352)

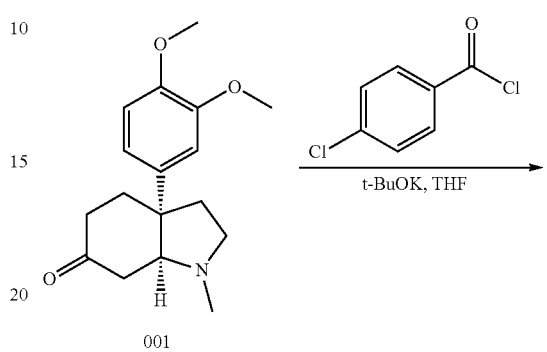

A mixture of 001(100 mg, 346 umol), (4-chlorobenzoyl) 4-chlorobenzoate (204 mg, 691 umol), and t-BuOK (1M in THF, 691 uL) in THF (1.50 mL) was degassed and purged with N$_2$ 3 times. The reaction mixture was allowed to stir at 25° C. for 1 hr under an atmosphere of N$_2$ and then concentrated in vacuo. The resulting residue was purified by prep-HPLC (FA condition: column: Phenomenex luna C$_{18}$ 150*25 mm*10 um; mobile phase: [water(FA)-ACN]; B %: 23%-53%, 10 min) to give 352 (60.0 mg, 40%) as off-white solid. LC-MS (ESI+) m/z 428.8 (M+H)+.

$^1$H NMR (400 MHz, CDCl$_3$) δ 8.00 (d, J=8.4 Hz, 2H), 7.44 (d, J=8.4 Hz, 2H), 6.86 (s, 3H), 5.90 (d, J=3.2 Hz, 1H), 3.91 (d, J=17.2 Hz, 6H), 3.69-3.57 (m, 1H), 3.49 (s, 1H), 2.84-2.58 (m, 4H), 2.46-2.28 (m, 3H), 2.15-1.93 (m, 2H), 1.91-1.79 (m, 1H).

Example 112

Synthesis of (3aS,7aS)-3a-(3,4-dimethoxyphenyl)-1-methyl-2,3,3a,4,5,7a-hexahydro-1H-indol-6-yl 4-fluorobenzoate (353)

Example 113

Synthesis of (3aS,7aS)-3a-(3,4-dimethoxyphenyl)-1-methyl-2,3,3a,4,5,7a-hexahydro-1H-indol-6-yl 4-cyanobenzoate (354)

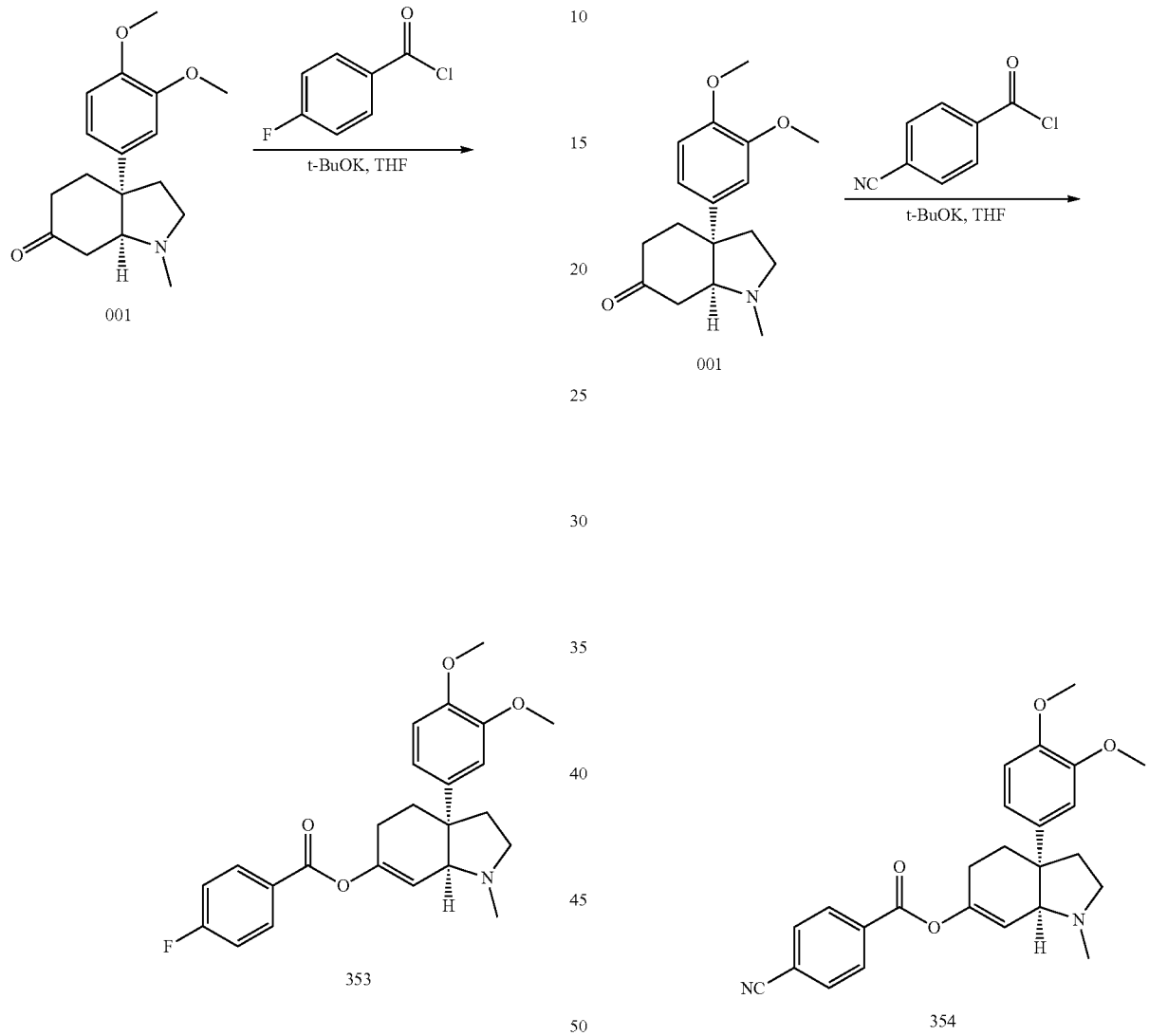

A mixture of 001 (100 mg, 346 umol), (4-fluorobenzoyl) 4-fluorobenzoate (181 mg, 691 umol), and t-BuOK (1M in THF, 691 uL) in THF (1.50 mL) was degassed and purged with $N_2$ 3 times. The reaction mixture was allowed to stir at 0~25° C. for 1 hr under an atmosphere of $N_2$ and then oncentrated in vacuo. The residue was purified by prep-HPLC (FA condition:column: Phenomenex luna $C_{18}$ 150*25 mm*10 um; mobile phase: [water(FA)-ACN]; B %: 23%-53%, 10 min) to give 353 (61.9 mg, 42%) as white gum.

LC-MS (ESI+) m/z 412.3 (M+H)+. $^1$H NMR (400 MHz, CDCl$_3$) δ 8.08 (dd, J=5.6, 8.4 Hz, 2H), 7.14 (t, J=8.4 Hz, 2H), 6.86 (s, 3H), 5.90 (d, J=3.2 Hz, 1H), 3.91 (d, J=17.2 Hz, 6H), 3.76-3.64 (m, 1H), 3.58 (s, 1H), 2.80 (d, J=8.4 Hz, 1H), 2.70 (s, 3H), 2.48-2.28 (m, 3H), 2.16-1.94 (m, 2H), 1.87 (d, J=13.6 Hz, 1H).

To a solution of 001 (200 mg, 691 umol) and 4-cyanobenzoyl chloride (229 mg, 1.38 mmol) in THF (2 mL) was added t-BuOK (1M in THF, 1.38 mL). The reaction mixture was allowed to stir at 25° C. for 1 hr and then concentrated in vacuo. The residue was purified by prep-HPLC (column: Phenomenex luna $C_{18}$ 150*25 mm*10 um; mobile phase: [water(FA)-ACN]; B %: 12%-42%, 10 min) to give 354 (62.3 mg, 21% yield) as a yellow solid. LC-MS (ESI$^+$) m/z 419.3 (M+H)$^+$ $^1$H NMR (400 MHz, CDCl$_3$) δ 8.17 (d, J=8.4 Hz, 2H), 7.77 (d, J=8.4 Hz, 2H), 6.90-6.80 m, 3H), 5.94 (dd, J=4.4 Hz, 1H), 3.91 (d, J=14.8 Hz, 6H), 3.79-3.69 (m, 1H), 3.63 (d, J=2.8 Hz, 1H), 2.83 (d, J=9.6 Hz, 1H), 2.72 (s, 3H), 2.47-2.32 (m, 3H), 2.16-2.06 (m, 1H), 2.06-1.96 (m, 1H), 1.88 (dd, J=13.2 Hz, 1H).

Example 114

Synthesis of (3aS,7aS)-3a-(3,4-dimethoxyphenyl)-1-methyl-2,3,3a,4,5,7a-hexahydro-1H-indol-6-yl 4-isopropylbenzoate (371)

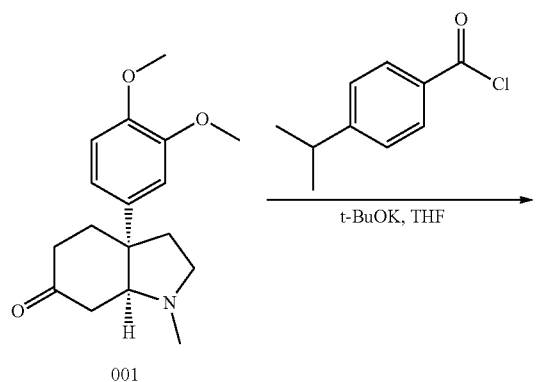

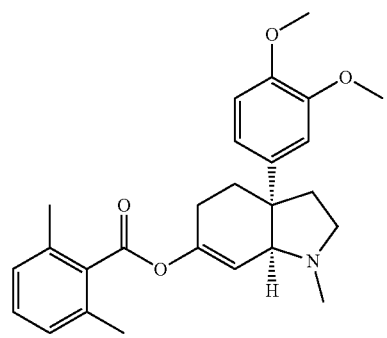

To a solution of 001 (150 mg, 518 umol) in THF (0.5 mL) was added t-BuOK (1M in THF, 1.04 mL). The reaction mixture was allowed to stir at 0° C. for 10 min and then 4-isopropylbenzoyl chloride (189 mg, 1.04 mmol) was added. The reaction mixture was allowed to stir at 25° C. for 2 hr and then was filtered and concentrated in vacuo. The resulting residue was purified by prep-HPLC (FA condition: column: Phenomenex luna $C_{18}$ $_{150*25}$ mm*10 um; mobile phase: [water (FA)-ACN]; B %: 24%-54%, 58 min) to give 371 (88.5 mg, 43%) as a white solid. LC-MS (ESI$^+$) m/z 436.3 (M+H)$^+$ $^1$H NMR (400 MHz, CDCl$_3$) δ 8.48 (s, 1H), 8.00 (d, J=8.4 Hz, 2H), 7.33 (d, J=8.4 Hz, 2H), 6.88 (s, 3H), 5.89 (d, J=3.2 Hz, 1H), 3.92 (d, J=17.2 Hz, 6H), 3.74 (dd, J=7.2, 10.0 Hz, 2H), 2.99 (s, 1H), 2.92 (dd, J=4.2, 8.4 Hz, 1H), 2.75 (s, 3H), 2.51-2.32 (m, 3H), 2.11 (d, J=3.2 Hz, 2H), 1.93-1.82 (m, 1H), 1.29 (d, J=6.8 Hz, 6H).

Example 115

Synthesis of (3aS,7aS)-3a-(3,4-dimethoxyphenyl)-1-methyl-2,3,3a,4,5,7a-hexahydro-1H-indol-6-yl 2,6-dimethylbenzoate (372)

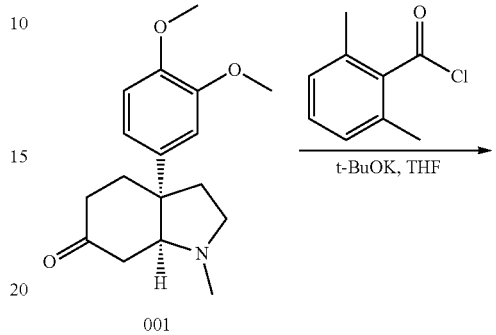

To a solution of 001 (120 mg, 414 umol) in THF (1.0 mL) was added t-BuOK (1M in THF, 829 uL). The mixture was allowed to stir at 0° C. for 10 min and then 2,6-dimethylbenzoyl chloride (139 mg, 829 umol) was added. The reaction mixture was allowed to stir at 25° C. for 2 hr and then filtered and concentrated in vacuo. The residue was purified by prep-HPLC (column: Phenomenex luna $C_{18}$ $_{150*25}$ mm*10 um; mobile phase: [water(FA)-ACN]; B %: 20%-50%, 10 min) to give 372 (86.7 mg, 72%) as a white solid. LC-MS (ESI$^+$) m/z 421.9 (M+H)$^+$ $^1$H NMR (400 MHz, CDCl$_3$) δ 7.22 (d, J=7.6 Hz, 1H), 7.06 (d, J=7.6 Hz, 2H), 6.96-6.77 (m, 3H), 5.98-5.87 (m, 1H), 3.92 (d, J=15.2 Hz, 6H), 3.70-3.51 (m, 2H), 2.91-2.78 (m, 1H), 2.70 (s, 3H), 2.44-2.40 (m, 2H), 2.37 (s, 6H), 2.21-1.99 (m, 3H), 1.93-1.83 (m, 1H).

Example 116

Synthesis of (3aS,7aS)-3a-(3,4-dimethoxyphenyl)-1-methyl-2,3,3a,4,5,7a-hexahydro-1H-indol-6-yl 2,3-dimethylbenzoate (373)

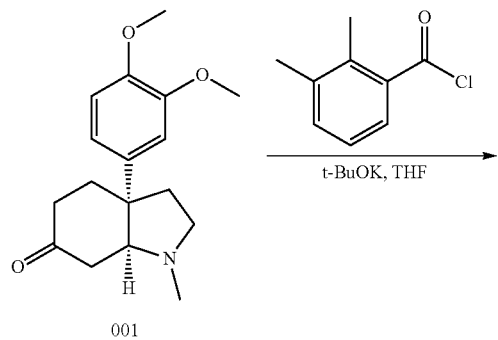

Example 117

Synthesis of (3aS,7aS)-3a-(3,4-dimethoxyphenyl)-1-methyl-2,3,3a,4,5,7a-hexahydro-1H-indol-6-yl 3-methylbenzoate (374)

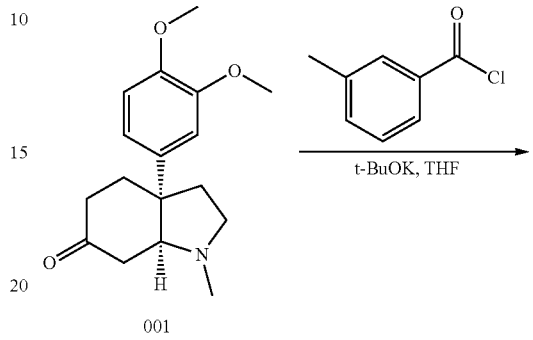

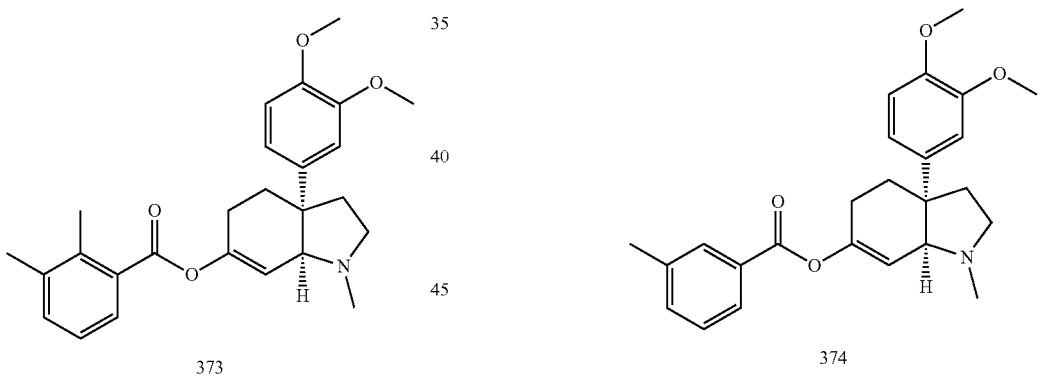

To a solution of 001 (150 mg, 518 umol) in THF (1.0 mL) was added t-BuOK (1M in THF, 1.04 mL) and 2,3-dimethylbenzoyl chloride (175 mg, 1.04 mmol) at 0° C. The reaction mixture was allowed to stir at 25° C. for 1 hr and then concentrated in vacuo. The residue was purified by prep-HPLC (column: Waters Xbridge BEH $C_{18}$ 100*30 mm*10 um; mobile phase: [water (ammonia hydroxide v/v)-ACN]; B %: 55%-85%, 2 min) to give 373 (83.5 mg, 55%) as a white solid.

LC-MS (ESI$^+$) m/z 422.3 (M+H)$^+$. $^1$H NMR (400 MHz, CDCl$_3$) δ 7.69 (d, J=7.8 Hz, 1H), 7.31 (br d, J=7.6 Hz, 1H), 7.14 (t, J=7.6 Hz, 1H), 6.96 (d, J=1.8 Hz, 1H), 6.94-6.89 (m, 1H), 6.88-6.83 (m, 1H), 5.86 (br d, J=4.4 Hz, 1H), 4.00-3.83 (m, 6H), 3.31-3.17 (m, 1H), 2.93 (br d, J=4.0 Hz, 1H), 2.53-2.37 (m, 6H), 2.33 (s, 3H), 2.30-2.16 (m, 3H), 2.02-1.93 (m, 2H), 1.86-1.60 (m, 2H).

To a solution of 001 (150 mg, 518 umol) and 3-methylbenzoyl chloride (160 g, 1.04 mmol, 137 uL) in THF (3 mL) was added t-BuOK (1M in THF, 1.04 mL). The reaction mixture was allowed to stir at 25° C. for 1 hour and then filtered. The filtrate was concentrated under reduced pressure. The residue was purified by prep-HPLC (column: Waters xbridge 150*25 mm 10 um; mobile phase: [water (NH4HCO3)-ACN]; B %: 45%-75%, 8 min) to give 374 (91.5 mg, 59%) as a yellow gum.

LC-MS (ESI$^+$) m/z 408.3 (M+H). $^1$H NMR (400 MHz, CDCl$_3$) δ=7.90-7.80 (m, 2H), 7.45-7.31 (m, 2H), 6.96-6.80 (m, 3H), 5.85 (d, J=4.4 Hz, 1H), 3.97-3.86 (m, 6H), 3.26-3.19 (m, 1H), 2.92 (d, J=4.4 Hz, 1H), 2.42 (d, J=4.0 Hz, 6H), 2.36-2.12 (m, 4H), 1.97 (d, J=6.8 Hz, 2H), 1.81 (d, J=3.2 Hz, 1H).

Example 118

Synthesis of (3aS,7aS)-3a-(3,4-dimethoxyphenyl)-1-methyl-2,3,3a,4,5,7a-hexahydro-1H-indol-6-yl 3-(tert-butyl)benzoate (375)

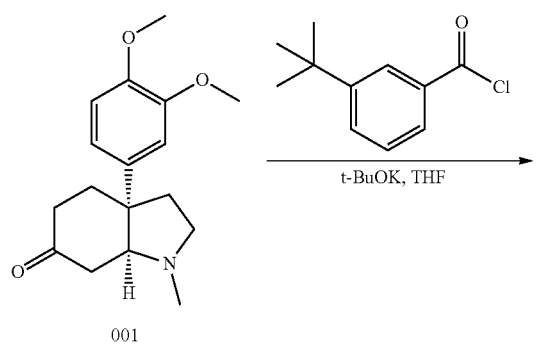

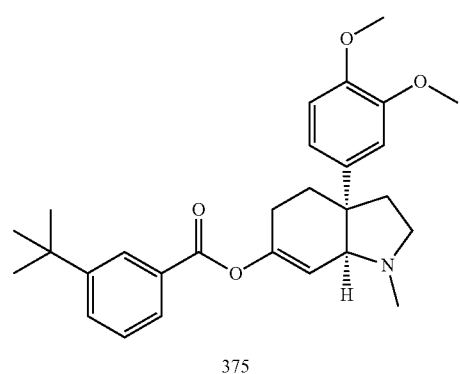

To a solution of 001 (150 mg, 518 umol) in THF (1.0 mL) was added t-BuOK (1M in THF, 1.04 mL) and 3-tert-butylbenzoyl chloride (204 mg, 1.04 mmol) at 0° C. The reaction mixture was allowed to stir at 25° C. for 2 hr and then concentrated in vacuo. The residue was purified by prep-HPLC (column: Phenomenex luna $C_{18}$ $_{150*25}$ mm*10 um; mobile phase: [water(FA)-ACN]; B %: 26%-56%, 8 min) to give 375 (107 mg, 71%) as a white solid. LC-MS (ESI$^+$) m/z 450.5 (M+H)$^+$. $^1$H NMR (400 MHz, CDCl$_3$) δ 8.47 (s, 1H), 8.08 (t, J=1.8 Hz, 1H), 7.88 (d, J=7.8 Hz, 1H), 7.70-7.57 (m, 1H), 7.40 (t, J=7.8 Hz, 1H), 6.87 (s, 3H), 5.95-5.82 (m, 1H), 3.94 (s, 3H), 3.89 (s, 3H), 3.77-3.62 (m, 2H), 2.98-2.80 (m, 1H), 2.73 (s, 3H), 2.52-2.29 (m, 3H), 2.20-1.95 (m, 2H), 1.92-1.82 (m, 1H), 1.36 (s, 9H).

Example 119

Synthesis of (3aS,7aS)-3a-(3,4-dimethoxyphenyl)-1-methyl-2,3,3a,4,5,7a-hexahydro-1H-indol-6-yl octanoate (395)

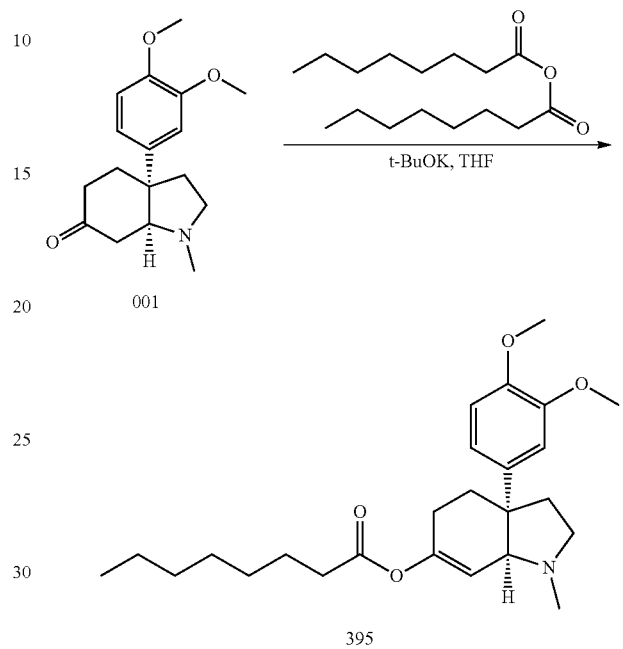

To a solution of 001 (150 mg, 518 umol) and octanoyl octanoate (280 mg, 1.04 mmol) in THF (2 mL) was added t-BuOK (1M in THF, 1.04 mL). The mixture was allowed to stir at 25° C. for 3 hr and then concentrated in vacuo. The residue was purified by prep-HPLC (column: Waters xbridge 150*25 mm 10 um; mobile phase: [water (NH$_4$HCO$_3$)-ACN]; B %: 50%-80%, 9 min) to give 395 (35.5 mg, 16%) as a colorless oil.

LC-MS (ESI$^+$) m/z. 416.6 (M+H)$^+$ $^1$H NMR (400 MHz, CDCl$_3$) δ 6.87 (s, 1H), 6.85-6.80 (m, 2H), 5.72-5.68 (m, 1H), 3.88 (d, J=12.0 Hz, 6H), 3.24 (t, J=7.6 Hz, 1H), 2.92 (s, 1H), 2.41 (s, 3H), 2.36 (t, J=7.6 Hz, 3H), 2.28-2.12 (m, 4H), 1.92-1.79 (m, 2H), 1.78-1.70 (m, 1H), 1.63 (m, 2H), 1.37-1.21 (m, 9H), 0.93-0.83 (m, 3H).

Example 120

Synthesis of (3aS,7aS)-3a-(3,4-dimethoxyphenyl)-1-methyl-2,3,3a,4,5,7a-hexahydro-1H-indol-6-yl 3-ethylhexanoate (398)

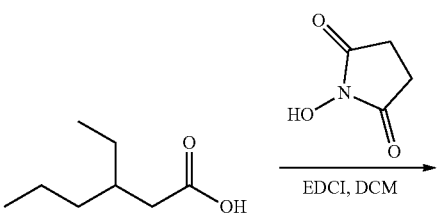

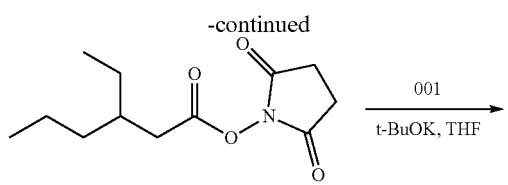

Step 1: Synthesis of (2,5-dioxopyrrolidin-1-yl) 3-ethylhexanoate

To a solution of 3-ethylhexanoic acid (50.0 mg, 346 umol) and 1-hydroxypyrrolidine-2,5-dione (59.8 mg, 520 umol) in DCM (2 mL) was added EDCI (99.7 mg, 520 umol) and DMAP (4.24 mg, 34.6 umol). The reaction mixture was allowed to stir at 25° C. for 30 min and then quenched by adding it to a cold saturated aqueous $NH_4Cl$ solution (3 ml). The aqueous solution was extracted with ethyl acetate (5 ml×2). The organic solutions were separated, combined, dried over anhydrous $Na_2SO_4$, filtered and concentrated under reduced pressure to give (2,5-dioxopyrrolidin-1-yl) 3-ethylhexanoate (166 mg) as white oil. $^1H$ NMR (400 MHz, $CDCl_3$) δ=2.93-2.83 (m, 4H), 2.54 (d, J=6.8 Hz, 2H), 2.03-1.85 (m, 1H), 1.50-1.30 (m, 6H), 0.98-0.82 (m, 6H).

Step 2: Synthesis of (3aS,7aS)-3a-(3,4-dimethoxyphenyl)-1-methyl-2,3,3a,4,5,7a-hexahydro-1H-indol-6-yl 3-ethylhexanoate (398)

To a solution of (2,5-dioxopyrrolidin-1-yl) 3-ethylhexanoate (83.3 mg, 345 umol) and 001 (50.0 mg, 172 umol) in THF (2 mL) was added t-BuOK (2M in THF, 172.8 uL). The reaction mixture was allowed to stir at 25° C. for 1 hr and concentrated in vacuo. The residue was purified by prep-HPLC (column: Phenomenex luna $C_{18}$ $_{150*25}$ mm*10 um; mobile phase: [water (FA)-ACN]; B %: 25%-55%, 8 min) to give 398 (8.18 mg, 6%) as white oil. LC-MS (ESI+) m/z 416.4 (M+H)+. $^1H$ NMR (400 MHz, $CDCl_3$) δ 6.92-6.76 (m, 3H), 5.70 (d, J=4.4 Hz, 1H), 3.88 (d, J=10.8 Hz, 6H), 3.36-3.15 (m, 1H), 3.08-2.80 (m, 1H), 2.44 (s, 3H), 2.35-2.13 (m, 6H), 1.93-1.81 (m, 3H), 1.44-1.17 (m, 7H), 0.99-0.82 (m, 6H).

Example 121

Synthesis of (3aS,7aS)-3a-(3,4-dimethoxyphenyl)-1-methyl-2,3,3a,4,5,7a-hexahydro-1H-indol-6-yl 2-methylheptanoate (400)

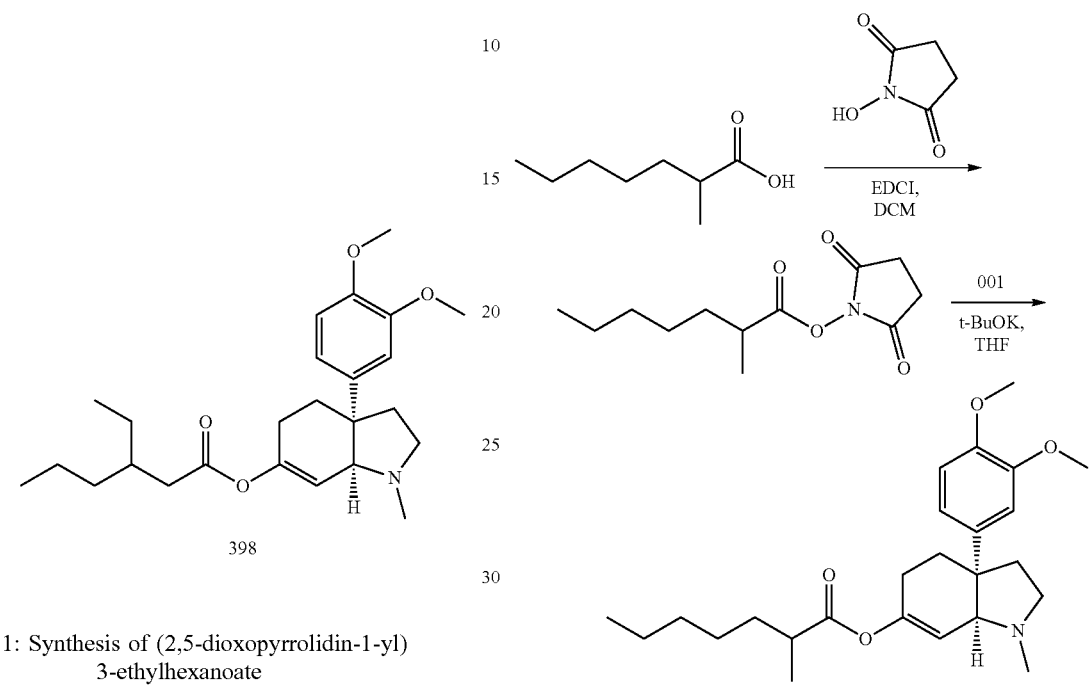

Step 1: Synthesis of (2,5-dioxopyrrolidin-1-yl) 2-methylheptanoate

To a solution of 2-methylheptanoic acid (1.0 g, 6.93 mmol) and 1-hydroxypyrrolidine-2,5-dione (877 mg, 7.63 mmol) in DCM (10 mL) was added EDCI (1.99 g, 10.4 mmol) and DMAP (84.7 mg, 693 umol). The reaction mixture was allowed to stir at 25° C. for 16 hr and then poured into water (20 mL) and extracted with ethyl acetate (60 mL). The organic layers were combined, dried by sodium sulfate, filtered and concentrated in vacuo to give (2,5-dioxopyrrolidin-1-yl) 2-methylheptanoate (1 g, 53%) as a off-white oil. $^1H$ NMR (400 MHz, $CDCl_3$) δ 2.85-2.62 (m, 5H), 1.79-1.64 (m, 1H), 1.57-1.43 (m, 1H), 1.40-1.31 (m, 2H), 1.29-1.15 (m, 7H), 0.90-0.75 (m, 3H).

Step 2: Synthesis of (3aS,7aS)-3a-(3,4-dimethoxyphenyl)-1-methyl-2,3,3a,4,5,7a-hexahydro-1H-indol-6-yl 2-methylheptanoate (400)

To a solution of 001 (200 mg, 691 umol) in THF (2.0 mL) was added t-BuOK (1M in THF, 1.38 mL). The reaction mixtgure was allowed to stir at 0° C. for 10 min and then (2,5-dioxopyrrolidin-1-yl) 2-methylheptanoate (333 mg, 1.38 mmol) was added. The reaction mixture was allowed to stir at 25° C. for 2 hr and then filtered and concentrated in vacuo. The residue was purified by prep-HPLC (FA condition: column: Phenomenex luna $C_{18}$ $_{150*25}$ mm*10 um; mobile phase: [water(FA)-ACN]; B %: 27%-57%, 58 min)

to give 400 (92.1 mg, 46%) as a yellow gum. LC-MS (ESI⁺) m/z 416.9 (M+H)⁺. ¹H NMR (400 MHz, CDCl₃) δ 6.95-6.78 (m, 3H), 5.70 (d, J=4.4 Hz, 1H), 3.90 (d, J=12.0 Hz, 6H), 3.24 (s, 1H), 2.92 (s, 1H), 2.49 (ddd, J=2.0, 7.2, 14.0 Hz, 1H), 2.42 (s, 3H), 2.38-2.30 (m, 1H), 2.29-2.13 (m, 3H), 1.90-1.81 (m, 2H), 1.79-1.62 (m, 2H), 1.48-1.39 (m, 1H), 1.37-1.26 (m, 6H), 1.18 (dd, J=2.4, 6.8 Hz, 3H), 0.89 (dt, J=3.6, 6.8 Hz, 3H).

Example 122

Synthesis of (3aS,7aS)-3a-(3,4-dimethoxyphenyl)-1-methyl-2,3,3a,4,5,7a-hexahydro-1H-indol-6-yl 2-ethylhexanoate (401)

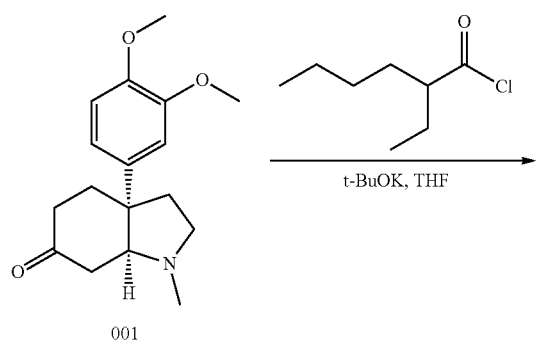

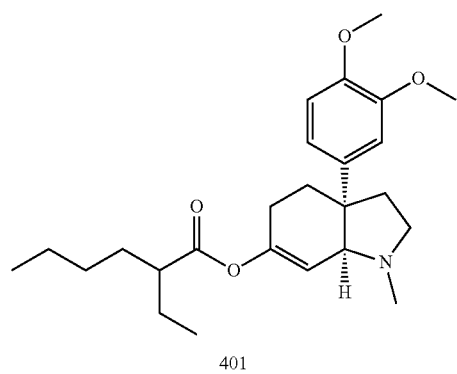

To a solution of 001 (100 mg, 346 umol) and 2-ethylhexanoyl chloride (112 mg, 691 umol, 120 uL) in THF (3 mL) was added t-BuOK (1M in THF, 691.2 uL). The reaction mixture was allowed to stir at 25° C. for 3 hr and then concentrated in vacuo to give a residue. The residue was purified by prep-HPLC (column: Welch Ultimate C₁₈ ₁₅₀*₂₅ mm*5 um; mobile phase: [water(FA)-ACN]; B %: 23%-53%, 10 min) to give 401 (80 mg, 39% yield) as a yellow gum. LC-MS (ESI⁺) m/z. 416.2 (M+H)⁺. ¹H NMR (400 MHz, CDCl₃) δ 6.94-6.75 (m, 3H), 5.69 (d, J=4.4 Hz, 1H), 3.88 (d, J=10.4 Hz, 6H), 3.37 (s, 1H), 3.24-3.04 (m, 1H), 2.51 (s, 3H), 2.36-2.18 (m, 4H), 1.76 (d, J=3.6 Hz, 1H), 1.71-1.43 (m, 5H), 1.38-1.19 (m, 6H), 1.00-0.82 (m, 6H).

Example 123

Synthesis of (3aS,7aS)-3a-(3,4-dimethoxyphenyl)-1-methyl-2,3,3a,4,5,7a-hexahydro-1H-indol-6-yl 2-methylpentanoate (402)

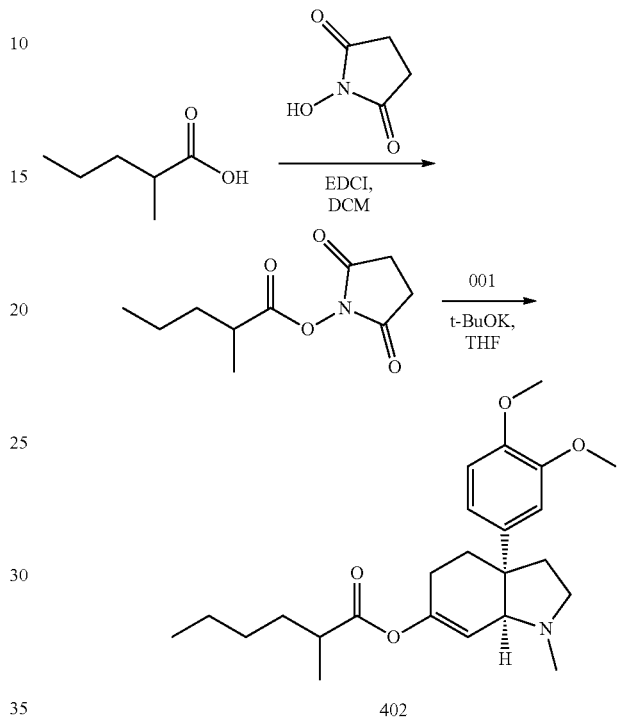

Step 1: Synthesis of (2,5-dioxopyrrolidin-1-yl) 2-methylpentanoate

To a solution of 2-methylpentanoic acid (1.00 g, 8.61 mmol) in DCM (5.0 mL) was added EDCI (2.48 g, 12.9 mmol) and DMAP (105 mg, 861 umol), followed by 1-hydroxypyrrolidine-2,5-dione (1.09 g, 9.47 mmol). The reaction mixture was allowed to stir at 25° C. for 2 hr and then poured into water (50 mL) and extracted with DCM (50 mL). The organic layers were combined, dried over sodium sulfate, filtered and concentrated in vacuo to give (2,5-dioxopyrrolidin-1-yl) 2-methylpentanoate (1.50 g, 65%) as a yellow solid. ¹H NMR (400 MHz, CDCl₃) δ 2.86-2.65 (m, 5H), 1.78-1.63 (m, 1H), 1.56-1.42 (m, 1H), 1.41-1.33 (m, 2H), 1.24 (d, J=7.0 Hz, 3H), 0.88 (t, J=7.4 Hz, 3H).

Step 2: Synthesis of (3aS,7aS)-3a-(3,4-dimethoxyphenyl)-1-methyl-2,3,3a,4,5,7a-hexahydro-1H-indol-6-yl 2-methylpentanoate (402)

To a solution of 001 (150 mg, 518 umol) in THF (1.0 mL) was added t-BuOK (1M in THF, 1.04 mL) and (2,5-dioxopyrrolidin-1-yl) 2-methylpentanoate (221 mg, 1.04 mmol) at 0° C. The reaction mixture was allowed to stir at 25° C. for 2 hr and then concentrated in vacuo. The residue was purified by prep-HPLC (column: Welch Ultimate C₁₈ ₁₅₀*₂₅ mm*5 um; mobile phase: [water(FA)-ACN]; B %: 17%-47%, 10 min) to give 402 (63.1 mg, 40%) as a yellow gum. LC-MS (ESI+) m/z 388.2 (M+H)⁺. ¹H NMR (400 MHz, CDCl$_3$) δ 8.47 (s, 1H), 6.83 (s, 3H), 5.77-5.65 (m, 1H), 3.88 (d, J=9.6 Hz, 6H), 3.64-3.48 (m, 1H), 3.40 (br s, 1H), 2.74-2.64 (m, 1H), 2.60 (s, 3H), 2.57-2.48 (m, 1H), 2.40-2.19 (m, 3H), 2.00-1.75 (m, 3H), 1.73-1.60 (m, 1H), 1.52-1.26 (m, 3H), 1.20-1.13 (m, 3H), 0.97-0.85 (m, 3H).

Example 124

Synthesis of (3aS,7aS)-3a-(3,4-dimethoxyphenyl)-1-methyl-2,3,3a,4,5,7a-hexahydro-1H-indol-6-yl 5-methoxypentanoate (404)

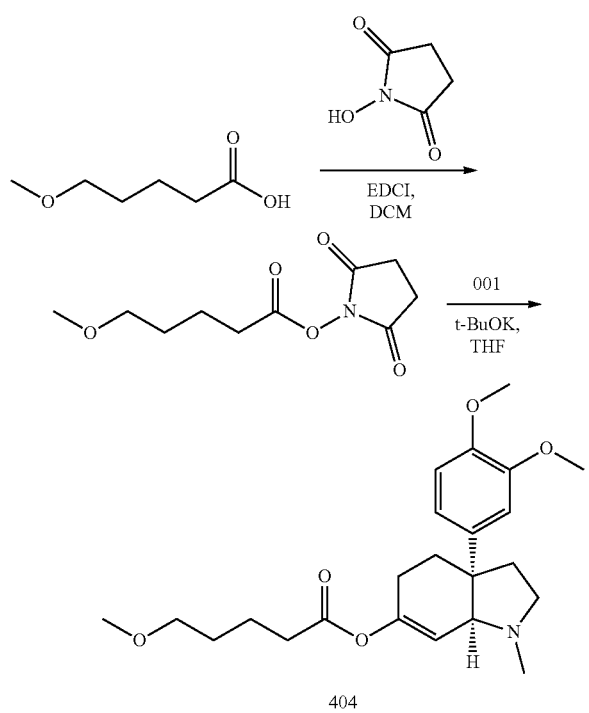

404

Step 1: Synthesis of (2,5-dioxopyrrolidin-1-yl) 5-methoxypentanoate

To the solution of 5-methoxypentanoic acid (2 g, 15.1 mmol) and 1-hydroxypyrrolidine-2,5-dione (1.74 g, 15.1 mmol) in THF (5 mL) was added EDCI (5.80 g, 30.2 mmol) and DMAP (185 mg, 1.51 mmol). The reaction mixture was allowed to stir 25° C. for 2 hr and then poured into water (50 mL) and extracted with ethyl acetate (30 mL). The organic solutions were combined, dried over sodium sulfate, filtered and concentrated in vacuo to give (2,5-dioxopyrrolidin-1-yl) 5-methoxypentanoate (2 g, 57%) as a white solid. $^1$H NMR (400 MHz, CDCl$_3$) δ=3.47-3.36 (m, 2H), 3.33-3.27 (m, 3H), 2.92-2.77 (m, 4H), 1.93-1.72 (m, 2H), 1.72-1.59 (m, 4H).

Step 2: Synthesis of (3aS,7aS)-3a-(3,4-dimethoxyphenyl)-1-methyl-2,3,3a,4,5,7a-hexahydro-1H-indol-6-yl 5-methoxypentanoate (404)

To a solution of 001 (300 mg, 1.16 mmol) in THF (3 mL) was added t-BuOK (1M in THF, 2.31 mL). The reaction mixture was allowed to stir at 0° C. for 30 min, then (2,5-dioxopyrrolidin-1-yl) 5-methoxypentanoate (795 mg, 3.47 mmol) was added. The reaction mixture was allowed to stir at 25° C. for 2 hr and then poured into water (30 mL) and extracted with ethyl acetate (30 mL). The organic solutions were combined, dried over sodium sulfate, filtered and concentrated in vacuo. The residue was purified by prep-HPLC(column: Phenomenex luna C$_{18}$ $_{150*25}$ mm*10 um; mobile phase: [water(FA)-ACN]; B %:12%-42%, 8 min) to give 404 (29.0 mg, 72 umol, 9.7%) as a yellow gum. LC-MS (ESI$^+$) m/z. 404.2 (M+H)$^+$. $^1$H NMR (400 MHz, CDCl$_3$) δ=6.82 (s, 3H), 5.72 (d, J=3.6 Hz, 1H), 3.88 (d, J=8.8 Hz, 6H), 3.59-3.44 (m, 1H), 3.39 (t, J=6.4 Hz, 2H), 3.32 (m, 4H), 2.70-2.53 (m, 4H), 2.42 (t, J=7.2 Hz, 2H), 2.37-2.28 (m, 3H), 1.97-1.83 (m, 2H), 1.81-1.67 (m, 3H), 1.66-1.57 (m, 2H).

Example 125

Synthesis of (3aS,7aS)-3a-(3,4-dimethoxyphenyl)-1-methyl-2,3,3a,4,5,7a-hexahydro-1H-indol-6-yl 2-methylbutanoate (425)

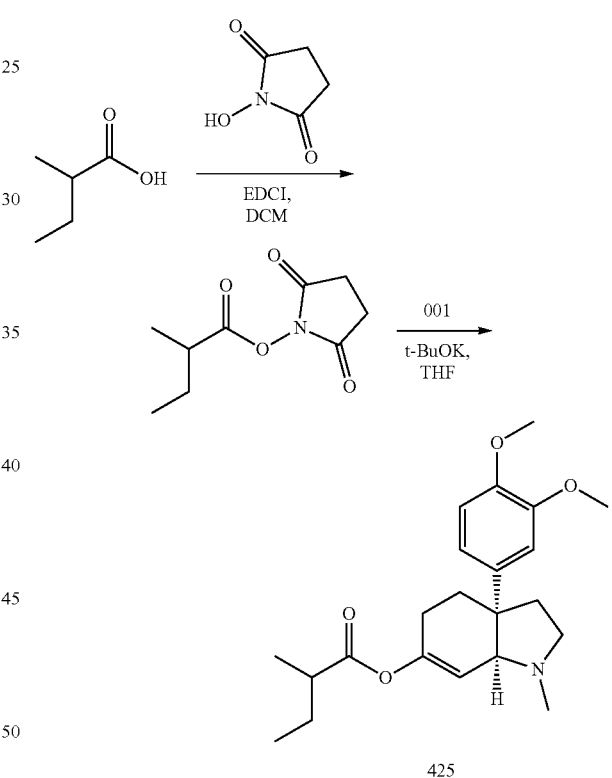

425

Step 1: Synthesis of (2,5-dioxopyrrolidin-1-yl) 2-methylbutanoate

To a solution of 2-methylbutanoic acid (1.00 g, 8.61 mmol, 1.07 mL) and 1-hydroxypyrrolidine-2,5-dione (1.49 g, 12.9 mmol) in DCM (7 mL) was added EDCI (2.48 g, 12.9 mmol). The reaction mixture was allowed to stir at 0-25° C. for 2 hr and then a saturated aqueous NH$_4$Cl solution (3 ml) was added. The aqueous solution was extracted with DCM (5 ml×2). The organic solutions were combined, dried over anhydrous Na$_2$SO$_4$, filtered and concentrated under reduced pressure to give (2,5-dioxopyrrolidin-1-yl) 2-methylbutanoate (1.67 g) as a white oil. $^1$H NMR (400 MHz, CDCl3) δ 2.75 (s, 4H), 2.69-2.58 (m, 1H), 1.77-1.65 (m, 1H), 1.63-1.51 (m, 1H), 1.23 (d, J=7.2 Hz, 3H), 1.16-1.07 (m, 1H), 0.95 (t, J=7.2 Hz, 3H).

Step 2: Synthesis of (3aS,7aS)-3a-(3,4-dimethoxyphenyl)-1-methyl-2,3,3a,4,5,7a-hexahydro-1H-indol-6-yl 2-methylbutanoate (425)

To a solution of 001 (150 mg, 519 umol) in THF (3 mL) was added dropwise t-BuOK (1M in THF, 1.04 mL) at 0° C. After the addition was complete, the reaction mixture was allowed to stir at 0° C. for 30 min and then (2,5-dioxopyrrolidin-1-yl) 2-methylbutanoate (207 mg, 1.04 mmol) was added dropwise at 0° C. The resulting mixture was allowed to stir at 25° C. for 2 hr and then concentrated in vacuo. The residue was purified by prep-HPLC (column: Phenomenex luna C$_{18}$ $_{150*25}$ mm*10 um; mobile phase: [water(FA)-ACN]; B %: 10%-40%, 10 min) to give 425 (70 mg, 45.7%) as a yellow oil. LC-MS (ESI$^+$) m/z 374.2 (M+H)$^+$. $^1$H NMR (400 MHz, CDCl3) δ 6.87-6.79 (m, 3H), 5.70 (dd, J=1.6, 4.4 Hz, 1H), 3.88 (d, J=10.8 Hz, 6H), 3.50-3.41 (m, 1H), 3.33-3.15 (m, 2H), 2.54 (s, 3H), 2.50-2.39 (m, 1H), 2.36-2.21 (m, 3H), 1.96-1.81 (m, 2H), 1.80-1.64 (m, 2H), 1.58-1.42 (m, 1H), 1.21-1.13 (m, 3H), 1.00-0.87 (m, 3H).

Example 126

Synthesis of (3aS,7aS)-3a-(3,4-dimethoxyphenyl)-1-methyl-2,3,3a,4,5,7a-hexahydro-1H-indol-6-yl 2-ethylbutanoate (426)

Step 1: Synthesis of (2,5-dioxopyrrolidin-1-yl)2-ethylbutanoate

A mixture of 2-ethylbutanoic acid (1.00 g, 8.6 mmol, 1.1 mL), 1-hydroxypyrrolidine-2,5-dione (1.50 g, 13 mmol), and EDCI (2.50 g, 13 mmol) in DCM (10 mL) was degassed and purged with N$_2$ 3 times. The reaction mixture was allowed to stir at 25° C. for 3 hours under an atmpsphere of N$_2$ and then quenched by the addition of water (10 mL) and extracted with DCM (10 mL×3). The organic solutions were combined, dried, filtered and concentrated to give (2,5-dioxopyrrolidin-1-yl)2-ethylbutanoate (1.67 g, 86%) as colorless liquid. $^1$H NMR (400 MHz, CDCl$_3$) δ 2.99-2.20 (m, 4H), 1.84-1.76 (m, 1H), 1.74-1.66 (m, 2H), 1.63-1.60 (m, 2H), 1.09-0.93 (m, 6H).

Step 2: Synthesis of (3aS,7aS)-3a-(3,4-dimethoxyphenyl)-1-methyl-2,3,3a,4,5,7a-hexahydro-1H-indol-6-yl 2-ethylbutanoate (426)

To a solution of 001 (200 mg, 691 umol) in THF (5.0 mL) was added dropwise t-BuOK (1M in THF, 1.4 mL) at 0° C. After the addition was complete, the mixture was allowed to stir at this temperature for 15 min, and then (2,5-dioxopyrrolidin-1-yl) 2-ethylbutanoate (295 mg, 1.4 mmol) was added. The reaction mixture was allowed to stir at 25° C. for 1 hr and then concentrated in vacuo. The residue was purified by prep-HPLC (FA condition: column: Phenomenex Luna C$_{18}$ $_{150*25}$ mm*10 um; mobile phase: [water(FA)-ACN]; B %: 13%-43%, 15 min) to give 426 (25.8 mg, 12%) as brown gum. LC-MS (ESI$^+$) m/z 388.3 (M+H)$^+$. $^1$H NMR (400 MHz, CDCl$_3$) δ 6.96-6.72 (m, 3H), 5.69 (d, J=4.4 Hz, 1H), 3.88 (d, J=11.2 Hz, 6H), 3.36-3.20 (m, 1H), 3.00 (s, 1H), 2.45 (s, 3H), 2.31-2.17 (m, 4H), 1.86 (d, J=6.0 Hz, 3H), 1.76 (dd, J=3.2, 12.6 Hz, 1H), 1.69-1.60 (m, 2H), 1.59-1.47 (m, 2H), 0.92 (dt, J=5.2, 7.2 Hz, 6H).

Example 127

Synthesis of (3aS,7aS)-3a-(3,4-dimethoxyphenyl)-1-methyl-2,3,3a,4,5,7a-hexahydro-1H-indol-6-yl 2,2-dimethylpentanoate (429)

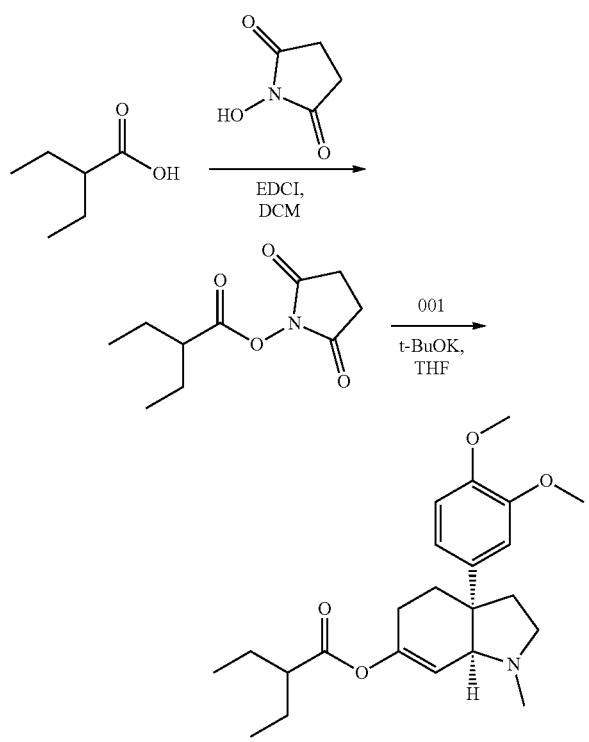

426

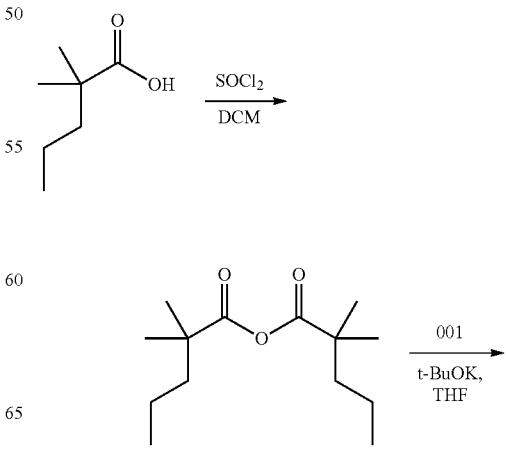

-continued

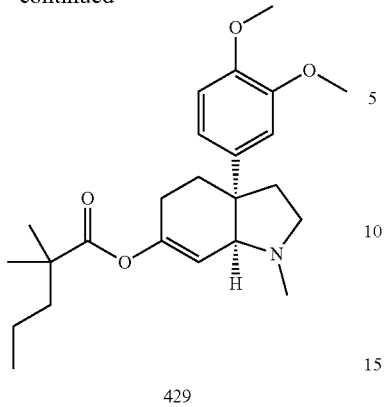

429

Step 1: Synthesis of 2,2-dimethylpentanoic anhydride

To a solution of 2,2-dimethylpentanoic acid (2 g, 15.3 mmol, 2.17 mL) in DCM (30 mL) was added DCC (2.54 g, 12.2 mmol, 2.49 mL). The mixture was allowed to stir at 25° C. for 10 minutes and then concentrated in vacuo. The residue was purified by column chromatography (SiO$_2$, Petroleum ether/Ethyl acetate=20/1 to 1/1) to give 2,2-dimethylpentanoic anhydride (830 mg) as white oil. $^1$H NMR (400 MHz, CDCl$_3$) δ 1.60-1.51 (m, 4H), 1.41-1.20 (m, 16H), 0.93 (t, J=7.2 Hz, 6H).

Step 2: Synthesis of (3aS,7aS)-3a-(3,4-dimethoxyphenyl)-1-methyl-2,3,3a,4,5,7a-hexahydro-1H-indol-6-yl 2,2-dimethylpentanoate (429)

To a solution of 001 (150 mg, 518 umol) and 2,2-dimethylpentanoyl 2,2-dimethylpentanoate (251 mg, 1.04 mmol) in THF (3 mL) was added t-BuOK (1M in THF, 518 uL). The mixture was allowed to stir at 25° C. for 1 hr and then concentrated in vacuo. The residue was purified by prep-HPLC (column: Phenomenex luna C$_{18}$ $_{150*25}$ mm*10 um; mobile phase: [water (FA)-ACN]; B %: 16%-46%, 10 min) to give 429 (92.4 mg) as white oil. LC-MS (ESI+) m/z 402.6 (M+H)$^+$. $^1$H NMR (400 MHz, CDCl$_3$) δ 6.83 (s, 3H), 5.67 (d, J=4.4 Hz, 1H), 3.88 (d, J=10.0 Hz, 6H), 3.60-3.50 (m, 1H), 3.42 (s, 1H), 2.82-2.66 (m, 1H), 2.61 (s, 3H), 2.42-2.19 (m, 3H), 1.97-1.74 (m, 3H), 1.61-1.45 (m, 2H), 1.34-1.12 (m, 8H), 0.90 (t, J=7.2 Hz, 3H).

Example 128

Synthesis of (3aS,7aS)-3a-(3,4-dimethoxyphenyl)-1-methyl-2,3,3a,4,5,7a-hexahydro-1H-indol-6-yl 2-ethyl-2-methylbutanoate (430)

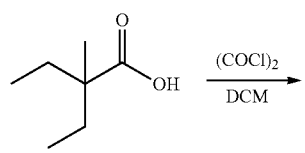

-continued

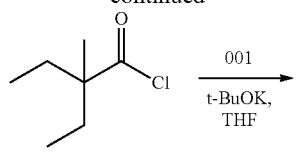

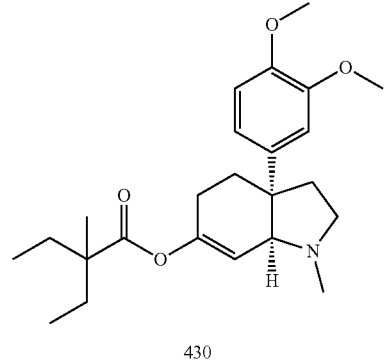

430

Step 1: Synthesis of 2-ethyl-2-methylbutanoyl chloride

To a solution of 2-ethyl-2-methyl-butanoic acid (400 mg, 3.07 mmol) in DCM (4 mL) was added (COCl)$_2$ (780 mg, 6.15 mmol, 538 uL) and DMF (22.5 mg, 307 umol, 23.6 uL) at 0° C. The mixture was allowed to stir at 25° C. for 17 hr. The reaction mixture was filtered and concentrated in vacuo to give 2-ethyl-2-methylbutanoyl chloride (100 mg) as a yellow liquid.

Step 2: Synthesis of (3aS,7aS)-3a-(3,4-dimethoxyphenyl)-1-methyl-2,3,3a,4,5,7a-hexahydro-1H-indol-6-yl 2-ethyl-2-methylbutanoate (430)

To a solution of 001 (100 mg, 346 umol) in THF (2 mL) was added t-BuOK (1M, 691 uL) at 0° C. over 10 min. To this mixture was added 2-ethyl-2-methylbutanoyl chloride (103 mg, 691 umol). The reaction mixture was allowed to stir at 25° C. for 2 hr and then filtered and concentrated in vacuo. The residue was purified by prep-HPLC (column: Phenomenex luna C$_{18}$ $_{150*25}$ mm*10 um; mobile phase: [water(FA)-ACN]; B %: 12%-42%,8 min) to give 430 (47 mg) as a yellow gum. LC-MS (ESI+) m/z 402.2 (M+H)$^+$. $^1$H NMR (400 MHz, CDCl$_3$) δ=6.93-6.72 (m, 3H), 5.74-5.62 (m, 1H), 3.88 (d, J=8.4 Hz, 6H), 3.76 (s, 2H), 3.10-2.88 (m, 1H), 2.76 (s, 3H), 2.53-2.27 (m, 3H), 2.09-1.78 (m, 3H), 1.77-1.62 (m, 2H), 1.57-1.41 (m, 2H), 1.11 (s, 3H), 0.97-0.73 (m, 6H).

Example 129

Synthesis of (3aS,7aS)-3a-(3,4-dimethoxyphenyl)-1-methyl-2,3,3a,4,5,7a-hexahydro-1H-indol-6-yl 3,3-dimethylbutanoate (431)

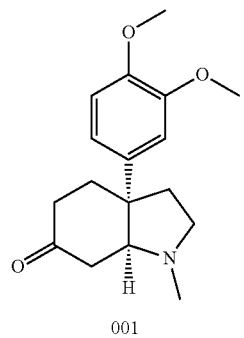

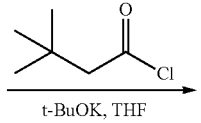

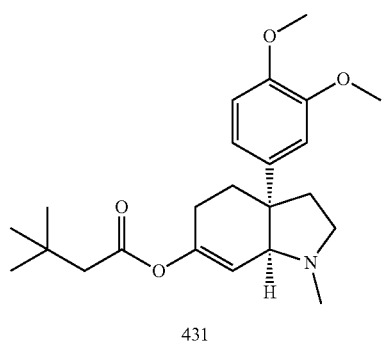

To a solution of 001 (150 mg, 518 umol) in THF (5 mL) was added t-BuOK (1M in THF, 1.04 mL) at 0° C. The reaction mixture was allowed to stir at 0° C. for 30 min. To the reaction mixture was added 3,3-dimethylbutanoyl chloride (140 mg, 1.04 mmol, 144 uL). The reaction mixture was allowed to stir at 25° C. for 1 hr and then filtered and concentrated in vacuo. The residue was purified by prep-HPLC (column: Waters xbridge 150*25 mm 10 um; mobile phase: [water(NH$_4$HCO$_3$)-ACN]; B %: 45%-75%, 8 min) to give 431 (70 mg) as a yellow gum. LC-MS (ESI$^+$) m/z 388.2 (M+H)$^+$. $^1$H NMR (400 MHz, CDCl$_3$) δ=6.90-6.69 (m, 3H), 5.65 (d, J=3.2 Hz, 1H), 3.83 (d, J=11.4 Hz, 6H), 3.28-3.12 (m, 1H), 2.90 (s, 1H), 2.51-2.04 (m, 9H), 1.81 (s, 2H), 1.74-1.66 (m, 1H), 0.99 (s, 9H).

Example 130

Synthesis of (3aS,7aS)-3a-(3,4-dimethoxyphenyl)-1-methyl-2,3,3a,4,5,7a-hexahydro-1H-indol-6-yl 2,2-dimethylbutanoate (428)

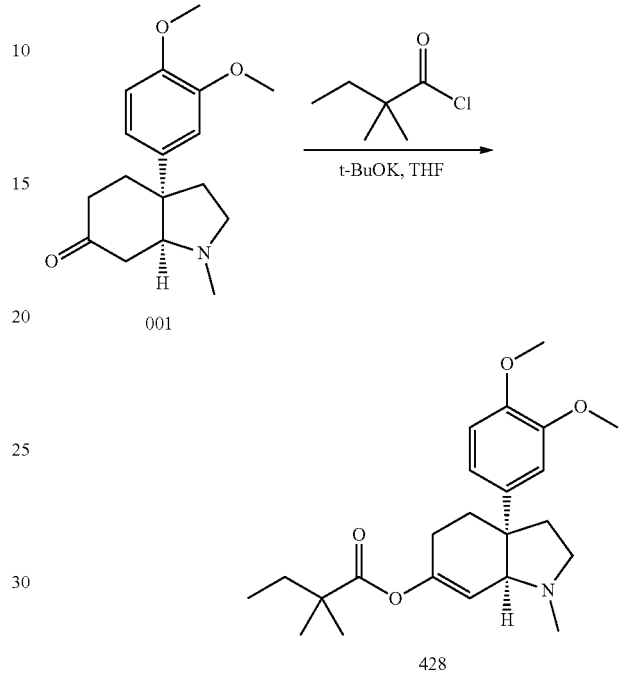

To a solution of 001(150 mg, 518 umol) in THF (1.0 mL) was added t-BuOK (1 M in THF, 1.04 mL). The reaction mixture was allowed to stir at 0° C. for 30 min, then 2,2-dimethylbutanoyl chloride (139 mg, 1.04 mmol) was added at 0° C. The reaction mixture was allowed to stir at 25° C. for 2 hr and then concentrated in vacuo. The residue was purified by prep-HPLC (column: Phenomenex luna C$_{18}$ 150*25 mm*10 um; mobile phase: [water(FA)-ACN]; B %: 18%-38%, 58 min) to give 428 (45.6 mg) as a yellow gum. LC-MS (ESI$^+$) m/z 388.3 (M+H)$^+$. $^1$H NMR (400 MHz, CDCl$_3$) δ 6.89-6.76 (m, 3H), 5.68 (d, J=4.8 Hz, 1H), 3.89 (d, J=9.2 Hz, 6H), 3.74-3.64 (m, 2H), 2.89 (br d, J=3.2 Hz, 1H), 2.72 (s, 3H), 2.48-2.28 (m, 3H), 2.03-1.87 (m, 2H), 1.86-1.77 (m, 1H), 1.67-1.53 (m, 2H), 1.19 (d, J=3.4 Hz, 6H), 0.86 (t, J=7.6 Hz, 3H).

Example 131

Synthesis of (3aS,7aS)-3a-(3,4-dimethoxyphenyl)-1-methyl-2,3,3a,4,5,7a-hexahydro-1H-indol-6-yl 2-propylpentanoate (427)

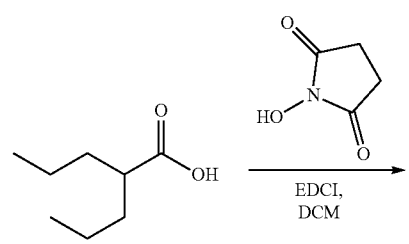

561

-continued

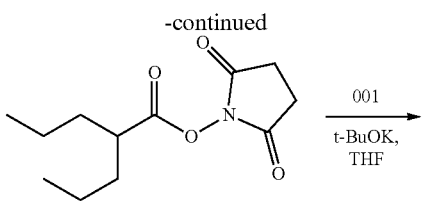

Step 1: Synthesis of 2,5-dioxopyrrolidin-1-yl 2-propylpentanoate

To a solution of 1-hydroxypyrrolidine-2,5-dione (877 mg, 7.62 mmol) and 2-propylpentanoic acid (1.0 g, 6.93 mmol, 1.11 mL) in DCM (10 mL) was added EDCI (1.99 g, 10.4 mmol) and DMAP (84.7 mg, 693 umol). The mixture was allowed to stir at 25° C. for 2 hr and then poured into water (20 mL). The solution was extracted with ethyl acetate (60 mL). The organic solutions were combined, dried over sodium sulfate, filtered and concentrated in vacuo to give 2,5-dioxopyrrolidin-1-yl 2-propylpentanoate (1.5 g) as a yellow oil. $^1$H NMR (400 MHz, CDCl$_3$) δ 2.84 (d, J=4.2 Hz, 4H), 2.75-2.64 (m, 1H), 1.73-1.67 (m, 1H), 1.65-1.37 (m, 7H), 0.96 (t, J=7.2 Hz, 6H).

Step 2: Synthesis of (3aS,7aS)-3a-(3,4-dimethoxyphenyl)-1-methyl-2,3,3a,4,5,7a-hexahydro-1H-indol-6-yl 2-propylpentanoate (427)

To a solution of 001 (150 mg, 518 umol) in THF (1.5 mL) was added t-BuOK (1 M, 1.04 mL). The reaction mixture was allowed to stir at 0° C. for 10 min and then 2,5-dioxopyrrolidin-1-yl2-propylpentanoate (250 mg, 1.04 mmol) was added. The reaction mixture was allowed to stir at 25° C. for 2 hr and then concentrated. The residue was purified by prep-HPLC (column: Welch Xtimate C$_{18}$ $_{150*25}$ mm*5 um; mobile phase: [water(NH$_3$H$_2$O)-ACN]; B %: 64%-94%, min) to give 427 (19.64 mg, 13% yield) as a yellow gum. LC-MS (ESI$^+$) m/z 416.2 (M+H)$^+$. $^1$H NMR (400 MHz, CDCl$_3$) δ 6.86-6.65 (m, 3H), 5.59 (d, J=4.4 Hz, 1H), 3.80 (d, J=10.8 Hz, 6H), 3.13 (t, J=7.6 Hz, 1H), 2.80 (s, 1H), 2.34-2.31 (m, 3H), 2.25-2.02 (m, 4H), 1.76 (d, J=6.8 Hz, 2H), 1.65 (d, J=3.2 Hz, 2H), 1.59-1.48 (m, 2H), 1.41-1.31 (m, 2H), 1.30-1.17 (m, 4H), 0.83 (dt, J=4.0, 7.2 Hz, 6H).

Example 132

Synthesis of (3aS,7aS)-3a-(3,4-dimethoxyphenyl)-1-methyl-2,3,3a,4,5,7a-hexahydro-1H-indol-6-yl 4-methylpentanoate (399)

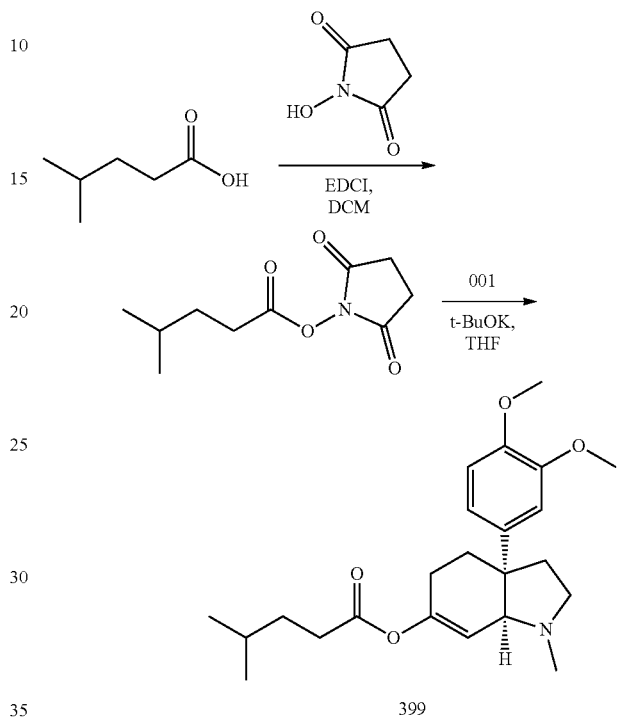

Step 1: Synthesis of 2,5-dioxopyrrolidin-1-yl 4-methylpentanoate

To a solution of 4-methylpentanoic acid (150 mg, 1.29 mmol, 162 uL) and 1-hydroxypyrrolidine-2,5-dione (222 mg, 1.94 mmol) in DCM (3 mL) was added EDCI (371 mg, 1.94 mmol) and DMAP (15.7 mg, 129 umol). The reaction mixture was allowed to stir at 25° C. for 2 hr. The reaction was quenched by the addition of an aqueous saturated solution of NH$_4$Cl (50 ml). The aqueous solution was extracted with DCM (5 ml×3). The organic solutions were was combined, dried over anhydrous Na$_2$SO$_4$, filtered and concentrated under reduced pressure to give 2,5-dioxopyrrolidin-1-yl 4-methylpentanoate (200 mg) as white oil. $^1$H NMR (400 MHz, CDCl$_3$) δ 2.83-2.74 (m, 4H), 2.58-2.49 (m, 2H), 1.62-1.54 (m, 3H), 0.87 (d, J=6.2 Hz, 6H).

Step 2: Synthesis of (3aS,7aS)-3a-(3,4-dimethoxyphenyl)-1-methyl-2,3,3a,4,5,7a-hexahydro-1H-indol-6-yl 4-methylpentanoate (399)

To a solution of 001 (120 mg, 414 umol) and 2,5-dioxopyrrolidin-1-yl 4-methylpentanoate (176 mg, 829 umol) in THF (3 mL) was added t-BuOK (1M in THF, 414 uL). The reaction mixture was allowed to stir at 25° C. for 2 hr and then concentrated in vacuo. The residue obtained was purified by prep-HPLC (column: Phenomenex luna C$_{18}$ $_{150*25}$ mm*10 um; mobile phase: [water (FA)-ACN]; B %: 18%-48%, 8 min) to give 399 (30 mg) as white oil. LC-MS (ESI+) m/z 388.3 (M+H)+. 1H NMR (400 MHz, CDCl3) δ 6.78-6.73 (m, 3H), 5.64 (dd, J=1.6, 4.4 Hz, 1H), 3.81 (d, J=10.4 Hz, 6H), 3.42-3.32 (m, 1H), 3.17 (s, 1H), 2.46 (s, 4H), 2.35-2.11 (m, 5H), 1.90-1.65 (m, 3H), 1.57-1.41 (m, 3H), 0.89-0.80 (m, 6H).

Example 133

Synthesis of 2-((3aS,7aS)-3a-(3,4-dimethoxyphenyl)-1-methyloctahydro-6H-indol-6-ylidene)-N-(3-hydroxyphenyl)hydrazine-1-carboxamide (251)

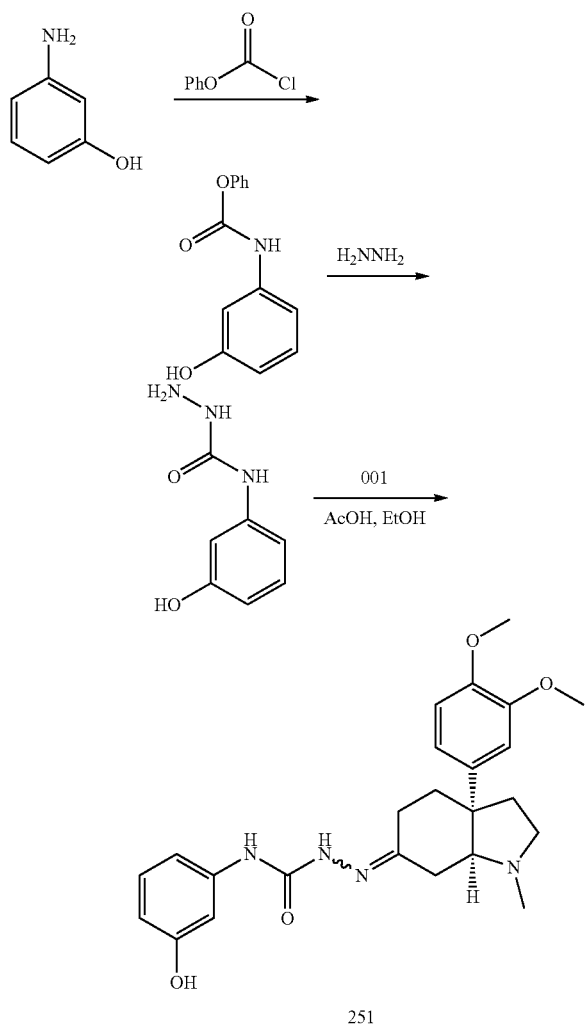

Step 1: Synthesis of phenyl (3-hydroxyphenyl)carbamate

To a solution of 3-aminophenol (1 g, 9.16 mmol) in THF (5.0 mL) and H2O (5.0 mL) was added NaHCO3 (769 mg, 9.16 mmol, 356 uL). Phenyl carbonochloridate (1.43 g, 9.16 mmol, 1.15 mL) was then added at 0° C. over 2 minutes. The reaction mixture was allowed to stir and warm to 20° C. over 5 minutes. The reaction mixture was diluted with ethyl acetate. The organic solution was separated and the aqueous solution was extracted with ethyl acetate (3×30 mL). The organic solutions were combined, washed with 5% hydrochloric acid (3×30 mL), dried over sodium sulfate, filtered and concentrated in vacuo to give phenyl phenyl (3-hydroxyphenyl) carbamate (1.5 g) as a yellow solid. LC-MS (ESI+) m/z 368.9 (M+H)+ 1H NMR (400 MHz, DMSO-d6) δ 10.10 (s, 1H), 9.76-8.84 (m, 1H), 7.47-7.37 (m, 2H), 7.31-7.13 (m, 3H), 7.12-7.00 (m, 2H), 6.97-6.89 (m, 1H), 6.71 (s, 1H), 6.50-6.38 (m, 1H).

Step 2: Synthesis of N-(3-hydroxyphenyl)hydrazinecarboxamide

To a solution of phenyl (3-hydroxyphenyl)carbamate (500 mg, 2.18 mmol) in ACN (5.0 mL) was added NH2NH2·H2O (272 mg, 5.45 mmol, 265 uL) in ACN (1.0 mL) over 5 minutes. The reaction mixture was allowed to stir at 20° C. for 4 hr and was then filtered and concentrated in vacuo. The crude product was purified by re-crystallization from EtOAc (5.0 mL) at 20° C. to give N-(3-hydroxyphenyl)hydrazinecarboxamide (350 mg) as a yellow solid. LC-MS (ESI+) m/z 168.1(M+H)+ 1H NMR (400 MHz, DMSO-d6) δ 8.48 (s, 1H), 7.33 (s, 1H), 7.11 (s, 1H), 7.05-6.89 (m, 1H), 6.80 (dd, J=1.2, 8.0 Hz, 1H), 6.32 (ddd, J=1.2, 2.4, 8.0 Hz, 1H), 4.31 (s, 2H).

Step 3: Synthesis of 2-((3aS,7aS)-3a-(3,4-dimethoxyphenyl)-1-methyloctahydro-6H-indol-6-ylidene)-N-(3-hydroxyphenyl)hydrazine-1-carboxamide (251)

A mixture of 001 (150 mg, 518 umol), 1-amino-3-(3-hydroxyphenyl)urea (103 mg, 622 umol) and AcOH (3.11 mg, 51.8 umol, 2.96 uL) in EtOH (2.0 mL) was degassed and purged with N2 for 3 times, and then the mixture was stirred at 40° C. for 1 hours under N2 atmosphere. On completion, the reaction mixture was filtered, concentrated in vacuo to give the residue. The crude product was purified by re-crystallization from EA (10 mL) at 25° C. and column chromatography (SiO2, DCM:MeOH=10:1) to give 251 (34.0 mg) as a white solid. LC-MS (ESI+) m/z 439.2 (M+H)+ 1H NMR (400 MHz, CDCl3) δ 8.21 (s, 1H), 7.54-7.42 (m, 1H), 7.16 (t, J=8.0 Hz, 1H), 6.85 (s, 3H), 6.78 (d, J=7.6 Hz, 1H), 6.57 (d, J=6.0 Hz, 1H), 3.90 (d, J=4.4 Hz, 6H), 3.08 (d, J=6.0 Hz, 1H), 2.94 (s, 1H), 2.82-2.53 (m, 2H), 2.42 (s, 3H), 2.39-2.28 (m, 2H), 2.23 (s, 1H), 2.18-2.07 (m, 2H), 2.06-1.90 (m, 2H).

Example 134

Synthesis of (3aS,7aS)-3a-(3,4-dimethoxyphenyl)-1-methyl-2,3,3a,4,5,7a-hexahydro-1H-indol-6-yl 3-(2-methoxyethoxy)propanoate (405)

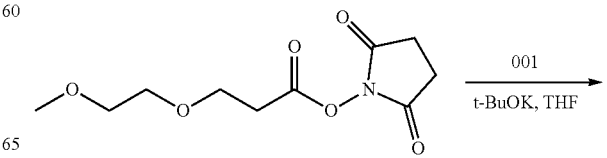

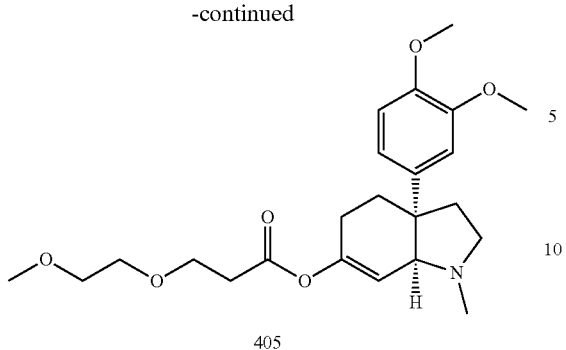

405

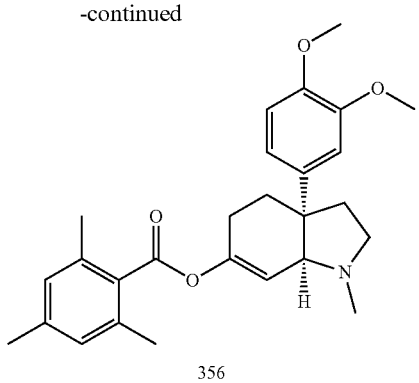

356

To a solution of 001 (200 mg, 691 umol) in THF (2.0 mL) was added LDA (2M in THF, 691 uL) and (2,5-dioxopyrrolidin-1-yl)3-(2-methoxyethoxy)propanoate (339 mg, 1.38 mmol) at 0° C. The mixture was allowed to stir at 0° C. for 2 hr. The mixture was poured into saturated aqueous NH$_4$Cl (100 mL) and extracted with ethyl acetate (100 mL). The organic solutions were separated, combined, dried over sodium sulfate, filtered and concentrated in vacuo. The residue was purified by prep-HPLC (column: Phenomenex luna C$_{18}$ $_{150*25}$ mm*10 um; mobile phase: [water(FA)-ACN]; B %: 7%-37%, 8 min) to give 405 (121 mg) as a yellow gum. LC-MS (ESI$^+$) m/z 420.1 (M+H)$^+$. $^1$H NMR (400 MHz, CDCl$_3$) δ 8.51-8.30 (m, 1H), 7.01-6.90 (m, 1H), 6.89-6.75 (m, 2H), 5.86-5.73 (m, 1H), 4.14-4.03 (m, 1H), 3.95-3.83 (m, 6H), 3.80-3.74 (m, 2H), 3.74-3.64 (m, 1H), 3.64-3.56 (m, 2H), 3.56-3.49 (m, 2H), 3.43-3.32 (m, 3H), 3.11-2.95 (m, 1H), 2.73-2.65 (m, 4H), 2.61 (s, 2H), 2.50-2.21 (m, 3H), 2.04-1.94 (m, 1H), 1.92-1.75 (m, 1H).

To a solution of 001 (100 mg, 345 umol) in THF (1.5 mL) was added t-BuOK (1M, 691 uL) and 2,4,6-trimethylbenzoyl chloride (94.7 mg, 518 umol). The reaction mixture was allowed to stir at 25° C. for 2 hr and then concentrated in vacuo. The residue was purified by prep-HPLC (column:

Phenomenex luna C$_{18}$ $_{150*25}$ mm*10 um; mobile phase: [water(FA)-ACN]; B %: 28%-58%, 58 min) to give 356 (150 mg) as a white solid. LC-MS (ESI+) m/z 436.4 (M+H)+. $^1$H NMR (400 MHz, CDCl$_3$) δ=8.42 (s, 1H), 6.94-6.82 (m, 5H), 6.05-5.83 (m, 1H), 3.90 (d, J=15.0 Hz, 6H), 3.59 (s, 2H), 2.91-2.76 (m, 1H), 2.68 (s, 3H), 2.50-2.35 (m, 3H), 2.34-2.27 (m, 9H), 2.11 (d, J=3.1 Hz, 2H), 1.94-1.82 (m, 1H).

Example 135

Synthesis of (3aS,7aS)-3a-(3,4-dimethoxyphenyl)-1-methyl-2,3,3a,4,5,7a-hexahydro-1H-indol-6-yl 2,4,6-trimethylbenzoate (356)

Example 136

Synthesis of (3aS,7aS)-3a-(3,4-dimethoxyphenyl)-1-methyl-2,3,3a,4,5,7a-hexahydro-1H-indol-6-yl 3-aminopropanoate (397)

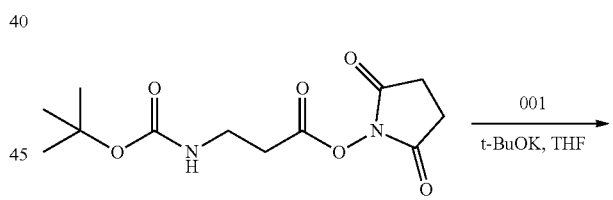

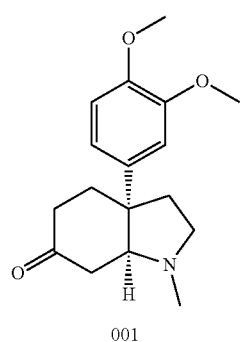

001

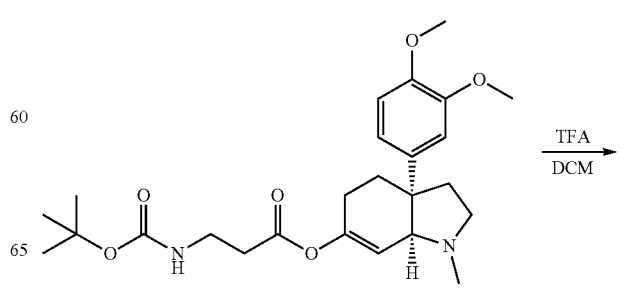

-continued

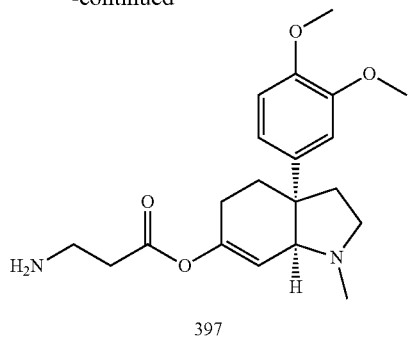

397

Step 1: Synthesis of (3aS,7aS)-3a-(3,4-dimethoxyphenyl)-1-methyl-2,3,3a,4,5,7a-hexahydro-1H-indol-6-yl 3-((tert-butoxyc arbonyl)amino)propanoate To a solution of 001 (150 mg, 518 umol) and (2,5-dioxopyrrolidin-1-yl) 3-(tert-butoxycarbonylamino)propanoate (593 mg, 2.07 mmol) in THF (4 mL) was added t-BuOK (2M in THF, 1.04 mL). The reaction mixture was allowed to stir at 25° C. for 3 hr and was then concentrated in vacuo. The residue was purified by prep-HPLC (column: Phenomenex luna $C_{18\ 150*25}$ mm*10 um; mobile phase: [water (FA)-ACN]; B %: 10%-40%,10 min) to give (3aS, 7aS)-3a-(3,4-dimethoxyphenyl)-1-methyl-2,3,3a,4,5,7a-hexahydro-1H-indol-6-yl 3-((tert-butoxycarbonyl)amino) propanoate (120 mg, 60%) as white oil. LC-MS (ESI$^+$) m/z 461.8 (M+H)$^+$. $^1$H NMR (400 MHz, CDCl$_3$) δ 6.88-6.69 (m, 1H), 5.98-4.77 (m, 1H), 4.07-3.69 (m, 2H), 3.57-3.31 (m, 3H), 2.63 (s, 1H), 2.49-2.16 (m, 8H), 1.45 (s, 9H).

Step 2: Synthesis of (3aS,7aS)-3a-(3,4-dimethoxyphenyl)-1-methyl-2,3,3a,4,5,7a-hexahydro-1H-indol-6-yl 3-aminopropanoate (397)

To a mixture of (3aS,7aS)-3a-(3,4-dimethoxyphenyl)-1-methyl-2,3,3a,4,5,7a-hexahydro-1H-indol-6-yl 3-((tert-butoxycarbonyl)amino)propanoate (50.0 mg, 108.56 umol) in DCM (2 mL) was added TFA (12.4 mg, 108 umol) in one portion at 25° C. under and atmosphere of N$_2$. The reactioin mixture was allowed to stir at 25° C. for 30 min and concentrated in vacuo. The residue was purified by prep-HPLC (column: Waters Atlantis T3 150*30 mm*5 um; mobile phase: [water (TFA)-ACN]; B %: 5%-35%, 15 min) to give 397 (19.9 mg, 60%) as white oil. LC-MS (ESI+) m/z 361.1 (M+H)$^+$. $^1$H NMR (400 MHz, CDCl$_3$) δ 8.64-8.19 (m, 2H), 6.84-6.84 (m, 1H), 6.91-6.66 (m, 2H), 6.06 (s, 1H), 4.18-4.03 (m, 1H), 3.94-3.80 (m, 7H), 3.32 (s, 2H), 3.10-2.78 (m, 6H), 2.51 (t, J=7.2 Hz, 2H), 2.31-2.22 (m, 1H), 2.45-2.22 (m, 4H), 2.07 (d, J=17.2 Hz, 1H), 1.90 (d, J=11.2 Hz, 1H), 1.83-1.71 (m, 1H).

Example A1

Hydrolysis Assay 50 uL of compound (10 mM) in DMSO was diluted into 950 uL of HCl aqueous solution (0.01 M) to a final concentration of 0.5 mM. The hydrolysis kinetics was under a certain temperature and measured by LCMS at a certain time interval. The corresponding LCMS chromatograms were recorded and the conversions were calculated. The hydrolysis conditions and the data were summarized in below table. LCMS spectra were obtained using Agilent 1200\G1956A or SHIMADZU LCMS-2020. Standard LCMS conditions were as follows (running time 1.55 minutes):

Acidic condition: Mobile Phase A: 0.0375% TFA in water (v/v). Mobile Phase B: 0.01875% TFA in acetonitrile (v/v); Column: Kinetex EVO C18 30*2.1 mm, 5 µm.

Basic condition: Mobile Phase A: 0.025% NH$_3$·H$_2$O in water (v/v). Mobile Phase B: Acetonitrile; Column: Kinetex EVO C18 2.1×30 mm, 5 µm.

Conversion (%)=peak area 1/(peak area 1+peak area 2)*100%, peak area 1 is the integration of hydrolyzed product, peak area 2 is the integration of starting material. Results are shown in Table 10.

TABLE 10

| Compound ID | Conditions | Time | Conversion (%) | Notes |
|---|---|---|---|---|
| 026 | pH = 2.0, 25° C., 0.5 mM, 0.01M HCl | 0-48 (h) | 0 | Stable; Mixture of two isomers |
| 037 | pH = 2.0, 37° C., 0.5 mM, 0.01M HCl | 10 (min) | 59 | Mixture of E/Z |
| | | 60 (min) | 84 | |
| | | 90 (min) | 87 | |
| 013 | pH = 2.0, 25° C., 0.5 mM, 0.01M HCl | 0-24 (h) | 0 | Stable |
| | pH = 2.0, 37° C., 0.5 mM, 0.01M HCl | 16 (h) | 17 | |
| | | 24 (h) | 22 | |
| | | 42 (h) | 35 | |
| | | 56 (h) | 50 | |
| | | 7 (d) | 77 | |
| | pH = 2.0, 50° C., 0.5 mM, 0.01M HCl | 10 (min) | 1 | |
| | | 40 (min) | 2 | |
| | | 120 (min) | 19 | |
| | | 22 (h) | 90 | |
| 001 | pH = 2.0, 25° C., 0.5 mM, 0.01M HCl | 0-24 (h) | 0 | Stable |
| | pH = 2.0, 40° C., 0.5 mM, 0.01M HCl | 0-24 (h) | 0 | Stable |
| | PH = 7.4, 25° C., 0.5 mM, PBS (20 mM) | 0-24 (h) | 0 | Stable |
| | PH = 7.4, 40° C., 0.5 mM, PBS (20 mM) | 0-24 (h) | 0 | Stable |
| 014 | pH = 2.0, 25° C., 0.5 mM, 0.01M HCl | 0-24 (h) | 0 | Stable |
| 036 | pH = 2.0, 37° C., 0.5 mM, 0.01M HCl | 0 | 0 | Hydrolyzed rapidly |
| | | 1 (min) | 100 | |

Figure 2:
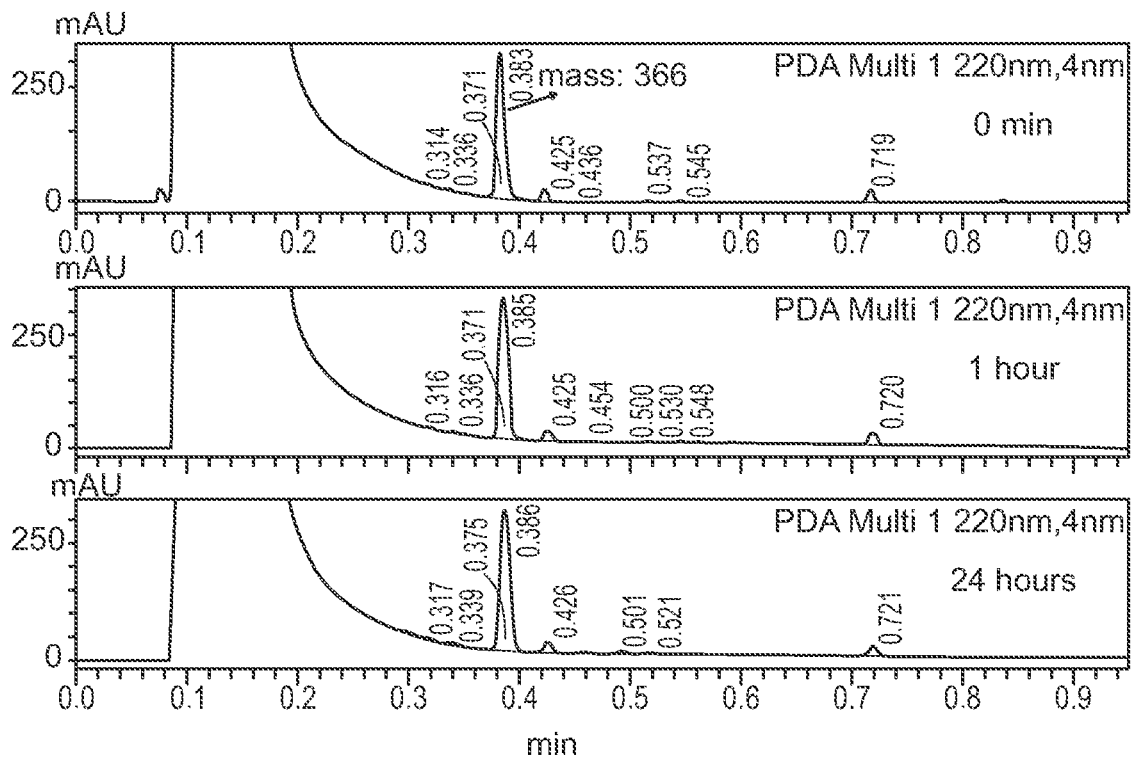
FIG. 2 is a series of LCMS graphs obtained from compound 014 in the acid hydrolysis assay of Example A1.

FIG. 1 is a series of LCMS graphs obtained from 013 in the acid hydrolysis assay of Example A1. FIG. 2 is a series of LCMS graphs obtained from 014 in the acid hydrolysis assay of Example A1

Example A2

Hydrolysis Assay

General Method Description of Hydrolysis Assay—Condition 1 (SGF)

50 uL of compound (10 mM) in DMSO was diluted into 950 uL of Simulated Gastric Fluid (SGF) with pepsin (pH 1.5) to a final concentration of 0.5 mM. The hydrolysis kinetics were conducted at 37° C. and measured by LCMS at a certain time interval.

General Method Description of Hydrolysis Assay—Condition 2 (DI Water)

50 uL of compound (10 mM) in DMSO was diluted into 950 uL of DI water to a final concentration of 0.5 mM. The hydrolysis kinetics were conducted at 25° C. and measured by LCMS at a certain time interval.

The corresponding LCMS chromatogram were recorded and the conversions were calculated by integration of each peak.

Note:

1) LCMS spectra were obtained using Agilent 1200\G1956A or SHIMADZU LCMS-2020. Standard LCMS conditions were as follows (running time 1.55 minutes):

Acidic condition: Mobile Phase A: 0.0375% TFA in water (v/v). Mobile Phase B: 0.01875% TFA in acetonitrile (v/v); Column: Kinetex EVO C18 30*2.1 mm, 5 μm.

Basic condition: Mobile Phase A: 0.025% $NH_3·H_2O$ in water (v/v). Mobile Phase B: Acetonitrile; Column: Kinetex EVO C18 2.1×30 mm, 5 μm.

2) Conversion (%)=peak area 1/(peak area 1+peak area 2)*100%, peak area 1 is the integration of hydrolyzed product, peak area 2 is the integration of starting material.

TABLE 11

| Compound | Time (min) | Condition 1 Conversion (%) | Condition 2 Conversion (%) |
|---|---|---|---|
| 26 | 1 | 0 | 0 |
|  | 5 | 0 | 0 |
|  | 30 | 0 | 0 |
|  | 1 (h) | 0 | 0 |
|  | 4 (h) | 0 | 0 |
|  | 24 (h) | 0 | 0 |
| 35 | 1 | 0 | Not Tested |
|  | 5 | 0 | NT |
|  | 30 | 5.4 | NT |
|  | 1 (h) | 13.1 | NT |
|  | 4 (h) | 35.2 | NT |
|  | 24 (h) | 38.9 | NT |
| 36 | 1 | 100 | NT |
|  | 5 | 100 | NT |
|  | 30 | 100 | NT |
|  | 1 (h) | 100 | NT |
|  | 4 (h) | 100 | NT |
|  | 24 (h) | 100 | NT |
| 37 | 1 | 0 | NT |
|  | 5 | 0 | NT |
|  | 30 | 82.3 | NT |
|  | 1 (h) | 89 | NT |
|  | 4 (h) | 89.2 | NT |
|  | 24 (h) | 89.5 | NT |
| 38 | 1 | 0 | NT |
|  | 5 | 0 | NT |
|  | 30 | 1.3 | NT |
|  | 1 (h) | 11.9 | NT |
|  | 4 (h) | 31.3 | NT |
|  | 24 (h) | 49.9 | NT |
| 43 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 44 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 45 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 46 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 69 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 70 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 80 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 81 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 109 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 110 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 111 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 113 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 114 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 157 | 1 | 100 | NT |
|  | 5 | 100 | NT |
|  | 30 | 100 | NT |
|  | 1 (h) | 100 | NT |
|  | 4 (h) | 100 | NT |
|  | 24 (h) | 100 | NT |
| 158 | 1 | 41.8 | 0 |
|  | 5 | 100 | 12.1 |
|  | 30 | 100 | 12.6 |
|  | 1 (h) | 100 | 13.7 |
|  | 4 (h) | 100 | 14.7 |
|  | 24 (h) | 100 | 51.1 |
| 159 | 1 | 77 | NT |
|  | 5 | 91 | NT |
|  | 30 | 100 | NT |
|  | 1 (h) | 100 | NT |
|  | 4 (h) | 100 | NT |
|  | 24 (h) | 100 | NT |
| 172 | 1 | 100 | 50* |
|  | 5 | 100 | 70* |
|  | 30 | 100 | 100 |

TABLE 11-continued

| Compound | Time (min) | Condition 1 Conversion (%) | Condition 2 Conversion (%) |
|---|---|---|---|
|  | 1 (h) | 100 | 100 |
|  | 4 (h) | 100 | 100 |
|  | 24 (h) | 100 | 100 |
| 174 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 190 | 1 | 0 | 0 |
|  | 5 | 8.30 | 0 |
|  | 30 | 82.97 | 0 |
|  | 1 (h) | 100 | 0 |
|  | 4 (h) | 100 | 0 |
|  | 24 (h) | 100 | 0 |
| 196 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 197 | 1 | 0 | 0 |
|  | 5 | 0 | 0 |
|  | 30 | 0 | 0 |
|  | 1 (h) | 0 | 0 |
|  | 4 (h) | 0 | 0 |
|  | 24 (h) | 0 | 0 |
| 198 | 1 | 0.86 | 0.2 |
|  | 5 | 1 | 0.21 |
|  | 30 | 1 | 0.22 |
|  | 1 (h) | 1 | 0.55 |
|  | 4 (h) | 1 | 0.89 |
|  | 24 (h) | 1 | 0.8 |
| 199 | 1 | 0 | 0 |
|  | 5 | 0 | 0 |
|  | 30 | 0 | 0 |
|  | 1 (h) | 4.2 | 0 |
|  | 4 (h) | 23.6 | 0 |
|  | 24 (h) | 27.3 | 0 |
| 200 | 1 | 0 | 0 |
|  | 5 | 0 | 0 |
|  | 30 | 0 | 0 |
|  | 1 (h) | 2.1 | 0 |
|  | 4 (h) | 27.7 | 0 |
|  | 24 (h) | 34.1 | 0 |
| 201 | 1 | 0 | 0 |
|  | 5 | 0 | 0 |
|  | 30 | 0 | 0 |
|  | 1 (h) | 0 | 0 |
|  | 4 (h) | 7.1 | 0 |
|  | 24 (h) | 14.7 | 0 |
| 202 | 1 | 0 | 0 |
|  | 5 | 0 | 0 |
|  | 30 | 0 | 0 |
|  | 1 (h) | 1.12/0 | 0 |
|  | 4 (h) | 3.01/6.42 | 0 |
|  | 24 (h) | 64.4/6.42 | 0 |
| 203 | 1 | 0 | 0 |
|  | 5 | 0 | 0 |
|  | 30 | 0 | 0 |
|  | 1 (h) | 0 | 0 |
|  | 4 (h) | 18.58 | 0 |
|  | 24 (h) | 26.48 | 0 |
| 204 | 1 | 100/0 | 0 |
|  | 5 | 100/0 | 0 |
|  | 30 | 0/100 | 0 |
|  | 1 (h) | 0/100 | 0 |
|  | 4 (h) | 0/100 | 0 |
|  | 24 (h) | 0/100 | 0 |
| 205 | 1 | 0 | 0 |
|  | 5 | 0 | 0 |
|  | 30 | 4.5 | 0 |
|  | 1 (h) | 9.4 | 0 |
|  | 4 (h) | 16.7 | 0 |
|  | 24 (h) | 19.3 | 0 |
| 206 | 1 | 0 | 0 |
|  | 5 | 0 | 0 |
|  | 30 | 1.41/0 | 0 |
|  | 1 (h) | 7.83/2.57 | 0 |
|  | 4 (h) | 0/77.75 | 0 |
|  | 24 (h) | 0/100 | 0 |
| 207 | 1 | 0 | 0 |
|  | 5 | 0 | 0 |
|  | 30 | 0 | 0 |
|  | 1 (h) | 0 | 0 |
|  | 4 (h) | 1.5 | 0 |
|  | 24 (h) | 7.9 | 0 |
| 208 | 1 | 0 | 0 |
|  | 5 | 0 | 0 |
|  | 30 | 0 | 0 |
|  | 1 (h) | 0 | 0 |
|  | 4 (h) | 11.5 | 0 |
|  | 24 (h) | 12 | 0 |
| 209 | 1 | 0 | 0 |
|  | 5 | 0 | 0 |
|  | 30 | 0 | 0 |
|  | 1 (h) | 0 | 0 |
|  | 4 (h) | 0 | 0 |
|  | 24 (h) | 0 | 0 |
| 210 | 1 | 0 | 0 |
|  | 5 | 0 | 0 |
|  | 30 | 3.48 | 0 |
|  | 1 (h) | 7.51 | 0 |
|  | 4 (h) | 14.75 | 0 |
|  | 24 (h) | 15.35 | 0 |
| 211 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 212 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 213 | 1 | 0 | NT |
|  | 5 | 0 | NT |
|  | 30 | 0 | NT |
|  | 1 (h) | 0 | NT |
|  | 4 (h) | 0 | NT |
|  | 24 (h) | 0 | NT |
| 215 | 1 | 0 | NT |
|  | 5 | 0 | NT |
|  | 30 | 6.1 | NT |
|  | 1 (h) | 15.2 | NT |
|  | 4 (h) | 25.8 | NT |
|  | 24 (h) | 46.8 | NT |
| 216 | 1 | 0 | 0 |
|  | 5 | 0 | 0 |
|  | 30 | 0 | 0 |
|  | 1 (h) | 0 | 0 |
|  | 4 (h) | 0 | 0 |
|  | 24 (h) | 0 | 0 |
| 219 | 1 | 100/0 | 0 |
|  | 5 | 100/0 | 0 |
|  | 30 | 0/100 | 0 |
|  | 1 (h) | 0/100 | 0 |
|  | 4 (h) | 0/100 | 0 |
|  | 24 (h) | 0/100 | 0 |
| 220 | 1 | 86.72% | 20.02% |
|  | 5 | 100% | 21.53% |
|  | 30 | 100% | 22.27% |
|  | 1 (h) | 100% | 55.36% |
|  | 4 (h) | 100% | 88.25% |
|  | 24 (h) | 100% | 89.93% |
| 221 | 1 | 0 | 0 |
|  | 5 | 0 | 0 |
|  | 30 | 2.9 | 0 |
|  | 1 (h) | 3.4 | 0 |

TABLE 11-continued

| Compound | Time (min) | Condition 1 Conversion (%) | Condition 2 Conversion (%) |
|---|---|---|---|
| | 4 (h) | 17.5 | 0 |
| | 24 (h) | 95.1 | 0 |
| 222 | 1 | 100 | 10 |
| | 5 | 100 | 20 |
| | 30 | 100 | 50 |
| | 1 (h) | 100 | 100 |
| | 4 (h) | 100 | 100 |
| | 24 (h) | 100 | 100 |
| 223 | 1 | 100 | 9.8 |
| | 5 | 100 | 10.4 |
| | 30 | 100 | 13.5 |
| | 1 (h) | 100 | 18.5 |
| | 4 (h) | 100 | 50.1 |
| | 24 (h) | 100 | 81.3 |
| 234 | 1 | 0 | 0 |
| | 5 | 0 | 0 |
| | 30 | 0 | 0 |
| | 1 (h) | 0 | 0 |
| | 4 (h) | 2.16 | 0 |
| | 24 (h) | 2.63 | 0 |
| 238 | 1 | 0 | NT |
| | 5 | 0 | NT |
| | 30 | 0 | NT |
| | 1 (h) | 0 | NT |
| | 4 (h) | 0 | NT |
| | 24 (h) | 0 | NT |
| 240 | 1 | 84 | 35.7 |
| | 5 | 100 | 30 |
| | 30 | 100 | 40.5 |
| | 1 (h) | 100 | 43.3 |
| | 4 (h) | 100 | 54.2 |
| | 24 (h) | 100 | 100 |
| 241 | 1 | 100 | 0 |
| | 5 | 100 | 28 |
| | 30 | 100 | 30 |
| | 1 (h) | 100 | 52 |
| | 4 (h) | 100 | 86 |
| | 24 (h) | 100 | 100 |
| 242 | 1 | 75.01 | 33.46 |
| | 5 | 95.02 | 36.51 |
| | 30 | 96.13 | 38.53 |
| | 1 (h) | 97.72 | 40.8 |
| | 4 (h) | 98.02 | 55.46 |
| | 24 (h) | 98.34 | 55.7 |
| 243 | 1 | 80.17 | 0 |
| | 5 | 100 | 0 |
| | 30 | 100 | 0 |
| | 1 (h) | 100 | 0 |
| | 4 (h) | 100 | 27.04 |
| | 24 (h) | 100 | 46.78 |
| 244 | 1 | 33.93 | 0 |
| | 5 | 100 | 0 |
| | 30 | 100 | 4.08 |
| | 1 (h) | 100 | 15.25 |
| | 4 (h) | 100 | 24.59 |
| | 24 (h) | 100 | 66.56 |
| 245 | 1 | 60 | 25 |
| | 5 | 100 | 35 |
| | 30 | 100 | 50 |
| | 1 (h) | 100 | 100 |
| | 4 (h) | 100 | 100 |
| | 24 (h) | 100 | 100 |
| 249 | 1 | 0 | 0 |
| | 5 | 70.48 | 0 |
| | 30 | 96.4 | 0 |
| | 1 (h) | 96.5 | 0 |
| | 4 (h) | 96.72 | 9.23 |
| | 24 (h) | 96.8 | 24.65 |
| 254 | 1 | 0 | 0 |
| | 5 | 2.4 | 0 |
| | 30 | 84.7 | 0 |
| | 1 (h) | 91.9 | 1.1 |
| | 4 (h) | 91.9 | 16.2 |
| | 24 (h) | 92 | 17.6 |
| 255 | 1 | 20.9 | 0 |
| | 5 | 65.2 | 0 |
| | 30 | 88.6 | 0 |
| | 1 (h) | 89.8 | 2.4 |
| | 4 (h) | 88.1 | 8.4 |
| | 24 (h) | 88 | 6 |
| 256 | 1 | 0 | 0 |
| | 5 | 0 | 0 |
| | 30 | 100 | 0 |
| | 1 (h) | 100% | 0 |
| | 4 (h) | 23% | 43% |
| | 24 (h) | 100% | 0 |
| 257 | 1 | 4.6 | 0 |
| | 5 | 54.1 | 0 |
| | 30 | 100 | 5 |
| | 1 (h) | 100 | 8 |
| | 4 (h) | 100 | 30 |
| | 24 (h) | 100 | 95 |
| 258 | 1 | 0 | 0 |
| | 5 | 0 | 0 |
| | 30 | 42.82 | 0 |
| | 1 (h) | 100 | 0 |
| | 4 (h) | 100 | 0 |
| | 24 (h) | 100 | 0 |
| 259 | 1 | 3.6 | 0 |
| | 5 | 4.1 | 0 |
| | 30 | 16.5 | 0 |
| | 1 (h) | 25 | 2 |
| | 4 (h) | 29.5 | 4.3 |
| | 24 (h) | 31.9 | 7.8 |
| 268 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 270 | 1 | 0 | 0 |
| | 5 | 0 | 0 |
| | 30 | 1 | 0 |
| | 1 (h) | 1 | 0 |
| | 4 (h) | 1 | 1 |
| | 24 (h) | 1 | 1 |
| 274 | 1 | 0 | 0 |
| | 5 | 0 | 0 |
| | 30 | 0 | 0 |
| | 1 (h) | 0 | 0 |
| | 4 (h) | 35.5 | 0 |
| | 24 (h) | 39.91 | 0 |
| 298 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 299 | 1 | 53 | 0 |
| | 5 | 100 | 0 |
| | 30 | 100 | 0 |
| | 1 (h) | 100 | 0 |
| | 4 (h) | 100 | 8 |
| | 24 (h) | 100 | 13 |
| 301 | 1 | 0 | 0 |
| | 5 | 0 | 0 |
| | 30 | 0 | 0 |
| | 1 (h) | 0 | 0 |
| | 4 (h) | 100 | 0 |
| | 24 (h) | 100 | 0 |
| 302 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 303 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |

TABLE 11-continued

| Compound | Time (min) | Condition 1 Conversion (%) | Condition 2 Conversion (%) |
|---|---|---|---|
| 304 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 305 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 306 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 309 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 310 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 311 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 312 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 313 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 314 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 315 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 316 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 317 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 334 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 355 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 363 | 1 | 0 | 0 |
| | 5 | 0 | 0 |
| | 30 | 0 | 0 |
| | 1 (h) | 2.1 | 0 |
| | 4 (h) | 27.1 | 0 |
| | 24 (h) | 46.7 | 8.1 |
| 365 | 1 | 0 | 0 |
| | 5 | 8.9 | 0 |
| | 30 | 47.1 | 10.11 |
| | 1 (h) | 77.4 | 11.33 |
| | 4 (h) | 94.1 | 12.6 |
| | 24 (h) | 100 | 17.4 |
| 366 | 1 | 0 | 0 |
| | 5 | 8.9 | 0 |
| | 30 | 47.1 | 10.11 |
| | 1 (h) | 77.4 | 11.33 |
| | 4 (h) | 94.1 | 12.6 |
| | 24 (h) | 100 | 17.4 |
| 367 | 1 | 100 | 5 |
| | 5 | 100 | 8.3 |
| | 30 | 100 | 11.5 |
| | 1 (h) | 100 | 11.92 |
| | 4 (h) | 100 | 13.32 |
| | 24 (h) | 100 | 20 |
| 370 | 1 | 20 | 0 |
| | 5 | 40 | 0 |
| | 30 | 100 | 0 |
| | 1 (h) | 100 | 10 |
| | 4 (h) | 100 | 30 |
| | 24 (h) | 100 | 70 |
| 214 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 246 | 1 | 100 | 40 |
| | 5 | 100 | 50 |
| | 30 | 100 | 60 |
| | 1 (h) | 100 | 75 |
| | 4 (h) | 100 | 100 |
| | 24 (h) | 100 | 100 |
| 251 | 1 | 6.91 | 0 |
| | 5 | 100 | 0 |
| | 30 | 100 | 0 |
| | 1 (h) | 100 | 0 |
| | 4 (h) | 100 | 0 |
| | 24 (h) | 100 | 15.18 |
| 252 | 1 | 0 | 21.5 |
| | 5 | 100 | 22 |
| | 30 | 100 | 26.1 |
| | 1 (h) | 100 | 28 |
| | 4 (h) | 100 | 50.1 |
| | 24 (h) | 100 | 70.1 |
| 253 | 1 | 0 | 0 |
| | 5 | 89.79 | 0 |
| | 30 | 100 | 0 |
| | 1 (h) | 100 | 0 |
| | 4 (h) | 100 | 3.38 |
| | 24 (h) | 100 | 28.89 |
| 260 | 1 | 25.8 | 0 |
| | 5 | 32.0 | 0 |
| | 30 | 65.5 | 0 |
| | 1 (h) | 73.6 | 13.4 |
| | 4 (h) | 89.1 | 24.1 |
| | 24 (h) | 90.5 | 14.0 |
| 271 | 1 | 100 | 78.3 |
| | 5 | 100 | 70.3 |

TABLE 11-continued

| Compound | Time (min) | Condition 1 Conversion (%) | Condition 2 Conversion (%) |
|---|---|---|---|
| | 30 | 100 | 82 |
| | 1 (h) | 100 | 85.7 |
| | 4 (h) | 100 | 94.5 |
| | 24 (h) | 100 | 100 |
| 275 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 2.17 | 0 |
| 276 | 1 | 0 | 0 |
| | 5 | 0 | 0 |
| | 30 | 0 | 0 |
| | 1 (h) | 2.77 | 0 |
| | 4 (h) | 5.48 | 0 |
| | 24 (h) | 5.5 | 0 |
| 281 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 300 | 1 | 0 | 0 |
| | 5 | 0 | 0 |
| | 30 | 0 | 0 |
| | 1 (h) | 0 | 0 |
| | 4 (h) | 0 | 0 |
| | 24 (h) | 0 | 0 |
| 361 | 1 | 10 | 0 |
| | 5 | 100 | 0 |
| | 30 | 100 | 0 |
| | 1 (h) | 100 | 0 |
| | 4 (h) | 100 | 45 |
| | 24 (h) | 100 | 100 |
| 364 | 1 | 10 | 0 |
| | 5 | 100 | 0 |
| | 30 | 14.91 | 0 |
| | 1 (h) | 16.09 | 35.78 |
| | 4 (h) | 77.07 | 47 |
| | 24 (h) | 90.5 | 78.89 |
| 369 | 1 | 30 | 0 |
| | 5 | 100 | 0 |
| | 30 | 100 | 0 |
| | 1 (h) | 100 | 0 |
| | 4 (h) | 100 | 45 |
| | 24 (h) | 100 | 50 |
| 293 | 1 | 0.0 | 0.0 |
| | 5 | 0.0 | 0.0 |
| | 30 | 0.0 | 0.0 |
| | 1 (h) | 0.0 | 0.0 |
| | 4 (h) | 0.0 | 0.0 |
| | 24 (h) | 0.0 | 0.0 |

Example A3

Plasma Stability Assay

Compound stability in mouse and human plasma was measured by incubating compound with mouse or human plasma at 37° C. in a microwell plate for sequential time points, monitoring pro-drug disappearance and metabolite appearance (mesembrine). A 20 mM stock solution of test compounds were prepared by dissolving appropriate amount of compounds in DMSO. These were diluted in DMSO to prepare a stock of 1 mM. A 1 mM stock was further diluted 200-folds in mice or human plasma (pre-warmed at 37° C. for 15 minutes) to attain a final concentration of 5 μM respectively (0.5% DMSO). Positive controls and test compounds spiked into 400 μL aliquot (n=2) mice or human plasma and were incubated in a $CO_2$ incubator at 37° C. An aliquot of 50 μL was withdrawn at 0, 0.25, 0.5, 1, 2, 4 hrs and immediately quenched with 400 μL of ice-cold acetonitrile containing internal standard followed by storing at minus 2-8° C. All the samples were thawed at room temperature. Samples were vortexed for 5 min followed by centrifugation at 4000 RPM for 15 min at 4° C. An aliquot of 100 μL was transferred to 96-well deep plate and submitted for analysis by LC-MS/MS. The concentrations of test compounds and positive control were quantified in the test samples using LC-MS/MS.

Results reported as % of prodrug compound remaining at time point, and % of metabolite (mesembrine, 001) accumulated at time point. The data is represented in the table below.

TABLE 12

| | | Mouse Plasma | | Human Plasma | |
|---|---|---|---|---|---|
| Compound | Time (min) | Prodrug (%) | Compound 001 (%) | Prodrug (%) | Compound 001 (%) |
| Compound of example 18 | 0.0 | 100.0 | 0 | 100.0 | 0 |
| | 15 | 98.6 | 0 | >99 | 0 |
| | 30 | 99.3 | 0 | >99 | 0 |
| | 60 | 86.4 | 0 | >99 | 0 |
| | 120 | 90.9 | 0 | >99 | 0 |
| | 240 | 63.9 | 0 | 93.6 | 0 |
| 268 | 0.0 | 100.0 | 84.7 | 100.0 | 73.4 |
| | 15 | 7.0 | 82.0 | 10.0 | 77.6 |
| | 30 | 2.8 | 85.0 | 6.8 | 87.4 |
| | 60 | 0.0 | 85.8 | 0.0 | 84.5 |
| | 120 | 0.0 | 78.4 | 0.0 | 89.2 |
| | 240 | 0.0 | 75.9 | 0.0 | 69.5 |
| 298 | 0.0 | 100.0 | NC | 100.0 | 1.8 |
| | 15 | 69.0 | 34.0 | >99 | 2.8 |
| | 30 | 46.1 | 44.5 | >99 | 4.0 |
| | 60 | 20.3 | 60.1 | 97.5 | 4.9 |
| | 120 | 5.1 | 64.3 | >99 | 8.9 |
| | 240 | 2.2 | 64.8 | 90.9 | 12.1 |
| 302 | 0.0 | 100.0 | 7.0 | 100.0 | 0.1 |
| | 15 | 58.2 | 31.2 | 95.3 | 0.5 |
| | 30 | 28.3 | 46.8 | 96.0 | 1.0 |
| | 60 | 5.5 | 60.7 | 94.4 | 2.2 |
| | 120 | 1.1 | 55.2 | 87.1 | 5.1 |
| | 240 | 0.9 | 62.1 | 75.8 | 10.6 |
| 303 | 0.0 | 100.0 | NC | 100.0 | 3.1 |
| | 15 | 0.3 | 93.3 | >99 | 6.4 |
| | 30 | 0.2 | 93.1 | 92.2 | 11.3 |
| | 60 | 0.1 | 89.5 | 84.9 | 17.7 |
| | 120 | 0.1 | 86.7 | 73.0 | 31.1 |
| | 240 | 0.1 | 85.4 | 49.7 | 44.2 |
| 304 | 0.0 | 100.0 | 0.3 | 100.0 | 0.2 |
| | 15 | 87.1 | 0.3 | >99 | 0.3 |
| | 30 | 88.6 | 0.4 | 97.8 | 0.2 |
| | 60 | 85.8 | 0.4 | 94.7 | 0.4 |
| | 120 | 84.3 | 0.6 | 99.9 | 0.5 |
| | 240 | 88.9 | 1.5 | 98.0 | 0.6 |
| 305 | 0.0 | 100.0 | NC | 100.0 | 0.2 |
| | 15 | 3.3 | 70.1 | >99 | 0.4 |
| | 30 | 1.1 | 65.6 | 96.2 | 1.2 |
| | 60 | 0.9 | 67.8 | 92.6 | 2.3 |
| | 120 | 0.9 | 63.6 | 97.5 | 5.0 |
| | 240 | 0.9 | 29.9 | 83.1 | 9.6 |
| 306 | 0.0 | 100.0 | NC | 100.0 | 3.0 |
| | 15 | 6.2 | 90.5 | 89.5 | 16.6 |
| | 30 | NC | 64.4 | 75.2 | 28.7 |
| | 60 | 1.6 | 90.5 | 53.7 | 46.0 |
| | 120 | 0.4 | 91.4 | 32.4 | 64.2 |
| | 240 | 0.1 | 89.8 | 13.8 | 77.9 |
| 307 | 0.0 | 100.0 | NC | 100.0 | 0.9 |
| | 15 | 18.1 | 73.4 | 88.5 | 1.6 |
| | 30 | 3.8 | 81.1 | 87.6 | 5.4 |
| | 60 | 0.1 | 86.3 | 83.0 | 9.0 |
| | 120 | 0.0 | 79.9 | 71.1 | 17.9 |
| | 240 | 0.0 | 79.0 | 57.5 | 29.6 |
| 308 | 0.0 | 100.0 | NC | 100.0 | NC |
| | 15 | 3.7 | 59.8 | 68.0 | 29.3 |
| | 30 | 1.5 | 60.0 | 43.8 | 36.8 |

TABLE 12-continued

| Compound | Time (min) | Mouse Plasma Prodrug (%) | Mouse Plasma Compound 001 (%) | Human Plasma Prodrug (%) | Human Plasma Compound 001 (%) |
|---|---|---|---|---|---|
|  | 60 | 0.1 | 58.3 | 14.1 | 47.4 |
|  | 120 | 0.0 | 57.7 | 2.3 | 50.7 |
|  | 240 | 0.0 | 58.2 | 0.7 | 50.8 |
| 309 | 0.0 | 100.0 | NC | 100.0 | 5.7 |
|  | 15 | 34.6 | 61.7 | 64.5 | 26.5 |
|  | 30 | 24.9 | 63.7 | 41.4 | 36.5 |
|  | 60 | 8.2 | 62.6 | 16.5 | 50.1 |
|  | 120 | 0.0 | 63.2 | 3.6 | 56.1 |
|  | 240 | 0.0 | 60.9 | 2.0 | 54.8 |
| 310 | 0.0 | 100.0 | NC | 100.0 | NC |
|  | 15 | 0.4 | 58.2 | 89.9 | NC |
|  | 30 | 0.1 | 62.2 | 84.5 | NC |
|  | 60 | 0.1 | 59.4 | 77.3 | 32.1 |
|  | 120 | 0.1 | 54.3 | 63.4 | 37.4 |
|  | 240 | 0.1 | 54.6 | 35.1 | 51.2 |
| 311 | 0.0 | 100.0 | 4.4 | 100.0 | 3.1 |
|  | 15 | 73.1 | 14.9 | 91.7 | 3.3 |
|  | 30 | 53.7 | 23.5 | 93.9 | 3.8 |
|  | 60 | 24.8 | 36.1 | 95.9 | 5.8 |
|  | 120 | 3.5 | 41.6 | 84.7 | 7.7 |
|  | 240 | 0.4 | 42.8 | 68.1 | 14.0 |
| 312 | 0.0 | 100.0 | NC | 100.0 | 0.0 |
|  | 15 | 3.5 | 66.1 | 8.1 | 68.9 |
|  | 30 | 1.6 | 70.8 | 6.2 | 70.1 |
|  | 60 | 2.2 | 64.4 | 20.9 | 66.5 |
|  | 120 | 2.8 | 61.7 | 10.5 | 68.0 |
|  | 240 | 0.8 | 61.5 | 13.8 | 68.4 |
| 313 | 0.0 | 100.0 | NC | 100.0 | 4.3 |
|  | 15 | 2.1 | 37.2 | 62.2 | 19.0 |
|  | 30 | 0.7 | 36.3 | 35.1 | 28.2 |
|  | 60 | 0.1 | 37.1 | 12.8 | 35.6 |
|  | 120 | 0.0 | 35.2 | 2.4 | 35.9 |
|  | 240 | 0.0 | 35.0 | 0.4 | 37.6 |
| 314 | 0.0 | 100.0 | NC | 100.0 | 4.0 |
|  | 15 | 1.1 | 68.2 | 16.9 | 32.8 |
|  | 30 | 1.5 | 69.0 | 2.3 | 71.0 |
|  | 60 | 0.9 | 67.5 | 0.1 | 82.0 |
|  | 120 | 1.0 | 67.1 | 0.0 | 76.2 |
|  | 240 | 1.5 | 68.3 | 0.0 | 70.9 |
| 315 | 0.0 | 100.0 | NC | 100.0 | 3.0 |
|  | 15 | 5.3 | 60.4 | 16.6 | 62.5 |
|  | 30 | 2.4 | 61.9 | 2.3 | 68.1 |
|  | 60 | 1.3 | 61.9 | 0.5 | 59.5 |
|  | 120 | 2.0 | 57.3 | 0.2 | 70.2 |
|  | 240 | 1.9 | 55.8 | 0.0 | 66.0 |
| 317 | 0.0 | 100.0 | NC | 100.0 | NC |
|  | 15 | 0.0 | 75.6 | 7.6 | 69.6 |
|  | 30 | 0.0 | 83.3 | 0.7 | 70.8 |
|  | 60 | 0.0 | 78.6 | 0.0 | 75.1 |
|  | 120 | 0.0 | 78.3 | 0.0 | 71.7 |
|  | 240 | 0.0 | 75.2 | 0.0 | 70.1 |
| 334 | 0.0 | 100.0 | NC | 100.0 | NC |
|  | 15 | 4.7 | 73.1 | 37.7 | 63.6 |
|  | 30 | 0.0 | 70.9 | 18.4 | 63.7 |
|  | 60 | 0.0 | 68.8 | 3.7 | 65.4 |
|  | 120 | 0.0 | 70.0 | 0.7 | 65.1 |
|  | 240 | 0.0 | 68.5 | 0.0 | 63.8 |
| 355 | 0.0 | 100.0 | 0.0 | 100.0 | 0.0 |
|  | 15 | 50.6 | 65.5 | >99 | 0.0 |
|  | 30 | 30.8 | 80.3 | >99 | 0.0 |
|  | 60 | 9.9 | 93.5 | >99 | 0.0 |
|  | 120 | 0.5 | 91.7 | >99 | 0.0 |
|  | 240 | 0.0 | 57.0 | 93.2 | 0.0 |
| 373 | 0.0 | 100 | 0.00 | 100 | 0 |
|  | 15 | 82 | 0.00 | 93.9 | 0 |
|  | 30 | 64 | 7.30 | 96.5 | 0 |
|  | 60 | 41 | 15.00 | 81.4 | 0 |
|  | 120 | 12 | 18.60 | 66.1 | 0 |
|  | 240 | 1 | 12.00 | 17.2 | 0 |
| 353 | 0.0 | 100 | 47.7 | 100 | 0 |
|  | 15 | 0 | 55 | 95.4 | 8.1 |
|  | 30 | 0 | 51.6 | 90.1 | 10.6 |
|  | 60 | 0 | 50.6 | 79.7 | 16.5 |
|  | 120 | 0 | 46.4 | 55.3 | 22.3 |
|  | 240 | 0 | 29.3 | 39.6 | 36.6 |
| 354 | 0.0 | 100 | 33.27 | 100 | 0.00 |
|  | 15 | 5 | 32.79 | 93 | 20.89 |
|  | 30 | 7 | 32.69 | 72 | 22.39 |
|  | 60 | 5 | 29.45 | 42 | 24.31 |
|  | 120 | 4 | 27.14 | 13 | 27.74 |
|  | 240 | 0 | 20.12 | 1 | 15.59 |
| 371 | 0.0 | 100 | 28.4 | 100 | 0.00 |
|  | 15 | 10 | 31.54 | 99 | 0.00 |
|  | 30 | 0 | 29.63 | 92 | 0.00 |
|  | 60 | 0 | 30.25 | 87 | 2.67 |
|  | 120 | 0 | 26.59 | 78 | 5.08 |
|  | 240 | 0 | 19.82 | 27 | 3.85 |
| 372 | 0.0 | 100 | 0 | 100 | 0.00 |
|  | 15 | 92 | 0 | 97 | 0.00 |
|  | 30 | 91 | 0 | 99 | 0.00 |
|  | 60 | 88 | 0 | 94 | 0.00 |
|  | 120 | 73 | 0 | 81 | 0.00 |
|  | 240 | 64 | 0 | 38 | 0.00 |
| 374 | 0.0 | 100 | 16.48 | 100 | 0.00 |
|  | 15 | 33 | 23.61 | 98 | 0.00 |
|  | 30 | 4 | 31.23 | 88 | 3.19 |
|  | 60 | 0 | 31.44 | 84 | 5.92 |
|  | 120 | 0 | 29.64 | 62 | 9.01 |
|  | 240 | 0 | 14.56 | 11 | 7.54 |
| 375 | 0.0 | 100 | 41.82 | 100 | 0.00 |
|  | 15 | 11 | 45.54 | >99 | 0.00 |
|  | 30 | 2 | 45.99 | >99 | 3.77 |
|  | 60 | 0 | 41.28 | 97 | 13.57 |
|  | 120 | 0 | 42.28 | 57 | 9.80 |
|  | 240 | 0 | 29.74 | 26 | 11.03 |
| 259 | 0.0 | 100 | 0 | 100 | 9.4 |
|  | 15 | 86.2 | 0.08 | >99 | 14.7 |
|  | 30 | 81.0 | 0.1 | 96.6 | 16.8 |
|  | 60 | 67.6 | 0.2 | 85.7 | 24.5 |
|  | 120 | 38.7 | 0.3 | 70.0 | 36.4 |
|  | 240 | 19.8 | 0.5 | 54.3 | 48.8 |
| 316 | 0.0 | 100 | 66.4 | 100 | 45.7 |
|  | 15 | 4.8 | 73.4 | 1.4 | 71.8 |
|  | 30 | 0.9 | 81.7 | 1.3 | 83.5 |
|  | 60 | 0 | 80.5 | 0.4 | 87.6 |
|  | 120 | 0 | 68.3 | 0.2 | 84.6 |
|  | 240 | 0 | 61.1 | 0.05 | 74.7 |
| 001 | 0.0 | 100.0 | N/A | 100.0 | N/A |
|  | 15 | >99 | N/A | >99 | N/A |
|  | 30 | 97.8 | N/A | >99 | N/A |
|  | 60 | >99 | N/A | >99 | N/A |
|  | 120 | >99 | N/A | >99 | N/A |
|  | 240 | >99 | N/A | >99 | N/A |
| 352 | 0.0 | 100.0 | 40.2 | 100.0 | 0.0 |
|  | 15 | 0.0 | 40.4 | 89.1 | 8.2 |
|  | 30 | 0.0 | 41.8 | 97.4 | 10.1 |
|  | 60 | 0.0 | 41.3 | 87.1 | 14.3 |
|  | 120 | 0.0 | 38.5 | 56.1 | 18.1 |
|  | 240 | 0.0 | 23.8 | 54.5 | 35.1 |

Example A4

Plasma Stability Assay

Compound stability in rat and human plasma was measured by incubating compound with rat or human plasma at 37° C. in a microwell plate for sequential time points, monitoring pro-drug disappearance and metabolite appearance (mesembrine, 001). A 1 mM stock solution of test compounds were prepared by dissolving appropriate amount of compounds in DMSO. The 1 mM stock was further diluted 200-folds in rat or human plasma to attain a final concentration of 10 μM respectively (0.5% DMSO). 50 uL aliquots of positive controls and test compounds spiked into rat or human plasma (n=2) were added to a pre-warmed plate (37° C.) and shaken at 50 rpm. At each respective time point, the reaction was stopped by adding 500 μL of acetonitrile containing internal standards (100 nM aprozolam, 200 nM caffeine, 100 nM tolbutamide). All samples were vortexed for 10 minutes, followed by centrifugation at 3,220 g for 30 minutes to precipitate proteins. 100 μL of the supernatant is transferred to a new plate. The supernatant will be diluted with ultrapure water according to the LC-MS signal response and peak shape. The concentrations of test compounds and positive control were quantified in the test samples using LC-MS/MS. Results reported as % of prodrug compound remaining at time point, and % of metabolite (mesembrine, 001) accumulated at time point. The data is represented in the table below.

TABLE 13

| Compound | Time (min) | Rat Plasma Prodrug (%) | Rat Plasma Compound 001 (%) | Human Plasma Prodrug (%) | Human Plasma Compound 001 (%) |
|---|---|---|---|---|---|
| 001 | 0.0 | N/A | 100.0 | N/A | 100.0 |
| | 10 | N/A | >99 | N/A | >99 |
| | 30 | N/A | >99 | N/A | >99 |
| | 60 | N/A | 97.3 | N/A | >99 |
| | 120 | N/A | >99 | N/A | >99 |
| | 240 | N/A | 98.3 | N/A | >99 |
| 026 | 0.0 | 100.0 | 96.2 | 100.0 | >99 |
| | 10 | 0.0 | >99 | 40.3 | >99 |
| | 30 | 0.0 | >99 | 23.5 | >99 |
| | 60 | 0.0 | >99 | 12.0 | >99 |
| | 120 | 0.0 | >99 | 3.4 | >99 |
| | 240 | 0.0 | >99 | 0.8 | >99 |
| 356 | 0.0 | 100.0 | 0.3 | 100.0 | 0.2 |
| | 10 | >99 | 0.4 | >99 | 0.3 |
| | 30 | >99 | 0.5 | >99 | 0.3 |
| | 60 | >99 | 0.5 | >99 | 0.3 |
| | 120 | >99 | 0.5 | >99 | 0.2 |
| | 240 | 95.8 | 0.5 | >99 | 0.3 |
| 371 | 0.0 | 100.0 | 46.5 | 100.0 | 7.2 |
| | 10 | 5.0 | >99 | >99 | 8.2 |
| | 30 | 0.2 | >99 | 94.4 | 9.5 |
| | 60 | 0.1 | >99 | 90.7 | 11.7 |
| | 120 | 0.0 | >99 | 91.3 | 14.6 |
| | 240 | 0.0 | >99 | 78.0 | 18.9 |
| 372 | 0.0 | 100.0 | 0.3 | 100.0 | 0.3 |
| | 10 | >99 | 0.5 | >99 | 0.3 |
| | 30 | >99 | 0.6 | >99 | 0.3 |
| | 60 | >99 | 0.7 | >99 | 0.3 |
| | 120 | 98.4 | 0.8 | >99 | 0.3 |
| | 240 | >99 | 0.8 | >99 | 0.3 |
| 373 | 0.0 | 100.0 | 3.4 | 100.0 | 0.3 |
| | 10 | 81.0 | 27.3 | 96.3 | 0.9 |
| | 30 | 58.4 | 60.9 | >99 | 1.2 |
| | 60 | 26.8 | 89.8 | 94.8 | 2.3 |
| | 120 | 5.2 | >99 | 89.9 | 3.5 |
| | 240 | 1.3 | >99 | 96.3 | 6.0 |
| 374 | 0.0 | 100.0 | 33.2 | 100.0 | 1.3 |
| | 10 | 9.7 | >99 | >99 | 3.4 |
| | 30 | 0.3 | >99 | >99 | 5.6 |
| | 60 | 0.1 | >99 | >99 | 9.1 |
| | 120 | 0.0 | >99 | >99 | 14.9 |
| | 240 | 0.0 | >99 | 95.4 | 25.1 |
| 395 | 0.0 | 100.0 | >99 | 100.0 | >99 |
| | 10 | 0.3 | >99 | 13.9 | >99 |
| | 30 | 0.1 | >99 | 3.5 | >99 |
| | 60 | 0.1 | >99 | 1.1 | >99 |
| | 120 | 0.1 | >99 | 0.3 | >99 |
| | 240 | 0.1 | >99 | 0.1 | >99 |
| 397 | 0.0 | 100.0 | >99 | 100.0 | 91.8 |
| | 10 | 10.5 | >99 | 2.2 | >99 |
| | 30 | 0.5 | >99 | 0.5 | 97.6 |
| | 60 | 0.1 | >99 | 0.1 | >99 |
| | 120 | 0.1 | >99 | 0.2 | >99 |
| | 240 | 0.1 | >99 | 0.0 | >99 |
| 398 | 0.0 | 100.0 | 44.8 | 100.0 | 8.7 |
| | 10 | 2.8 | 80.9 | 96.4 | 25.9 |
| | 30 | 0.7 | 78.7 | 85.0 | 43.1 |
| | 60 | 0.1 | 81.8 | 72.4 | 51.9 |
| | 120 | 0.0 | 91.6 | 51.6 | 77.5 |
| | 240 | 0.0 | 78.2 | 25.5 | 88.6 |
| 399 | 0.0 | 100.0 | >99 | 100.0 | >99 |
| | 10 | 0.0 | >99 | 5.6 | >99 |
| | 30 | 0.0 | >99 | 1.1 | >99 |
| | 60 | 0.0 | >99 | 0.5 | >99 |
| | 120 | 0.0 | >99 | 0.3 | >99 |
| | 240 | 0.0 | >99 | 0.2 | >99 |
| 400 | 0.0 | 100.0 | 23.3 | 100.0 | 37.9 |
| | 10 | 12.6 | >99 | 34.7 | 92.0 |
| | 30 | 0.6 | >99 | 11.6 | >99 |
| | 60 | 0.1 | >99 | 5.2 | >99 |
| | 120 | 0.1 | >99 | 2.3 | >99 |
| | 240 | 0.0 | >99 | 1.9 | >99 |
| 401 | 0.0 | 100.0 | 2.8 | 100.0 | 1.2 |
| | 10 | 84.5 | 27.0 | 95.9 | 2.1 |
| | 30 | 55.8 | 52.7 | >99 | 3.5 |
| | 60 | 33.8 | 70.3 | 96.6 | 4.4 |
| | 120 | 16.3 | 76.8 | 94.4 | 5.6 |
| | 240 | 3.3 | 85.7 | 93.4 | 8.9 |
| 402 | 0.0 | 100.0 | 41.8 | 100.0 | 51.1 |
| | 10 | 3.5 | >99 | 11.3 | >99 |
| | 30 | 0.1 | >99 | 2.9 | >99 |
| | 60 | 0.0 | >99 | 2.1 | >99 |
| | 120 | 0.0 | >99 | 1.6 | >99 |
| | 240 | 0.0 | >99 | 1.1 | >99 |
| 404 | 0.0 | 100.0 | >99 | 100.0 | >99 |
| | 10 | 0.3 | >99 | 22.9 | >99 |
| | 30 | 0.3 | >99 | 11.5 | >99 |
| | 60 | 0.3 | >99 | 7.6 | >99 |
| | 120 | 0.3 | >99 | 3.8 | >99 |
| | 240 | 0.2 | >99 | 1.6 | >99 |
| 405 | 0.0 | 100.0 | 71.4 | 100.0 | 79.0 |
| | 10 | 0.1 | 91.8 | >99 | 84.1 |
| | 30 | 0.0 | 88.2 | 95.0 | 77.6 |
| | 60 | 0.1 | 86.9 | 87.0 | 93.0 |
| | 120 | 0.0 | 81.2 | 65.7 | 94.1 |
| | 240 | 0.0 | 81.4 | 46.7 | 93.8 |
| 425 | 0.0 | 100.0 | 23.0 | 100.0 | 83.5 |
| | 10 | 4.4 | 94.3 | 6.5 | 86.8 |
| | 30 | 0.1 | 94.5 | 4.8 | 89.9 |
| | 60 | 0.0 | 96.5 | 4.0 | 89.7 |
| | 120 | 0.0 | 96.8 | 3.0 | 84.9 |
| | 240 | 0.0 | 96.4 | 1.9 | 89.1 |
| 426 | 0.0 | 100.0 | 3.6 | 100.0 | 1.2 |
| | 10 | 70.2 | 40.9 | 87.1 | 2.7 |
| | 30 | 33.2 | 87.9 | 80.3 | 5.1 |
| | 60 | 9.5 | >99 | 79.2 | 7.2 |
| | 120 | 0.9 | >99 | 73.6 | 10.3 |
| | 240 | 0.1 | >99 | 66.4 | 13.4 |
| 427 | 0.0 | 100.0 | 2.6 | 100.0 | 0.3 |
| | 10 | 93.6 | 19.3 | >99 | 0.8 |
| | 30 | 73.4 | 46.9 | 96.6 | 1.0 |
| | 60 | 43.9 | 69.9 | 96.9 | 1.4 |
| | 120 | 16.0 | 95.8 | 95.5 | 2.0 |
| | 240 | 2.3 | >99 | 91.2 | 3.2 |
| 428 | 0.0 | 100.0 | 1.5 | 100.0 | 1.7 |
| | 10 | 90.3 | 14.5 | 82.9 | 8.2 |
| | 30 | 69.9 | 37.8 | 74.5 | 15.7 |
| | 60 | 41.7 | 60.6 | 69.1 | 23.7 |
| | 120 | 18.1 | 83.6 | 56.8 | 36.4 |
| | 240 | 3.9 | >99 | 46.0 | 47.1 |
| 429 | 0.0 | 100.0 | 1.2 | 100.0 | 0.6 |
| | 10 | 90.4 | 11.3 | >99 | 2.9 |
| | 30 | 83.9 | 27.5 | 96.3 | 6.3 |
| | 60 | 71.9 | 49.8 | 95.3 | 10.4 |
| | 120 | 50.8 | 79.6 | 91.8 | 17.4 |
| | 240 | 26.2 | >99 | 84.6 | 26.7 |
| 430 | 0.0 | 100.0 | 0.2 | 100.0 | 0.0 |
| | 10 | 98.2 | 0.8 | >99 | 0.1 |
| | 30 | 98.3 | 1.7 | >99 | 0.1 |
| | 60 | 97.1 | 2.6 | >99 | 0.2 |

TABLE 13-continued

| Compound | Time (min) | Rat Plasma Prodrug (%) | Rat Plasma Compound 001 (%) | Human Plasma Prodrug (%) | Human Plasma Compound 001 (%) |
|---|---|---|---|---|---|
| | 120 | 94.1 | 4.2 | >99 | 0.3 |
| | 240 | 92.8 | 6.7 | 95.9 | 0.4 |
| 431 | 0.0 | 100.0 | 1.7 | 100.0 | 1.5 |
| | 10 | 74.5 | 28.8 | 82.1 | 11.6 |
| | 30 | 45.7 | 70.6 | 69.0 | 23.4 |
| | 60 | 16.5 | >99 | 62.8 | 35.0 |
| | 120 | 2.3 | >99 | 52.6 | 52.3 |
| | 240 | 0.2 | >99 | 37.4 | 68.9 |

Example B1

SERT Inhibition Assay

SERT inhibition was measured using a Neruotransmitter Transportation Fluorescence assay. Briefly, stable 5HTT cells were prepared in a 384 microwell plate. Compounds were prepared by in assay buffer (20 mM HEPES in HBSS, 0.1% BSA). The compounds were added to the plated cells and incubated for 30 minutes at 37° C. 25 µL of dye solution (Molecular Devices Neurotransmitter Transporter Uptake Assay Kit) was added per well and incubated for 30 minutes at 37° C. The plates were then read on a plate reader.

The in vitro SERT inhibition was measured for the compounds listed in the table below. The results are provided as follows: A: $IC_{50}$<=50 nM or lower; B: 50 nM<$IC_{50}$<=100 nM; C: 100 nM<$IC_{50}$<=500 nM; D: 500 nM<IC50<=1 micromolar; E: IC50>1 micromolar. Results are shown in Table 14.

TABLE 14

| Compound | SERT $IC_{50}$ (nM) |
|---|---|
| 036 | A |
| 038 | A |
| 026 | E |
| 035 | A |
| 037 | A |
| 045 | E |
| 046 | C |
| 070 | C |
| 080 | A |
| 081 | A |
| 109 | A |
| 043 | A |
| 044 | E |
| 110 | A |
| 111 | A |
| 157 | A |
| 158 | A |
| 159 | A |
| 242 | A |
| 258 | A |
| 303 | A |
| 317 | A |
| 372 | A |
| 373 | A |

Example B2

Pharmacokinetics of 043 and 001

Total twelve male mice were used in this study. Animals were administered through oral route with solution formulation of 043 at 75 mg/kg dose. The formulation vehicle used was normal saline. Blood samples (approximately 60 µL) were collected under light isoflurane anesthesia from a set of two mice at 0.25, 0.5, 1, 2, 4 and 8 h. The blood samples were collected at each time point in labeled micro centrifuge tube containing $K_2$EDTA as anticoagulant and PMSF (100 mM; 10 µL/mL of blood) as a stabilizer. Plasma samples were separated by centrifugation of whole blood and stored below −70° C. until bioanalysis. Following blood collection, immediately animals were sacrificed followed by abdominal vena-cava was cut open and whole body was perfused from heart using 10 mL of normal saline. Brain samples were collected from set of two mice at 0.25, 0.5, 1, 2, 4 and 8 h. After isolation, brain samples were rinsed three times in ice cold normal saline (for 5-10 seconds/rinse using ~10-20 mL normal saline in disposable petri dish for each rinse) and dried on blotting paper. Brain samples were homogenized using ice-cold phosphate buffer saline (pH-7.4) and PMSF (100 mM; 10 µL/mL of blood) as a stabilizer. Brain homogenates were stored below −70±10° C. until analysis. Total homogenate volume was three times of the brain weight.

The plasma and brain concentration-time data of 043 and 001 was used for the pharmacokinetic analysis. Plasma and brain samples were quantified by fit-for-purpose LC-MS/MS method.

LLOQ: 043-01N: 1.03 ng/mL for plasma and 2.06 ng/mL for brain; 001: 2.04 ng/mL for plasma and brain.

The extraction procedure for plasma/brain samples and the spiked plasma/brain calibration standards were identical:

A 25 µL of study sample plasma/brain (dilution applied to some samples) or spiked plasma calibration standard was added to individual pre-labeled micro-centrifuge tubes followed by 100 µL of internal standard prepared in acetonitrile (Glipizide-500 ng/mL) was added except for blank, where 100 µL of acetonitrile was added. Samples were vortexed for 5 minutes. Samples were centrifuged for 10 minutes at a speed of 4000 rpm at 4° C. Following centrifugation, 100 µL of clear supernatant was transferred in 96 well plates and analyzed using LC-MS/MS.

Following a single oral at 75 mg/kg dose administration of 043 in male $C_{57}BL/6$ Mice, peak plasma concentrations were observed at 0.50 h, suggesting rapid absorption. Brain concentrations were quantifiable up to 4 h with brain exposure-Kp was <1.

Figure 5A:
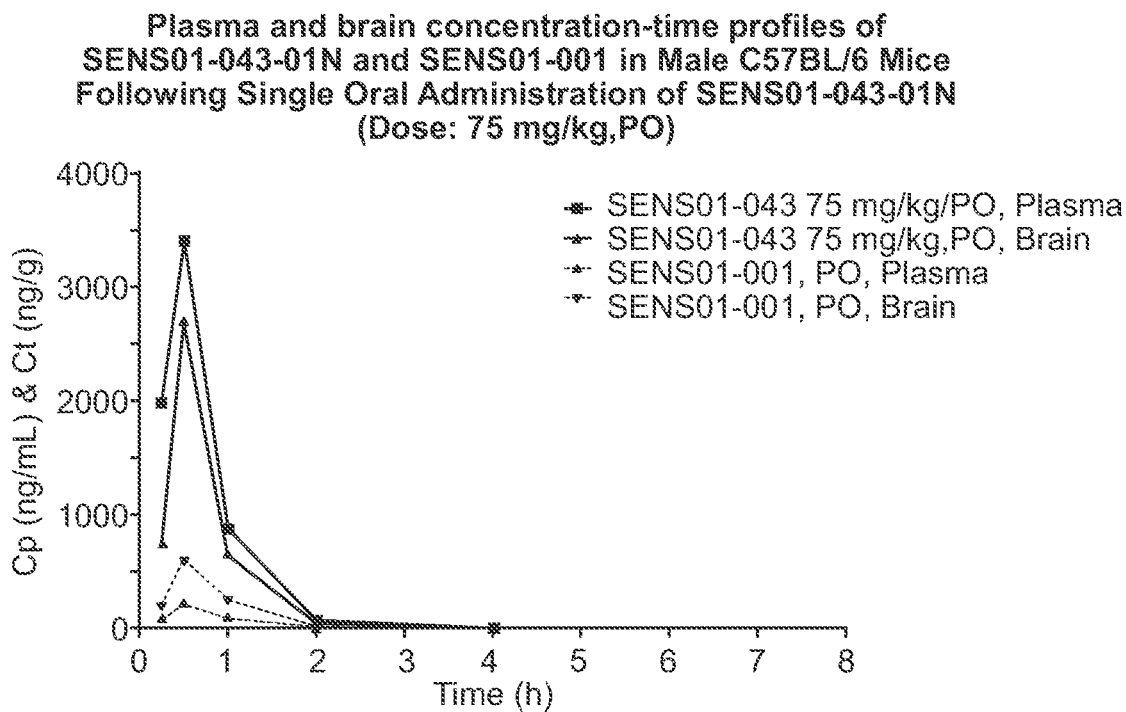
FIGS. 5A and 5B are graphs showing the plasma and brain concentrations-time profiles (mean) of 043 and 001 in male C57BL/6 mice following a single oral administration of 043 (Dose: 75 mg/kg) shown in a linear scale (FIG. 5A) and a semi-log scale (FIG. 5B). Prodrug compound 043 efficiently converts to 001 in vivo.
Figure 5B:
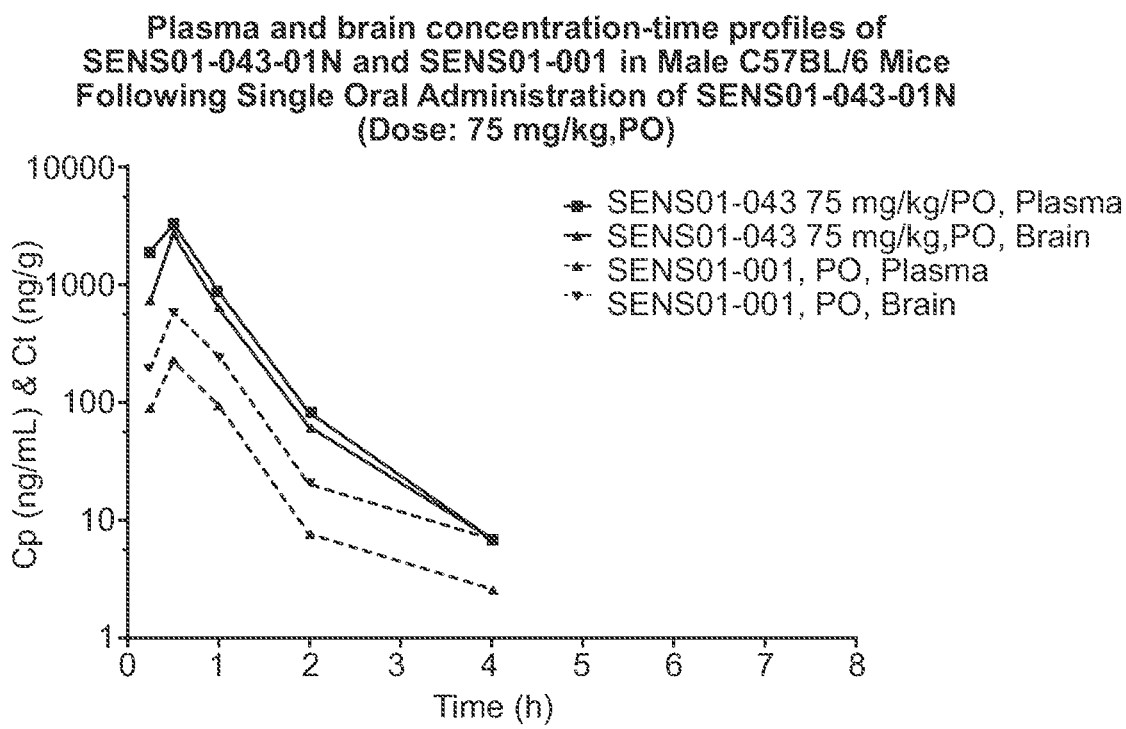

Following a single oral at 75 mg/kg dose administration of 043 in male $C_{57}BL/6$ Mice, peak plasma concentrations of 001 were observed at 0.50 h, suggesting rapid absorption of metabolite. Brain concentrations were quantifiable up to 4 h with brain exposure-Kp was 2.55. The results are summarized in Table 15 and shown in FIGS. 5A and 5B, which show plasma and brain levels of 001 (mesembrine) and prodrug compound 043 in mice following 75 mg/kg po administration of compound 043 in mice. Prodrug compound 043 efficiently converts to 001 in vivo. Dashed lines represent concentrations of 001 in plasma (▲) and brain (▼) following administration of 043. These data indicate mesembrine prodrugs with modification to the ketone, can efficiently hydrolyze and convert to mesembrine in vivo and allow duration of action to be improved.

TABLE 15

Pharmacokinetic data of 043 and 001 in male C57BL/6 mice following a single oral administration of 043 (Dose: 75 mg/kg, PO)

| Analyte | Matrix | Route | Dose (mg/kg) | $T_{max}$ (h) | $C_{max}$ (ng/mL) | $AUC_{last}$ (h*ng/mL) | | |
|---|---|---|---|---|---|---|---|---|
| 043 | Plasma | PO | 75 | 0.50 | 3392.53 | 2555.07 | | — |
| 001 | Plasma | PO | — | 0.50 | 230.83 | 195.38 | | |

| | Matrix | Route | Dose (mg/kg) | $T_{max}$ (h) | $C_{max}$ (ng/mL) | $AUC_{last}$ (h*ng/mL) | Brain-Kp ($C_{max}$) | Brain-Kp ($AUC_{last}$) |
|---|---|---|---|---|---|---|---|---|
| 043 | Brain | PO | 75 | 0.50 | 2684.81 | 1787.23 | 0.79 | 0.70 |
| 001 | Brain | PO | — | 0.50 | 602.12 | 498.04 | 2.61 | 2.55 |

General Procedure for Intravenous Pharmacokinetic Study in Mice:

Male $C_{57}BL6$ mice were used to evaluate each compound, with n=3 mice/time point. Animals were administered through intravenous route with solution formulation at 2 mg/kg dose. The formulation vehicle used was 1% NMP and 99% normal saline. Blood samples (approximately 60 μL) were collected under light isoflurane anesthesia from a set of three mice at each time point. The blood samples were collected at each time point in labeled micro centrifuge tube containing $K_2EDTA$ as anticoagulant and phenyl methyl sulfonyl fluoride [PMSF (100 mM; 10 μL/mL of blood)] as a stabilizer. Plasma samples were separated by centrifugation of whole blood and stored below −70° C. until bioanalysis. Following blood collection, immediately, animals were sacrificed, and vena-cava was cut open and blood was drained. Whole body was perfused from heart using 10 mL of normal saline. Brain samples were collected from set of three mice at each time point. After isolation, brain samples were rinsed three times in ice cold normal saline (for 5-10 seconds/rinsed using ~10-20 mL normal saline in disposable petri dish for each rinse), dried on blotting paper and weighed. Brain samples were homogenized using 2 volumes of ice-cold PBS (pH-7.4) of brain weight. Total homogenate volume was three times of the brain weight. Brain homogenates were stored below −70±10° C. until analysis. Concentrations of compound (or compound and metabolite) in mouse plasma and brain samples were determined by fit for purpose LC-MS/MS method.

Example B3

Pharmacokinetics of 001 in Mice (iv)

Figure 6:
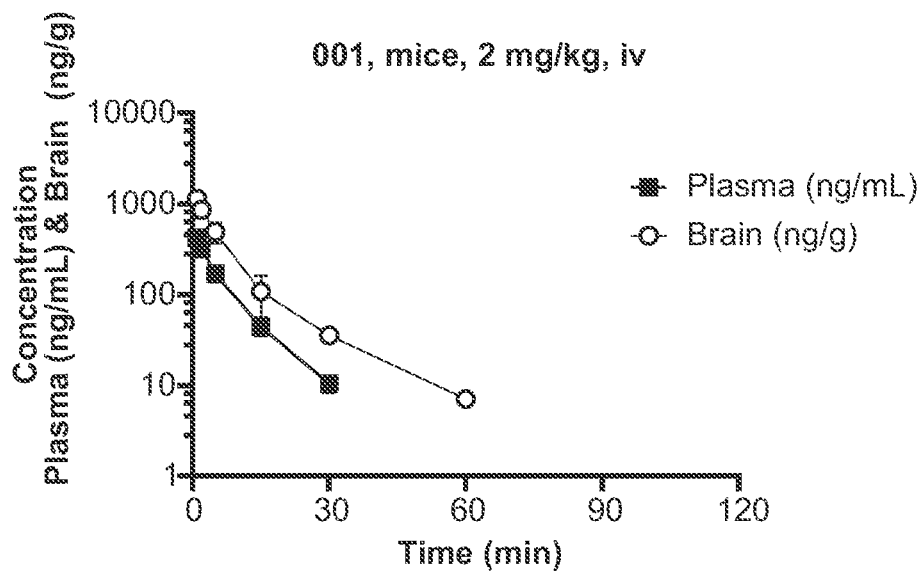
FIG. 6 is a graph showing the plasma and brain concentration-time profile (mean±SD) of 001 (mesembrine) in male C57BL/6 mice (n=3 per time point) following single intravenous administration of 001 (Dose: 2 mg/kg). 001 falls below limit of quantification after 30 min in plasma, and 60 min in brain.

Plasma and brain concentration-time profile (mean±SD) of 001 (mesmebrine) in male $C_{57}BL/6$ mice (n=3 per time point) following single intravenous administration of 001 (dose: 2 mg/kg). Plasma and brain samples were collected from set of three mice at each time point: 1, 2, 5, 15, 30, 60, 120, 180 min. Plasma levels of 001 not detectable at 60, 120, 180 min. Brain levels of 001 not detectable at 120, 180 min. The results are shown in FIG. 6, which shows plasma and brain levels of 001 following 2 mg/kg iv administration of compound 001 in mice. 001 falls below limit of quantification after 30 min in plasma, and 60 min in brain. Rapidly decreasing concentrations of 001 indicate fast clearance of the drug, hampering its potential as an oral therapeutic. This duration of action is insufficient for QD (once per day) or BID (twice per day) dosing.

Example B4

Pharmacokinetics of 001 in Mice Following 317 Administration (iv)

Figure 7:
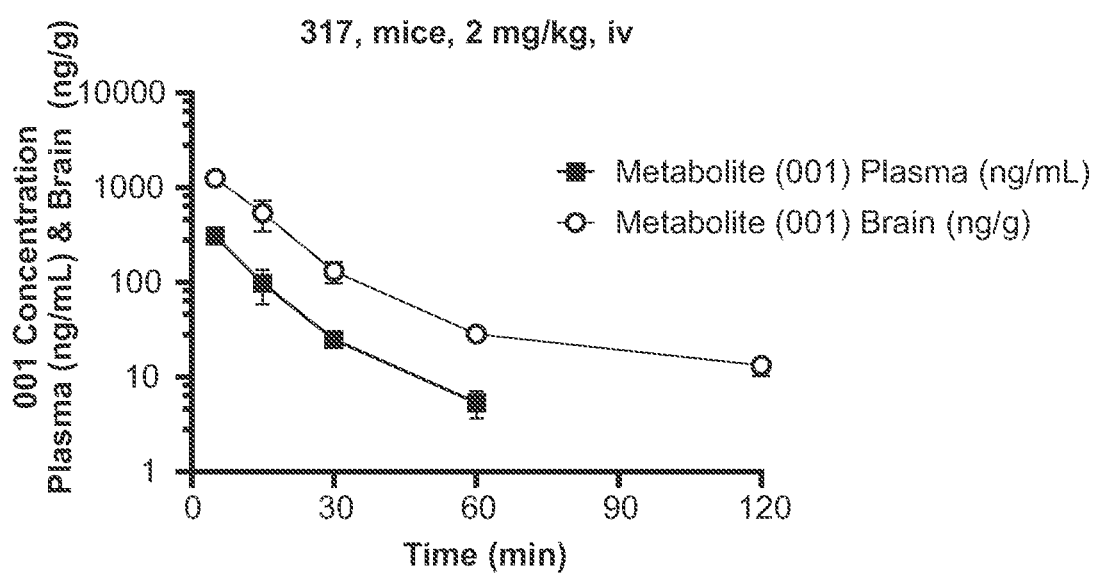
FIG. 7 is a graph showing the plasma and brain concentrations-time profiles (mean) of compound 317 following i.v. administration of the compound (Dose: 2 mg/kg). Compound 317 converts to 001 in vivo, providing quantifiable levels of 001 up to 60 min in plasm and 2 hours in brain.

The plasma and brain concentration-time data of 317 and 001 were used for the pharmacokinetic analysis. Plasma and brain concentration-time profile (mean±SD) of 001 (mesmebrine) in male $C_{57}BL/6$ mice (n=3 per time point) following single intravenous administration of pro-drug 317 (dose: 2 mg/kg). Plasma and brain samples were collected from set of three mice at each time point: 5, 15, 30, 60, 120 min. Plasma levels of 001 not detectable at 120 min. Plasma, CSF and brain samples were quantified by fit-for-purpose LC-MS/MS method. The results are shown in FIG. 7, which Plasma and brain levels of 001 following 2 mg/kg iv administration of compound 317 in mice. Compound 317 converts to 001 in vivo, providing quantifiable levels of 001 up to 60 min in plasm and 2 hours in brain. These data demonstrate that mesembrine prodrugs with a lipophilic enol ester (propionate) can provide extended levels of 001 in brain, as indicated by 2 hour brain concentration. These data also show a 2× improvement of 001 brain Tlast (time of last measurable concentration) compared to mesembrine dosing.

Example B5

Pharmacokinetics of 001 in Mice Following 334 Administration (iv)

Figure 8:
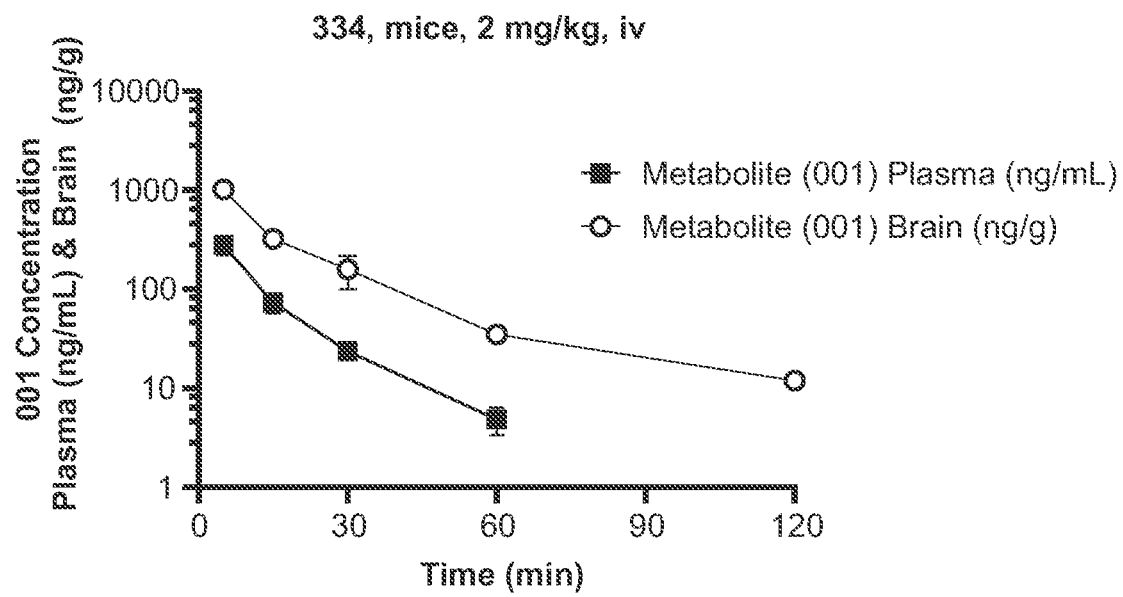
FIG. 8 is a graph showing the plasma and brain concentrations-time profiles (mean) of compound 334 following i.v. administration of the compound (Dose: 2 mg/kg). Compound 334 converts to 001 in vivo, providing quantifiable levels of 001 up to 60 min in plasma and 2 hours in brain.

The plasma and brain concentration-time data of 334 and 001 were used for the pharmacokinetic analysis. Plasma and brain concentration-time profile (mean±SD) of 001 (mesmebrine) in male $C_{57}BL/6$ mice (n=3 per time point) following single intravenous administration of pro-drug 334 (dose: 2 mg/kg). Plasma and brain samples were collected from set of three mice at each time point: 5, 15, 30, 60, 120 min. Plasma levels of 001 not detectable at 120 min. Plasma, CSF and brain samples were quantified by fit-for-purpose LC-MS/MS method. The results are shown in FIG. 8, which shows Plasma and brain levels of 001 following 2 mg/kg iv administration of compound 334 in mice. Compound 334 converts to 001 in vivo, providing quantifiable levels of 001 up to 60 min in plasm and 2 hours in brain. These data demonstrate that a mesembrine-prodrug with lipophilic enol ester and increased steric bulk (3-methylbutanoate) can provide increased concentration (compared to 317 in FIG. 7), while providing extended levels of 001 in brain, as indicated by the 2-hour brain time point.

TABLE 16

| Compound ID | Matrix | $C_0$ (ng/mL) | $AUC_{last}$ (h * ng/mL) |
|---|---|---|---|
| Mesembrine (001) | Plasma | 561 | 51 |
| 334 (001 measured) | Plasma | 354 | 134 |
| 317 (001 measured) | Plasma | 535 | 92 |
| Mesembrine (001) | Brain | 1498 | 150 |
| 334 (001 measured) | Brain | 1752 | 357 |
| 317 (001 measured) | Brain | 1884 | 425 |

Pharmacokinetic data comparing 001 levels following administration of 001 or prod-drug 317 or pro-drug 334 in male $C_{57}BL/6$ mice following a single intravenous administration (Dose: 2 mg/kg, IV).

General Procedure for Oral Dose Pharmacokinetic Study in Mice:

Total thirty-five male mice were used for each study with n=5 mice/time point. Animals were administered through oral route with solution formulation at 10 mg/kg dose. The formulation vehicle used was normal saline. Blood samples (approximately 60 μL) were collected under light isoflurane anesthesia from a set of five mice at 0.083, 0.25, 0.50, 1.0, 1.5, 2.0 and 3.0 h. The blood samples were collected at each time point in labeled micro centrifuge tube containing K2EDTA as anticoagulant. Plasma samples were separated by centrifugation of whole blood and stored below −70° C. until bioanalysis. Following blood collection, immediately animals were sacrificed followed by abdominal vena-cava was cut open and whole body was perfused from heart using 10 mL of normal saline. Brain samples were collected from set of five mice at 0.083, 0.25, 0.50, 1.0, 1.5, 2.0 and 3.0 h. After isolation, brain samples were rinsed three times in ice cold normal saline (for 5-10 seconds/rinsed using ~10-20 mL normal saline in disposable petri dish for each rinse), dried on blotting paper and weighed. Brain samples were homogenized using ice-cold phosphate buffer saline (pH-7.4). Brain homogenates were stored below −70±10° C. until analysis. Total homogenate volume was three times of the brain weight.

Example B6

Pharmacokinetics of 001 in Mice (po)

Figure 9:
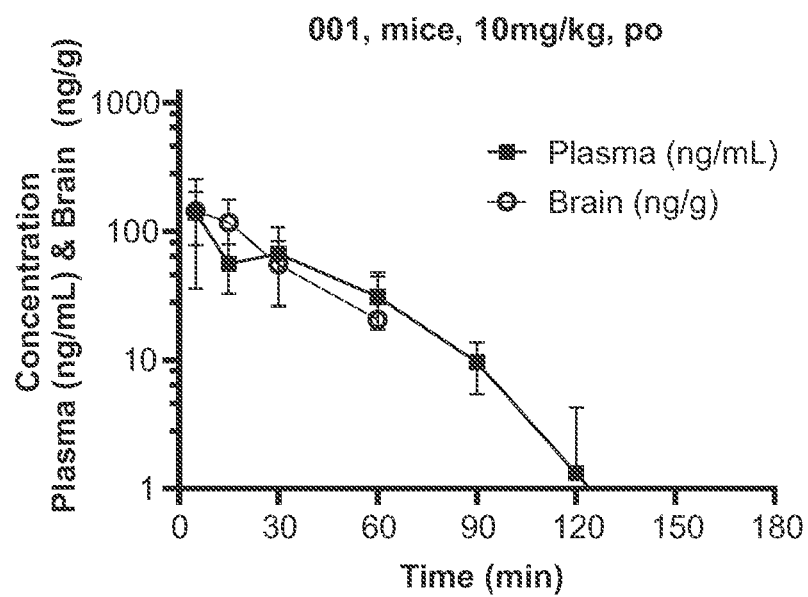
FIG. 9 is a graph showing the plasma and brain concentrations-time profiles (mean) of compound 001 following oral administration of the compound (Dose: 10 mg/kg). 001 is quantifiable up to 60 min in brain and 2 hours in plasma.

The plasma and brain concentration-time data of 001 was used for the pharmacokinetic analysis. Plasma and brain concentration-time profile (mean±SD) of 001 (mesembrine) in male $C_{57}BL/6$ mice (n=5 per time point) following oral administration of 001 (dose: 10 mg/kg, po). Plasma and brain samples were collected from set of three mice at each time point: 5, 15, 30, 60, 90, 120, 180 min. Plasma levels of 001 not detectable at 180 min. Brain levels of 001 not detectable at 90, 120, 180 min. Plasma and brain samples were quantified by fit-for-purpose LC-MS/MS method. The results are shown in FIG. 9, which shows plasma and brain levels of 001 following 10 mg/kg po administration of compound 001 in mice. 001 is quantifiable up to 60 min in brain and 2 hours in plasma. These data demonstrate 001 has poor bioavailability (%F<10%) and fast clearance in mice. Oral dose of 001 provides low systemic concentrations compared to i.v. dosing, likely due to high first pass effect. This is further evidence that 001 has a rapid onset but short duration of action in vivo, compounded by poor bioavailability, warranting prodrugs that can overcome these deficiencies.

Example B7

Pharmacokinetics of 001 in Mice Following 305 Administration (po)

Figure 10:
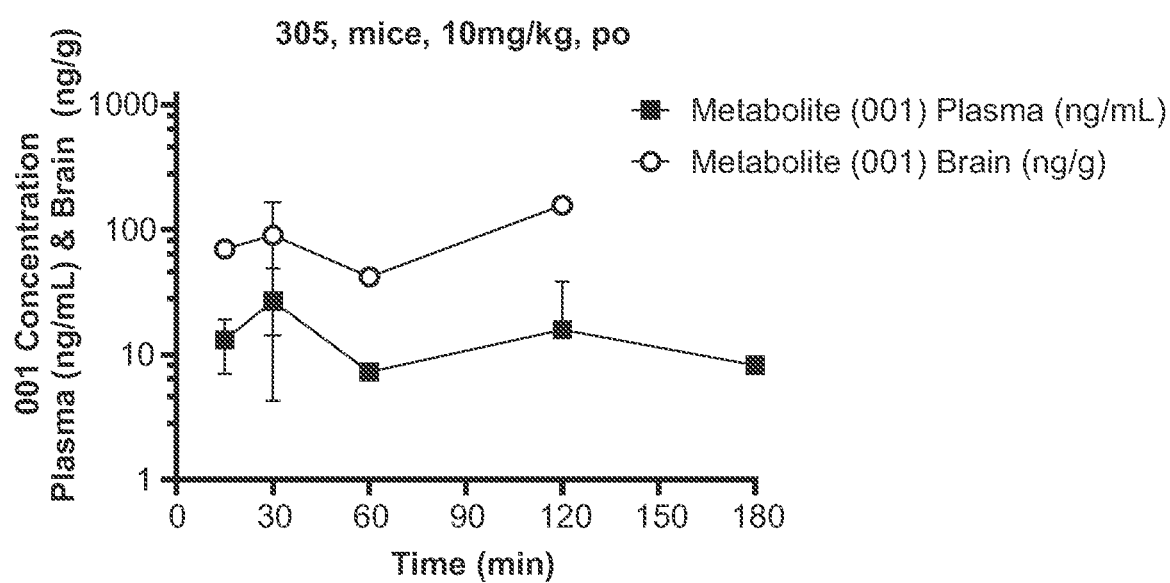
FIG. 10 is a graph showing mesembrine produced as a metabolite from an administered mesembrine prodrug in mice, and shows the plasma and brain concentrations-time profiles (mean) of compound 305 following oral administration of the compound (Dose: 10 mg/kg). 001 is quantifiable up to 3 hours in brain and 2 hours in plasma.

Plasma and brain concentration-time profile (mean±SD) of 001 (mesmebrine) in male $C_{57}BL/6$ mice (n=2 per time point) following oral administration of 305 (dose: 10 mg/kg, po). Plasma and brain samples were collected from set of three mice at each time point: 15, 30, 60, 120, 180 min. Brain levels of 001 not detectable at 180 min. The results are shown in FIG. 10, which shows plasma and brain levels of 001 as a metabolite following 10 mg/kg po administration of compound 305 in mice. 001 is quantifiable up to 3 hours in brain and 2 hours in plasma. These time-concentration plots demonstrate slow but continual release of 001 in vivo (as indicated by steady concentrations over time) following oral dose of prodrug due to increased lipophilicity and steric bulk (tert-butyl(benzoate)) of the prodrug moiety. Prodrug compound 305 provides extended concentrations of 001 over time compared to the equivalent oral dose of mesembrine.

Example B8

Figure 11A:
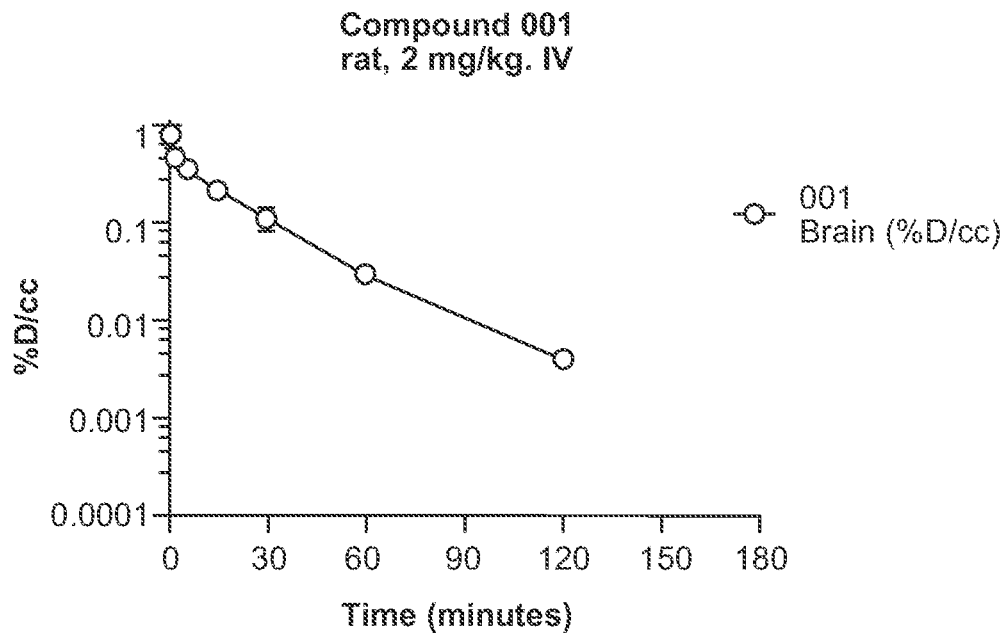
FIG. 11A is a graph showing the brain levels of 001 (mesembrine), and shows a % D/cc-time profile for compound 001 (i.v. Dose: 2 mg/kg). In rats, 001 brain levels fall below limit of quantification after 2 hours.
Figure 11B:
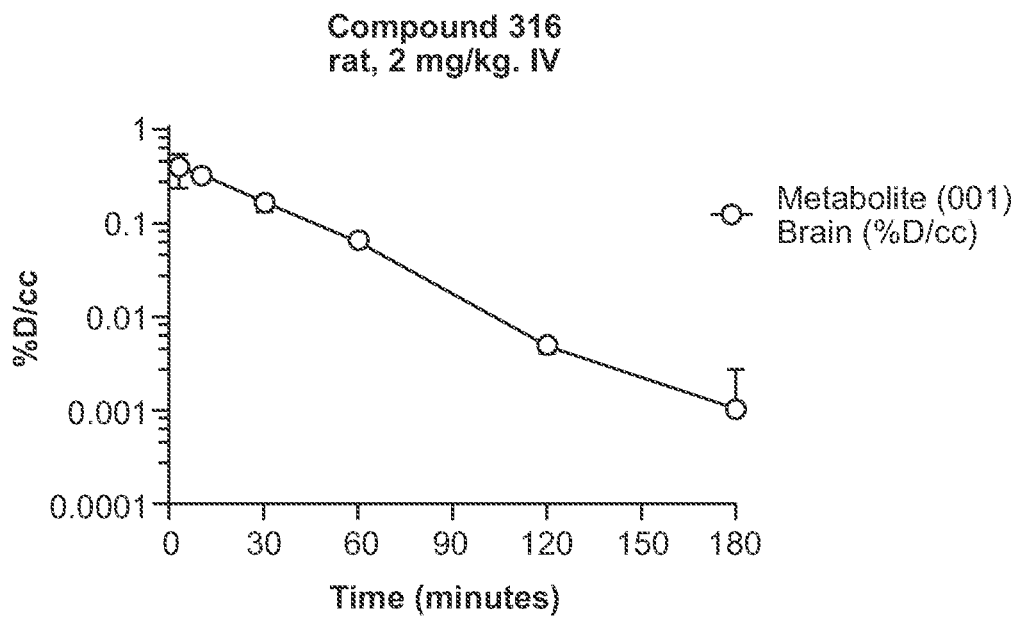
FIG. 11B is a graph showing the brain levels of 001 (mesembrine) produced as a metabolite from compound 316 shows a % D/cc-time profile for compound 316 (i.v. Dose: 2 mg/kg). Compound 316 converts to 001 in vivo in rat, and 001 brain levels are quantifiable up to 3 hours.
Figure 12:
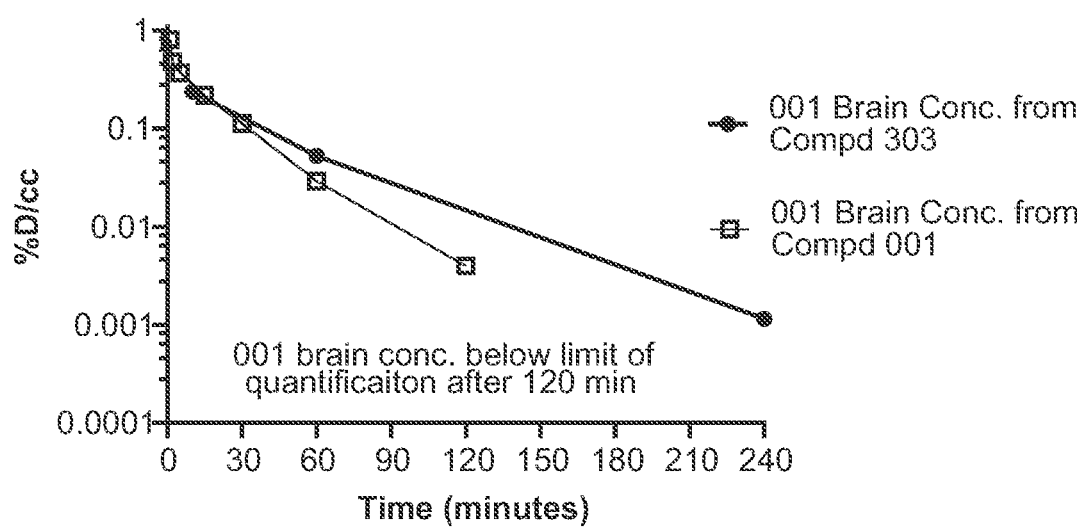
FIG. 12 is a graph of the brain levels of 001 (mesembrine) produced as a metabolite from compound 303 compared to administration of 001, and shows that administration of prodrug compound 303 extends concentration of 001 in rat brain (2 mg/kg Compd 303, iv), compared to compound 001 administration (2 mg/kg, iv). Compound 303 converts to 001 in vivo in rat, and 001 brain levels were quantifiable up to 4 hours, compared to just 2 hours when 001 is administered.

Pharmacokinetic Studies of Prodrug and Metabolite (001) Following Intravenous Administration in Male SD Rat 2 mg/kg of compound was administered intravenously to male SD rats (formulated in 1% NMP and 99% saline v/v). Plasma and brain samples were collected at 9 time points (n=3 per time point) from 0-4 hours post dose, to measure concentrations of prodrug and metabolite (001). Brain samples were homogenized with PBS (W/V, 1:3). Plasma/brain samples were mixed with acetonitrile containing internal standard. The samples were vortexed then centrifuged at 4 degrees Celsius for 15 minutes. The supernatant was diluted with water (1:2 V/V) and analyzed by LC/MS/MS for quantitative analysis. Concentration of parent/prodrug and metabolite (001) in brain were calculated for each time point. Area under the curve (AUC) was calculated and divided by dose to account for molecular weight difference of prodrug and metabolite (AUC/D). The Brain AUC ratio was calculated by dividing the Brain AUC/D for each prodrug and metabolite (001) by the Brain AUC/D obtained from Study ID #1. A brain AUC ratio >1.0 indicates an increase in brain concentration of 001 following administration of prodrug. Compound 001 Limit of Quantification: 0.00016% D/cc (0.5 ng/mL). Results are shown in FIGS. 11A, 11B, and 12. FIG. 11A shows brain levels of 001 following 2 mg/kg iv administration of compound 001 in rat. In rats, 001 brain levels fall below limit of quantification after 2 hours. Further evidence of the drug's rapid clearance and short duration of action. FIG. 11B shows brain levels of 001 as a metabolite following 2 mg/kg iv administration of compound 316 in rat. Compound 316 converts to 001 in vivo in rat, and 001 brain levels are quantifiable up to 3 hours. These data further demonstrate that mesembrine-prodrugs with a lipophilic enol ester and increased steric bulk (3-methylpentanoate) can provide increased concentration while providing extended levels of 001 in brain, as indicated by 3-hour brain time point (in comparison, mesembrine concentration at 3-hour time point was below quantifiable levels, FIG. 11A). FIG. 12 shows brain levels of 001 as a metabolite following 2 mg/kg iv administration of compound 303, overlaid with brain levels of 001 following 2 mg/kg iv administration of 001 in rat. Compound 303 converts to 001 in vivo in rat, and 001 brain levels were quantifiable up to 4 hours, compared to just 2 hours when 001 is administered. In comparison to mesembrine (001), prodrug compound 303 provides a flatter curve of 001 concentration (●) with slower clearance due to gradual conversion of 303 to 001 in vivo. The time-concentration profile of 001 from compound 303 administration, provides extended concentrations and potentially longer duration of action of 001 in vivo compared to dosing of mesembrine (001). Consistent with compound 305, compound 303 has a lipophilic aromatic prodrug moiety (4-methylbenzoate).

TABLE 17

| Study ID | Compound Administered | Compound Detected | Brain AUC ratio |
|---|---|---|---|
| 1 | 001 | 001 | 1.00 |
| 2 | 268 | 268 | 0.01 |
|   |   | 001 | 1.21 |
| 3 | 298 | 298 | 1.20 |
|   |   | 001 | 0.42 |
| 4 | 303 | 303 | 0.31 |
|   |   | 001 | 1.21 |
| 5 | 316 | 316 | 0.18 |
|   |   | 001 | 1.22 |
| 6 | 317 | 317 | BLQ |
|   |   | 001 | 1.10 |
| 7 | 334 | 334 | 0.14 |
|   |   | 001 | 1.19 |

The invention claimed is:

1. A compound of formula (I):

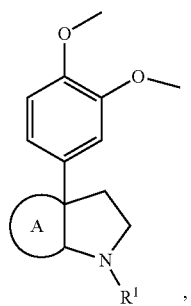

(I)

or a pharmaceutically acceptable salt thereof, wherein
R$^1$ is or C$_1$-C$_7$alkyl or H; and
ring A

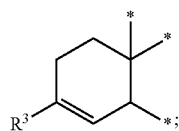

wherein * denotes the attachment points of ring A to the compound of formula (I), and wherein
R$^3$ is —OSi(C$_1$-C$_6$ alkyl)$_3$, —OC(O)C$_1$-C$_6$ alkyl, —OC(O)C$_2$-C$_6$ alkenyl, —OC(O)C$_3$-C$_{10}$ cycloalkyl, —OC(O)phenyl, —OC(O)-5- to 7-membered heteroaryl, wherein each hydrogen atom in C$_1$-C$_6$ alkyl, C$_2$-C$_6$ alkenyl, C$_3$-C$_{10}$ cycloalkyl, phenyl, and 5- to 7-membered heteroaryl is optionally substituted by halogen, C$_1$-C$_6$ alkyl, C$_1$-C$_3$ alkoxy, nitro, —N(C$_1$-C$_3$ alkyl)$_2$, C$_1$-C$_3$ haloalkyl, cyano, phenyl, phenoxy or —O(CH$_2$)$_p$OCH$_3$; and
p is 2, 3, or 4.

2. The compound of claim 1, wherein the compound is of formula (IIIb-1)

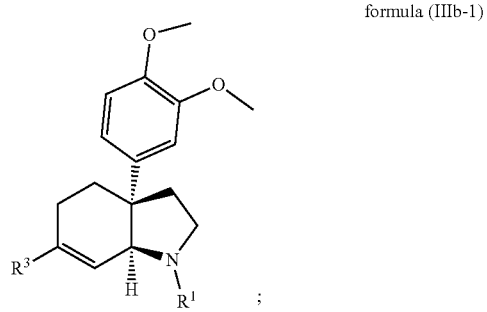

formula (IIIb-1)

or a pharmaceutically acceptable salt thereof.

3. The compound of claim 1, wherein R$^3$ is —OC(O)C$_1$-C$_6$ alkyl.

4. The compound of claim 1, wherein R$^3$ is —OC(O)CH$_3$.

5. The compound of claim 1, wherein R$^3$ is

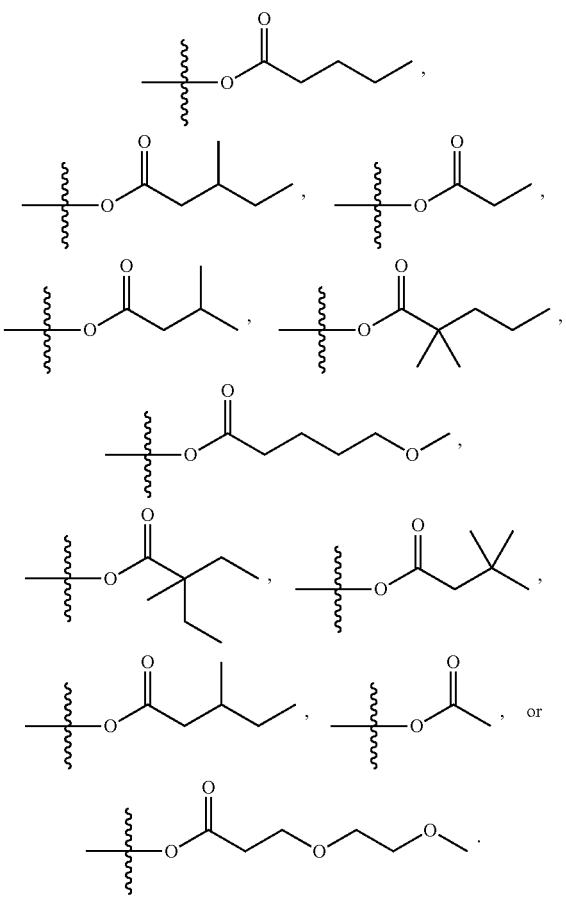

6. The compound of claim 1, wherein R$^3$ is —OC(O)—C$_2$-C$_6$ alkenyl; wherein the C$_2$-C$_6$ alkenyl is isopropenyl or butenyl.

7. The compound of claim 1, wherein the compound is a compound of formula (IIIb-1)

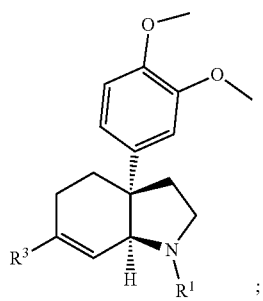

formula (IIIb-1)

or a pharmaceutically acceptable salt thereof, wherein:
$R^1$ is methyl; and
$R^3$ is —OC(O)$C_1$-$C_6$ alkyl, —OC(O)(cyclohexyl), —OC(O)phenyl, or —OC(O)-(6-membered heteroaryl), wherein each hydrogen atom in $C_1$-$C_6$ alkyl, cyclohexyl, phenyl, and 6-membered heteroaryl is optionally substituted by $C_1$-$C_6$ alkyl, $C_1$-$C_3$ alkoxy, or —O(CH$_2$)$_p$OCH$_3$; and
p is 2, 3, or 4.

8. The compound of claim 7, wherein $R^3$ is —OC(O)$C_1$-$C_6$ alkyl, and the $C_1$-$C_6$ alkyl is unsubstituted.

9. The compound of claim 7, wherein the $C_1$-$C_6$ alkyl is substituted by methoxy.

10. A compound of formula (IIIb-1)

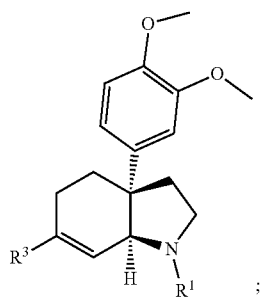

formula (IIIb-1)

or a pharmaceutically acceptable salt thereof, wherein:
$R^1$ is methyl; and
$R^3$ is —OC(O)$C_1$-$C_6$ alkyl, wherein the $C_1$-$C_6$ alkyl is unsubstituted; or
$R^3$ is —OC(O)phenyl, wherein the phenyl is optionally monosubstituted with an unsubstituted $C_1$-$C_6$ alkyl.

11. The compound of claim 10, wherein $R^3$ is —OC(O)$C_1$-$C_6$ alkyl.

12. The compound of claim 1, wherein the compound is

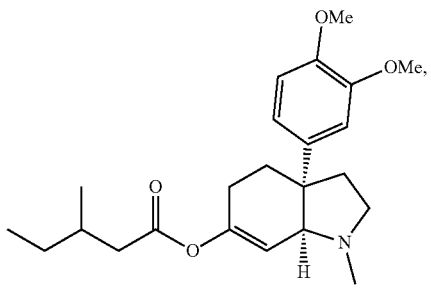 [SMILES: CCC(C)CC(=O)OC1=C[C@@H]2N(C)CC[C@]2(c2ccc(OC)c(OC)c2)CC1]

or a pharmaceutically acceptable salt thereof.

13. The compound of claim 1, wherein the compound is

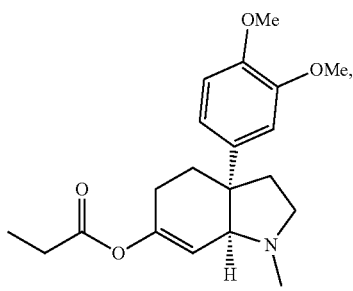 [SMILES: CCC(=O)OC1=C[C@@H]2N(C)CC[C@]2(c2ccc(OC)c(OC)c2)CC1]

or a pharmaceutically acceptable salt thereof.

14. The compound of claim 1, wherein the compound is

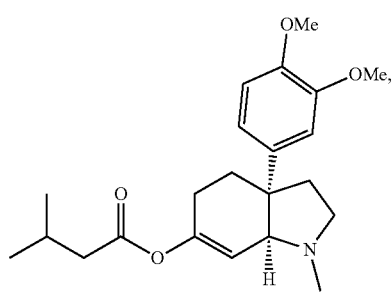 [SMILES: COc1ccc([C@@]23CCC(OC(=O)CC(C)C)=C[C@@H]2N(C)CC3)cc1OC]

or a pharmaceutically acceptable salt thereof.

15. The compound of claim 1, wherein the compound is

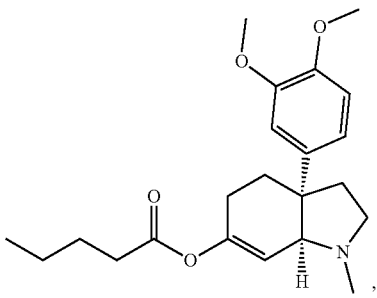 [SMILES: CCCCC(=O)OC1=C[C@@H]2N(C)CC[C@]2(c2ccc(OC)c(OC)c2)CC1]

or a pharmaceutically acceptable salt thereof.

16. The compound of claim 1, wherein the compound is

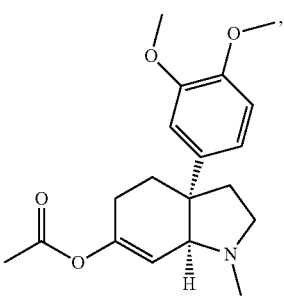 [SMILES: COc1ccc([C@@]23CCC(OC(C)=O)=C[C@@H]2N(C)CC3)cc1OC]

or a pharmaceutically acceptable salt thereof.

17. A compound of the formula:

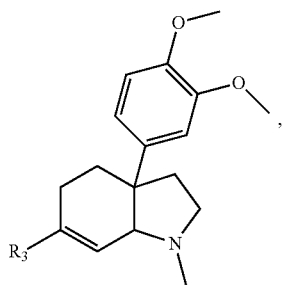

or a pharmaceutically acceptable salt thereof, wherein $R^3$ is —OC(O)alkyl optionally substituted by alkoxy, —OH, halogen, or -O(CH$_2$)$_p$CH$_3$; and p is 2, 3, or 4.

18. The compound of claim 17, wherein $R^3$ is —OC(O)alkyl substituted by fluoro, —OH, methoxy or -O(CH$_2$)$_p$OCH$_3$; and p is 2, 3, or 4.

19. The compound of claim 18, wherein $R^3$ is —OC(O)alkyl substituted by fluoro, methoxy, or —O(CH$_2$)$_2$OCH$_3$.

20. The compound of claim 17, selected from the group consisting of:

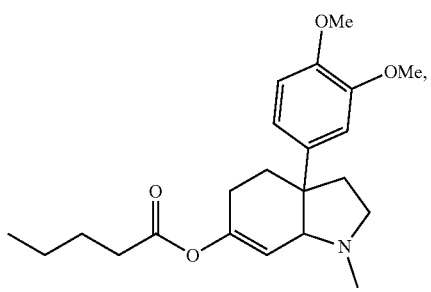

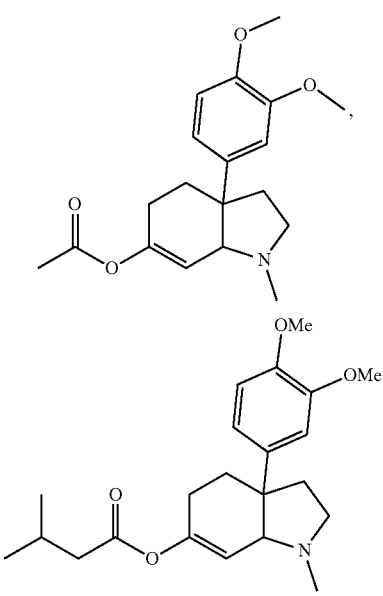

-continued

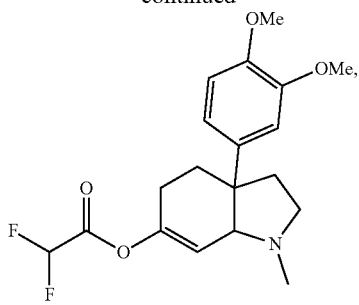

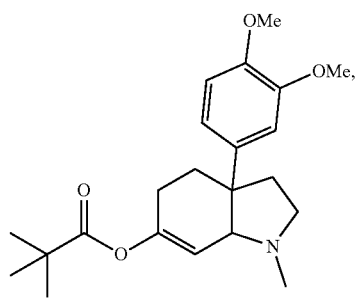

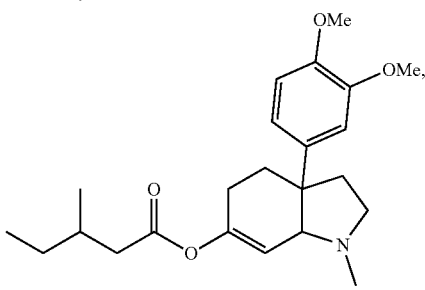

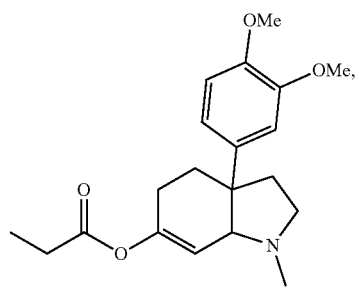

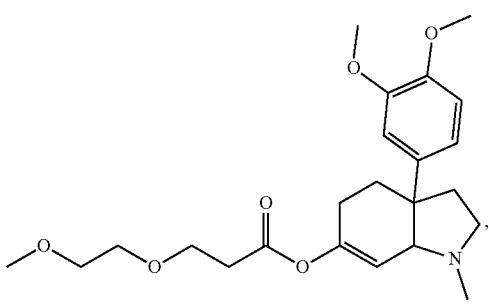 [SMILES: COCCOCCC(=O)OC1=CC2N(C)CCC2(c2ccc(OC)c(OC)c2)CC1]

595
-continued
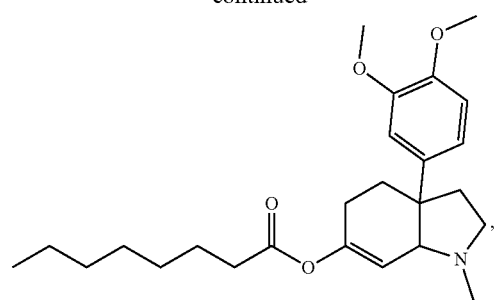
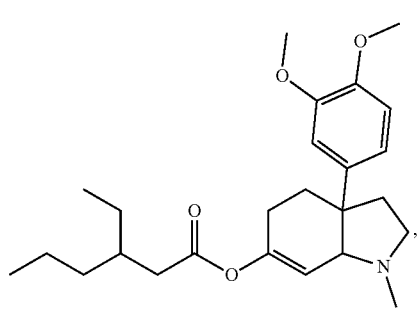
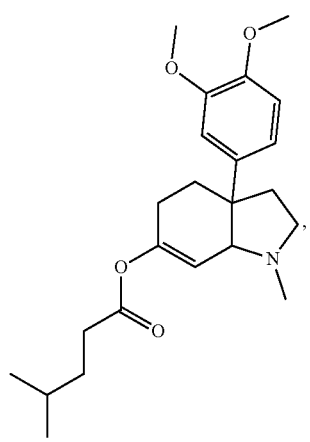
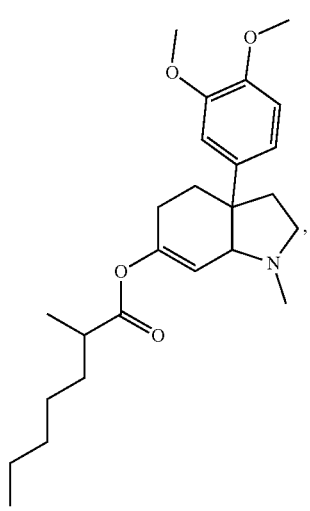
596
-continued
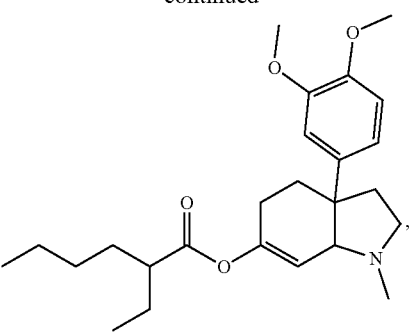
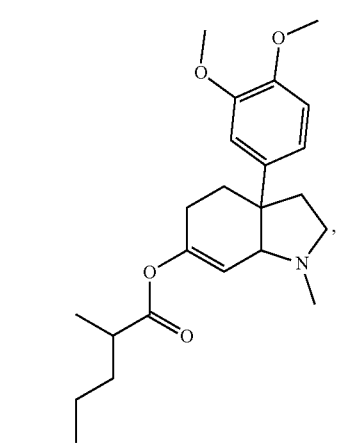
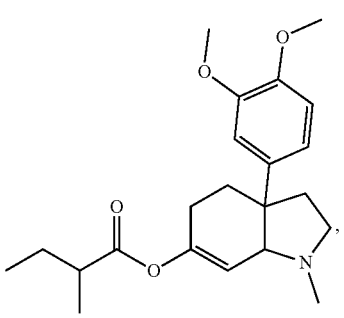
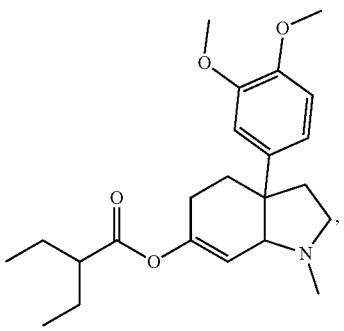

597
-continued
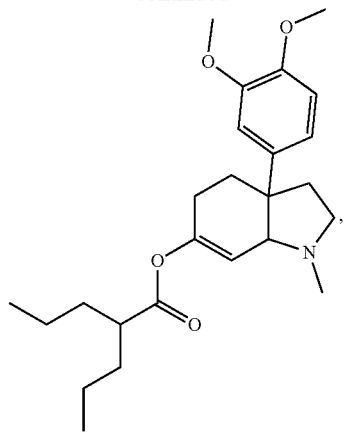
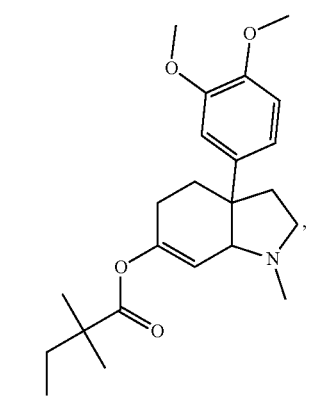
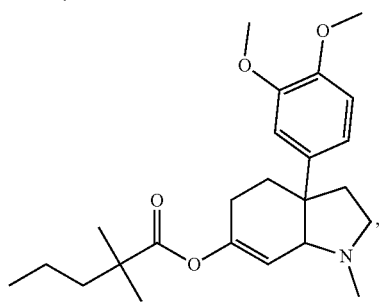
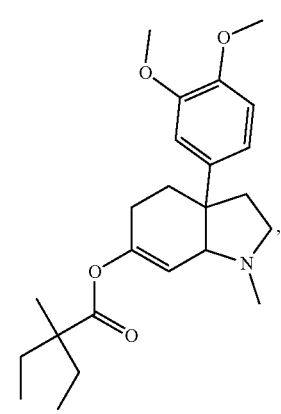
598
-continued
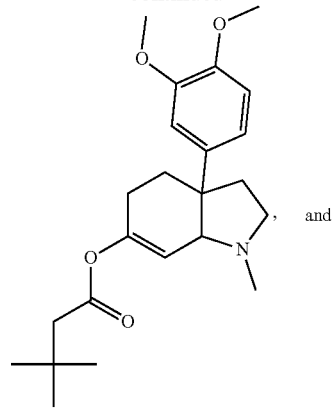
and
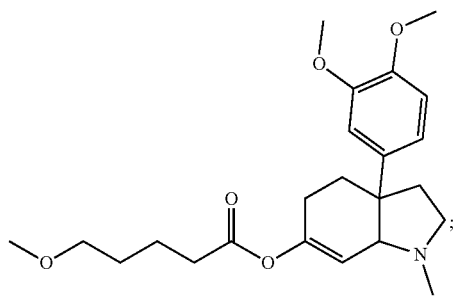
or a pharmaceutically acceptable salt thereof.
21. The compound of claim 17, selected from the group consisting of:
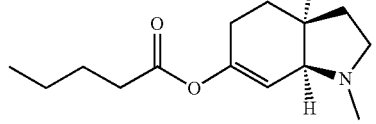
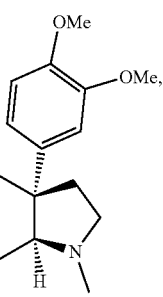
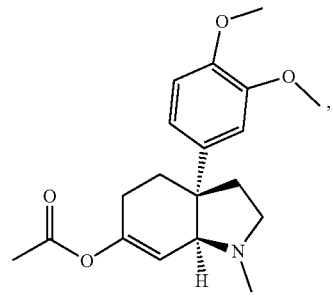

599
-continued
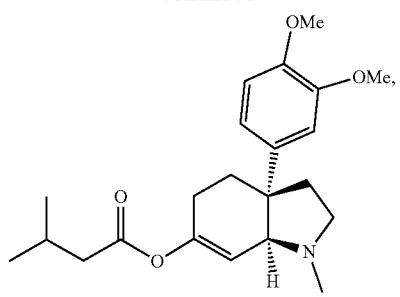
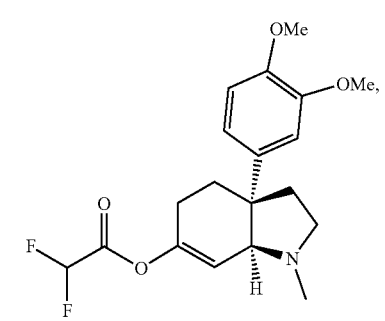
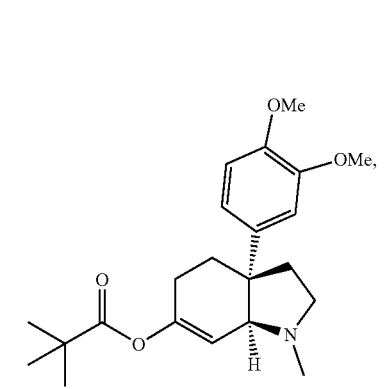
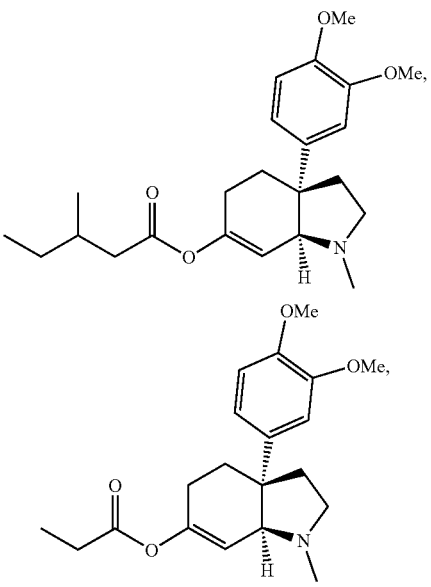
600
-continued
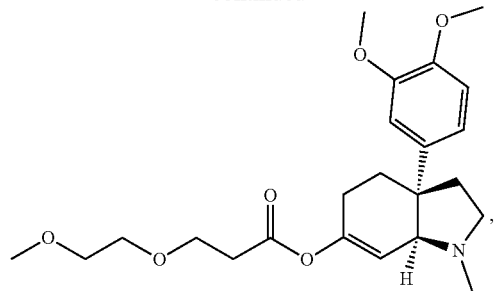
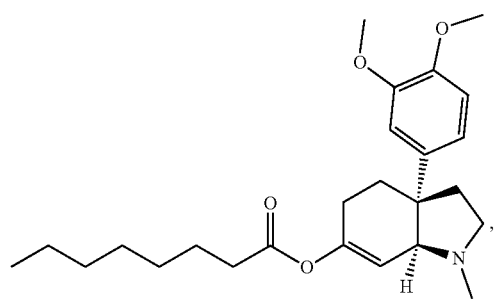
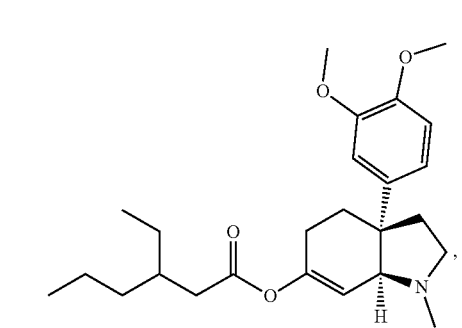
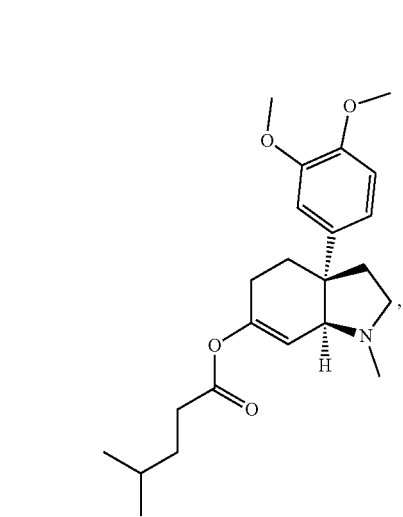

601
-continued
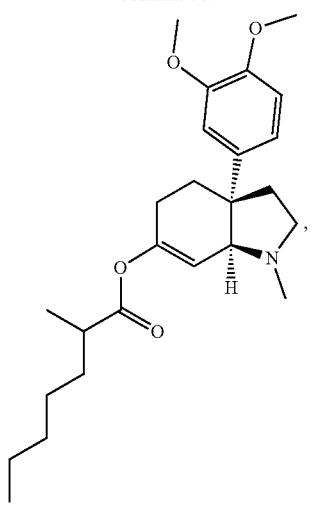
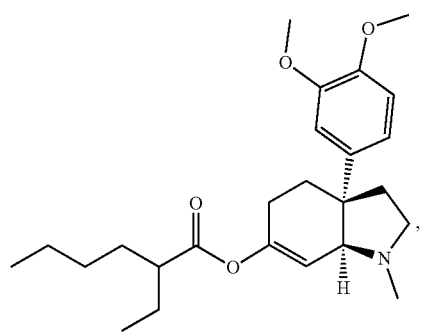
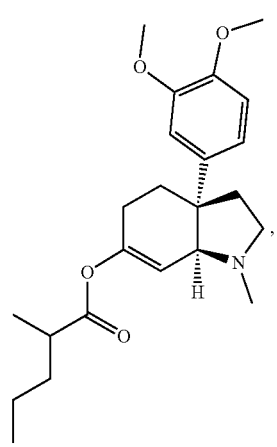
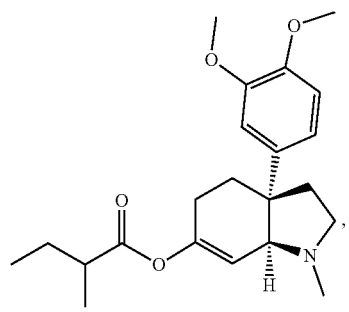
602
-continued
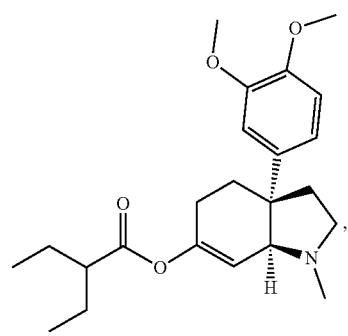
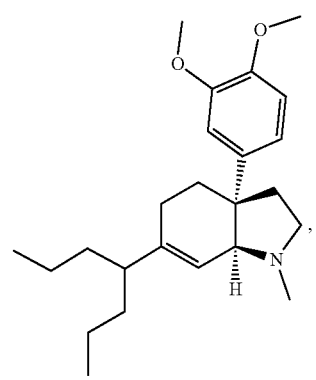
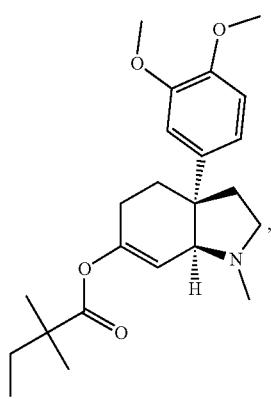

603
-continued
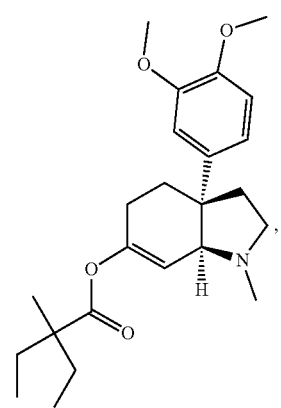
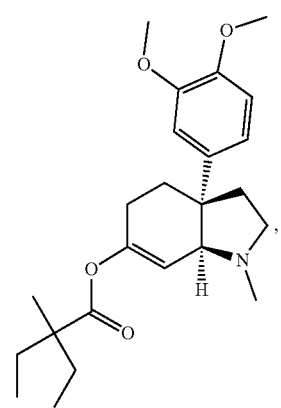
604
-continued
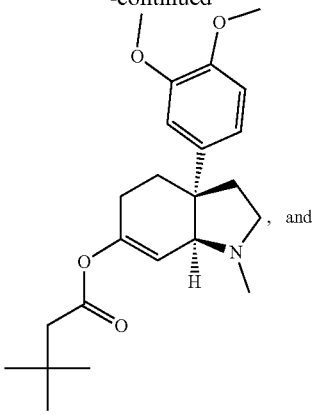, and
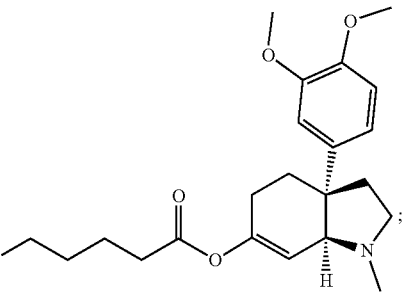
or a pharmaceutically acceptable salt thereof.
* * * * *